US010011838B2

(12) United States Patent
Lang et al.

(10) Patent No.: US 10,011,838 B2
(45) Date of Patent: Jul. 3, 2018

(54) YEAST STRAIN AND MICROBIAL METHOD FOR PRODUCTION OF PENTACYCLIC TRITERPENES AND/OR TRITERPENOIDS

(71) Applicant: NOVOZYMES A/S, Bagsvaerd (DK)

(72) Inventors: Christine Lang, Berlin (DE); Anna Lewandowski, Berlin (DE)

(*) Notice: Subject to any disclaimer, the term of this patent is extended or adjusted under 35 U.S.C. 154(b) by 0 days.

(21) Appl. No.: 15/118,489

(22) PCT Filed: Feb. 6, 2015

(86) PCT No.: PCT/EP2015/052516
§ 371 (c)(1),
(2) Date: Aug. 12, 2016

(87) PCT Pub. No.: WO2015/121168
PCT Pub. Date: Aug. 20, 2015

(65) Prior Publication Data
US 2017/0130233 A1    May 11, 2017

(30) Foreign Application Priority Data

Feb. 12, 2014 (EP) .................... 14154917

(51) Int. Cl.
*C12N 1/15* (2006.01)
*C12N 1/19* (2006.01)
*C12N 15/52* (2006.01)
*C12N 15/61* (2006.01)
*C12N 15/53* (2006.01)
*C12N 9/90* (2006.01)
*C12N 9/02* (2006.01)
*C12P 15/00* (2006.01)
*C12P 7/42* (2006.01)
*C12P 5/00* (2006.01)
*C12N 15/81* (2006.01)

(52) U.S. Cl.
CPC .......... *C12N 15/52* (2013.01); *C12N 9/0042* (2013.01); *C12N 9/0071* (2013.01); *C12N 9/90* (2013.01); *C12N 15/81* (2013.01); *C12P 5/007* (2013.01); *C12P 7/42* (2013.01); *C12P 15/00* (2013.01); *C12Y 106/02004* (2013.01); *C12Y 504/99041* (2013.01)

(58) Field of Classification Search
None
See application file for complete search history.

(56) References Cited

FOREIGN PATENT DOCUMENTS

WO    WO 2012116783 A2 *  9/2012 ........... C12N 9/0004
WO    2013/167751 A1    11/2013

OTHER PUBLICATIONS

GenBank, Accession No. U49919, 1999, www.ncbi.nlm.gov.*
GenBank, Accession No. BT008426, 2003, www.ncbi.nlm.gov.*
GenBank, Accession No. FN995113, 2011, www.ncbi.nlm.gov.*
Li et al., Increase of betulinic acid production in *Saccharomyces cerevisiae* by balancing fatty acids and betulinic acid forming pathways, Appl. Microbiol. Biotechnol., Jan. 2014, 98, 3081-89.*
GenBank, Accession No. XM_003602850, 2011, www.ncbi.nlm.nih.gov.*
GenBank, Accession No. BAA86930, 2000, www.ncbi.nlm.gov.*
GenBank, Accession No. BAJ84106, 2011, www.ncbi.nlm.gov.*
Li et al., Increase of betulinic acid production in *Saccharomyces cerevisiae* by balancing fatty acids and betulinic acid forming pathways further report, Appl. Microbiol. Biotechnol., 2014, 98, 3081-89.*
Tessa Moses et al.:"Bioengineering of plant (tri)terpenoids: from metabolic engineering of plants to synthetic biology in vivo and in vitro", New Phytologist, May 14, 2013, pp. 1-17, XP55074828.
Fukushima Ery O et al.:"CYP716A Subfamily Members are Multifunctional Oxidases in Triterpenoid Biosynthesis", Plant and Cell Physiology, Bd. 52, No. 12, Dec. 2011, pp. 2050-2061, XP002738814.
Seki H et al.:"Licorice beta-amyrin 11-oxidase, a cytochrome P450 with a key role in the biosynthesis of the triterpene sweetener glycyrrhizin", Proceedings of the national academy of sciences, National Academy of sciences, US, Bd.105, No. 37, Sep. 16, 2008, pp. 14204-14209, XP008131547.
Shibuya M et al.:"Two branches of the lupeol synthase gene in the molecular evolution of plant oxidosqualene cyclases", European Journal of Biochemistry, Wiley-Blackwell publishing Ltd, GB, Bd.266, No. 1, Nov. 1, 1999, pp. 302-307, XP002191880.
Zhang H et al.:"Oxidosqualene cyclases from cell suspension cultures of *Betula platyphylla* var. *japonica*: molecular evolution of oxidosqualene cyclases in higher plants", Biological & Pharmaceutical Bulletin (of Japan), Pharmaceutical Society of Japan, Tokyo, JP, Bd.26, No. 5, Jan. 1, 2003, pp. 642-650, XP002980653.

* cited by examiner

*Primary Examiner* — Tekchand Saidha
*Assistant Examiner* — Todd M Epstein
(74) *Attorney, Agent, or Firm* — Eric J. Fechter

(57) ABSTRACT

The invention relates to a yeast strain and to a method for microbial production of pentacyclic triterpenes and/or triterpenoids in yeast. More particularly, the invention relates to a modified yeast strain for production of pentacyclic triterpenoids comprising at least one copy of a gene for encoding an oxidosqualene cyclase, at least one copy of a gene for encoding an NADPH-cytochrome P450 reductase and/or at least one copy of a gene for encoding a cytochrome P450 monooxygenase.

36 Claims, 2 Drawing Sheets

Figure 1:
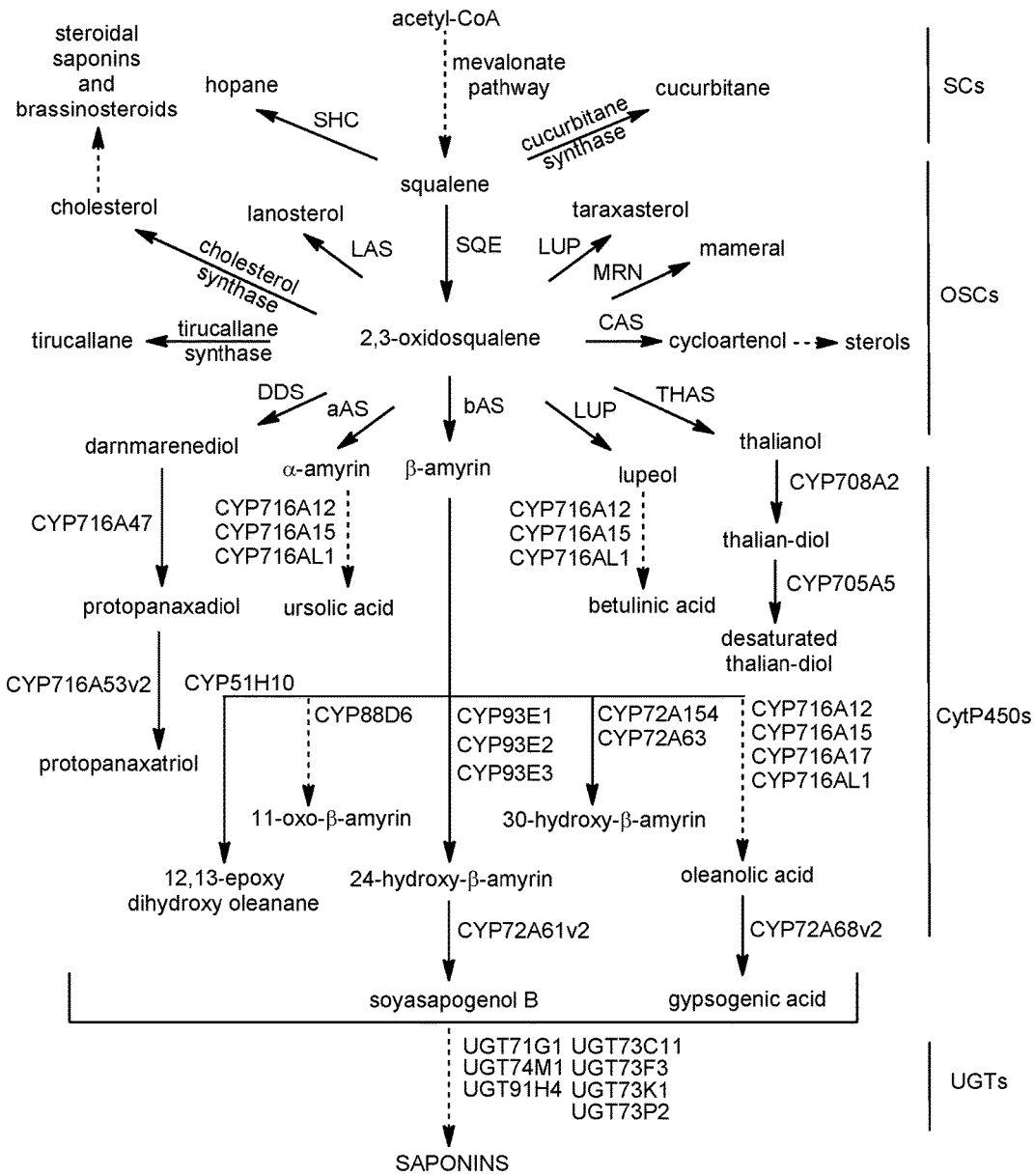

YEAST STRAIN AND MICROBIAL METHOD FOR PRODUCTION OF PENTACYCLIC TRITERPENES AND/OR TRITERPENOIDS

CROSS-REFERENCE TO RELATED APPLICATIONS

This is the U.S. national stage of International application PCT/EP2015/052516, filed Feb. 6, 2015 designating the United States and claims priority to EP 14154917.0, filed Feb. 12, 2014.

DESCRIPTION

The invention relates to a yeast strain and a method for microbial production of pentacyclic triterpenes and/or triterpenoids in yeast. In particular, the invention relates to a modified yeast strain for production of pentacyclic triterpenoids comprising at least one copy of a gene for encoding an oxidosqualene cyclase, at least one copy of a gene for encoding a NADPH-cytochrome P450 reductase and/or at least one copy of a gene for encoding a cytochrome P450 monooxygenase.

BACKGROUND OF THE INVENTION

Terpenoids are a group of substances including natural substances or related compounds which are structurally derived from isoprene. They differ from similar terpenes in that they contain functional groups, whereas terpenes are pure hydrocarbons.

Cyclic triterpenes are a diverse group of secondary metabolites which result from the metabolic pathway of squalene. They occur principally in plants and are of considerable interest to the pharmaceutical and food industries on account of their biological (inter alia antifungal, antibacterial, anti-inflammatory, antioxidative, antiviral and anti-tumoral) activities. Pentacyclic triterpenes constitute a particularly relevant sub-group of cyclic triterpenes. The basic structures of pentacyclic triterpenes consist of 5-ring systems with different substitution patterns of the methyl groups; in this case the rings A to D are 6-membered and ring E is five- or six-membered.

Nowadays, triterpenoids are generally obtained from higher plants by complex extraction processes (WO 2011/074766 A2, WO 2011/074766 A3R4, Muffler et al., 2011). However, in this resource they are only present in very small amounts, so that in the past it was hardly possible to commercialize and industrialize these substances (Madsen et al., 2011; Fukushima et al., 2011).

Furthermore, the chemical synthesis of biologically active triterpenes is likewise not economically viable and lasting on account of the complex structures.

The microbial production of triterpenes or triterpenoids is not yet established. It has already been shown (Moses et al., 2013) that the synthesis of pentacyclic triterpenoids in *Saccharomyces cerevisiae* (*S. cerevisiae*) is possible in principle after heterologous expression of corresponding genes (Moses et al. 2013).

Some genes which catalyze the synthesis of triterpenes are already known (Fukushima et al., 2011, Philips et al., 2006, Wang et al., 2011). These genes code for enzymes which catalyze the synthesis of for example cycloartenol or lanosterol (non-pentacyclic triterpenes) or lupeol or β-amyrin (pentacyclic triterpenes), but also corresponding secondary products (Huang et al., 2012, Kirby et al., 2008).

Lupeol or α/β-amyrin constitute the most important starting substances for the biosynthesis of a plurality of pentacyclic triterpenes. These compounds include, for example, betulinic acid, ursolic acid and oleanolic acid, which are of considerable interest to the pharmaceutical and food industries on account of their inter alia antibacterial, antiviral, anti-inflammatory and anti-tumoral activities (Fukushima et al., 2011; Saleem et al., 2009; Siddique et al., 2011; Holanda et al., 2008; Melo et al., 2011; Chintharlapalli et al., 2011; Shanmugam et al., 2011, Suzuki et al., 2002).

The production of the triterpenoid lupeol and betulinic acid in yeast is described in CN102433347. *S. cerevisiae* strains are known from Fukushima et al., 2011, which produce oleanolic acid, ursolic acid or betulinic acid. *S. cerevisiae* strains are known from Huang et al., 2012, which produce between 0.045 and 0.1 mg/L oleanolic acid, ursolic acid or betulinic acid. Dai et al., 2013, describe the synthesis of the triterpenoid protopanaxadiol with the overexpression of the tHMG1 gene as well as a NADPH-cytochrome P450 reductase in *S. cerevisiae*. In order to increase squalene and 2,3-oxidosqualene, the following genes were overexpressed: tHGMG1, ERG20, ERG9 and ERG1. In Fukushima et al., 2013, the synthesis of the pentacyclic triterpenoids soyasapogenol B, gypsogenic acid and 4-epi-hederagenin in *S. cerevisiae* is described. In Kunii et al., 2012, the oxidation of beta-amyrin to 12,13-epoxy in *S. cerevisiae* is described. In Seki et al., 2008, the oxidation of beta-amyrin to 11-oxo-beta-amyrin in *S. cerevisiae* with a yield of 1.6 mg/L is described.

It is known from Wang et al., 2011, that approximately 50 oxidosqualene cyclases from plants, which catalyze the cyclization of 2,3-oxidosqualene in different triterpene alcohols, were cloned and characterized by means of heterologous gene expression in yeast. From Kirby et al., 2008, an *S. cerevisiae* strain is known which expresses a beta-amyrin synthase of the plant *Artemisia annua* and produces 6 mg/L of the triterpenoid beta-amyrin and also expresses the tHMG1 gene.

It is known that the overexpression of the HMG-CoA reductase in yeast leads to the enrichment of the triterpene squalene (Polakowski et al., 1998). Furthermore, overexpressed genes from the ergosterol biosynthesis lead to the accumulation of sterols in the yeast *Saccharomyces cerevisiae* (Veen et al., 2003).

Li et al., 2013, constructed *S. cerevisiae* strains which produce the pentacyclic triterpenoid betulinic acid in different quantities (0.01-1.92 mg $L^{-1}$ $OD^{-1}$). However, the achieved quantities are in no way sufficient for production on an industrial scale.

Phytochemicals such as terpenes and sterols currently make up a large proportion of active substances obtained from plants. The annual turnover is approximately 12.4 billion USO (Raskin et al., 2002). In this case there is great interest in betulinic acid, which has proved successful as an inhibitor of melanoma and other cancer cells (Pisha et al., 1995; Sunder et al., 2000). An equally important role is played by several derivatives of betulinic acid which are currently at the center of various clinical studies for the treatment of the HIV virus. The great interest in betulinic acid is accounted for above all by the therapeutically application of betulinic acid and betulinic acid derivatives against cancer or HIV (DE69908397T2, DE1971376884, DE19713768A 1, DE69634951 T2, DE69633398T2).

In addition to the outdated and inefficient synthetic production (Ruzicka et al., 1938), nowadays betulinic acid is obtained by extraction from higher plants, for example from the bark of *Picramnia pentandra* (Ruzicka et al., 1938),

*Arbutus menziesii* (Robinson et al., 1970) or *Ziziphus mauritiana* (Pisha et al., 1995) and in particular *Platanus occidentalis*. In this case in spite of continuous improvement of the extraction process large quantities of organic solvent are consumed. In this connection one of the most recent processes is described in US2007/0149490A1, in which the betulinic acid is obtained from the bark of, the plane tree by means of chemical extraction. It can be seen from the document that large quantities of organic solvents as well as large quantities of energy are consumed in order to obtain betulinic acid.

Furthermore, the pentacyclic triterpenes and/or triterpenoids in plant resources only occur in the form of mixtures, so that the purification of individual components is very complex.

In order to estimate the future annual world requirement for betulinic acid a comparison may be made with taxol, which is used in cancer therapy. Betulinic acid also has, in addition to other applications (anti-inflammatory, antibacterial, antiviral), the potential for use in cancer therapy. The annual world requirement for taxol is currently approximately 1000 kg (Cameron et al., 2002). However, it must be noted that, by comparison with betulinic acid, taxol is used in much smaller doses for therapy.

Thus the disadvantages of the prior art reside above all in the fact that large quantities of solvent and energy are required by the previously available industrial processes for production of triterpenes and triterpenoids, in particular betulinic acid. Moreover, these are particularly time-consuming and expensive production processes. The described processes for microbial production currently do not achieve a yield which enables production on an industrial scale.

Therefore, the object of the invention was to provide a strain and a method for microbial production of pentacyclic triterpenoids.

DESCRIPTION OF THE INVENTION

The object is achieved by the independent claims. Particularly advantageous embodiments are set out in the dependent claims.

In a first preferred embodiment the invention relates to a modified yeast strain for production of pentacyclic triterpenoids, comprising
i. at least one copy of a gene for encoding an oxidosqualene cyclase, wherein the gene comprises a sequence selected from the group comprising nucleic acids according to accession number AB055511 (SEQ ID NO: 1), AB025343 (SEQ ID NO: 2), AB663343 (SEQ ID NO: 3), NM_179572 (SEQ ID NO: 4), AB181245 (SEQ ID NO: 5), DQ268869 (SEQ ID NO: 6), AB025345 (SEQ ID NO: 7), AB116228 (SEQ ID NO: 8), JQ087376 (SEQ ID NO: 9), HM623871 (SEQ ID NO: 10), AB289586 (SEQ ID NO: 11), AB055512 (SEQ ID NO: 12) and nucleic acid sequence variants with at least 70% sequence identity to SEQ ID NO: 1 to 12, or wherein the gene comprises a sequence which codes for an amino acid sequence according to SEQ ID NO: 54 to 65, or for an amino acid sequence variant with at least 85% sequence identity to SEQ ID NO: 54 to 65;
and/or
ii. at least one copy of a gene for encoding an NADPH-cytochrome P450 reductase, wherein the gene comprises a sequence selected from the group comprising nucleic acids according to accession number AB433810 (SEQ ID NO: 13), X66016 (SEQ ID NO: 14), X69791 (SEQ ID NO: 15), XM_003602850 (SEQ ID NO: 16), NM_001179172 (SEQ ID NO: 17), X66017 (SEQ ID NO: 18), JN594507 (SEQ ID NO: 19), DQ984181 (SEQ ID NO: 20), DQ318192 (SEQ ID NO: 21), AF302496 (SEQ ID NO: 22), AF302497 (SEQ ID NO: 23), AF302498 (SEQ ID NO: 24), L07843 (SEQ ID NO: 25), AF024635 (SEQ ID NO: 26), AF024634 (SEQ ID NO: 27), FJ719368 (SEQ ID NO: 28), FJ719369 (SEQ ID NO: 29) and nucleic acid sequence variants with at least 70% sequence identity to SEQ ID NO: 13 to 29; or wherein the gene comprises a sequence which codes for an amino acid sequence according to SEQ ID NO: 66 to 82, or for an amino acid sequence variant with at least 85% sequence identity to SEQ ID NO: 66 to 82;

and/or iii. at least one copy of a gene for encoding a cytochrome P450 monooxygenase, wherein the gene comprises a sequence selected from the group comprising nucleic acids according to accession number AB619802 (SEQ ID NO: 30), AB619803 (SEQ ID NO: 31), DQ335781 (SEQ ID NO: 32), JN565975 (SEQ ID NO: 33), XM_002331391 (SEQ ID NO: 34), XM_003525274 (SEQ ID NO: 35), JF803813 (SEQ ID NO: 36), XM_004139039 (SEQ ID NO: 37), GU997666 (SEQ ID NO: 38), JX036032 (SEQ ID NO: 39), XM_002522891 (SEQ ID NO: 40), AM457725 (SEQ ID NO: 41), XM_002265988 (SEQ ID NO: 42), XM_002527956 (SEQ ID NO: 43), BT147421 (SEQ ID NO: 44), XM_003530477 (SEQ ID NO: 45), BT096613 (SEQ ID NO: 46), XM_002309021 (SEQ ID NO: 47), BT051785 (SEQ ID NO: 48), XM_002513137 (SEQ ID NO: 49), XM_002264607 (SEQ ID NO: 50), XM_002324633 (SEQ ID NO: 51), XM_003531801 (SEQ ID NO: 52), XM_002280933 (SEQ ID NO: 53) and nucleic acid sequence variants with at least 70% sequence identity to SEQ ID NO: 30 to 53, or wherein the gene comprises a sequence which codes for an amino acid sequence according to SEQ ID NO: 83 to 105, or for an amino acid sequence variant with at least 85% sequence identity to SEQ ID NO: 83 to 105.

The modified yeast strain according to the invention for production of pentacyclic triterpenoids preferably comprises:
at least one copy of a gene for encoding an oxidosqualene cyclase according to i., wherein a copy of a gene for encoding a NADPH-cytochrome P450 reductase according to ii. or a copy of a gene for encoding a cytochrome P450 monooxygenase according to iii. are not present (e.g. for the production of lupeol);
at least one copy of a gene for encoding an oxidosqualene cyclase according to i. and at least one copy of a gene for encoding a cytochrome P450 monooxygenase according to iii., wherein a copy of a gene for encoding a NADPH-cytochrome P450 reductase according to ii. is not present;
a combination of at least one copy of a gene for encoding an oxidosqualene cyclase according to i. and at least one copy of a gene for encoding a NADPH-cytochrome P450 reductase according to ii. and at least one copy of a gene for encoding a cytochrome P450 monooxygenase according to iii.

In particular, the invention comprises yeast strains which have one of the following combinations of gene
- AB025343 (OEW), XM_003602850 (MTR), AB619802 (CYP716A15)
- AB025343 (OEW), XM_003602850 (MTR), AB619803 (CYP716A17)
- AB025343 (OEW), XM_003602850 (MTR), AB619803 (CYP716A9)
- AB025343 (OEW), X69791 (CrCPR), AB619802 (CYP716A15)
- AB025343 (OEW), X69791 (CrCPR), XM_003525274 (Cytochrome P450 71682-like)
- AB025343 (OEW), X69791 (CrCPR), XM_002331391 (CYP716A9)
- AB025343 (OEW), X69791 (CrCPR), AB619803 (CYP716A17)
- AB025343 (OEW), AB433810 (LjCPR1), AB619802 (CYP716A15)
- AB025343 (OEW), AB433810 (LjCPR1), XM_004139039 (cytochrome P450 71681-like)
- AB025343 (OEW), X66016 (ATR1) und JN565975 (CYP716AL1)

In this case it is preferable that the following combinations are not selected:
- AB663343 (GuLUP1), AB433810 (LjCPR1) and DQ335781 (CYP716A12);
- AB663343 (GuLUP1), AB433810 (LjCPR1) and AB619802 (CYP716A15);
- NM_179572 (AtLUP1), X66016 (ATR1) und JN565975 (CYP716AL1).

The remaining combinations exhibited a substantially higher yield of pentacyclic triterpenoids, so that these are preferred.

In particular, the invention comprises yeast strains which have an intracellular concentration of pentacyclic triterpenoids of more than 1 mg per gram of dry biomass, preferably more than 2 mg per gram of dry biomass, CH2OY.

In particular, the invention comprises yeast strains which have an intracellular concentration of lupeol of more than 5 mg per gram of dry biomass, preferably more than 7 mg per gram of dry biomass.

Therefore, in several embodiments the yeast strains according to the present invention are characterized in that they have an intracellular concentration of pentacyclic triterpenoids of more than 1, 2, 3, 4, 5, 6 or 7 mg per gram of dry biomass.

The technical problem of producing substantially more pentacyclic triterpenoids in yeast has been solved by, on the one hand, selection of different gene combinations and, on the other hand, by the use of new genes. In the light of the prior art if was extremely surprising that relatively large quantities of pentacyclic triterpenoids can be produced in yeast by the genes according to the invention.

A measurement of the intracellular concentration of the pentacyclic triterpenoids is possible without difficulties for a person skilled in the art in the field of microbiology. The following methods can be used for this: Most pentacyclic triterpenoids are hydrophobic and can accumulate in cells. In a first step the cells can be harvested by means of various processes such as for example centrifugation, filtration, crossflow filtration, chromatography (e.g. affinity chromatography, ion exchange chromatography, size exclusion chromatography) or by scraping of solid surfaces or culture plates. The cell pellet can be achieved in any way, preferably by means of centrifugation, filtration or crossflow filtration. Alternatively, the cells can fall with time. Optionally the cells are washed in any manner known from the prior art such as for example centrifugation, filtration or crossflow filtration. The cell pellet may be dried or not dried. The cells can be lysed in any manner known from the prior art. The cells can be lysed by means of mechanical action such as for example homogenization (for example with the aid of a Potter or a Downs homogenizer) or by means of pressure treatment (for example with the aid of a French press) or by means of ultrasound or by means of detergents or by means of lytic phages. Optionally, pentacyclic triterpenoids can be extracted by means of extraction with solvents, for example with organic solvents. Optionally, the organic solvent could then be evaporated. Alternatively or additionally, pentacyclic triterpenoids can be isolated or measured as a function of their chemical nature by means of chromatography methods (for example phase chromatography, ion exchange chromatography, reversed phase chromatography, size exclusion chromatography, high performance liquid chromatography (HPLC), ultra-high performance liquid chromatography (UHPLC), fast protein liquid chromatography (FPLC)) or by means of electrophoresis or by means of capillary electrophoresis (CE) or by means of distillation.

The above-mentioned methods can likewise be used for the production and isolation of the pentacyclic triterpenoids, for example in the method according to the invention for production of pentacyclic triterpenoids.

In Tables 7 to 14 several preferred gene combinations are disclosed which, independently of the yeast strain or type of genetic modification of the strain, lead to advantageous yields.

In particular, the invention comprises yeast strains which have the following gene combinations:

In further embodiments of the invention the following genes or gene combinations lead to an intracellular concentration of lupeol of more than 10 mg per gram of dry biomass:

| OSC gene | CPR gene | CYP gene | CYP gene accession |
|---|---|---|---|
| GuLUP1 | — | — | — |
| RcLUS1 | — | — | — |
| OEW | — | — | — |
| OEW | LjCPR1 | B1 | XM_004139039 |

In further embodiments of the invention the following genes or gene combinations lead to an intracellular concentration of lupeol of more than 7.5 mg per gram of dry biomass:

| OSC gene | CPR gene | CYP gene | CYP gene accession |
|---|---|---|---|
| GuLUP1 | — | — | — |
| RcLUS1 | — | — | — |
| OEW | — | — | — |
| OEW | LjCPR1 | B1 | XM_004139039 |
| OEW | CrCPR | B2 | XM_003525274 |
| OEW | ATR1 | AL1 | JN565975 |
| OEW | CrCPR | A9 | XM_002331391 |
| OEW | LjCPR1 | A41 | JF803813 |
| OEW | LjCPR1 | AL1 | JN565975 |
| OEW | LjCPR1 | B2 | XM_003525274 |
| OEW | CrCPR | A17 | AB619803 |
| OEW | LjCPR1 | A15 | AB619802 |
| OEW | ATR1 | A9 | XM_002331391 |
| OEW | MTR | A17 | AB619803 |
| OEW | CrCPR | AL1 | JN565975 |

In further embodiments of the invention the following genes or gene combinations lead to an intracellular concentration of lupeol of more than 5 mg per gram of dry biomass:

| OSC gene | CPR gene | CYP gene | CYP gene accession |
|---|---|---|---|
| GuLUP1 | — | — | — |
| RcLUS1 | — | — | — |
| OEW | — | — | — |
| OEW | LjCPR1 | B1 | XM_004139039 |
| OEW | CrCPR | B2 | XM_003525274 |
| OEW | ATR1 | AL1 | JN565975 |
| OEW | CrCPR | A9 | XM_002331391 |
| OEW | LjCPR1 | A41 | JF803813 |
| OEW | LjCPR1 | AL1 | JN565975 |
| OEW | LjCPR1 | B2 | XM_003525274 |
| OEW | CrCPR | A17 | AB619803 |
| OEW | LjCPR1 | A15 | AB619802 |
| OEW | ATR1 | A9 | XM_002331391 |
| OEW | MTR | A17 | AB619803 |
| OEW | CrCPR | AL1 | JN565975 |
| OEW | MTR | B2 | XM_003525274 |
| OEW | ATR1 | B2 | XM_003525274 |
| OEW | LjCPR1 | A17 | AB619803 |
| OEW | LjCPR1 | A9 | XM_002331391 |
| OEW | NCP1 | B2 | XM_003525274 |
| OEW | LjCPR1 | A12 | DQ335781 |
| OEW | CrCPR | A15 | AB619802 |
| OEW | NCP1 | A9 | XM_002331391 |
| OEW | MTR | A9 | XM_002331391 |
| OEW | NCP1 | A17 | AB619803 |
| OEW | NCP1 | A15 | AB619802 |
| OEW | MTR | A12 | DQ335781 |
| OEW | ATR1 | A15 | AB619802 |
| OEW | ATR1 | A17 | AB619803 |
| OEW | LjCPR1 | A41 | JF803813 |

In further embodiments of the invention the following genes or gene combinations lead to an intracellular concentration of betulin of more than 10 mg per gram of dry biomass:

| OSC gene | CPR gene | CYP gene | CYP gene accession |
|---|---|---|---|
| OEW | MTR | A15 | AB619802 |
| OEW | CrCPR | A15 | AB619802 |
| OEW | LjCPR1 | A15 | AB619802 |

In further embodiments of the invention the following genes or gene combinations lead to an intracellular concentration of betulin of more than 3 mg per gram of dry biomass:

| OSC gene | CPR gene | CYP gene | CYP gene accession |
|---|---|---|---|
| OEW | MTR | A15 | AB619802 |
| OEW | CrCPR | A15 | AB619802 |
| OEW | LjCPR1 | A15 | AB619802 |
| OEW | LjCPR1 | B2 | XM_003525274 |

In further embodiments of the invention the following genes or gene combinations lead to an intracellular concentration of betulin of more than 1 mg per gram of dry biomass:

| OSC gene | CPR gene | CYP gene | CYP gene accession |
|---|---|---|---|
| OEW | MTR | A15 | AB619802 |
| OEW | CrCPR | A15 | AB619802 |
| OEW | LjCPR1 | A15 | AB619802 |
| OEW | LjCPR1 | B2 | XM_003525274 |
| OEW | LjCPR1 | A17 | AB619803 |
| OEW | CrCPR | B2 | XM_003525274 |
| OEW | MTR | B2 | XM_003525274 |
| OEW | CrCPR | A17 | AB619803 |
| OEW | MTR | A17 | AB619803 |
| OEW | MTR | A12 | DQ335781 |

In further embodiments of the invention the following genes or gene combinations lead to an intracellular concentration of betulin aldehyde of more than 3 mg per gram of dry biomass:

| OSC gene | CPR gene | CYP gene | CYP gene accession |
|---|---|---|---|
| OEW | MTR | A15 | AB619802 |
| OEW | MTR | A17 | AB619803 |
| OEW | LjCPR1 | A17 | AB619803 |

In further embodiments of the invention the following genes or gene combinations lead to an intracellular concentration of betulin aldehyde of more than 2 mg per gram of dry biomass:

| OSC gene | CPR gene | CYP gene | CYP gene accession |
|---|---|---|---|
| OEW | MTR | A15 | AB619802 |
| OEW | MTR | A17 | AB619803 |
| OEW | LjCPR1 | A17 | AB619803 |
| OEW | CrCPR | A17 | AB619803 |
| OEW | CrCPR | A15 | AB619802 |
| OEW | LjCPR1 | B2 | XM_003525274 |

In further embodiments of the invention the following genes or gene combinations lead to an intracellular concentration of betulin aldehyde of more than 1 mg per gram of dry biomass:

| OSC gene | CPR gene | CYP gene | CYP gene accession |
|---|---|---|---|
| OEW | MTR | A15 | AB619802 |
| OEW | MTR | A17 | AB619803 |
| OEW | LjCPR1 | A17 | AB619803 |
| OEW | CrCPR | A17 | AB619803 |
| OEW | CrCPR | A15 | AB619802 |
| OEW | LjCPR1 | B2 | XM_003525274 |
| OEW | MTR | B2 | XM_003525274 |
| OEW | LjCPR1 | A15 | AB619802 |
| OEW | CrCPR | B2 | XM_003525274 |

In further embodiments of the invention the following genes or gene combinations lead to an intracellular concentration of betulinic acid of more than 5 mg per gram of dry biomass:

| OSC gene | CPR gene | CYP gene | CYP gene accession |
|---|---|---|---|
| OEW | MTR | A17 | AB619803 |
| OEW | MTR | A15 | AB619802 |

In further embodiments of the invention the following genes or gene combinations lead to an intracellular concentration of betulin of more than 2 mg per gram of dry biomass:

| OSC gene | CPR gene | CYP gene | CYP gene accession |
|---|---|---|---|
| OEW | MTR | A17 | AB619803 |
| OEW | MTR | A15 | AB619802 |
| OEW | CrCPR | A15 | AB619802 |
| OEW | CrCPR | A17 | AB619803 |
| OEW | MTR | B2 | XM_003525274 |

In further embodiments of the invention the following genes or gene combinations lead to an intracellular concentration of betulinic acid of more than 1 mg per gram of dry biomass:

| OSC gene | CPR gene | CYP gene | CYP gene accession |
|---|---|---|---|
| OEW | MTR | A17 | AB619803 |
| OEW | MTR | A15 | AB619802 |
| OEW | CrCPR | A15 | AB619802 |
| OEW | CrCPR | A17 | AB619803 |
| OEW | MTR | B2 | XM_003525274 |
| OEW | LjCPR1 | A17 | AB619803 |
| OEW | LjCPR1 | B2 | XM_003525274 |
| OEW | CrCPR | B2 | XM_003525274 |

The yield of pentacyclic triterpenoids can be expressed—as an alternative to the intracellular concentration in mg per g of dry biomass—as mg per liter of culture medium. It may be that several gene combinations lead to the limited intracellular concentration of pentacyclic triterpenoids per gram of dry biomass on account of a sub-optimal growth rate. Nevertheless, such gene combinations can prove advantageous when they lead to a relatively high yield of pentacyclic triterpenoid per liter of culture medium.

In further embodiments of the invention the following genes or gene combinations lead to a concentration of lupeol of more than 100 mg per gram of dry biomass:

| OSC gene | CPR gene | CYP gene | CYP gene accession |
|---|---|---|---|
| OEW | CrCPR | B2 | XM_003525274 |
| OEW | — | — | — |
| OEW | LjCPR1 | A41 | JF803813 |
| OEW | LjCPR1 | AL1 | JN565975 |
| OEW | ATR1 | AL1 | JN565975 |
| OEW | CrCPR | A9 | XM_002331391 |
| OEW | MTR | A17 | AB619803 |
| OEW | LjCPR1 | B1 | XM_004139039 |
| OEW | CrCPR | AL1 | JN565975 |
| OEW | LjCPR1 | B2 | XM_003525274 |
| OEW | CrCPR | A17 | AB619803 |
| OEW | ATR1 | A9 | XM_002331391 |
| OEW | LjCPR1 | A15 | AB619802 |
| OEW | NCP1 | B2 | XM_003525274 |
| OEW | MTR | B2 | XM_003525274 |
| OEW | ATR1 | B2 | XM_003525274 |
| OEW | LjCPR1 | A9 | XM_002331391 |
| OEW | LjCPR1 | A17 | AB619803 |
| OEW | LjCPR1 | A12 | DQ335781 |

In further embodiments of the invention the following gene or gene combinations lead to a concentration of betulin of more than 50 mg per liter of culture medium:

| OSC gene | CPR gene | CYP gene | CYP gene accession |
|---|---|---|---|
| OEW | MTR | A15 | AB619802 |
| OEW | CrCPR | A15 | AB619802 |
| OEW | LjCPR1 | A15 | AB619802 |
| OEW | LjCPR1 | B2 | XM_003525274 |

In further embodiments of the invention the following genes or gene combinations lead to a concentration of betulinaldehyde of more than 25 mg per liter of culture medium:

| OSC gene | CPR gene | CYP gene | CYP gene accession |
|---|---|---|---|
| OEW | MTR | A15 | AB619802 |
| OEW | LjCPR1 | A17 | AB619803 |
| OEW | CrCPR | A17 | AB619803 |
| OEW | CrCPR | A15 | AB619802 |
| OEW | LjCPR1 | B2 | XM_003525274 |
| OEW | MTR | B2 | XM_003525274 |

In further embodiments of the invention the following gene or gene combinations lead to a concentration of betulinic acid of more than 25 mg per liter of culture medium:

| OSC gene | CPR gene | CYP gene | CYP gene accession |
|---|---|---|---|
| OEW | MTR | A15 | AB619802 |
| OEW | CrCPR | A15 | AB619802 |
| OEW | CrCPR | A17 | AB619803 |
| OEW | MTR | B2 | XM_003525274 |
| OEW | LjCPR1 | A17 | AB619803 |
| OEW | MTR | A17 | AB619803 |

A measurement of the concentration of the pentacyclic triterpenoids per liter of culture medium is possible without difficulties for a person skilled in the art in the field of microbiology. The above-mentioned methods can be used for this:

In the context of the invention pentacyclic triterpenoids differ from triterpenes by at least one functional group. In the prior art there is often no clear distinction between the two terms, so that compounds with functional groups are also designated as triterpenes. Such compounds also constitute triterpenoids in the context of the invention.

The pentacyclic triterpenes and the terpenoids derived therefrom are divided into groups or types or series and associated with the underlying $C_{30}$ terpane. Names given to these terpanoid types include the following $C_{30}H_{52}$ basic structures: bauerane type, friedelane type, gammacerane type, glutinane type, hopane type, lupane type, multiflorane type, oleanane type, 18α-oleanane type, taraxerane type and ursane type.

The pentacyclic triterpenes and/or triterpenoids are preferably defined by a structure according to one of the formulae I, II or III, namely:

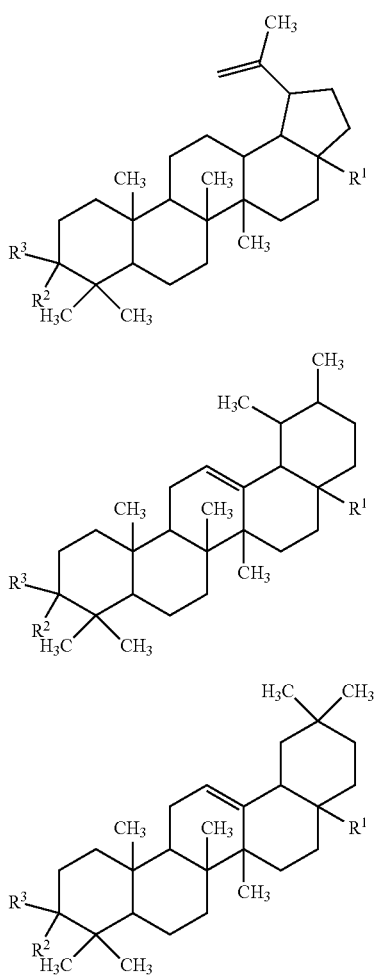

I

II

III wherein:
R1: Me, CH₂OH, CH₂OY¹, CH₂O—X—OH, CH₂O—X—OY¹, CH₂O—X—Y², CH₂O—X—Y³, CH₂NHY¹, CH₂NY¹₂, CH₂Y³, CH₂NH—X—OH, CH₂NH—X—Y², CH₂NH—X—Y³, CH₂NH—X—OY¹, CH₂OC(O)—OY¹, CH₂O—X—OY¹, CO₂Y¹, COY³, COY², CHO, CH=N(CH₂)ₘ(O(CH₂)m)nR4, or CH=N(CH₂)m(O(CH₂)m)nY²;
R2, R3: H, OH, OY¹, O—X—OH, O—X—OY¹, O—X—Y², Y³, NHY¹, NY¹₂, Y³, NH—X—OH, NH—X—Y², NH—X—Y³, NY¹—X—OY¹, NY¹—X—OH, NY¹—X—Y², NY¹—X—Y³ or NY¹—X—OY¹; provided that one of R2 or R3 is H, or that R2 and R3 together constitute carbonyl oxygen;
R4: H, OH, OY¹ or Y³;
Y¹: H, alkyl having 1-30 C atoms, linear or branched, cycloalkyl with 3-30 C atoms, alkanyl having 3-30 C atoms, oxyalkyl having 4-30 C atoms, phenylalkyl with 7-30 C atoms or phenoxyalkyl having 7-30 C atoms;
Y²: NH₂, NHY¹ or NY¹₂;
Y³: —(O(CH₂)m)nR4 or —(O(CH2)m)nY², wherein m=2-4 and n=1-230;
X: —OC(CH₂)pCO—, wherein p=1-22.

It was not to be expected that the production of pentacyclic triterpenoids in yeast can take place on an industrial scale. The results of previous research on this topic did not render such a possibility in anyway obvious.

The production of pentacyclic triterpenoids in yeast is particularly advantageous, since they exhibit no or only very little formation of further cyclic triterpenes (apart from sterols). Since in this case these are not native metabolites of yeast, few forms of mixtures are produced, so that the purification of the target products is simplified by a multiple.

The gene for encoding an oxidosqualene cyclase is preferably selected from Table 1. The gene for encoding an NADPH-cytochrome P450 reductase is preferably selected from Table 2. The gene for encoding a cytochrome P450 monooxygenase is preferably selected from Table 3. Above all in the compilation of these tables a majority of the inventive step is based on this application. In the prior art there were no clues to the combination of these genes.

In this case the genes are preferably transformed into the yeast strain, wherein the genes are functionally connected by promoter sequences which allow the expression of these genes in yeasts.

TABLE 1

Oxidosqualene cyclases (OSCs)

| Original organism | Gene name | OSC gene | Accession [Bp] |
|---|---|---|---|
| Betula platyphylla (var. Japonica) | OSCBPW | AB055511 | 2268 |
| Olea europaea | OEW | AB025343 | 2277 |
| Glycyrrhiza uralensis | GuLUP1 | AB663343 | 2277 |
| Arabidopsis thaliana | AtLUP1 | NM_179572 | 2274 |
| Lotus japonicus | OSC3 | AB181245 | 2268 |
| Ricinus communis | RcLUS1 | DQ268869 | 2310 |
| Taraxacum officinale | TRW | AB025345 | 2277 |
| Glycyrrhiza glabra | GgLUS1 | AB116228 | 2277 |
| Eleutherococcus trifoliatus | EtLUS | JQ087376 | 2292 |
| Kalanchoe daigremontiana | KdLUS | HM623871 | 2298 |
| Bruguiera gymnorhiza | BgLUS | AB289586 | 2286 |
| Betula platyphylla (var. Japonica) | OSCBPY | AB055512 | 2340 |

The gene OSCBPW AB055511 from *Betula platyphylla* (var. *Japonica*) (birch) has been described by Zhang et al., 2003. Birch bark contains large quantities of betulin. The gene belongs to the lupeol synthase family.

The gene OEW AB025343 from *Olea europaea* (olive tree) has been described by Shibuya et al., 1999. OEW transformants accumulate lupeol as exclusive product. This gene also belongs to the lupeol synthase family.

GuLUP1 AB663343 from *Glycyrrhiza uralensis* (licorice) has been described by Fukushima et al., 2011. Fukushima describes a co-expression with LjCPR1 and CYP716A12/CYP716A15.

AtLUP1 NM_179572 from *Arabidopsis thaliana* (mouse-ear cress or also thale cress) has been described by Huang et al., 2012, Husselstein-Muller et al., 2001, and Herrera et al., 1998. In this case Huang et al. describes a co-expressed with ATR1 and CYP716AL1.

The gene OSC3 AB181245 from *Lotus japonicus* (bird's foot trefoil) was described in 2006 by Sawai et al.

The gene RcLUS1 DQ268869 from *Ricinus communis* (castor oil plant) has been described by Guhling et al., 2006 and Gallo et al., 2009. This gene is not known as part of the lupeol synthase family and constitutes a highly specific LUS which is responsible for the production of lupeol in the *Ricinus* strain.

The gene TRW AB025345 from *Taraxacum officinale* was described in 1999 by Shibuya et al.

The gene GgLUS1 AB116228 from *Glycyrrhiza glabra* was described in 2004 by Hayashi et al.

The gene GgLUS1 JQ087376 from *Eleutherococcus trifoliatus* was described in 2012 by Ma et al.

KdLUS HM623871 from *Kalanchoe daigremontiana* have been described by Wang et al., 2010.

The gene BgLUS AB289586 from *Bruguiera gymnorhiza* has been described by Basyuni et al., 2007.

OSCBPY AB055512 from *Betula platyphylla* (var. *Japonica*) (birch) has been described by Zhang et al., 2003 and Phillips et al., 2006.

Table 2: NADPH-cytochrome P450 reductases (CPRs) EC 1.6.2.4

TABLE 2

NADPH-cytochrome P450 reductases (CPRs) EC 1.6.2.4

| Original organism | Gene name | CPR gene Accession | ORF length [Bp] |
|---|---|---|---|
| *Lotus japonicus* | LjCPR1 | AB433810 | 2121 |
| *Arabidopsis thaliana* | ATR1 | X66016 | 2079 |
| *Catharanthus roseus* | CrCPR | X69791 | 2145 |
| *Medicago truncatula* | MTR_3g100160 | XM_003602850 | 2079 |
| *Saccharomyces cerevisiae* | NCP1 (CPR1) | NM_001179172 | 2076 |
| *Arabidopsis thaliana* | ATR2 | X66017 | 2039 |
| *Artemisia annua* | CPR | JN594507 | 2115 |
| *Artemisia annua* | CPR | DQ984181 | 2115 |
| *Artemisia annua* | CPR | DQ318192 | 2115 |
| Hybrid poplar | CPR Isoform 1 | AF302496 | 2079 |
|  | CPR Isoform 2 | AF302497 | 2139 |
|  | CPR Isoform 3 | AF302498 | 2139 |
| *Vigna radiata* | VrCPR | L07843 | 2073 |
| *Petroselinum crispum* Petersilie | PcCPR1 | AF024635 | 2100 |
|  | PcCPR2 | AF024634 | 2046 |
| *Gossypium hirsutum* (cultivar CRI12) | GhCPR1 | FJ719368 | 2082 |
|  | GhCPR2 | FJ719369 | 2133 |

The gene LjCPR1 AB433810 from *Lotus japonicus* (bird's foot trefoil) has been described by Seki et al., 2008. In Fukushima et al., 2011 a co-expression with GuLUP1 and CYP716A12/CYP716A15 is disclosed.

The genes ATR1 X66016 and ATR2 X66017 out of *Arabidopsis thaliana* (mouse-ear cress) have been described by Pompon et al., 1996, Urban et al., 1997 and Urbank, 2012. Huang et al., 2012 describes a co-expression of ATR1 with AtLUP1 and CYP716AL1. Moreover, a low FMN affinity is known by means of ATR2 (Louerat-Oriou et al., 1998).

CrCPR X69791 from *Catharanthus roseus* (dogbane) has been described by Meijer et al., 1993 and Jensen et al., 2010. The corresponding CYP protein is known and has been tested.

The corresponding CYP protein of MTR_3g100160 XM_003602850 from *Medicago truncatula* (medick) is also known and has been tested.

The gene NCP1 (CPR1) NM_001179172 from *Saccharomyces cerevisiae* is known from Murakami et al., 1990 and Pompon et al., 1996.

The genes CPR JN594507, DQ984181 and DQ318192 from *Artemisia annua* have been described by Misra et al., 2012, or Yang et al., 2008 or Ro et al., 2006.

The CPR isoforms 1 (AF302496), 2 (AF302497) and 3 (AF302498) from Hybrid poplar (*Populus trichocarpa*× *Populus deltoides*) have been described by Ro et al., 2002.

The gene VrCPR L07843 from *Vigna radiata* (mung bean) has been described by Shet et al., 1993 and Urban et al., 1997.

The genes PcCPR1 AF024635 and PcCPR2 AF024634 from *Petroselinum crispum* (parsley) were described in 1997 by Koopmann et al.

The genes GhCPR1 FJ719368 and GhCPR2 FJ719369 from *Gossypium hirsutum* ((cultivar CR112) cotton) have been described by Yang et al., 2010.

TABLE 3

Cytochrome P450 monooxygenases (CYPs)

| Original organism | Gene name | CYP gene Accession | ORF length [Bp] |
|---|---|---|---|
| *Vitis vinifera* | CYP716A15 | AB619802 | 1443 |
| *Vitis vinifera* | CYP716A17 | AB619803 | 1443 |
| *Medicago truncatula* | CYP716A12 | DQ335781 | 1440 |
| *Catharanthus roseus* | CYP716AL1 | JN565975 | 1443 |
| *Populus trichocarpa* | CYP716A9 | XM_002331391 | 1446 |
| *Glycine max* | Predicted: Cytochrome P450 716B2-like (LOC100801007) | XM_003525274 | 1449 |
| *Bupleurum chinense* | CYP716A41 | JF803813 | 1449 |
| *Cucumis sativus* Gurke | Predicted: cytochrome P450 716B1-like | XM_004139039 | 1452 |
| *Panax notoginseng* | cytochrome P450 | GU997666 | 1446 |
| *Panax ginseng* | CYP716A52v2 | JX036032 | 1446 |
| *Ricinus communis* | cytochrome P450, putative | XM_002522891 | 1443 |
| *Vitis vinifera* | VITISV_041935 | AM457725 | 1443 |
| *Vitis vinifera* | Predicted: cytochrome P450 716B2 | XM_002265988 | 1443 |
| *Ricinus communis* | cytochrome P450, putative | XM_002527956 | 1416 |
| *Medicago truncatula* | unknown | BT147421 | 1440 |
| *Glycine max* | Predicted: *Glycine max* cytochrome P450 716B2-like (LOC100813159) | XM_003530477 | 1449 |
| *Glycine max* | unknown | BT096613 | 1335 |
| *Vitis vinifera* | Predicted: cytochrome P450 716B2 (LOC100242305) | XM_002280933 | 1449 |
| *Populus trichocarpa* | CYP716A8 (POPTR_0006s08560g) | XM_002309021 | 1455 |
| *Medicago truncatula* | unknown | BT051785 | 1440 |
| *Ricinus communis* | cytochrome P450, putative | XM_002513137 | 1434 |
| *Vitis vinifera* | cytochrome P450 716B2-like (LOC100265713) | XM_002264607 | 1458 |
| *Populus trichocarpa* | POPTR_0018s13390g | XM_002324633 | 1455 |
| *Glycine max* | cytochrome P450 716B2-like (LOC100815640), transcript variant X1 | XM_003531801 | 1449 |

The gene CYP716A15 AB619802 from *Vitis vinifera* (grapevine) has been described by Fukushima et al., 2011. Fukushima describes a co-expression with GuLUP1 and LjCPR1.

The gene CYP716A17 AB619803 from *Vitis vinifera* (grapevine) produces oleanolic acid with β-amyrin as substrate and has been described by Fukushima et al., 2011.

The gene CYP716A12 DQ335781 from *Medicago truncatula* (medick) has been described by Fukushima et al., 2011. Fukushima describes a co-expression with GuLUP1 and LjCPR1.

The gene CYP716AL 1 JN565975 from *Catharanthus roseus* (dogbane) has been described by Huang et al., 2012. Huang describes a co-expression with AtLU P1 and ATR 1.

The gene CYP716A9 XM_002331391 originates from *Populus trichocarpa* (poplar).

The gene cytochrome P450 716B2-like (LOC100801007) XM_003525274 originates from *glycine max* (soybean), which contains soyasaponins of the oleanane type.

CYP716A41 JF803813 from *Bupleurum chinense* (hare's ear) has been described by Pistelli et al., 2005, and contains saikosaponins of the oleanane type. Moreover, 8upleurum flavum is known tocontain betulin and betulinic acid.

The gene cytochrome P450 716S1-like XM_004139039 from *Cucumis sativus* (cucumber) has been described by Zhou et al., 2012. Ursolic acid has been identified in *Cucumis sativus* roots.

CYP716A52v2 JX036032 from *Panax ginseng* with the products erythrodiol and oleanolic acid has been described by Han et al., 2013. CYP716A52v2 is a β-amyrin 28-oxidase.

The genes cytochrome P450 GU997666 from *Panax notoginseng*, cytochrome P450 XM_002522891 from *Ricinus communis*, VITISV_041935 AM457725 from *Vitis vinifera*, cytochrome P450 71682 XM_002265988 from *Vitis vinifera*, cytochrome P450, XM_002527956 from *Ricinus communis*, BT147421 from *Medicago truncatula*, *Glycine max* cytochrome P450 71682-like (LOC100813159) XM_003530477 from *Glycine max*, BT096613 from *Glycine max*, cytochrome P450 71682 (LOC100242305) from *Vitis vinifera*, CYP716A8 (POPTR_0006s08560g) XM_002309021 from *Populus trichocarpa*, BT051785 from *Medicago truncatula*, cytochrome P450, XM_002513137 from *Ricinus communis*, cytochrome P450 71682-like (LOC100265713) XM_002264607 from *Vitis vinifera*, POPTR_0018s13390g XM_002324633 from *Populus trichocarpa* and cytochrome P450 71682-like (LOC100815640), transcript variant X1 XM_003531801 from *Glycine max* have likewise been included in Table 3.

The following genes have not yet been transformed into yeast in the prior art: X69791, XM_003602850, L07843, FJ719368, FJ719369, AB619803, XM_002331391, XM_003525274, JF803813, XM_004139039, GU997666, XM_002522891, AM457725, XM_002265988, XM_002527956, 8T147421, XM_003530477, BT096613, XM_002280933, XM_002309021, BT051785, XM_002513137, XM_002264607, XM_002324633, XM_003531801. Therefore, a person skilled in the art could not have foreseen that precisely these genes and combinations thereof with one another and with genes for encoding an oxidosqualene cyclase could lead to a yield from the production of triterpenoids in yeasts which is increased by a multiple.

It is preferable that the yeast strain comprises at least one copy of a gene for encoding a NADPH-cytochrome P450 reductase, wherein the gene comprises a sequence selected from the group comprising nucleic acids according to Accession Number X69791, XM_003602850, L07843, FJ719368, FJ719369, or sequence variants with analogous functions. Since theses sequences are not necessary for the production of, for example, lupeol it was completely surprising that these gene sequences lead to a particularly high and stable yield.

Moreover, it is preferable that the yeast strain comprises at least one copy of a gene for encoding a cytochrome P450 monooxygenase, wherein the gene comprises a sequence selected from the group comprising nucleic acids according to Accession Number AB619802, AB619803, DQ335781, JN565975, XM_002331391, XM_003525274, JF803813, XM_004139039, GU997666, JX036032, XM_002522891, AM457725, XM_002265988, XM_002527956, BT147421, XM_003530477, BT096613, XM_002280933, XM_002309021, BT051785, XM_002513137, XM_002264607, XM_002324633, XM_003531801.

Surprisingly, the use of these genes in combination with any gene from Table 1 and Table 2, but preferably X69791, XM_003602850, L07843, FJ719368, FJ719369, gave particularly good results with regard to the yield and the growth rate of the yeasts.

Furthermore, it is preferable that the strain produces betulin. Numerous pharmacological effects are described for betulin. Betulin has an inter alia anti-inflammatory, antibacterial, antiviral, hepatoprotective, antitumor and, moreover, cholesterol-lowering activity. Due to this broad spectrum of activity betulin is of particular interest for science and the pharmaceutical industry. Therefore, the increased production by the yeast strains according to the invention is particularly significant.

It may also be preferable that an increased enrichment of the preliminary stage, lupeol, is achieved. This can be achieved by a corresponding choice of the genes to be transformed. In addition to its antiprotozoic and antimicrobial action, lupeol also exhibits anti-inflammatory characteristics as well as an inhibition of growth of tumor cells. Moreover, lupeol can be used as an adjuvant therapeutic agent. Thus lupeol likewise constitutes an interesting substance which in the past could only be synthesized at substantial expense. The industrial production in yeast therefore constitutes a major advantage by comparison with the prior art. A number of pharmaceutically relevant triterpenes/triterpenoids can be produced from lupeol. It is particularly preferable to use yeast strains which overproduce lupeol for the production of betulin, betulin aldehyde and/or betulinic acid. The intermediate product lupeol or also the by-product β-amyrin are themselves molecules which, if simply available, are of great commercial interest.

The invention preferably relates to a "toolbox" with the aid of which an increased microbial production of pentacyclic triterpenoids, preferably betulin, betulin aldehyde and/or betulinic acid, is possible. In this case a "tool" is the strain construction. In this case first of all a yeast strain is constructed which, because of an optimized lipid metabolism, enriches large quantities of acetyl-CoA and/or 2,3-oxidosqualene. A strain which overproduces acetyl-CoA and/or 2,3-oxidosqualene constitutes an outstanding platform for the production of a number of biologically highly active triterpenes/triterpenoids. Betulinic acid as target substance has been selected as a pentacyclic triterpenoid which is particularly relevant from an ecological and economic viewpoint. Therefore, starting from a platform strain producing acetyl-CoA and/or 2,3-oxidosqualene, with the second "tool", the use of the selected genes from Tables 1, 2 and 3 and above all the combination thereof, further biosynthetic metabolic enzymes have been expressed for the purpose of the overproduction of betulinic acid.

It is particularly preferable that the yeast strain betulin aldehyde is produced.

Moreover, it is preferable that the yeast strain betulinic acid is produced.

In contrast to conventional active substances, betulinic acid has proved to be non-toxic for eukaryotic cells and laboratory animals. The good compatibility of betulinic acid by comparison with other natural substances such as taxol has been highlighted in Pisha et al. (1995). Later works have shown the very good compatibility of betulinic acid in studies on mice, where medication of up to 500 mg/kg hadno toxic effects (Udeani et al., 1999). The pharmacological in vivo action (mouse model) including the good compatibility of betulinic acid is described in an article by Mullauer et al. (2010) on page 8 ("Betulinic acidic in vivo").

Betulinic acid is inter alia an inhibitor of melanoma and other cancer cells. Moreover, several derivatives of betulinic acid are currently at the center of various clinical studies for the treatment of HIV and AIDS. Therefore, it is a great advance for science and research that betulinic acid can now be produced in large quantities more cost-effectively and more simply by the invention.

Surprisingly, substantially higher concentrations of pentacyclic triterpenoids can be produced by the selected gene combinations by a respective gene from Table 1, 2 and 3, which contain some new genes which have not previously been used in yeasts.

Surprisingly, the quantity produced is dependent upon the strain. This was shown inter alia using the example of lupeol. Thus the claimed strains showed particularly good results with regard to yield and purity of the products.

With the same gene combination CEN.PK strains, for example, behaved differently from AH22 strains.

By targeted genetic modifications *S. cerevisiae* strains could be constructed which enable the synthesis and enrichment of pentacyclic triterpenoids in large quantities due to the widening of the post-squalene biosynthesis path in the yeast *S. cerevisiae*.

The yeast can be selected from the group consisting of *Saccharomyces cerevisiae, Saccharomyces delbruckii, Saccharomyces italicus, Saccharomyces ellipsoideus, Saccharomyces fermentati, Saccharomyces kluyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosei, Saccharomyces rouxii, Saccharomyces uvarum* and *Saccharomycodes ludwigii*, as well as yeasts of the genus *Kluyveromyces* such as *K. lactis K. marxianus* var. *marxianus*, *K. thermotolerans*, as well as yeasts of the genus *Candida* such as *Candida utilis, Candida tropicalis, Candida albicans, Candida lipolytica* and *Candida versatilis*, as well as yeasts of the genus *Pichia* such as *Pichia stipidis, Piachia pastoris* and *Pichia sorbitophila*, as well as yeasts of the genera *Cryptococcus, Debaromyces, Hansenula, Saccharomycecopsis, Saccharomycodes, Schizosaccharomyces, Wickerhamia, Debayomyces, Hanseniaspora, Kloeckera, Zygosaccharomyces, Ogataea, Kuraishia, Komagataella, Metschnikowia, Williopsis, Nakazawaea, Cryptococcus, Torulaspora, Bullera, Rhodotorula, Yarrowia, Willopsis* and *Sporobolomyces*.

Moreover, the yeast strain is particularly preferably *Saccharomyces cerevisiae*.

It has proved particularly advantageous that the yeast strain comprises a tHMG1 expression cassette.

It has been shown that a further improvement of the yield can be achieved by the modification of genes of the pre- and post-squalene biosynthesis path. In this case genes of the pre- and post-squalene biosynthesis path were either overexpressed, downregulated, inhibited or deleted, in order ultimately to increase the production of pentacyclic triterpenoids.

In the context of the invention the basic strain, preferably *S. cerevisiae*, can be modified in different ways in order additionally to lead to an increased production of triterpenoids. An advantageous starting point for modification is the amount of acetyl-CoA. Acetyl-CoA is converted to squalene, which in turn constitutes a preliminary stage in the triterpenoid synthesis. It is therefore desirable to provide a large amount of acetyl-CoA. One possibility for modification is to reduce undesirable side reactions. This can take place, for example, by means of the reduction of the alcohol dehydrogenase activity in order to decrease the synthesis of ethanol from acetaldehyde, for example by deletion of one or more of the isoenzymes Adh1, Adh3, Adh4, Adh5. A further possibility is the inactivation or repression of ACC1 (acetyl-CoA carboxylase) in order to decrease the synthesis of fatty acids from acetyl-CoA.

Moreover, it is advantageous to reduce the fatty acid biosynthesis by decreasing the expression of FAS1 and/or FAS2 or to reduce the glyoxylate cycle by modification of at least one of the genes CIT2, ICL1, MLS1, MDH3, HAP2, HAP3, HAP4 and HAP5. The person skilled in the art knows how these genes can be modified in order to arrive at the desired result without exercising inventive skill himself.

In the context of the invention, moreover, a reduction of the pyruvate dehydrogenase activity can take place by modification of the sub-units of the PDH complex PDA 1, PDB1, LAT1, LPD1 and PDX1.

Moreover, the reduction of the transport of pyruvate into the mitochondria in order to prevent/reduce the loss of pyruvate in the citrate cycle, by deletion/modification of MPC1, YIA6 or YEA6, has proved advantageous. Furthermore, it is possible to achieve a reduction of the transport of acetyl-CoA into the mitochondria by decreasing the activity of the carnitine shuttle by genetic modification of the genes YAT1, YAT2 or CRC1.

Undesirable side reactions are suppressed by said modifications, so that the production of pentacyclic triterpenoids can proceed under optimized conditions and thus a higher yield can be achieved.

In addition to the suppression of side reactions it is also possible to effect an increase in the cytosolic acetyl-CoA concentration. Acetyl-CoA constitutes the building block for the synthesis of lipids i.A., so that a large quantity of acetyl-CoA is desirable. One possibility is the heterologous expression of an acetylating acetyl-CoA synthase (EC 1.2.1.10) which converts cytosolic acetaldehyde into acetyl-CoA. In this case it is additionally preferable if a simultaneous enrichment of acetaldehyde occurs, for example, by decreasing the alcohol dehydrogenase activity or by decreasing the acetaldehyde dehydrogenase activity (ALD6).

An overexpression of the yeast genes pyruvate decarboxylase (PDC1, PDC5, and/or PDC6) and acetaldehyde dehydrogenase (ALD6) and acetyl-CoA synthetase (ACS1 and/or ACS2) has given good results. Alternatively, heterologous genes can also be used.

A third possibility for optimizing the basic strain is to increase the gene activities in the upper sterol metabolic pathway. This can take place, for example, by an overexpression of the yeast genes ERG9, ERG20, ERG1, ERGS.

It is also possible to decrease the gene activities in the lower sterol metabolic pathway. The reduction and/or elimination of the activity of ERG7 has proved particularly advantageous here.

Moreover, it is preferable to use all heterologous gene sequences in a codon-optimized form in order to achieve a substantial expression. A person skilled in the art is capable of implementing this without exercising inventive skill himself.

In the context of the invention the modification possibilities listed above can also be combined with one another in order to arrive at further preferred strains.

Furthermore, it is preferable that the strain is a *Saccharomyces cerevisiae* CEN.PK.

Moreover, it is preferable that the yeast strain is a CEN.PK111-61A strain.

Moreover, it is preferable that the yeast strain is a AH22tH3ura8 strain.

The invention makes it possible to produce large quantities of betulinic acid in yeast. As a result it is possible to make savings both on the large quantities of solvents and also on the large quantities of energy required in the prior art for production because of the multiple distillation steps. In addition to these ecologically relevant facts the acquisition of bark is not economically viable and sustainable, since these trees are not suitable for cultivation in plantations. Furthermore, a tree 20 years old with a height of 10 meters only sheds a few kilograms of bark per year. In order to obtain 1 kg of betulinic acid the annual production of bark from approximately 30 plane trees would have to be processed. If cultivation in plantations were possible, a usable area of at least 300 square meters would be required for the production of 1 kg of betulinic acid. However, the actual area is significantly higher, since plantation cultivation of plane trees is not possible. A product concentration of, for example, 10% and more based on the dry biomass could be achieved by the invention. Therefore a usable area of only approximately 20 square meters per kg of betulinic acid (for sugar) would be required with the new biotechnological process. With the conventional method using willow bark a multiple of the area from 300 square meters per kg of betulinic acid is required.

A further crucial advantage is that pentacyclic triterpenes/triterpenoids in plant resources only occur in the form of mixtures, so that the purification of individual components is very complex. In contrast to this, in yeast there is very little or no formation of further cyclic triterpenes/triterpenoids (apart from sterols), since these do not constitute native metabolites in yeast. As a result a high degree of purity of the pentacyclic triterpenes is achieved in yeast during the synthesis, which substantially reduces the purification costs for the product. A further significant disadvantage of the plant-based production is the fluctuations in quality and quantity of the plants or trees which occur due to unforeseeable environmental influences in particular in open-air cultivation. Especially for the pharmaceutical industry this frequently constitutes a problem, because a constant raw material quality is crucially important for the subsequent quality of the product. Moreover, crop failures can lead to major shortages of the product. A remarkable example of this is the scarcity of the anti-malaria active substance artemisinin which occurred in 2005 due to crop failures and the lack of alternative resources, and which led to a dramatic undersupply in the third world (McNeil et al., 2004). All these problems are solved by the strains according to the invention.

Major savings on resources can be made by the use of a microbial production process. On the one hand natural plant resources can be protected and limitations due to limited occurrence of the resources can be eliminated. Furthermore, savings are made on processing aids, since higher concentrations and higher degrees of purity are to be expected in yeast. In addition, polluting and expensive purification processes can be replaced.

In a further advantageous embodiment the invention relates to a method for producing a previously described modified yeast strain comprising the following steps:

a) Provision of a *Saccharomyces cerevisiae* strain, b) transformation with a vector comprising a gene for encoding an oxidosqualene cyclase, (wherein the gene comprises a sequence selected from the group comprising nucleic acids according to Accession Number AB055511, AB025343, AB663343, NM_179572, AB181245, DQ268869, AB025345, AB116228, JQ087376, HM623871, AB289586, AB055512) and/or c) transformation of a vector comprising a gene for encoding an NADPH-cytochrome P450 reductase (wherein the gene comprises a sequence selected from the group comprising nucleic acids according to Accession Number AB433810, X66016, X69791, XM_003602850, NM_001179172, X66017, JN594507, DQ984181, DQ318192, AF302496, AF302497, AF302498, L07843, AF024635, AF024634, FJ719368, FJ719369), and/or d) transformation of a vector comprising a gene for encoding a cytochrome P450 monooxygenase, (wherein the gene comprises a sequence selected from the group comprising nucleic acids according to Accession Number AB619802, AB619803, DQ335781, JN565975, XM_002331391, XM_003525274, JF803813, XM_004139039, GU997666, JX036032, XM_002522891, AM457725, XM_002265988, XM_002527956, BT147421, XM_003530477, BT096613, XM_002309021, BT051785, XM_002513137, XM_002264607, XM_002324633, XM_003531801, XM_002280933.)

Methods for producing a previously described modified yeast strain comprising the steps only b), b) and c), b) and d), or b), c) and d) are particularly preferable. Furthermore, the yeast strains resulting therefrom are to be regarded as a subject of the invention.

It is preferable that the method additionally comprises the step of transformation with a vector comprising the tHMG1-gene.

According to the invention any known vector can be used as vector with any possible transformation method, such as for example a linear vector, a circular vector, a viral vector or a bacterial vector. The vector preferably comprises linear DNA or circular DNA, more preferably circular DNA, in particular a plasmid. The vector can be introduced into the cell by any method and can preferably be transformed in combination with transfection reagents (for example, lithium acetate, polyethylenimine (PEI), fugenes, LT-1, jet-PEI, transfectamine, lipofectamine, UptiFectin, PromoFectin, Geneporter, Hilymax, carbon nanofibers, carbon nanotubes of cell-penetrating peptides (CPP), protein transduction domains (PTDs), liposomes, DEAE-dextran, dendrimers). The transformation can optionally be carried out with electroporation, a gene gun, optical transfection, electro-transfer, impalefection, magnetofection and/or magnet-assisted transfection.

The vector is preferably a circular DNA vector, particularly preferably the vector is a plasmid. The plasmid may be any known plasmid, such as e.g. YEpH2, pUC19, pMA or pMK. The vector may also be a linear expression cassette, which possibly cannot be integrated into the genome of the target cell.

Moreover, the object of the invention was to develop a method which enables the microbial production of substantially more pentacyclic triterpenoids in yeast. Therefore, in several embodiments the method according to the invention is characterized in that the pentacyclic triterpenoids produced by the method are inter alia anti-inflammatory, and have an intracellular concentration of more than 1, 2, 3, 4 or 5 mg per gram of dry biomass.

Another preferred embodiment of the invention relates to a method for producing pentacyclic triterpenoids, wherein a previously described modified yeast strain is used for the production.

For the heterologous gene expression in yeast and thus the synthesis of pentacyclic triterpenoids via a cyclical intermediate product, the plant genes from the groups (Tables 1-3) were selected in different combinations and introduced into a suitable yeast strain.

An important advantage of the invention is that a particularly environmentally friendly production process has been provided for the microbial production of pentacyclic triterpenoids. Thus by the invention, in addition to the construction of a yeast strain which produces and enriches pentacyclic triterpenoid (preferably betulin, betulin aldehyde and/or betulinic acid), the establishment of an environmentally friendly and lasting fermentation and purification process can also be provided. Thus it is now possible, for example, to produce 20 g betulinic acid by means of the newly established production process.

By the triterpene/triterpenoid production process according to the invention, preferably in order to save on resources, waste materials and by-products from the sugar industry (for example, molasses) or biodiesel production (for example, glycerol) are used as substrates. For isolation of betulinic acid an already established and environmentally friendly method of autolysis is adapted to the process.

In the new method, instead of organic solvents water is predominantly used in accordance with the principles of Green Chemistry. Approximately 2000 liters of water are used for the production of 1 kg of betulinic acid. From the ecological, ecotoxicological and health point of view water is more tolerable than organic solvents.

Organic solvents may only be required during extraction. Because of the higher product concentration the requirement for organic solvents is 70 to 90% lower than in the comparison process based on plane trees.

Regardless of the ecological advantages, it may also be established that the new method exhibits a higher mass index (starting materials in kg/kg product) than the reference method from the prior art.

The invention has in particular the following advantages:
- prevention of direct intervention in nature by obtaining the bark
- decreasing transport routes by central production without costly acquisition of biomass
- use of waste products or by-products as substrate (by-products of the sugar industry or biodiesel production)
- high space-time yield and resulting low environmental pollution (through low energy consumption due to small reactor volumes)
- high and adjustable product concentration enables low organic solvent consumption
- high and constant quality of the product due to independence from environmental influences simple production and approval of the method by choice of the industrially established host *Saccharomyces cerevisiae*
- simple possibility of reacting to fluctuating or rising demand The following gene sequences are particularly preferably used for encoding oxidosqualene cyclase (OSCs):

SEQ ID No 1. *Betula platyphylla* OSCBPW mRNA fur Lupeolsynthase, complete cds, AB055511
ATGTGGAAGTTGAAGATAGCGGAAGGAGGGCCAGGGCTGGTGAGCGGAAA
TGATTTCATCGGGCGGCAACACTGGGAATTCGACCCGGATGCCGGCACTC
CCCAAGAGCGTGCTGAAGTTGAAAAGGTCCGGGAGGAGTTCACCAAAAAT
CGGTTTCAGATGAAACAAAGCGCTGATCTTTTGATGAGGATGCAGCTTAG
GAAGGAGAACCCATGCCAACCAATTCCACCACCAGTGAAAGTGAAAGAAA
CAGAGGTGATAACAGAGGAAGCAGTGATTACTACACTGAGAAGATCACTA
AGCTTTTATTCCTCCATTCAAGCTCATGATGGCCACTGGCCTGGTGAATC
TGCTGGCCCCTTGTTTTTCCTTCAACCCTTTGTAATGGCATTATACATCA
CTGGAGATCTCAATACTATTTTTTCCCCAGCACACCAGAAGGAAATTATT
CGATACTTGTATAATCATCAGAACGAAGATGGAGGCTGGGGGTTCCATAT
AGAGGGTCACAGCACAATGTTTGGGTCAGCTTTGAGCTACATTGCCTTGA
GAATACTTGGAGAGGGACTTGAAGATGGTGAAGATGGGGCTATGGCTAAA
AGCCGGAAATGGATTCTTGACCATGGTGGTTTAGTGGCTATTCCTTCATG
GGGAAAGTTTTGGGTCACGGTACTGGGACTGTATGAGTGGTCAGGCTGCA
ATCCACTGCCCCCAGAGTTCTGGTTTCTTCCTGATATCTTTCCCATACAT
CCAGGTAAAATGTTATGCTACTGTCGCTTGGTTTACATGCCAATGTCTTA
TTTATATGGGAAGAGGTTTGTTGGTCCAATCACTGGATTGATTCAATCAC
TTAGACAAGAGTTATATAACGAGCCTTACCATCAAATTAACTGGAATAAA
GCCCGGAGTACAGTTGCAAAGGAGGATCTCTACTATCCGCATCCCCTCAT
ACAAGATCTGCTATGGGATTTCTTCACCATGTAGCCGAGCCTGTCCTGA
CGCGTTGGCCCTTTTCAATGCTGAGAGAAGGCACTCAAAGCTGCAATT
GGTCATGTACATTATGAGGACGAGAACAGCAAATACCTTTGCATTGGAAG
CGTTGAAAAGGTATTATGTTTGATTGCCTGTTGGGCTGAAGATCCAAATG
GGGAGGCATACAAGCTTCATCTAGGAAGGATTCCAGACAACTATTGGGTT
GCTGAAGATGGCTTAAAAATTCAGAGTTTCGGCTGTCAGATGTGGGATGC
GGGTTTTGCTATTCAAGCAATTCTCTCTTGCAATTTAAACGAAGAGTATT
GGCCAACACTTCGTAAAGCACATGAGTTTGTAAAGGCTTCACAGGTCCCA
GAAAACCCTTCTGGGGACTTCAAAGCCATGTACCGCCACATAAACAAAGG
AGCATGGACATTCTCGATGCAGGACCATGGATGGCAGGTCTCTGACTGCA
CCGCTGAAGGGCTGAAGGTTGCAATCTTGTTCTCGCAAATGCCTCCGGAC
CTTGTTGGGGAAAAAATTGAGAAAGAGCGGTTATATGATGCTGTGAATGT
CATTCTTTCTCTACAAAGTAGCAATGGTGGTTTCCCAGCATGGGAGCCTC
AAAGAGCATATGGTTGGTTGGAGAAGTTCAACCCCACGGAATTCTTTGAA
GATACCCTTATTGAGCGAGAGTACGTAGAGTGCACTTCACCTGCAGTTCA
TGGTCTGGCACTCTTTAGGAAGTTCTATCCCCGGCACCGGGGGACGGAGA
TAGATAGTAGCATTTACAGGGGAATTCAATACATTGAAGACGTGCAAGAA
CCTGATGGATCATGGTATGGTCATTGGGGGATTTGCTACACCTACGGTAC
ATGGTTTGCTGTAGGGGCACTGGCAGCTTGTGGAAGAAACTACAAAAATT
GTCCTGCATTGCGCAAATCTTGTGAATTTTTGCTATCAAAGCAGCTACCT
AATGGTGGATGGGGAGAAAGTTACCTATCAAGCCAAAACAAGGTGTGGAC
GAATATAGAAGGCAACCGTGCAAATTTGGTCCAAACAGCATGGGCCTTGT -continued

TATCCCTCATTGATGCTAGGCAGGCCGAGATAGATCCAACACCAATTCAT

CGTGGAGTAAGAGTATTGATCAATTCACAGATGGAAGATGGTGACTTTCC

TCAACAGGAAATCACTGGAGTATTTATGCGAAACTGCACACTAAACTACT

CATCATATAGAAACATTTTTCCGATATGGGCTCTTGGAGAATATCGGAGG

CGAGTTCTATTTGCATGA

SEQ ID No 2. *Olea europaea* OEW mRNA for lupeol
synthase, complete cds, AB025343
ATGTGGAAGTTGAAGATTGCTGATGGAACAGGGCCGTGGCTTACAACAAC

CAATAATCATATTGGAAGACAGCATTGGGAATTCGATCCTGAGGCTGGAA

CTCCAGATGAACGAGTCGAGGTTGAAAGACTGCGTGAAGAGTTCAAGAAG

AACAGATTTCGAACTAAACAAAGTGCTGATTTGCTGATGCGTATGCAGCT

TGTGAAGGAGAACCAACGTGTTCAAATCCCACCAGCGATCAAAATCAAAG

AAACAGAAGGTATAACAGAGGAAGCAGTGATAACTACTCTAAGAAGAGCC

ATAAGTTTCTATTCCACAATTCAAGCTCACGATGGCCACTGGCCAGCTGA

ATCCGCCGGCCCTTTGTTTTTCCTCCCTCCTTTGGTCTTAGCCTTGTATG

TGACTGGAGCAATCAATGTTGTTCTATCGCGAGAACATCAGAAAGAGATT

ACACGATACATATACAATCATCAGAATGAAGATGGAGGTTGGGGGATACA

TATAGAGGGTCATAGCACCATGTTTGGTTCTGTGCTTAGCTACATTACGC

TTAGGTTGCTAGGAGAAGGACAAGAAGATGGTGAAGACAAGGCCGTAGCT

AGAGGTCGAAAATGGATACTTGACCATGGTGGCGCCGTGGGGATACCATC

GTGGGGTAAGTTTTGGCTTACGGTGCTCGGAGTATACGAGTGGGATGGCT

GCAACCCAATGCCCCCAGAATTCTGGCTGCTTCCCAATTTTTCCCCAATT

CATCCAGGAAAGATGTTGTGTTATTGTCGGTTGGTATACATGCCCATGTC

ATATTTGTATGGCAAGAGGTTTGTTGGACCAATTACTGGATTGGTGCTAT

CACTAAGGCAAGAGATTTATACTGAACCTTATCATGGAATAAATTGGAAT

AGGGCAAGGAACACCTGTGCAAAGGAGGATCTTTACTACCCACACCCTCT

GGCACAAGATATGCTTTGGGGATTCCTCCATCATTTTGCCGAGCCAGTTC

TAACTCGATGGCCGTTTTCTAAACTAAGAGAAGGCTTTAAAAGTTGCA

ATGGAGCATGTTCATTATGAGGACATGAACAGCAGATACCTTTGCATTGG

ATGTGTAGAGAAGGTGTTATGTCTTATTGCTTGTTGGGTAGAAGATCCTA

ATTCTGAAGCATACAAAAGACATATAGCACGTATACCTGATTACTTCTGG

GTCGCCGAAGATGGCCTGAAAATGCAGAGTTTTGGGTGTCAAATGTGGGA

TGCAGCTTTTGCTATTCAAGCCATATTATCATCCAATCTAGCTGAAGAGT

ACGGGCCGACCCTCATGAAAGCACACAACTTTGTGAAAGCCTCACAGGTC

CAAGAAAATCCATCTGGAGATTTTAATGAAATGTATCGTCACACTTCTAA

AGGCGCCCTGGACATTTTCTATGCAAGATCATGGTTGGCAAGTCTCAGATT

GTACAGCTGAAGGACTTAAGGCCGCACTCTTATTCTCGCAAATGCCTATA

GAACTAGTTGGAGCAGAAATCGAAACAGGACATTTATATGATGCTGTAAA

TGTCATTTTGACCCTTCAGAGTGCTAGTGGCGGTTTTCCAGCATGGGAGC

CTCAGAAAGCATATCGATGGTTGGAGAAGCTCAACCCTACAGAGTTTTTT

GAAGATGTTCTTATAGAGCGAGATTATGTAGAGTGCACATCATCAGCAGT

CCAAGCCTTAAAGCTCTTTAAGCAGTTGCATCCAGGACACAGAAGAAAGG

-continued

AAATAGCAAGCTGCATCTCAAAAGCAATACAATACATCGAAGCTACTCAA

AATCCTGATGGTTCATGGGATGGTAGTTGGGGAATATGCTTTACGTATGG

CACGTGGTTTGCAGTAGAGGGCTTGGTCGCTTGTGGGAAAAATTATCATA

ACTCTCCCACACTACGGAGAGCATGTGAATTTTTGTTGTCGAAACAATTA

CCGGATGGTGGATGGAGTGAAAGCTACCTTTCGAGCTCGAACAAGGTATA

TACTAATCTTGAAGGTAATCGGTCAAATTTGGTGCAAACCTCATGGGCTC

TGTTGTCTCTCATCAAAGCTGGGCAGGTCGAGATTGATCCTGGGCCTATA

CATCGTGGAATAAAACTGCTAGTAAATTCACAAATGGAAGATGGTGACTT

TCCTCAAGAGGAAATTACAGGAGCATTCATGAAGAATTGTACTCTGAACT

ATTCATCGTACCGGAATATCTTTCCAATATGGGCTCTCGGTGAGTATCGT

CGTCGGATTCTTCATGCACAAACATAG

SEQ ID No 3. *Glycyrrhiza uralensis* GuLUP1 mRNA for
lupeol synthase, complete cds, AB663343
ATGTGGAAGCTGAAGATAGGAGAAGGAGGAGCGGGGTTGATTTCCGTGAA

CAACTTCATCGGACGGCAACACTGGGAGTTCGATCCAAATGCAGGAACTC

CACAGGAACACGCTGAGATTGAAAGGCTACGCCGGGAATTCACCAAAAAC

CGTTTTTCCATCAAACAAAGCGCTGACCTCTTGATGAGAATGCAGCTCAG

AAAGGAGAACCATTACGGCACCAATAATAATATTCCAGCAGCAGTGAAAT

TGAGTGACGCAGAGAACATAACGGTGGAAGCATTGGTTACAACAATTAGA

AGGGCTATCAGTTTCTATTCCTCAATTCAAGCCCATGATGGACACTGGCC

TGCAGAATCTGCTGGCCCTCTCTTTTTCCTTCAACCATTGGTAATGGCCC

TATATATTACAGGATCCCTTGATGACGTTTTAGGACCTGAACATAAGAAG

GAAATTGTTCGCTATTTGTATAATCATCAGAATGAAGATGGTGGGTGGGG

ATTCCATATAGAGGGTCATAGCACAATGTTTGGATCTGCATTGAGCTACG

TTGCATTAAGGATACTTGGAGAAGGGCCTGAAGACAAGGCAATGGCCAAA

GGCAGAAAATGGATCCTCGACCACGGTGGTTTAGTTGCTATTCCATCATG

GGGAAAGTTCTGGGTCACGGTACTTGGAGCTTATGAGTGGTCAGGCTGCA

ATCCACTTCCACCAGAGTTATGGCTTCTGCCCAAATTCACCCCTTTTCAT

CCAGGAAAATGTTGTGCTACTGTCGCTTGGTTTACATGCCCATGTCATA

TTTATATGGGAAGAAGTTCGTGGGCCCTATCACTGCCTTAATCAGATCAC

TACGAGAAGAATTGTACAATGAGCCTTATAATCAAATTAACTGGAATACA

GCTCGAAACACTGTTGCTAAGGAGGATCTCTACTACCCACATCCTCTGAT

CCAAGATATGTTATGGGATTTCTTTATCACGTGGGAGAGCGTTTTCTGA

ATTGCTGGCCCTTTTCCATGCTTAGACGGAAGGCATTAGAAATCGCAATT

AATCATGTACATTACGAGGACGAGAACAGTAGATACCTTTGCATTGGCAG

TGTAGAGAAGGTGTTATGTTTGATTGCGCGTTGGGTTGAAGATCCCAACT

CAGAGGCATACAAACTTCATTTAGCCCGAATCCCTGATTACTTCTGGCTC

GCTGAAGATGGCTTGAAAATCCAGAGCTTTGGGTGCCAGATGTGGGATGC

AGCATTCGCTATACAAGCAATACTTGCCTGTAATGTGAGTGAGGAGTATG

GACCTACGCTCCGGAAAGCACACCACTTCGTGAAGGCTTCGCAGGTTCGC

GAAAACCCATCCGGTGACTTCAACGCAATGTACAGACACATTTCGAAAGG

-continued

AGCATGGACATTCTCAATGCATGATCACGGTTGGCAAGTCTCTGACTGCA
CCGCAGAAGGACTAAAGGCTGCACTGCTATTGTCAGAAATGCCAAGTGAA
CTAGTTGGGGGGAAAATGGAAACAGAGCGCTTCTACGACGCTGTTAATGT
CATCCTCTCTCTACAAAGCAGTAATGGCGGGTTCCCTGCTTGGGAGCCTC
AGAAAGCGTACCGTTGGTTAGAGAAATTCAATCCAACTGAATTCTTTGAA
GACACTATGATTGAGGGGAGTATGTTGAGTGCACTGGATCCGCAATGCA
AGGGTTGGCTCTCTTCAGAAAGCAATACCCACAGCACAGAAGCAAGGAAA
TAGATCGCTGCATTGCCAAAGCAATCCGTTACATAGAAAACATGCAAAAT
CCTGATGGCTCTTGGTATGGGTGTTGGGGAATTTGCTATACATACGGTAC
ATGGTTTGCCGTGGAGGGACTAACGGCCTGTGGGAAGAACTGCCACAACA
GTCTTTCCTTGCGAAAAGCTTGTCAATTCTTGTTGTCAAAGCAGCTTCCT
AATGCGGGGTGGGGAGAAAGTTACTTGTCAAGCCAAAACAAGGTGTATAC
AAACCTAGAAGGAAACCGTGCAAATTTAGTTCAAAGTTCGTGGGCTTTGT
TGTCCCTTACTCATGCAGGGCAGGCCGAGATAGATCCTACACCCATACAC
CGTGGAATGAAGTTACTCATCAATTCACAAATGGAAGATGGAGACTTCCC
ACAGCAGGAGATTACAGGAGTATTTATGAGGAACTGTACCCTGAACTACT
CATCGTATCGAAACATCTTTCCCATATGGGCTATGGGAGAGTATCGTCGC
CAAGTCTTGTGTGCTCACAGTTATTGA

SEQ ID No 4. *Arabidopsis thaliana* lupeol synthase
1 (LUP1) mRNA, complete cds, NM_179572
ATGTGGAAGTTGAAGATAGGAAAGGGAAATGGAGAAGATCCGCATTTATT
CAGCAGCAATAACTTCGTCGGACGTCAAACATGGAAGTTTGATCACAAAG
CCGGCTCACCGGAGGAACGAGCTGCCGTCGAAGAAGCTCGCCGGGGTTTC
TTGGATAACCGTTTTCGTGTTAAAGGTTGCAGTGATCTATTGTGGCGAAT
GCAATTTCTAAGAGAAGAAATTCGAACAAGGCATACCACAACTAAAAG
CTACTAACATAGAAGAAATAACGTATGAAACAACGACAAATGCATTACGA
AGAGGCGTTCGTTACTTCACGGCTTTGCAAGCCTCCGACGGCCATTGGCC
GGGAGAAATCACCGGTCCGCTTTTCTTCCTTCCTCCTCTCATATTTTGTT
TGTACATTACCGGACATCTGGAGGAAGTATTCGATGCTGAACATCGCAAA
GAGATGCTAAGACATATCTATTGTCACCAGAACGAAGATGGTGGATGGGG
ATTACACATCGAAAGCAAGAGTGTTATGTTCTGCACCGTGTTGAATTACA
TATGTTTACGTATGCTTGGAGAAAATCCTGAACAAGACGCATGCAAACGA
GCTAGACAATGGATTCTTGACCGCGGTGGAGTGATCTTTATTCCTTCTTG
GGGGAAATTTTGGCTCTCGATACTTGGAGTCTATGATTGGTCTGGAACTA
ATCCGACGCCACCAGAACTCTTGATGCTGCCTTCTTTTCTTCCAATACAT
CCAGGGAAAATTTTGTGTTATAGCCGGATGGTTAGTATACCTATGTCGTA
TCTATATGGGAAGAGGTTTGTTGGTCCAATTACACCTCTTATTTTACTCT
TGCGCGAAGAACTTTACTTGGAACCTTATGAAGAAATCAATTGGAAAAAA
AGTCGACGTCTATATGCAAAAGAAGACATGTATTATGCTCATCCTTTGGT
TCAAGATTTGTTATCTGACACTCTTCAAAACTTTGTGGAGCCTTTACTTA
CACGTTGGCCATTGAACAAGCTTGTGAGGGAAAAAGCTCTTCAGCTTACT
ATGAAACACATACACTATGAAGACGAAAATAGCCATTACATAACCATTGG -continued ATGTGTTGAAAAGGTACTGTGCATGCTAGCTTGTTGGGTTGAAAATCCGA
ATGGAGATTATTTCAAGAAGCATCTGGCTAGAATTCCAGATTATATGTGG
GTCGCTGAAGATGGAATGAAAATGCAGAGCTTTGGATGTCAACTGTGGGA
TACTGGATTTGCTATTCAAGCTTTGCTTGCAAGTAATCTCCCTGATGAAA
CTGATGATGCACTAAAGAGAGGACATAATTACATAAAGGCATCTCAGGTT
AGAGAAAACCCTTCAGGTGATTTTAGGAGCATGTACCGCCACATTTCGAA
AGGAGCATGGACATTTTCTGATCGAGATCATGGATGGCAAGTTTCAGATT
GTACAGCTGAAGCTTTAAAGTGTTGCCTGCTGCTTTCCATGATGTCAGCT
GATATCGTCGGCCAGAAAATAGATGATGAACAATTATATGACTCTGTTAA
CCTCTTGCTGTCTTTACGAGCGGAAATGGAGGTGTCAATGCGTGGGAGC
CATCCCGTGCATATAAATGGTTGGAACTGCTCAATCCTACAGAATTCATG
GCTAATACCATGGTCGAGCGGGAGTTTGTGGAATGCACCTCATCTGTTAT
ACAAGCACTTGATCTATTTAGAAAATTGTATCCAGATCACAGGAAGAAAG
AGATCAACAGGTCCATCGAAAAAGCTGTGCAATTTATACAAGACAATCAA
ACACCAGACGGTTCATGGTACGGAAATTGGGGTGTTTGCTTCATTTACGC
TACTTGGTTTGCTCTTGGAGGCCTAGCAGCAGCTGGTGAAACTTACAACG
ATTGTTTAGCTATGCGCAATGGTGTCCACTTTTTGCTCACGACACAAAGA
GATGATGGAGGTTGGGGTGAAAGCTATTTATCATGCTCCGAACAGAGATA
TATACCATCAGAAGGAGAAAGATCAAACCTTGTGCAAACATCATGGGCTA
TGATGGCTCTAATTCATACGGACAGGCTGAGAGAGATTTGATTCCTCTT
CATCGTGCTGCCAAACTTATCATCAATTCACAACTTGAAAACGGCGATTT
TCCTCAACAGGAAATAGTAGGAGCGTTCATGAATACATGCATGCTACACT
ATGCTACATACAGAAACACCTTCCCATTATGGGCACTCGCAGAATACCGA
AAAGTTGTGTTTATCGTTAATTAA SEQ ID No 5. *Lotus japonicus* OSC3 mRNA for lupeol
synthase, complete cds, AB181245
ATGTGGAAGTTGAAGGTAGCAGAAGGAGGAAAAGGGTTGGTTTCTGTGAG
CAATTTCATCGGAAGGCAACACTGGGTGTTCGACCCAAATGCAGGGACAC
CACAAGAACATGAGGAGATTGAAAGGATGCGCCAAGAATTCACCAAAAAT
CGATTCTCCATCAAACAAAGTGCAGACCTCTTGATGAGAATGCAGCTGAG
AAAGGAGAACCCTTGTGGGCCCATCCCACCAGCAGTTAAATTGAGAGATG
TGGAAAAGGTAACTGCAGAAGCATTGATCACTACAATTAGAAGGTCCATC
ACCTTTTATTCTTCAATTCAAGCCCATGATGGCCACTGGCCTGCTGAATC
TGCAGGCCATTATTCTTCGTTCAACCTTTGGTAATGGCACTGTACATTA
CAGGATCCCTTGATGATGTATTAGGACCTCAACACAAGAAGGAAATTATT
CGATATTTGTATAATCATCAGAACGAAGATGGGGTTGGGGATTCCACAT
AGAGGGTCATAGTACCATGTTTGGATCTGCATTGAGCTACATTGCATTGA
GGGTACTTGGACAAAGCCTTGAAGATGGTGAGGACATGGCAGTGGCCAGA
GGCAGAAAATGGATCCTCGATCATGGCGGTTTAGTAGCTATTCCATCATG
GGGAAAGTTCTGGGTCACGGTGCTAGGGGTTTATGAGTGGTCAGGGTGCA
ATCCCCTTCCACCAGAGTTCTGGCTTCTACCCAAAATTTTCCCTATTCAT

```
CCAGGGAAAATGTTATGTTACTGTCGCTTAGTTTACATGCCCATGTCATA
TTTATATGGAAAGAAGTTTGTAGGCCCAATCACTGCCTTAGTCAGATCAC
TAAGAAAAGAATTGTACAATGAGCCTTATGATCGAGTTGACTGGAATAAG
GCCCGCAACACTGTTGCTAAGGAGGATCTATACTATCCCCATCCTCTAAT
CCAAGACATGTTATGGGATTTCTTCATCATGTGGGAGAGCGTGTTCTGA
ACACTTGGCCATTTTCAATGCTAAGCAGAAGGCAATAGAAGTTGCTATT
AATCATGTACGTTACGAGGATGAGACCACTAGGTACCTTTGCATTGGAAG
TGTAGAGAAGGTGTTATATTTGATTGCGCGTTGGGTTGAAGACCCCAACT
CAGAGGCTTACAAACTTCATTTAGCCCGAATCCCTGATTACTTCTGGCTT
GCAGAAGATGGCTTGAAAATCCAGAGTTTTGGCTGCCAAATGTGGGATGC
AGCATTTGCTATTCAAGCAATACTGAGTGGTAATGTGAGTGAAGAGTATG
GACCAACATTAAAGAAAGCACACCACTTTGTGAAGGCTTCGCAGGTACGT
GAAAACCCATCCGGTGACTTCAAAGCAATGTACAGACACATTTCCAAAGG
GGCATGGACATTCTCAATGCATGATCATGGATGGCAAGTCTCTGATTGCA
CAGCAGAAGGACTAAAGGTTGCACTCCTACTGTCAGAAATGTCAGATGAT
CTAGTTGGGGCAAAAATGGAAACAGAGCAATTCTATGATGCTGTTAATGT
CATCCTCTCTCTACAAAGCAGCAATGGTGGTTTCCCTGCTTGGGAGCCTC
AAAGAGCCTACCAATGGTTAGAGAAATTCAATCCAACTGAATTCTTTGAA
GAAACTCTGATTGAGGGGAGTATGTAGAGTGCACTGGTTCAGCAATGCA
AGCCCTGGCTCTTTTCAGAAAGCTATACCCGAAGCATAGGCGAAAGGAAA
TAGATCGCTGCATTTCCAAAGCAATCCGATACATTGAAAACACACAAAAT
CCTGATGGGTCTTGGTATGGTTGCTGGGGAATTTGCTACACTTATGGTAC
CTGGTTTGCAGTGGAAGGACTAACAGCTTGTGGGAAGAACTTCCAAAATA
GTGTTACCTTGCGTAGAGCATGTAAATTTTTGTTGTCAAAGCAGCTTCCT
AATGGAGGGTGGGGAGAAAGTTACTTGTCAAGCCAAGACAAGGTGTACAC
AAACATTGAAGGAAAACGTGCAAATTTGGTTCAAAGTTCATGGGCTTTGT
TGTCACTTATGCGTGCTGGGCAGGCTGAGATAGATCCGACACCAATTCAC
CGTGGAATAAGGTTACTCATTAATTCACAAATGGATGATGGAGACTTCCC
ACAACAGGAGATTACAGGAGTATTTATGAGGAACTGTACCCTAAACTACT
CATCATATCGAAACATCTTTCCTATATGGGCTCTTGGAGAGTACCGTCGC
AGAGTCTTATGTGCATGA
SEQ ID No 6. Ricinus communis lupeol synthase
mRNA, complete cds, DQ268869
ATGTGGCGAATTAAAATAGCTGAGGGAGGAAATAACCCTTATATTTATAG
CACAAACAATTTTCAGGGAAGGCAAATTTGGGTATTTGATCCTAATGCTG
GTACTCCTGAAGAACAAGCCGAGGTTGAAGAAGCTCGTCAAAACTTCTGG
AAAAATCGATTTCAGGTCAAGCCTAACTCTGATCTCCTTTGGCAACTCCA
GTTTCTAAGGGAGAAAAATTTAAGCAAAAAATTCCAAAAGTAAAGGTTG
AAGATGGCGAGGAGATCACAAGTGAAATAGCTGCAGCCGCTTTGAGGAGA
AGCGTCCACTTGTTTTCGGCCTTGCAGGCAAGCGATGGCCATTGGTGTGC
AGAAAATGGAGGCCTGCTGTTCTTTTTGCCTCCCCTTGGTTTTGCTGTCT
ACATTACAGGACACCTTAATACTGTATTTTCTCCAGAGCATCGCAAAGAA
ATCCTCCGTTACATATACTGTCATCAGAATGAAGATGGTGGATGGGGAAT
ACACATTGAAGGTCACAGCACTATGTTTTGCACAGTTCTTAATTATATAT
GTATGCGTATACTTGGTGAAGCACGTGATGGTGGAATAGAAATGCTTGT
GAAAGAGGGCGAAAATGGATACTCGATCATGGTGGTGCAACTGGTATATC
TTCTTGGGGAAAGACATGGCTTTCGATACTTGGTGTGTACGAGTGGGATG
GGACCAATCCCATGCCCCAGAGTTTTGGGCCTTTCCATCTTCTTTTCCC
TTACACCCAGCAAAAATGTTTTGTTACTGTCGGATCACTTACATGCCAAT
GTCGTACTTGTACGGGAAGAGGTTTGTTGGTCCAATCACACCACTCATTC
TACAAATAAGAGAAGAAATCTATAATGAACCTTACAACAAAATCAAGTGG
AATAGTGTGCGTCATTTATGTGCAAAGGAAGACAACTATTTTCCACATCC
AACGATACAGAAACTGTTATGGGATGCTCTGTATACATTTAGCGAGCCTC
TATTCTCTCGTTGGCCCTTCAACAAATTGAGAGAGAAGGCTCTCAAGATA
ACAATGGATCACATTCATTATGAAGATCACAACAGTCGGTACATCACTAT
TGGATGCGTTGAGAAGCCGTTATGCATGCTTGCCTGTTGGATTGAAGATC
CTCATGGGAAGCGTTTAAGAAGCACCTTGCCAGAATTGCAGATTACATA
TGGGTTGGAGAAGATGGAATAAAGATGCAGAGTTTCGGAAGTCAAACATG
GGACACAAGTCTAGCTCTTCAGGCCCTGATAGCTAGCGACCTCTCTCATG
AAATAGGACCTACACTAAAACAAGGACACGTCTTCACGAAGAATTCTCAG
GCAACTGAGAACCCTTCGGGCGACTTCAGAAAAATGTTTCGTCATATCTC
CAAAGGAGCTTGGACATTCTCTGATAAAGATCAAGGATGGCAAGTTTCTG
ATTGTACAGCAGAAAGCTTGAAGTGCTGCCTACTTTTCTCAATGATGCCT
CCCGAAATTGTTGGTGAGAAAATGGAACCTGAAAAGGTCTATGATTCAGT
CAATGTCATACTTTCTCTTCAGAGCCAAAATGGTGGTTTCACAGCTTGGG
AGCCAGCAAGAGCAGGATCATGGATGGAGTGGCTCAACCCTGTAGAGTTC
ATGGAGGATCTTGTCGTTGAGCACGAGTATGTGGAGTGCACTTCATCAGC
AATCCAAGCACTAGTTCTTTTTAAAAAATTATATCCCCGACACAGGAACA
AAGAGATTGAAAATTGTATCATAAATGCTGCGCAGTTCATTGAAAATATA
CAAGAACCTGATGGTTCATGGTATGGAAATTGGGGGATATGCTTCTCTTA
TGGTACCTGGTTTGCACTGAAAGGATTAGCTGCTGCTGGAAGGACATATG
AAAATTGTTCTGCTATTCGTAAAGGTGTTGATTTTCTACTAAAATCACAA
AGAGATGATGGTGGATGGGCAGAGAGTTATCTTTCATGTCCAAAGAAGGT
GTATGTTCCTTTTGAGGGTAATCGATCAAATCTAGTTCAAACTGCTTGGG
CAATGATGGGTTTGATTTATGAGGACAGGCCAAAAGAGACCCTATGCCT
CTTCATCGCGCTGCAAAGTTATTAATTAATTCTCAAACAGATCTTGGTGA
TTTTCCTCAACAGGAACTTACAGGAGCATTCATGAGGAATTGCATGCTGC
ACTATGCACTATTTAGGAATACTTTTCCCATTTGGGCTTTGGCAGAATAT
CGGCGACATGTCTTATTCCCTTCTGCTGGATTTGGTTTTGGATTCACCAA
TAATTTATGA
```

SEQ ID No 7. *Taraxacum officinale* TRW mRNA for lupeol synthase, complete cds, AB025345
ATGTGGAAGCTGAAAATAGCAGAAGGTGGTGATGATGAGTGGCTGACCAC
CACCAACAACCACGTCGGCCGTCAGCACTGGCAGTTTGATCCGGATGCTG
GAACCGAAGAGGAACGTGCTGAGATTGAAAAGATTCGTCTCAACTTCAAA
CTTAATCGTTTTCAATTCAAACAAAGTGCCGACTTGTTAATGCGTACTCA
ACTAAGAAAAGAGAACCCAATCAATAAATACCGGATGCAATAAAATTGA
ATGAAACAGAAGAAGTGACAAATGACGCAGTGACAACTACACTCAAAAGA
GCCATTAGCTTTTACTCCACCATTCAAGCCCATGATGGGCACTGGCCAGC
TGAGTCTGCTGGCCCTTTGTTCTTCCTTCCTCCATTGGTAATAGCACTAT
ATGTGACTGGAGCAATGAATGATATTCTAACACCCGCACATCAGCTAGAA
ATAAAACGTTACATATACAATCATCAGAATGAAGATGGAGGTTGGGGATT
ACATATAGAGGGTCATAGCACAATATTTGGATCAGTACTTAGTTACATAA
CTTTAAGATTACTTGGGGAAGAAGCTGATAGTGTTGCAGAGGACATGGCT
TTGGTTAAGGGGCGTAAATGGATCCTTGACCATGGTGGTGCAGTTGGGAT
TCCTTCATGGGGAAAGTTTTGGCTTACGATACTTGGAGTATACGAATGGG
GAGGCTGTAATCCTATGCCACCCGAATTTGGCTCATGCCTAAGTTTTTC
CCAATTCATCCAGGCAAAATGTTGTGTTATTGTCGCTTAGTTTACATGCC
CATGTCGTACTTATACGGCAAAAGATTTGTGGGAAAAATAACCGAGTTGG
TTCGAGACCTAAGGCAAGAGCTTTATACGGACCCTTATGATGAGATTAAT
TGGAATAAAGCACGAAACACGTGTGCAAAGGAAGATCTCTACTATCCACA
CCCTTTTGTTCAAGATATGGTATGGGTGTACTTCATAATGTTGTTGAAC
CTGTATTAACAAGTCGTCCGATTTCCACACTAAGAGAAAAGGCTTTGAAA
GTCGCAATGGATCATGTTCACTATGAAGATAAGAGCAGTAGATATCTTTG
CATTGGATGTGTGGAAAAGGTGTTATGCTTGATTGCAACGTGGGTGGAAG
ATCCAAATGGTGATGCATATAAACGTCATCTTGCTAGAATTCCTGACTAC
TTTTGGGTTGCTGAGGATGGGATGAAAATGCAGAGTTTTGGATGTCAAAT
GTGGGATGCAGCATTTGCTATTCAAGCTATTTTTCAAGTAATCTAACAG
AAGAATACGGCCCGACTCTTAAAAAAGCACACGAGTTTGTAAAAGCATCA
CAGGTTCGTGATAATCCTCCTGGAGATTTCAGTAAAATGTACCGACATAC
TTCTAAGGGTGCATGGACATTTTCCATACAAGACCACGGTTGGCAAGTCT
CTGATTGTACCGCAGAAGGCTTGAAGGTTTCACTTTTGTACTCCCAAATG
AACCCAAAACTAGTGGGCGAAAAAGTTGAAACGGAGCATCTCTACGACGC
TGTCAATGTCATTCTTTCATTACAAAGTGAAAATGGTGGCTTTCCTGCTT
GGGAACCACAAAGGGCGTACGCTTGGCTGGAGAAATTCAACCCCACTGAA
TTCTTTGAAGATGTGTTGATTGAGCGAGAGTATGTTGAATGCACTTCATC
TGCAATCCAAGGTTTGACACTCTTCAAGAAGTTGCACCCAGGGCACAGAA
CCAAGGAGATCGAGCATTGTATATCAAGAGCTGTAAAGTACGTTGAAGAC
ACACAAGAAAGTGATGGTTCATGGTATGGTTGTTGGGGAATTTGCTACAC
CTATGGTACATGGTTTGCGGTAGATGCGCTAGTAGCTTGTGGGAAGAACT
ATCATAACTGTCCCGCTCTTCAAAAAGCTTGCAAATTTCTGTTATCCAAA CAACTTCCGGATGGTGGATGGGGAGAGAGTTATCTTTCGAGCTCAAATAA
GGTGTATACGAATTTGGAGGGAAATCGTTCGAATTTAGTGCATACATCAT
GGGCTTTAATATCCCTTATTAAAGCTGGACAGGCTGAAATTGATCCTACA
CCAATATCTAATGGCGTACGGCTTCTCATCAATTCACAAATGGAAGAAGG
GGACTTTCCTCAACAGGAAATCACAGGAGTGTTCATGAAGAACTGTAACC
TCAATTACTCATCATTTCGAAATATTTTTCCCATATGGGCACTTGGTGAA
TATCGTCGTATTGTTCAAAATATATGA SEQ ID No 8. *Glycyrrhiza glabra* GgLUS1 mRNA for lupeol synthase, complete cds, AB116228
ATGTGGAAGCTGAAGATAGGAGAAGGAGGAGCGGGGTTGATTTCCGTGAA
CAACTTCATCGGACGGCAACACTGGGAGTTCGATCCAAATGCAGGAACTC
CACAGGAACACGCTGAGATTGAAAGGCTACGCCGGGAATTCACCAAAAAC
CGTTTTTCCATCAAACAAAGCGCTGACCTCTTGATGAGAATGCAGCTCAG
AAAGGAGAACCATTACGGCACCAATAATAATATTCCAGCAGCAGTGAAAT
TGAGTGACGCAGAGAACATAACGGTGGAAGCATTGGTTACAACAATTACA
AGGGCTATCAGTTTCTATTCCTCAATTCAAGCCCATGATGGACACTGGCC
TGCAGAATCTGCTGGGCCTCTCTTTTTCCTTCAACCATTGGTAATGGCCC
TATATATTACAGGATCCCTTGATGACGTTTTAGGACCTGAACATAAGAAG
GAAATTGTTCGCTATTTGTATAATCATCAGAATGAAGATGGTGGGTGGGG
ATTCCATATAGAGGGTCATAGCACAATGTTTGGATCTGCATTGAGCTACG
TTGCATTAAGGATACTTGGAGAAGGGCCTCAAGACAAGGCAATGGCCAAA
GGCAGAAAATGGATCCTCGACCACGGTGGTTTAGTTGCTATTCCATCATG
GGGAAAGTTCTGGGTCACGGTACTTGGAGCTTATGAGTGGTCAGGCTGCA
ATCCACTTCCACCAGAGTTATGGCTTCTGCCCAAATTCGCCCCTTTTCAT
CCAGGAAAATGTTGTGCTACTGTCGCTTGGTTTACATGCCCATGTCATA
TTTATATGGGAAGAAGTTCGTGGGCCCTATCACTGCCTTAATCAGATCAC
TACGAGAAGAATTGTACAATGAGCCTTATAATCAAATTAACTGGAATACA
GCTCGAAACACTGTTGCTAAGGAGGATCTCTACTACCCACATCCTCTGAT
CCAAGATATGTTATGGGGATTTCTTTATCACGTGGGAGAGCGTTTTCTGA
ATTGCTGGCCCTTTTCCATGCTTAGACGGAAGGCATTAGAAATCGCAATT
AATCATGTACATTACGAGGACGAGAACAGTAGATACCTTTGCATTGGCAG
TGTAGAGAAGGTGTTATGTTTGATTGCGCGTTGGGTTGAAGATCCCAACT
CAGAGGCATACAAACTTCATTTAGCCCGAATCCCTGATTACTTCTGGCTC
GCTGAAGATGGCTTGAAAATCCAGAGCTTTGGGTGCCAGATGTGGGATGC
AGCATTCGCTATACAAGCAATACTTGCCTGTAATGTGAGTGAGGAGTATG
GACCTACGCTCCGAAAGCACACCACTTCGTGAAGGCTTCGCAGGTTCGC
GAAAACCCATCCGGTGACTTCAACGCAATGTACAGACACATTTCGAAAGG
AGCATGGACATTCTCAATGCATGATCACGGTTGGCAAGTCTCTGACTGCA
CCGCAGAAGGACTAAAGGCTGCACTGCTATTGTCAGAAATGCCAAGTGAA
CTAGTTGGGGGAAAATGGAAACAGAGCGCTTCTACGACGCTGTTAATGT
CATCCTCTCTCTACAAAGCAGTAATGGCGGGTTCCCTGCTTGGGAGCCTC
AGAAAGCGTACCGTTGGTTAGAGAAATTCAATCCAACTGAATTCTTTGAA -continued

```
GACACTATGATTGAGAGGGAGTATGTTGAGTGCACTGGATCCGCAATGCA
AGGGTTGGCTCTCTTCAGAAAGCAATTCCCACAGCACAGAAGCAAGGAAA
TAGATCGCTGCATTGCCAAAGCAATCCGTTACATAGAAACATGCAAAAT
CCTGATGGCTCTTGGTATGGGTGTTGGGGAATTTGCTATACATACGGTAC
ATGGTTTGCCGTGGAGGGACTAACGGCCTGTGGGAAGAACTGCCACAACA
GTCTTTCCTTGCGAAAAGCTTGTCAATTCTTGTTGTCAAAGCAGCTTCCT
AATGCGGGGTGGGGAGAAAGTTACTTGTCAAGCCAAAACAAGGTGTATAC
AAACCTAGAAGGAAACCGTGCAAATTTAGTTCAAAGTTCGTGGGCTTTGT
TGTCCCTTACTCATGCAGGGCAGGCCGAGATAGATCCTACACCCATACAC
CGTGGAATGAAGTTACTCATCAATTCACAAATGGAAGATGGAGACTTCCC
ACAGCAGGAGATTACAGGAGTATTTATGAGGAACTGTACCCTGAACTACT
CATCGTATCGAAACATCTTTCCCATATGGGCTATGGGAGAGTATCGTCGC
CAAGTCTTGTGTGCTCACAGTTATTGA
```

SEQ ID No 9. *Eleutherococcus trifoliatus* lupeol
synthase mRNA, complete cds, JQ087376
```
ATGTGGAAGCTGAAGATAGCCGAAGGAGATAAAAATGACCCGTATTTGTA
CAGCACCAATAATTTTGTCGGCCGGCAAACATGGGAGTTCGACCCGGATT
ATGTGGGTAGCCCCGGAGAGCTAGAGGAGGTGGAAGAGGCTCGGCGTCAG
TTTTGGGAGAACAGGTACAAGGTCAAGCCTTGTGGCGATCTCCTCTGGCG
TATGCAGTTCCTAAGAGAGAAGAATTTCAAACAAACAATCCCCCAAGTGA
AGGTAGGAGATGACGAGGCAGTTACTTATGACGCCGCCACTACGACACTC
CGAAGGGCCGTCCACTTCTTTTCAGCTTTGCAGGCCAGCGACGGTCATTG
GCCTGCCGAGATCGCCGGACCTCTCTTTTTCCTTCCGCCCTTGGTGATGT
GTGTATATATCACAGGGCATCTTGATACAGTGTTCCCAGCAAACATCGA
AAAGAAATTCTTCGCTACATATATTGTCATCAAAATGAAAATGGCGGGGG
GGGATTACATATTGAGGGGCATAGCACCATGTTCGGCACAACTTTTAGCT
ACATTTGTATGCGTATACTTGGAAAAGGACCCGATGGTGGTGTAAACAAT
GCATGTGCCAAAGGCCGAAAATGGATCCTTGACCACGGCAGTGCAACCGC
TATACCTTCATGGGCAAGACTTGGCTTTCGATACTTGGTGTATATGAAT
GGACGGGAAGCAACCCAATGCCCCCGGAATTCGGCTTCTCCCTTCTTCC
CTTTCTGTGCACCCAGCTAAAATGTTGTGTTATTGCCGGATGGTTTACTT
GCCAATGTCATATTTATATGGGAAGAGGTTTGTTGGGCCAATCACTCCTC
TCATTTTACAATTAAAAGAAGAACTTTATGCTCAACCCTACAATGAAATC
AGGTGGGGAAAAGTACGTCATGTGTGTGCCAAGGAGGACATCTACTATCC
TCACCCTTTAATACAAGACCTGCTATGGGATAGTCTCCATGTATTAGCTG
AACCTCTTTTAACTCGTTGGCCATTTAACAAGTTGAGAGAGAAAGCTTTG
CAGACTACCATGAAACACATTCACTATGAAGATGAGAACAGTCGATATAT
TACCATTGGATGTGTGGAAAAGATTTTGTGTATGCTTGCTTGTTGGGTTG
AGGATCCAAATGGAGATTATTTCAAGAAACACCTTGCAAGGATTCCAGAT
TATTTATGGGTTGCTGAAGATGGAATGAAGATGCAGAGTTTTGGTAGTCA
GGAATGGGATATAGGTTTTGGCATTCAAGCATTGTTGGCTAGTGATCTCA
```

-continued
```
CTCATGAACTTGGACCTACTCTTATGAAAGGACACGACTTCATCAAAAAG
TCCCAGGTCAAGGATAATCCTTCCGGTGACTTCAAAAGCATGTATCGCCA
CATTTCTAAAGGATCGTGGACCTTCTCAGATCAAGATCACGGATGGCAAG
TTTCTGATTGTACTGCAGAAGGATTAAAGTGTTGCCTTATTTTCTCAACA
ATGCCAGAGGAAATCGTTGGCAAGAAATGGAACCAGAACTACTGTATAA
TTCTGTTAATGTATTGCTTTCCCTACAGAGCAAAAATGGTGGGGTAGCAG
CATGGGAGCCTGCAACAGCACAGGACTGGTTAGAGTTGTTCAATCCTACG
GAATTCTTTGCAGACACCATCATTGAGCACGAGTATGTAGAGTGCACTTC
ATCGGCAATCCAAGCCCTGACTCTGTTTAAAAAGTTATATCCTGGGCACC
GAAAGAAGGAGATAGATAATTTTATTACGAATGCCATTCGTTTCATTGAA
GACATACAAATACCTGATGGTTCATGGTATGGAAACTGGGGTGTGTGTTT
TACTTACGGTACCTGGTTTGCTCTTGGGGGGCTAGCGGCAGGTGGAAAGA
CATACAACAATTGTGCAGCTGTTCGTAAAGCTGTTAATTTTCTACTCGAA
TCACAATTGGATGATGGCGGTTGGGGAGAAAGCCATCTTTCTTGCCCCAG
AAAGGTATATGTACCATTAGAAGGAAACCGCTCAAATTTGGTGCATACTG
GATGGGCCTTAATGGGACTGATTCATTCTGGGCAGGCCGAGAGAGACCCA
ACACCTCTTCACCGTGCAGCCAAGTTATTGATCAATTCCCAGATGGAAGA
TGGTGATTTTCCCCAACAGGAAATAACCGGAGCTTTTATGAAGAATTGCA
TGTTGCACTATGCAGTTTATCGAAATATATACCCATTGTGGGCTTTAGCA
GAGTATCGGAGGCGGGTACCATTACCGACCCTAGGTGCCTAA
```

SEQ ID No 10. *Kalanchoe daigremontiana* lupeol
synthase mRNA, complete cds, HM623871
```
ATGTGGAAGTTAAAGATAGCGGACGGAGGGAGTAACCCTTACATCTTCAC
CACCAACAATTTTGTGGGAAGGCAGATATGGGAATTTGACCCCCAAGCCA
CCGACCCTCAGCAACTAGCTAAAGTCGAAGCTGCTCGTCTCGATTTCTAC
CATAACCGCTATAAACTCAAACCCAATTCCGATCTCCTCTGGCGCATGCA
GTTTCTTGAGGAGAAAGCTTTCACACAAACTATACCACAAGTTAAAGTTG
AGGATGGTGAAGAGGTTAGTTACGAGGCAGTAACTGCAGCACTGAGAAGA
GGAGTCCATCTCTATTCAGCTCTCCAAGCTAGTGATGGCCACTGGCCAGC
TGAAAATGCTGGCCCTATGTTTTTCATGCCCCCTATGGTTATGTGTCTAT
ACATCACTGGACATCTTAATGCCATATTCACGGAAGAACATCGAAGTGAA
ACTCTTCGTTACATATATTATCATCAGAATGAAGATGGTGGCTGGGGGTT
TCATATTGAGGGCCACAGCACCATGTTTGGTACAGTTCTAAACTATATAT
GTATGCGGTTGCTGGAGAGGGGCCTGAAGGAGGTCAAGACAATGCTGTT
TCCAGAGGAAGGAAGTGGATCCTCGACCATGGTGGTGCCACCTCCATTCC
ATCATGGGAAAGACTGGCTTTCGATTATGGGCTTGTGTGACTGGTCTG
GATGCAATCCCATGCCCCCCGAGTTTTGGCTTCTTCCTTCCTATCTTCCT
ATGCATCCAGGCAAATGTGGTGCTACTGCCGAATGGTCTACATGCCGAT
GTCATATTTATATGGTAAAAGATTCACAGCTCGTATCACACCACTCATTC
TTCAGTTGAGAGAAGAAATTCACATTCAACCATACGACCAAATCGACTGG
AAAAAAGTGCGACATGTGTGTTGTAAGGAGGATATGTACTATCCACATCC
ACTACTTCAAGACTTGTTATGGGACACTCTCTATCTCACTACTGAGCCTC
```

-continued

TCCTTACTCGCTGGCCACTGAACAAACTGATCAGGAAAAGAGCTCTGCAG

ACGACAATGAAACATATACACTATGAAGATGAGAATAGCAGATACATCAC

GATTGGCTGTGTCGAGAAGGTTTTGTGCATGCTTGCTTGCTGGGTTGAAG

ATCCAAATGGAGATTATTTTAAAAAACATTTAGCTAGAATTCCAGACTAT

TTATGGATTGCTGAAGATGGCATGAAGATGCAGAGTTTCGGAAGTCAGCA

CTGGGATACAGCCTTTTCTATCCAAGCACTACTGGCTAGTAACATGGCTG

AAGAAATCGGAATAACACTTGCAAAAGGCCACGATTTTATTAAGAAATCT

CAGGTGAAAGACAACCCTTCTGGTGACTTCAAAGGCATGTACCGTCACAT

TTCAAAGGGGCATGGACATTTTCAGATCAAGATCATGGATGGCAAGTTT

CAGATTGCACGGCAGAGGGCCTGAAGTGTTGTCTGCTTTTCTCAATGATG

CAACCTGAGGTTGTGGGTGAGAGCATGGCACCAGAGAGCCTGTACMCTCA

GTAAATGTTCTCCTCTCTTGCAGAGCCAGAACGGTGGATTACCAGCCTG

GGAGCCAGCAGGTGCACCCGAGTGGTTGGAGCTTCTAAACCCGACCGAGT

TTTTTGAGAACATTGTAATTGAGCACGAGTACGTCGAGTGCACTAGCTCG

GCAGTTCAGGCTTTAGTCCTTTTCAAAAAGCTATACCCCCTACATCGTAG

AAAAGAAGTGGAAAGATTTATCACAAACGGTGCGAAATACCTTGAAGATA

TACAGATGCCTGATGGGTCATGGTATGGGAACTGGGGAGTTTGCTTCACC

TATGGTGCATGGTTTGCTCTTGAAGGATTGTCAGCTGCTGGAAAGACATA

CAACAATTGTGCAGCAGTCCGCAAAGGCGTTGACTTTCTACTAAACATTC

AACTTGAAGACGGTGGGTGGGGAGAGAGTTACCAATCATGTCCAGACAAG

AAATATGTTCCTCTAGAAGATAATAGATCAAATCTGGTTCAAACTTCATG

GGCGTTAATGGGTCTAATTTACGCCGACAGGCTGATAGGGATCCAACTC

CTCTTCACCGGGCTGCACAATTACTGATTAACTCGCAGTTGGAAGATGGA

GATTTTCCGCAACAAGAAATAACTGGAGTGTTTCAGAGGAACTGCATGTT

GCATTATGCAGCATACAGAAACATATTCCCTCTCTGGGCCCTTGCTGAGT

ATAGAAGACAGATTCAGTTACATTCAGAGGCTACCAAAATGGTCTAA

SEQ ID No 11. *Bruguiera gynnnorhiza* BgLUS mRNA for lupeol synthase, complete cds, AB289586
ATGTGGAGGCTTAAGATTGCAGAGGGTGGCAACAACCCTTACATATACAG

CACAAACAATTTCGTGGGAAGGCAAACATGGGAGTTTGACCCTGAAGCTG

GGACCCCTGAGGAGCGAGCCCAGGTTGAAGAGGCTCGTGAAAATTTCTGG

AGGGACCGCTTTCTCATCAAGCCCAGCTCCGACCTCCTTTGGCGATTCCA

GTTTCTGAGTGAGAAAAGTTTAAACAAAGGATTCCACAAGTGAAGGTTC

AGGATGGTGAGGAAATCACACGTGAAATTGCCACAACCGCATTGAGGAGG

AGCGTCCATTTGGTTTCTGCCTTGCAGGCCAGCGATGGGCATTGGTGCGC

AGAAAATTCTGGCCCCATGTTCTTTGTTCCTCCTATGGTTTTTTCTCTGT

ATATCACAGGACATCTTAATGCTGTATTCTCTGCAGAGCACTGCAAAGAG

ATTCTGAGATACATATACTGTCATCCGAATGAGGATGGTGGGTGGGGATT

ACACATAGAGGGTCACAGCGCCATGTTCTCCACAGTTCTGAATTACAATT

GGCTGGGGAAACTTGGCGAGGGACGAGATGGTGGGAAAGACAATGCTTGC

GAAAGAGCGCGAAGGAGGATTCTTGATCACGGTAGTGCAACTGCAATCAG

CTCCTGGGGAAAGACATGGCTGGCGATACTTGGTGTGTATGAATGGGATG

GTTGCAACCCAATGCCTCCAGAATTTTGGGCCTTCCCCACTTTTTTCCCA

ATACATCCAGCAAGAATGTTATGCTACTGTCGGCTCACTTACATGGCCAT

GTCATACCTGTATGGGAAGAAATTTGTCGGTCCAATCACACCTCTAATTT

TACAACTGAGGGAGGAAATCTACAATGAACCATATGACCAAATCAATTGG

AGCAGAATGCGCCATTTGTGTGCAAAAGAGGATAACTACTATGCCCACAC

TCTAACACAAATCATTTTGTGGGATGCAATTTACATGTTGGGCGAACCTC

TTCTCAAGCGCTGGCCATTCAACAAATTGAGAGAGAAGGCTCTCAAAATA

ACAATGGATCACATTCATTATGAAGATGAAAACAGTCAATACATTACAAT

TGGGAGTGTTGAAAAGCCATTACTCATGCTTGCTTGCTGGCATGAAGATC

CCAATGGTGATGCTTTTAAGAAGCACCTCGCCAGAATACCAGATTATGTT

TGGCTTGGTGAAGATGGAATAAAGATTCAGAGTTTTGGCAGCCAAGTGTG

GGATACAAGTTTTGTTCTCCAAGCTTTGATTGCTAGCAATCTTCCCAGTG

AAACAGGACCTACACTTGAGAAAGGGCACAATTTCATAAAGAACTCTCAG

GTCACCCAGAACCCTTCTGGTGACTTCAGAAGAATGTTTCGTCATATCTC

TAAAGGGTCATGGACATTCTCTGACAAAGATCACGGATGGCAAGTTTCTG

ATTGCACTGCAGAAAGCCTGAAGTGTTGTCTACTTTTCTCGATGATGCCC

CCTGAACTTGTGGGTGAGAAGATGGGACCTCAGCGGATGTACGATGCCGT

CAATGTGATAATTTCTCTTCAGAGTAAAAATGGTGGCTGTTCAGCCTGGG

AGCCAGCAGGAGCTGGGTCGTGGATGGAGTGGCTTAACCCTGTGGAATTT

CTAGCGGACCTTGTTATCGAACATGAGTATGTTGAGTGCACTTCATCATC

GTTGCAAGCATTAGTTCTATTCAAGAAGTTATATCCTGAGCACAGGAGGA

AAGAGATTGAAATTTTATACTAAATGCTGTAAGATTCACTGAAGAAATT

CAACAGCCTGATGGATCATGGTATGGAAATTGGGGAATATGCTTCCTTTC

TGGGTACATGGTTTGGACTTAAAGGGCTGGCTGCTGCTGGCAAGACTTACT

ACAATTGCACTGCTGTGCGTAAAGGGGTCGAATTTCTACTCCAAACACAA

CGAGACGATGGTGGATGGGGAGAGAGTTACCTTTCATGCCCAAAGAAGAT

CTACGTACCTCTTGAGGGAAACCGATCAAATTTGGTACAAACTGCACTGG

CCATGATGGGCTTAATTCTTGGTGGGCAGGGTGAGAGAGACCCTACACCC

CTTCATCGAGCTGCAAAGTTGTTGATCAATTCTCAAACAGAACTTGGTGA

TTTTCCTCAGCAGGAACTCTCAGGTTGTTTCATGAGGAATTGCATGTTGC

ACTATTCAGAATATAGGGACATCTTTCCAACGTGGGCTAGCAGAATAC

TGCAAGCTTTTTCCATTGCCTTCCAAAAATGATTGA

SEQ ID No 12. *Betula platyphylla* OSCBPY mRNA for beta-amyrin synthase, complete cds, AB055512
ATGTGGAGGCTTAAGATCGCAGACGGTGGGAGTGACCCTATATCTACTC

TACAAACAACTTTGTTGGGAGGCAGACATGGGAGTTTGACCCTCAGGCTG

GTTCCCCACAAGAGCGGGCTGAGGTTGAAGAGGCTCGTCGGAATTTCTAC

GACAACCGGTATCAGGTCAAACCTAGTGGTGATCTCCTATGGCGAATGCA

GTTTCTTAAGGAGAAAAACTTCAAACAAACAATTCCTCCAGTAAAGGTTG

AGGATGGAGAGGAAATCACATATGAAAAGTCCACAGCTGCATTGAGAAGG

GCCGTCCATTTCTATTCGGCCTTGCAAGCTAGTGATGGCCATTGGCCTGC

-continued

```
TGAAAATGCCGGTCCATTATTTTTCCTTCCCCCCTTGGTTATGTGTATGT

ACATTACAGGACATCTTAATACTGTGTTCCCTGCTGAGCATCAAAAGGAA

ATCCTTCGATACATATACTATCATCAGAATGAAGATGGTGGGTGGGGATT

ACACATAGAGGGTCACAGCACCATGTTTTGCACTGCTCTCAGCTACATCT

GTATGCGCATACTCGGGGAAGGGCCTGATGGTGGTCAGGACAATGCTTGT

GCAAGAGCGCGAAAGTGGATCCTTGATCATGGTGGTGTAACACACATGCC

TTCTTGGGGAAAGACCTGGCTTTCGATACTTGGTATATTCGAGTGGATTG

GAAGCAACCCAATGCCTCCAGAATTTTGGATCCTTCCTTCATTTCTTCCC

ATGCATCCAGCCAAAATGTGGTGCTACTGCCGCATGGTGTACATGCCTAT

GTCATACCTCTATGGGAAAAGGTTTGTAGGCCCAATCACACCTCTCATTC

TTCAATTGAGGGAGGAACTCTACACTCAACCTTACCACCAAGTTAACTGG

AAGAAAGTGCGTCATCTATGTGCAAAGGAGGATATCTACTATCCCCACCC

TTTGATACAAGATCTATTGTGGGATAGTCTATACATATTCACTGAGCCTC

TTCTAACTCGTTGGCCCTTTAACAAGCTGGTCAGAGAGAAGGCTCTTCAA

GTAACAATGAAGCACATTCATTATGAAGATGAGAACAGTCGATACATCAC

CATTGGATGCGTGGAAAAGGTCCTCTGTATGCTTGCTTGTTGGGTTGAAG

ATCCAAATGGGGATTATTTCAAGAAACATATTGCTAGGATACCAGATTAC

ATATGGGTTGCTGAAGATGAATCAAGATGCAGAGTTTTGGAAGTCAAGA

GTGGGATACCGGTTTTGCTATTCAAGCTTTGCTTGCTAGTAATCTAACTG

ATGAAATTGGACCTACACTTGCGAGAGGGCACGACTTCATAAAGAAATCT

CAGGTCAAGGACAACCCTTCTGGAGACTTTGAAAGCATGCACCGTCACAT

TTCTAAAGGATCATGGACTTTCTCTGATCAAGATCATGGATGGCAAGTTT

CTGATTGCACTGCCGAAGGTTTGAAGTGTTGCTTGCTTTTCTCCATTATG

CCACCAGAAATTGTTGGTGAGAAAATGGAACCTGAGCAATTGTATGATTC

TGTAAATGTCCTACTTTCTCTACAGAGTAAAAATGGTGGTTTAGCTGCCT

GGGAACCAGCAGGAGCCCAAGAATGGTTGGAATTGCTTAATTCCACAGAA

TTCTTTGCGGACATTGTCATTGAGCATGAGTACATTGAGTGCACTGCATC

AGCAATGCAAACTTTAGTTTTGTTTAAGAAGTTATACCCCGGGCACCGNA

AGAAAGAGATCGAAAATTTCATAAAAAATGCTGCTCAGTTCCTTCAAGTC

ATACAAATGCCTGATGGTTCATGGTATGGAAATTGGGGAGTTTGCTTCAC

ATATGGTACATGGTTTGCACTTGGAGGATTGGCTGCAGTTGGCAAGACTT

ACAACAATTGTCTAGCCGTGCGCAGAGCTGTTGATTTTCTACTCAGAGCA

CAAAGAGATAATGGTGGTTGGGGAGAGAGCTATCTCTCATGTCCAAAGAA

GGAGTATGTACCTCTTGAAGGAAACAAATCAAATTTGGTACATACTGCAT

GGGCAATGATGGGTCTCATTCATGCTGGACAGGCTGAAAGAGACCCAACA

CCTCTTCACCGCGCAGCAAAGTTGATAATTAATTCTCAACTCGAAGATGG

AGATTTTCCTCAACAGGAAATCACTGGAGTCTTTATGAAGAACTGTATGT

TACACTATGCAGCATACAAAAATATTTACCCACTGTGGGCTCTGGCAGAA

TACCGCAAGCATGTCCCATTGCCATTAGGAAAAAATTTAAATCAAGTAGT

GAACTGTATAGGTCAATCACTATATAAGAAGTATAAATAA
```

The following gene sequences are particularly preferably used for encoding NADPH-cytochrome P450 reductase (CPRs):

```
SEQ ID No 13. Lotus japonicus LjCPR1 mRNA for
cytochrome P450 reductase, complete cds, AB433810
ATGGAAGAATCAAGCTCCATGAAGATTTCGCCTCTGGATCTGATGTCCG

CCATGATCAAGGGCACACTCGACCCTTCCAACGTCTCCTCCACCTCCGG

CGCCGGCTCCGTCTTCCTCGAGAATCGTGAGTTCGTCATGGTGCTTACC

ACCTCCATCGCCGTCCTCATCGGATGCGTCGTCGTTTTCATTTGGCGCA

GATCCACCGGTAACAAGGCTAAGTCCATCGAGCCTCCCAAGCGCGTCGT

CGAGAAGCTTAGCGACGAGGCTGAGGTTGACGACGGTACCAGAAAGGTC

ACCATCTTCTTCGGTACTCAGACTGGTACTGCTGAAGGATTCGCCAAGG

CGATTGCGGAAGAGGCAAAAGTGCGATACGAAAAAGCCAAGTTCAAAAT

TGTTGATATGGATGATTATGCCCAGGACGATGATGAGTATGAGGAAAAG

CTCAAGAAAGAGACACTGGCACTTTTCTTCTTAGCTACATATGGTGATG

GTGAGCCAACTGATAATGCGGCGAGATTTTACAAATGGTTTCTGGAGGG

AGATGAGAAAGAAGAAGGATGGCTTCGAAATCTTGAGTATGCTGTTTTT

GGTCTGGGGAACAGGCAGTATGAGCATTTTAATAAGGTCGCCATTGAAG

TGGATGATAAGCTTGCTGATTTTGGTGGGAAGCGTCTTGTCAAAGTAGG

TCTAGGAGATGATGATCAATGCATAGAAGATGACTTTACTGCATGGAAA

GAAGAATTGTGGCCAGCATTGGATGAATTGCTTAGAGGTGATGATGATA

CAACTGTGTCTACACCCTATACGGCTGCTGTGTTGGAGTATCGTGTTGT

TATTCATGATCCATTAGATGCATCTGTCGATGAAAAGAAGTGGCATAAT

GTTAATGGCCATGCTATTGTGGATGCTAACATCCAGTCAGGTCAAATG

TGGCTGTGCGAAAGGAGCTTCATACTCCTGTGTCAGATCGTTCTTGCAC

ACATTTAGAATTTGACATTTCAGGCACTGGAGTTGCATATGAAACAGGG

GACCATGTTGGTGTTTACTGTGAGAATTTATCTGAAACTGTGGAAGAAG

CAGTAAGGTTACTAGGTTTGTCACCAGATACCTATTTCTCCGTCCATAC

TGATGATGAAGATGGGAAACCACTTAGTGGAAGCTCCTTGCCACCTACT

TTCCCACCATGTACTTTAAGAACAGCAATTGCCCGATATGCAGATGTCT

TGAGTTCACCCAAAAAGTCTGTTTTGCTTGCCTTAGCTGCTCATGCATC

TAATCCATCTGAAGCCGACCGCCTACGACATCTTGCTTCACCTGCTGGA

AAGGATGAATATTCAGAGTGGGTGATTGCCAGTCAAAGAAGTCTCCTTG

AGGTCATGGCTGAATTTCCATCAGCCAAACCTCCAATTGGTGTCTTTTT

CGCAGCAATTGCTCCTCGCCTGCAGCCAAGATTTTATTCGATCTCATCA

TCTCCTAGGATGGCTCCATCCAGAATTCACGTTACCTGTGCATTAGTGA

ATGATAAAATGCCCACTGGTAGGATTCATAGGGGAGTGTGTTCAACATG

GATGAAGAATTCTGTGCCATTGGAGAAAAGTCAGGACTGCAGTTGGGCT

CCAATATTTGTTAGACAGTCCAATTTTAAACTCCCTGCTGATAATAAAG

TGCCTATAATCATGATAGGTCCTGGCACAGGATTGGCTCCTTTCAGGGG

TTTCTTGCAGGAAAGATTAGCTCTGAAAGAGGATGGAGCTGAACTTGGC

CCCTCCGTTTTATTCTTCGGATGCAGGAATCGTCAAATGGACTACATCT
```

```
ATGAAGATGAGTTGAACCACTTTGTCAACAGTGGTGCGCTTTCTGAGCT
CATTGTTGCCTTCTCACGGAGGGACCTACCAAGGAATATGTGCAACAT
AAAATGATGGAGAAGGCTTCGGATATTTGGAACATGATATCTCAGGGAG
CTTACATTTATGTGTGTGGGGATGCCAAGGGCATGGCTAGGGATGTGCA
CCGTACTCTGCACACAATTTTGCAAGAGCAGGGTTCTCTCGATAGTTCC
AAGGCTGAGGGTATGGTTAAGAACCTACAATTGAATGGTAGGTATTTGC
GTGATGTATGGTGA
```

SEQ ID No 14. A.thaliana ATR1 mRNA for NADPH-cytochrome P450 reductase, X66016

```
ATGACTTCTGCTTTGTATGCTTCCGATTTGTTTAAGCAGCTCAAGTCAA
TTATGGGGACAGATTCGTTATCCGACGATGTTGTACTTGTGATTGCAAC
GACGTCTTTGGCACTAGTAGCTGGATTTGTGGTGTTGTTATGGAAGAAA
ACGACGGCGGATCGGAGCGGGGAGCTGAAGCCTTTGATGATCCCTAAGT
CTCTTATGGCTAAGGACGAGGATGATGATTTGGATTTGGGATCCGGGAA
GACTAGAGTCTCTATCTTCTTCGGTACGCAGACTGGAACAGCTGAGGGA
TTTGCTAAGGCATTATCCGAAGAAATCAAAGCGAGATATGAAAAAGCAG
CAGTCAAAGTCATTGACTTGGATGACTATGCTGCCGATGATGACCAGTA
TGAAGAGAAATTGAAGAAGGAAACTTTGGCATTTTTCTGTGTTGCTACT
TATGGAGATGGAGAGCCTACTGACAATGCTGCCAGATTTTCAAAATGGT
TTACGGAGGAAAATGAACGGGATATAAAGCTTCAACAACTAGCATATGG
TGTGTTTGCTCTTGGTAATCGCCAATATGAACATTTTAATAAGATCGGG
ATAGTTCTTGATGAAGAGTTATGTAAGAAAGGTGCAAAGCGTCTTATTG
AAGTCGGTCTAGGAGATGATGATCAGAGCATTGAGGATGATTTTAATGC
CTGGAAAGAATCACTATGGTCTGAGCTAGACAAGCTCCTCAAAGACGAG
GATGATAAAGTGTGGCAACTCCTTATACAGCTGTTATTCCTGAATACC
GGGTGGTGACTCATGATCCTCGGTTTACAACTCAAAAATCAATGGAATC
AAATGTGGCCAATGGAAATACTACTATTGACATTCATCATCCCTGCAGA
GTTGATGTTGCTGTGCAGAAGGAGCTTCACACACATGAATCTGATCGGT
CTTGCATTCATCTCGAGTTCGACATATCCAGGACGGGTATTACATATGA
AACAGGTGACCATGTAGGTGTATATGCTGAAAATCATGTTGAGATAGTT
GAAGAAGCTGGAAAATTGCTTGGCCACTCTTTAGATTTAGTATTTTCCA
TACATGCTGACAAGGAAGATGGCTCCCCATTGGAAAGCGCAGTGCCGCC
TCCTTTCCCTGGTCCATGCACACTTGGGACTGGTTTGGCAAGATACGCA
GACCTTTTGAACCCTCCTCGAAAGTCTGCGTTAGTTGCCTTGGCGGCCT
ATGCCACTGAACCAAGTGAAGCCGAGAAACTTAAGCACCTGACATCACC
TGATGGAAAGGATGAGTACTCACAATGGATTGTTGCAAGTCAGAGAAGT
CTTTTAGAGGTGATGGCTGCTTTTCCATCTGCAAAACCCCCACTAGGTG
TATTTTTTGCTGCAATAGCTCCTCGTCTACAACCTCGTTACTACTCCAT
CTCATCCTGCCAAGATTGGGCGCCAAGTAGAGTTCATGTTACATCCGCA
CTAGTATATGGTCCAACTCCTACTGGTAGAATCCACAAGGGTGTGTGTT
CTACGTGGATGAAGAATGCAGTTCCTGCGGAGAAAAGTCATGAATGTAG
TGGAGCCCCAATCTTTATTCGAGCATCTAATTTCAAGTTACCATCCAAC
```

```
CCTTCAACTCCAATCGTTATGGTGGGACCTGGGACTGGGCTGGCACCTT
TTAGAGGTTTTCTGCAGGAAAGGATGGCACTAAAAGAAGATGGAGAAGA
ACTAGGTTCATCTTTGCTCTTCTTTGGGTGTAGAAATCGACAGATGGAC
TTTATATACGAGGATGAGCTCAATAATTTTGTTGATCAAGGCGTAATAT
CTGAGCTCATCATGGCATTCTCCCGTGAAGGAGCTCAGAAGGAGTATGT
TCAACATAAGATGATGGAGAAGGCAGCACAAGTTTGGGATCTAATAAAG
GAAGAAGGATATCTCTATGTATGCGGTGATGCTAAGGGCATGGCGAGGG
ACGTCCACCGAACTCTACACACCATTGTTCAGGAGCAGGAAGGTGTGAG
TTCGTCAGAGGCAGAGGCTATAGTTAAGAAACTTCAAACCGAAGGAAGA
TACCTCAGAGATGTCTGGTGA
```

SEQ ID No 15. Catharanthus roseus cpr mRNA for NADPH-ferrihemoprotein reductase, X69791

```
ATGGATTCTAGCTCGGAGAAGTTGTCGCCGTTCGAATTGATGAGCGCGA
TCTTGAAGGGAGCTAAATTAGATGGGTCTAACTCTTCAGATTCTGGCGT
AGCTGTGTCGCCGGCAGTTATGGCTATGTTGTTGGAGAATAAGGAGTTA
GTGATGATTTTGACTACTTCAGTGGCGGTTTTGATCGGTTGTGTCGTAG
TTTTGATATGGCGGCGATCTTCCGGATCGGGTAAAAAAGTCGTGGAGCC
TCCGAAGCTCATAGTGCCTAAATCTGTTGTAGAACCGGAGGAAATTGAT
GAAGGGAAGAAGAAATTTACCATATTTTTTGGAACACAAACTGGAACAG
CTGAAGGCTTCGCTAAGGCTCTAGCTGAGGAAGCCAAAGCTCGATATGA
AAAGGCAGTTATCAAAGTGATTGATATAGATGATTATGCGGCTGATGAT
GAAGAATACGAGGAGAAATTCAGAAAAGAGACCTTGGCATTTTTCATCT
TGGCCACGTATGGAGATGGTGAGCCAACCGACAATGCTGCAAGGTTCTA
CAAATGGTTTGTAGAGGGAAATGATAGAGGGACTGGCTAAAGAATCTG
CAATATGGAGTTTTTGGCCTTGGTAACAGACAATATGAGCATTTCAACA
AGATTGCTAAAGTGGTGGATGAGAAAGTTGCTGAACAGGGTGGTAAGCG
GATTGTTCCATTGGTTCTGGGAGACGATGACCAGTGCATTGAAGATGAC
TTTGCTGCATGGCGTGAGAATGTATGGCCTGAGTTGGATAACTTGCTCC
GGGATGAGGATGATACAACTGTTTCTACAACCTACACTGCTGCTATTCC
AGAATATCGTGTTGTGTTCCCTGACAAATCAGATTCACTTATTTCAGAA
GCAAATGGCCATGCCAATGGTTATGCTAATGGCAACACCGTATATGATG
CCCAGCATCCTTGCAGATCTAATGTTGCAGTGAGGAAGGAGCTTCATAC
TCCAGCATCTGATCGTTCTTGCACCCATTTGGATTTTGACATTGCTGGC
ACTGGCCTTTCATATGGAACTGGAGATCATGTTGGAGTGTACTGTGATA
ATCTATCTGAAACCGTGGAGGAGGCTGAGAGATTACTGAATTTACCCCC
AGAAACTTATTTCTCGCTTCATGCTGATAAAGAGGATGGAACCCCACTT
GCTGGGAGCTCATTGCCTCCTCCTTTCCCACCTTGTACTCTAAGAACCG
CCCTCACTCGTTATGCAGATCTCTTAAATACTCCTAAGAAGTCTGCTTT
GTTAGCTCTAGCAGCTTATGCATCTGATCCAAATGAGGCCGATCGTCTA
AAATATCTTGCTTCTCCAGCCGGAAAGGATGAATATGCTCAGTCACTAG
TTGCAAATCAGAGAAGCCTCCTCGAGGTCATGGCTGAATTTCCATCAGC
```

-continued

AAAGCCTCCTCTTGGAGTATTCTTTGCAGCAATTGCTCCACGCCTCCAA

CCCAGATTCTATTCTATATCGTCTTCTCCAAGGATGGCACCATCTAGAA

TTCATGTCACTTGTGCACTTGTTTATGAAAAAACACCTGGAGGACGAAT

TCACAAGGGTGTGTGTTCGACATGGATGAAGAATGCCATTCCATTGGAG

GAAAGCCGTGACTGCAGCTGGGCTCCTATCTTTGTCAGGCAGTCTAACT

TCAAACTCCCTGCCGATCCTAAAGTGCCTGTTATAATGATCGGCCCTGG

TACTGGACTAGCTCCCTTCAGAGGATTCCTTCAGGAAAGATTAGCTCTG

AAGGAAGAAGGAGCTGAACTTGGTACTGCAGTTTTCTTTTTTGGATGCA

GGAACCGCAAAATGGATTACATCTATGAAGATGAGCTAAACCATTTCCT

TGAAATTGGTGCACTTTCCGAGCTACTTGTTGCTTTCTCACGTGAGGGA

CCCACTAAGCAGTATGTGCAACACAAGATGGCAGAAAAGGCTTCTGATA

TTTGGAGGATGATTTCTGATGGAGCATATGTTTACGTCTGCGGTGATGC

CAAAGGCATGGCCAGGGATGTCCACAGAACTCTCCACACCATTGCTCAA

GAGCAGGGATCGATGGATAGCACACAGGCTGAGGGTTTTGTGAAGAATC

TGCAAATGACCGGAAGGTATCTCCGAGATGTCTGGTGA

SEQ ID No 16. *Medicago truncatula* NADPH cytochrome P450 reductase (MTR_3g100160) mRNA, complete cds, XM_003602850

ATGACTTCTTCCAATTCCGATTTAGTCCGTACAATCGAATCCGTACTCG

GAGTTTCCCTCGGCGACTCCGTTTCAGATTCGGTTGTTCTCATCGTTAC

CACCTCCGCCGCCGTCATAATTGGACTTCTCGTTTTTCTATGGAAGAAA

TCTTCGGATCGGAGCAAAGAGTTGAAACCGGTTATAGTTCCTAAGTCCT

TGGTGAAAGAAGAAGATGATGATGCTGATATTGCTGATGGAAAAACCAA

AGTTACCGTTTTCTTTGGTACTCAAACTGGTACTGCTGAAGGATTCGCT

AAGGCATTGGCAGAGGAGATCAAGGCAAGATATGAAAAAGCATTTGTCA

AAGTTGTTGATATGGATGACTATGCAGCGGATGATGATCAATATGAAGA

GAAGCTGAAGAAAGAAACTTGCATTTTTCATGCTGGCGACTTATGGA

GATGGAGAGCCAACTGACAATGCCGCAAGATTCTATAAATGGTTTACTG

AGGGTAAAGACGAGAGGGGAACCTGGCTTAACAGCTCACATATGGTGT

TTTTGGCCTAGGTAACAGGCAATATGAACATTTTAACAAGATAGGTAAA

GTTGTTGACGACGATCTCAGTGAACAAGGGGCAAAGCGTCTTGTTCCAC

TTGGAATGGGTGATGATGATCAATCCATTGAGGATGATTTTAATGCCTG

GAAAGAATCTCTGTGGCCTGAGTTGGATCAGTTGCTCCGAGATGAGGAT

GATGTAAATACTGTGTCTACTCCTTATACAGCTGCTATTTCTGAATATC

GAGTAGTGTTTCACGACCCCACTGTCACGCCGTCCTACGAGAATCACTT

TAACGCGGCAAATGGGGGTGCTGTATTTGATATTCATCATCCTTGTAGG

GCGAATGTCGCTGTTCGAAGGGAGCTTCATAAACCTCAGTCTGACCGTT

CTTGTATACATTTGGAGTTTGATGTATCAGGGACCGGCGTAACATACGA

AACTGGAGACCATGTGGGTGTTTATGCTGATAACTGTGATGAAACTGTT

AAAGAAGCTGGGAAGTTGTTGGGTCAGGATTTAGATTTGCTGTTTTCTC

TTCACACTGATAATGAGGATGGCACTTCCCTAGGTGGTTCTCTTCTACC

TCCTTTCCCTGGTCCTTGCACAGTTCGCACTGCATTAGCACGTTATGCA

SEQ ID No 17. *Saccharomyces cerevisiae* S288c Ncp1p (NCP1), mRNA, NM_001179172

GATCTCTTGAACCCCCCACGAAAGGCTGCTTTAATTGCATTAGCTGCTC

ATGCTTCCGAGCCTAGTGAAGCAGAAAGATTGAAGTTTCTCTCATCTCC

TCAGGGAAAGGATGAATACTCCAAATGGGTTGTTGGAAGCCATAGAACT

CTTCTTGAGGTGATGGCTGATTTTCCATCAGCAAAACCACCCCTTGGTG

TGTTTTTTGCTGCCATAGCCCCTCGTTTACAACCTCGTTATTATTCTAT

TTCATCATCTCCTAGGTTTGCCCCACAAAGGGTACACGTAACTTGTGCC

CTGGTAGAAGGTCCAACTCCAACTGGCAGAATTCACAAAGGAGTATGTT

CAACCTGGATGAAGAATGCTATTCCCTCAGAGGAAAGCCGTGACTGTAG

CTGGGCTCCCATTTTTATCAGGCCATCGAATTTCAAGCTACCTGCTGAT

CCTTCAATTCCTATTATTATGGTTGGACCTGGTACTGGTTTAGCACCTT

TTAGGGGATTTTTACAGGAGAGATTTGCTCTCAAAGAGGACGGTGTTCA

ACTTGGTCCTGCATTACTATTCTTCGGGTGCAGGAACCGTCAAATGGAT

TTTATATATGAGGAAGAGCTGAATAATTTTGTGGAACAAGGTTCTCTGT

CAGAGTTGATAGTTGCATTCTCTAGAGAGGGGCCTGAAAAGGAGTATGT

TCAACACAAAATGATGGATAAAGCATCATACTTCTGGAGTCTCATTTCT

CAGGGAGGTTATCTTTATGTATGTGGTGATGCCAAGGGCATGGCCAGAG

ATGTTCATCGAACTCTTCACACCATTGTCCAGCAGCAGGAAAATGCAGA

CTCTTCAAAGGCGGAGGCTACGGTGAAAAAACTCCAGATGGATGGACGC

TACCTTAGGGATGTCTGGTGA

SEQ ID No 17. *Saccharomyces cerevisiae* S288c Ncp1p (NCP1), mRNA, NM_001179172

ATGCCGTTTGGAATAGACAACACCGACTTCACTGTCCTGGCGGGCTAG

TGCTTGCCGTGCTACTGTACGTAAAGAGAAACTCCATCAAGGAACTGCT

GATGTCCGATGACGGAGATATCACAGCTGTCAGCTCGGGCAACAGAGAC

ATTGCTCAGGTGGTGACCGAAAACAACAAGAACTACTTGGTGTTGTATG

CGTCGCAGACTGGGACTGCCGAGGATTACGCCAAAAAGTTTTCCAAGGA

GCTGGTGGCCAAGTTCAACCTAAACGTGATGTGCGCAGATGTTGAGAAC

TACGACTTTGAGTCGCTAAACGATGTGCCCGTCATAGTCTCGATTTTTA

TCTCTACATATGGTGAAGGAGACTTCCCCGACGGGGCGGTCAACTTTGA

AGACTTTATTTGTAATGCGGAAGCGGGTGCACTATCGAACCTGAGGTAT

AATATGTTTGGTCTGGGAAATTCTACTTATGAATTCTTTAATGGTGCCG

CCAAGAAGGCCGAGAAGCATCTCTCCGCCGCGGGCGCTATCAGACTAGG

CAAGCTCGGTGAAGCTGATGATGGTGCAGGAACTACAGACGAAGATTAC

ATGGCCTGGAAGGACTCCATCCTGGAGGTTTTGAAAGACGAACTGCATT

TGGACGAACAGGAAGCCAAGTTCACCTCTCAATTCCAGTACACTGTGTT

GAACGAAATCACTGACTCCATGTCGCTTGGTGAACCCTCTGCTCACTAT

TTGCCCTCGCATCAGTTGAACCGCAACGCAGACGGCATCCAATTGGGTC

CCTTCGATTTGTCTCAACCGTATATTGCACCCATCGTGAAATCTCGCGA

ACTGTTCTCTTCCAATGACCGTAATTGCATCCACTCTGAATTTGACTTG

TCCGGCTCTAACATCAAGTACTCCACTGGTGACCATCTTGCTGTTTGGC

CTTCCAACCCATTGGAAAAGGTCGAACAGTTCTTATCCATATTCAACCT

GGACCCTGAAACCATTTTTGACTTGAAGCCCCTGGATCCCACCGTCAAA

-continued
GTGCCCTTCCCAACGCCAACTACTATTGGCGCTGCTATTAAACACTATT
TGGAAATTACAGGACCTGTCTCCAGACAATTGTTTTCATCTTTGATTCA
GTTCGCCCCAACGCTGACGTCAAGGAAAAATTGACTCTGCTTTCGAAA
GACAAGGACCAATTCGCCGTCGAGATAACCTCCAAATATTTCAACATCG
CAGATGCTCTGAAATATTGTCTGATGGCGCCAAATGGGACACCGTACC
CATGCAATTCTTGGTCGAATCAGTTCCCCAAATGACTCCTCGTTACTAC
TCTATCTCTTCCTCTTCTCTGTCTGAAAAGCAAACCGTCCATGTCACCT
CCATTGTGGAAAACTTTCCTAACCCAGAATTGCCTGATGCTCCTCCAGT
TGTTGGTGTTACGACTAACTTGTTAAGAAACATTCAATTGGCTCAAAAC
AATGTTAACATTGCCGAAACTAACCTACCTGTTCACTACGATTTAAATG
GCCCACGTAAACTTTTCGCCAATTACAAATTGCCCGTCCACGTTCGTCG
TTCTAACTTCAGATTGCCTTCCAACCCTTCCACCCCAGTTATCATGATC
GGTCCAGGTACCGGTGTTGCCCCATTCCGTGGGTTTATCAGAGAGCGTG
TCGCGTTCCTCGAATCACAAAAGAAGGGCGGTAACAACGTTTCGCTAGG
TAAGCATATACTGTTTTATGGATCCCGTAACACTGATGATTTCTTGTAC
CAGGACGAATGGCCAGAATACGCCAAAAAATTGGATGGTTCGTTCGAAA
TGGTCGTGGCCCATTCCAGGTTGCCAAACACCAAAAAAGTTTATGTTCA
AGATAAATTAAAGGATTACGAAGACCAAGTATTTGAAATGATTAACAAC
GGTGCATTTATCTACGTCTGTGGTGATGCAAAGGGTATGGCCAAGGGTG
TGTCAACCGCATTGGTTGGCATCTTATCCCGTGGTAAATCCATTACCAC
TGATGAAGCAACAGAGCTAATCAAGATGCTCAAGACTTCAGGTAGATAC
CAAGAAGATGTCTGGTAA SEQ ID No 18. *A.thaliana* mRNA ATR2 for NADPH-
cytochrome P450 reductase, X66017
ATGTCCTCTTCTTTCTTCGTCAACCTCCATGATCGATCTCATGGCAG
CAATCATCAAAGGAGAGCCTGTAATTGTCTCCGACCCAGCTAATGCCTC
CGCTTACGAGTCCGTAGCTGCTGAATTATCCTCTATGCTTATAGAGAAT
CGTCAATTCGCCATGATTGTTACCACTTCCATTGCTGTTCTTATTGGTT
GCATCGTTATGCTCGTTTGGAGGAGATCCGGTTCTGGGAATTCAAAACG
TGTCGAGCCTCTTAAGCCTTTGGTTATTAAGCCTCGTGAGGAAGAGATT
GATGATGGGCGTAAGAAAGTTACCATCTTTTTCGGTACACAAACTGGTA
CTGCTGAAGGTTTTGCAAAGGCTTTAGGAGAAGAAGCTAAAGCAAGATA
TGAAAAGACCAGATTCAAAATCGTTGATTTGGATGATTACGCGGCTGAT
GATGATGAGTATGAGGAGAAATTGAAGAAAGAGGATGTGGCTTTCTTCT
TCTTAGCCACATATGGAGATGGTGAGCCTACCGACAATGCAGCGAGATT
CTACAAATGGTTCACCGAGGGGAATGACAGAGGAGAATGGCTTAAGAAC
TTGAAGTATGGAGTGTTTGGATTAGGAAACAGACAATATGAGCATTTTA
ATAAGGTTGCCAAAGTTGTAGATGACATTCTTGTCGAACAAGGTGCACA
GCGTCTTGTACAAGTTGGTCTTGGAGATGATGACCAGTGTATTGAAGAT
GACTTTACCGCTTGGCGAGAAGCATTGTGGCCCGAGCTTGATACAATAC
TGAGGGAAGAAGGGGATACAGCTGTTGCCACACCATACACTGCAGCTGT -continued
GTTAGAATACAGAGTTTCTATTCACGACTCTGAAGATGCCAAATTCAAT
GATATAACATTGGCAAATGGGAATGGTTACACTGTGTTTGATGCTCAAC
ATCCTTACAAAGCAAATGTCGCTGTTAAAAGGGAGCTTCATACTCCCGA
GTCTGATCGTTCTTGTATCCATTTGGAATTTGACATTGCTGGAAGTGGA
CTTACGATGAAACTTGGAGATCATGTTGGTGTACTTTGTGATAACTTAA
GTGAAACTGTAGATGAAGCTCTTAGATTGCTGGATATGTCACCTGATAC
TTATTTCTCACTTCACGCTGAAAAAGAAGACGGCACACCAATCAGCAGC
TCACTGCCTCCTCCCTTCCCACCTTGCAACTTGAGAACAGCGCTTACAC
GATATGCATGTCTTTTGAGTTCTCCAAAGAAGTCTGCTTTAGTTGCGTT
GGCTGCTCATGCATCTGATCCTACCGAAGCAGAACGATTAAAACACCTT
GCTTCACCTGCTGGAAAGGATGAATATTCAAAGTGGGTAGTAGAGAGTC
AAAGAAGTCTACTTGAGGTGATGGCCGAGTTTCCTTCAGCCAAGCCACC
ACTTGGTGTCTTCTTCGCTGGAGTTGCTCCAAGGTTGCAGCCTAGGTTC
TATTCGATATCATCATCGCCCAAGATTGCTGAAACTAGAATTCACGTCA
CATGTGCACTGGTTTATGAGAAAATGCCAACTGGCAGGATTCATAAGGG
AGTGTGTTCCACTTGGATGAAGAATGCTGTGCCTTACGAGAAGAGTGAA
AAACTGTTCCTCGGGCGGCCGATATTTGTTAGGCAATCCAACTTCAAGC
TTCCTTCTGATTCTAAGGTACCGATCATCATGATCGGTCCAGGGACTGG
ATTAGCTCCATTCAGAGGATTCCTTCAGGAAAGACTAGCGTTGGTAGAA
TCTGGTGTTGAACTTGGGCCATCAGTTTTGTTCTTTGGATGCAGAAACC
GTAGAATGGATTTCATCTACGAGGAAGAGCTCCAGCGATTTGTTGAGAG
TGGTGCTCTCGCAGAGCTAAGTGTCGCCTTCTCTCGTGAAGGACCCACC
AAAGAATACGTACAGCACAAGATGATGGACAAGGCTTCTGATATCTGGA
ATATGATCTCTCAAGGAGCTTATTTATATGTTTGTGGTGACGCCAAAGG
CATGGCAAGAGATGTTCACAGATCTCTCCACACAATAGCTCAAGAACAG
GGGTCAATGGATTCAACTAAAGCAGAGGGCTTCGTGAAGAATCTGCAAA
CGAGTGGAAGATATCTTAGAGATGTATGGTAA SEQ ID No 19. *Artemisia annua* cytochrome P450
reductase (CPR) mRNA, complete cds, JN594507
ATGCAATCAACAACTTCCGTTAAGTTATCTCCCTTCGATCTAATGACGG
CGTTACTTAACGGCAAGGTATCGTTCGACACATCAAACACATCCGATAC
GAATATTCCGTTAGCGGTGTTTATGGAGAATCGTGAGCTTTTGATGATT
TTAACTACTTCAGTTGCGGTGTTGATCGGATGCGTTGTGGTGCTTGTGT
GGAGACGGTCGTCGTCGGCGGCGAAGAGAGCGGCGGAGTCGCCGGTGAT
TGTTGTGCCGAAGAAAGTGACGGAGGATGAGGTTGATGATGGACGGAAG
AAAGTTACTGTGTTTTTTGGAACTCAGACTGGTACTGCTGAAGGTTTTG
CTAAGGCGCTTGTTGAAGAAGCTAAAGCGCGATATGAAAAGGCGGTGTT
TAAAGTGATTGATTTGGATGATTATGCTGCTGAAGATGATGAGTATGAG
GAGAAGTTAAAGAAAGAATCTCTTGCTTTTTTCTTTTTAGCTACGTATG
GAGATGGTGAGCCGACAGATAATGCTGCTAGATTCTATAAATGGTTTAC
CGAGGGTGAAGAGAAAGGTGAATGGCTTGAAAAGCTTCAATACGCAGTG
TTTGGACTTGGTAACAGACAGTATGAGCATTTCAACAAGATTGCGAAGG -continued

```
TGGTCGATGAAAAACTTACGGAACAGGGTGCAAAGCGCCTTGTTCCTGT
TGGCATGGGAGACGACGATCAATGTATTGAAGACGACTTCACTGCATGG
AAAGAGTTGGTGTGGCCTGAGTTGGATCAATTACTTCGTGATGAGGATG
ATACATCTGTTGCCACCCCATACACAGCTGCTGTTGCAGAATACCGTGT
TGTGTTCCATGATAAACCAGAGACATATGATCAGGATCAACTGACAAAT
GGCCATGCTGTTCATGATGCTCAACATCCATGCAGATCCAATGTAGCTG
TCAAAAAGGAGCTCCATTCCCCTCTATCTGACCGTTCTTGCACTCATTT
GGAATTTGATATCTCTAATACTGGATTATCGTATGAAACTGGGGACCAT
GTTGGAGTCTACGTTGAGAATCTAAGTGAAGTTGTGGACGAAGCTGAAA
AATTAATAGGTTTACCGCCGCACACTTATTTCTCAATACACGCTGATAA
CGAAGACGGGACACCACTTGGTGGAGCCTCTTTGCCACCTCCTTTCCCT
CCATGCACTTTAAGAAAAGCATTGGCTTCCTATGCCGATGTTTTGAGCT
CTCCTAAAAAGTCAGCTTTGCTTGCTTTAGCTGCTCATGCTACTGATTC
TACTGAAGCTGATAGACTGAAATTTCTTGCGTCTCCTGCGGGAAAGGAT
GAATATGCTCAGTGGATAGTTGCAAGCCACAGAAGTCTCCTTGAGGTCA
TGGAGGCCTTCCCATCAGCTAAGCCTCCGCTTGGTGTTTTTTTTGCATC
TGTCGCCCCACGTTTGCAGCCGAGATACTATTCCATTTCTTCTTCCCCA
AGTTTGCGCCAAATAGGATTCATGTAACTTGTGCATTAGTGTATGAGC
AAACACCATCAGGCCGCGTTCACAAGGGAGTCTGTTCAACATGGATGAA
GAATGCTGTGCCTATGACAGAAAGCCAGGATTGCAGTTGGGCCCCAATT
TATGTTAGAACATCCAATTTCAGACTTCCTTCTGATCCTAAGGTCCCAG
TTATCATGATTGGCCCAGGCACTGGATTGCTCCATTTAGAGGTTTCCT
TCAGGAAAGGTTAGCTCAGAAGGAAGCTGGGACTGAGCTCGGAACAGCC
ATCTTATTCTTCGGATGCAGGAATCGCAAAGTGGATTTCATATATGAGG
ACGAGCTTAATAATTTCGTGGAGACTGGGGCTCTTTCCGAGCTTGTTAC
GGCCTTCTCTCGTGAAGGTGCCACTAAGGAGTACGTGCAACACAAGATG
ACTCAGAAGACTTCGGATATCTGGAATTTACTCTCTGAGGGAGCATATT
TGTATGTTTGCGGTGATGCCAAAGGCATGGCCAAAGATGTACATCGGAC
TCTGCACACTATTGTGCAAGAACAGGGATCTCTAGACTCCTCAAAGGCG
GAGCTCTACGTGAAGAATCTACAAATGGCAGGAAGATATCTCCGTGATG
TATGGTAA

SEQ ID No 20. Artennisia annua cytochrome P450
reductase mRNA, complete cds, DQ984181
ATGCAATCAACAACTTCCGTTAAGTTATCTCCCTTCGATCTAATGACGG
CGTTACTTAACGGCAAGGTATCGTTCGACACATCAAACACATCGGATAC
GAATATTCCGTTAGCGGTGTTTATGGAGAATCGTGAGCTTTTGATGATT
TTAACTACTTCGGTTGCGGTTTTGATCGGATGCGTTGTGGTGCTTGTGT
GGAGACGGTCGTCGTCGGCGGCGAAGAAAGCGGCGGAGTCGCCGGTGAT
TGTTGTGCCGAAGAAAGTGACGGAGGATGAGGTTGATGATGGACGGAAG
AAAGTTACTGTGTTTTTTGGAACTCAGACTGGTACTGCTGAAGGTTTTG
CTAAGGCGCTTGTTGAAGAAGCTAAAGCGCGATATGAAAAGGCGGTGTT
```

SEQ ID No 21. Artennisia annua cytochrome P450
reductase mRNA, complete cds, DQ318192
```
ATGCAATCAACAACTTCCGTTAAGTTATCTCCCTTCGATCTAATGACGG
CGTTACTTAACGGCAAGGTATCGTTCGACACATCAAACACATCGGATAC
GAATATTCCGTTAGCGGTGTTTATGGAGAATCGTGAGCTTTTGATGATT
TTAACTACTTCGGTTGCGGTGTTGATCGGATGCGTTGTGGTGCTTGTGT
```

TAAAGTGATTGATTTGGATGATTATGCTGCTGAGGACGATGAGTATGAG
GAGAAGTTAAAGAAAGAATCTCTTGCTTTTTTCTTTTTAGCTACGTATG
GAGATGGTGAGCCGACAGATAATGCTGCTAGATTCTATAAATGGTTTAC
CGAGGGTGAAGAGAAAGGTGAATGGCTTGACAAGCTTCAATACGCAGTG
TTTGGACTTGGTAACAGACAGTATGAGCATTTCAACAAGATTGCGAAGG
TGGTCGATGAAAAACTTGTGGAGCAGGGTGCAAAGCGCCTTGTTCCTGT
TGGCATGGGAGACGATGATCAATGTATTGAAGACGACTTCACTGCATGG
AAAGAGTTGGTGTGGCCTGAGTTGGATCAATTACTTCGTGATGAGGATG
ATACATCTGTTGCCACTCCATACACAGCTGCTGTTGCAGAATACCGTGT
TGTGTTCCATGATAAACCAGAGACATATGATCAGGATCAACTGACAAAT
GGCCATGCTGTTCATGATGCTCAACATCCATGCAGATCCAATGTCGCTG
TCAAAAAGGAGCTCCATTCCCCTCTATCTGACCGGTCTTGCACTCATTT
GGAATTTGATATCTCTAATACTGGATTATCGTATGAAACTGGGGACCAT
GTTGGAGTCTACGTTGAGAATCTAAGTGAAGTTGTGGACGAAGCTGAAA
AATTAATAGGTTTACCGCCGCACAOTTATTTCTCAGTACACGCTGATAA
CGAAGACGGGACACCACTTGGTGGAGCCTCTTTGCCACCTCCTTTCCCT
CCATGCACTTTAAGAAAAGCATTGGCTTCCTATGCCGATGTTTTGAGCT
CTCCTAAAAAGTCAGCTTTGCTTGCTTTAGCTGCTCATGCTACTGATTC
TACTGAAGCTGATAGACTGAAATTTCTTGCGTCTCCTGCGGGAAAGGAT
GAATATGCTCAGTGGATAGTTGCAAGCCACAGAAGTCTCCTTGAGGTCA
TGGAGGCCTTCCCATCAGCTAAGCCTCCGCTTGGTGTTTTTTTTGCATC
TGTCGCCCCACGTTTGCAGCCGAGATACTATTCCATTTCTTCTTCCCCA
AGGTTTGCGCCAAATAGGATTCATGTAACTTGTGCATTAGTGTATGAGC
AAACACCATCAGGCCGCGTTCACAAGGGAGTCTGTTCAACATGGATGAA
GAATGCCGTGCCTATGACAGAAAGCCAGGATTGCAGTTGGGCCCCAATT
TATGTTAGAACATCCAATTTCAGACTTCCTTCTGATCCTAAGGTCCCAG
TTATCATGATTGGCCCAGGCACTGGATTGCTCCATTTAGAGGTTTCCT
TCAGGAAAGGTTAGCTCAGAAGGAAGCTGGGACTGAGCTCGGAACAGCC
ATCTTATTCTTCGGATGCAGGAATCGCAAAGTGGATTTCATATATGAGG
ACGAGCTTAATAATTTCGTGGAGACTGGGGCTCTTTCCGAGCTTGTTAC
GGCCTTCTCTCGTGAAGGTGCCACTAAGGAGTACGTGCAACACAAGATG
ACTCAGAAGGCTTCGGATATCTGGAATTTACTCTCTGAGGGAGCATATT
TGTATGTTTGCGGTGATGCCAAAGGCATGGCCAAAGATGTACATCGGAC
TCTGCACACTATTGTGCAAGAACAGGGATCTCTAGACTCCTCAAAGGCG
GAGCTCTACGTGAAGAATCTACAAATGGCAGGAAGATATCTCCGTGATG
TATGGTAA
```

SEQ ID No 21. *Artennisia annua* cytochrome P450
reductase mRNA, complete cds, DQ318192
```
ATGCAATCAACAACTTCCGTTAAGTTATCTCCCTTCGATCTAATGACGG
CGTTACTTAACGGCAAGGTATCGTTCGACACATCAAACACATCGGATAC
GAATATTCCGTTAGCGGTGTTTATGGAGAATCGTGAGCTTTTGATGATT
TTAACTACTTCGGTTGCGGTGTTGATCGGATGCGTTGTGGTGCTTGTGT
```

-continued

```
GGAGACGGTCGTCGTCGGCGGCGAAGAAAGCGGCGGAGTCGCCGGTGAT
TGTTGTGCCGAAGAAAGTGACGGAGGATGAGGTTGATGACGGACGGAAG
AAAGTTACTGTGTTTTTTGGAACTCAGACTGGTACTGCTGAAGGTTTTG
CTAAGGCGCTTGTTGAAGAAGCTAAAGCGCGATATGAAAAGGCGGTGTT
TAAAGTGATTGATTTGGATGATTATGCTGCTGAAGATGATGAGTATGAG
GAGAAGTTAAAGAAAGAATCTCTTGCTTTTTTCTTTTTAGCTACGTATG
GAGATGGTGAGCCGACAGATAATGCTGCTAGATTCTATAAATGGTTTAC
CGAGGGTGAAGAGAAAGGTGAATGGCTTGACAAGCTTCAATACGCAGTG
TTTGGACTTGGTAACAGACAGTATGAGCATTTCAACAAGATTGCGAAGG
TGGTCGATGAAAAACTTGTGGAGCAGGGTGCAAAGCGCCTTGTTCCTGT
TGGCATGGGAGACGATGATCAATGTATCGAAGACGACTTCACTGCATGG
AAAGAGTTGGTGTGGCCTGAGTTGGATCAATTACTTCGTGATGAGGATG
ATACATCTGTTGCCACTCCATACACAGCTGCTGTTGGAGAATACCGTGT
TGTGTTCCATGACAAACCAGAGACATATGATCAGGATCAACTGACAAAT
GGCCATGCTGTTCATGATGCTCAACATCCATGCAGATCCAATGTCGCTG
TCAAAAAGGAGCTCCATTCCCCTCTATCTGACCGGTCTTGCACTCATTT
GGAATTTGATATCTCTAATACTGGATTATCGTATGAAACTGGGGACCAT
GTTGGAGTCTACGTTGAGAATCTAAGTGAAGTTGTGGACGAAGCTGAAA
AATTAATAGGTTTACCGCCGCACACTTATTTCTCAGTACATACTGATAA
CGAAGACGGGACACCACTTGGTGGAGCCTCTTTGCCACCTCCTTTCCCT
CCATGCACTTTAAGAAAAGCATTGGCTTCCTATGCCGATGTTTTGAGCT
CTCCTAAAAAGTCAGCTTTGCTTGCTTTAGCTGCTCATGCTACTGATTC
TACTGAAGCTGATAGACTGAAATTTTTGCGTCTCCTGCTGGAAAGGAT
GAATATGCTCAGTGGATAGTTGCAAGCCACAGAAGTCTCCTTGAGGTCA
TGGAGGCCTTCCCATCAGCTAAGCCTCCGCTTGGTGTTTTTTTTGCATC
TGTCGCCCCACGTTTGCAGCCGAGATACTATTCCATTTCTTCTTCCCCA
AAGTTTGCGCCAAATAGGATTCATGTAACTTGTGCATTAGTGTATGAGC
AAACACCATCAGGCCGCGTTCACAAGGGAGTCTGTTCAACATGGATGAA
GAATGCCGTGCCTATGACAGAAAGCCAGGATTGCAGTTGGGCCCCAATT
TATGTTAGAACATCCAATTTCAGACTTCCTTCTGATCCTAAGGTCCCAG
TTATCATGATTGGCCCAGGCACTGGATTGGCTCCATTTAGAGGTTTCCT
TCAGGAAAGGTTAGCTCAGAAGGAAGCTGGGACTGAGCTCGGAACAGCC
ATCTTATTCTTCGGATGCAGGAATCGCAAAGTGGATTTCATATATGAGG
ACGAGCTTAATAATTTCGTGGAGACGGGGGCTCTTTCCGAGCTTGTTAC
GGCCTTCTCTCGTGAAGGTGCCACTAAGGAGTACGTGCAACACAAGATG
ACTCAGAAGGCTTCGGATATCTGGAATTTACTCTCTGAGGGAGCATATT
TGTATGTTTGCGGTGATGCCAAAGGCATGGCCAAAGATGTACATCGGAC
TCTGCACACTATTGTGCAAGAACAGGGATCTCTAGACTCCTCAAAGGCG
GAGCTCTACGTGAAGAATCTACAAATGGCAGGAAGATATCTCCGTGATG
TATGGTAA
```

SEQ ID No 22. Hybrid poplar (*Populus trichocarpa* x *P. deltoides*) NADPH-cytochrome P450 oxydoreductase isoform 1 mRNA, complete cds, AF302496

```
ATGAGTTCAGGTGGTTCAAATTTGGCGAGGTTCGTTCAATCAGTGCTAG
GGATATCTTTTGGCGACTCCCTGTCTGACTCAGTTGTTGTGATAATTAC
CACGTCGTTTGCTGCTCTAGTTGGATTGGTGGTGCTTGTATTGAAGAGA
TCGTCCGATCGGAGCAAAGACGTCAAGCCGTTGGTGGTTCCTAAGTCAC
TTTCAATTAAGGACGAGGAGGATGAGTCCGAGGCTCTGGGTGGGAAAAC
TAAGGTTACTATCTTTTATGGGACTCAGACCGGAACTGCGGAGGGTTTT
GCTAAGGCTTTAGCTGAAGAGGTCAAAGCAAGATATGAGAAAGCAGCTG
TTAAAGTGTTTGACCTGGATGATTATGCTATGGAAGATGATCAATATGA
AGAAAAATTGAAGAAAGAGACTTTGGCATTATTCATGGTTGCCACTTAT
GGAGATGGAGAGCCAACTGATAACGCTGCGAGATTTATAAGTGGTTTA
CTGAGGGAAATGAAAGGGGAATCTGGCTTCAACAGCTTTCTTATGGTGT
TTTTGGTCTTGGTAACCGTCAATATGAACATTTTAATAAGATAGCGAAG
GTGCTTGATGACCTGCTCTATAACAAGGAGGAAAGCGTCTCGTTCCTG
TTGGTCTTGGCGACGATGATCAATGCATAGAGGATGATTTTCTGCTTG
GAAAGAATTTTTGTGGCCTGAGCTAGACCAGTTGCTCAGAGATGAAGAT
GATGTGAATGCTCCATCTACTCCTTATACAGCTGCTATACCTGAATATC
GATTAGTGATTCATGATCCTTCTATAATATCTGTTGAGGATAAATTCTC
AAACTTGGCAAATGGGAATGTGTCTTTTGATATTCACCATCCATGCAGA
GTCAATGTTGCTGTCCAAAAAGAGCTTCACAAAGCAGAGTCTGACCGGT
CTTGCATACATCTGGAATTTGACATCACAGGGACTGGAATTACATATGA
AACTGGAGACCATTTGGGGGTGTATGCTGAGAATAGTGATGAAACTGTT
GAAGAAGCAGGGAAGTTGCTAGATAAACCTTTAGATTGTTGTTTTCTA
TTCATGCTGATAATGAGGATGGCACAGCTATTGGAAGCTCATTGCCGCC
TCCTTTCCCAGGTCCCTGCACACTTCACACTGCATTGGCATGCTATGCA
GATCTCTTGAGCCCTCCTAAAAAGGCTGCTTTGCTTTGGCTGCTC
ATGCCAGTGAACCTAGCGAGGCAGATAGACTCAAGTTTTTATCATCACC
GCAAGGAAAGAATGAATACTCTCACTGGGTCATGGCAAGTCAGAGAAGT
CTTCTCGAGGTAATGGCTGAGTTCCCATCTTCGAAACCTCCCCTTGGTA
TCTTTTTTGCTGCAGTGGCTCCTCGCCTACAGCCTCGCTACTATTCTAT
CTCATCCTCTCCTAGATATACTCCCAATAGAGTACATGTGACCTGTGCT
TTAGTATATGGTCCAACTCCCACTGGTAGAATTCACAAAGGGGTGTGTT
CAACTTGGATGAAGAATGCAGTTCCTCTGGAGAAAAGTTATGAATGTAG
TTGGGCTCCCATTTTCACCAGAACATCTAATTTCAAGTTACCAGCAGAT
CCTTCAACTCCAATTATAATGGTGGGTCCTGGTACTGGATTGGCACCTT
TCAGAGGATTTTTACAGGAAAGAATAGCCCTGAAAGAGGATGGTGTGAA
GCTTGGTCCCGCCCTGCTTTTCTTTGGATGCAGAAATCGCCGAATGGAT
TTCATATATGAGGATGAGCTCAATAATTTTGTCGAGCAAGGTGTGATAT
CCGAGTTGATAGTTGCATTCTCAAGGGAGGGGCCACAGAAGGAATATGT
TCAACATAAGATGGTGGATAGAGCAGCAGAGATATGGACTATAATTTCT
```

-continued

CAAGGAGGTTATTTTTACGTGTGCGGTGATGCCAAGGGTATGGCTAGAG

ATGTTCATAGGACTCTGCACACTATTGTGCAAGAGCAGGGAGGCCTGGA

CTCGTCGAAAACCGAGTCTATGGTGAAGAAGCTCCAAATGGAAGGACGG

TATCTAAGAGATGTCTGGTGA

SEQ ID No 23. Hybrid poplar (*Populus trichocarpa*
x *P. deltoides*) NADPH-cytochrome P450
oxydoreductase isoform 2 mRNA, complete cds,
AF302497

ATGCAATCATCAAGCAGCTCGATGAAAGTGTCACCACTTGAACTTATGC

AAGCCATAATCAAAGGCAAAGTGGACCCAACAAATGTTTCATCGGAATC

CGGTGGTTCTGCTGCTGAGATGGCAACTTTGATCCGCGAGAATCGTGAG

TTTGTTATTATCTTAACTACTTCCATAGCGGTTTTGATCGGCTACGTTG

TCGTTTTAATTTGGAGAAGATCATCCGGCTATCAGAAACCTAAAGTCCC

TGTCCCTCCTAAGCCGTTGATTGTTAAAGACCTCGAACCTGAAGTTGAT

GATGGCAAGAAAAAGGTCACCATCTTTTTCGGCACCCAAACTGGTACTG

CTGAAGGATTTGCTAAGGCTCTAGCTGAGGAGGCAAAAGCTCGGTATGA

GAAGGCTATATTTAAAACTGTTGATTTGGATGATTATGCGGAGGATGAC

GATGAATACGAAGAGAAATTGAAGAAAGAGTCTCTGGCCATTTTCTTCT

TGGCCACATATGGAGATGGTGAGCCTACAGATAACGCCGCGAGGTTTTA

TAAATGGTTTACAGATGGCAATGAGAGGGGGGAATGGCTTAAGGAACTT

CCATATGCTGTTTTTGGTCTTGGCAACAGGCAATACGAGCATTTTAATA

AGATTGCCATAGTGGTGGATAAAATCCTTGGCAACCAGGGTGGGAAGCA

GCTTGTTCCAGTGGGTCTTGGTGATGATGATCAATGCATGGAAGATGAC

TTTGCCGCATGGCGAGAATTGTTGTGGCCTGAGTTGGACCAGTTGCTTC

TTGATGGGATGATCCAACTGGTGTTTCTACCCCTTATACTGCTGCCGT

GGCAGAATATCGGGTTGTATTGCATGACCCTGAAGATGCACCATTAGAG

GATGATAACTGGAGTAATGCGAATGGTCATGCTATTTATGATGCTCAGC

ATCCATGCAGGGCTAATGTTACTGTGAGGAGGGAGCTTCATACCCCTGC

ATCTGATCGTTCATGTACCCATTTGGAGTTCGACATATCTGGCACTGGA

CTTGTATATGGAACTGGTGATCATGTTGGTGTGTACTGTGAAAATCTAA

GTGAAATTGTTGAGGAAGCACTGCAGTTGTTGGGTTTATCGCCAGATAT

TTACTTCACTATCCATACTGATAATGAGGATGGCACACCACTTAGTGGA

AGTGCCTTGCCACCTCCATTCCCATCGTCCACCTTAAGAACAGCTCTAA

CTCGATATGCTGATCTTTTGAGTTCACCCAAAAAGTCTGCTTTAATGGC

TTTAGCAGCTCATGCTACTAATCCAACCGAAGCTGATCGGCTAAGACAT

CTTGCATCACCTGCTGGAAAGGATGAATATGCACAATGGATAGTTGCAA

ATCATAGAAGCCTCCTGGAAGTCATGGCTGAATTTCCATCAGCCAAACC

CCCACTTGGAGTCTTCTTTGCTTCAGTTGCCCCGCGATTGCTGCCAAGA

TACTATTCTATTTCATCATCTCCAAGCATGGCACCTTCAAGGATTCATG

TTACATGTGCACTGGTTCTTGAGAAAACACCAGCAGGTCGAATTCACAA

AGGAGTGTGCTCAACTTGGATGAAGAATGCTGTGCCTTTAGAGAAAGC

CATGATTGCAGCTGGGCACCTATTTTTGTTAGACAATCAAACTTCAAAC

TTCCAGCAGATACTAAAGTTCCCATCATTATGATTGGCCCTGGAACTGG

TTTAGCTCCTTTCAGGGGTTTCCTTCAGGAAAGATTAGCCCAGAAAGAA

GCAGGAGCAGAACTGGGATCCTCTGTATTATTCTTTGGTTGCAGGAACC

GTCAAATGGATTTATCTATGAAGATGAGCTCAACAATTTCGTTGAAAG

TGGTGCACTTTCTGAACTATCTGTAGCCTTCTCACGTGAGGGACCTACC

AAGGAATATGTGCAGCATAAGATGATGCAGAAGGCTTCTGATATCTGGA

ACATGATTTCTCAAGGAGGATATTTATATGTTTGTGGAGATGCCAAGGG

CATGGCTAAAGATGTCCACAGAACTCTCCACACTATCGTGCAAGAGCAG

GGATCTCTTGACAACTCCAAGACAGAGAGCTTTGTGAAGGGTCTGCAAA

TGAATGGCAGGTATCTGCGTGATGTATGGTAA

SEQ ID No 24. Hybrid poplar (*Populus trichocarpa*
x *P. deltoides*) NADPH-cytochrome P450
oxydoreductase isoform 3 mRNA, complete cds,
AF302498

ATGGAGTCATCAAGCAGCTCGATCAAAGTGTCTCCACTTGATCTTATGC

AAGCCATAATCAAAGGCAAAGTGGACCCCGCGAATGTTTCATCGGAGTC

CGGTGGTTCTGTTGCTGAGGTAGCAACTTTGATCCTCGAGAATCGTGAG

TTTGTTATGATCTTAACTACTTCCATCGCTGTTTTGATCGGCTGCGTCG

TCGTTTTGATTTGGAGAAGATCATCTGGGTATCAGAGACCCAAAGTACC

TGTGCCTCCCAAGCCCTTGATTGTTAAAGACCTTGAACCTGAAGTTGAC

GATGGCAAGAAAAAGGTCACCATCTTTTTCGGCACCCAAACCGGTACGG

CAGAAGGATTTGCTAAGGCTCTAGCTGAGGAGGCAAAAGCTCGGTATGA

CAAGGCTACATTTAAAACTGTTGATATGGATGATTACGCGGGTGATGAT

GATGAATACGAAGAGAAATTGAAGAAGAGGATCTGGTTATTTTCTTCT

TGGCCACATACGGAGATGGTGAGCCTACTGATAATGCGGCAAGGTTCTA

CAAATGGTTTACAGAGGGAAATGAGAGAGGGGAATGGCTCAAGGACCTT

CCATATGCAGTTTTTGGCCTTGGCAACAGGCAGTACGAGCATTTTAACA

AGATTGCTATAGTGGTGGATAAAATCTTTGCTGACCAGGGTGGGAAGCG

CCTTGCCCCAGTGGGTCTTGGTGATGATGATCAATGCATGGAAGATGAC

TTTGCTGCATGGCGGGAATTGTTGTGGCCTGAGATGGACCAGTTGCTTC

TTGATGGAGACGATCCAACAGCTGTTTCTACTCCTTATGCTGCCACTGT

ATCAGAATATCGGGTTGTATTCCATAGCCCTGAAGATGCCCCATTAGAG

GATGATAACTGGAGTAATGCAAATGGCCATGCTGTCTATGATGCTCAGC

ATCCATGCAGGGCTAATGTTGCTGTGAGGAGGGAGCTTCATACCCCGGC

ATCTGATCGTTCATGTACCCATCTGGAGTTTGAAATATCAGGCACCGGA

CTTGCATATGGAACTGGGGATCATGTTGGTGTGTACTGTGAAAATCTAA

GTGAAACTGTAGAGGAAGCACTGCAGTTGTTGGGTTTATCACCAGATAC

TTATTTCTCTATCCACAATGATAATGAGGATGGCACGCCACTTAGTGGA

GGCGCCTTGCCACCTCCATTCCCACCGTCCACCTTAAAAACTGCTCTAG

CTCGATATGCTGATCTTTTGAGTTTGCCCAAAAAGTCTGCTCTAATGGC

TTTAGCAGCTCATGCTACTGATCCAACAGAAGCTGATCGACTAAGGCAT

CTTGCATCGCCTGCTGGGAAGGATGAATATGCACAATTGTTAGTTGCAA

ATCAGAGAAGCCTCCTTGAGGTCATGGCTGAATTTCCATCAGCCAAGCC

-continued

CCCACTTGGTGTCTTCTTTGCTTCAGTTGCACCTCGGTTGCAGCCAAGA

TACTACTCTATTTCATCATCTCCAAGGATGGCTCCATCAAGAATTCATG

TTACATGTGCACTGGTTCTTGAGAAAACACTAGGAGGTCGTATTCACAA

AGGAGTTTGCTCAACTTGGATGAAGAACGTGTGCCTCTGGAGAAAAGC

CATGATTGCAGCTGGGCACCTGTTTTTGTTAGGCAATCAAACTTCAAAC

TTCCAGCAGATGCTAAAGTTCCCATCATTATGATTGGCCCTGGAACTGG

TTTAGCTCCCTTCAGAGGTTTCCTCCAGGAAAGATTAGCCCTGAAAGAA

GCAGGATCAGAACTGGGATCCTCTGTATTATTCTTTGGTTGCAGGAACC

GCAAAATGGATTTTATCTATGAAGACGAGCTCAACAACTTCGTTGAAAG

TGGTGCACTTTCTGAACTAGTTGTTGCCTTCTCCCGTGAGGGACCTACC

AAGGAATACGTGCAGCATAAGATGATGCAGAAGGCTTCTGATATCTGGA

ACATGATTTCACAAGGTGGATATTTATATGTTTGTGGTGATGCCAAAGG

CATGGCTAAAGATGTCCACAGAGCGCTCCACACTATTGTGCAAGAGCAG

GGATCCCTTGACAACTCGAAGACGAAAGCTTTGTGAAGAGTCTGCAAA

TGAATGGCAGGTATCTACGTGATGTATGGTAA

SEQ ID No 25. *Vigna radiata* NADPH cytochrome P450
mRNA, complete cds, L07843
ATGGCTTCCAATTCCGATTTGGTGCGCGCCGTTGAGTCGTTCCTTGGCG

TTTCTCTAGGAGATTCCGTTTCGGATTCGCTGCTTCTCATCGCCACCAC

CTCCGCGGCGGTTGTAGTCGGTCTTCTCGTGTTTTTATGGAAGAAATCT

TCGGATCGGAGCAAGGAGGTGAAGCCGGTGGTTGTGCCGAGGGATTTAA

TGATGGAGGAGGAAGAGGAAGTTGACGTTGCCGCCGGCAAGACTAAGGT

CACCATTTTCTTCGGTACTCAGACCGGTACTGCTGAAGGCTTTGCTAAG

GCGTTGGCAGAGGAGATCAAGGCAAGGTATGAAAAAGCGGCTGTCAAAG

TTGTTGACCTGGATGACTATGCAGCTGATGATGATCTATATGAGGAGAA

GCTGAAGAAAGAGAGTCTTGTATTTTTCATGCTAGCAACTTACGGGGAT

GGAGAACCAATAGACAATGCTGCAAGATTCTACAAATGGTTTACTGAGG

GGAAAGACGAAAGGGGAATCTGGCTTCAAAAACTCACCTATGGAGTTTT

CGGCCTAGGTAACAGGCAATACGAACATTTTAATAAGATAGGTAAAGTT

GTGGATGAAGAACTTGCTGAACAAGGTGCAAAGCGTCTAGTTGCAGTTG

GATTAGGTGATGATGATCAATCCATTGAAGATGATTTTCTGCCTGGAA

AGAAAGTTTATGGTCTGAGTTGGATCAGTTGCTCAGAGATGAGGATGAT

GCTAATACTGTCTCTACTCCCTATACAGCTGCTATTCTTGAATACCGAG

TAGTGATTCACGATCCCACTGCAGCATCAACCTATGATAATCACTCAAC

CGTGGCAAATGGGAATACTGAGTTTGATATTCATCATCCTTGCAGGGTG

AATGTTGCTGTACAAAAGGAGCTTCACAAACCTGAGTCTGATCGTTCTT

GCATACATTTGGAATTTGATATATCGGGGACGAGCATAACATATGATAC

TGGAGACCATGTGGGTGTTTATGCTGAGAACTGCAATGAAACTGTCGAA

GAAACTGGGAAGTTGTTGGGTCAGAATTTGGATCTATTTTTTTCTCTTC

ACACAGACAAGGATGATGGCACTTCCCTAGGTGGTTCTCTCCTACCTCC

TTTCCCTGGCCCTTGTTCACTGCGAACTGCATTAGCACGTTATGCTGAT

CTCTTGAACCCCCCACGAAAGGCTGCTTTACTTGCATTGGCTACTCATG

CCTCTGAACCTAGCGACGAAAGATTAAAGTTCCTTTCATCTCCTCAGGG

GAAGGATGAGTATTCCAAATGGGTGGTTGGAAGCCAGAGGAGTCTCGTT

GAGGTGATGGCTGAGTTTCCATCAGCAAAACCTCCTCTTGGTGTGTTTT

TTGCTGCAATAGCCCCTCGTTTACAGCCTCGTTATTATTCTATTTCATC

CTCTCCAAGGTTTGCTCCTCAAAGGGTACATGTAACTTGTGCTTTGGTG

TATGGTCCAACTCCCACTGGTAGAATTCACAAAGGTGTATGTTCAACTT

GGATGAAGAATGCTATTCCCTCAGAAAAAAGTCAAGACTGTAGCTCGGC

TCCTATTTTTATTAGGCCATCAAATTTCAAGCTTCCAGTTGATCATTCA

ATACCTATTATTATGGTTGGACCTGGTACCGGTCTTGCACCCTTTCAGGG

GATTTTTGCAGGAAAGATATGCTCTCAAAGAGGATGGTGTTCAACTTGG

CCCTGCATTACTCTTCTTTGGATGTAGAAATCGTCAAATGGATTTCATT

TATGAGGATGAGCTAAAGAGTTTTGTGGAACAAGGTTCTCTTTCAGAAT

TGATAGTTGCATTCTCTAGAGAGGGGCTGAAAAGGAATATGTTCAACA

CAAGATGATGGACAAAGCTGCGCACCTTTGGAGTTTGATTTCTCAAGGA

GGTTATCTTTACGTCTGTGGAGATGCCAAGGGCATGGCCAGAGATGTCC

ATCGAACTCTTCATTCCATTGTCCAGGAGCAGGAAAACGTGGACTCAAC

AAAAGCTGAAGCTATAGTGAAAAAACTCCAGATGGACGGACGTTACCTT

AGAGATGTATGGTGA

SEQ ID No 26. *Petroselinum crispum* NADPH
cytochrome P450 reductase (CPR1) mRNA, complete
cds, AF024635
ATGCAATCGGAATCAATGGAAGTGTCGCCGGTGGATTTGCTGGCGTCGA

TTCTGAAGATTGATTCGGTTGAATCGATGACGTTGCTGCTCGAGAACCG

TGACGTCTTGATGTTACTTACGACGTCGTTTGCGGTGTTGATTGGATTA

GGATTGGTGATGATGTGGCGGAGATCAACGACGATGACGAAGAGCGCGA

AGAAGCTCGAGCCGGCGAAGATTGTGATCCCGAAATTTGAAATGGAGGA

GGAAGTTGATGACGGTAAAAAGAAGGTTACGATTTTTTACGGTACTCAG

ACCGGTACTGCTGAAGGTTTTGCTAAGGCACTTGCGGAGGAGGCGAAAG

CAAGATATCAGGATGCTATCTTTAAAACTATTGATTTGGATGATTATGC

GGGTGATGATGACGAGTATGAGACGAAACTTAAGAAAGAATCTATGGTG

TTCTTCTTCTTAGCCACGTATGGTGATGGTGAACCAACCGACAATGCAG

CGAGATTTTACAAGTGGTTTTGTGAGGGCAAAGAGAGGGGAGTGGCT

TAACAATCTTCAATATGGTGTGTTTGGCCTTGGCAACAGGCAATATGAG

CATTTCAACAAGATTGCAGTGGTTGTGGATGACGGCCTTGTTGAGCAGG

GTGCCAAGCGTCTTGTTCCAGTTGGTATGGGAGATGACGACCAATGTAT

TGAAGATGACTTTACTGCATGGCGGGAGTTAGTCTGGCCTGAGTTGGAT

CAACTGCTCTTGGACGAGGAGTCTAAGGCTGCTGCAACTCCATATACAG

CTGCTGTGCTAGAATATCGTGTTCAGTTTTATAATCAAACTGATACATC

ATCTCCACTGGTTCGGAGTATGAGCAAATTAAATGGCCATGCTGTATAT

GATGCTCAACATCCCTGCAGGGCTAATGTGGCTGTAAGAAGAGAGCTTC

ATACACCTGCATCGGATCGTTCCTGCACCCATCTGGAGTTCGATATTTC

-continued

CTCTACTGGACTTGCATATGAAACTGGTGACCATGTAGGAGTCTACACT

GAAAATCTGATTGAAATTGTTGAGGAGGCTGAAAGATTGATTGATATAT

CGCCAGATACTTATTTCTCCATTCATACTGAAAATGAAGATGGAACACC

CCTTAGTGGGGGATCCCTGCCACCCCCTTTCCCCCATGCAGCTTTAGA

ACTGCACTTACTAGATATGCAGATCTTTTGAGTACTCCAAAGAAGTCTG

CTTTAGTTGCGTTGGCGGCTCATGCATCTGATCCTAGCGAAGCTGAACG

ATTGAGATTTCTTGCATCTCCTGTTGGAAAGGATGAATATGCGCAGTGG

CTCGTCGCTAGTCAGAGGAGCCTGCTAGAAGTCTTGGCTGCGTTTCCAT

CAGCCAAACCCCCATTGGGAGTTTTCTTTGCATCTGTTGCCCCACGCTT

GCAGCCCAGATACTATTCCATCTCTTCCTCACCAAGGATGGCTCCATCA

AGAATTCATGTAACTTGTGCATTAGTTCACGAGACAACGCCTGCAGGAA

GAATACACAAAGGGCTCTGTTCTACTTGGATGAAGAATGCTGTCTCATT

GGAGGATGCCCATGTGAGTAGCTGGGCTCCTATTTTTGTTAGGCAATCA

AACTTCAGGCTTCCAACTGATTCGAAAGTACCTATTATTATGATTGGTC

CTGGCACCGGGTTGGCTCCTTTTAGGGGTTTCATGCAGGAAAGGTTAGC

TCTTAAGGAATCTGGAGCAGAACTTGGATCTGCAGTACTGTACTTTGGA

TGCAGGAATAGAAAATTGGATTTCATTTACGAGGATGAGCTTAATCACT

TTGTTGAAACTGGTGCAATATCTGAGATGGTTGTTGCTTTCTCACGTGA

GGGTCCTGCTAAGGAATATGTCCAACATAAGATGAGTCAAAAGGCTTCA

GAGATATGGGACATGATATCTCATGGAGCATATATTTATGTCTGTGGTG

ATGCCAAAGGCATGGCCAGAGACGTGCACAGGATGCTCCACACAATTGC

ACAAGAGCAGGGAGCTCTGGACAGTAGCCATGCAGAGAGCTTGGTGAAA

AATCTTCATATGAGTGGAAGATATTTACGTGATGTATGGTAA

SEQ ID No 27. *Petroselinum crispum* NADPH
cytochrome P450 reductase (CPR2) mRNA, complete
cds, AF024634

ATGGGTGGTGAGAGCTTGGCCACGTCACTGCCGGCGACGCTCCTCGAGA

ATCGTGACCTGTTAATGCTCCTCACCACGTCAATCGCCGTTTTGATTGG

ATGCGCTGTCGTTTTGGTGTGGCGCAGATCGAGCCTGCGATCGGTTAAA

TCAGTTGAGCCGCCGAAGCTGATTGTACCGAAAGTTGAAATTGAAGATG

AAGTTGATGACGGTAAAAAGAAAGTTACCGTGTTTTTCGGCACTCAAAC

TGGTACTGCTGAAGGCTTTGCTAAGGCTTTTGCGGAGGAGGCGAAAGCG

CGGTACGAGAAGGCGAAATTCAGAGTTGTTGATTTAGATGATTATGCGG

CGGAGGATGAGGAGTACGAGGCGAAATTTAAGAAGGAATCTTTTGCGTT

TTTCTTCTTAGCTACATATGGTGACGGTGAGCCAACTGACAATGCGGCT

AGATTCTATAAGTGGTTTTCGGAGGGTGAAGAGAAAGGAGATTGGTTAA

ATAAGCTTCAATATGGAGTGTTTGGCCTTGGAAATAGGCAGTACGAACA

TTTTAACAAGATCGCGAAAGTTGTTGACGATGGTCTTGCAGATCAGGGA

GCCAAGCGTATTGTGAAGTGGGTATGGGTGATGATGATCAATGCATTG

AAGATGACTTCACCGCATGGCGGGAATTGGTCTGGCCTGAATTGGATAA

GTTGCTTTTGGATGAGGATGACACATCTGCTGCAACTCCTTACACAGCT

GCTGTTTTGGAATATCGGGTTGTGGTTTATGACCAACTTGATACAGCTA

-continued

CACTGGATCGGAGTTTAAGTACCCAAAATGGCCATACAGTTCATGATGC

TCAACATCCGTGCAGGTCTAGCGTAGCTGCAAAGAAAGAGCTTCATAAA

CCTGCATCTGATCGTTCGTGCATTCACTTGGAGTTTGACATTTCACACA

CCGGGCTTGCATATGAAACTGGTGACCACGTCGGGGTCTACTGTGAGAA

TCTGGTTGAAATTGTTGAGGAGGCTGAAAAGCTATTAGGCATGCAACCA

AACACTTACTTCTCTGTCCATATTGACGACGAAGATGGAACACCACTTA

CTGGAGGCTCTCTGCCACCTCCCTTCCCGCCATGCACTGTGAGAAGTGC

ACTGGCAAAATATGCAGATCTTTTGAGCTCTCCGAAGAAGTCTGCCTTG

CTTGCTCTGGCGGCACATGCTTCTGATCCTACCGAGGCTGACCGATTAA

GATTGTTAGCATCTCCTGCTGGAAAGGATGAATATGCACAATGGGTAGT

TGCTAGCCACAGAAGCCTTCTTGAAGTCTTGGCTGAATTTCCATCAGCC

AAACCCCCACTGGGAGTATTCTTTGCATCAGTTGCACCACGCTTGCAGC

CCAGATACTATTCTATCTCTTCTTCACCAAGGATGGTACCATCAAGGAT

TCATGTTACTTGTGCTTTAGTTTATGAGAAAACACCTACGGGGCGAATT

CACAAAGGAGTGTGTTCAACTTGGATGAAGAATGCTGTTTCTTTGGAGG

AAAGCCATGATTGCAGTTGGGCACCCATTTTTGTTAGACAATCCAACTT

CAAGCTTCCTTCTGATACGAAAGTCCCCATCATTATGATTGGCCCTGGA

ACTGGATTAGCTCCTTTCAGGGGTTTCCTGCAGGAAAGGCAAGCTCTGA

AGGATGCTGGAGCAGAGCTGGGAACTGCTGTGTTATACTTTGGGTGCAG

GAATAGAAATTTGGATTTTATTTACGAGGATGAGCTAAATAAGTTTGTC

GAAAGTGGTTCAATCTCTGAGCTAATTGTAGCTTTCTCACGTGAGGGGC

CCACTAAGGAGTATGTGCAACATAAGATGTTGCAGAAAGCGTCAGAGAT

CTGGAACTTGATTTCTGAGGGTGCATATATTTATGTCTGCGGTGATGCA

AAAGGCATGGCCAGGGATGTCCATCGCATGCTTCACACAATTGCACAGG

AGCAGGGAGCTCTTGACAGCAGCAAGGCGGAGAGCTGGGTTAAGAACCT

TCAAATGACTGGGAGGTATCTTCGTGATGTATGGTAA

SEQ ID No 28. *Gossypium hirsutum* cultivar CRI12
NADPH: cytochrone P450 reductase (CPR1)
mRNA, complete cds, FJ719368

ATGAGTTCGAGTTCCGATTTGGTGGGTTTTGTTGAATCGGTATTGGGAG

TGTCGTTAGAGGGTTCGGTAACGGATTCTATGATAGTGATCGCGACGAC

GTCGTTAGCGGTGATTCTGGGCTTTTGGTGTTTTTCTGGAAGAAATCG

GGTTCCGAACGGACCGTGATGTCAAACCGTTGGTGGCACCTAAGCCTG

TTTCACTCAAGGACGAGGAAGACGACGACGCCGTTATCGCTGCCGGCAA

AACTAAAGTTACCATTTTCTACGGCACACAGACGGGAACGGCCGAGGGA

TTTGCTAAGGCTTTAGCCGAAGAGATCAAGGCAAGATATGAGAAAGCTG

CTGTCAAAGTTGTTGACCTGGATGATTATGCCATGGACGATGAACAATA

CGAAGAGAAGCTGAAAAAGGAGACTTTAGCTTTTTTCATGGTGGCCACT

TATGGAGACGGAGAGCCAACCGATAACGCTGCTAGGTTTTACAAATGGT

TTACTGAGGGAAATGAAAGGCTGCCGTGGCTTCAACAACTCACATATGG

TGTATTTGGTCTGGGTAACCGTCAATATGAACATTTTAATAAGATAGCA

AAGGTGCTTGATGAGCAACTTTCCGAACAAGGTGCTAAACGTCTTATTG

```
AAGTTGGTCTTGGAGATGATGATCAATGCATTGAAGATGATTTTACTGC
ATGGAGAGAACTGCTCTGGCCAGAGTTAGATCAACTGCTTAGAGATGAA
GATGATGAAAATGCTACOTCTACCCCGTATACGGCAGCTATTCCTGAAT
ATAGAGTAGTGGTTCATGATCCTGCTGTGATGCACGTAGAGGAGAATTA
CTCAAATAAGGCAAATGGGAATGCTACATATGACCTCCACCATCCATGC
AGAGTTAATGTTGCCGTTCAGAGAGAGCTCCACAAGCCTGAATCTGATC
GCTCCTGTATTCATTTGGAGTTTGACATATCAGGGACTGGTATCACATA
TGAAACCGGAGATCACGTTGGTGTCTACGCGGATAATTGCGTTGAGACT
GTTGAGGAAGCTGCAAGATTGTTGGGTCAACCTCTGGATTTGCTATTTT
CTATACACACTGACAATGAGGACGGCACATCTGCTGGAAGCTCATTGCC
GCCACCTTTTGCCAGTCCATGTACACTGCGAATGGCATTGGCACGATAT
GCAGATCTTTTAAACCCTCCACGGAAGGCTGCTTTGATTGCCTTGGCTG
CTCATGCCACTGAACCCAGTGAAGCAGAAAAGCTTAAGTTCTTATCGTC
ACCACAGGGGAAGGATGAGTACTCACAATGGGTTGTTGCAAGTCAGAGA
AGTCTTCTTGAGGTTATGGCTGAGTTCCCATCAGCAAAACCTCCTCTTG
GTGTATTTTTTGCTGCAGTAGCTCCTCGTTTACAGCCTCGTTATTATTC
TATCTCATCCTCCCCTAGGTTTGTACCTGCCAGGGTTCATGTAACCTGC
GCTTTAGTTTATGGTCCAACTCCAACTGGAAGAATTCACCGGGGTGTGT
GCTCAACATGGATGAAGAATGCAGTTCCTTTAGAGAAAAGCAATGATTG
TAGCTGGGCTCCTATTTTTATTCGGCAATCCAATTTTAAGCTACCAGCA
GATCCTTCAGTTCCAATCATCATGGTTGGACCCGGGACTGGATTGGCAC
CTTTCAGAGGTTTTCTACAGGAAAGATTGGTCCTCAAAGAAGATGGTGC
AGAACTTGGCTCTTCTCTACTCTTTTTGGATGTAGGAATCGGCGAATG
GATTTCATTTATGAGGATGAGCTCAATAACTTTGTGGAACAAGGTGCCC
TTTCTGAGCTTGTTGTTGCATTTTCACGAGAAGGTCCGCAGAAGGAATA
TGTTCAACACAAAATGATGGATAAAGCTGCAGATATATGGAACCTAATT
TCTAAGGGTGGATATCTTTATGTTTGTGGTGATGCCAAGGGTATGGCAA
GAGATGTTCATCGCACTTTGCACACTATTATTCAGGAGCAGGAAAATGT
GGATTCATCAAAGGCGGAGTCTATGGTGAAGAAACTCCAGATGGACGGA
CGATACCTTAGAGATGTGTGGTGA
SEQ ID No 29. Gossypium hirsutum cultivar CRI12
NADPH: cytochronne P450 reductase (CPR2)
mRNA, complete cds, FJ719369
ATGGATTCTTCATCATCATCATCATCTTCAGGTCCCTCACCTCTCGATC
TCATGTCGGCTTTAGTCAAGGCCAAAATGGACCCTTCCAACGCTTCCTC
CGACTCTGCTGCTCAAGTAACCACCGTCCTTTTCGAGAACAGAGAGTTC
GTTATGATTTTAACTACCTCCATTGCTGTGCTCATCGGCTGCGTCGTCA
TTTTGATCTGGCGTAGATCCGCTTCTCAAAAGCCTAAACAAATCCAGCT
TCCTCTTAAGCCTTCGATCATTAAAGAACCAGAACTTGAAGTTGACGAT
GGAAAGAAAAAAGTCACCATCCTCTTCGGTACTCAAACCGGCACCGCCG
AAGGCTTCGCTAAGGCTCTAGTCGAGGAGGCAAAAGCACGCTATGAAAA
GGCGACTTTTAATATTGTAGATTTGGATGATTATGCAGCAGATGATGAA
```

GAATACGAGGAGAAGATGAAGAAAGATAATTTGGCTTTCTTCTTCTTGG
CCACTTATGGAGACGGTGAGCCAACAGATAATGCAGCCAGGTTCTATAA
ATGGTTCACTGAGGGAAAAGAGAGGGGAGAATGGCTTCAGAACATGAAG
TATGGGATTTTCGGCCTTGGTAACAAACAGTATGAACATTTTAACAAGG
TTGCAAAGGTGGTTGATGAACTCCTTACCGAGCAGGGAGCGAAGCGCAT
AGTTCCTTTGGGTCTTGGAGATGATGACCAATGCATAGAAGATGACTTC
ACTGCATGGCGTGAATTAGTGTGGCCCGAGTTAGATCAGCTTCTGCGTG
ATGAAGATGATGCAACTGTTTCTACCCCGTACACTGCTGCTGTTTTGGA
ATACCGTGTTGTATTTTATGATCCTGCAGATGCACCCCTTGAGGATAAG
AACTGGAGTAATGCAAATGGTCATGCTACTTATGATGCTCAACATCCTT
GCAGGTCTAATGTGGCTGTGAGGAAGGAGCTTCATGCTCCTGAATCTGA
TCGGTCTTGCACCCACCTTGAATTTGACATTGCTGGAACTGGACTTTCA
TACGAGACAGGCGATCATGTCGGTGTTTACTGTGAGAACCTGGATGAAG
TTGTAGATGAAGCATTGAGTTTACTGGGCTTATCACCCGACACTTATTT
CTCTGTTCACACTGATAAAGAGGATGGTACACCACTTGGTGGAAGTTCT
TTACCTTCTTCTTTCCCCCCTTGTACTCTGAGAACAGCACTGGCACGAT
ATGCTGATCTTTTGAGCTCGCCAAAAAAGGCTGCCTTACTTGCTTTGGC
TGCTCATGCCTCTGATCCAACTGAAGCCGATCGACTAAGACACCTTGCA
TCACCTGCTGGAAAGGATGAGTATGCTCAATGGATTGTTGCAAACCAGA
GAAGTCTCCTTGAGGTCATGGCGGAATTTCCTTCAGCCAAGCCTCCACT
TGGTGTTTTCTTTGCAGCTGTTGCTCCAAGGTTGCAGCCTAGATATTAT
TCGATATCATCCTCACCAAGGTTGGCACCATCAAGGATTCATGTAACTT
GTGCATTGGTTTATGAGAAAACGCCAACAGGTCGTATTCACAAAGGTGT
TTGTTCAACTTGGATGAAGAATGCTGTGTCCTCGGGGAAAAGCGATGAC
TGCGGCTGGGCACCCATTTTTGTCAGGCAATCAAACTTTAAACTTCCTT
CAGATACTAAAGTGCCCATCATAATGATTGGTCCTGGTACTGGATTGGC
TCCTTTCAGGGGATTCCTTCAGGAAAGGCTTGCACTGAAAGAAGCTGGT
GCTGAGTTGGGTCCATCTGTATTGTTCTTTGGCTGCAGAAACCGGAAAA
TGGATTTCATATATGAAGATGAGCTCAACAACTTTGTCAACAGTGGTGC
ACTATCTGAGCTTGTGGTTGCCTTTTCACGTGAGGGACCTACCAAGGAA
TATGTGCAACATAAAATGATGGAGAAGGCCAAGGACATATGGGACATGA
TTTCTCAGGGAGGTTACCTGTATGTGTGTGGTGATGCCAAGGGCATGGC
TAGAGATGTTCATCGAGCTCTTCACACTATTTTCCAAGAGCAGGGATCA
CTAGACAGCTCAAAGGCTGAGAGCATGGTGAAAAATCTGCAAATGAGCG
GCAGGTACCTACGCGATGTATGGTGA

The following gene sequences are particularly preferably used for encoding cytochrome P450 monooxygenase (CYPs):

SEQ ID No 30. Vitis vinifera CYP716A15 mRNA for
cytochrome P450, complete cds, AB619802
ATGGAGGTGTTCTTCCTCTCCCTGCTCCTCATCTTTGTGCTCTCAGTCT
CCATCGGACTTCACTTGCTCTTCTACAAGCATAGATCCCACTTCACTGG

CCCCAATCTCCCTCCTGGCAAGATTGGTTGGCCTATGGTTGGTGAAAGC

CTTGAATTCCTCTCCACCGGCTGGAAAGGCCACCCGGAAAAATTCATCT

TCGATCGCATCTCCAAATACTCCTCTGAAGTCTTCAAGACCTCCCTCCT

CGGAGAGCCTGCTGCCGTCTTTGCTGGCGCTGCGGGCAACAAGTTTTTG

TTCTCCAACGAAAACAAACTTGTTCATGCGTGGTGGCCTAGCTCTGTCG

ACAAGGTCTTCCCCTCCTCCACCCAAACCTCATCCAAAGAGGAGGCCAA

GAAGATGAGGAAGTTGCTCCCTCAGTTCTTTAAGCCTGAAGCCTTGCAA

CGTTACATTGGCATCATGGATCACATTGCGCAGAGGCATTTTGCTGATA

GCTGGGACAACAGAGATGAAGTCATTGTATTTCCACTGGCCAAGAGGTT

CACTTTCTGGCTAGCTTGCCGCCTGTTTATGAGCATAGAAGATCCTGCC

CACGTCGCTAAATTTGAAAAGCCCTTCCATGTCTTGGCCTCAGGACTCA

TCACCGTCCCAATTGACTTGCCTGGGACACCTTTCCACCGCGCTATCAA

GGCCTCCAACTTCATCAGAAAGGAGCTTAGAGCCATCATCAAGCAAGG

AAGATCGATCTGGCTGAGGGCAAGGCCTCACAAAATCAAGATATATTGT

CCCACATGCTTCTGGCTACAGATGAAGATGGATGCCACATGAATGAAAT

GGAAATTGCTGATAAAATCCTCGGTTTGTTGATTGGTGGCCATGACACT

GCCAGTGCTGCCATTACATTCCTTATCAAGTACATGGCTGAGCTGCCTC

ACATCTACGAGAAAGTCTACGAGGAGCAAATGGAAATTGCCAATTCAAA

AGCACCAGGTGAATTGCTGAACTGGGATGATGTTCAAAACATGAGATAT

TCATGGAATGTTGCCTGTGAAGTGATGAGACTTGCACCCCCACTCCAAG

GAGCTTTCCGGGAAGCAATCACTGACTTCGTGTTCAACGGTTTCTCCAT

TCCTAAGGGTTGGAAGCTGTACTGGAGCGCAAACTCAACCCACAAAAGC

CCAGAATGCTTCCCTCAACCCGAAAATTTTGACCCTACAAGATTTGAAG

GAAACGGGCCTGCTCCTTACACATTCGTTCCCTTTGGTGGCGGACCTAG

GATGTGCCCTGGTAAAGAGTACGCCCGCTTGGAAATACTAGTCTTCATG

CACAACGTGGTTAAAAGGTTCAAATGGGATAAATTGCTTCCTGATGAGA

AGATAATCGTTGACCCCATGCCCATGCCTGCTAAGGGACTTCCAGTTCG

CCTCCATCCTCACAAACCATAG

SEQ ID No 31. *Vitis vinifera* CYP716A17 mRNA for Cytochrome P450, complete cds, AB619803
ATGGAGGTGTTCTTCCTCTCCCTGCTCCTCATCTCTGTGCTCTCAGTCT

CCATCAGACTTTACTTGCTCTTATACAAGCATAGATCCCACTTCACTGG

CCCCAATCTCCCTCCTGGCAAGATTGGTTGGCCAATGGTTGGTGAAAGC

CTTGAATTCCTCTCCACCGGCTGGAAAGGCCACCCGGAAAAATTCATCT

TCGATCGCATCTCCAAATACTCCTCTGAAGTCTTCAAGACCTCCCTCCT

CGGAGAGCCTGCTGCCGTCTTTGCTGGCGCTGCGGGCAACAAGTTTTTG

TTCTCCAACGAAAACAAACTTGTTCATGCATGGTGGCCTAGCTCCGTCG

ACAAGGTCTTCCCCTCCTCCACCCAAACCTCATCCAAAGAGGAGGCCAA

GAAGATGAGGAAGTTGCTCCCTCAGTTCTTTAAGCCTGAAGCCTTGCAA

CGTTACACCGGCATCATGGATCACATTGCACAGAGGCATTTTGCTGATA

GCTGGGACAACAGAGATGAAGTCATTGTATTTCCACTGGCCAAGAGGTT

CACTTTCTGGCTAGCTTGCCGCCTGTTTATGAGCATAGAAGATCCTGCC

CACGTCGCTAAATTTGAAAAGCCCTTCCACGTCTTGGCCTCAGGACTCA

TCACCATCCCAATTGACCTGCCTGGGACACCTTTCCACCGCGCTATCAA

GGCCTCCAACTTCATCAGAAAGGAGCTTAGAGCCATCATCAAGCAAGG

AAGATCGATCTGGCTGAGAGCAAGGCCTCAAAAACTCAAGATATATTGT

CCCACATGCTTCTGGCTACAGATGAAGATGGATGCCACATGAATGAAAT

GAGTATTGCTGATAAAATCCTCGGTTTGTTGATTGGTGGCCATGACACT

GCCAGTTCTGCCATTACATTCCTTGTCAAGTACATGGCTGAGCTGCCTC

ACATCTACGAGAAAGTCTACAAGGAGCAAATGGAAATTGCCAATTCAAA

AGCACCAGGTGAATTGCTGPACTGGGATGATGTTCAAAAGATGAGATAT

TCATGGAATGTTGCCTGTGAAGTGATGAGACTTGCACCCCCACTCCAAG

GAGCTTTCCGGGAAGCAATCACTGACTTCGTGTTCAACGGTTTCTCCAT

TCCTAAGGGTTGGAAGCTGTACTGGAGCGCAAACTCAACCCACAAAAGC

CTAGAATGCTTCCCTCAACCCGAAAATTTTGACCCTACAAGATTTGAAG

GAGCCGGGCCTGCTCCTTACACATTCGTTCCCTTTGGTGGCGGACCTAG

GATGTGCCCTGGTAAAGAGTACGCCCGCTTGGAGATACTTATCTTCATG

CACAACTTGGTTAAAAGGTTCAAATGGGATAAATTGCTTCCTGATGAGA

AGATAATCGTTGACCCCATGCCCATGCCTGCTAAGGGACTTCCAGTTCG

CCTCCATCCTCACAAACCATAG

SEQ ID No 32. *Medicago truncatula* cytochrome P450 monooxygenase CYP716A12 (CYP716A12) mRNA, complete cds, DQ335781
ATGGAGCCTAATTTCTATCTCTCCCTTCTCCTTCTCTTTGTCACTTTCA

TATCTCTCTCTCTTTTTTTCATATTCTACAAACAGAAATCTCCATTAAA

TTTGCCACCTGGTAAAATGGGTTACCCAATCATAGGTGAAAGCCTTGAG

TTCTTATCAACAGGATGGAAAGGACATCCTGAAAAATTCATTTTCGACC

GTATGCGTAAATATTCCTCAGAACTCTTTAAAACATCAATCGTAGGAGA

ATCTACGGTGGTTTGTTGCGGAGCAGCAAGTAACAAGTTTTTGTTTTCA

AACGAGAATAAACTTGTGACTGCATGGTGGCCAGATAGTGTAAACAAA

TCTTCCCTACTACTTCTCTTGACTCTAACTTGAAGGAAGAATCCATCAA

GATGAGAAATTGCTTCCACAATTCTTTAAACCCGAAGCTCTACAACGT

TATGTTGGTGTCATGGATGTTATTGCTCAAAGACATTTTGTTACTCATT

GGGATAATAAAAATGAAATCACCGTCTACCCCTTGGCCAAGAGGTACAC

CTTTTTGTTAGCTTGTCGGTTGTTCATGAGCGTTGAAGACGAGAATCAT

GTAGCAAAATTTAGTGATCCATTTCAGTTAATTGCGGCCGGAATCATAT

CTCTACCAATTGATTTGCCAGGAACACCATTCAACAAAGCTATAAAGGC

CTCAAACTTTATAAGAAAGGAGTTGATTAAGATCATAAAGCAAAGGAGG

GTAGATTTGGCAGAAGGGACAGCATCACCAACACAAGATATATTGTCTC

ACATGTTGTTGACAAGTGATGAAAATGGAAGAGTATGAATGAACTTAA

TATTGCTGATAAGATTCTTGGCCTTTTGATCGGAGGACATGACACTGCT

AGCGTCGCATGCACTTTCCTTGTCAAATATCTCGGCGAGTTACCTCACA

TTTATGATAAAGTCTATCAAGAGCAAATGGAAATTGCAAAATCGAAACC

-continued
AGCAGGAGAATTGTTGAATTGGGATGACCTGAAGAAAATGAAATACTCT

TGGAACGTAGCTTGTGAAGTAATGAGACTTTCCCCTCCACTCCAAGGAG

GTTTCAGGGAAGCCATCACTGACTTTATGTTCAATGGATTCTCAATTCC

TAAGGGATGGAAGCTTTATTGGAGTGCAAATTCAACACATAAGAACGCA

GAATGTTTTCCCATGCCAGAGAAATTTGACCCAACAAGATTTGAAGGAA

ATGGACCAGCTCCTTATACTTTTGTTCCCTTTGGTGGAGGACCAAGGAT

GTGTCCTGGAAAAGAGTATGCAAGATTAGAAATACTTGTTTTCATGCAC

AATTTGGTGAAAAGGTTTAAGTGGGAAAAGGTGATTCCAGATGAGAAGA

TTATTGTTGATCCATTCCCCATCCCTGCAAAGGATCTTCCAATTCGCCT

TTATCCACACAAAGCTTAA

SEQ ID No 33. Catharanthus roseus cytochrome P450
(CYP716AL1) mRNA, complete cds, JN565975
ATGGAGATCTTCTATGTCACTCTCCTTAGCTTATTCGTTCTCCTTGTTT

CCCTTTCCTTTCATTTCCTCTTCTACAAAAACAAATCAACCTTGCCGGG

ACCGTTACCTCCGGGCCGGACCGGCTGGCCGATGGTGGGAGAAAGTCTT

CAATTTCTCTCAGCGGGCTGGAAAGGCCATCCTGAAAAATTCATATTTG

ATCGTATGGCTAAGTATTCTTCGAATGTCTTTAGGTCACATCTACTAGG

TGAACCTGCCGCGGTATTTGTGGTGCAATTGGAAATAAATTTTTATTC

TCAAATGAAAATAAACTTGTTCAAGCATGGTGGCCTGATTCAGTAAACA

AAGTTTTCCCATCTTCAAATCAAACTTCTTCAAAAGAAGAAGCTATTAA

AATGCGAAAGATGCTTCCGAATTTTCTTAAACCGGAAGCTTTACAACGT

TACATAGGTTTAATGGACCAAATTGCCCAAAAACATTTTTCTTCCGGTT

GGGAAAATAGGGAACAAGTTGAAGTTTTTCCTTTAGCCAAAAATTATAC

TTTTTGGTTAGCTTCAAGATTATTTGTTAGTGTTGAAGATCCAATTGAA

GTTGCAAAATTACTTGAACCCTTTAATGTTTTGGCCTCGGGACTAATTT

CTGTCCCTATTGATTTGCCTGGTACACCTTTTAATCGTGCTATAAAGGC

ATCAAATCAAGTAAGAAAAATGCTTATTTCTATAATTAAACAAAGAAAA

ATTGATTAGCTGAAGGAAAAGCATCTCCAACACAAGATATTTGTCAC

ATATGCTTTTAACAAGTGATGAAAATGGTAAATTCATGCATGAATTGGA

TATTGCTGATAAAATCCTTGGTTTGTTAATTGGTGGACATGATACTGCA

AGTTCTGCATGTACTTTTATTGTCAAGTTTCTTGGAGAATTGCCAGAGA

TATATGAAGGAGTTTATAAAGAACAAATGGAGATTGCCAACTCAAAAGC

CCCTGGTGAATTCTTGAATTGGGAAGATATTCAAAAGATGAAATATTCA

TGGAATGTAGCATGTGAAGTGTTGAGACTTGCACCACCTCTCCAAGGTG

CTTTTAGAGAAGCCCTAAATGATTTCATGTTCCATGGATTCTCTATTCC

AAAAGGATGGAAGATTTACTGGAGTGTGAATTCAACACACAGAAATCCA

GAATGTTTTCCAGATCCACTTAAATTTGACCCGTCAAGATTTGATGGAT

CTGGACCTGCTCCATATACATTTGTACCATTTGGTGGAGGACCAAGAAT

GTGCCCTGGAAAAGAATACGCTAGGCTGGAAATTCTGGTTTTTATGCAT

AATCTTGTGAAGAGATTCAAGTGGGAAAAAATTATCCCAAATGAAAGA

TTGTTGTTGATCCAATGCCAATTCCTGAAAAAGGACTTCCTGTTCGACT

TTATCCTCACATTAATGCATAA

SEQ ID No 34. Populus trichocarpa cytochrome P450
(CYP716A9), mRNA, XM_002331391
ATGGAGCTTCTCTTCCTCTCACTCCTCCTCGCCCTCTTTGTTTCCTCCG

TCACTATTCCCCTCTTTCTCATCTTTTACAATCATCGATCCCAGAACAG

CCACCCCAACCTCCCTCCAGGCAAGCTAGGCCTTCCCCTTGTTGGAGAA

AGCTTTGAGTTCTTGGCCACGGGATGGAAAGGCCATCCTGAAAAGTTCA

TCTTTGATCGCATAGCTAAATACTCATCTCACATCTTCAAGACAAATAT

TCTTGGTCAACCAGCAGTTGTCTTTTGTGGTGTTGCTTGTAACAAGTTT

TTGTTTTCCAATGAGAACAAGCTCGTTGTATCCTGGTGGCCCGACTCTG

TTAACAAAATCTTTCCCTCTTCACTTCAAACATCATCTAAAGAGGAAGC

CAAGAAAATGAGAWCTTCTCCCTCAGTTCTTGAAACCTGAGGCCTTGCA

AGGATACATTGGTATCATGGATACCATTGCACAAAGACACTTCGCCTCG

GAATGGGAACATAAAGAACAAGTGCTGGTGTTCCCTTTGTCAAAGAATT

ACACCTTTCGTTTGGCTTGTAGATTGTTTCTGAGTATTGAAGATCCAAG

CCACGTAGCTAAATTTTCTGACCCCTTTAATCTTTTAGCCTCGGGTATC

ATTTCCATCCCCATTGATTTGCCCGGGACTCCATTCAACCGAGCTATCA

AAGCCTCAAACTTCATCAGAACTGAGCTTTTAGCTTTTATAAGACAAAG

AAAGAAGGATCTTGCAGAGGGAAAAGCTTCCCCCACGCAGGATATATTG

TCACACATGTTGTTGACATGTGATGAAAATGGAAAATGCATGAATGAGC

TTGATATTGCTGATAAGATCATTGGATTGTTGATTGGTGGGCATGATAC

AGCCAGCGCTGCTTGTACCTTCATTGTCAAGTATCTTGCAGAGCTTCCA

CATATATATGAGGAAGTTTACAAGGAACAAATGGAGATAGCCAAATCCA

AAACTCCTGGTGAATTCTTGAATTGGGATGACATTCAGAAGATGAAATA

CTCATGGAAAGTAGCTTGTGAAGTGATGAGGATCTCACCACCGCTTCAA

GGTGCTTTTAGGGAAGCTCTCAATGATTTCATTTTCAATGGCTTTACCA

TTCCAAAGGGTTGGAAGTTATATTGGAGCACCAACTCAACCCATAGAGA

TCCCGTCTACTTTCCTGAACCTGAGAAATTTGATCCTAGGAGGTTTGAA

GGAAGTGGGCCAGCTCCATACACGTTTGTCCCCTTCGGTGGAGGACCTC

GGATGTGCCCTGGAAAGGAGTATGCTCGCTTGGAAATACTCGTTTTCAT

GCATAATTTGGTCAGAAGGTTTAAATTTGATAAGTTGATTCAAGATGAA

AAGATTGTAGTGAATCCACTGCCAATCCCTGATAAAGGACTTCCTGTTC

GCCTTCATCCTCACAAGGCCTAG

SEQ ID No 35.: Glycine max cytochrome P450 716B2-
like (LOC100801007), mRNA, XM_003525274
ATGGACCATAATAACTTGTACCTCTCCCTCCTTCTCCTCTTCGTTTCTT

TCGTGACCCTCTCCCTCTTCTTCCTCTTCTACAAACACAGGTCTCCATT

CGTGGCCCCGAACCTGCCACCTGGAGCAACCGGTTACCCGGTGATCGGG

GAGAGCCTGGAGTTCCTGTCAACAGGATGGAAGGGTCATCCGGAGAAGT

TCATCTTCGACCGGATGATCAGGTACTCCTCCCAACTGTTCAAGACCTC

CATCTTCGGGGAACCCGCGGTCATATTCTGTGGGCCACCTGCAACAAG

TTCTTGTTCTCTAACGAGAACAAGCTTGTTCAGCTGGTGGCCCAACA

GCGTCAACAAGGTGTTCCCCTCCACGCTTCAGAGCAACTCCAAAGAAGA

GTCCAAAAAGATGAGGAAGTTGCTCCCTCAGTTCCTCAAGCCCGAGGCT

CTCCAACGCTACGTTGGCATCATGGACACCATCGCTCAAAACCACTTCG

CTTCCCTTTGGGACAACAAGACGGAACTCACCGTCTATCCCTTGGCTAA

GAGGTACACGTTCTTGTTGGCTTGTCGTTTGTTTATGAGCGTTGAGGAT

GTGAATCACGTAGCAAAATTTGAGAACCCTTTTCACCTGTTGGCGTCTG

GAATCATATCAGTGCCTATTGATCTTCCTGGAACGCCGTTCAACAAAGC

AATCAAGGCAGCAAACGCAATCAGGAAGGAACTGTTAAAGATCATTAGA

CAGAGGAAGGTTGATTTAGCTGAAGGAAAAGCTTCACCAACACAAGACA

TTTTATCTCACATGTTGTTAACATGCAATGAGAATGGACAATTCATGAA

TGAATTGGATATTGCCGACAAGATTCTTGGCCTTTTGATTGGAGGCCAT

GACACTGCTAGTGCTGCATGCACTTTCATTGTCAAATATCTTGCTGAAC

TCCCTCACATTTATGATAGTGTCTATCAAGAACAAATGGAAATCGCAAA

ATCGAAATTGCCCGGAGAGTTATTGAATTGGGATGATATCAACAGGATG

AAGTATTCTTGGAATGTAGCTTGTGAAGTAATGAGAATCGCTCCTCCAC

TTCAAGGAGGTTTTAGGGAAGCTATCAATGACTTTATTTTCAATGGCTT

CTCAATTCCAAAGGGATGGAAGTTGTATTGGAGTGCAAATTCAACACAT

AAAAATCCGGAATACTTTCCAGAGCCAGAGAAATTCGATCCAACTAGAT

TCGAAGGACAAGGGCCAGCTCCTTTTACTTTTGTACCATTTGGTGGAGG

ACCAAGGATGTGCCCCGGAAAAGAGTATGCTCGATTGGAAATATTGGTT

TTCATGCACAACCTAGTGAAGAGGTTTAAGTGGGAAAAATTGATTCCAG

ATGAGAAGATTATCGTTGATCCCTTGCCCGTACCTGCAAAGAACCTCCC

AATTCGTCTTCATCCTCACAAACCCTGA

SEQ ID No 36. *Bupleurunn chinense* cytochrome P450
CYP716A41 mRNA, complete cds, JF803813
ATGATGATGTACTTGTATTTTCAGTCATCAGCATTCTTGTTCTACTTC

CTTGTGTATGGCTCTTCTTCTTACACTCGAACAGAAAATCAACCCAACA

ATCATACAAATCTCTCCCACCAGGAGAAACGGGCTATTTTCTCATCGGA

GAAAGCTTAGAATTTCTGTCCACAGGAAGGAAAGGCCATCCTGAAAAGT

TCATTTTTGATCGCATGACAAAGTACGCCTCTAAAATTTTCAAATCATC

GCTATTTGGAGAGAAACAATAGTCTTTTGTGGTGCTGCTAACAACAAG

TTTTTGTTTTCTGACGAAAACAAGCTGGTGCAGTCGTGGTGGCCTAACT

CCGTAAACAAACTCTTCCCTTCCTCTACACAAACTTCTTCGAAAGAAGA

AGCCATCAAAATGAGGAAAATGCTTCCAAACTTCTTCAAACCCGAGGCC

TTGCAAAGATATGTTGGTGTTATGGATGAAATAGCTCAAAAACACTTTG

ATTCTTGTTGGGAAAACAAACACGGTCATTGTTGCACCTCTCACCAA

GCGTTTCACCTTTTGGCTTGCTTGTCGTTTGTTTGTCAGCCTTGAAGAT

CCTACACAGGTAGCTAAATTTGCTGAGCCTTTCAATCTATTGGCCTCTG

GAGTTTTTTCTATTCCTATTGATTTACCGGGAACAGCATTCAATCGAGC

TATTAAAGCCTCTAACTTCATTCGAAAAACGCTTATTGGCATCATTAAA

AAAAGAAAGGTTGATTTAGAGGATGGAACTGCATCAGCCACACAAGATA

TTTTGTCGCATATGCTCTTGACAAGCGATGAGACTGGAAAGTTCATGAC

TGAAGCCGATATTGCTGATAAAATATTAGGTTTGTTGATAGGAGGTCAT

GATACTGCTAGCTCTGCTTGTGCTTTGATTGTCAAGTATCTTGCTGAAC

TCCCTCACATATATGATGGAGTCTATAGAGAGCAAATGGAAATTGCAAA

ATCTAAATCTCCAGGGGAGTTGCTAAACTGGGATGATGTACAAAAGATG

AAATATTCATGGAATGTAGCATGTGAAGTTTTGAGACTTGCACCACCCC

TCCAAGGAAGTTTTAGAGAAGTACTTTCTGATTTCATGCACAATGGTTT

CTCCATACCCAAGGGATGGAAGATCTATTGGAGTGCGAATTCGACACAT

AAAAGTTCAGAATATTTCCCAGAGCCAGAAAAGTTTGATCCGAGACGAT

TTGAAGGGTCAGGACCAGCACCCTACACATTTGTGCCATTTGGAGGTGG

ACCAAGAATGTGCCCTGGAAAAGAATATGGTAGATTGGAGATACTTGTA

TTCATGCACCACTTGGTGAAGAGGTTCAGATGGCAAAAAATATATCCTC

TGGAGAAGATTACTGTTAATCCAATGCCTTTCCCTGACAAGGATCTTCC

AATTCGCCTATTTCCTCACAAAGCATAG

SEQ ID No 37.: *Cucumis sativus* cytochrome P450
716B1-like (LOC101206033), mRNA, XM_004139039
ATGGAGCTTTTCCTCATCTCTCTCTTAATCCTTTTGTTCTTCTTTCTTT

CTCTTACTCTTTTCATCCTCTTCCACAATCACAAATCCTTATTCTCTTA

TCCCAACACTCCTCCTGGCGCCATCGGCCTTCCCATACTCGGCGAGAGC

GTCGAGTTCTTATCATCTGGTTGGAAAGGCCATCCTGAGAAGTTCATCT

TCGATCGTTTGAATAAGTACAAGTCAGATGTGTTCAAAACCTCGATCGT

GGGAGTTCCAGCCGCCATTTTCTGCGGCCCTATTTGTAACAAGTTCCTC

TTCTCTAACGAGAATAAACTGGTTACTCCTTGGTGGCCAGATTCCGTGA

ACAAGATCTTCCCCTCTACAACTCAGACTAGCACCAAAGAAGAAGCTAA

GAAACTCAAGAAACTCCTTCCGCAATTCCTTAAACCCGAAGCGCTTCAG

CGTTATATTGGAATTATGGACGAACTTGCTGAACGCCATTTCAATTCCT

TTTGGAAGAACAGAGAAGAGGTCCTCGTGTTTCCTCTTGCTAAAAGCTT

CACATTCTCAATAGCGTGCCGACTGTTCATGAGCGTGGAAGATGAAATT

CACGTGGAGAGATTATCGGGACCATTCGAGCACATTGCAGCAGGAATCA

TATCGATGCCGATCGATTTACCAGGAACGCCATTCAATAGAGCAATAAA

GGCGTCAAAGTTCATCAGAAAGGAAGTGGTGGCGATCGTGAGGCAGAGG

AAACAGGATTTGGCGGAAGGAAAGGCGTTGGCGACGCAGGATATTTTGT

CCCACATGCTTCTAACGTGCGATGAGAATGGTGTGTACATGAACGAATC

AGATATCACCGATAAGATTCTTGGGTTGTTGATCGGCGGCCATGACACT

GCCAGTGTTGCATGCACCTTCATCGTTAAGTTCCTCGCTGAGCTTCCTC

ATATCTACGATGCTGTATATACAGAGCAAATGGAAATAGCAAGAGCAAA

AGCGGAAGGGGAAACGTTGAAGTGGGAAGACATTAAGAAGATGAAATAT

TCATGGAATGTGGCTTGTGAGGTTCTAAGAATTGCTTCCCCACTCCAAG

GTGCCTTTAGGGAAGCCTTAAGTGACTTCGTTTTCAATGGTTTTTTCAT

TCCCAAGGGTTGGAAGCTATATTGGAGTGCAAACTCGACACACAAAAAC

CCCGAGTACTTCCCAGAACCTTATAAGTTCGATCCGGGAAGATTTGAAG

GAAATGGACCATTACCCTACACATTTGTGCCGTTTGGGGGAGGGCCAAG

GATGTGCCCTGGTAAGGAGTATGCAAAGCTTGAGATTTTGGTGTTCATG

-continued

CATAATTTGGTGAAGAGATTCAAATGGACAAAGCTTCTTGAAAATGAAA

ACATCATTGTTAACCCAATGCCAATCCCTCAAAAAGGTCTCCCAGTTCG

CCTTTTTCCTCATCAACCTCTTTCTCTTTAA

SEQ ID No 38. *Panax notoginseng* clone 00445n
cytochrome P450 mRNA, complete cds, GU997666
ATGGAACTCTTCTATGTCCCTCTCCTCTCCCTCTTTGTTCTCTTCATCT

CTTTATCATTCCACTTCCTCTTCTACAAGTCCAAATCCAGCTCCTCCGT

CGGGCTTCCTCTCCCGCCGGGCAAGACCGGATGGCCCATTATCGGCGAG

AGCTACGAGTTTCTCTCCACGGGGTGGAAAGGCTACCCGGAGAAGTTTA

TATTTGACCGTATGACCAAGTACTCCTCAAATGTCTTTAAAACCTCTAT

TTTCGGAGAGCCCGCCGCAGTATTCTGCGGCGCGKCTTGTAACAAGTTC

TTGTTCTCGAACGAAAACAAGCTTGTTCAGGCGTGGTGGCCTGACTCCG

TAAACAAAGTTTTTCCTTCTTCAACTCAAACCTCTTCGAAAGAAGAGGC

GATTAAGATGCGAAAATGCTGCCAAACTTCTTTAAACCGGAGGCCTTG

CAGCGCTACATCGGCCTCATGGACCAAATCGCTGCAAAGCACTTTGAAT

CCGGTTGGGAAAATAAAGACGAAGTGGTTGTATTTCCCCTGGCAAAATC

CTAYACGTTTTGGATCGCGTGTAAGGTATTTGTTAGCGTAGAGGAACCT

GCGCAGGTTGCGGAGCTGTTGGAACCATTTAGCGCGATTGCTTCTGGGA

TTATATCCGTGCCAATAGATTTGCCCGGCACGCCGTTTAACAGTGCCAT

AAAATCATCGAAAATTGTTAGGAGAAAGCTTGTGGGATTATTAACCAG

AGGAAAATTGATTTAGGGGAGGGAAAGGCTTCACCAACACAAGACATAT

TGTCACACATGTTGTTGACGAGTGATGAAAGTGGCAAGTTTATGGGTGA

GGGGGAAATTGCTGATAAGATATTGGGGTTGTTGATTGGAGGACATGAC

ACTGCAAGTTCTGCATGTACTTTTGTTGTCAAGTTTCTTGCTGAGCTGC

CTCAGATTTATGRGGGAGTCTACCAGGAGCAAATGGAGATAGTGAAATC

TAAAAAGGCAGGAGAATTATTGAAGTGGGAGGACATACAAAAGATGAAA

TATTCGTGGAATGTAGCCTGTGAAGTGCTGAGACTTGCACCACCCCTTC

AAGGAGCTTTTAGAGAAGCCCTCTCCGATTTCACCTACAACGGTTTCTC

AATCCCCAAAGGCTGGAAGCTATATTGGAGTGCAAATTCAACCCACAGA

AACTCAGAAGTTTTCCCGGAGCCACTAAAATTTGATCCATCAAGATTCG

ACGGAGCCGGGCCGCCGCCGTTCTCGTTCGTGCCGTTCGGCGGCGGGCC

GAGAATGTGCCCCGGAAAAGAGTATGCCCGGCTGGAAATACTGGTGTTT

ATGCACCATCTTGTCAAGAGGTTCAAGTGGGAAAAGGTTATTCCTGATG

AGAAAATTGTTGTTAATCCCATGCCAATTCCTGCCAACGGACTTCCTGT

TCGCCTATTTCCACACAAAGCCTAA

SEQ ID No 39. *Panax ginseng* cytochrome P450
CYP716A52v2 mRNA, complete cds, JX036032
ATGGAACTCTTCTATGTCCCTCTCCTCTCACTCTTTGTTCTCTTCATCT

CTTTATCATTCCACTTCCTCTTCTACAAGTCCAAACCCAGCTCCTCCGG

CGGGTTTCCTCTCCCGCCGGGCAAGACTGGGTGGCCCATTATTGGAGAG

AGCTACGAGTTTCTCTCCACGGGATGAAAGGCTACCCGGAGAAGTTCA

TATTTGACCGTATGACCAAGTACTCCTCAAATGTCTTTAAAACCTCTAT

TTTCGGAGAGCCCGCCGCAGTATTCTGCGGCGCGGCTTGTAACAAGTTC

TTGTTCTCGAACGAGAATAAGCTTGTTCAGGCCTGGTGGCCTGACTCCG

TGAACAAAGTTTTTCCTTCATCAACCCAAACCTCTTCGAAAGAAGAGGC

GATTAAGATGCGAAAATGCTGCCAAACTTCTTTAAACCGGAGGCTTTG

CAGCGCTACATCGGCCTCATGGACCAAATCGCTGCAAATCACTTTGAAT

CCGGTTGGGAAAATAAAAACGAAGTGGTTGTATTTCCCCTGGCAAAATC

CTACACGTTTTGGATCGCGTGTAAGGTATTTGTTAGCGTAGAGGAACCT

GCGCAGGTTGCGGAGCTGTTGGAACCATTCAGCGCGATTGCTTCTGGGA

TTATATCCGTCCCAATAGATTTGCCCGGCACGCCGTTTAACAGTGCCAT

AAAATCATCGAAAATTGTTAGGAGGAAGCTTGTGGGGATTATTAAGCAG

AGGAAAATTGATTTAGGGGAGGGAAAGGCTTCAGCAACACAAGACATAT

TGTCACACATGCTGTTGACAAGTGATGAAAGTGGCAAGTTTATGGGTGA

GGGGGATATTGCCGATAAGATATTGGGGTTGTTGATTGGAGGCCATGAC

ACTGCAAGTTCTGCATGTACTTTTGTTGTCAAGTTTCTTGCTGAGCTGC

CTCAGATTTATGAGGGAGTCTACCAGGAGCAAATGGAGATAGTGAAATC

TAAAAAGGCAGGAGAATTATTGAAGTGGGAGGACATACAAAAGATGAAA

TATTCGTGGAATGTAGCCTGTGAAGTGCTGAGACTTGCACCACCTCTTC

AAGGAGCTTTTAGAGAAGCCCTCTCCGATTTCACCTACAACGGTTTCTC

AATCCCTAAAGGCTGGAAGCTATATTGGAGTGCAAATTCAACCCACATA

AACTCAGAAGTTTTCCCGGAGCCACTAAAATTTGATCCATCAAGATTCG

ACGGAGCCGGGCCGCCGCCGTTCTCGTTCGTGCCGTTCGGCGGCGGGCC

GAGAATGTGCCCCGGAAAAGAGTATGCCCGGCTGGAAATACTGGTGTTT

ATGCACCATCTTGTCAAGAGGTTCAAGTGGGAAAAGGTTATTCCTGATG

AGAAAATTGTTGTTAATCCCATGCCAATTCCTGCCAACGGACTTCCTGT

TCGCCTATTTCCACACAAAGCCTAA

SEQ ID No 40. *Ricinus communis* cytochrome P450,
putative, mRNA, XM_002522891
ATGGACCACTTCTATCTTACCCTTCTTTTCCTCTTCGTTTCCTTCATCA

CCTTTTCAATTTTTATCATATTTTACAAGCACAAATCTCAATACAATTA

TCCAAGTCTTCCTCCAGGGAAGCCTGGCCTCCCTTTTGTTGGTGAAAGC

CTTGAATTTTGTCTTCAGGTTGGAAGGGTCACCCTGAAAAGTTTGTGT

TTGATAGAACTTCTAAATATTCTTCTGAGATTTTTAAAACTAATCTTCT

TGGCCAACCTGCTGCTGTCTTCTGTGGTGCTTCTGCCAACAAGTTTTTG

TTCTCCAATGAAAACAAGCTTGTTCAGGCCTGGTGGCCTGATTCTGTTA

ACAAAATATTCCCTTCTTCTCTTCAAACTTCTTCTAAAGAAGAAGCCAT

TAAAATGAGAAAGCTTCTCCCTCAGTTCATGAAACCTGAAGCCCTCCAG

CGTTATATTGGTATCATGGATACAATTGCTCAGAGGCACTTGCTTCGG

GATGGGAAAAAAAAAATGAAGTAGTTGTGTTTCCTCTAGCGAAGAATTA

CACCTTCTGGTTAGCGTGCAGACTGTTTGTCAGCCTGGAAGATCCAGAT

CACATCGCTAAATTTGCAGACCCTTTTCAGGAATTGGCTTCAGGAATCA

TTTCCGTGCCAATAGATTTGCCTGGAACACCATTCAGAAGAGCAATCAA

AGCTTCAAACTTCATCAGGAAAGAGCTTATAAGTATTATAAAGCAAAGA

```
AAGATTGATCTAGCAGAAGGGAAAGCTTCTGGTACACAGGATATATTGT
CCCATATGTTGTTAACATCAGATGAGGATGGAAAGTTTATGAATGAGAT
GGATATTGCCGACAAAATTCTTGGATTGCTGATTGGTGGGCATGATACT
GCTAGTGCTGCTTGTACTTTCATTATCAAGTACCTTGCTGAGCTCCCTC
AAATCTATGATGCAGTTTACAAAGAGCAAATGGAGATTGCAAAATCAAA
AGGAGAAGGAGAGTTGTTGAATTGGGAAGACATACAGAAGATGAAATAT
TCATGGAATGTGGCATGTGAAGTTATGAGAGTTGCACCACCCCTTCAAG
GTGCTTTCAGGGAAGCTATCAATGACTTTATCTTTAATGGCTTCTATAT
TCCAAAAGGCTGGAAGCTATATTGGAGTGCAAACTCAACACACAAAAGT
GCAACATACTTTGAAGAACCAGAGAAATTTGATCCAAGTAGATTTGAAG
GGAAAGGACCAGCCCCATACACATTTGTACCATTTGGAGGAGGACCAAG
AATGTGCCCTGGGAAAGAGTATGCTAGACTGGAAATTCTTGTTTTCATG
CATAATCTGGTCAAAAGATTCAATTTCCAAAAGATAATTCCTGATGAGA
ACATCATTGTTAATCCTTTGCCTATCCCTGCTAAGGGTCTTCCAGTTCG
CCTTCTTCCTCATCAAATTTAG

SEQ ID No 41. Vitis vinifera contig VV78X175946.8,
whole genome shotgun sequence, AM457725
ATGGAGGTGTTCTTCCTCTCCCTGCTCCTCATCTGTGTGCTCTCAGTCT
CCATCAGACTTTACTTGCTCTTATACAAGCATAGATCCCACTTCACTGG
CCCCAATCTCCCTCCTGGCAAGATTGGTTGGCCAATGGTTGGTGAAAGC
CTTGAATTCCTCTCCACCGGCTGGAAAGGCCACCCGGAAAAATTCATCT
TCGATCGCATCTCCAAATACTCCTCTGAAGTCTTCAAGACCTCCCTCCT
CGGAGAGCCTGCTGCCGTCTTTGCTGGCGCTGCGGGCAACAAGTTTTTG
TTCTCCAACGAAAACAAACTTGTTCATGCGTGGTGGCCTAGCTCTGTCG
ACAAGGTCTTCCCCTCCTCCACCCAAACCTCATCCAAAGAGGAGGCCAA
GAAGATGAGGAAGTTGCTCCCTCAGTTCCTTAAGCCTGAAGCCTTGCAA
CGTTACACCGGCATCATGGATCACATTGCACAGAGGCATTTTGCTGATA
GCTGGGACAACAGAGATGAAGTCATTGTATTTCCACTGGCCAAGAGGTT
CACTTTCTGGCTAGCTTGCCGCCTGTTTATGAGCATAGAAGATCCTGCC
CACGTCGCTAAATTTGAAAAGCCCTTCCACGTCTTGGCCTCRGGACTCA
TCACCATCCCAATTGACCTGCCTGGGACACCTTTCCACCGCGCTATCAA
GGCCTCCAACTTCATCAGAAAGGAGCTTAGAGCCATCATCAAGCAAAGG
AAGATCGATCTGGCTGAGAGCAAGGCCTCAAAAACTCAAGATATATTGT
CCCACATGCTTCTGGCTACAGATGAAGATGGATGCCACATGAATGAAAT
GARTATTGCTGATAAAATCCTCGGTTTGTTGATTGGTGGCCATGACACT
GCCAGTTCTGCCATTACATTCCTTGTCAAGTACATGGCTGAGCTGCCTC
ACATCTACGAGAAAGTCTACAAGGAGCAAATGGAAATTGCCAATTCAAA
AGCACCAGGTGAATTGCTGAACTGGGATGATGTTCAAAAGATGAGATAT
TCATGGAATGTTGCCTGTGAAGTGATGAGACTTGCACCCCACTCCAAG
GAGCTTTCCGGGAAGCAATCACTGACTTCGTGTTCAATGGTTTCTCCAT
TCCTAAGGGTTGGAAGCTGTACTGGAGCGCAAACTCAACCCACAAAGC
CTAGAATGCTTCCCTCAACCCGAAAAATTTGACCCTACAAGATTTGAAG
GAGCCGGGCCTGCTCCTTACACATTCGTTCCCTTTGGTGGCGGACCTAG
GATGTGCCCTGGTAAAGAGTACGCCCGCTTGGARATACTTATCTTCATG
CACAACTTGGTTAAAAGGTTCAAATGGGATAAATTGCTTCCTGATGAGA
AGATAATCGTTGACCCCATGCCCATGCCTGCTAAGGGACTTCCAGTTCG
CCTCCATCCTCACAAACCATAG SEQ ID No 42.: Vitis vinifera cytochrome P450
716B2-like (LOC100262400), mRNA, XM_002265988
ATGGAGGTGTTCTTCCTCTCCCTGCTCCTCATCTGTGTGCTCTCAGTCT
CCATCGGACTTCAGTTCCTCTTCTACAAGCACAGATCCCACTTCACTGG
CCCCAACCTCCCCCCTGGCAGGATTGGTTGGCCTATGGTTGGTGAAAGC
CTTGAATTCCTCTCCACCGGCTGGAAAGGCCACCCGGAAAAATTCATCT
TCGATCGCATCTCCAAATACTCCTCTGAAGTCTTCAAGACCTCCCTCCT
CGGAGAGCCTGCTGCCGTCTTTGCTGGCGCTGCGGGCAACAAGTTTTTG
TTCTCCAACGAAAACAAGCTTGTTCATGCGTGGTGGCCTAGCTCCGTGG
ACAAGGTCTTCCCCTCCTCCACCCAAACCTCATCCAAAGAGGAGGCCAA
GAAGATGAGGAAGTTGCTCCCTCGGTTCCTTAAGCCTGAAGCCTTGCAA
CGTTACATCGGCATCATGGATACACATTGCGCAGAGGCACTTTGCTGATA
GCTGGGACAACAGAGATGAAGTCATTGTGTTTCCACTGTCCAAGAGGTT
CACTTTCTGGCTAGCTTGCCGCCTCTTTATGAGCATAGAAGATCCTGAC
CACATCGCTAAATTTGAAAAGCCCTTCCATGTCTTGGCCTCAGGACTCA
TCACCGTCCCGATTGACTTGCCTGGGACACCTTTCCACCGCGCTATCAA
GGCCTCCAACTTCATCAGAAAGGAGCTTAGAGCCATCATCAAGCAAAGG
AAGATCGATCTGGCCGAGGGAAAAGCCTCACCAACTCAAGATATATTGT
CCGACCTGCTTCTGGCCACAGATGAAGATGGACGCCACATGAACGAAAT
TAATATTGCTGATAAAATCCTTGGCTTGTTGATTGGTGGCCATGATACG
GCCAGTTCTGCCATTACATTCATTGTTAAGTACATGGCTGAGCTGCCTC
ATATGTACGAGAAAGTCTACGAAGAGCAAATGGAAATTGCCAATTCAAA
AGCACCAGGTGAATTATTGAACTGGGATGATGTTCAAAAGATGAGATAT
TCATGGAATGTTGCTTGTGAAGTGATGAGACTTGCACCCCACTCCAAG
GAGCTTTCCGAGAAGCAATCACTGACTTCGTGTTCAATGGTTTCTCCAT
TCCTAAGGGTTGGAAGTTGTACTGGAGCACAAGCTCAACCCACAAAAGC
CCAAAATGCTTCCCTGAACCTGAAAAATTTGACCCTACAAGATTTGAAG
GAGCTGGGCCTGCTCCTTACACATTCGTTCCCTTTGGTGGTGGACCTAG
GATGTGCCCTGGTAAAGAGTACGCCCGCTTGGAAATACTTGTCTTCATG
CATAACGTGGTTAAAAGGTTCAAATGGGATAAATTGCTTCCTGATGAGA
AGATAATAATTGACCCCATGCGCATGCCTGCTAAGGGACTTCCAGTTCG
CCTCCGTCTTCACAAACCATAA SEQ ID No 43. Ricinus communis cytochrome P450,
putative, mRNA, XM_002527956
ATGTTTCCCTTTGCCGTCCTCCTCATCGCTCTTTTCAATCTCATACCTCA
TCTTCAAACACAAGTCCAACGCCTCCAGCAGGAAGAATCTCCCACCTGG
CAATACCGGTTGGCCTCTCATAGGCGAAAGCATAGAGTTCCTAAGCACC
```

```
GGGCGAAAGGGTCACCCGGAGAAGTTCATATTTGACCGAATGGAGAAGT
TCTCGAGCAAGGTGTTCAAGACCTCATTGCTTCTGGAGCCGGCAGCAGT
GTTTTGTGGGGCAGCAGGGAACAAGTTCTTGTTCTCCAATGAGAATAAA
CTAGTCACTGCATGGTGGCCTAACTCTGTTAATAAAATCTTCCCATCCT
CTCTCCAAACCTCTTCACAGGAGGAATCCAAGAGAATGAGAAAGCTTCT
TCCTCAATTTCTGAAGCCAGAAGCTCTTCAAAGATATATAAGTATCATG
GATGTTATTGCACAAAGACATTTCGCATTCGGATGGAACAACAAACAAC
AAGTGACAGTTTTCCCTCTAGCTAAGATGTATACTTTCTGGTTAGCCTG
TCGGTTGTTTCTAAGCATGGAAGACCGGGAAGAAGTCGAAAAGTTTGCA
AAGCCATTCGATGTATTGGCATCAGGTATTATATCGATACCTATTGATT
TTCCAGGGACGCCATTTAACCGAGGGATCAAAGCATCAAATGAGGTAAG
AAGGGAGCTGATAAAGATGATCGAACAGAGGAAGATTGATCTAGCCGAG
AATAAGGCATCCCCAACACAGGATATATTGTCTCACATGCTAACCACAG
CAGACGAGTACATGAATGAAATGGATATAGCTGATAAGATTCTTGGTTT
GCTTATTGGAGGCCACGACACAGCCAGTGCTGCCATAACGTTTGTTGTC
AAGTATCTTGCGGAGATGCCTCAAGTCTACAATAAGGTGTTAGAGGAAC
AAATGGAGATTGCGAAAGCAAAAGCAGCTGGAGAGCTGTTGAACTGGGA
AGACATCCAAAAGATGAGATATTCATGGAACGTAGCATGTGAAGTGATG
AGACTTGCTCCTCCGCTACAAGGAGCCTTTAGAGAGGCCATGACAGACT
TCACCTATGCAGGTTTCACTATTCCTAAAGGATGGAAGTTGTACTGGGG
TGCTAACTCTACACACAGAAACCCCGAGTGTTTCCCAGAACCAGAAAAG
TTCGACCCCTCAAGGTTTGAAGGCAAGGGACCTGCCCCTTACACATTCG
TTCCTTTTGGAGGCGGACCCAGAATGTGCCCTGGAAAAGAATATGCTAG
ATTGGAGATCCTCGTTTTCATGCACAACATTGTCAAAAGTTCAGATGG
GAGAAGCTGCTTCCTGAAGAGAAGATTATTGTTGATCCTCTCCCGATTC
CCGCTAAAGGCCTTCCCCTTCGTCTTCATCCCACACCTCCTAG
```

SEQ ID No 44. *Medicago truncatula* clone JCVI-FLMt-11H3 unknown mRNA, BT147421
```
ATGGAGCCTAATTTCTATCTCTCCCTTCTCCTTCTCTTTGTCACTTTCA
TATCTCTCTCTCTTTTTTTCATATTCTACAAACAGAAATCTCCATTAAA
TTTGCCACCTGGTAAAATGGGTTACCCAATCATAGGTGAAAGCCTTGAG
TTCTTATCAACAGGATGGAAAGGACATCCTGAAAAATTCATTTTCGACC
GTATGCGTAAATATTCCTCAGAACTCTTTAAAACATCAATCGTAGGAGA
ATCTACGGTGGTTTGTTGCGGAGCAGCAAGTAACAAGTTTTGTTTTCA
AACGAGAATAAACTTGTGACTGCATGGTGGCCAGATAGTGTAAACAAAA
TCTTCCCTACTACTTCTCTTGACTCTAACTTGAAGGAAGAATCCATCAA
GATGAGAAAATTGCTTCCACAATTCTTTAAACCCGAAGCTCTACAACGT
TATGTTGGTGTCATGGATGTTATTGCTCAAAGACATTTTGTTACTCATT
GGGATAATAAAAATGAAACCACCGTCTACCCCTTGGCCAAGAGGTACAC
CTTTTTGTTAGCTTGTCGGTTGTTCATGAGCGTTGAAGACGAGAATCAT
GTAGCAAAATTTAGTGATCCATTTCAGTTAATTGCGGCCGGAATCATAT
CTCTACCAATTGATTTGCCAGGAACACCATTCAACAAAGCTATAAAGGC
```

```
CTCAAACTTTATAAGAAAGGAGTTGATTAAGATCATAAAGCAAAGGAGG
GTAGATTTGGCAGAAGGGACAGCATCACCAACACAAGATATATTGTCTC
ACATGTTGTTGACAAGTGATGAAAATGGAAAGAGTATGAATGAACTTAA
TATTGCTGATAAGATTCTTGGCCTTTTGATCGGAGGACATGACACTGCT
AGCGTCGCATGCACTTTCCTTGTCAAATATCTCGGCGAGTTACCTCACA
TTTATGATAAAGTCTATCAAGAGCAAATGGAAATTGCAAATCGAAACC
AGCAGGAGAATTGTTGAATTGGGATGACCTGAAGAAAATGAAATACTCT
TGGAACGTAGCTTGTGAAGTAATGAGACTTTCCCCTCCACTCCAAGGAG
GTTTCAGGGAAGCCATCACTGACTTTATGTTCAATGGATTCTCAATTCC
TAAGGGATGGAAGCTTTATTGGAGTGCAAATTCAACACATAAGAACGCA
GAATGTTTTCCCATGCCAGAGAAATTTGACCCAACAAGATTTGAAGGAA
ATGGACCAGCTCCTTATACTTTTGTTCCCTTTGGTGGAGGACCAAGGAT
GTGTCCTGGAAAAGAGTATGCAAGATTAGAAATACTTGTTTTCATGCAC
AATTTGGCGAAAAGGTTTAAGTGGGAAAAGGTGATTCCAGATGAGAAGA
TTATTGTTGATCCATTCCCCATCCCTGCAAAGGATCTTCCAATTCGCCT
TTATCCACACAAAGCTTAA
```

SEQ ID No 45.: *Glycine max* cytochrome P450 716B2-like (LOC100813159), mRNA, XM_003530477
```
ATGGAGGATAATAACTTGCATCTCTCCCTCCTTCTCCTCTTCGTTTCTA
TAGTGACCCTCTCCCTCTTCGTCCTCTTCTACAAGCACAGGTCTGCATT
TGCGGCCCCGAACCTGCCACCGGGAGCCACCGGTTACCCGGTGATCGGG
GAGAGCCTGGAGTTCCTGTCCACAGGATGGAAGGGTCATCCGGAGAAGT
TCATCTTCGACCGGATGATCAGGTACTCCTCCCAGCTGTTCAAGACCTC
CATCCTGGGGAACCGGCGGTAATATTCTGTGGGCCACCTGCAACAAG
TTCTTATTTTCGAACGAGAACAAGCTTGTTGCAGCGTGGTGGCCCAACA
GCGTCAACAAGGTGTTCCCCACCACGCTTCTTAGCAACTCCAAACAAGA
GTCCAAAAAGATGAGGAAGTTGCTCCCTCAGTTCCTTAAGCCCGAGGCT
CTCCAACGCTACGTTGGAATCATGGACACCATTGCTCGAAACCACTTCG
CTTCCCTTTGGGACAACAAGACGGAACTCACCGTCTATCCCTTGGCCAA
GAGGTACACGTTCTTGTTGGCTTGTCGTTTGTTTATGAGCATTGAGGAC
GTGAATCACGTAGCAAAATTTGAGAACCCTTTTCACCTGTTGGCGTCTG
GAATCATATCAGTGCCTATTGATCTTCCCGGAACGCCGTCAACAAAGC
AATTAAAGCAGCAAACGCAATCAGGAAGGAGCTGTTGAAGATCATTAGA
CAGAGGAAGGTGGATTTAGCTGAAGGGAAAGCATCGCCAACACAAGACA
TTTTGTCTCATATGTTGTTAACATGCGATGAGAAGGGACAGTTCATGAA
TGAATTGGATATTGCCGACAAGATTCTTGGCCTTTTGATTGGAGGCCAT
GACACTGCTAGTGCTGCAATCACTTTCATTGTCAAATATCTTGCTGAAC
TCCCTCACATTTATGATAGAGTCTATCAAGAGCAAATGGAAATTGCAAA
ACTGAAATCGCCAGGAGAGTTATTGAATTGGGATGATGTCAACAGGATG
CAGTATTCTTGGAATGTAGCTTGTGAAGTAATGAGAATCGCTCCTCCAC
TTCAAGGAGGTTTTAGGGAAGCTATCAATGACTTTATTTTCGATGGCTT
```

TTCAATACCAAAGGGATGGAAGTTGTATTGGAGTGCAAATTCAACACAT
AAAAGTCCAGAATATTTTCCAGAGCCAGAGAAATTCGATCCAACTAGAT
TCGAAGGACAAGGGCCAGCTCCTTATACTTTTGTACCATTTGGTGGAGG
ACCAAGGATGTGCCCCGGAAAAGAGTATGCTCGATTGGAAATATTGGTT
TTCATGCACAACCTAGTGAAGAGGTTTAAGTGGCAAAAATTGATTCCAG
ATGAGAAAATTATCGTTGATCCCTTGCCCATACCTGCAAAGAACCTTCC
AATTCGTCTTCATCCTCACAAACCCTGA

SEQ ID No 46. Soybean clone JCVI-FLGm-20N8
unknown mRNA, BT096613
ATGGAGGATAATAACTTGCATCTCTCCCTCCTTCTCCTCTTCGTTTCTA
TAGTGACCCTCTCCCTCTTCGTCCTCTTCTACAAGCACAGGTCTGCATT
TGCGGCCCCGAACCTGCCACCGGGAGCCACCGGTTACCCGGTGATCGGG
GAGAGCCTGGAGTTCCTGTCCACAGGATGGAAGGGTCATCCGGAGAAGT
TCATCTTCGACCGGATGATCAGGTACTCCTCCCAGCTGTTCAAGACCTC
CATCCTGGGGGAACCGGCGGTAATATTCTGTGGGGCCACCTGCAACAAG
TTCTTATTTTCGAACGAGAACAAGCTTGTTGCAGCGTGGTGGCCCAACA
GCGTCAACAAGGTGTTCCCCACCACGCTTCTTAGCAACTCCAAACAAGA
GTCCAAAAGATGAGGAAGTTGCTCCCTCAGTTCCTTAAGCCCGAGGCT
CTCCAACGCTACGTTGGAATCATGGACACCATTGCTCGAAACCACTTCG
CTTCCCTTTGGGACAACAAGACGGAACTCACCGTCTATCCCTTGGCCAA
GAGGTACACGTTCTTGTTGGCTTGTCGTTTGTTTATGAGCATTGAGGAC
GTGAATCACGTAGCAAAATTTGAGAACCCTTTTCACCTGTTGGCGTCTG
GAATCATATCAGTGCCTATTGATCTTCCCGGAACGCCGTTCAACAAAGC
AATTAAAGCAGCGAACGCAATCAGGAAGGAGCTGTTGAAGATCATTAGA
CAGAGGAAGGTGGATTTAGCTGAAGGGAAAGCATCGCCAACACAAGACA
TTTTGTCTCATATGTTGTTAACATGCGATGAGAAGGGACAGTTCATGAA
TGAATTGGATATTGCCGACAAGATTCTTGGCCTTTTGATTGGAGGCCAT
GACACTGCTAGTGCTGCAATCACTTTCATTGTCAAATATCTTGCTGAAC
TCCCTCACATTTATGATAGAGTCTATCAAGAGCAAATGGAAATTGCAAA
ACTGAAATCGCCAGGAGAGTTATTGAATTGGGATGATGTCAACAGGATG
CAGTATTCTTGGAATGTAGCTTGTGAAGTAATGAGAATCGCTCCTCCAC
TTCAAGGAGGTTTTAGGGAAGCTATCAATGACTTTATTTTCGATGGCTT
TTCAATACCAAAGGGATGGAAGTTGTATTGGAGTGCAAATTCAACACAT
AAAAGTCCAGAATATTTTCCAGAGCCAGAGAAATTCGATCCAACTAGAT
TCGAAGGACAAGGGCCAGCTCCTTACACTTTTGTACCATTTGGTGGAGG
ACCAAGGATGTGCCCCGGAAAAGAGTATGCTCGATTGGAAATATTGGTT
TTCATGTACAAC SEQ ID No 47.: *Vitis vinifera* cytochrome P450
716B2-like (LOC100242305), mRNA, XM_002280933
ATGGAGCTCTCTTTACTCCACATACTTCCATGGGCCACCCTCTTCACCA
CTCTTTCTCTTTCATTCCTCATCTACAAGCTCATGATCATCTCCCATGG
CACACCCAGAAACCTTCCGTCCGGCAATACCGGTCTGCCCTATATCGGA
GAAAGCATCCAGTTCCTCTCCAATGGCAGAAAGGGTCATCCCGAGAAGT TCATTTCTGAGAGAATGTTGAAGTTCTCATCCAAAGTTTTCAAGACCTC
ACTCTTCGGAGAAACTGCTGCAGTCTTCTGTGGCTCGGCCGGGAACAAG
TTCTTGTTCTCCAACGAGAACAAGCTTGTGACCGCATGGTGGCCGAGCT
CCGTAAACAAAATCTTCCCTTCCTCTCTGCAAACCTCCTCGCAGGAAGA
ATCAAAGAAAATGAGAAAGCTGCTTCCGGGCTTTCTCAAACCCGAAGCC
CTCCAAAGATATATCAGTATCATGGACGTGATAGCTCAGAGGCACTTTG
AGTCCAGCTGGAACAACAAGGAAGAAGTCACAGTCTTCCCGCTAGCCAA
GATGTTCACATTCTGGCTGGCTTGTCGTCTGTTTTTGAGCGTAGAAGAC
CCCGACCATGTCGAAAAGCTTGCAGAGCCCTTCAACGAACTGGCCGCCG
GAATCATAGCCCTACCTATTGATTTGCCTGGGACGTCATTTAACAAGGG
GATCAAAGCTTCAAACCTGGTCAGAAAGGAGCTTCATGCAATAATCAAG
AAGAGGAAGATGAATCTTGCGGACAACAAGGCGTCGACGACGCAGGACA
TATTGTCACATATGCTTCTCACTTGTGATGAGAATGGAGAGTACATGAA
TGAAGAGGATATAGCTGATAAAATTCTTGGGTTGCTCGTCGGAGGTCAT
GACACAGCCAGTGCTACCATTACTTTTATTGTCAAGTTTCTTGCAGAGC
TGCCTCATGTTTACGATGAAGTTTTCAAGGAACAAATGGAGATAGCAAA
ATCAAAGGCCCCAGGTGAGCTGTTGAATTGGGAGGACATTCCAAAGATG
AGGTATTCATGGAATGTAGCATGTGAAGTGATGAGACTGGCACCACCCG
TTCAAGGAGCTTTCCGAGAAGCCATGAATGACTTCATCTTCGAGGGTTT
CTCCATTCCAAAGGGATGGAAGCTGTACTGGAGCACGCACTCGACCCAC
CGGAACCCGGAGTTCTTCCCCAAGCCGGAAAAATTCGACCCCTCGAGGT
TTGACGGAAAGGGACCAGCCCCTTACACCTATGTGCCTTTCGGAGGAGG
ACCCAGGATGTGCCCTGGCAAAGAGTATGCTAGATTGGAAGTACTAGTG
TTCATGCACAATTTAGTGAGAAGGTTCAAATGGGAGAAGCTGCTGCCAG
ATGAAGAGATTATAGTAGACCCCATGCCCATTCCTGCAAAAGGCCTTCC
CATTCGCCTCCATCATCACCAACCCTAG SEQ ID No 48. *Populus trichocarpa* hypothetical
protein (POPTR_0006s08560g) mRNA, complete cds,
XM_002309021
ATGGAACTTCCCTTCATCTCCCTGCTTCCCTATGGAATCCTCTTCATCA
TCTCTGCAGTTTCACTATCATACCTCATAAACAAACACAAATATTATCT
CTCCTCCCTCAACAACCTCCCGCCTGGTAATACCGGTTTGCCATTAATC
GGTGAAAGTCTGGAGTTCCTGACCACGGGGCAAAAGGGTCAGCCGGAGA
AGTTCATATTAGACAGAATGGCAAAGTTCTCATCCAAAGTCTTCAAAAC
CTCGTTGTTTTGTGAACCAACTGCAGTATTCTGTGGTGCAGCAGGGAAC
AAGTTCTTGTTCTCTAATGAGAATAAGCTTGTCACTGCATGGTGGCCTG
ATTCGTCAACAAAATCTTCCCTTCCTCTCAACAAACTTCTTCACAAGA
AGAATCCAAGAAAATGAGAAAGCTTTTCCCACTTTTTTTCAAGCCAGAA
TCACTTCAAAGATATATTAGTGTGATGGATGTGATTGCACAAAGGCACT
TGGCTTCTGATTGGAAGGCAAACAGGAAGTCAGTGTTTCCCTCTGGC
TAAGACGTACACTTTTGGTTAGCTTGCCGCTTATTTCTAAGCATGAAA
GATCCTGAGGAAGTCCAAAAGTTCGCCAAACCCCTTCAATGATTTAGCCG

CTGGGATTATATCCATACCCATTGATTTGCCCTGGACACCCTTTAATCG

CGGGGTCAAAGCATCAAATGTGGTGCACAAGGAGCTTCTAAAGATCATA

AAGCAGAGGAAGATTGATCTAGCGGAGAACAAGGCATCCCCCACACAAG

ATATACTGTCCCATATGCTAACCACAGCAGACGATAATGGGCAATGCAT

GAAAAAGATCGATATTGCCGATAAGATACTTGGTTTGCTTGTTGGAGGT

CACGACACAGCCAGTGCTGCTATAACTTTTATTGTCAAGTATCTTGCAG

AGTTGCCTCATGTCTACAACAAGCTCTTGGAAGAACAAAGAGAGATCGC

AAAAACGAAAACACCTGGAGAGCTGTTGAATTGGGAGGACATACAAAGG

ATGAGATATTCATGGAACGTTGCCTGTGAAGTGATGAGAGTTGCTCCCC

CACTCCAAGGAGCTTTCCGAGAGGCCATGACCGAGTTCAACTACGCAGG

TTTTACAATTCCGAAGGGATGGAAGCTGTATTGGAGCGCAAACACTACA

CACAAAAATCCTGAATGTTTCCCTGAGCCAGAGAATTTTGACCCATCAA

GATTCGAAGGCAATGGACCGGCCCCATACACCTTTGTTCCATTTGGAGG

AGGTCCTAGGATGTGTCCAGGCAAAGAATATGCTAGACTGGAAATACTT

GTTTTCTTGCACAACTTGGTTAAAAAGTTCAGATGGGAGAAGCTGCTTC

CTAAAGAGAGGATAATTGTAGATCCAATGCCAATACCTTCAAAAGGCCT

TCCGATCCGCCTCCACCCTCACGAGGCTGCCTAA

SEQ ID No 49. Medicago truncatula clone MTYP5_F6_
F7_F81G-0-7 unknown mRNA, BT051785
ATGGAGCCTAATTTCTATCTCTCCCTTCTCCTTCTCTTTGTCACTTTCA

TATCTCTCTCTCTTTTTTTCATATTCTACAAACAGAAATCTCCATTAAA

TTTGCCACCTGGTAAAATGGGTTACCCAATCATAGGTGAAAGCCTTGAG

TTCTTATCAACAGGATGGAAAGGACATCCTGAAAAATTCATTTTCGACC

GTATGCGTAAATATTCCTCAGAACTCTTTAAAACATCAATCGTAGGAGA

ATCTACGGTGGTTTGTTGCGGAGCAGCAAGTAACAAGTTTTTGTTTTCA

AACGAGAATAAACTTGTGACTGCATGGTGGCCAGATAGTGTAAACAAAA

TCTTCCCTACTACTTCTCTTGACTCTAACTTGAAGGAAGAATCCATCAA

GATGAGAAAATTGCTTCCACAATTCTTTAAACCCGAAGCTCTACAACGT

TATGTTGGTGTCATGGATGTTATTGCTCAAAGACATTTTGTTACTCATT

GGGATAATAAAAATGAAACCACCGTCTACCCCTTGGCCAAGAGGTACAC

CTTTTTGTTAGCTTGTCGGTTGTTCATGAGCGTTGAAGACGAGAATCAT

GTAGCAAATTTAGTGATCCATTTCAGTTAATTGCGGCCGGAATCATAT

CTCTACCAATTGATTTGCCAGGAACACCATTCAACAAAGCTATAAAGGC

CTCAAACTTTATAAGAAGGAGTTGATTAAGATCATAAAGCAAAGGAGG

GTAGATTTGGCAGAAGGGACAGCATCACCAACACAAGATATATTGTCTC

ACATGTTGTTGACAAGTGATGAAAATGGAAAGAGTATGAATGAACTTAA

TATTGCTGATAAGATTCTTGGCCTTTTGACCGGAGGACATGACACTGCT

AGCGTCGCATGCACTTTCCTTGTCAAATATCTCGGCGAGTTACCTCACA

TTTATGATAAAGTCTATCAAGAGCAAATGGAATTGCAAAATCGAAACC

AGCAGGAGAATTGTTGAATTGGGATGACCTGAAGAAAATGAAATACTCT

TGGAACGTAGCTTGTGAAGTAATGAGACTTTCCCCTCCACTCCAAGGAG

GTTTCAGGGAAGCCATCACTGACTTTATGTTCAATGGATTCTCAATTCC

TAAGGGATGGAAGCTTTATTGGAGTGCAAATTCAACACATAAGAACGCA

GAATGTTTTCCCATGCCAGAGAAATTTGACCCAACAAGATTTGAAGGAA

ATGGACCAGCTCCTTATACTTTTGTTCCCTTTGGTGGAGGACCAAGGAT

GTGTCCTGGAAAAGAGTATGCAAGATTAGAAATACTTGTTTTCATGCAC

AATTTGGCGAAAAGGTTTAAGTGGGAAAAGGTGATTCCAGATGAGAAGA

TTATTGTTGATCCATTCCCCATCCCTGCAAAGGATCTTCCAATTCGCCT

TTATCCACACAAAGCTTAA

SEQ ID No 50. Ricinus communis cytochrome P450,
putative, mRNA, XM_002513137
ATGGAGTTGTTCTTTCTCATAGCCTTAACCCTTTTCATTATTCTTGTCA

CTCTTCCAATTCTGGCTGTCTTATACAGACCAAATATTATCAATCTACC

ACCAGGCAAGACGGGCTTGCCATACATAGGAGAGAGCCTGGAATTTCTT

TCCACAGGCAGAAAAGGTCATCCTGAGAAGTTTTTATCAGATAGAATGG

AAAAATTCTCACGTCAAGTTTTCAGGACTTCAATTCTTGGTGAACAAAC

TGCAGTCGTCTGTGGCGCACAAGGCAACAAGTTCTTGTTCTCTAATGAG

AACAAGCTTGTCACTGCTTGGTGGCCAAAATCAATCCTGAGACTCTTCC

CTTCCTCTAATCAAAGCACTATCCTAGCTGAAGGCATGAGGATGAGGAA

GATGCTACCTCACTTTCTCAAACCTGAGGCCCTGCAAAGATACATAGGT

GTAATGGACCATATGCACAAGTTCACTTTCAGGATAGCTGGGAAAACA

AGCAAGAAGTCACAGTTTATCCGCTTGCAAAGATGTATACATTTTCAGT

TGCTTGCAAAGTGTTCTTGAGCATGGATGACCCAAAGGAGGTCGCAAAG

TTCGCTGCTCCTTTCAATGATATGGCCTCAGGAATTATTTCTATTCCTA

TCAATTTTCCTGGAACATCTTTCAATCGTGGACTCAAGGCCTCGAAGAT

TATAAGGAACGAAATGTTGCGTATGATTAAGCAAAGAAGAAAAGATCTT

GCTGAGAATAAAGCAACTCCTATGCAAGATATACTGTCCCATATGCTGG

TAGCAACTGATGAAGAAGGTCAGAGATTGGGAGAAGTTGGGATTGCTGA

TAAGATCATCTCTTTGCTCATTGGTGGCCACGACACAGCAAGTGCTACA

ATCACTTTCGTTGTCAAGTTTCTTGCCGAGCTCCCAGATATCTACGATC

AAGTCTTGAAAGAGCAATTGGAGATTGCTAAATCAAAAGAACCAGGAGA

ATTATTGACCTGGAAGACATTCAGAAGATGAAGTACTCGTGGAATGTT

GCTTGTGAAGTAATGAGATTAGCCCCACCTCTTCAGGGTTCTTTCAGAG

AAGCCTTACATGACTTCGACTATGCTGGTTTCTCTATTCCAAAGGGTTG

GAAATTATATTGGAGCACACATACAACACACAAAAATCCAGAATATTTT

TCGGATCCTGAAAAGTTTGATCCTTCAAGATTTGAAGGATCAGGGCCAG

CACCTTACACATTTGTTCCATTTGGAGGAGGGCCAAGGATGTGTCCTGG

AAAAGAGTATGCAAGATTGGAAATTCTTGTTTTCATGCACAATATAGCG

AAGAGGTTCAAGTGGAACAAGGTTATTCCTGACGAGAAAATTGTTGTTG

ACCCCATGCCAATACCAGCTAAAGGCCTTCCAGTTCACCTCTATCCTCA

AAAACATGAGTAA

SEQ ID No 51.: *Vitis vinifera* cytochrome P450 716B2-like (LOC100265713), mRNA, XM_002264607
ATGATCATGCAGCAAAGCGACATGGAGCTCTTGCTCCTCCTTTCTCC

TCCTCATGGCTCTCTCTCTCTTTTTGGATTCGCTTCTTTGTCCATAA

ACTCGAAAAAAGCAGTGGTATTAACCTGCCTCCAGGGAAAATGGGTTTT

CCATTCATTGGTGAAAGTCTAGAATTCCTTCGGATGGGCAGGAAGGGAA

CCCCTGAAAGGTTCATTCAAGATAGGATGGCCAAATACTCAACCCAGAT

CTTCAAAACTTGCTTACTCGGAGAACCAACTGCAGTTGTGTGTGGGCT

GCTGGAAACAAGTTGTTGTTCTCCAACGAGAACAAGCTTGTTACTTCAT

GGTGGCCGCGCTCTGTGGAGAAGATATTTCCCTCTTCTCTTCAGACTTC

GACCAAAGAAGAGTCCATGAAAACTCGTAAGTTGCTTCCAGCCTTTCTC

AAACCCGAGGCGTTGCAAAAGTATGTGGGGATCATGGATTCCATAGCGA

AGTGGCATTTGGATAACCACTGGGACTTGAATGAAACCGTTACTGTTTT

CCCTCTTGCCAAGCAATACACCTTCATGGTGGCTTGTAGATTGTTCTTG

AGCATAGATGACCCTAAGCACATTGCAAAATTCGCTAACCCATTTCATA

TTTTGGCTGCTGGGGTCATGTCAATACCTATAAACTTCCCTGGGACCCC

ATTCAACCGTGCTATCAAGGCTGCGGATTCCGTAAGAAAGGAGCTCAGA

GCAATAATCAAGCAAAGGAAAATTCAAGTTTTAGCGGGGAAAAGTTCAT

CCTCTAAGCATGATATACTGTCCCATATGCTCACCACAACAGATGAGAA

TGGACAGTTCTTGAATGAGATGGACATTGCGGATAAGATACTTGGTTTG

CTAATTGGTGGCCATGACACTGCAAGTGCTGTCATAACTTTCATCATCA

AGTATCTTGCAGAGTTGCCACAAGTCTACAATGAGGTTTTAAAGGAGCA

AATGGAGGTTGCAGCCGGGAAGAAAAGTGGAGAGATGCTTGATTGGGAG

GACATACAAAGATGAAGTATTCATGGAATGTGGCAAATGAAGTAATGA

GGCTGGCACCACCACTTCAAGGTAGTTTCCGAGAGGCCATAACTGACTT

CACCTATGCTGGTTTCTCCATTCCCAAAGGGTGGAAGTTGTACTGGAGC

ACAAATGCAACACACAAGAACCCTGACTACTTCCCTGATCCGGAGAAAT

TTGATCCTTCAAGGTTTGAAGGAAATGGACCCATTCCTTACACCTATGT

TCCTTTCGGAGGAGGACCACGAATGTGCCCTGGGAAGAGTATGCTCGT

TTGGAAATACTTGTTTTCATACACAATGTTGTGAGACGGTTCAGTTGGT

ATAAACTGCATCCAAATGAAGATGTCATAGTGGATCCAATGCCAATGCC

TGCAAAAGGACTTCCCATTCGCCTTCGTCACCATTAA

SEQ ID No 52. *Populus trichocarpa* hypothetical protein (POPTR_0018s13390g) mRNA, complete cds, XM_002324633
ATGGAGACTCTCTATTTCATCCTTCTCCTCTTTGTCCCCATCATTCTCT

CCCTCGTTGCCATAATTTACAAGCACAGATACCAGGATAAACTCCAAAA

CGTTCCTCCAGGCAATCTAGGCCTCCCTTTTGTGGGAGAGAGCCTAGAT

TTCCTGTCAAAAGGATGGAAAGGTTGCCCAGAAAACTTCATATTCGATC

GCATTCGGAAATATTCGTCAGAAATATTCAAAACAAATCTTTTTCTTCA

GCCTGTAGTGATGTTAAATGGTGTTGCCGGAAACAAGTTCTTATTCTCC

AACGAGAACAGACTTGTTGAAACATGGTGGCCTGATTTTGTGAACAGGA

TATTCCATCTGCAGTAGAAACGTCACCCAAAGAAGAAGCGAAAAGAAT

GCGTAGGTTGTTCCCTCGATTCTTGAAACCTGAGGCCTTGCAGAGGTAT

ATAGGTACCATGGATATGGTTACCAAAAGACACTTTGCCTTGGAGTGGG

GAAACAAAGCAGAGGTGGTTGTCTTCCCTCTGGCAAAAAGCTACACATT

CGAGTTGGCTTGCCGCTTGTTTCTAAGTATTGAAGATCCCAGCCACATA

GCCAGATTTTCCCACCCATTCAACCAAATAACCTCTGGTATTTTTACCA

TCCCCATTGATTTTCCTGGAACTCCATTTAATCGAGCCATCAAGGCCTC

AAAGTTAATCAGAATTGAGCTTTTGGCCATTATCAGGCAAAGAAAGAAG

GATCTTGCAGAAGGAAAGGCATCCCCAACCCAGGACATTTTGTCACACA

TGCTGTTGAGCAATGATGCGGATGGAAAGTACATGAATGAGGTGCAGAT

TTCTGACAAGATTCTTGCATTATTGATGGGTGGACATGAAAGCACTGCT

GCTTCTTGTACTTTCATTGTCAAATATCTTGCTGAGCTGCCTCATATCT

ATGAAGCAGTTTACAAGGAACAAGCTGAGATCATTAAATCCAAAGCACC

CGGTGAGTTGTTGAATTGGGATGACATTCAAAAGATGAAATATTCATGG

AATGTAGCTTGTGAAACGTTGAGACTCTCACCACCGCTTATTGGTAACT

TCAAAGAAGCCATCAAGGACTTCACATTCAACGGGTTCTCCATCCCAAA

GGGCTGGAAGGCAAGTCATTTTCTCACTTTGTATTGGAGTGCAAGCTCG

ACCCATAAAAATCCTGAATACTTTTCTGAGCCTGAAAAGTTCGATCCCA

GTAGATTTGAAGGGAAAGGACCAGCTCCTTACACGTTTATTCCATTTGG

TGGAGGACCAAGGATGTGCCCTGGAAATGAATATGCTCGATTAGAAATT

CTTGTTTTCATGCATAACTTGGTGAAGAGGTTCAAATTTGAAAGATTGA

TTCTCGATGAGAAGATAGTATTCGATCCAACGCCAAAACCAGAAATGGG

ACTTCCAGTTCGTCTGCTTCCTCACAAAGCTTGA

SEQ ID No 53.: *Glycine max* cytochrome P450 716B2-like (LOC100815640), transcript variant X1, mRNA; XM_003531801
ATGGAGCAGTTGTACTACCTCACCCTTGTGCTACTGTTTGTGTCCTTCG

TCTCTGTCTCTTTTTTCATCATTTTCTACAGGCATCGTTCTCCGTTCAG

CGTCCCAACTTGCCGCCGGGGAAGGCGGGGTTTCCGGTGATCGGCGAG

AGCCTGGAGTTTCTGTCGGCGGGACGGAAGGGGCTTCCGGAGAAGTTCT

TCTCCGATCGCATGACAGAGTACTCTTCCAAAGTGTTCAAGACCTCCAT

CTTAGGGGAGCCTACAGTGATTTTCTGTGGAGCCGCATGTAACAAGTTC

TTGTTTTCTAACGAGAACAAACACGTCATTTCGTGGTGGCCTGAAAATG

TCAAGAAGTTGTTCCCAACGAATATTCAAACAAACTCTAAGGAAGAAGC

CAAGAAGTTGAGAAACATTCTCCCTCAGTTCCTCAGCGCCAAAGCCATC

CAACGTTACGTTGGTATTATGGACACTGTTGCCCAAAGCACACTTTGCTC

TGGAGTGGGAGAACAACACCCAAGTCACCGTATTGCCCTTGGCCAAGAG

GTATACCTTTGGGGTGGCTAGCCGTGTGTTCATGAGCATTGATGATTTG

AATCAAGTGGCGAAATTGGCAGAACCTTTAAATCAGGTGAATGCAGGAA

TTATATCAATGCCCATTAACTTCCCCGGAACTGTGTTCAACCGAGGAAT

CAAGGCCTCCAAGTTCATTAGGAGGGAGCTGTTGAGGATTGTCAAGCAG

AGGAAGGTGGAACTAGCTAATGGAATGTCCACACCAACACAAGACATTT

TGTCTCACATGCTAATATATTGTGATGAGAATGGACAATATTTGGCTGA

-continued

```
ACATGATATTGTCAACAAGATCCTTGGCTTGCTGATAGGTAGCCATGAA

ACCACAAGTACTGTTTGCACTTTCGTTGTCAAATACCTTGCCGAGCTCC

CTCAAAATATTTATGAAAATGTCTATCAAGAACAAATGGCGATTGCAAA

ATCCAAAGCTCCAGGAGAGTTGTTGAATTGGGATGACATCCAGAAGATG

AAATATTCATGGAATGTAGCTTGTGAAGTAATAAGGCTTAACCCTCCAG

CCCAAGGAGCTTTTAGGGAAGCCATCAATGACTTTATCTTCGATGGATT

CTCAATTCCAAAAGGCTGGAAGTTGTATTGGAGTGCAAATTCAACTCAC

AAAAATCCAGAGTACTTCCCTGAGCCAGAGAAATTTGATCCAAGCAGAT

TTGAAGGAACTGGACCAGCTCCTTATACTTATGTGCCATTTGGTGGAGG

GCCAAGTATGTGCCCTGGAAAAGAGTATGCGCGAATGGAACTATTGGTG

TTCATGCACAACTTAGTGAAGAGGTTCAAGTGTGAAACTCTTTTTCCTA

ATGGAAATGTTACTTATAACCCTACGCCTATTCCTGCCAAGGGCCTTCC

TGTTCGTCTTATTCCTCACCGATCATGA
```

Moreover, it is preferable that modifications of the above-mentioned sequences, so-called sequence variants, are selected, wherein these modified sequences have a sufficient sequence identity with the above-mentioned sequences in order to be functionally analogous thereto. In this case a sequence identity of at least 70%, preferably 75%, 80% or 85%, particularly preferably 90% or 95% is advantageous. The sequence identity between two sequences can be analyzed by conventional methods, for example with NCBI Blast or Clustal.

In a preferred embodiment the functionally analogous sequence variants code for the same amino acid sequences which are encoded by the sequences SEQ ID NO: 1 to 53 explicitly referred to.

The invention therefore comprises the application of nucleic acid sequences, as well as yeast strains comprising such sequences which code for one or more of the above-mentioned enzymes (preferably according to one of the sequences SEQ ID NO: 54 to 105). The nucleic acid sequences are preferably selected from the group comprising:
a) a nucleic acid molecule comprising a nucleotide sequence according to SEQ ID NO: 1 to SEQ ID NO: 53;
b) a nucleic acid molecule which is complementary to a nucleotide sequence according to a),
c) a nucleic acid molecule which hybridizes with a nucleotide sequence according to a) or b) under stringent conditions (hybridization conditions are known to a person skilled in the art, and are described, for example, in Sam brook, Molecular Cloning, Ed. 1-3, Cold Spring Harbor, N.Y.);
d) a nucleic acid molecule comprising a nucleotide sequence which exhibits a sufficient sequence identity in order to be functionally analogous to a nucleotide sequence according to a), b) or c);
e) a nucleic acid molecule which as a result of the genetic code is degenerated to a nucleotide sequence according to a) to c); and
f) a nucleic acid molecule according to a nucleotide sequence according to a) to e), which by deletions, additions, substitutions, translocations, inversions and/or insertions is modified and functionally analogous to a nucleotide sequence according to a) to e).

In a preferred embodiment of the invention the application of a nucleic acid sequence is provided, which exhibits a sufficient sequence identity in order to be functionally analogous with the nucleic acid sequence according to point a), b) and/or c). In the context of the invention this means that, in order to be functionally analogous to said nucleotide sequences or to sequences hybridizing with these nucleotide sequences, the sequence variant can effectively cause the required production of the pentacyclic triterpenoids in the same or similar quantities. Functionally analogous sequences in the context of the invention are all sequences which the person skilled in the art can identify as equivalent by routine tests.

In particular, the present invention comprises nucleic acid sequences and the use thereof, as well as yeast strains also comprising sequences which code for the following amino acid sequences (according to the sequences SEQ ID NO: 54 to 105):

```
Oxidosqualene cyclases (OSCs)
>gi|18147594|dbj|BAB83087.1| lupeol synthase
[Betula platyphylla] SEQ ID No 54:
MWKLKIAEGGPGLVSGNDFIGRQHWEFDPDAGTPQERAEVEKVREEFTKN

RFQMKQSADLLMRMQLRKENPCQPIPPPVKVKETEVITEEAVITTLRRSL

SFYSSIQAHDGHWPGESAGPLFFLQPFVMALYITGDLNTIFSPAHQKEII

RYLYNHQNEDGGWGFHIEGHSTMFGSALSYIALRILGEGLEDGEDGAMAK

SRKWILDHGGLVAIPSWGKFWVTVLGLYEWSGCNPLPPEFWFLPDIFPIH

PGKMLCYCRLVYMPMSYLYGKRFVGPITGLIQSLRQELYNEPYHQINWNK

ARSTVAKEDLYYPHPLIQDLLWGFLHHVAEPVLTRWPFSMLREKALKAAI

GHVHYEDENSKYLCIGSVEKVLCLIACWAEDPNGEAYKLHLGRIPDNYWV

AEDGLKIQSFGCQMWDAGFAIQAILSCNLNEEYWPTLRKAHEFVKASQVP

ENPSGDFKAMYRHINKGAWTFSMQDHGWQVSDCTAEGLKVAILFSQMPPD

LVGEKIEKERLYDAVNVILSLQSSNGGFPAWEPQRAYGWLEKFNPTEFFE

DTLIEREYVECTSPAVHGLALFRKFYPRHRGTEIDSSIYRGIQYIEDVQE

PDGSWYGHWGICYTYGTVVFAVGALAACGRNYKNCPALRKSCEFLLSKQL

PNGGWGESYLSSQNKVWINIEGNRANLVQTAWALLSLIDARQAEIDPTPI

HRGVRVLINSQMEDGDFPQQEITGVFMRNCTLNYSSYRNIFPIWALGEYR

RRVLFA

>gi|6456434|dbj|BAA86930.1| lupeol synthase
[Olea europaea] SEQ ID No 55:
MWKLKIADGTGPWLTTTNNHIGRQHWEFDPEAGTPDERVEVERLREEFKK

NRFRTKQSADLLMRMQLVKENQRVQIPPAIKIKETEGITEEAVITTLRRA

ISFYSTIQAHDGHWPAESAGPLFFLPPLVLALYVTGAINVVLSREHQKEI

TRYIYNHQNEDGGWGIHIEGHSTMFGSVLSYITLRLLGEGQEDGEDKAVA

RGRKWILDHGGAVGIPSWGKFWLTVLGVYEWDGCNPMPPEFWLLPNFSPI

HPGKMLCYCRLVYMPMSYLYGKRFVGPITGLVLSLRQEIYTEPYHGINWN

RARNTCAKEDLYYPHPLAQDMLWGFLHHFAEPVLTRWPFSKLREKALKVA

MEHVHYEDMNSRYLCIGCVEKVLCLIACWVEDPNSEAYKRHIARIPDYFW

VAEDGLKMQSFGCQMWDAAFAIQAILSSNLAEEYGPTLMKAHNFVKASQV

QENPSGDFNEMYRHTSKGAWTFSMQDHGWQVSDCTAEGLKAALLFSQMPI
```

ELVGAEIETGHLYDAVNVILTLQSASGGFPAWEPQKAYRWLEKLNPTEFF

EDVLIERDYVECTSSAVQALKLFKQLHPGHRRKEIASCISKAIQYIEATQ

NPDGSWDGSWGICFTYGTWFAVEGLVACGKNYHNSPTLRRACEFLLSKQL

PDGGWSESYLSSSNKVYTNLEGNRSNLVQTSWALLSLIKAGQVEIDPGPI

HRGIKLLVNSQMEDGDFPQEEITGAFMKNCTLNYSSYRNIFPIWALGEYR

RRILHAQT

>gi|360038892|dbj|BAL41371.1| lupeol synthase
[*Glycyrrhiza uralensis*] SEQ ID No 56:
MWKLKIGEGGAGLISVNNFIGRQHWEFDPNAGTPQEHAEIERLRREFTKN

RFSIKQSADLLMRMQLRKENHYGTNNNIPAAVKLSDAENITVEALVTTIR

RAISFYSSIQAHDGHWPAESAGPLFFLQPLVMALYITGSLDDVLGPEHKK

EIVRYLYNHQNEDGGWGFHIEGHSTMFGSALSYVALRILGEGPEDKAMAK

GRKWILDHGGLVAIPSWGKFWVTLGAYEWSGCNPLPPELWLLPKFTPFH

PGKMLCYCRLVYMPSYLYGKKFVGPITALIRSLREELYNEPYNQINWNT

ARNTVAKEDLYYPHPLIQDMLWGFLYHVGERFLNCWPFSMLRRKALEIAI

NHVHYEDENSRYLCIGSVEKVLCLIARWVEDPNSEAYKLHLARIPDYFWL

AEDGLKIQSFGCQMWDAAFAIQAILACNVSEEYGPTLRKAHHFVKASQVR

ENPSGDFNAMYRHISKGAWTFSMHDHGWQVSDCTAEGLKAALLLSEMPSE

LVGGKMETERFYDAVNVILSLQSSNGGFPAWEPOKAYRWLEKFNPTEFFE

DTMIEREYVECTGSAMQGLALFRKQYPQHRSKEIDRCIAKAIRYIENMQN

PDGSWYGCWGICYTYGTVVFAVEGLTACGKNCHNSLSLRKACQFLLSKQL

PNAGWGESYLSSQNKVYTNLEGNRANLVQSSWALLSLTHAGQAEIDPTPI

HRGMKLLINSQMEDGDFPQQEITGVFMRNCTLNYSSYRNIFPIWAMGEYR

RQVLCAHSY

>gi|30699380|ref|NP_849903.1| lupeol synthase 1
[*Arabidopsis thaliana*] SEQ ID No 57:
MWKLKIGKGNGEDPHLFSSNNFVGRQTWKFDHKAGSPEERAAVEEARRGF

LDNRFRVKGCSDLLWRMQFLREKKFEQGIPQLKATNIEEITYETTTNALR

RGVRYFTALQASDGHWPGEITGPLFFLPPLIFCLYITGHLEEVFDAEHRK

EMLRHIYCHQNEDGGWGLHIESKSVMFCTVLNYICLRMLGENPEQDACKR

ARQWILDRGGVIflPSWGKFWLSILGVYDWSGTNPTPPELLMLPSFLPIH

PGKILCYSRMVSIPMSYLYGKRFVGPITPLILLLREELYLEPYEEINWKK

SRRLYAKEDMYYAHPLVQDLLSDTLQNFVEPLLTRWPLNKLVREKALQLT

MKHIHYEDENSHYITIGCVEKVLCMLACWVENPNGDYFKKHLARIPDYMW

VAEDGMKMQSFGCQLWDTGFAIQALLASNLPDETDDALKRGHNYIKASQV

RENPSGDFRSMYRHISKGAWTFSDRDHGWQVSDCTAEALKCCLLLSMMSA

DIVGQKIDDEQLYDSVNLLLSLQSGNGGVNAWEPSRAYKWLELLNPTEFM

ANTMVEREFVECTSSVIQALDLFRKLYPDHRKKEINRSIEKAVQFIQDNQ

TPDGSWYGNWGVCFIYATWFALGGLAAAGETYNDCLAMRNGVHFLLTTQR

DDGGWGESYLSCSEQRYIPSEGERSNLVQTSWAMMALIHTGQAERDLIPL

HRAAKLIINSQLENGDFPQQEIVGAFMNTCMLHYATYRNTFPLWALAEYR

KVVFIVN

>gi|83016477|dbj|BAE53430.1| lupeol synthase
[*Lotus japonicus*] SEQ ID No 58:
MWKLKVAEGGKGLVSVSNFIGRQHWVFDPNAGTPQEEHEEIERMRQEFTKN

RFSIKQSADLLMRMQLRKENPCGPIPPAVKLRDVEKVTAEALITTIRRSI

TFYSSIQAHDGHWPAESAGPLFFVQPLVMALYITGSLDDVLGPQHKKEII

RYLYNHQNEDGGWGFHIEGHSTMFGSALSYIALRVLGQSLEDGEDMAVAR

GRKWILDHGGLVAIPSWGKFWVTLGVYEWSGCNPLPPEFWLLPKIFPIH

PGKMLCYCRLVYMPMSYLYGKKFVGPITALVRSLRKELYNEPYDRVDWNK

ARNTVAKEDLYYPHPLIQDMLWGFLHHVGERVLNTVVPFSMLRQKAIEVA

INHVRYEDETTRYLCIGSVEKVLYLIARWVEDPNSEAYKLHLARIPDYFW

LAEDGLKIQSFGCQMWDAAFAIQAILSGNVSEEYGPTLKKAHHFVKASQV

RENPSGDFKAMYRHISKGAWTFSMHDHGWQVSDCTAEGLKVALLLSEMSD

DLVGAKMETEQFYDAVNVILSLQSSNGGFPAWEPQRAYQWLEKFNPTEFF

EETLIEREYVECTGSAMQALALFRKLYPKHRRKEIDRCISKAIRYIENTQ

NPDGSWYGCWGICYTYGTVVFAVEGLTACGKNFQNSVTLRRACKFLLSKQ

LPNGGWGESYLSSQDKVYTNIEGKRANLVQSSWALLSLMRAGQAEIDPTP

IHRGIRLLINSQMDDGDFPQQEITGVFMRNCTLNYSSYRNIFPIWALGEY

RRRVLCA

>gi|82468803|gb|ABB76766.1| lupeol synthase
[*Ricinus communis*] SEQ ID No 59:
MWRIKIAEGGNNPYIYSTNNFQGRQIWVFDPNAGTPEEQAEVEEARQNFW

KNRFQVKPNSDLLWQLQFLREKNFKQKIPKVKVEDGEEITSEIAAAALRR

SVHLFSALQASDGHWCAENGGLLFFLPPLVFAVYITGHLNTVFSPEHRKE

ILRYIYCHONEDGGWGIHIEGHSTMFCTVLNYICMRILGEARDGGIENAC

ERGRKWILDHGGATGISSWGKTWLSILGVYEWDGTNPMPPEFWAFPSSFP

LHPAKMFCYCRITYMPSYLYGKRFVGPITPLILQIREEIYNEPYNKIKW

NSVRHLCAKEDNYFPHPTIQKLLWDALYTFSEPLFSRWPFNKLREKALKI

TMDHIHYEDHNSRYITIGCVEKPLCMLACWIEDPHGEAFKKHLARIADYI

WVGEDGIKMQSFGSQTWDTSLALQALIASDLSHEIGPTLKQGHVFTKNSQ

ATENPSGDFRKMFRHISKGAWTFSDKDQGWQVSDCTAESLKCCLLFSMMP

PEIVGEKMEPEKVYDSVNILSLQSNQGGFTAWEPARAGSWMEWLNPVEF

MEDLVVEHEYVECTSSAIQALVLFKKLYPRHRNKEIENCIINAAQFIENI

QEPDGSWYGNWGICFSYGTWFALKGLAAAGRTYENCSAIRKGVDFLLKSQ

RDDGGWAESYLSCPKKVYVPFEGNRSNLVQTAWAMMGLIYGGQAKRDPMP

LHRAAKLLINSQTDLGDFPQQELTGAFMRNCMLHYALFRNTFPIWALAEY

RRHVLFPSAGFGFGFTNNL

>gi|6456467|dbj|BAA86932.1| lupeol synthase
[*Taraxacum officinale*] SEQ ID No 60:
MWKLKIAEGGDDEWLTTTNNHVGRQHWQFDPDAGTEEERAEIEKIRLNFK

LNRFQFKQSADLLMRTQLRKENPINKIPDAIKLNETEEVTNDAVTTTLKR

AISFYSTIQAHDGHWPAESAGPLFFLPPLVIALYVTGAMNDILTPAHQLE

IKRYIYNHQNEDGGWGLHIEGHSTIFGSVLSYITLRLLGEEADSVAEDMA

LVKGRKWILDHGGAVGIPSWGKFWLTILGVYEWGGCNPMPPEFWLMPKFF

-continued
PIHPGKMLCYCRLVYMPMSYLYGKRFVGKITELVRDLRQELYTDPYDEIN

WNKARNTCAKEDLYYPHPFVQDMVWGVLHNVVEPVLTSRPISTLREKALK

VAMDHVHYEDKSSRYLCIGCVEKVLCLIATWVEDPNGDAYKRHLARIPDY

FWVAEDGMKMQSFGCQMWDAAFAIQAIFSSNLTEEYGPTLKKAHEFVKAS

QVRDNPPGDFSKMYRHTSKGAWTFSIQDHGWQVSDCTAEGLKVSLLYSQM

NPKLVGEKVETEHLYDAVNVILSLQSENGGFPAWEPQRAYAWLEKFNPTE

FFEDVLIEREYVECTSSAIQGLTLFKKLHPGHRTKEIEHCISRAVKYVED

TQESDGSWYGCWGICYTYGTWFAVDALVACGKNYHNCPALQKACKFLLSK

QLPDGGWGESYLSSSNKVYTNLEGNRSNLVHTSWALISLIKAGQAEIDPT

PISNGVRLLINSQMEEGDFPQQEITGVFMKNCNLNYSSFRNIFPIWALGE

YRRIVQNI

>gi|41687978|dbj|BAD08587.1| lupeol synthase
[Glycyrrhiza glabra] SEQ ID No 61:
MWKLKIGEGGAGLISVNNFIGRQHWEFDPNAGTPQEHAEIERLRREFTKN

RFSIKQSADLLMRMQLRKENHYGTNNNIPAAVKLSDAENITVEALVTTIT

RAISFYSSIQAHDGHWPAESAGPLFFLQPLVMALYITGSLDDVLGPEHKK

EIVRYLYNHQNEDGWGFHIEGHSTMFGSALSYVALRILGEGPQDKAMAK

GRKWILDHGGLVAIPSWGKFWVTVLGAYEWSGCNPLPPELWLLPKFAPFH

PGKMLCYCRLVYMPSYLYGKKFVGPITALIRSLREELYNEPYNQINWNT

ARNTVAKEDLYYPHPLIQDMLWGFLYHVGERFLNCWPFSMLRRKALEIAI

NHVHYEDENSRYLCIGSVEKVLCLIARWVEDPNSEAYKLHLARIPDYFWL

AEDGLKIQSFGCQMWDAAFAIQAILACNVSEEYGPTLRKAHHFVKASQVR

ENPSGDFNAMYRHISKGAWTFSMHDHGWQVSDCTAEGLKAALLLSEMPSE

LVGGKMETERFYDAVNVILSLQSSNGGFPAWEPQKAYRWLEKFNPTEFFE

DTMIEREYVECTGSAMQGLALFRKQFPQHRSKEIDRCIAKAIRYIENMQN

PDGSWYGCWGICYTYGTWFAVEGLTACGKNCHNSLSLRKACQFLLSKQLP

NAGWGESYLSSQNKVYTNLEGNRANLVQSSWALLSLTHAGQAEIDPTPIH

RGMKLLINSQMEDGDFPQQEITGVFMRNCTLNYSSYRNIFPIWAMGEYRR

QVLCAHSY

>gi|392621787|gb|AFM82492.1| lupeol synthase
[Eleutherococcus trifoliatus] SEQ ID No 62:
MWKLKIAEGDKNDPYLYSTNNFVGRQTWEFDPDYVGSPGELEEVEEARRQ

FWENRYKVKPCGDLLWRMQFLREKNFKQTIPQVKVGDDEAVTYDAATTTL

RRAVHFFSALQASDGHWPAEIAGPLFFLPPLVMCVYITGHLDTVFPAKHR

KEILRYIYCHQNENGGGGLHIEGHSTMFGTTFSYICMRILGKGPDGGVNN

ACAKGRKWILDHGSATAIPSWGKTINLSILGVYEWTGSNPMPPEFWLLPS

SLSVHPAKMLCYCRMVYLPMSYLYGKRFVGPITLILQLKEELYAQPYNE

IRWGKVRHVCAKEDIYYPHPLIQDLLWDSLHVLAEPLLTRWPFNKLREKA

LQTTMKHIHYEDENSRYITIGCVEKILCMLACWVEDPNGDYFKKHLARIP

DYLWVAEDGMKMQSFGSQEWDIGFGIQALLASDLTHELGPTLMKGHDFIK

KSQVKDNPSGDFKSMYRHISKGSWIFSDQDHGWQVSDCTAEGLKCCLIFS

TMPEEIVGKKMEPELLYNSVNVLLSLQSKNGGVAAWEPATAQDWLELFNP

TEFFADTIIEHEYVECTSSAIQALTLFKKLYPGHRKKEIDNFITNAIRFI

EDIQIPDGSWYGNWGVCFTYGTWFALGGLAAGGKTYNNCAAVRKAVNFLL

ESQLDDGGWGESHLSCPRKVYVPLEGNRSNLVHTGWALMGLIHSGQAERD

PTPLHRAAKLLINSQMEDGDFPQQEITGAFMKNCMLHYAVYRNIYPLWAL

AEYRRRVPLPTLGA

>gi|300807980|gb|ADK35126.1| lupeol synthase
[Kalanchoe daigremontiana] SEQ ID No 63:
MWKLKIADGGSNPYIFTTNNFVGRQIWEFDPQATDPQQLAKVEAARLDFY

HNRYKLKPNSDLLWRMQFLEEKAFTQTIPQVKVEDGEEVSYEAVTAALRR

GVHLYSALQASDGHWPAENAGPMFFMPPMVMCLYITGHLNAIFTEEHRSE

TLRYIYYHQNEDGGWGFHIEGHSTMFGTVLNYICMRLLGEGPEGGQDNAV

SRGRKWILDHGGATSIPSWGKTWLSIMGLCDWSGCNPMPPEFWLLPSYLP

MHPGKMWCYCRMVYMPMSYLYGKRFTARITPLILQLREEIHIQPYDQIDW

KKVRHVCCKEDMYYPHPLLQDLLWDTLYLTTEPLLTRWPLNKLIRKRALQ

TTMKIHYEDENSRYITIGCVEKVLCMLACWVEDPNGDYFKKHLARIPDY

LWIAEDGMKMQSFGSQHWDTAFSIQALLASNMAEEIGITLAKGHDFIKKS

QVKDNPSGDFKGMYRHISKGAWIFSDQDHGWQVSDCTAEGLKCCLLFSMM

QPEVVGESMAPESLYNSVNVLLSLQSQNGGLPAWEPAGAPEWLELLNPTE

FFENIVIEHEYVECTSSAVQALVLFKKLYPLHRRKEVERFITNGAKYLED

IQMPDGSWYGNWGVCFTYGAWFALEGLSAAGKTYNNCAAVRKGVDFLLNI

QLEDGGWGESYQSCPDKKYVPLEDNRSNLVQTSWALMGLIYAGQADRDPT

PLHRAAQLLINSQLEDGDFPQQEITGVFQRNCMLHYAAYRNIFPLWALAE

YRRQIQLHSEATKMV

>gi|157679393|dbj|BAF80444.1| Lupeol synthase
[Bruguiera gymnorhiza] SEQ ID No 64:
MWRLKIAEGGNNPYIYSTNNFVGRQTWEFDPEAGTPEERAQVEEARENFW

RDRFLIKPSSDLLWRFQFLSEKKFKQRIPQVKVQDGEEITREIATTALRR

SVHLVSALQASDGHWCAENSGPMFFVPPMVFSLYITGHLNAVFSAEHCKE

ILRYIYCHPNEDGGWGLHIEGHSAMFSTVLNYNWLGKLGEGRDGGKDNAC

ERARRRILDHGSATAISSWGKTWLAILGVYEWDGCNPMPPEFWAFPTFFP

IHPARMLCYCRLTYMAMSYLYGKKFVGPITPLILQLREEIYNEPYDQINW

SRMRHLCAKEDNYYAHTLTQIILWDAIYMLGEPLLKRWPFNKLREKALKI

TMDHIHYEDENSQYITIGSVEKPLLMLACWHEDPNGDAFKKHLARIPDYV

WLGEDGIKIQSFGSQVWDTSFVLQALIASNLPSETGPTLEKGHNFIKNSQ

VTQNPSGDFRRMFRHISKGSWTFSDKDHGWQVSDCTAESLKCCLLFSMMP

PELVGEKMGPQRMYDAVNVIISLQSKNGGCSAWEPAGAGSWMEWLNPVEF

LADLVIEHEYVECTSSSLQALVLFKKLYPEHRRKEIEIFILNAVRFTEEI

QQPDGSWYGNWGICFLSGTWFGLKGLAAAGKTYYNCTAVRKGVEFLLQTQ

RDDGGWGESYLSCPKKIYVPLEGNRSNLVQTALAMMGLILGGQGERDPTP

LHRAAKLLINSQTELGDFPQQELSGCFMRNCMLHYSEYRDIFPTWALAEY

CKLFPLPSKND

>gi|18147596|dbj|BAB83088.1| beta-amyrin synthase [Betula platyphylla] SEQ ID No 65:
MWRLKIADGGSDPYIYSTNNFVGRQTVVEFDPQAGSPQERAEVEEARRNF
YDNRYQVKPSGDLLWRMQFLKEKNFKQTIPPVKVEDGEEITYEKSTAALR
RAVHFYSALQASDGHWPAENAGPLFFLPPLVMCMYITGHLNTVFPAEHQK
EILRYIYYHQNEDGGWGLHIEGHSTMFCTALSYICMRILGEGPDGGQDNA
CARARKWILDHGGVTHMPSWGKTWLSILGIFEWIGSNPMPPEFWILPSFL
PMHPAKMWCYCRMVYMPMSYLYGKRFVGPITPLILQLREELYTQPYHQVN
WKKVRHLCAKEDIYYPHPLIQDLLWDSLYIFTEPLLTRWPFNKLVREKAL
QVTMKHIHYEDENSRYITIGCVEKVLCMLACWVEDPNGDYFKKHIARIPD
YIWVAEDGIKMQSFGSQEWDTGFAIQALLASNLTDEIGPTLARGHDFIKK
SQVKDNPSGDFESMHRHISKGSWTFSDQDHGWQVSDCTAEGLKCCLLFSI
MPPEIVGEKMEPEQLYDSVNVLLSLQSKNGGLAAWEPAGAQEWLELLNST
EFFADIVIEHEYIECTASAMQTLVLFKKLYPGHRKKEIENFIKNAAQFLQ
VIQMPDGSWYGNWGVCFTYGTWFALGGLAAVGKTYNNCLAVRRAVDFLLR
AQRDNGGWGESYLSCPKKEYVPLEGNKSNLVHTAWAMMGLIHAGQAERDP
TPLHRAAKLIINSQLEDGDFPQQEITGVFMKNCMLHYAAYKNIYPLWALA
EYRKHVPLPLGKNLNQVVNCIGQSLYKKYKD NADPH-cytochrome P450 Reduktase (CPRs):

>gi|197209812|dbj|BAG68945.1| cytochrome P450 reductase [Lotus japonicus] SEQ ID No 66:
MEESSSMKISPLDLMSAMIKGTLDPSNVSSTSGAGSVFLENREFVMLTT
SIAVLIGCVVVFIWRRSTGNKAKSIEPPKRVVEKLSDEAEVDDGTRKVTI
FFGTQTGTAEGFAKAIAEEAKVRYEKAKFKIVDMDDYAQDDDEYEEKLKK
ETLALFFLATYGDGEPTDNAARFYKWFLEGDEKEEGWLRNLEYAVFGLGN
RQYEHFNKVAIEVDDKLADFGGKRLVKVGLGDDDQCIEDDFTAWKEELWP
ALDELLRGDDDTTVSTPYTAAVLEYRVVIHDPLDASVDEKKWHNVNGHAI
VDAQHPVRSNVAVRKELHTPVSDRSCTHLEFDISGTGVAYETGDHVGVYC
ENLSETVEEAVRLLGLSPDTYFSVHTDDEDGKPLSGSSLPPTFPPCTLRT
AIARYADVLSSPKKSVLLALAAHASNPSEADRLRHLASPAGKDEYSEWVI
ASQRSLLEVMAEFPSAKPPIGVFFAAIAPRLQPRFYSISSSPRMAPSRIH
VTCALVNDKMPTGRIHRGVCSTWMKNSVPLEKSQDCSWAPIFVRQSNFKL
PADNKVPIIMIGPGTGLAPFRGFLQERLALKEDGAELGPSVLFFGCRNRQ
MDYIYEDELNHFVNSGALSELIVAFSREGPTKEYVQHKMMEKASDIWNMI
SQGAYIYVCGDAKGMARDVHRTLHTILQEQGSLDSSKAEGMVKNLQLNGR
YLRDVW >gi|16187|emb|CAA46814.1| NADPH-ferrihemoprotein reductase [Arabidopsis thaliana] SEQ ID No 67:
MTSALYASDLFKQLKSIMGTDSLSDDVVLVIATTSLALVAGFVVLLWKKT
TADRSGELKPLMIPKSLMAKDEDDDLDLGSGKTRVSIFFGTQTGTAEGFA
KALSEEIKARYEKAAVKVIDLDDYAADDDQYEEKLKKETLAFFCVATYGD
GEPTDNAARFSKWFTEENERDIKLQQLAYGVFALGNRQYEHFNKIGIVLD
EELCKKGAKRLIEVGLGDDDQSIEDDFNAWKESLWSELDKLLKDEDDKSV
ATPYTAVIPEYRVVTHDPRFTTQKSMESNVANGNTTIDIHHPCRVDVAVQ
KELHTHESDRSCIHLEFDISRTGITYETGDHVGVYAENHVEIVEEAGKLL
GHSLDLVFSIHADKEDGSPLESAVPPPFPGPCTLGTGLARYADLLNPPRK
SALVALAAYATEPSEAEKLKHLTSPDGKDEYSQWIVASQRSLLEVMAAFP
SAKPPLGVFFAAIAPRLQPRYYSISSCQDWAPSRVHVTSALVYGPTPTGR
IHKGVCSTWMKNAVPAEKSHECSGAPIFIRASNFKLPSNPSTPIVMVGPG
TGLAPFRGFLQERMALKEDGEELGSSLLFFGCRNRQMDFIYEDELNNFVD
QGVISELIMAFSREGAQKEYVQHKMMEKAAQVWDLIKEEGYLYVCGDAKG
MARDVHRTLHTIVQEQEGVSSSEAEAIVKKLQTEGRYLRDVW >gi|18139|emb|CAA49446.1| NADPH-ferrihemoprotein reductase [Catharanthus roseus] SEQ ID No 68:
MDSSSEKLSPFELMSAILKGAKLDGSNSSDSGVAVSPAVMAMLLENKELV
MILTTSVAVLIGCVVVLIWRRSSGSGKKVVEPPKLIVPKSVVEPEEIDEG
KKKFTIFFGTQTGTAEGFAKALAEEEAKARYEKAVIKVIDIDDYAADDEEY
EEKFRKETLAFFILATYGDGEPTDNAARFYKWFVEGNDRGDWLKNLQYGV
FGLGNRQYEHFNKIAKVVDEKVAEQGGKRIVPLVLGDDDQCIEDDFAAWR
ENVWPELDNLLRDEDDTTVSTTYTAAIPEYRVVFPDKSDSLISEANGHAN
GYANGNTVYDAQHPCRSNVAVRKELHTPASDRSCTHLDFDIAGTGLSYGT
GDHVGVYCDNLSETVEEAERLLNLPPETYFSLHADKEDGTPLAGSSLPPP
FPPCTLRTALTRYADLLNTPKKSALLALAAYASDPNEADRLKYLASPAGK
DEYAQSLVANQRSLLEVMAEFPSAKPPLGVFFAAIAPRLQPRFYSISSSP
RMAPSRIHVICALVYEKTPGGRIHKGVCSTWMKNAIPLEESRDCSWAPIF
VRQSNFKLPADPKVPVIMIGPGTGLAPFRGFLQERLALKEEGAELGTAVF
FFGCRNRKMDYIYEDELNHFLEIGALSELLVAFSREGPTKQYVQHKMAEK
ASDIWRMISDGAYVYVCGDAKGMARDVHRTLHTIAQEQGSMDSTQAEGFV
KNLQMTGRYLRDVW >gi|357465233|ref|XP_003602898.1| NADPH cytochrome P450 reductase [Medicago truncatula] SEQ ID No 69:
MTSSNSDLVRTIESVLGVSLGDSVSDSVVLIVTTSAAVIIGLLVFLWKKS
SDRSKELKPVIVPKSLVKEEDDDADIADGKTKVTVFFGTQTGTAEGFAKA
LAEEIKARYEKAFVKVVDMDDYAADDDQYEEKLKKETLAFFMLATYGDGE
PTDNAARFYKWFTEGKDERGTWLQQLTYGVFGLGNRQYEHFNKIGKVVDD
DLSEQGAKRLVPLGMGDDDQSIEDDFNAWKESLWPELDQLLRDEDDVNTV
STPYTAAISEYRVVFHDPTVTPSYENHFNAANGGAVFDIHHPCRANVAVR
RELHKPQSDRSCIHLEFDVSGTGVTYETGDHVGVYADNCDETVKEAGKLL
GQDLDLLFSLHTDNEDGTSLGGSLLPPFPGPCTVRTALARYADLLNPPRK
AALIALAAHASEPSEAERLKFLSSPQGKDEYSKWVVGSHRTLLEVMADFP
SAKPPLGVFFAAIAPRLQPRYYSISSSPRFAPQRVHVTCALVEGPTPTGR
IHKGVCSTWMKNAIPSEESRDCSWAPIFIRPSNFKLPADPSIPIIMVGPG
TGLAPFRGFLQERFALKEDGVQLGPALLFFGCRNRQMDFIYEEELNNFVE
QGSLSELIVAFSREGPEKEYVQHKMMDKASYFWSLISQGGYLYVCGDAKG
MARDVHRTLHTIVQQQENADSSKAEATVKKLQMDGRYLRDVW >gi|6321832|ref|NP_011908.1| Ncp1p [*Saccharomyces cerevisiae* S288c] SEQ ID No 70:
MPFGIDNTDFTVLAGLVLAVLLYVKRNSIKELLMSDDGDITAVSSGNRDI
AQVVTENNKNYLVLYASQTGTAEDYAKKFSKELVAKFNLNVMCADVENYD
FESLNDVPVIVSIFISTYGEGDFPDGAVNFEDFICNAEEAGALSNLRYNMF
GLGNSTYEFFNGAAKKAEKHLSAAGAIRLGKLGEADDGAGTTDEDYMAWK
DSILEVLKDELHLDEQEAKFTSQFQYTVLNEITDSMSLGEPSAHYLPSHQ
LNRNADGIQLGPFDLSQPYIAPIVKSRELFSSNDRNCIHSEFDLSGSNIK
YSTGDHLAVWPSNPLEKVEQFLSIFNLDPETIFDLKPLDPTVKVPFPTPT
TIGAAIKHYLEITGPVSRQLFSSLIQFAPNADVKEKLTLLSKDKDQFAVE
ITSKYFNIADALKYLSDGAKWDTVPMQFLVESVPQMTPRYYSISSSSLSE
KQTVHVTSIVENFPNPELPDAPPVVGVTTNLLRNIQLAQNNVNIAETNLP
VHYDLNGPRKLFANYKLPVHVRRSNFRLPSNPSTPVIMIGPGTGVAPFRG
FIRERVAFLESQKKGGNNVSLGKHILFYGSRNTDDFLYQDEWPEYAKKLD
GSFEMVVAHSRLPNTKKVYVQDKLKDYEDQVFEMINNGAFIYVCGDAKGM
AKGVSTALVGILSRGKSITTDEATELIKMLKTSGRYQEDVW >gi|161891|emb|CAA46815.1| NADPH-ferrihemoprotein reductase [*Arabidopsis thaliana*] SEQ ID No 71:
MSSSSSSSTSMIDLMAAIIKGEPVIVSDPANASAYESVAAELSSMLIENR
QFAMIVTTSIAVLIGCIVMLVWRRSGSGNSKRVEPLKPLVIKPREEEIDD
GRKKVTIFFGTQTGTAEGFAKALGEEAKARYEKTRFKIVDLDDYAADDDE
YEEKLKKEDVAFFFLATYGDGEPTDNAARFYKWFTEGNDRGEWLKNLKYG
VFGLGNRQYEHFNKVAKVVDDILVEQGAQRLVQVGLGDDDQCIEDDFTAW
REALWPELDTILREEGDTAVATPYTAAVLEYRVSIHDSEDAKFNDITLAN
GNGYTVFDAQHPYKANVAVKRELHTPESDRSCIHLEFDIAGSGLTMKLGD
HVGVLCDNLSETVDEALRLLDMSPDTYFSLHAEKEDGTPISSSLPPPFPP
CNLRTALTRYACLLSSPKKSALVALAAHASDPTEAERLKHLASPAGKDEY
SKWVVESQRSLLEVMAEFPSAKPPLGVFFAGVAPRLQPRFYSISSSPKIA
ETRIHVTCALVYEKMPTGRIHKGVCSTWMKNAVPYEKSEKLFLGRPIFVR
QSNFKLPSDSKVPIIMIGPGTGLAPFRGFLQERLALVESGVELGPSVLFF
GCRNRRMDFIYEEELQRFVESGALAELSVAFSREGPTKEYVQHKMMDKAS
DIWNMISQGAYLYVCGDAKGMARDVHRSLHTIAQEQGSMDSTKAEGFVKN
LQTSGRYLRDVW >gi|397771304|gb|AF064618.1| cytochrome P450 reductase [*Artemisia annua*] SEQ ID No 72:
MQSTTSVKLSPFDLMTALLNGKVSFDTSNTSDTNIPLAVFMENRELLMIL
TTSVAVLIGCVVVLVWRRSSAAKRAAESPVIVVPKKVTEDEVDDGRKKV
TVFFGTQTGTAEGFAKALVEEAKARYEKAVFKVIDLDDYAAEDDEYEEKL
KKESLAFFFLATYGDGEPTDNAARFYKWFTEGEEKGEWLEKLQYAVFGLG
NRQYEHFNKIAKVVDEKLTEQGAKRLVPVGMGDDDQCIEDDFTAWKELVW
PELDQLLRDEDDTSVATPYTAAVAEYRVVFHDKPETYDQDQLTNGHAVHD
AQHPCRSNVAVKKELHSPLSDRSCTHLEFDISNTGLSYETGDHVGVYVEN
LSEVVDEAEKLIGLPPHTYFSIHADNEDGTPLGGASLPPPFPPCTLRKAL ASYADVLSSPKKSALLALAAHATDSTEADRLKFLASPAGKDEYAQWIVAS
HRSLLEVMEAFPSAKPPLGVFFASVAPRLQPRYYSISSSPKFAPNRIHVT
CALVYEQTPSGRVHKGVCSTWMKNAVPMTESQDCSWAPIYVRTSNFRLPS
DPKVPVIMIGPGTGLAPFRGFLQERLAQKEAGTELGTAILFFGCRNRKVD
FIYEDELNNFVETGALSELVTAFSREGATKEYVQHKMTQKTSDIWNLLSE
GAYLYVCGDAKGMAKDVHRTLHTIVQEQGSLDSSKAELYVKNLQMAGRYL
RDVW >gi|115499487|gb|AB198819.1| cytochrome P450 reductase [*Artemisia annua*] SEQ ID No 73:
MQSTTSVKLSPFDLMTALLNGKVSFDTSNTSDTNIPLAVFMENRELLMIL
TTSVAVLIGCVVVLVWRRSSSAAKKAAESPVIVVPKKVTEDEVDDGRKKV
TVFFGTQTGTAEGFAKALVEEAKARYEKAVFKVIDLDDYAAEDDEYEEKL
KKESLAFFFLATYGDGEPTDNAARFYKWFTEGEEKGEWLDKLQYAVFGLG
NRQYEHFNKIAKVVDEKLVEQGAKRLVPVGMGDDDQCIEDDFTAWKELVW
PELDQLLRDEDDTSVATPYTAAVAEYRVVFHDKPETYDQDQLTNGHAVHD
AQHPCRSNVAVKKELHSPLSDRSCTHLEFDISNTGLSYETGDHVGVYVEN
LSEVVDEAEKLIGLPPHTYFSVHADNEDGTPLGGASLPPPFPPCTLRKAL
ASYADVLSSPKKSALLALAAHATDSTEADRLKFLASPAGKDEYAQWIVAS
HRSLLEVMEAFPSAKPPLGVFFASVAPRLQPRYYSISSSPRFAPNRIHVT
CALVYEQTPSGRVHKGVCSTWMKNAVPMTESQDCSWAPIYVRTSNFRLPS
DPKVPVIMIGPGTGLAPFRGFLQERLAQKEAGTELGTAILFFGCRNRKVD
FIYEDELNNFVETGALSELVTAFSREGATKEYVQHKMTQKASDIWNLLSE
GAYLYVCGDAKGMAKDVHRTLHTIVQEQGSLDSSKAELYVKNLQMAGRYL
RDVW >gi|83854017|gb|ABC47946.1| cytochrome P450 reductase [*Artemisia annua*] SEQ ID No 74:
MQSTTSVKLSPFDLMTALLNGKVSFDTSNTSDTNIPLAVFMENRELLMIL
TTSVAVLIGCVVVLVWRRSSSAAKKAAESPVIVVPKKVTEDEVDDGRKKV
TVFFGTQTGTAEGFAKALVEEAKARYEKAVFKVIDLDDYAAEDDEYEEKL
KKESLAFFFLATYGDGEPTDNAARFYKWFTEGEEKGEWLDKLQYAVFGLG
NRQYEHFNKIAKVVDEKLVEQGAKRLVPVGMGDDDQCIEDDFTAWKELVW
PELDQLLRDEDDTSVATPYTAAVGEYRVVFHDKPETYDQDQLTNGHAVHD
AQHPCRSNVAVKKELHSPLSDRSCTHLEFDISNTGLSYETGDHVGVYVEN
LSEVVDEAEKLIGLPPHTYFSVHTDNEDGTPLGGASLPPPFPPCTLRKAL
ASYADVLSSPKKSALLALAAHATDSTEADRLKFFASPAGKDEYAQWIVAS
HRSLLEVMEAFPSAKPPLGVFFASVAPRLQPRYYSISSSPKFAPNRIHVT
CALVYEQTPSGRVHKGVCSTVMKNAVPMTESQDCSWAPIYVRTSNFRLP
SDPKVPVIMIGPGTGLAPFRGFLQERLAQKEAGTELGTAILFFGCRNRKV
DFIYEDELNNFVETGALSELVTAFSREGATKEYVQHKMTQKASDIWNLLS
EGAYLYVCGDAKGMAKDVHRTLHTIVQEQGSLDSSKAELYVKNLQMAGRY
LRDVW >gi|13183562|gb|AAK15259.1| AF302496_1 NADPH-
cytochrome P450 oxydoreductase isoform 1 [*Populus
trichocarpa x Populus deltoides*] SEQ ID No 75:
MSSGGSNLARFVQSVLGISFGDSLSDSVVVIITTSFAALVGLVVVLVLKRS

SDRSKDVKPLVVPKSLSIKDEEDESEALGGKTKVTIFYGTQTGTAEGFAK

ALAEEVKARYEKAAVKVFDLDDYAMEDDQYEEKLKKETLALFMVATYGDG

EPTDNAARFYKWFTEGNERGIWLQQLSYGVFGLGNRQYEHFNKIAKVLDD

LLYEQGGKRLVPVGLGDDDQCIEDDFSAWKEFLWPELDQLLRDEDDVNAP

STPYTAAIPEYRLVIHDPSIISVEDKFSNLANGNVSFDIHHPCRVNVAVQ

KELHKAESDRSCIHLEFDITGTGITYETGDHLGVYAENSDETVEEAGKLL

DKPLDLLFSIHADNEDGTAIGSSLPPPFPGPCTLHTALACYADLLSPPKK

AALLALAAHASEPSEADRLKFLSSPQGKNEYSHWVMASQRSLLEVMAEFP

SSKPPLGIFFAAVAPRLQPRYYSISSSPRYTPNRVHVTCALVYGPTPTGR

IHKGVCSTWMKNAVPLEKSYECSWAPIFTRTSNFKLPADPSTPIIMVGPG

TGLAPFRGFLQERIALKEDGVKLGPALLFFGCRNRRMDFIYEDELNNFVE

QGVISELIVAFSREGPQKEYVQHKMVDRAAEIWTIISQGGYFYVCGDAKG

MARDVHRTLHTIVQEQGGLDSSKTESMVKKLQMEGRYLRDVW

>gi|13183564|gb|AAK15260.1| AF302497_1 NADPH-
cytochrome P450 oxydoreductase isoform 2 [*Populus
trichocarpa x Populus deltoides*] SEQ ID No 76:
MqSSSSSMKVSPLELMQAIIKGKVDPINVSSESGGSAAEMATLIRENREF

VIILTTSIAVLIGYVVVLIWRRSSGYQKPKVPVPPKPLIVKDLEPEVDDG

KKKVTIFFGTQTGTAEGFAKALAEEEAKARYEKAIFKTVDLDDYAEDDDEY

EEKLKKESLAIFFLATYGDGEPTDNAARFYKWFTDGNERGEWLKELPYAV

FGLGNRQYEHFNKIAIVVDKILGNQGGKQLVPVGLGDDDQCMEDDFAAWR

ELLWPELDQLLLDGDDPTGVSTPYTAAVAEYRVVLHDPEDAPLEDDNWSN

ANGHAIYDAQHPCRANVTVRRELHTPASDRSCTHLEFDISGTGLVYGTGD

HVGVYCENLSEIVEEALQLLGLSPDIYFTIHTDNEDGTPLSGSALPPPFP

SSTLRTALTRYADLLSSPKKSALMALAAHATNPTEADRLRHLASPAGKDE

YAQWIVANHRSLLEVMAEFPSAKPPLGVFFASVAPRLLPRYYSISSSPSM

APSRIHVTCALVLEKTPAGRIHKGVCSTVVMKNAVPLEKSHDCSWAPIFV

RQSNFKLPADTKVPIIMIGPGTGLAPFRGFLQERLAQKEAGAELGSSVLF

FGCRNRQMDFIYEDELNNFVESGALSELSVAFSREGPTKEYVQHKMMQKA

SDIWNMISQGGYLYVCGDAKGMAKDVHRTLHTIVQEQGSLDNSKTESFVK

GLQMNGRYLRDVW

>gi|13183566|gb|AAK15261.1| AF302498_1 NADPH-
cytochrome P450 oxydoreductase isoform 3 [*Populus
trichocarpa x Populus deltoides*] SEQ ID No 77:
MESSSSSIKVSPLDLMQAIIKGKVDPANVSSESGGSVAEVATLILENREF

VMILTTSIAVLIGCVVVLIWRRSSGYQRPKVPVPPKPLIVKDLEPEVDDG

KKKVTIFFGTQTGTAEGFAKALAEEEAKARYDKATFKTVDMDDYAGDDDEY

EEKLKKEDLVIFFLATYGDGEPTDNAARFYKWFTEGNERGEWLKDLPYAV

FGLGNRQYEHFNKIAIVVDKIFADQGGKRLAPVGLGDDDQCMEDDFAAWR

ELLWPEMDQLLLDGDDPTAVSTPYAATVSEYRVVFHSPEDAPLEDDNWSN

ANGHAVYDAQHPCRANVAVRRELHTPASDRSCTHLEFEISGTGLAYGTGD

HVGVYCENLSETVEEALQLLGLSPDTYFSIHNDNEDGTPLSGGALPPPFP

PSTLKTALARYADLLSLPKKSALMALAAHATDPTEADRLRHLASPAGKDE

YAQLLVANQRSLLEVMAEFPSAKPPLGVFFASVAPRLQPRYYSISSSPRM

APSRIHVICALVLEKTLGGRIHKGVCSTVVMKNAVPLEKSHDCSWAPVFV

RQSNFKLPADAKVPIIMIGPGTGLAPFRGFLQERLALKEAGSELGSSVLF

FGCRNRKMDFIYEDELNNFVESGALSELVVAFSREGPTKEYVQHKMMQKA

SDIWNMISQGGYLYVCGDAKGMAKDVHRALHTIVQEQGSLDNSKTESFVK

SLQMNGRYLRDVW

>gi|295448|gb|AAA34240.1| NADPH cytochrome P450
[*Vigna radiata*] SEQ ID No 78:
MASNSDLVRAVESFLGVSLGDSVSDSLLLIATTSAAVVVGLLVFLWKKSS

DRSKEVKPVVVPRDLMMEEEEEVDVAAGKTKVTIFFGTQTGTAEGFAKAL

AEEIKARYEKAAVKVVDLDDYAADDDLYEEKLKKESLVFFMLATYGDGEP

IDNAARFYKWFTEGKDERGIWLQKLTYGVFGLGNRQYEHFNKIGKVVDEE

LAEQGAKRLVAVGLGDDDQSIEDDFSAWKESLWSELDQLLRDEDDANTVS

TPYTAAILEYRVVIHDPTAASTYDNHSTVANGNTEFDIHHPCRVNVAVQK

ELHKPESDRSCIHLEFDISGTSITYDTGDHVGVYAENCNETVEETGKLLG

QNLDLFFSLHTDKDDGTSLGGSLLPPFPGPCSLRTALARYADLLNPPRKA

ALLALATHASEPSDERLKFLSSPQGKDEYSKWVVGSQRSLVEVMAEFPSA

KPPLGVFFAAIAPRLQPRYYSISSSPRFAPQRVHVTCALVYGPTPTGRIH

KGVCSTVVMKNAIPSEKSQDCSSAPIFIRPSNFKLPVDHSIPIIMVGPGT

GLAPFRGFLQERYALKEDGVQLGPALLFFGCRNRQMDFIYEDELKSFVEQ

GSLSELIVAFSREGAEKEYVQHKMMDKAAHLWSLISQGGYLYVCGDAKGM

ARDVHRTLHSIVQEQENVDSTKAEAIVKKLQMDGRYLRDVW

>gi|2809387|gb|AAB97737.1| NADPH cytochrome P450
reductase [*Petroselinum crispum*] SEQ ID No 79:
MQSESMEVSPVDLLASILKIDSVESMILLLENRDVLMLLTTSFAVLIGLG

LVMMWRRSTTMTKSAKKLEPAKIVIPKFEMEEEVDDGKKKVTIFYGTQTG

TAEGFAKALAEEEAKARYQDAIFKTIDLDDYAGDDDEYETKLKKESMVFFF

LATYGDGEPTDNAARFYKWFCEGKERGEWLNNLQYGVFGLGNRQYEHFNK

IAVVVDDGLVEQGAKRLVPVGMGDDDQCIEDDFTAWRELVWPELDQLLLD

EESKAAATPYTAAVLEYRVQFYNQTDTSSPLVRSMSKLNGHAVYDAQHPC

RANVAVRRELHTPASDRSCTHLEFDISSTGLAYETGDHVGVYTENLIEIV

EEAERLIDISPDTYFSIHTENEDGTPLSGGSLPPPFPPCSFRTALTRYAD

LLSTPKKSALVALAAHASDPSEAERLRFLASPVGKDEYAQWLVASQRSLL

EVLAAFPSAKPPLGVFFASVAPRLQPRYYSISSSPRMAPSRIHVTCALVH

ETTPAGRIHKGLCSTVVMKNAVSLEDAHVSSWAPIFVRQSNFRLPTDSKV

PIIMIGPGTGLAPFRGFMQERLALKESGAELGSAVLYFGCRNRKLDFIYE

DELNHFVETGAISEMVVAFSREGPAKEYVQHKMSQKASEIWDMISHGAYI

YVCGDAKGMARDVHRMLHTIAQEQGALDSSHAESLVKNLHMSGRYLRDVW

>gi|2809385|gb|AAB97736.1| NADPH cytochrome P450 reductase [Petroselinum crispum] SEQ ID No 80:
MGGESLATSLPATLLENRDLLMLLTTSIAVLIGCAVVLVWRRSSLRSVKS
VEPPKLIVPKVEIEDEVDDGKKKVTVFFGTQTGTAEGFAKAFAEEEAKARY
EKAKFRVVDLDDYAAEDEEYEAKFKKESFAFFFLATYGDGEPTDNAARFY
KWFSEGEEKGDWLNKLQYGVFGLGNRQYEHFNKIAKVVDDGLADQGAKRI
VEVGMGDDDQCIEDDFTAWRELVWPELDKLLLDEDDTSAATPYTAAVLEY
RVVVYDQLDTATLDRSLSTQNGHTVHDAQHPCRSSVAAKKELHKPASDRS
CIHLEFDISHTGLAYETGDHVGVYCENLVEIVEEAEKLLGMQPNTYFSVH
IDDEDGTPLTGGSLPPPFPPCTVRSALAKYADLLSSPKKSALLALAAHAS
DPTEADRLRLLASPAGKDEYAQWVVASHRSLLEVLAEFPSAKPPLGVFFA
SVAPRLQPRYYSISSSPRMVPSRIHVTCALVYEKTPTGRIHKGVCSTWMK
NAVSLEESHDCSWAPIFVRQSNFKLPSDTKVPIIMIGPGTGLAPFRGFLQ
ERQALKDAGAELGTAVLYFGCRNRNLDFIYEDELNKFVESGSISELIVAF
SREGPTKEYVQHKMLQKASEIWNLISEGAYIYVCGDAKGMARDVHRMLHT
IAQEQGALDSSKAESWVKNLQMTGRYLRDVW >gi|224551850|gb|ACN54323.1| NADPH: cytochronne P450 reductase [Gossypium hirsutum] SEQ ID No 81:
MSSSSDLVGFVESVLGVSLEGSVTDSMIVIATTSLAVILGLLVFFWKKSG
SERSRDVKPLVAPKPVSLKDEEDDDAVIAAGKTKVTIFYGTQTGTAEGFA
KALAEEIKARYEKAAVKVVDLDDYAMDDEQYEEKLKKETLAFFMVATYGD
GEPTDNAARFYKWFTEGNERLPWLQQLTYGVFGLGNRQYEHFNKIAKVLD
EQLSEQGAKRLIEVGLGDDDQCIEDDFTAWRELLWPELDQLLRDEDDENA
TSTPYTAAIPEYRVVVHDPAVMHVEENYSNKANGNATYDLHHPCRVNVAV
QRELHKPESDRSCIHLEFDISGTGITYETGDHVGVYADNCVETVEEAARL
LGQPLDLLFSIHTDNEDGTSAGSSLPPPFASPCTLRMALARYADLLNPPR
KAALIALAAHATEPSEAEKLKFLSSPQGKDEYSQWVVASQRSLLEVMAEF
PSAKPPLGVFFAAVAPRLQPRYYSISSSPRFVPARVHVTCALVYGPTPTG
RIHRGVCSTWMKNAVPLEKSNDCSWAPIFIRQSNFKLPADPSVPIIMVGP
GTGLAPFRGFLQERLVLKEDGAELGSSLLFFGCRNRRMDFIYEDELNNFV
EQGALSELVVAFSREGPQKEYVQHKMMDKAADIWNLISKGGYLYVCGDAK
GMARDVHRTLHTIIQEQENVDSSKAESMVKKLQMDGRYLRDVW >gi|224551852|gb|ACN54324.1| NADPH: cytochronne P450 reductase [Gossypium hirsutum] SEQ ID No 82:
MDSSSSSSSGPSPLDLMSALVKAKMDPSNASSDSAAQVTTVLFENREFV
MILTTSIAVLIGCVVILIWRRSASQKPKQIQLPLKPSIIKEPELEVDDGK
KKVTILFGTQTGTAEGFAKALVEEAKARYEKATFNIVDLDDYAADDEEYE
EKMKKDNLAFFFLATYGDGEPTDNAARFYKWFTEGKERGEWLQNMKYGIF
GLGNKQYEHFNKVAKVVDELLTEQGAKRIVPLGLGDDDQCIEDDFTAWRE
LVWPELDQLLRDEDDATVSTPYTAAVLEYRVVFYDPADAPLEDKNWSNAN
GHATYDAQHPCRSNVAVRKELHAPESDRSCTHLEFDIAGTGLSYETGDHV
GVYCENLDEVVDEALSLLGLSPDTYFSVHTDKEDGTPLGGSSLPSSFPPC
TLRTALARYADLLSSPKKAALLALAAHASDPTEADRLRHLASPAGKDEYA QWIVANQRSLLEVMAEFPSAKPPLGVFFAAVAPRLQPRYYSISSSPRLAP
SRIHVTCALVYEKTPTGRIHKGVCSTWMKNAVSSGKSDDCGWAPIFVRQS
NFKLPSDTKVPIIMIGPGTGLAPFRGFLQERLALKEAGAELGPSVLFFGC
RNRKMDFIYEDELNNFVNSGALSELVVAFSREGPTKEYVQHKMMEKAKDI
WDMISQGGYLYVCGDAKGMARDVHRALHTIFQEQGSLDSSKAESMVKNLQ
MSGRYLRDVW Cytochrome P450 Monooxygenases (CYPs):
>gi|326324797|dbj|BAJ84106.1| cytochrome P450 [Vitis vinifera] SEQ ID No 83:
MEVFFLSLLLIFVLSVSIGLHLLFYKHRSHFTGPNLPPGKIGWPMVGESL
EFLSTGWKGHPEKFIFDRISKYSSEVFKTSLLGEPAAVFAGAAGNKFLFS
NENKLVHAWWPSSVDKVFPSSTQTSSKEEAKKMRKLLPQFFKPEALQRYI
GIMDHIAQRHFADSWDNRDEVIVFPLAKRFTFWLACRLFMSIEDPAHVAK
FEKPFHVLASGLITVPIDLPGTPFHRAIKASNFIRKELRAIIKQRKIDLA
EGKASQNQDILSHMLLATDEDGCHMNEMEIADKILGLLIGGHDTASAAIT
FLIKYMAELPHIYEKVYEEQMEIANSKAPGELLNWDDVQNMRYSWNVACE
VMRLAPPLQGAFREAITDFVFNGFSIPKGWKLYWSANSTHKSPECFPQPE
NFDPTRFEGNGPAPYTFVPFGGGPRMCPGKEYARLEILVFMHNVVKRFKW
DKLLPDEKIIVDPMPMPAKGLPVRLHPHKP >gi|326324799|dbj|BAJ84107.1| Cytochrome P450 [Vitis vinifera] SEQ ID No 84:
MEVFFLSLLLISVLSVSIRLYLLLYKHRSHFTGPNLPPGKIGWPMVGESL
EFLSTGWKGHPEKFIFDRISKYSSEVFKTSLLGEPAAVFAGAAGNKFLFS
NENKLVHAWWPSSVDKVFPSSTQTSSKEEAKKMRKLLPQFLKPEALQRYT
GIMDHIAQRHFADSWDNRDEVIVFPLAKRFTFWLACRLFMSIEDPAHVAK
FEKPFHVLASGLITIPIDLPGTPFHRAIKASNFIRKELRAIIKQRKIDLA
ESKASKTQDILSHMLLATDEDGCHMNEMSIADKILGLLIGGHDTASSAIT
FLVKYMAELPHIYEKVYEEQMEIANSKAPGELLNWDDVQKMRYSWNVACE
VMRLAPPLQGAFREAITDFVFNGFSIPKGWKLYWSANSTHKSLECFPQPE
KFDPIRFEGAGAPYTFVPFGGGPRMCPGKEYARLEILIFMHNLVKRFKW
DKLLPDEKIIVDPMPMPAKGLPVRLHPHKP >gi|84514135|gb|ABC59076.1| cytochrome P450 monooxygenase CYP716A12 [Medicago truncatula] SEQ ID No 85:
MEPNFYLSLLLLFVTFISLSLFFIFYKQKSPLNLPPGKMGYPIIGESLEF
LSTGWKGHPEKFIFDRMRKYSSELFKTSIVGESTVVCCGAASNKFLFSNE
NKLVTAWWPDSVNKIFPTTSLDSNLKEESIKMRKLLPQFFKPEALQRYVG
VMDVIAQRHFVTHWDNKNEITVYPLAKRYTFLLACRLFMSVEDNHVAKF
SDPFQLIAAGIISLPIDLPGTPFNKAIKASNFIRKELIKIIKQRRVDLAE
GTASPTQDILSHMLLTSDENGKSMNELNIADKILGLLIGGHDTASVACTF
LVKYLGELPHIYDKVYQEQMEIAKSKPAGELLNWDDLKKMKYSWNVACEV
MRLSPPLQGGFREAITDFMFNGFSIPKGWKLYWSANSTHKNAECFPMPEK
FDPTRFEGNGPAPYTFVPFGGGPRMCPGKEYARLEILVFMHNLVKRFKWE
KVIPDEKIIVDPFPIPAKDLPIRLYPHKA >gi|365927744|gb|AEX07773.1| cytochrome P450
[Catharanthus roseus] SEQ ID No 86:
MEIFYVTLLSLFVLLVSLSFHFLFYKNKSTLPGPLPPGRTGWPMVGESLQ

FLSAGWKGHPEKFIFDRMAKYSSNVFRSHLLGEPAAVFCGAIGNKFLFSN

ENKLVQAWWPDSVNKVFPSSNQTSSKEEAIKMRKMLPNFLKPEALQRYIG

LMDQIAQKHFSSGWENREQVEVFPLAKNYTFWLASRLFVSVEDPIEVAKL

LEPFNVLASGLISVPIDLPGTPFNRAIKASNQVRKMLISIIKQRKIDLAE

GKASPTQDILSHMLLTSDENGKFMHELDIADKILGLLIGGHDTASSACTF

IVKFLGELPEIYEGVYKEQMEIANSKAPGEFLNWEDIQKMKYSWNVACEV

LRLAPPLQGAFREALNDFMFHGFSIPKGWKIYWSVNSTHRNPECFPDPLK

FDPSRFDGSGPAPYTFVPFGGGPRMCPGKEYARLEILVFMHNLVKRFKWE

KIIPNEKIVVDPMPIPEKGLPVRLYPHINA

>gi|224118706|ref|XP_002331427.1| cytochrome P450
[Populus trichocarpa] SEQ ID No 87:
MELLFLSLLLALFVSSVTIPLFLIFYNHRSQNSHPNLPPGKLGLPLVGES

FEFLATGWKGHPEKFIFDRIAKYSSHIFKTNILGQPAVVFCGVACNKFLF

SNENKLVVSWWPDSVNKIFPSSLQTSSKEEAKKMRKLLPQFLKPEALQGY

IGIMDTIAQRHFASEWEHKEQVLVFPLSKNYTFRLACRLFLSIEDPSHVA

KFSDPFNLLASGIISIPIDLPGTPFNRAIKASNFIRTELLAFIRQRKKDL

AEGKASPTQDILSHMLLTCDENGKCMNELDIADKIIGLLIGGHDTASAAC

TFIVKYLAELPHIYEEVYKEQMEIAKSKTPGEFLNWDDIQKMKYSWKVAC

EVMRISPPLQGAFREALNDFIFNGFTIPKGWKLYVVSTNSTHRDPVYFPE

PEKFDPRRFEGSGPAPYTFVPFGGGPRMCPGKEYARLEILVFMHNLVRRF

KFDKLIQDEKIVVNPLPIPDKGLPVRLHPHKA

>gi|356513241|ref|XP_003525322.1|: cytochrome P450
716B2-like [Glycine max] SEQ ID No 88:
MDHNNLYLSLLLLFVSFVTLSLFFLFYKHRSPFVAPNLPPGATGYPVIGE

SLEFLSTGWKGHPEKFIFDRMIRYSSQLFKTSIFGEPAVIFCGATCNKFL

FSNENKLVAAWWPNSVNKVFPSTLQSNSKEESKKMRKLLPQFLKPEALQR

YVGIMDTIAQNHFASLWDNKTELTVYPLAKRYTFLLACRLFMSVEDVNHV

AKFENPFHLLASGIISVPIDLPGTPFNKAIKAANAIRKELLKIIRQRKVD

LAEGKASPTQDILSHMLLTCNENGQFMNELDIADKILGLLIGGHDTASAA

CTFIVKYLAELPHIYDSVYQEQMEIAKSKLPGELLNWDDINRMKYSWNVA

CEVMRIAPPLQGGFREAINDFIFNGFSIPKGWKLYWSANSTHKNPEYFPE

PEKFDPTRFEGQGPAPFTVPFGGGPRMCPGKEYARLEILVFMHNLVKRF

KWEKLIPDEKIIVDPLPVPAKNLPIRLHPHKP

>gi|388827893|gb|AFK79029.1| cytochrome P450
CYP716A41 [Bupleurum chinense] SEQ ID No 89:
MMMYLYFSVISILVLLPCVWLFFLHSNRKSTQQSYKSLPPGETGYFLIGE

SLEFLSTGRKGHPEKFIFDRMTKYASKIFKSSLFGEKTIVFCGAANNKFL

FSDENKLVQSWWPNSVNKLFPSSTQTSSKEEAIKMRKMLPNFFKPEALQR

YVGVMDEIAQKHFDSCWENKHTVIVAPLTKRFTFWLACRLFVSLEDPTQV

AKFAEPFNLLASGVFSIPIDLPGTAFNRAIKASNFIRKTLIGIIKKRKVD

LEDGTASATQDILSHMLLTSDETGKFMTEADIADKILGLLIGGHDTASSA

CALIVKYLAELPHIYDGVYREQMEIAKSKSPGELLNWDDVQKMKYSWNVA

CEVLRLAPPLQGSFREVLSDFMHNGFSIPKGWKIYWSANSTHKSSEYFPE

PEKFDPRRFEGSGPAPYTFVPFGGGPRMCPGKEYGRLEILVFMHHLVKRF

RWQKIYPLEKITVNPMPFPDKDLPIRLFPHKA

>gi|449442637|ref|XP_004139087.1|: cytochrome P450
716B1-like [Cucumis sativus] SEQ ID No 90:
MELFLISLLILLFFFLSLTLFILFHNHKSLFSYPNTPPGAIGLPILGESV

EFLSSGWKGHPEKFIFDRLNKYKSDVFKTSIVGVPAAIFCGPICNKFLFS

NENKLVTPWWPDSVNKIFPSTTQTSTKEEAKKLKKLLPQFLKPEALQRYI

GIMDELAERHFNSFWKNREEVLVFPLAKSFTFSIACRLFMSVEDEIHVER

LSGPFEHIAAGIISMPIDLPGTPFNRAIKASKFIRKEVVAIVRQRKQDLA

EGKALATQDILSHMLLTCDENGVYMNESDITDKILGLLIGGHDTASVACT

FIVKFLAELPHIYDAVYTEQMEIARAKAEGETLKWEDIKKMKYSWNVACE

VLRIASPLQGAFREALSDFVFNGFFIPKGWKLYWSANSTHKNPEYFPEPY

KFDPGRFEGNGPLPYTFVPFGGGPRMCPGKEYAKLEILVFMHNLVKRFKW

TKLLENENIIVNPMPIPQKGLPVRLFPHQPLSL

>gi|332071098|gb|AED99868.1| cytochrome P450
[Panax notoginseng] SEQ ID No 91:
MELFYVPLLSLFVLFISLSFHFLFYKSKSSSSVGLPLPPGKTGWPIIGES

YEFLSTGWKGYPEKFIFDRMTKYSSNVFKTSIFGEPAAVFCGAXCNKFLF

SNENKLVQAWWPDSVNKVFPSSTQTSSKEEAIKMRKMLPNFFKPEALQRY

IGLMDQIAAKHFESGWENKDEVVVFPLAKSYTFWIACKVFVSVEEPAQVA

ELLEPFSAIASGIISVPIDLPGTPFNSAIKSSKIVRRKLVGIINQRKIDL

GEGKASPTQDILSHMLLTSDESGKFMGEGEIADKILGLLIGGHDTASSAC

TFVVKFLAELPQIYXGVYQEQMEIVKSKKAGELLKWEDIQKMKYSWNVAC

EVLRLAPPLQGAFREALSDFTYNGFSIPKGWKLYWSANSTHRNSEVFPEP

LKFDPSRFDGAGPPPFSFVPFGGGPRMCPGKEYARLEILVFMHHLVKRFK

WEKVIPDEKIWNPMPIPANGLPVRLFPHKA

>gi|397741002|gb|AF063032.1| cytochrome P450
CYP716A52v2 [Panax ginseng] SEQ ID No 92:
MELFYVPLLSLFVLFISLSFHFLFYKSKPSSSGGFPLPPGKTGWPIIGES

YEFLSTGWKGYPEKFIFDRMTKYSSNVFKTSIFGEPAAVFCGAACNKFLF

SNENKLVQAWWPDSVNKVFPSSTQTSSKEEAIKMRKMLPNFFKPEALQRY

IGLMDQIAANHFESGWENKNEVVVFPLAKSYTFWIACKVFVSVEEPAQVA

ELLEPFSAIASGIISVPIDLPGTPFNSAIKSSKIVRRKLVGIIKQRKIDL

GEGKASATQDILSHMLLTSDESGKFMGEGDIADKILGLLIGGHDTASSAC

TFVVKFLAELPQIYEGVYQEQMEIVKSKKAGELLKWEDIQKMKYSWNVAC

EVLRLAPPLQGAFREALSDFTYNGFSIPKGWKLYVVSANSTHINSEVFPE

PLKFDPSRFDGAGPPPFSFVPFGGGPRMCPGKEYARLEILVFMHHLVKRF

KWEKVIPDEKIVVNPMPIPANGLPVRLFPHKA

>gi|255563874|ref|XP_002522937.1| cytochrome P450,
putative [Ricinus communis] SEQ ID No 93:
MDHFYLTLLFLFVSFITFSIFIIFYKHKSQYNYPSLPPGKPGLPFVGESL

EFLSSGWKGHPEKFVFDRTSKYSSEIFKTNLLGQPAAVFCGASANKFLFS

NENKLVQAWWPDSVNKIFPSSLQTSSKEEAIKMRKLLPQFMKPEALQRYI

```
GIMDTIAQRHFASGWEKKNEVVVFPLAKNYTFWLACRLFVSLEDPDHIAK

FADPFQELASGIISVPIDLPGTPFRRAIKASNFIRKELISIIKQRKIDLA

EGKASGTQDILSHMLLTSDEDGKFMNEMDIADKILGLLIGGHDTASAACT

FIIKYLAELPQIYDAVYKEQMEIAKSKGEGELLNWEDIQKMKYSWNVACE

VMRVAPPLQGAFREAINDFIFNGFYIPKGWKLYVVSANSTHKSATYFEEP

EKFDPSRFEGKGPAPYTFVPFGGGPRMCPGKEYARLEILVFMHNLVKRFN

FQKIIPDENIIVNPLPIPAKGLPVRLLPHQI
```

>gi|147784145|emb|CAN72302.1| hypothetical protein
VITISV_041935 [*Vitis vinifera*] SEQ ID No 94:

```
MEVFFLSLLLICVLSVSIRLYLLLYKHRSHFIGPNLPPGKIGWPMVGESL

EFLSTGWKGHPEKFIFDRISKYSSEVFKTSLLGEPAAVFAGAAGNKFLFS

NENKLVHAWWPSSVDKVFPSSTQTSSKEEAKKMRKLLPQFLKPEALQRYT

GIMDHIAQRHFADSWDNRDEVIVFPLAKRFTFWLACRLFMSIEDPAHVAK

FEKPFHVLASGLITIPIDLPGTPFHRAIKASNFIRKELRAIIKQRKIDLA

ESKASKTQDILSHMLLATDEDGCHMNEMXIADKILGLLIGGHDTASSAIT

FLVKYMAELPHIYEKVYKEQMEIANSKAPGELLNWDDVQKMRYSWNVACE

VMRLAPPLQGAFREAITDFVFNGFSIPKGWKLYWSANSTHKSLECFPQPE

KFDPTRFEGAGPAPYTFVPFGGGPRMCPGKEYARLEILIFMHNLVKRFKW

DKLLPDEKIIVDPMPMPAKGLPVRLHPHKP
```

>gi|225460666|ref|XP_002266024.1|: beta-amyrin
28-oxidase [*Vitis vinifera*] SEQ ID No 95:

```
MEVFFLSLLLICVLSVSIGLQFLFYKHRSHFTGPNLPPGRIGWPMVGESL

EFLSTGWKGHPEKFIFDRISKYSSEVFKTSLLGEPAAVFAGAAGNKFLFS

NENKLVHAWWPSSVDKVFPSSTQTSSKEEAKKMRKLLPRFLKPEALQRYI

GIMDHIAQRHFADSWDNRDEVIVFPLSKRFTFWLACRLFMSIEDPDHIAK

FEKPFHVLASGLITVPIDLPGTPFHRAIKASNFIRKELRAIIKQRKIDLA

EGKASPTQDILSDLLLATDEDGRHMNEINIADKILGLLIGGHDTASSAIT

FIVKYMAELPHMYEKVYEEQMEIANSKAPGELLNWDDVQKMRYSWNVACE

VMRLAPPLQGAFREAITDFVFNGFSIPKGWKLYWSTSSTHKSPKCFPEPE

KFDPTRFEGAGPAPYTFVPFGGGPRMCPGKEYARLEILVFMHNVVKRFKW

DKLLPDEKIIIDPMRMPAKGLPVRLRLHKP
```

>gi|255574173|ref|XP_002528002.1| cytochrome P450,
putative [*Ricinus communis*] SEQ ID No 96:

```
MFPFAVLLIALSISYLIFKHKSNASSRKNLPPGNTGWPLIGESIEFLSTG

RKGHPEKFIFDRMEKFSSKVFKTSLLLEPAAVFCGAAGNKFLFSNENKLV

TAWWPNSVNKIFPSSLTSSQEESKRMRKLLPQFLKPEALQRYISIMDVI

AQRHFAFGWNNKQQVTVFPLAKMYTFWLACRLFLSMEDREEVEKFAKPFD

VLASGIISIPIDFPGTPFNRGIKASNEVRRELIKMIEQRKIDLAENKASP

TQDILSHMLTTADEYMNEMDIADKILGLLIGGHDTASAAITFVVKYLAEM

PQVYNKVLEEQMEIAKAKAAGELLNWEDIQKMRYSWNVACEVMRLAPPLQ

GAFREAMTDFTYAGFTIPKGWKLYWGANSTHRNPECFPEPEKFDPSRFEG

KGPAPYTFVPFGGGPRMCPGKEYARLEILVFMHNIVKKFRWEKLLPEEKI

IVDPLPIPAKGLPLRLHPHTS
```

>gi|356523805|ref|XP_003530525.1|: cytochrome P450
716B2 [*Glycine max*] SEQ ID No 97:

```
MEDNNLHLSLLLLFVSIVTLSLFVLFYKHRSAFAAPNLPPGATGYPVIGE

SLEFLSTGWKGHPEKFIFDRMIRYSSQLFKTSILGEPAVIFCGATCNKFL

FSNENKLVAAWWPNSVNKVFPTTLLSNSKQESKKMRKLLPQFLKPEALQR

YVGIMDTIARNHFASLWDNKTELTVYPLAKRYTFLLACRLFMSIEDVNHV

AKFENPFHLLASGIISVPIDLPGTPFNKAIKAANAIRKELLKIIRQRKVD

LAEGKASPTQDILSHMLLTCDEKGQFMNELDIADKILGLLIGGHDTASAA

ITFIVKYLAELPHIYDRVYQEQMEIAKLKSPGELLNWDDVNRMQYSWNVA

CEVMRIAPPLQGGFREAINDFIFDGFSIPKGWKLYWSANSTHKSPEYFPE

PEKFDPTRFEGQGPAPYTFVPFGGGPRMCPGKEYARLEILVFMHNLVKRF

KWQKLIPDEKIIVDPLPIPAKNLPIRLHPHKP
```

>gi|255641079|gb|ACU20818.1| unknown, partial
[*Glycine max*] SEQ ID No 98:

```
MEDNNLHLSLLLLFVSIVTLSLFVLFYKHRSAFAAPNLPPGATGYPVIGE

SLEFLSTGWKGHPEKFIFDRMIRYSSQLFKTSILGEPAVIFCGATCNKFL

FSNENKLVAAWWPNSVNKVFPTTLLSNSKQESKKMRKLLPQFLKPEALQR

YVGIMDTIARNHFASLWDNKTELTVYPLAKRYTFLLACRLFMSIEDVNHV

AKFENPFHLLASGIISVPIDLPGTPFNKAIKAANAIRKELLKIIRQRKVD

LAEGKASPTQDILSHMLLTCDEKGQFMNELDIADKILGLLIGGHDTASAA

ITFIVKYLAELPHIYDRVYQEQMEIAKLKSPGELLNWDDVNRMQYSWNVA

CEVMRIAPPLQGGFREAINDFIFDGFSIPKGWKLYWSANSTHKSPEYFPE

PEKFDPTRFEGQGPAPYTFVPFGGGPRMCPGKEYARLEILVFMYN
```

>gi|225429866|ref|XP_002280969.1|: beta-amyrin
28-oxidase [*Vitis vinifera*] SEQ ID No 99:

```
MELSLLHILPWATLFTTLSLSFLIYKLMIISHGTPRNLPSGNTGLPYIGE

SIQFLSNGRKGHPEKFISERMLKFSSKVFKTSLFGETAAVFCGSAGNKFL

FSNENKLVTAWWPSSVNKIFPSSLQTSSQEESKKMRKLLPGFLKPEALQR

YISIMDVIAQRHFESSWNNKEEVTVFPLAKMFTFWLACRLFLSVEDPDHV

EKLAEPFNELAAGIIALPIDLPGTSFNKGIKASNLVRKELHAIIKKRKMN

LADNKASTTQDILSHMLLTCDENGEYMNEEDIADKILGLLVGGHDTASAT

ITFIVKFLAELPHVYDEVFKEQMEIAKSKAPGELLNWEDIPKMRYSWNVA

CEVMRLAPPVQGAFREAMNDFIFEGFSIPKGWKLYWSTHSTHRNPEFFPK

PEKFDPSRFDGKGPAPYTYVPFGGGPRMCPGKEYARLEVLVFMHNLVRRF

KWEKLLPDEKIIVDPMPIPAKGLPIRLHHHQP
```

>gi|224090683|ref|XP_002309057.1| hypothetical
protein POPTR_0006s08560g [*Populus trichocarpa*]
SEQ ID No 100:

```
MELPFISLLPYGILFIISAVSLSYLINKHKYYLSSLNNLPPGNTGLPLIG

ESLEFLTTGQKGQPEKFILDRMAKFSSKVFKTSLFCEPTAVFCGAAGNKF

LFSNENKLVTAWWPDSVNKIFPSSQQTSSQEESKKMRKLFPLFFKPESLQ

RYISVMDVIAQRHLASDWEGKQEVSVFPLAKTYTFWLACRLFLSMEDPEE

VQKFAKPFNDLAAGIISIPIDLPWTPFNRGVKASNVVHKELLKIIKQRKI

DLAENKASPTQDILSHMLTTADDNGQCMKKIDIADKILGLLVGGHDTASA

AITFIVKYLAELPHVYNKLLEEQREIAKTKTPGELLNWEDIQRMRYSWNV
```

-continued
ACEVMRVAPPLQGAFREAMTEFNYAGFTIPKGWKLYWSANTTHKNPECFP

EPENFDPSRFEGNGPAPYTFVPFGGGPRMCPGKEYARLEILVFLHNLVKK

FRWEKLLPKERIIVDPMPIPSKGLPIRLHPHEAA

>gi|217072174|gb|ACJ84447.1| unknown [Medicago
truncatula] SEQ ID No 101:
MEPNFYLSLLLLFVTFISLSLFFIFYKQKSPLNLPPGKMGYPIIGESLEF

LSTGWKGHPEKFIFDRMRKYSSELFKTSIVGESTVVCCGAASNKFLFSNE

NKLVTAWWPDSVNKIFPTTSLDSNLKEESIKMRKLLPQFFKPEALQRYVG

VMDVIAQRHFVTHWDNKNETTVYPLAKRYTFLLACRLFMSVEDENHVAKF

SDPFQLIAAGIISLPIDLPGTPFNKAIKASNFIRKELIKIIKQRRVDLAE

GTASPTQDILSHMLLTSDENGKSMNELNIADKILGLLTGGHDTASVACTF

LVKYLGELPHIYDKVYQEQMEIAKSKPAGELLNWDDLKKMKYSWNVACEV

MRLSPPLQGGFREAITDFMFNGFSIPKGWKLYWSANSTHKNAECFPMPEK

FDPTRFEGNGPAPYTFVPFGGGPRMCPGKEYARLEILVFMHNLAKRFKWE

KVIPDEKIIVDPFPIPAKDLPIRLYPHKA

>gi|255544242|ref|XP_002513183.1| cytochrome P450,
putative [Ricinus communis] SEQ ID No 102:
MELFFLIALTLFIILVTLPILAVLYRPNIINLPPGKTGLPYIGESLEFLS

TGRKGHPEKFLSDRMEKFSRQVFRTSILGEQTAVVCGAQGNKFLFSNENK

LVTAWWPKSILRLFPSSNQSTILAEGMRMRKMLPHFLKPEALQRYIGVMD

HMAQVHFQDSWENKQEVIVYPLAKMYTFSVACKVFLSMDDPKEVAKFAAP

FNDMASGIISIPINFPGTSFNRGLKASKIIRNEMLRMIKQRRKDLAENKA

TPMQDILSHMLVATDEEGQRLGEVGIADKIISLLIGGHDTASATITFVVK

FLAELPDIYDQVLKEQLEIAKSKEPGELLTVVEDIQKMKYSWNVACEVMR

LAPPLQGSFREALHDFDYAGFSIPKGWKLYWSTHTTHKNPEYFSDPEKFD

PSRFEGSGPAPYTFVPFGGGPRMCPGKEYARLEILVFMHNIAKRFKWNKV

IPDEKIVVDPMPIPAKGLPVHLYPQKHE

>gi|731408064|ref|XP_002264643.3|: beta-amyrin 28-
oxidase-like [Vitis vinifera] SEQ ID No 103:
MVSFDLLYSNLIFCLLFSAIASIQMIMQQSDMELLLLSFLLLMALSLSFW

IRFFVHKLEKSSGINLPPGKMGFPFIGESLEFLRMGRKGTPERFIQDRMA

KYSTQIFKTCLLGEPTAVVCGAAGNKLLFSNENKLVTSWWPRSVEKIFPS

SLQTSTKEESMKTRKLLPAFLKPEALQKYVGIMDSIAKWHLDNHWDLNET

VTVFPLAKQYTFMVACRLFLSIDDPKHIAKFANPFHILAAGVMSIPINFP

GTPFNRAIKAADSVRKELRAIIKQRKIQVLAGKSSSSKHDILSHMLTTTD

ENGQFLNEMDIADKILGLLIGGHDTASAVITFIIKYLAELPQVYNEVLKE

QMEVAAGKKSGEMLDWEDIQKMKYSWNVANEVMRLAPPLQGSFREAITDF

TYAGFSIPKGWKLYWSTNATHKNPDYFPDPEKFDPSRFEGNGPIPYTYVP

FGGGPRMCPGKEYARLEILVFIHNVVRRFSWYKLHPNEDVIVDPMPMPAK

GLPIRLRHH

>gi|224142653|ref|XP_002324669.1| hypothetical
protein POPTR_0018s13390g [Populus trichocarpa]
SEQ ID No 104:
METLYFILLLFVPIILSLVAIIYKHRYQDKLQNVPPGNLGLPFVGESLDF

LSKGWKGCPENFIFDRIRKYSSEIFKTNLFLQPVVMLNGVAGNKFLFSNE

-continued
NRLVETWWPDFVNRIFPSAVETSPKEEAKRMRRLFPRFLKPEALQRYIGT

MDMVTKRHFALEWGNKAEVVVFPLAKSYTFELACRLFLSIEDPSHIARFS

HPFNQITSGIFTIPIDFPGTPFNRAIKASKLIRIELLAIIRQRKKDLAEG

KASPTQDILSHMLLSNDADGKYMNEVQISDKILALLMGGHESTAASCTFI

VKYLAELPHIYEAVYKEQAEIIKSKAPGELLNWDDIQKMKYSWNVACETL

RLSPPLIGNFKEAIKDFTFNGFSIPKGWKASHFLTLYWSASSTHKNPEYF

SEPEKFDPSRFEGKGPAPYTFIPFGGGPRMCPGNEYARLEILVFMHNLVK

RFKFERLILDEKIVFDPTPKPEMGLPVRLLPHKA

>gi|356526487|ref|XP_003531849.1|: cytochrome P450
716B2 isoform X1 [Glycine max] SEQ ID No 105:
MEQLYYLTLVLLFVSFVSVSFFIIFYRHRSPFSVPNLPPGKAGFPVIGES

LEFLSAGRKGLPEKFFSDRMTEYSSKVFKTSILGEPTVIFCGAACNKFLF

SNENKHVISWWPENVKKLFPTNIQTNSKEEAKKLRNILPQFLSAKAIQRY

VGIMDTVAQRHFALEWENNTQVTVLPLAKRYTFGVASRVFMSIDDLNQVA

KLAEPLNQVNAGIISMPINFPGTVFNRGIKASKFIRRELLRIVKQRKVEL

ANGMSTPTQDILSHMLIYCDENGQYLAEHDIVNKILGLLIGSHETTSTVC

TFVVKYLAELPQNIYENVYQEQMAIAKSKAPGELLNWDDIQKMKYSWNVA

CEVIRLNPPAQGAFREAiNDFIFDGFSIPKGWKLYWSANSTHKNPEYFPE

PEKFDPSRFEGTGPAPYTYVPFGGGPSMCPGKEYARMELLVFMHNLVKRF

KCETLFPNGNVTYNPTPIPAKGLPVRLIPHR

The invention therefore comprises the application of nucleic acid sequences, as well as yeast strains comprising such sequences which code for proteins, wherein the proteins have a sufficient sequence identity to the above-mentioned sequences (SEQ ID NO: 54 to 105) in order to be functionally analogous thereto. In this case, a sequence identity of at least 70%, preferably 75% or 80%, particularly preferably 85%, 90% or 95% sequence identity is advantageous. In the context of the invention this means that, in order to be functionally analogous to said amino acid sequences, the sequence variant can effectively cause the required production of the pentacyclic triterpenoids in the same or similar quantities. Functionally analogous sequences in the context of the invention are all sequences which the person skilled in the art can identify as equivalent by routine tests. The sequence identity between two sequences can be analyzed by conventional methods, for example with NCBI Blast or Clustal.

EXAMPLES

The invention will be explained below with reference to several examples and drawings, but without being limited to these.

FIG. 1 shows the biosynthesis of triterpenoids in *S. cerevisiae*. Enzymes have already been expressed in yeast and compounds have been detected (Moses et al., 2013). The illustration shows an overall view of the pre- and post-squalene biosynthesis path as well as the broadening of the metabolic pathway in order to establish the synthesis of pentacyclic triterpenoids in the yeast *Saccharomyces cerevisiae* using the example of betulinic acid. It can be seen from the illustration that for the synthesis of pentacyclic triterpenoids 1, 2 or 3 genes have been established in the metabolism of the yeast. The corresponding enzymes are designated as oxidosqualene cyclase (OSC), NADPH-cytochrome P450 reductase (CPR) and cytochrome P450 monooxygenase (CYP). In a first step 2,3-oxidosqualene is cyclized by means of a multifunctional or monofunctional OSC. In a second step the intermediate product is oxidized three times by means of a CYP and CPR in order to arrive at the end product.

Figure 2:
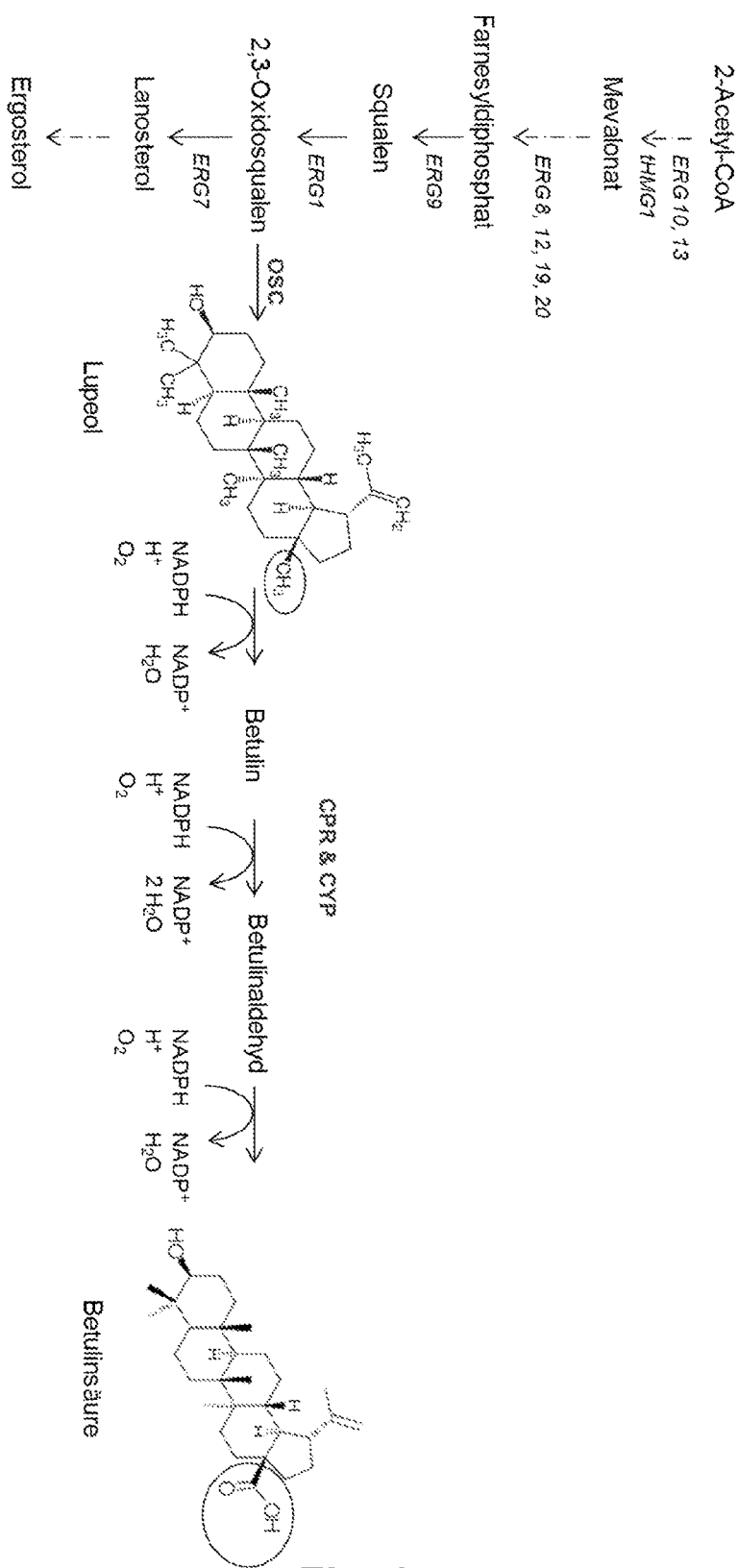

FIG. 2 shows the pre- and post-squalene biosynthesis path in the yeast *Saccharomyces cerevisiae* as well as the broadening of the metabolic pathway in order to establish the synthesis of pentacyclic triterpenoids using the example of betulinic acid. The heterologous genes to be expressed for the synthesis are shown in red in the illustration and are designated as oxidosqualene cyclase (OSC), NADPH-cytochrome P450 reductase (CPR) and cytochrome P450 monooxygenase (CYP).

In order to ensure high conversion rates of the heterologous genes or the enzymes formed and thus also to ensure high titers of pentacyclic triterpenoids, a plurality of genes were tested for each heterologous enzyme reaction in different combinations for determination of the optimal genes and combination therewith with high productivity.

The cyclic triterpenoids have been extracted from yeast and examined by means of GC-MS.

Strain Construction

The construction of the strains is based on the strain CEN.PK111-61A (MATalpha; ura3-52; leu2-3_112; TRP1; his3deltaI; MAL2-8C; SUC2) and also on the strain AH22tH3ura8 (Polakowski et al., 1998).

TABLE 4

Overall view of the plasmids used for the strain construction

| Plasmid name | Marker | OSC gene | CPR gene | CYP gene | CYP gene accession |
|---|---|---|---|---|---|
| pTT1-leer | URA3 | — | — | — | — |
| pTT1-OEW | URA3 | OEW (Oe) | — | — | — |
| pTT1-GuLUP1 | URA3 | GuLUP1 (Gu) | — | — | — |
| pTT1-RcLUS1 | URA3 | RcLUS1 (Rc) | — | — | — |
| pTT2-leer | LEU2 | — | — | — | — |
| pTT2-LjCPR1-A15 | LEU2 | — | LjCPR1 (Lj) | CYP716A15 (Vv) | AB619802 |
| pTT2-LjCPR1-A17 | LEU2 | — | LjCPR1 (Lj) | CYP716A17 (Vv) | AB619803 |
| pTT2-LjCPR1-A12 | LEU2 | — | LjCPR1 (Lj) | CYP716A12 (Mt) | DQ335781 |
| pTT2-LjCPR1-AL1 | LEU2 | — | LjCPR1 (Lj) | CYP716AL1 (Cr) | JN565975 |
| pTT2-LjCPR1-A9 | LEU2 | — | LjCPR1 (Lj) | CYP716A9 (Pt) | XM_002331391 |
| pTT2-LjCPR1-B2 | LEU2 | — | LjCPR1 (Lj) | Predicted: Cytochrome P450 716B2-like (LOC100801007) (Gm) | XM_003525274 |
| pTT2-LjCPR1-A41 | LEU2 | — | LjCPR1 (Lj) | CYP716A41 (Bc) | JF803813 |
| pTT2-LjCPR1-B1 | LEU2 | — | LjCPR1 (Lj) | Predicted: cytochrome P450 716B1-like (Cs) | XM_004139039 |
| pTT2-ATR1-AL1 | LEU2 | — | ATR1 (At) | CYP716AL1 (Cr) | JN565975 |
| pTT2-ATR1-A15 | LEU2 | — | ATR1 (At) | CYP716A15 (Vv) | AB619802 |
| pTT2-ATR1-A17 | LEU2 | — | ATR1 (At) | CYP716A17 (Vv) | AB619803 |
| pTT2-ATR1-A9 | LEU2 | — | ATR1 (At) | CYP716A9 (Pt) | XM_002331391 |
| pTT2-ATR1-B2 | LEU2 | — | ATR1 (At) | Predicted: Cytochrome P450 716B2-like (LOC100801007) (Gm) | XM_003525274 |
| pTT2-CrCPR-AL1 | LEU2 | — | CrCPR (Cr) | CYP716AL1 (Cr) | JN565975 |
| pTT2-CrCPR-A15 | LEU2 | — | CrCPR (Cr) | CYP716A15 (Vv) | AB619802 |
| pTT2-CrCPR-A17 | LEU2 | — | CrCPR (Cr) | CYP716A17 (Vv) | AB619803 |
| pTT2-CrCPR-A9 | LEU2 | — | CrCPR (Cr) | CYP716A9 (Pt) | XM_002331391 |
| pTT2-CrCPR-B2 | LEU2 | — | CrCPR (Cr) | Predicted: Cytochrome P450 716B2-like (LOC100801007) (Gm) | XM_003525274 |
| pTT2-MTR-A15 | LEU2 | — | MTR_3g100160 (Mt) | CYP716A15 (Vv) | AB619802 |
| pTT2-MTR-A17 | LEU2 | — | MTR_3g100160 (Mt) | CYP716A17 (Vv) | AB619803 |
| pTT2-MTR-A9 | LEU2 | — | MTR_3g100160 (Mt) | CYP716A9 (Pt) | XM_002331391 |
| pTT2-MTR-B2 | LEU2 | — | MTR_3g100160 (Mt) | Predicted: Cytochrome P450 716B2-like (LOC100801007) (Gm) | XM_003525274 |
| pTT2-MTR-A12 | LEU2 | — | MTR_3g100160 (Mt) | CYP716A12 (Mt) | DQ335781 |
| pTT2-NCP1-A15 | LEU2 | — | NCP1 (Sc) | CYP716A15 (Vv) | AB619802 |
| pTT2-NCP1-A17 | LEU2 | — | NCP1 (Sc) | CYP716A17 (Vv) | AB619803 |
| pTT2-NCP1-A9 | LEU2 | — | NCP1 (Sc) | CYP716A9 (Pt) | XM_002331391 |

TABLE 4-continued

Overall view of the plasmids used for the strain construction

| Plasmid name | Marker | OSC gene | CPR gene | CYP gene | CYP gene accession |
|---|---|---|---|---|---|
| pTT2-NCP1-B2 | LEU2 | — | NCP1 (Sc) | Predicted: Cytochrome P450 716B2-like (LOC100801007) (Gm) | XM_003525274 |

Gu, *Glycyrrhiza uralensis*; Oe, *Olea europaea*; Re *Ricinus communis*; Lj, *Lotus japonicas*; Cr, *Catharanthus roseus*; Vv, *Vitis vinifera*; Pt, *Populus trichocarpa*; Gm, *Glycine max*; Bc, *Bupleurum chinense*, Cs, *Cucumis sativus*; Mt, *Medicago truncatula*; At, *Arabidopsis thaliana*; Sc, *Saccharomyces cerevisiae*

Gu, *Glycyrrhiza uralensis*; Oe, *Olea europaea*; Re *Ricinus communis*; Lj, *Lotus japonicas*; Cr, *Catharanthus roseus*; Vv, *Vitis vinifera*; Pt, *Populus trichocarpa*; Gm, *Glycine max*; Be, *Bupleurum chinense*, Cs, *Cucumis sativus*; Mt, *Medicago truncatula*; At, *Arabidopsis thaliana*; Sc, *Saccharomyces cerevisiae*

TABLE 5

Overall view of the basic strains for the strain construction

| Name | Genotype |
|---|---|
| CEN.PK111-61A | MATalpha; ura3-52; leu2-3_112; TRP1; his3delta1; MAL2-8C; SUC2 |
| CEN.PK2U | CEN.PK111-61A ura3::tHMG1 |
| AH22tH3ura8 | MATa; leu2-3,112; Δcan1; ura3::tHMG1 |

Example 1: Overexpression of the Gene tHMG1 in the Gene Locus URA3

The tHMG1-integration module (cADH1pr-tHMG1-TRP1t-loxP-kanMX-loxP) has been synthesized by GeneArt and cloned in a pMK vector by means of the restriction sites AseI and PacI. The tHMG1-gene (t=truncated) codes for a truncated HMG-CoA reductase, which consists only of the catalytic sub-unit of the protein consists and thus is no longer subject to the feedback inhibition by sterol intermediates. A pMK-vector with a kanamycin resistance was used. For the genomic integration the tHMG1 module from the pMK plasmid was amplified by means of PCR with the following primers:

URA3_tHMG1_fw:
5'ATGTCGAAAGCTACATATAAGGAACGTGCTGCTACTCATCCAGTCAG
GCACCGTGTATGAAATC

URA3_tHMG_rev:
5TTAGTITTGCTGGCCGCATCTICTCAAATATGCTTCCCAGGGATCTG
ATATCACCTAATAACTTC The 4.5 kbp fragment contains the KanMX-marker (for the resistance of geneticin G418 in yeasts) flanked by loxP-sides (for the recovery of the marker), the tHMG1-gene under the control of a constitutive ADH1 promoter and TRP1 terminator as well as homologous sequences for the URA3 gene locus (the first and last 40 bp to the coding region of the URA3). The strain *Saccharomyces cerevisiae* CEN.PK111-61A was used for the transformation by means of homologous recombination at the gene locus URA3. After the transformation by means of the lithium-acetate method according to Gietz et al. (1992), the strain was plated for selection on YE agar plates with geneticin 418. The strain CEN.PK2U is constructed in this way.

YE medium: 0.5% yeast extract; 2% glucose; pH 6.3. For agar plates 1.5% agar was added to the medium. The glucose is produced as a 40% glucose solution and autoclaved separately. After the autoclaving are being 25 ml glucose solution are added to the medium.

Example 2: Expression of the Gene GuLUP1 for the Production of Cyclic Triterpenes (for Example, Lupeol)

The gene GuLUP1 optimized by GenScript codon was synthesized for the yeast and cloned in a pUC57 vector by means of the restriction site EcoRV. The pUC57 vector contains an ampicillin resistance gene and an origin of replication pMB1 for the replication in *E. coli*. For the cloning the gene GuLUP1 from the pUC57 plasmid was amplified by means of PCR with the following primers:

GuLUP_SacI_fw:
5'GACTGACTGAGCTCAAAAATGIGGAAATTAAAAATCGGTGAAGGTGGT
GC

GuLUP_NotI_rev:
5'GACTGACTGCGGCCGCCTATTAGTAAGAATGGGCGCACAAGACTTGTC

The amplified fragment has a size of 2.277 kbp.

Simultaneously with this a gene cassette from GeneArt was synthesized and cloned in a pMA vector via the interface Kp. This gene cassette contains a CEN/ARS sequence for an autonomous replication in yeast, the URA3 selection marker for yeast, MR sequences (URA3 recovery by means of the selection on agar plates with 5-FOA) and flanked regions which are homologous with the integration locus 5'YHRCdelta14 and enable the genomic integration the gene cassette into the integration locus 5'YHRCdelta14. The pMA vector contains an ampicillin resistance gene as selection marker for *E. coli* and an origin of replication Col El for the replication in *E. coli*.

The amplified fragment (gene: GuLUP1) was cloned by means of the restriction sites SacI and NotI in the pMA vector under the control of a ENO1 promoter and ENO1 terminator. The resulting plasmid is designated pTT1-GuLUP1.

The plasmid was transformed into competent *E. coli* cells. The selection took place by means of ampicillin resistance on LB agar plates.

LB medium: 1% casein peptone; 0.5% yeast extract; 1% NaCl; pH 7.0. For agar plates 1.5% agar was added to the medium.

Antibiotic: Ampicillin (Boehringer, Mannheim) 100 µg/ml

The strain *Saccharomyces cerevisiae* CEN.PK2U from example 1 and the strain AH22tH3ura8 were used for the episomal transformation. After the transformation by means of the lithium-acetate method according to Gietz et al. (1992), the strains were plated for selection on WMVIII agar plates without uracil.

Example 3: Cultivation Conditions for the Evaluation of the Strains

Standard cultivation of the yeast *S. cerevisiae*
1. Preculture: 20 ml WMVIII medium: (Lang and Looman, 1995) in a 100 ml Erlenmeyer flask 0.1% (v:v) from a glycerol stock were injected. The yeasts were cultured at 28° C. and 150 rpm for 72 hours on an orbital shaker.
2. Main culture: 50 ml WMVIII medium in a 250 ml baffled flask were injected from the preculture to a start value of $OD_{600}$=0.5. The yeasts were cultured at 28° C. and 150 rpm for 72 hours on an orbital shaker.

Strains having the genetic background of CEN.PK111-61A and CEN.PK2U are auxotrophic for uracil, histidine and leucine. Therefore, the medium was supplemented with uracil (100 mg/l), histidine (100 mg/l) and with leucine (400 mg/l). In order to exert a selection pressure on a transformed plasmid, the corresponding supplement in the medium was omitted.

Strains having the genetic background of AH22tH3ura8 are auxotrophic for uracil, histidine and leucine. Therefore, the medium was supplemented with uracil (100 mg/l) and with leucine (400 mg/l). In order to exert a selection pressure on a transformed plasmid, the corresponding supplement in the medium was omitted.

Components of WMVIII medium for 1 liter according to Lang and Looman, 1995: 250 mg $NH_4H_2PO_4$; 2.8 g $NH_4Cl$; 250 mg $MgCl_2\times 6H_2O$; 100 mg $CaCl_2\times 2H_2O$; 2 g $KH_2PO_4$; 550 mg $MgSO_4\times 7H_2O$; 75 mg mesa-inositol; 10 g Na-glutamate with the following change: 50 glucose instead of sucrose are produced as a 40% glucose solution and autoclaved separately.

After the autoclaving 125 ml glucose solution, 1 ml sterile filtered trace elements and 4 ml sterile filtered vitamins are added to the medium.

Trace elements: 1000× concentrated: 1.75 g $ZnSO_4\times 7 H_2O$; 0.5 g $FeSO_4\times 7 H_2O$; 0.1 g $CuSO_4\times 5 H_2O$; 0.1 g $MnCl_2\times 4 H_2O$; 0.1 g $NaMoO_4\times 2 H_2O$ for 1 liter.

Vitamin solution: 250× concentrated: 2.5 g nicotinic acid; 6.25 g pyridoxine; 2.5 g thiamine; 0.625 g biotin; 12.5 g Ca-pantothenate for 1 liter.

For agar plates 1.5% agar was added to the medium.
Medium supplements: Leucine (400 mg/l); histidine (100 mg/l); uracil (100 mg/l). The stock solutions are produced and sterile filtered with a concentration of 20 mg/ml.

Example 4: Growth and Productivity Analysis (Identification and Quantification of Cyclic Triterpenes)

The cultivation is carried out according to example 3.
Determination of the Dry Biomass (BTS)
For determination of the dry biomass, two times 2 ml culture volume were transferred into previously conditioned and balanced 2 ml reaction vessels. The cells were centrifuged at 18620×g for 5 minutes and washed with 1 ml water. Then the cell pellet was dried in a drying cabinet for 24 hours at 80° C. The samples cooled in the desiccator for 30 minutes before the weighing took place.
Sample Preparation
a) Yeast strains transformed with the genes for a OSC, CPR and CYP on a pTT1 and pTT2 plasmid:

In a duplicate determination 800 µl of culture broth of a main culture are transferred into a 2 ml reaction vessel. The extraction can be continued directly or the samples can also be frozen at −20° C. and extracted at a later time.
b) Yeast strains transformed with the gene for a OSC on a pTT1 plasmid:
In a duplicate determination 250 µl of culture broth of a main culture are transferred into a 1.5 ml reaction vessel. The extraction can be continued directly or the samples can also be frozen at −20° C. and extracted at a later time.
Extraction
Yeast strains transformed with the genes for a OSC, CPR and CYP on a pTT1 and pTT2 plasmid: The extraction agent chloroform/methanol (4+1) is mixed with stigmasterol to a concentration of 50 µg/ml. In the first step 800 µl culture broth are admixed with 80 µl 1M HCl, 250 µl glass beads (0.4-0.6 mm) and 800 µl extraction agent and then shaken for 20 minutes in the TissueLyser II at 30 Hz. After subsequent centrifugation for 5 minutes at 18000×g the organic phase is transferred into a new 1.5 ml reaction vessel. The removed organic phase is vaporized under a vacuum (SpeedVac; 35° C.; 0.1 mbar; 30 minutes). The vaporized samples are dissolved in 100 µl N-methyl-N-trimethylsilyltrifluoracetamide (MSTFA, Sigma) and transferred into brown GC vials provided with glass inserts. The samples are derivatized for 1 hour at 80° C. The prepared samples and thus the identification and the quantification of cyclic triterpenes were carried out by means of GC-MS.

Yeast Strains Transformed with the Gene for a OSC on a pTT1 Plasmid:
The extraction agent chloroform/methanol (4+1) is mixed with stigmasterol to a concentration of 50 µg/ml. In the first step 250 µl culture broth are admixed with 25 µl 1M HCl, 250 µl glass beads and 400 µl extraction agent and then shaken for 20 minutes in the TissueLyser II at 30 Hz. After subsequent centrifugation for 5 minutes at 18000×g, 250 µl of organic phase are transferred into a new 1.5 ml reaction vessel. The removed organic phase is vaporized under a vacuum (SpeedVac; 35° C.; 0.1 mbar; 30 minutes). The vaporized samples are dissolved in 250 µl chloroform and 100 µl are transferred into brown GC vials provided with glass inserts. The prepared samples and thus the identification and the quantification of cyclic triterpenes were carried out by means of GC-MS.

Production of the External Standard (ESTD)
For quantitative determination of pentacyclic triterpenes such as, for example, lupeol and betulinic acid by gas chromatography, a series of dilutions is produced with the respective substances. The ESTDs, like the samples, additionally contain stigmasterol in a concentration of 50 µg/ml as internal standard. The ESTDs are produced in chloroform. Similar to the samples, the ESTDs are measured in a brown GC vial with MSTFA for 1 hour at 80° C., derivatized or underivatized, by means of GC-MS.

Conditions for the gas chromatography (GC)
The GC analysis was carried out with an Agilent 6890N gas chromatograph (Agilent, Waldbronn) equipped with an Autosampler Agilent 7683B. An Agilent 5975 VL mass spectrometer was used as detector. The following conditions were selected: The column used was a 30 m long HP-5MS column (Agilent) with an internal diameter of 0.25 mm and a film thickness of 0.25 µm. Helium served as the mobile phase. The GC/MS system was operated with a temperature program (150° C. for 0.5 min, 40° C./min to 280° C., 2° C./min to 310° C., 40° C./min to 340° C., 340° C. for 2.5 min) in the splitless mode. The injector temperature was 280° C., and the temperature of the detector (MS Quadrupole) was 150° C. The injection volume of the samples was 1 µl.

Example 5: Strain-Dependent Yield of Pentacyclic Triterpenes

The gas chromatographic analysis of the pentacyclic triterpenes is set out in Table 6. The dry biomass (BTS) as well as the volumetric and specific product yield are set out in the tables. The strains were cultured as in Example 3. The quantities produced using the example of lupeol, betulin, betulin aldehyde and betulinic acid are dependent upon the strain. With the same gene combination, CEN.PK strains behaved differently from AH22 strains.

TABLE 6

Comparison of the yield of cyclic triterpenes between the CEN.PK2U and AH22tH3ura8 transformed with the plasmids pTT1-OEW and pTT2-LjCPR1-B2

| Strain | OSC gene | CPR gene | CYP gene | CYP gene Accession | BTS g/l | Lupeol mg/l | Lupeol mg/g | Betulin mg/l | Betulin mg/g |
|---|---|---|---|---|---|---|---|---|---|
| CEN.PK2U | OEW | LjCPR1 | B2 | XM_003525274 | 11.20 | 81.00 | 7.23 | n.d. | n.d. |
| AH22th3ura8 | OEW | LjCPR1 | B2 | XM_003525274 | 13.82 | 118.29 | 8.56 | 51.43 | 3.72 |

| strain | OSC gene | CPR gene | CYP gene | CYP gene Accession | betulin aldehyde mg/l | betulin aldehyde mg/g | betulinic acid mg/l | betulinic acid mg/g |
|---|---|---|---|---|---|---|---|---|
| CEN.PK2U | OEW | LjCPR1 | B2 | XM_003525274 | k.A. | k.A. | n.d. | n.d. |
| AH22th3ura8 | OEW | LjCPR1 | B2 | XM_003525274 | 28.79 | 2.08 | 22.25 | 1.61 |

Example 6: Influence of the HMG-CoA Reductase

In Table 7 the dry biomass and the lupeol productivities of CEN.PK111-61A and CEN.PK2U are transformed with the plasmid pTT1-OEW as well as with the deregulated HMG-CoA reductase. The strains were cultured as in Example 3, but with different main cultivation times (48 hours, 72 hours and 93 hours respectively). The lupeol productivity of the CEN.PK2U is higher than that of CEN.PK111-61A. This shows that the deregulation of the HMG-CoA reductase has a positive influence on the production of triterpenoids.

TABLE 7

Comparison of the productivities of CEN.PK111-61A and CEN.PK2U transformed with the plasmid pTT1-OEW

| strain | OSC gene | CPR gene | CYP gene | 48 h BTS g/l | 48 h Lupeol mg/l | 48 h Lupeol mg/g | 72 h BTS g/l | 72 h Lupeol mg/L | 72 h Lupeol mg/g | 93 h BTS g/l | 93 h Lupeol mg/l | 93 h Lupeol mg/g |
|---|---|---|---|---|---|---|---|---|---|---|---|---|
| CEN.PK111-61A | OEW | — | — | 5.50 | 38.61 | 7.02 | 11.32 | 83.18 | 7.35 | 10.55 | 88.38 | 8.38 |
| CEN.PK2U | OEW | — | — | 10.60 | 92.03 | 8.68 | 11.78 | 129.90 | 11.02 | 11.87 | 125.84 | 10.60 |

TABLE 8

Comparison of the productivities between AH22th3ura8 and AH22th3ura8Δare1Δare2

| strain | OSC gene | CPR gene | CYP gene | clone | 48 h BTS g/l | 48 h Lupeol mg/l | 48 h Lupeol mg/g | 72 h BTS g/l | 72 h Lupeol mg/L | 72 h Lupeol mg/g | 93 h BTS g/l | 93 h Lupeol mg/l | 93 h Lupeol mg/g |
|---|---|---|---|---|---|---|---|---|---|---|---|---|---|
| AH22th3ura8 | GuLUP1 | — | — | K1 | 11.00 | 74.86 | 6.81 | 13.25 | 126.77 | 9.57 | 12.90 | 133.54 | 10.35 |
| AH22th3ura8 Δare1Δare2 | GuLUP1 | — | — | K1 | 10.43 | 60.96 | 5.84 | 11.90 | 90.37 | 7.59 | 11.82 | 96.74 | 8.19 |

Example 7: Yields of Lupeol, Betulin, Betulin Aldehyde and Betulinic Acid after Episomal Expression of Different OSC, CPR and CYP Genes in Different Yeast Strains

TABLE 9

| | | | | | | BTS | Lupeol | | Betulin | | betulin aldehyde | | betulinic acid | |
|---|---|---|---|---|---|---|---|---|---|---|---|---|---|---|
| strain | OSC gene | CPR gene | CYP gene | CYP gene accession | | g/l | mg/l | mg/g | g/l | mg/L | mg/g | g/l | mg/l | mg/g |
| CEN.PK111-61A | OEW | — | — | — | | 11.32 | 83.18 | 7.35 | n.d | n.d. | n.d | n.d. | n.d | n.d. |
| CEN.PK111-61A | OEW | LjCPR1 | A9 | XM_002331391 | | 10.68 | 63.14 | 5.91 | 4.56 | 0.43 | k.A. | k.A. | n.d | n.d. |
| CEN.PK2U | OEW | — | — | — | | 11.78 | 129.89 | 11.02 | n.d | n.d. | n.d | n.d. | n.d | n.d. |
| CEN.PK2U | GuLUP1 | — | — | — | | 10.93 | 53.15 | 4.86 | n.d | n.d. | n.d | n.d. | n.d | n.d. |
| CEN.PK2U | AtLUP1 | — | — | — | | 3.42 | 10.74 | 3.14 | n.d | n.d. | n.d | n.d. | n.d | n.d. |
| CEN.PK2U | RcLUS1 | — | — | — | | 3.00 | 34.03 | 11.34 | n.d | n.d. | n.d | n.d. | n.d | n.d. |
| CEN.PK2U | OEW | LjCPR1 | A12 | DQ335781 | | 13.84 | 76.43 | 5.52 | 10.80 | 0.78 | k.A. | k.A. | n.d | n.d. |
| CEN.PK2U | OEW | LjCPR1 | AL1 | JN565975 | | 12.33 | 76.91 | 6.24 | n.d. | n.d. | k.A. | k.A. | n.d | n.d. |
| CEN.PK2U | OEW | LjCPR1 | A15 | AB619802 | | 11.74 | 65.15 | 5.55 | 43.24 | 3.68 | k.A. | k.A. | 3.79 | 0.32 |
| CEN.PK2U | OEW | LjCPR1 | A17 | AB619803 | | 12.13 | 72.19 | 5.95 | 15.39 | 1.27 | k.A. | k.A. | 4.48 | 0.37 |
| CEN.PK2U | OEW | LjCPR1 | A9 | XM_002331391 | | 12.93 | 82.18 | 6.36 | 6.89 | 0.53 | k.A. | k.A. | 3.82 | 0.30 |
| CEN.PK2U | OEW | LjCPR1 | B1 | XM_004139039 | | 11.00 | 47.94 | 4.36 | n.d | n.d. | k.A. | k.A. | n.d | n.d. |
| CEN.PK2U | OEW | LjCPR1 | A41 | JF803813 | | 12.43 | 65.12 | 5.24 | 0.87 | 0.07 | k.A. | k.A. | n.d | n.d. |
| CEN.PK2U | OEW | LjCPR1 | B2 | XM_003525274 | | 11.20 | 81.00 | 7.23 | n.d | n.d. | k.A. | k.A. | n.d | n.d. |
| CEN.PK2U | OEW | ATR1 | AL1 | JN565975 | | 13.42 | 127.73 | 9.52 | n.d | n.d. | k.A. | k.A. | nd | nd |
| CEN.PK 2U | OEW | ATR1 | A15 | AB619802 | | 14.52 | 80.41 | 5.54 | 10.18 | 0.70 | n.d | n.d. | 0.43 | 0.03 |
| CEN.PK 2U | OEW | ATR1 | A17 | AB619803 | | 14.81 | 78.41 | 5.29 | 7.08 | 0.48 | 3.54 | 0.24 | 0.95 | 0.06 |
| CEN.PK 2U | OEW | ATR1 | A9 | XM_002331391 | | 14.30 | 115.95 | 8.11 | 0.36 | 0.02 | n.d | n.d. | n.d | n.d. |
| CEN.PK 2U | OEW | ATR1 | B2 | XM_003525274 | | 14.47 | 106.90 | 7.39 | n.d | n.d. | n.d | n.d. | n.d | n.d. |
| CEN.PK 2U | OEW | MTR | A15 | AB619802 | | 13.12 | 47.02 | 3.58 | 101.57 | 7.74 | 26.33 | 2.01 | 27.31 | 2.08 |
| CEN.PK 2U | OEW | MTR | A17 | AB619803 | | 15.39 | 124.75 | 8.11 | 18.75 | 1.22 | 19.96 | 1.30 | 23.93 | 1.56 |
| CEN.PK 2U | OEW | MTR | A17 | AB619803 | | 3.58 | 24.78 | 6.91 | 6.30 | 1.76 | 12.08 | 3.37 | 26.82 | 7.48 |
| CEN.PK 2U | OEW | MTR | A9 | XM_002331391 | | 14.72 | 90.65 | 6.16 | 2.89 | 0.20 | n.d | n.d. | n.d | n.d. |
| CEN.PK 2U | OEW | MTR | B2 | XM_003525274 | | 15.48 | 76.08 | 4.92 | 7.03 | 0.45 | 3.62 | 0.23 | 3.46 | 0.22 |
| CEN.PK 2U | OEW | MTR | A12 | DQ335781 | | 15.18 | 89.38 | 5.89 | 23.99 | 1.58 | 9.07 | 0.60 | 1.56 | 0.10 |
| CEN.PK 2U | OEW | CrCPR | AL1 | JN565975 | | 15.04 | 119.22 | 7.93 | n.d | n.d. | n.d | n.d. | n.d | n.d. |
| CEN.PK 2U | OEW | CrCPR | A15 | AB619802 | | 15.88 | 75.50 | 4.76 | 50.28 | 3.17 | 5.74 | 0.36 | 5.70 | 0.36 |
| CEN.PK 2U | OEW | CrCPR | A17 | AB619803 | | 15.54 | 91.11 | 5.86 | 12.59 | 0.81 | 7.44 | 0.48 | 3.98 | 0.26 |
| CEN.PK 2U | OEW | CrCPR | A9 | XM_002331391 | | 14.56 | 127.42 | 8.75 | 1.23 | 0.08 | n.d | n.d. | n.d | n.d. |
| CEN.PK 2U | OEW | CrCPR | B2 | XM_003525274 | | 15.59 | 89.78 | 5.76 | 4.77 | 0.31 | 2.27 | 0.15 | 0.89 | 0.06 |
| CEN.PK 2U | OEW | NCP1 | A15 | AB619802 | | 15.74 | 94.68 | 6.02 | 2.42 | 0.15 | n.d | n.d. | n.d | n.d. |
| CEN.PK 2U | OEW | NCP1 | A17 | AB619803 | | 15.82 | 96.78 | 6.12 | 2.41 | 0.15 | n.d | n.d. | n.d | n.d. |
| CEN.PK 2U | OEW | NCP1 | A9 | XM_002331391 | | 15.21 | 94.07 | 6.18 | 0.04 | 0.00 | n.d | n.d. | n.d | n.d. |
| CEN.PK 2U | OEW | NCP1 | B2 | XM_003525274 | | 15.92 | 109.22 | 6.86 | 0.48 | 0.03 | n.d | n.d. | n.d | n.d. |

TABLE 10

| | | | | | | BTS | Lupeol | | Betulin | | betulin aldehyde | | betulinic acid | |
|---|---|---|---|---|---|---|---|---|---|---|---|---|---|---|
| strain | OSC gene | CPR gene | CYP gene | CYP gene accession | | g/l | mg/l | mg/g | g/l | mg/L | mg/g | g/l | mg/l | mg/g |
| AH22th3ura8 | OEW | — | — | — | | 12.82 | 126.48 | 9.87 | n.d | n.d. | n.d | n.d. | n.d | n.d. |
| AH22th3ura8 | OEW | LjCPR1 | A12 | DQ335781 | | 15.17 | 100.59 | 6.63 | 85.13 | 0.56 | k.A. | k.A. | 5.18 | 0.03 |
| AH22th3ura8 | OEW | LjCPR1 | AL1 | JN565975 | | 14.89 | 127.74 | 8.58 | 1.95 | 0.01 | k.A. | k.A. | n.d | n.d. |
| AH22th3ura8 | OEW | LjCPR1 | A15 | AB619802 | | 14.02 | 115.42 | 8.24 | 154.69 | 11.04 | 22.09 | 1.58 | 12.90 | 0.92 |
| AH22th3ura8 | OEW | LjCPR1 | A17 | AB619803 | | 14.32 | 103.00 | 7.19 | 38.42 | 2.68 | 44.33 | 3.10 | 28.12 | 1.96 |
| AH22th3ura8 | OEW | LjCPR1 | A9 | XM_002331391 | | 15.13 | 106.77 | 7.06 | 11.05 | 0.07 | k.A. | k.A. | n.d | n.d. |
| AH22th3ura8 | OEW | LjCPR1 | B1 | XM_004139039 | | 11.44 | 121.81 | 10.65 | n.d | n.d. | k.A. | k.A. | n.d | n.d. |
| AH22th3ura8 | OEW | LjCPR1 | A41 | JF803813 | | 14.90 | 128.53 | 8.63 | n.d | n.d. | k.A. | k.A. | n.d | n.d. |
| AH22th3ura8 | OEW | LjCPR1 | B2 | XM_003525274 | | 13.82 | 118.29 | 8.56 | 51.43 | 3.72 | 28.79 | 2.08 | 22.25 | 1.61 |
| AH22th3ura8 | OEW | MTR | A15 | AB619802 | | 14.61 | 61.91 | 4.24 | 276.46 | 18.93 | 63.85 | 4.37 | 92.17 | 6.31 |
| AH22th3ura8 | OEW | MTR | A17 | AB619803 | | 14.53 | 104.66 | 7.20 | 26.08 | 1.79 | 43.11 | 2.97 | 55.44 | 3.81 |
| AH22th3ura8 | OEW | MTR | B2 | XM_003525274 | | 14.54 | 108.51 | 7.47 | 32.52 | 2.24 | 25.37 | 1.75 | 29.53 | 2.03 |
| AH22th3ura8 | OEW | CrCPR | A15 | AB619802 | | 13.96 | 91.43 | 6.55 | 190.98 | 13.68 | 33.40 | 2.39 | 37.60 | 2.69 |
| AH22th3ura8 | OEW | CrCPR | A17 | AB619803 | | 14.28 | 117.76 | 8.25 | 31.22 | 2.19 | 42.71 | 2.99 | 34.90 | 2.44 |
| AH22th3ura8 | OEW | CrCPR | B2 | XM_003525274 | | 14.08 | 135.49 | 9.63 | 35.47 | 2.52 | 21.58 | 1.53 | 16.17 | 1.15 | n.d.: Concentration bellow the limits of detection
k.A.: no details

In Tables 9 and 10 the dry biomass substances (BTS) and the formed concentrations of the triterpenoids lupeol, betulin, betulin aldehyde and betulinic acid after 72 hours' cultivation in WMVIII medium are shown. Tests were performed on the influence of the expression of different OSC, CPR and CYP genes in the strains AH22th3ura8, CEN.PK2U and CEN.PK111-61A, which were transformed with the genes for the CPR and CYP enzymes on the pTT2 plasmid and/or with the gene for the OSC enzyme on the pTT1 plasmid.

In Tables 11, 12, 13 and 14 the preferred combinations of genes and the respective yields (independently of the yeast strain) of the pentacyclic triterpenoids are shown.

TABLE 11

Lupeol yield

| OSC gene | CPR gene | CYP gene | CYP gene accession | mg/l | mg/g |
|---|---|---|---|---|---|
| GuLUP1 | — | — | — | 67.50 | 12.66 |
| RcLUS1 | — | — | — | 34.03 | 11.34 |
| OEW | — | — | — | 129.89 | 11.02 |
| OEW | LjCPR1 | B1 | XM_004139039 | 121.81 | 10.65 |
| OEW | CrCPR | B2 | XM_003525274 | 135.49 | 9.63 |
| OEW | ATR1 | AL1 | JN565975 | 127.73 | 9.52 |
| OEW | CrCPR | A9 | XM_002331391 | 127.42 | 8.75 |
| OEW | LjCPR1 | A41 | JF803813 | 128.53 | 8.63 |
| OEW | LjCPR1 | AL1 | JN565975 | 127.74 | 8.58 |
| OEW | LjCPR1 | B2 | XM_003525274 | 118.29 | 8.56 |
| OEW | CrCPR | A17 | AB619803 | 117.76 | 8.25 |
| OEW | LjCPR1 | A15 | AB619802 | 115.42 | 8.24 |
| OEW | ATR1 | A9 | XM_002331391 | 115.95 | 8.11 |
| OEW | MTR | A17 | AB619803 | 124.75 | 8.11 |
| OEW | CrCPR | AL1 | JN565975 | 119.22 | 7.93 |
| OEW | MTR | B2 | XM_003525274 | 108.51 | 7.47 |
| OEW | ATR1 | B2 | XM_003525274 | 106.90 | 7.39 |
| OEW | LjCPR1 | A17 | AB619803 | 103.00 | 7.19 |
| OEW | LjCPR1 | A9 | XM_002331391 | 106.77 | 7.06 |
| OEW | NCP1 | B2 | XM_003525274 | 109.22 | 6.86 |
| OEW | LjCPR1 | A12 | DQ335781 | 100.59 | 6.63 |
| OEW | CrCPR | A15 | AB619802 | 91.43 | 6.55 |
| OEW | NCP1 | A9 | XM_002331391 | 94.07 | 6.18 |
| OEW | MTR | A9 | XM_002331391 | 90.65 | 6.16 |
| OEW | NCP1 | A17 | AB619803 | 96.78 | 6.12 |
| OEW | NCP1 | A15 | AB619802 | 94.68 | 6.02 |
| OEW | MTR | A12 | DQ335781 | 89.38 | 5.89 |
| OEW | ATR1 | A15 | AB619802 | 80.41 | 5.54 |
| OEW | ATR1 | A17 | AB619803 | 78.41 | 5.29 |
| OEW | LjCPR1 | A41 | JF803813 | 65.12 | 5.24 |

TABLE 12

Betulin

| OSC gene | CPR gene | CYP gene | CYP gene accession | mg/l | mg/g |
|---|---|---|---|---|---|
| OEW | MTR | A15 | AB619802 | 276.46 | 18.93 |
| OEW | CrCPR | A15 | AB619802 | 190.98 | 13.68 |
| OEW | LjCPR1 | A15 | AB619802 | 154.69 | 11.04 |
| OEW | LjCPR1 | B2 | XM_003525274 | 51.43 | 3.72 |
| OEW | LjCPR1 | A17 | AB619803 | 38.42 | 2.68 |
| OEW | CrCPR | B2 | XM_003525274 | 35.47 | 2.52 |
| OEW | MTR | B2 | XM_003525274 | 32.52 | 2.24 |
| OEW | CrCPR | A17 | AB619803 | 31.22 | 2.19 |
| OEW | MTR | A17 | AB619803 | 26.08 | 1.79 |
| OEW | MTR | A12 | DQ335781 | 23.99 | 1.58 |

TABLE 13 betulin aldehyde

| OSC gene | CPR gene | CYP gene | CYP gene accession | mg/l | mg/g |
|---|---|---|---|---|---|
| OEW | MTR | A15 | AB619802 | 63.85 | 4.37 |
| OEW | MTR | A17 | AB619803 | 12.08 | 3.37 |
| OEW | LjCPR1 | A17 | AB619803 | 44.33 | 3.10 |
| OEW | CrCPR | A17 | AB619803 | 42.71 | 2.99 |
| OEW | CrCPR | A15 | AB619802 | 33.40 | 2.39 |
| OEW | LjCPR1 | B2 | XM_003525274 | 28.79 | 2.08 |
| OEW | MTR | B2 | XM_003525274 | 25.37 | 1.75 |
| OEW | LjCPR1 | A15 | AB619802 | 22.09 | 1.58 |
| OEW | CrCPR | B2 | XM_003525274 | 21.58 | 1.53 |

TABLE 14 betulinic acid

| OSC gene | CPR gene | CYP gene | CYP gene accession | mg/l | mg/g |
|---|---|---|---|---|---|
| OEW | MTR | A17 | AB619803 | 26.82 | 7.48 |
| OEW | MTR | A15 | AB619802 | 92.17 | 6.31 |
| OEW | CrCPR | A15 | AB619802 | 37.60 | 2.69 |
| OEW | CrCPR | A17 | AB619803 | 34.90 | 2.44 |
| OEW | MTR | B2 | XM_003525274 | 29.53 | 2.03 |
| OEW | LjCPR1 | A17 | AB619803 | 28.12 | 1.96 |
| OEW | LjCPR1 | B2 | XM_003525274 | 22.25 | 1.61 |
| OEW | CrCPR | B2 | XM_003525274 | 16.17 | 1.15 |

REFERENCES

WO 2011/074766 A2
WO 2011/074766 A3R4
CN 102433347
WO2012/116783 A2
Cameron, S. I. and Smith, R. F., In Proceedings of the 29th Annual Meeting of the Plant Growth Regulation Society of America (ed. Halifax, N. S.), Bringing 'Blue Sky Biology' Down to Earth: Linking Natural Products Research with Commercialization, 2002, pp. 31-39
Chintharlapalli S, Papineni S, Lei P, Pathi S, Safe S. Betulinic acid inhibits colon cancer cell and tumor growth and induces proteasome-dependent and -independent down-regulation of specificity proteins (Sp) transcription factors. BMC Cancer. 2011 Aug. 24; 11:371. PubMed PMID: 21864401 PubMed Central PMCID: PMC3170653.
Fukushima E O, Seki H, Ohyama K, Ono E, Umemoto N, Mizutani M, Saito K, Muranaka T. CYP716A Subfamily Members are Multifunctional Oxidases in Triterpenoid Biosynthesis. Plant Cell Physiol. 2011 Oct. 28. [Epub ahead of print] PubMed PMID: 22039103.
Holanda Pinto S A, Pinto L M, Cunha G M, Chaves M H, Santos F A, Rao V S. Anti-inflammatory effect of alpha, beta-Amyrin, a pentacyclic triterpene from Protium heptaphyllum in rat model of acute periodontis. Inflammopharmacology. 2008 February; 16(1):48-52. PubMed PMID: 18046512.
Huang et al. 2012, Molecular characterization of the pentacyclic triterpenoid biosynthetic pathwa) in Catharanthus roseu. Planta 2012, 236:1571-1581.
Kirby et al. Engineering triterpene production in Saccharomyces cerevisiae—beta-amyrin synthase from Artemisia annua. FEBS J. 275(8):1852-1859, 2008
Li J, Zhang Y. Increase of betulinic acid production in Saccharomyces cerevisiae by balancing fatty acids and betulinic acid forming pathway. Appl Microbial Biotechnol. 2013

Muffler et al. Biotransformation of triterpenes. Process Biochem. 46(1): 1-15, 2011

Madsen K M, Udatha G D, Semba S, Otero J M, Koetter P, Nielsen J, Ebizuka Y, Kushiro T, Panagiotou G. Linking genotype and phenotype of Saccharomyces cerevisiae strains reveals metabolic engineering targets and leads to triterpene hyper-producers. PLoS One. 2011 Mar. 18; 6(3):e14763. PubMed PMID: 21445244; PubMed Central PMCID: PMC3060802.

McNeil et al. Plant shortage leaves campaigns against malaria at risk. New York Times 14 November, 2004

Melo C M, Morais T C, Tome A R, Brito G A, Chaves M H, Rao V S, Santos F A. Anti-inflammatory effect of a,13-amyrin, a triterpene from Protium heptaphyllum, on cerulein-induced acute pancreatitis in mice. Inflamm Res. 2011 July; 60(7):673-81. Epub 2011 Mar. 12. PubMed PMID: 21400110.

Philips D R, Rasbery J M, Bartel B, Matsuda S P T. Biosynthetic diversity in plant triterpenes cyclization. Current Opinion in Plant Biology. 2006 Apr. 3; 9:305-314.

Pisha et al. Discovery of betulinic acid as a selective inhibitor of human melanoma that functions by induction of apoptosis. Nat Med 1(10):1046-1051, 1995

Polakowski et al. Overexpression of a cytosolic hydroxymethylglutaryl-CoA reductase leads to squalene accumulation in yeast. Appl Microbial Biotechnol. 49(1):66-71, 1998

Raskin et al. Plants and human health in the twenty-first century. Trends Biotechnol. 20(12):522-531, 2002

Ruzicka et al. Helv. Chim. Acta 21, 1076-1078, 1938

Robinson et al. Betulinic acid from Arbutus menziesii. Phytochemistry 9(4):907-909, 1970

Saleem M, Murtaza I, Tarapore R S, Suh Y, Adhami V M, Johnson J J, Siddiqui I A, Khan N, Asim M, Hafeez B B, Shekhani M T, Li B, Mukhtar H. Lupeol inhibits proliferation of human prostate cancer cells by targeting beta-catenin signaling. Carcinogenesis. 2009 May; 30(5):808-17. Epub 2009 Feb. 20. PubMed PMID: 19233958.

Shanmugam M K, Rajendran P, Li F, Nema T, Vali S, Abbasi T, Kapoor S, Sharma A, Kumar A P, Ho P C, Hui K M, Sethi G. Ursolic acid inhibits multiple cell survival pathways leading to suppression of growth of prostate cancer xenograft in nude mice. J Mol Med (Berl). 2011 July; 89(7):713-27. doi: 10.1007/s00109-011-0746-2. Epub 2011 Apr. 5. PubMed PMID: 21465181.

Siddique H R, Saleem M. Beneficial health effects of lupeol triterpene: a review of preclinical studies. Life Sci. 2011 Feb. 14; 88(7-8):285-93. Epub 2010 Nov. 29. Review. PubMed PMID: 21118697.

Sunder et al. Use of betulinic acid and its derivatives for inhibiting cancer growth and a method for monitoring this. U.S. Pat. No. 6,048,847, 2000

Suzuki H, Achnine L, Xu R, Matsuda S P, Dixon R A. A genomics approach to the early stages of triterpene saponin biosynthesis in Medicago truncatula. Plant J. 2002 December; 32(6):1033-48. PubMed PMID: 12492844

Veen et al. Combined overexpression of genes of the ergosterol biosynthetic pathway leads to accumulation of sterols in Saccharomyces cerevisiae. FEMS Yeast Res. 4, 87-95, 2003

Wang Z, Guhling 0, Yao R, Li F, Yeats T H, Rose J K, Jetter R. Two oxidosqualene cyclases responsible for biosynthesis of tomato fruit cuticular triterpenoids. Plant Physiol. 2011 January; 155(1):540-52. Epub 2010 Nov. 8. PubMed PMID: 21059824; PubMed Central PMCID: PMC3075788.

---

SEQUENCE LISTING

<160> NUMBER OF SEQ ID NOS: 105

<210> SEQ ID NO 1
<211> LENGTH: 2268
<212> TYPE: DNA
<213> ORGANISM: Betula platyphylla

<400> SEQUENCE: 1

```
atgtggaagt tgaagatagc ggaaggaggg ccagggctgg tgagcggaaa tgatttcatc      60
gggcggcaac actgggaatt cgaccgggat gccggcactc cccaagagcg tgctgaagtt     120
gaaaaggtcc gggaggagtt caccaaaaat cggtttcaga tgaaacaaag cgctgatctt     180
ttgatgagga tgcagcttag gaaggagaac ccatgccaac caattccacc accagtgaaa     240
gtgaaagaaa cagaggtgat aacagaggaa gcagtgatta ctacactgag aagatcacta     300
agcttttatt cctccattca agctcatgat ggccactggc ctggtgaatc tgctggcccc     360 ttgttttttcc ttcaaccctt tgtaatggca ttatacatca ctggagatct caatactatt     420
ttttccccag cacaccagaa ggaaattatt cgatacttgt ataatcatca gaacgaagat     480
ggaggctggg ggttccatat agagggtcac agcacaatgt ttgggtcagc tttgagctac     540
attgccttga gaatacttgg agagggactt gaagatggtg aagatggggc tatggctaaa     600
agccggaaat ggattcttga ccatggtggt ttagtggcta ttccttcatg gggaaagttt     660
tgggtcacgg tactgggact gtatgagtgg tcaggctgca atccactgcc cccagagttc     720
tggtttcttc ctgatatctt tcccatacat ccaggtaaaa tgttatgcta ctgtcgcttg     780
```

```
gtttacatgc caatgtctta tttatatggg aagaggtttg ttggtccaat cactggattg    840
attcaatcac ttagacaaga gttatataac gagccttacc atcaaattaa ctggaataaa    900
gcccggagta cagttgcaaa ggaggatctc tactatccgc atcccctcat acaagatctg    960
ctatggggat tcttcacca gtagccgag cctgtcctga cgcgttggcc cttttcaatg     1020
ctgagagaga aggcactcaa agctgcaatt ggtcatgtac attatgagga cgagaacagc   1080 aaatacctttt gcattggaag cgttgaaaag gtattatgtt tgattgcctg ttgggctgaa   1140
gatccaaatg gggaggcata caagcttcat ctaggaagga ttccagacaa ctattgggtt   1200
gctgaagatg gcttaaaaat tcagagtttc ggctgtcaga gtgggatgc gggttttgct    1260 attcaagcaa ttctctcttg caatttaaac gaagagtatt ggccaacact tcgtaaagca   1320
catgagtttg taaaggcttc acaggtccca gaaaacccttt ctggggactt caaagccatg   1380
taccgccaca taaacaaagg agcatggaca ttctcgatgc aggaccatgg atggcaggtc   1440
tctgactgca ccgctgaagg gctgaaggtt gcaatcttgt tctcgcaaat gcctccggac   1500
cttgttgggg aaaaaattga gaaagagcgg ttatatgatg ctgtgaatgt cattctttct   1560
ctacaaagta gcaatggtgg tttcccagca tgggagcctc aaagagcata tggttggttg   1620
gagaagttca accccacgga attctttgaa gatacccctta ttgagcgaga gtacgtagag   1680
tgcacttcac ctgcagttca tggtctggca ctctttagga agttctatcc ccggcaccgg   1740
gggacggaga tagatagtag catttacagg ggaattcaat acattgaaga cgtgcaagaa   1800
cctgatggat catggtatgg tcattggggg atttgctaca cctacggtac atggtttgct   1860
gtaggggcac tggcagcttg tggaagaaac tacaaaaatt gtcctgcatt gcgcaaatct   1920
tgtgaatttt tgctatcaaa gcagctacct aatggtggat ggggagaaag ttacctatca   1980
agccaaaaca aggtgtggac gaatatagaa ggcaaccgtg caaatttggt ccaaacagca   2040
tgggccttgt tatccctcat tgatgctagg caggccgaga tagatccaac accaattcat   2100
cgtggagtaa gagtattgat caattcacag atggaagatg gtgactttcc tcaacaggaa   2160
atcactggag tatttatgcg aaactgcaca ctaaactact catcatatag aaacattttt   2220
ccgatatggg ctcttggaga atatcggagg cgagttctat ttgcatga                2268
```

<210> SEQ ID NO 2
<211> LENGTH: 2277
<212> TYPE: DNA
<213> ORGANISM: Olea europaea

<400> SEQUENCE: 2

```
atgtggaagt tgaagattgc tgatggaaca gggccgtggc ttacaacaac caataatcat    60
attggaagac agcattggga attcgatcct gaggctggaa ctccagatga acgagtcgag   120
gttgaaagac tgcgtgaaga gttcaagaag aacagatttc gaactaaaca aagtgctgat   180
ttgctgatgc gtatgcagct tgtgaaggag aaccacgtg ttcaaatccc accagcgatc    240
aaaatcaaag aaacagaagg tataacagag gaagcagtga taactactct aagaagagcc   300
ataagtttct attccacaat tcaagctcac gatggccact ggccagctga atccgccggc   360 cctttgttttt tcctccctcc tttggtctta gccttgtatg tgactggagc aatcaatgtt   420
gttctatcgc gagaacatca gaaagagatt acacgataca tatacaatca tcagaatgaa   480
gatggaggtt gggggataca tatagagggt catagcacca tgtttggttc tgtgcttagc   540
tacattacgc ttaggttgct aggagaagga caagaagatg gtgaagacaa ggccgtagct   600
agaggtcgaa aatggatact tgaccatggt ggcgccgtgg ggataccatc gtggggtaag   660
```

```
ttttggctta cggtgctcgg agtatacgag tgggatggct gcaacccaat gcccccagaa      720
ttctggctgc ttcccaattt ttcccccaatt catccaggaa agatgttgtg ttattgtcgg      780
ttggtataca tgcccatgtc atatttgtat ggcaagaggt tgttggacc aattactgga       840 ttggtgctat cactaaggca agagatttat actgaacctt atcatggaat aaattggaat      900
agggcaagga acacctgtgc aaaggaggat ctttactacc cacaccctct ggcacaagat      960
atgctttggg gattcctcca tcattttgcc gagccagttc taactcgatg ccgttttct      1020 aaactaagag agaaggcttt aaaagttgca atggagcatg ttcattatga ggacatgaac     1080
agcagatacc tttgcattgg atgtgtagag aaggtgttat gtcttattgc ttgttgggta     1140
gaagatccta attctgaagc atacaaaaga catatagcac gtatacctga ttacttctgg     1200
gtcgccgaag atggcctgaa aatgcagagt tttgggtgtc aaatgtggga tgcagctttt     1260
gctattcaag ccatattatc atccaatcta gctgaagagt acgggccgac cctcatgaaa     1320
gcacacaact ttgtgaaagc ctcacaggtc caagaaaatc catctggaga ttttaatgaa     1380
atgtatcgtc acacttctaa aggcgcctgg acattttcta tgcaagatca tggttggcaa     1440
gtctcagatt gtacagctga aggacttaag gccgcactct tattctcgca aatgcctata     1500
gaactagttg gagcagaaat cgaaacagga catttatatg atgctgtaaa tgtcattttg     1560
acccttcaga gtgctagtgg cggttttcca gcatgggagc ctcagaaagc atatcgatgg     1620
ttggagaagc tcaaccctac agagttttt gaagatgttc ttatagagcg agattatgta      1680
gagtgcacat catcagcagt ccaagcctta aagctcttta agcagttgca tccaggacac     1740
agaagaaagg aaatagcaag ctgcatctca aaagcaatac aatacatcga agctactcaa     1800
aatcctgatg gttcatggga tggtagttgg ggaatatgct ttacgtatgg cacgtggttt     1860
gcagtagagg gcttggtcgc ttgtgggaaa aattatcata actctcccac actacggaga     1920
gcatgtgaat ttttgttgtc gaaacaatta ccgatggtg gatggagtga agctaccttt     1980
tcgagctcga acaaggtata tactaatctt gaaggtaatc ggtcaaattt ggtgcaaacc     2040
tcatgggctc tgttgtctct catcaaagct gggcaggtcg agattgatcc tgggcctata     2100
catcgtggaa taaaactgct agtaaattca caaatggaag atggtgactt tcctcaagag     2160
gaaattacag gagcattcat gaagaattgt actctgaact attcatcgta ccggaatatc     2220
tttccaatat gggctctcgg tgagtatcgt cgtcggattc ttcatgcaca aacatag       2277
```

<210> SEQ ID NO 3
<211> LENGTH: 2277
<212> TYPE: DNA
<213> ORGANISM: Glycyrrhiza uralensis

<400> SEQUENCE: 3

```
atgtggaagc tgaagatagg agaaggagga gcggggttga tttccgtgaa caacttcatc       60
ggacggcaac actgggagtt cgatccaaat gcaggaactc acaggaaaca cgctgagatt      120
gaaaggctac gccgggaatt caccaaaaac cgttttttcca tcaaacaaag cgctgaccctc    180 ttgatgagaa tgcagctcag aaaggagaac cattacggca ccaataataa tattccagca     240
gcagtgaaat tgagtgacgc agagaacata acggtggaag cattggttac aacaattaga     300
agggctatca gtttctattc ctcaattcaa gcccatgatg acactggcc tgcagaatct       360 gctggccctc tcttttttcct tcaaccattg gtaatggccc tatatattac aggatcccctt    420 gatgacgttt taggacctga acataagaag gaaattgttc gctatttgta taatcatcag      480
```

```
aatgaagatg gtgggtgggg attccatata gagggtcata gcacaatgtt tggatctgca      540
ttgagctacg ttgcattaag gatacttgga gaagggcctg aagacaaggc aatggccaaa      600
ggcagaaaat ggatcctcga ccacggtggt ttagttgcta ttccatcatg gggaaagttc      660
tgggtcacgg tacttggagc ttatgagtgg tcaggctgca atccacttcc accagagtta      720
tggcttctgc ccaaattcac ccctttcat ccaggaaaaa tgttgtgcta ctgtcgcttg       780
gtttacatgc ccatgtcata tttatatggg aagaagttcg tgggccctat cactgcctta      840
atcagatcac tacgagaaga attgtacaat gagccttata atcaaattaa ctggaataca      900
gctcgaaaca ctgttgctaa ggaggatctc tactacccac atcctctgat ccaagatatg      960
ttatggggat ttcttatca cgtgggagag cgttttctga attgctggcc cttttccatg      1020
cttagacgga aggcattaga aatcgcaatt aatcatgtac attacgagga cgagaacagt      1080
agataccttt gcattggcag tgtagagaag gtgttatgtt tgattgcgcg ttgggttgaa      1140
gatcccaact cagaggcata caaacttcat ttagcccgaa tccctgatta cttctggctc      1200
gctgaagatg gcttgaaaat ccagagcttt gggtgccaga tgtgggatgc agcattcgct      1260
atacaagcaa tacttgcctg taatgtgagt gaggagtatg gacctacgct ccggaaagca      1320
caccacttcg tgaaggcttc gcaggttcgc gaaaacccat ccggtgactt caacgcaatg      1380
tacagacaca tttcgaaagg agcatggaca ttctcaatgc atgatcacgg ttggcaagtc      1440
tctgactgca ccgcagaagg actaaaggct gcactgctat tgtcagaaat gccaagtgaa      1500
ctagttgggg ggaaaatgga aacagagcgc ttctacgacg ctgttaatgt catcctctct      1560
ctacaaagca gtaatggcgg gttccctgct tgggagcctc agaaagcgta ccgttggtta      1620
gagaaattca atccaactga attctttgaa gacactatga ttgagaggga gtatgttgag      1680
tgcactggat ccgcaatgca agggttggct ctcttcagaa agcaataccc acagcacaga      1740
agcaaggaaa tagatcgctg cattgccaaa gcaatccgtt acatagaaaa catgcaaaat      1800
cctgatggct cttggtatgg gtgttgggga atttgctata catacggtac atggtttgcc      1860
gtggagggac taacggcctg tgggaagaac tgccacaaca gtctttcctt gcgaaaagct      1920
tgtcaattct tgttgtcaaa gcagcttcct aatgcgggt ggggagaaag ttacttgtca       1980
agccaaaaca aggtgtatac aaacctagaa ggaaaccgtg caaatttagt tcaaagttcg      2040
tgggctttgt tgtcccttac tcatgcaggg caggccgaga tagatcctac acccatacac      2100
cgtggaatga agttactcat caattcacaa atggaagatg gagacttccc acagcaggag      2160
attacaggag tatttatgag gaactgtacc ctgaactact catcgtatcg aaacatcttt      2220
cccatatggg ctatgggaga gtatcgtcgc caagtcttgt gtgctcacag ttattga        2277

<210> SEQ ID NO 4
<211> LENGTH: 2274
<212> TYPE: DNA
<213> ORGANISM: Arabidopsis thaliana

<400> SEQUENCE: 4
atgtggaagt tgaagatagg aaagggaaat ggagaagatc cgcatttatt cagcagcaat       60
aacttcgtcg acgtcaaac atggaagttt gatcacaaag ccggctcacc ggaggaacga       120
gctgccgtcg aagaagctcg ccggggtttc ttggataacc gttttcgtgt taaaggttgc      180
agtgatctat tgtggcgaat gcaatttcta agagagaaga aattcgaaca aggcatacca      240
caactaaaag ctactaacat agaagaaata acgtatgaaa caacgacaaa tgcattacga      300
agaggcgttc gttacttcac ggctttgcaa gcctccgacg gccattggcc gggagaaatc      360
```

```
accggtccgc ttttcttcct tcctcctctc atattttgtt tgtacattac cggacatctg    420
gaggaagtat tcgatgctga acatcgcaaa gagatgctaa gacatatcta ttgtcaccag    480
aacgaagatg gtggatgggg attacacatc gaaagcaaga gtgttatgtt ctgcaccgtg    540
ttgaattaca tatgtttacg tatgcttgga gaaaatcctg aacaagacgc atgcaaacga    600
gctagacaat ggattcttga ccgcggtgga gtgatcttta ttccttcttg ggggaaattt    660
tggctctcga tacttggagt ctatgattgg tctggaacta atccgacgcc accagaactc    720
ttgatgctgc cttctttcct tccaatacat ccagggaaaa ttttgtgtta tagccggatg    780
gttagtatac ctatgtcgta tctatatggg aagaggtttg ttggtccaat tacacctctt    840
attttactct tgcgcgaaga actttacttg gaaccttatg aagaaatcaa ttggaaaaaa    900
agtcgacgtc tatatgcaaa agaagacatg tattatgctc atcctttggt tcaagatttg    960
ttatctgaca ctcttcaaaa ctttgtggag cctttactta cacgttggcc attgaacaag   1020
cttgtgaggg aaaaagctct tcagcttact atgaaacaca tacactatga agacgaaaat   1080
agccattaca taaccattgg atgtgttgaa aaggtactgt gcatgctagc ttgttgggtt   1140
gaaaatccga tggagatta tttcaagaag catctggcta gaattccaga ttatatgtgg   1200
gtcgctgaag atgaatgaa atgcagagc tttggatgtc aactgtggga tactggatttt   1260 gctattcaag ctttgcttgc aagtaatctc cctgatgaaa ctgatgatgc actaaagaga   1320
ggacataatt acataaaggc atctcaggtt agagaaaacc cttcaggtga ttttaggagc   1380
atgtaccgcc acattccgaa aggagcatgg acattttctg atcgagatca tggatggcaa   1440
gtttcagatt gtacagctga agctttaaag tgttgcctgc tgctttccat gatgtcagct   1500
gatatcgtcg ccagaaaat agatgatgaa caattatatg actctgttaa cctcttgctg   1560
tctttacaga gcggaaatgg aggtgtcaat gcgtgggagc catcccgtgc atataaatgg   1620
ttggaactgc tcaatcctac agaattcatg gctaatacca tggtcgagcg ggagtttgtg   1680
gaatgcacct catctgttat acaagcactt gatctattta gaaaattgta tccagatcac   1740
aggaagaaag agatcaacag gtccatcgaa aaagctgtgc aatttataca agacaatcaa   1800
acaccagacg gttcatggta cggaaattgg ggtgttttgct tcatttacgc tacttggttt   1860
gctcttggag gcctagcagc agctggtgaa acttacaacg attgtttagc tatgcgcaat   1920
ggtgtccact ttttgctcac gacacaaaga gatgatgag gttggggtga agctatttta   1980
tcatgctccg aacagagata tataccatca gaaggagaaa gatcaaacct tgtgcaaaca   2040
tcatgggcta tgatggctct aattcatacg ggacaggctg agagagattt gattcctctt   2100
catcgtgctg ccaaacttat catcaattca caacttgaaa acggcgattt tcctcaacag   2160
gaaatagtag gagcgttcat gaatacatgc atgctacact atgctacata cagaaacacc   2220
ttcccattat gggcactcgc agaataccga aaagttgtgt ttatcgttaa ttaa         2274
```

<210> SEQ ID NO 5
<211> LENGTH: 2268
<212> TYPE: DNA
<213> ORGANISM: Lotus japonicus

<400> SEQUENCE: 5

```
atgtggaagt tgaaggtagc agaaggagga aaagggttgg tttctgtgag caatttcatc     60
ggaaggcaac actgggtgtt cgacccaaat gcagggacac cacaagaaca tgaggagatt    120
gaaaggatgc gccaagaatt caccaaaaat cgattctcca tcaaacaaag tgcagacctc    180
```

```
ttgatgagaa tgcagctgag aaaggagaac ccttgtgggc ccatcccacc agcagttaaa        240
ttgagagatg tggaaaaggt aactgcagaa gcattgatca ctacaattag aaggtccatc        300
accttttatt cttcaattca agcccatgat ggccactggc ctgctgaatc tgcaggccca        360
ttattcttcg ttcaaccttt ggtaatggca ctgtacatta caggatccct tgatgatgta        420
ttaggacctc aacacaagaa ggaaattatt cgatatttgt ataatcatca gaacgaagat        480
gggggttggg gattccacat agagggtcat agtaccatgt ttggatctgc attgagctac        540
attgcattga gggtacttgg acaaagcctt gaagatggtg aggacatggc agtggccaga        600
ggcagaaaat ggatcctcga tcatggcggt ttagtagcta ttccatcatg ggaaagttc         660 tgggtcacgg tgctaggggt ttatgagtgg tcagggtgca atccccttcc accagagttc        720
tggcttctac ccaaaatttt ccctattcat ccagggaaaa tgttatgtta ctgtcgctta        780
gtttacatgc ccatgtcata tttatatgga aagaagtttg taggcccaat cactgcctta        840
gtcagatcac taagaaaaga attgtacaat gagccttatg atcgagttga ctggaataag        900
gcccgcaaca ctgttgctaa ggaggatcta tactatcccc atcctctaat ccaagacatg        960
ttatggggat tcttcatca gtgggagag cgtgttctga cacttggcc attttcaatg           1020 ctaagacaga aggcaataga agttgctatt aatcatgtac gttacgagga tgagaccact        1080
aggtaccttt gcattggaag tgtagagaag gtgttatatt tgattgcgcg ttgggttgaa        1140
gaccccaact cagaggctta caaacttcat ttagcccgaa tccctgatta cttctggctt        1200
gcagaagatg gcttgaaaat ccagagtttt ggctgccaaa tgtgggatgc agcatttgct        1260
attcaagcaa tactgagtgg taatgtgagt gaagagtatg gaccaacatt aaagaaagca        1320
caccactttg tgaaggcttc gcaggtacgt gaaaacccat ccggtgactt caaagcaatg        1380
tacagacaca tttccaaagg ggcatggaca ttctcaatgc atgatcatgg atggcaagtc        1440
tctgattgca cagcagaagg actaaaggtt gcactcctac tgtcagaaat gtcagatgat        1500
ctagttgggg caaaaatgga aacagagcaa ttctatgatg ctgttaatgt catcctctct        1560
ctacaaagca gcaatggtgg tttccctgct tgggagcctc aaagagccta ccaatggtta        1620
gagaaattca atccaactga attctttgaa gaaactctga ttgagaggga gtatgtagag        1680
tgcactggtt cagcaatgca agccctggct cttttcagaa agctataccc gaagcatagg        1740
cgaaaggaaa tagatcgctg catttccaaa gcaatccgat acattgaaaa cacacaaaat        1800
cctgatgggt cttggtatgg ttgctgggga atttgctaca cttatggtac ctggtttgca        1860
gtggaaggac taacagcttg tgggaagaac ttccaaaata gtgttacctt gcgtagagca        1920
tgtaaatttt tgttgtcaaa gcagcttcct aatggagggt ggggagaaag ttacttgtca        1980
agccaagaca aggtgtacac aaacattgaa ggaaaacgtg caaatttggt tcaaagttca        2040
tgggctttgt tgtcacttat gcgtgctggg caggctgaga tagatccgac accaattcac        2100
cgtggaataa ggttactcat taattcacaa atggatgatg agacttccc acaacaggag         2160 attacaggag tatttatgag gaactgtacc ctaaactact catcatatcg aaacatcttt        2220
cctatatggg ctcttggaga gtaccgtcgc agagtcttat gtgcatga                    2268
```

<210> SEQ ID NO 6
<211> LENGTH: 2310
<212> TYPE: DNA
<213> ORGANISM: Ricinus communis

<400> SEQUENCE: 6

```
atgtggcgaa ttaa

| | |
|---|---|
| tttcagggaa ggcaaatttg ggtatttgat cctaatgctg gtactcctga agaacaagcc | 120 |
| gaggttgaag aagctcgtca aaacttctgg aaaaatcgat ttcaggtcaa gcctaactct | 180 |
| gatctccttt ggcaactcca gtttctaagg gagaaaaatt ttaagcaaaa aattccaaaa | 240 |
| gtaaaggttg aagatggcga ggagatcaca agtgaaatag ctgcagccgc tttgaggaga | 300 |
| agcgtccact tgttttcggc cttgcaggca agcgatggcc attggtgtgc agaaaatgga | 360 |
| ggcctgctgt tcttttttgcc tcccttggtt tttgctgtct acattacagg acaccttaat | 420 |
| actgtatttt ctccagagca tcgcaaagaa atcctccgtt acatatactg tcatcagaat | 480 |
| gaagatggtg gatggggaat acacattgaa ggtcacagca ctatgttttg cacagttctt | 540 |
| aattatatat gtatgcgtat acttggtgaa gcacgtgatg gtggaataga aatgcttgt | 600 |
| gaaagagggc gaaatggat actcgatcat ggtggtgcaa ctggtatatc ttcttgggga | 660 |
| aagacatggc tttcgatact tggtgtgtac gagtgggatg ggaccaatcc catgccccca | 720 |
| gagttttggg cctttccatc ttcttttccc ttacacccag caaaaatgtt ttgttactgt | 780 |
| cggatcactt acatgccaat gtcgtacttg tacgggaaga ggtttgttgg tccaatcaca | 840 |
| ccactcattc tacaaataag agaagaaatc tataatgaac cttacaacaa atcaagtgg | 900 |
| aatagtgtgc gtcatttatg tgcaaaggaa gacaactatt ttccacatcc aacgatacag | 960 |
| aaactgttat gggatgctct gtatacattt agcgagcctc tattctctcg ttggcccttc | 1020 |
| aacaaattga gagagaaggc tctcaagata caatggatc acattcatta tgaagatcac | 1080 |
| aacagtcggt acatcactat tggatgcgtt gagaagccgt tatgcatgct tgcctgttgg | 1140 |
| attgaagatc ctcatgggga agcgtttaag aagcaccttg ccagaattgc agattacata | 1200 |
| tgggttggag aagatggaat aaagatgcag agtttcggaa gtcaaacatg ggacacaagt | 1260 |
| ctagctcttc aggccctgat agctagcgac ctctctcatg aaataggacc tacactaaaa | 1320 |
| caaggacacg tcttcacgaa gaattctcag gcaactgaga acccttcggg cgacttcaga | 1380 |
| aaaatgtttc gtcatatctc caaggagct tggacattct ctgataaaga tcaaggatgg | 1440 |
| caagtttctg attgtacagc agaaagcttg aagtgctgcc tacttttctc aatgatgcct | 1500 |
| cccgaaattg ttggtgagaa aatggaacct gaaaaggtct atgattcagt caatgtcata | 1560 |
| ctttctcttc agagccaaaa tggtggtttc acagcttggg agccagcaag agcaggatca | 1620 |
| tggatggagt ggctcaaccc tgtagagttc atggaggatc ttgtcgttga gcacgagtat | 1680 |
| gtggagtgca cttcatcagc aatccaagca ctagttcttt ttaaaaaatt atatccccga | 1740 |
| cacaggaaca aagagattga aaattgtatc ataaatgctg cgcagttcat tgaaaatata | 1800 |
| caagaacctg atggttcatg gtatggaaat tgggggatat gcttctctta tggtacctgg | 1860 |
| tttgcactga aggattagc tgctgctgga aggacatatg aaaattgttc tgctattcgt | 1920 |
| aaaggtgttg atttctctact aaaatcacaa agagatgatg gtggatgggc agagagttat | 1980 |
| ctttcatgtc caagaaggt gtatgttcct tttgagggta atcgatcaaa tctagttcaa | 2040 |
| actgcttggg caatgatggg tttgatttat ggaggacagg ccaaaagaga ccctatgcct | 2100 |
| cttcatcgcg ctgcaaagtt attaattaat tctcaaacag atcttggtga ttttcctcaa | 2160 |
| caggaactta caggagcatt catgaggaat tgcatgctgc actatgcact atttaggaat | 2220 |
| acttttccca tttgggcttt ggcagaatat cggcgacatg tcttattccc ttctgctgga | 2280 |
| tttggttttg gattcaccaa taatttatga | 2310 |

<210> SEQ ID NO 7

<211> LENGTH: 2277
<212> TYPE: DNA
<213> ORGANISM: Taraxacum officinale

<400> SEQUENCE: 7

```
atgtggaagc tgaaaatagc agaaggtggt gatgatgagt ggctgaccac caccaacaac      60
cacgtcggcc gtcagcactg cagtttgat  ccggatgctg aaccgaaga  ggaacgtgct     120
gagattgaaa agattcgtct caacttcaaa cttaatcgtt ttcaattcaa acaaagtgcc     180
gacttgttaa tgcgtactca actaagaaaa gagaacccaa tcaataaaat accggatgca     240
ataaaattga atgaaacaga agaagtgaca atgacgcag  tgacaactac actcaaaaga     300
gccattagct tttactccac cattcaagcc catgatgggc actggccagc tgagtctgct     360
ggcccttttgt tcttccttcc tccattggta atagcactat atgtgactgg agcaatgaat     420
gatattctaa cacccgcaca tcagctagaa ataaaacgtt acatatacaa tcatcagaat     480
gaagatggag gttggggatt acatatagag ggtcatagca caatatttgg atcagtactt     540
agttacataa ctttaagatt acttgggaa  gaagctgata gtgttgcaga ggacatggct     600
ttggttaagg ggcgtaaatg gatccttgac catggtggtg cagttgggat tccttcatgg     660
ggaaagtttt ggcttacgat acttggagta tacgaatggg gaggctgtaa tcctatgcca     720
cccgaattt  ggctcatgcc taagttttt  ccaattcatc caggcaaaat gttgtgttat     780
tgtcgcttag tttacatgcc catgtcgtac ttatacggca aaagatttgt gggaaaaata     840
accgagttgg ttcgagacct aaggcaagag ctttatacgg acccttatga tgagattaat     900
tggaataaag cacgaaacac gtgtgcaaag gaagatctct actatccaca ccctttttgtt     960
caagatatgg tatggggtgt acttcataat gttgttgaac ctgtattaac aagtcgtccg    1020
atttccacac taagagaaaa ggctttgaaa gtcgcaatgg atcatgttca ctatgaagat    1080
aagagcagta gatatctttg cattggatgt gtggaaaagg tgttatgctt gattgcaacg    1140
tgggtggaag atccaaatgg tgatgcatat aaacgtcatc ttgctagaat tcctgactac    1200
ttttggttg  ctgaggatgg gatgaaaatg cagagttttg gatgtcaaat gtgggatgca    1260
gcatttgcta ttcaagctat tttttcaagt aatctaacag aagaatacgg cccgactctt    1320
aaaaaagcac acgagtttgt aaaagcatca caggttcgtg ataatcctcc tggagatttc    1380
agtaaaatgt accgacatac ttctaagggt gcatggacat tttccataca agaccacggt    1440
tggcaagtct ctgattgtac cgcagaaggc ttgaaggttt cacttttgta ctcccaaatg    1500
aacccaaaac tagtgggcga aaagttgaa  acggagcatc tctacgacgc tgtcaatgtc    1560
attcttcat  tacaaagtga aatggtggc  tttcctgctt gggaaccaca aagggcgtac    1620
gcttggctgg agaaattcaa ccccactgaa ttctttgaag atgtgttgat tgagcgagag    1680
tatgttgaat gcacttcatc tgcaatccaa ggtttgacac tcttcaagaa gttgcaccca    1740
gggcacagaa ccaaggagat cgagcattgt atatcaagag ctgtaaagta cgttgaagac    1800
acacaagaaa gtgatggttc atggtatggt tgttggggaa tttgctacac ctatggtaca    1860
tggtttgcgg tagatgcgct agtagcttgt gggaagaact atcataactg tcccgctctt    1920
caaaaagctt gcaaatttct gttatccaaa caacttccgg atggtggatg gggagagagt    1980
tatctttcga gctcaaataa ggtgtatacg aatttggagg gaaatcgttc gaatttagtg    2040
catacatcat gggctttaat atcccttatt aaagctggac aggctgaaat tgatcctaca    2100
ccaatatcta atggcgtacg gcttctcatc aattcacaaa tggaagaagg ggactttcct    2160
caacaggaaa tcacaggagt gttcatgaag aactgtaacc tcaattactc atcatttcga    2220
```

| | |
|---|---:|
| aatatttttc ccatatgggc acttggtgaa tatcgtcgta ttgttcaaaa tatatga | 2277 |

<210> SEQ ID NO 8
<211> LENGTH: 2277
<212> TYPE: DNA
<213> ORGANISM: Glycyrrhiza glabra

<400> SEQUENCE: 8

| | |
|---|---:|
| atgtggaagc tgaagatagg agaaggagga gcggggttga tttccgtgaa caacttcatc | 60 |
| ggacggcaac actgggagtt cgatccaaat gcaggaactc cacaggaaca cgctgagatt | 120 |
| gaaaggctac gccgggaatt caccaaaaac cgttttttcca tcaaacaaag cgctgacctc | 180 |
| ttgatgagaa tgcagctcag aaaggagaac cattacggca ccaataataa tattccagca | 240 |
| gcagtgaaat tgagtgacgc agagaacata acggtggaag cattggttac aacaattaca | 300 |
| agggctatca gtttctattc ctcaattcaa gcccatgatg acactggcc tgcagaatct | 360 |
| gctgggcctc tcttttttcct tcaaccattg gtaatggccc tatatattac aggatcccttt | 420 |
| gatgacgttt taggacctga acataagaag gaaattgttc gctatttgta taatcatcag | 480 |
| aatgaagatg gtgggtgggg attccatata gagggtcata gcacaatgtt tggatctgca | 540 |
| ttgagctacg ttgcattaag gatacttgga aagggcctc aagacaaggc aatggccaaa | 600 |
| ggcagaaaat ggatcctcga ccacggtggt ttagttgcta ttccatcatg gggaaagttc | 660 |
| tgggtcacgg tacttggagc ttatgagtgg tcaggctgca atccacttcc accagagtta | 720 |
| tggcttctgc ccaaattcgc ccctttttcat ccaggaaaaa tgttgtgcta ctgtcgcttg | 780 |
| gtttacatgc ccatgtcata tttatatggg aagaagttcg tgggccctat cactgcctta | 840 |
| atcagatcac tacgagaaga attgtacaat gagcctttata atcaaattaa ctggaataca | 900 |
| gctcgaaaca ctgttgctaa ggaggatctc tactacccac atcctctgat ccaagatatg | 960 |
| ttatggggat ttcttttatca cgtgggagag cgttttctga attgctggcc cttttccatg | 1020 |
| cttagacgga aggcattaga aatcgcaatt aatcatgtac attacgagga cgagaacagt | 1080 |
| agatacctttt gcattggcag tgtagagaag gtgttatgtt tgattgcgcg ttgggttgaa | 1140 |
| gatcccaact cagaggcata caaacttcat ttagcccgaa tccctgatta cttctggctc | 1200 |
| gctgaagatg gcttgaaaat ccagagcttt gggtgccaga tgtgggatgc agcattcgct | 1260 |
| atacaagcaa tacttgcctg taatgtgagt gaggagtatg acctacgct ccggaaagca | 1320 |
| caccacttcg tgaaggcttc gcaggttcgc gaaaacccat ccggtgactt caacgcaatg | 1380 |
| tacagacaca tttcgaaagg agcatggaca ttctcaatgc atgatcacgg ttggcaagtc | 1440 |
| tctgactgca ccgcagaagg actaaaggct gcactgctat tgtcagaaat gccaagtgaa | 1500 |
| ctagttgggg ggaaaatgga acagagcgc ttctacgacg ctgttaatgt catcctctct | 1560 |
| ctacaaagca gtaatggcgg gttccctgct tgggagcctc agaaagcgta ccgttggtta | 1620 |
| gagaaattca atccaactga attctttgaa gacactatga ttgagaggga gtatgttgag | 1680 |
| tgcactggat ccgcaatgca agggttggct ctcttcagaa agcaattccc acagcacaga | 1740 |
| agcaaggaaa tagatcgctg cattgccaaa gcaatccgtt acatagaaaa catgcaaaat | 1800 |
| cctgatggct cttggtatgg gtgttgggga atttgctata catacggtac atggtttgcc | 1860 |
| gtggagggac taacggcctg tgggaagaac tgccacaaca gtctttcctt gcgaaaagct | 1920 |
| tgtcaattct tgttgtcaaa gcagcttcct aatgcgggt ggggagaaag ttacttgtca | 1980 |
| agccaaaaca aggtgtatac aaacctagaa ggaaaccgtg caaatttagt tcaaagttcg | 2040 |

```
tgggctttgt tgtcccttac tcatgcaggg caggccgaga tagatcctac acccatacac    2100
cgtggaatga agttactcat caattcacaa atggaagatg gagacttccc acagcaggag    2160
attacaggag tatttatgag gaactgtacc ctgaactact catcgtatcg aaacatcttt    2220
cccatatggg ctatgggaga gtatcgtcgc caagtcttgt gtgctcacag ttattga      2277
```

<210> SEQ ID NO 9
<211> LENGTH: 2292
<212> TYPE: DNA
<213> ORGANISM: Eleutherococcus trifoliatus

<400> SEQUENCE: 9

```
atgtggaagc tgaagatagc cgaaggagat aaaaatgacc cgtatttgta cagcaccaat     60
aattttgtcg gccggcaaac atgggagttc gacccggatt atgtgggtag ccccggagag    120
ctagaggagg tggaagaggc tcggcgtcag ttttgggaga acaggtacaa ggtcaagcct    180
tgtggcgatc tcctctggcg tatgcagttc ctaagagaaa gaatttcaa acaaacaatc    240 ccccaagtga aggtaggaga tgacgaggca gttacttatg acgccgccac tacgacactc    300
cgaagggccg tccacttctt ttcagctttg caggccagcg acggtcattg gcctgccgag    360
atcgccggac ctctcttttt ccttccgccc ttggtgatgt gtgtatatat cacagggcat    420
cttgatacag tgttcccagc aaaacatcga aagaaattc ttcgctacat atattgtcat    480
caaaatgaaa atggcggggg gggattacat attgaggggc atagcaccat gttcggcaca    540
acttttagct acatttgtat gcgtatactt ggaaaaggac ccgatggtgg tgtaaacaat    600
gcatgtgcca aaggccgaaa atggatcctt gaccacggca gtgcaaccgc tataccttca    660
tggggcaaga cttggctttc gatacttggt gtatatgaat ggacgggaag caacccaatg    720 ccccccggaat tctggcttct cccttcttcc ctttctgtgc acccagctaa atgttgtgt    780 tattgccgga tggtttactt gccaatgtca tatttatatg ggaagaggtt tgttgggcca    840
atcactcctc tcattttaca attaaaagaa gaactttatg ctcaacccta caatgaaatc    900
aggtggggaa aagtacgtca tgtgtgtgcc aaggaggaca tctactatcc tcacccttta    960
atacaagacc tgctatggga tagtctccat gtattagctg aacctctttt aactcgttgg   1020
ccatttaaca agttgagaga gaaagctttg cagactacca tgaaacacat tcactatgaa   1080
gatgagaaca gtcgatatat taccattgga tgtgtggaaa agattttgtg tatgcttgct   1140
tgttgggttg aggatccaaa tggagattat ttcaagaaac ccttgcaag gattccagat   1200 tatttatggg ttgctgaaga tggaatgaag atgcagagtt ttggtagtca ggaatgggat   1260
ataggttttg gcattcaagc attgttggct agtgatctca ctcatgaact tggacctact   1320
cttatgaaag gacacgactt catcaaaaag tcccaggtca aggataatcc ttccggtgac   1380
ttcaaaagca tgtatcgcca catttctaaa ggatcgtgga ccttctcaga tcaagatcac   1440
ggatggcaag tttctgattg tactgcagaa ggattaaagt gttgccttat tttctcaaca   1500
atgccagagg aaatcgttgg caagaaaatg gaaccagaac tactgtataa ttctgttaat   1560
gtattgcttt ccctacagag caaaaatggt ggggtagcag catgggagcc tgcaacagca   1620
caggactggt tagagttgtt caatcctacg gaattctttg cagacaccat cattgagcac   1680
gagtatgtag agtgcacttc atcggcaatc caagccctga ctctgtttaa aaagttatat   1740
cctgggcacc gaaagaagga gatagataat tttattacga atgccattcg tttcattgaa   1800
gacatacaaa tacctgatgg ttcatggtat ggaaactggg gtgtgtgttt tacttacggt   1860
acctggtttg ctcttggggg gctagcggca ggtggaaaga catacaacaa ttgtgcagct   1920
```

| | |
|---|---|
| gttcgtaaag ctgttaattt tctactcgaa tcacaattgg atgatggcgg ttggggagaa | 1980 |
| agccatcttt cttgccccag aaaggtatat gtaccattag aaggaaaccg ctcaaatttg | 2040 |
| gtgcatactg gatgggcctt aatgggactg attcattctg gcaggccga gagagaccca | 2100 |
| acacctcttc accgtgcagc caagttattg atcaattccc agatgaaga tggtgatttt | 2160 |
| ccccaacagg aaataaccgg agcttttatg aagaattgca tgttgcacta tgcagtttat | 2220 |
| cgaaatatat acccattgtg ggctttagca gagtatcgga ggcgggtacc attaccgacc | 2280 |
| ctaggtgcct aa | 2292 |

<210> SEQ ID NO 10
<211> LENGTH: 2298
<212> TYPE: DNA
<213> ORGANISM: Kalanchoe daigremontiana

<400> SEQUENCE: 10

| | |
|---|---|
| atgtggaagt taaagatagc ggacggaggg agtaaccctt acatcttcac caccaacaat | 60 |
| tttgtgggaa ggcagatatg ggaatttgac ccccaagcca ccgaccctca gcaactagct | 120 |
| aaagtcgaag ctgctcgtct cgatttctac cataaccgct ataaactcaa acccaattcc | 180 |
| gatctcctct ggcgcatgca gtttcttgag gagaaagctt tcacacaaac tataccacaa | 240 |
| gttaaagttg aggatggtga agaggttagt tacgaggcag taactgcagc actgagaaga | 300 |
| ggagtccatc tctattcagc tctccaagct agtgatggcc actggccagc tgaaaatgct | 360 |
| ggccctatgt ttttcatgcc ccctatggtt atgtgtctat acatcactgg acatcttaat | 420 |
| gccatattca cggaagaaca tcgaagtgaa actcttcgtt acatatatta tcatcagaat | 480 |
| gaagatggtg gctgggggtt tcatattgag ggccacagca ccatgtttgg tacagttcta | 540 |
| aactatatat gtatgcggtt gcttggagag gggcctgaag gaggtcaaga caatgctgtt | 600 |
| tccagaggaa ggaagtggat cctcgaccat ggtggtgcca cctccattcc atcatgggga | 660 |
| aagacttggc tttcgattat gggcttgtgt gactggtctg gatgcaatcc catgcccccc | 720 |
| gagttttggc ttcttccttc ctatcttcct atgcatccag gcaaaatgtg gtgctactgc | 780 |
| cgaatggtct acatgccgat gtcatattta tatggtaaaa gattcacagc tcgtatcaca | 840 |
| ccactcattc ttcagttgag agaagaaatt cacattcaac catacgacca aatcgactgg | 900 |
| aaaaagtgc gacatgtgtg ttgtaaggag gatatgtact atccacatcc actacttcaa | 960 |
| gacttgttat gggacactct ctatctcact actgagcctc tccttactcg ctggccactg | 1020 |
| aacaaactga tcaggaaaag agctctgcag acgacaatga acatataca ctatgaagat | 1080 |
| gagaatagca gatacatcac gattggctgt gtcgagaagg ttttgtgcat gcttgcttgc | 1140 |
| tgggttgaag atccaaatgg agattatttt aaaaaacatt tagctagaat tccagactat | 1200 |
| ttatggattg ctgaagatgg catgaagatg cagagtttcg gaagtcagca ctgggataca | 1260 |
| gccttttcta tccaagcact actggctagt aacatggctg aagaaatcgg aataacactt | 1320 |
| gcaaaaggcc acgattttat taagaaatct caggtgaaag acaaccctc tggtgacttc | 1380 |
| aaaggcatgt accgtcacat ttcaaagggg gcatggacat tttcagatca agatcatgga | 1440 |
| tggcaagttt cagattgcac ggcagagggc ctgagtgtt gtctgctttt ctcaatgatg | 1500 |
| caacctgagg ttgtgggtga gagcatggca ccagagagcc tgtacaactc agtaaatgtt | 1560 |
| ctcctctctt tgcagagcca gaacggtgga ttaccagcct gggagccagc aggtgcaccc | 1620 |
| gagtggttgg agcttctaaa cccgaccgag ttttttgaga acattgtaat tgagcacgag | 1680 |

| | |
|---|---|
| tacgtcgagt gcactagctc ggcagttcag gctttagtcc ttttcaaaaa gctataccc | 1740 |
| ctacatcgta gaaagaagt ggaaagattt atcacaaacg gtgcgaaata ccttgaagat | 1800 |
| atacagatgc ctgatgggtc atggtatggg aactggggag tttgcttcac ctatggtgca | 1860 |
| tggtttgctc ttgaaggatt gtcagctgct ggaaagacat acaacaattg tgcagcagtc | 1920 |
| cgcaaaggcg ttgactttct actaaacatt caacttgaag acggtgggtg gggagagagt | 1980 |
| taccaatcat gtccagacaa gaaatatgtt cctctagaag ataatagatc aaatctggtt | 2040 |
| caaacttcat gggcgttaat gggtctaatt tacgccggac aggctgatag ggatccaact | 2100 |
| cctcttcacc gggctgcaca attactgatt aactcgcagt tggaagatgg agattttccg | 2160 |
| caacaagaaa taactggagt gtttcagagg aactgcatgt tgcattatgc agcatacaga | 2220 |
| aacatattcc ctctctgggc ccttgctgag tatagaagac agattcagtt acattcagag | 2280 |
| gctaccaaaa tggtctaa | 2298 |

<210> SEQ ID NO 11
<211> LENGTH: 2286
<212> TYPE: DNA
<213> ORGANISM: Bruguiera gymnorhiza

<400> SEQUENCE: 11

| | |
|---|---|
| atgtggaggc ttaagattgc agagggtggc aacaacccctt acatatacag cacaaacaat | 60 |
| ttcgtgggaa ggcaaacatg ggagtttgac cctgaagctg ggacccctga ggagcgagcc | 120 |
| caggttgaag aggctcgtga aaatttctgg agggaccgct ttctcatcaa gcccagctcc | 180 |
| gacctccttt ggcgattcca gtttctgagt gagaaaaagt ttaaacaaag gattccacaa | 240 |
| gtgaaggttc aggatggtga ggaaatcaca cgtgaaattg ccacaaccgc attgaggagg | 300 |
| agcgtccatt tggtttctgc cttgcaggcc agcgatgggc attggtgcgc agaaaattct | 360 |
| ggccccatgt tctttgttcc tcctatggtt ttttctctgt atatcacagg acatcttaat | 420 |
| gctgtattct ctgcagagca ctgcaaagag attctgagat acatatactg tcatccgaat | 480 |
| gaggatggtg ggtggggatt acacatagag ggtcacagcg ccatgttctc cacagttctg | 540 |
| aattacaatt ggctggggaa acttggcgag ggacgagatg gtgggaaaga caatgccttgc | 600 |
| gaaagagcgc gaaggaggat tcttgatcac ggtagtgcaa ctgcaatcag ctcctgggga | 660 |
| aagacatggc tggcgatact tggtgtgtat gaatgggatg gttgcaaccc aatgcctcca | 720 |
| gaattttggg ccttccccac ttttttccca atacatccag caagaatgtt atgctactgt | 780 |
| cggctcactt acatggccat gtcatacctg tatgggaaga aatttgtcgg tccaatcaca | 840 |
| cctctaattt tacaactgag ggaggaaatc tacaatgaac catatgacca aatcaattgg | 900 |
| agcagaatgc gccatttgtg tgcaaaagag gataactact atgccacac tctaacacaa | 960 |
| atcattttgt gggatgcaat ttacatgttg ggcgaacctc ttctcaagcg ctggccattc | 1020 |
| aacaaattga gagagaaggc tctcaaaata caatggatc acattcatta tgaagatgaa | 1080 |
| aacagtcaat acattacaat tgggagtgtt gaaaagccat tactcatgct tgcttgctgg | 1140 |
| catgaagatc ccaatggtga tgcttttaag aagcacctcg ccagaatacc agattatgtt | 1200 |
| tggcttggtg aagatggaat aaagattcag agttttggca gccaagtgtg ggatacaagt | 1260 |
| tttgttctcc aagctttgat tgctagcaat cttcccagtg aaacaggacc tacacttgag | 1320 |
| aaagggcaca atttcataaa gaactctcag gtcacccaga acccttctgg tgacttcaga | 1380 |
| agaatgtttc gtcatatctc taagggtca tggacattct ctgacaaaga tcacggatgg | 1440 |
| caagttttctg attgcactgc agaaagcctg aagtgttgtc tacttttctc gatgatgccc | 1500 |

```
cctgaacttg tgggtgagaa gatgggacct cagcggatgt acgatgccgt caatgtgata    1560
atttctcttc agagtaaaaa tggtggctgt tcagcctggg agccagcagg agctgggtcg    1620
tggatggagt ggcttaaccc tgtggaattt ctagcggacc ttgttatcga acatgagtat    1680
gttgagtgca cttcatcatc gttgcaagca ttagttctat tcaagaagtt atatcctgag    1740
cacaggagga aagagattga aattttata ctaaatgctg taagattcac tgaagaaatt    1800
caacagcctg atggatcatg gtatggaaat tggggaatat gcttcctttc tggtacatgg    1860
tttggactta aagggctggc tgctgctggc aagacttact acaattgcac tgctgtgcgt    1920
aaaggggtcg aatttctact ccaaacacaa cgagacgatg gtggatgggg agagagttac    1980
ctttcatgcc caagaagat ctacgtacct cttgagggaa accgatcaaa tttggtacaa    2040
actgcactgg ccatgatggg cttaattctt ggtgggcagg gtgagagaga ccctacaccc    2100
cttcatcgag ctgcaaagtt gttgatcaat tctcaaacag aacttggtga ttttcctcag    2160
caggaactct caggttgttt catgaggaat tgcatgttgc actattcaga atataggac    2220 atctttccaa cgtgggctct agcagaatac tgcaagcttt ttccattgcc ttccaaaaat    2280
gattga                                                              2286

<210> SEQ ID NO 12
<211> LENGTH: 2340
<212> TYPE: DNA
<213> ORGANISM: Betula platyphylla
<220> FEATURE:
<221> NAME/KEY: misc_feature
<222> LOCATION: (1749)..(1749)
<223> OTHER INFORMATION: n is a, c, g, or t

<400> SEQUENCE: 12
atgtggaggc ttaagatcgc agacggtggg agtgacccct atatctactc tacaaacaac      60
tttgttggga ggcagacatg ggagtttgac cctcaggctg gttccccaca agagcgggct     120
gaggttgaag aggctcgtcg gaatttctac gacaaccggt atcaggtcaa acctagtggt     180
gatctcctat ggcgaatgca gtttcttaag gagaaaaact tcaaacaaac aattcctcca     240
gtaaaggttg aggatggaga ggaaatcaca tatgaaaagt ccacagctgc attgagaagg     300
gccgtccatt tctattcggc cttgcaagct agtgatggcc attggcctgc tgaaaatgcc     360
ggtccattat ttttccttcc cccccttggtt atgtgtatgt acattacagg acatcttaat     420
actgtgttcc ctgctgagca tcaaaaggaa atccttcgat acatatacta tcatcagaat     480
gaagatggtg gtgggggatt acacatagag ggtcacagca ccatgttttg cactgctctc     540
agctacatct gtatgcgcat actcggggaa gggcctgatg gtggtcagga caatgcttgt     600
gcaagagcgc gaaagtggat ccttgatcat ggtggtgtaa cacacatgcc ttcttgggga     660
aagacctggc tttcgatact tggtatattc gagtggattg gaagcaaccc aatgcctcca     720
gaattttgga tccttccttc attctttccc atgcatccag ccaaaatgtg gtgctactgc     780
cgcatggtgt acatgcctat gtcataccct catgggaaaa ggtttgtagg cccaatcaca     840
cctctcattc ttcaattgag ggaggaactc tacactcaac cttaccacca agttaactgg     900
aagaaagtgc gtcatctatg tgcaaggag gatatctact atccccaccc tttgatacaa     960
gatctattgt gggatagtct atacatattc actgagcctc ttctaactcg ttggcccttt    1020
aacaagctgg tcagagagaa ggctcttcaa gtaacaatga agcacattca ttatgaagat    1080
gagaacagtc gatacatcac cattggatgc gtggaaaagg tcctctgtat gcttgcttgt    1140
```

```
tgggttgaag atccaaatgg ggattatttc aagaaacata ttgctaggat accagattac    1200 atatggttg ctgaagatgg aatcaagatg cagagttttg gaagtcaaga gtgggatacc     1260
ggttttgcta ttcaagcttt gcttgctagt aatctaactg atgaaattgg acctacactt    1320
gcgagagggc acgacttcat aaagaaatct caggtcaagg acaacccttc tggagacttt    1380
gaaagcatgc accgtcacat ttctaaagga tcatggactt tctctgatca agatcatgga    1440
tggcaagttt ctgattgcac tgccgaaggt ttgaagtgtt gcttgctttt ctccattatg    1500
ccaccagaaa ttgttggtga aaaatggaa cctgagcaat gtatgattc tgtaaatgtc      1560 ctactttctc tacagagtaa aaatggtggt ttagctgcct gggaaccagc aggagcccaa    1620
gaatggttgg aattgcttaa ttccacagaa ttctttgcgg acattgtcat tgagcatgag    1680
tacattgagt gcactgcatc agcaatgcaa actttagttt tgtttaagaa gttatacccc    1740
gggcaccgna agaaagagat cgaaaatttc ataaaaaatg ctgctcagtt ccttcaagtc    1800
atacaaatgc ctgatggttc atggtatgga aattggggag tttgcttcac atatggtaca    1860
tggtttgcac ttggaggatt ggctgcagtt ggcaagactt acaacaattg tctagccgtg    1920
cgcagagctg ttgattttct actcagagca caaagagata atggtggttg gggagagagc    1980
tatctctcat gtccaaagaa ggagtatgta cctcttgaag gaaacaaatc aaatttggta    2040
catactgcat gggcaatgat gggtctcatt catgctggac aggctgaaag agacccaaca    2100
cctcttcacc gcgcagcaaa gttgataatt aattctcaac tcgaagatgg agattttcct    2160
caacaggaaa tcactggagt ctttatgaag aactgtatgt tacactatgc agcatacaaa    2220
aatatttacc cactgtgggc tctggcagaa taccgcaagc atgtcccatt gccattagga    2280
aaaaatttaa atcaagtagt gaactgtata ggtcaatcac tatataagaa gtataaataa    2340
```

<210> SEQ ID NO 13
<211> LENGTH: 2121
<212> TYPE: DNA
<213> ORGANISM: Lotus japonicus

<400> SEQUENCE: 13

```
atggaagaat caagctccat gaagatttcg cctctggatc tgatgtccgc catgatcaag      60
ggcacactcg acccttccaa cgtctcctcc acctccggcg ccggctccgt cttcctcgag     120
aatcgtgagt cgtcatggt gcttaccacc tccatcgccg tcctcatcgg atgcgtcgtc      180
gttttcattt ggcgcagatc caccggtaac aaggctaagt ccatcgagcc tcccaagcgc     240
gtcgtcgaga agcttagcga cgaggctgag gttgacgacg gtaccagaaa ggtcaccatc     300
ttcttcggta ctcagactgg tactgctgaa ggattcgcca aggcgattgc ggaagaggca     360
aaagtgcgat acgaaaaagc caagttcaaa attgttgata tggatgatta tgcccaggac     420
gatgatgagt atgaggaaaa gctcaagaaa gagacactgg cacttttctt cttagctaca     480
tatggtgatg tgagccaac tgataatgcg gcgagatttt acaaatggtt tctggaggga     540
gatgagaaag aagaaggatg gcttcgaaat cttgagtatg ctgttttttgg tctggggaac    600 aggcagtatg agcattttaa taaggtcgcc attgaagtgg atgataagct tgctgatttt     660
ggtgggaagc gtcttgtcaa agtaggtcta ggagatgatg atcaatgcat agaagatgac    720
tttactgcat ggaaagaaga attgtggcca gcattggatg aattgcttag aggtgatgat    780
gatacaactg tgtctacacc ctatacggct gctgtgttgg agtatcgtgt tgttattcat     840
gatccattag atgcatctgt cgatgaaaag aagtggcata atgttaatgg ccatgctatt    900
gtggatgctc aacatccagt caggtcaaat gtggctgtgc gaaaggagct tcatactcct    960
```

```
gtgtcagatc gttcttgcac acatttagaa tttgacattt caggcactgg agttgcatat    1020
gaaacagggg accatgttgg tgtttactgt gagaatttat ctgaaactgt ggaagaagca    1080
gtaaggttac taggtttgtc accagatacc tatttctccg tccatactga tgatgaagat    1140
gggaaaccac ttagtggaag ctccttgcca cctactttcc caccatgtac tttaagaaca    1200
gcaattgccc gatatgcaga tgtcttgagt tcacccaaaa agtctgtttt gcttgcctta    1260
gctgctcatg catctaatcc atctgaagcc gaccgcctac gacatcttgc ttcacctgct    1320
ggaaaggatg aatattcaga gtgggtgatt gccagtcaaa gaagtctcct tgaggtcatg    1380
gctgaatttc catcagccaa acctccaatt ggtgtctttt tcgcagcaat tgctcctcgc    1440
ctgcagccaa gattttattc gatctcatca tctcctagga tggctccatc cagaattcac    1500
gttacctgtg cattagtgaa tgataaaatg cccactggta ggattcatag gggagtgtgt    1560
tcaacatgga tgaagaattc tgtgccattg gagaaaagtc aggactgcag ttgggctcca    1620
atatttgtta gacagtccaa ttttaaactc cctgctgata taaagtgcc  tataatcatg    1680 ataggtcctg gcacaggatt ggctcctttc aggggtttct tgcaggaaag attagctctg    1740
aaagaggatg gagctgaact tggcccctcc gttttattct tcggatgcag gaatcgtcaa    1800
atggactaca tctatgaaga tgagttgaac cactttgtca acagtggtgc gctttctgag    1860
ctcattgttg ccttctcacg ggagggacct accaaggaat atgtgcaaca taaaatgatg    1920
gagaaggctt cggatatttg aacatgata  tctcagggag cttacattta tgtgtgtggg    1980
gatgccaagg gcatggctag ggatgtgcac cgtactctgc acacaatttt gcaagagcag    2040
ggttctctcg atagttccaa ggctgagggt atggttaaga acctacaatt gaatggtagg    2100
tatttgcgtg atgtatggtg a                                             2121

<210> SEQ ID NO 14
<211> LENGTH: 2079
<212> TYPE: DNA
<213> ORGANISM: Arabidopsis thaliana

<400> SEQUENCE: 14
atgacttctg ctttgtatgc ttccgatttg tttaagcagc tcaagtcaat tatggggaca      60
gattcgttat ccgacgatgt tgtacttgtg attgcaacga cgtcttttggc actagtagct    120 ggatttgtgg tgttgttatg gaagaaaacg acggcggatc ggagcgggga gctgaagcct    180
ttgatgatcc ctaagtctct tatggctaag gacgaggatg atgatttgga tttgggatcc    240
gggaagacta gagtctctat cttcttcggt acgcagactg gaacagctga gggatttgct    300
aaggcattat ccgaagaaat caaagcgaga tatgaaaaag cagcagtcaa agtcattgac    360
ttggatgact atgctgccga tgatgaccag tatgaagaga aattgaagaa ggaaactttg    420 gcattttct gtgttgctac ttatggagat ggagagccta ctgacaatgc tgccagattt    480
tcaaaatggt ttacggagga aaatgaacgg atataaagc ttcaacaact agcatatggt    540
gtgtttgctc ttggtaatcg ccaatatgaa cattttaata agatcgggat agttcttgat    600
gaagagttat gtaagaaagg tgcaaagcgt cttattgaag tcggtctagg agatgatgat    660
cagagcattg aggatgattt taatgcctgg aaagaatcac tatggtctga gctagacaag    720
ctcctcaaag acgaggatga taaagtgtg gcaactcctt atacagctgt tattcctgaa    780
taccgggtgg tgactcatga tcctcggttt acaactcaaa aatcaatgga atcaaatgtg    840
gccaatggaa atactactat tgacattcat catccctgca gagttgatgt tgctgtgcag    900
```

| | |
|---|---|
| aaggagcttc acacacatga atctgatcgg tcttgcattc atctcgagtt cgacatatcc | 960 |
| aggacgggta ttacatatga aacaggtgac catgtaggtg tatatgctga aaatcatgtt | 1020 |
| gagatagttg aagaagctgg aaaattgctt ggccactctt tagatttagt attttccata | 1080 |
| catgctgaca aggaagatgg ctccccattg gaaagcgcag tgccgcctcc tttccctggt | 1140 |
| ccatgcacac ttgggactgg tttggcaaga tacgcagacc ttttgaaccc tcctcgaaag | 1200 |
| tctgcgttag ttgccttggc ggcctatgcc actgaaccaa gtgaagccga gaacttaag | 1260 |
| cacctgacat cacctgatgg aaaggatgag tactcacaat ggattgttgc aagtcagaga | 1320 |
| agtcttttag aggtgatggc tgcttttcca tctgcaaaac ccccactagg tgtatttttt | 1380 |
| gctgcaatag ctcctcgtct acaacctcgt tactactcca tctcatcctg ccaagattgg | 1440 |
| gcgccaagta gagttcatgt tacatccgca ctagtatatg gtccaactcc tactggtaga | 1500 |
| atccacaagg gtgtgtgttc tacgtggatg aagaatgcag ttcctgcgga gaaaagtcat | 1560 |
| gaatgtagtg gagccccaat ctttattcga gcatctaatt tcaagttacc atccaaccct | 1620 |
| tcaactccaa tcgttatggt gggacctggg actgggctgg caccttttag aggttttctg | 1680 |
| caggaaagga tggcactaaa agaagatgga gaagaactag gttcatcttt gctcttcttt | 1740 |
| gggtgtagaa atcgacagat ggactttata tacgaggatg agctcaataa ttttgttgat | 1800 |
| caaggcgtaa tatctgagct catcatggca ttctcccgtg aaggagctca gaaggagtat | 1860 |
| gttcaacata agatgatgga gaaggcagca caagtttggg atctaataaa ggaagaagga | 1920 |
| tatctctatg tatgcggtga tgctaagggc atggcgaggg acgtccaccg aactctacac | 1980 |
| accattgttc aggagcagga aggtgtgagt cgtcagagg cagaggctat agttaagaaa | 2040 |
| cttcaaaccg aaggaagata cctcagagat gtctggtga | 2079 |

<210> SEQ ID NO 15
<211> LENGTH: 2145
<212> TYPE: DNA
<213> ORGANISM: Catharanthus roseus

<400> SEQUENCE: 15

| | |
|---|---|
| atggattcta gctcggagaa gttgtcgccg ttcgaattga tgagcgcgat cttgaaggga | 60 |
| gctaaattag atgggtctaa ctcttcagat tctggcgtag ctgtgtcgcc ggcagttatg | 120 |
| gctatgttgt tggagaataa ggagttagtg atgattttga ctacttcagt ggcggttttg | 180 |
| atcggttgtg tcgtagtttt gatatggcgg cgatcttccg gatcgggtaa aaaagtcgtg | 240 |
| gagcctccga agctcatagt gcctaaatct gttgtagaac cggaggaaat tgatgaaggg | 300 |
| aagaagaaat ttaccatatt ttttggaaca caaactggaa cagctgaagg cttcgctaag | 360 |
| gctctagctg aggaagccaa agctcgatat gaaaaggcag ttatcaaagt gattgatata | 420 |
| gatgattatg cggctgatga tgaagaatac gaggagaaat tcagaaaaga gaccttggca | 480 |
| tttttcatct tggccacgta tggagatggt gagccaaccg acaatgctgc aaggttctac | 540 |
| aaatggtttg tagagggaaa tgatagaggg gactggctaa agaatctgca atatggagtt | 600 |
| tttggccttg gtaacagaca atatgagcat tcaacaagat tgctaaagt ggtggatgag | 660 |
| aaagttgctg aacagggtgg taagcggatt gttccattgg ttctgggaga cgatgaccag | 720 |
| tgcattgaag atgactttgc tgcatggcgt gagaatgtat ggcctgagtt ggataacttg | 780 |
| ctccggggat aggatgatac aactgttttct acaacctaca ctgctgctat tccagaatat | 840 |
| cgtgttgtgt tccctgacaa atcagattca cttatttcag aagcaaatgg ccatgccaat | 900 |
| ggttatgcta atggcaacac cgtatatgat gcccagcatc cttgcagatc taatgttgca | 960 |

```
gtgaggaagg agcttcatac tccagcatct gatcgttctt gcacccattt ggattttgac    1020
attgctggca ctggccttc atatggaact ggagatcatg ttggagtgta ctgtgataat    1080
ctatctgaaa ccgtggagga ggctgagaga ttactgaatt tacccccaga aacttatttc    1140
tcgcttcatg ctgataaaga ggatggaacc ccacttgctg ggagctcatt gcctcctcct    1200
ttcccacctt gtactctaag aaccgccctc actcgttatg cagatctctt aaatactcct    1260
aagaagtctc ctttgttagc tctagcagct tatgcatctg atccaaatga ggccgatcgt    1320
ctaaaatatc ttgcttctcc agccggaaag gatgaatatg ctcagtcact agttgcaaat    1380
cagagaagcc tcctcgaggt catggctgaa tttccatcag caaagcctcc tcttggagta    1440
ttctttgcag caattgctcc acgcctccaa cccagattct attctatatc gtcttctcca    1500
aggatggcac catctagaat tcatgtcact tgtgcacttg tttatgaaaa aacacctgga    1560
ggacgaattc acaagggtgt gtgttcgaca tggatgaaga atgccattcc attggaggaa    1620
agccgtgact gcagctgggc tcctatcttt gtcaggcagt ctaacttcaa actccctgcc    1680
gatcctaaag tgcctgttat aatgatcggc cctggtactg gactagctcc cttcagagga    1740
ttccttcagg aaagattagc tctgaaggaa gaaggagctg aacttggtac tgcagttttc    1800 tttttggat gcaggaaccg caaaatggat tacatctatg aagatgagct aaaccatttc    1860
cttgaaattg gtgcactttc cgagctactt gttgctttct cacgtgaggg acccactaag    1920
cagtatgtgc aacacaagat ggcagaaaag gcttctgata tttggaggat gatttctgat    1980
ggagcatatg tttacgtctg cggtgatgcc aaaggcatgg ccagggatgt ccacagaact    2040
ctccacacca ttgctcaaga gcagggatcg atggatagca cacaggctga gggttttgtg    2100
aagaatctgc aaatgaccgg aaggtatctc cgagatgtct ggtga                    2145

<210> SEQ ID NO 16
<211> LENGTH: 2079
<212> TYPE: DNA
<213> ORGANISM: Medicago truncatula

<400> SEQUENCE: 16
atgacttctt ccaattccga tttagtccgt acaatcgaat ccgtactcgg agtttccctc      60
ggcgactccg tttcagattc ggttgttctc atcgttacca cctccgccgc cgtcataatt     120
ggacttctcg ttttctatg gaagaaatct tcggatcgga gcaaagagtt gaaaccggtt     180
atagttccta gtccttggt gaaagaagaa gatgatgatg ctgatattgc tgatggaaaa     240
accaaagtta ccgttttctt tggtactcaa actggtactg ctgaaggatt cgctaaggca     300
ttggcagagg agatcaaggc aagatatgaa aaagcatttg tcaaagttgt tgatatggat     360
gactatgcag cggatgatga tcaatatgaa gagaagctga gaaagaaac tcttgcattt     420 ttcatgctgg cgacttatgg agatggagag ccaactgaca atgccgcaag attctataaa     480
tggtttactg agggtaaaga cgagagggga acctggcttc aacagctcac atatggtgtt     540
tttggcctag gtaacaggca atatgaacat tttaacaaga taggtaaagt tgttgacgac     600
gatctcagtg aacaagggc aaagcgtctt gttccacttg gaatgggtga tgatgatcaa     660
tccattgagg atgattttaa tgcctggaaa gaatctctgt ggcctgagtt ggatcagttg     720
ctccgagatg aggatgatgt aaatactgtg tctactcctt atacagctgc tatttctgaa     780
tatcgagtag tgtttcacga ccccactgtc acgccgtcct acgagaatca ctttaacgcg     840
gcaaatgggg gtgctgtatt tgatattcat catccttgta gggcgaatgt cgctgttcga     900
```

```
agggagcttc ataaacctca gtctgaccgt tcttgtatac atttggagtt tgatgtatca    960
gggaccggcg taacatacga aactggagac catgtgggtg tttatgctga taactgtgat   1020
gaaactgtta aagaagctgg gaagttgttg ggtcaggatt tagatttgct gttttctctt   1080
cacactgata atgaggatgg cacttcccta ggtggttctc ttctacctcc tttccctggt   1140
ccttgcacag ttcgcactgc attagcacgt tatgcagatc tcttgaaccc cccacgaaag   1200
gctgctttaa ttgcattagc tgctcatgct tccgagccta gtgaagcaga aagattgaag   1260
tttctctcat ctcctcaggg aaaggatgaa tactccaaat gggttgttgg aagccataga   1320
actcttcttg aggtgatggc tgattttcca tcagcaaaac caccccttgg tgtgttttt   1380
gctgccatag cccctcgttt acaacctcgt tattattcta tttcatcatc tcctaggttt   1440
gccccacaaa gggtacacgt aacttgtgcc ctggtagaag gtccaactcc aactggcaga   1500
attcacaaag gagtatgttc aacctggatg aagaatgcta ttccctcaga ggaaagccgt   1560
gactgtagct gggctcccat ttttatcagg ccatcgaatt tcaagctacc tgctgatcct   1620
tcaattccta ttattatggt tggacctggt actggtttag cacctttag gggattttta   1680
caggagagat ttgctctcaa agaggacggt gttcaacttg gtcctgcatt actattcttc   1740
gggtgcagga accgtcaaat ggattttata tatgaggaag agctgaataa ttttgtggaa   1800
caaggttctc tgtcagagtt gatagttgca ttctctagag aggggcctga aaaggagtat   1860
gttcaacaca aaatgatgga taaagcatca tacttctgga gtctcatttc tcagggaggt   1920
tatctttatg tatgtggtga tgccaagggc atggccagag atgttcatcg aactcttcac   1980
accattgtcc agcagcagga aaatgcagac tcttcaaagg cggaggctac ggtgaaaaaa   2040
ctccagatgg atggacgcta ccttagggat gtctggtga                         2079
```

<210> SEQ ID NO 17
<211> LENGTH: 2076
<212> TYPE: DNA
<213> ORGANISM: Saccharomyces cerevisiae

<400> SEQUENCE: 17

```
atgccgtttg aatagacaa caccgacttc actgtcctgg cggggctagt gcttgccgtg     60
ctactgtacg taaagagaaa ctccatcaag gaactgctga tgtccgatga cggagatatc    120
acagctgtca gctcgggcaa cagagacatt gctcaggtgg tgaccgaaaa caacaagaac    180
tacttggtgt tgtatgcgtc gcagactggg actgccgagg attacgccaa aaagttttcc    240
aaggagctgg tggccaagtt caacctaaac gtgatgtgcg cagatgttga gaactacgac    300
tttgagtcgc taaacgatgt gcccgtcata gtctcgattt ttatctctac atatggtgaa    360
ggagacttcc ccgacggggc ggtcaacttt gaagacttta tttgtaatgc ggaagcgggt    420
gcactatcga acctgaggta taatatgttt ggtctgggaa attctactta tgaattcttt    480
aatggtgccg ccaagaaggc cgagaagcat ctctccgccg cgggcgctat cagactaggc    540
aagctcggtg aagctgatga tggtgcagga actacagacg aagattacat ggcctggaag    600
gactccatcc tggaggtttt gaaagacgaa ctgcatttgg acgaacagga agccaagttc    660
acctctcaat tccagtacac tgtgttgaac gaaatcactg actccatgtc gcttggtgaa    720
ccctctgctc actatttgcc ctcgcatcag ttgaaccgca acgcagacgg catccaattg    780
ggtcccttcg atttgtctca accgtatatt gcacccatcg tgaaatctcg cgaactgttc    840
tcttccaatg accgtaattg catccactct gaatttgact tgtccggctc taacatcaag    900
tactccactg gtgaccatct tgctgtttgg ccttccaacc cattggaaaa ggtcgaacag    960
```

```
ttcttatcca tattcaacct ggaccctgaa accattttg acttgaagcc cctggatccc    1020
accgtcaaag tgcccttccc aacgccaact actattggcg ctgctattaa acactatttg    1080
gaaattacag acctgtctc cagacaattg ttttcatctt tgattcagtt cgcccccaac    1140
gctgacgtca aggaaaaatt gactctgctt tcgaaagaca aggaccaatt cgccgtcgag    1200
ataacctcca atatttcaa catcgcagat gctctgaaat atttgtctga tggcgccaaa    1260
tgggacaccg tacccatgca attcttggtc gaatcagttc cccaaatgac tcctcgttac    1320
tactctatct cttcctcttc tctgtctgaa aagcaaaccg tccatgtcac ctccattgtg    1380
gaaaactttc ctaacccaga attgcctgat gctcctccag ttgttggtgt tacgactaac    1440
ttgttaagaa acattcaatt ggctcaaaac aatgttaaca ttgccgaaac taacctacct    1500
gttcactacg atttaaatgg cccacgtaaa cttttcgcca attacaaatt gcccgtccac    1560
gttcgtcgtt ctaacttcag attgccttcc aacccttcca ccccagttat catgatcggt    1620
ccaggtaccg tgttgcccc attccgtggg tttatcagag agcgtgtcgc gttcctcgaa    1680
tcacaaaaga agggcggtaa caacgtttcg ctaggtaagc atatactgtt ttatggatcc    1740
cgtaacactg atgatttctt gtaccaggac gaatggccag aatacgccaa aaaattggat    1800
ggttcgttcg aaatggtcgt ggcccattcc aggttgccaa acaccaaaaa agtttatgtt    1860
caagataaat taaggatta cgaagaccaa gtatttgaaa tgattaacaa cggtgcattt    1920
atctacgtct gtggtgatgc aaagggtatg gccaagggtg tgtcaaccgc attggttggc    1980
atcttatccc gtggtaaatc cattaccact gatgaagcaa cagagctaat caagatgctc    2040
aagacttcag gtagatacca agaagatgtc tggtaa                             2076

<210> SEQ ID NO 18
<211> LENGTH: 2139
<212> TYPE: DNA
<213> ORGANISM: Arabidopsis thaliana

<400> SEQUENCE: 18
atgtcctctt cttcttcttc gtcaacctcc atgatcgatc tcatggcagc aatcatcaaa      60
ggagagcctg taattgtctc cgacccagct aatgcctccg cttacgagtc cgtagctgct     120
gaattatcct ctatgcttat agagaatcgt caattcgcca tgattgttac cacttccatt     180
gctgttctta ttggttgcat cgttatgctc gtttggagga atccggttc tgggaattca     240 aaacgtgtcg agcctcttaa gcctttggtt attaagcctc gtgaggaaga gattgatgat     300
gggcgtaaga aagttaccat cttttcggt acacaaactg gtactgctga aggttttgca     360
aaggctttag gagaagaagc taaagcaaga tatgaaaaga ccagattcaa aatcgttgat     420
ttggatgatt acgcggctga tgatgatgag tatgaggaga aattgaagaa agaggatgtg     480
gctttcttct tcttagccac atatggagat ggtgagccta ccgacaatgc agcgagattc     540
tacaaatggt tcaccgaggg gaatgacaga ggagaatggc ttaagaactt gaagtatgga     600
gtgtttggat taggaaacag acaatatgag cattttaata aggttgccaa agttgtagat     660
gacattcttg tcgaacaagg tgcacagcgt cttgtacaag ttggtcttgg agatgatgac     720
cagtgtattg aagatgactt taccgcttgg cgagaagcat tgtggcccga gcttgataca     780
atactgaggg aagaagggga tacagctgtt gccacaccat acactgcagc tgtgttagaa     840
tacagagttt ctattcacga ctctgaagat gccaaattca atgatataac attggcaaat     900
gggaatggtt acactgtgtt tgatgctcaa catccttaca agcaaatgt cgctgttaaa     960
```

-continued

```
agggagcttc atactcccga gtctgatcgt tcttgtatcc atttggaatt tgacattgct    1020
ggaagtggac ttacgatgaa acttggagat catgttggtg tactttgtga taacttaagt    1080
gaaactgtag atgaagctct tagattgctg gatatgtcac ctgatactta tttctcactt    1140
cacgctgaaa aagaagacgg cacaccaatc agcagctcac tgcctcctcc cttcccacct    1200
tgcaacttga aacagcgct tacacgatat gcatgtcttt tgagttctcc aaagaagtct    1260
gctttagttg cgttggctgc tcatgcatct gatcctaccg aagcagaacg attaaaacac    1320
cttgcttcac ctgctggaaa ggatgaatat tcaaagtggg tagtagagag tcaaagaagt    1380
ctacttgagg tgatggccga gtttccttca gccaagccac cacttggtgt cttcttcgct    1440
ggagttgctc caaggttgca gcctaggttc tattcgatat catcatcgcc caagattgct    1500
gaaactagaa ttcacgtcac atgtgcactg gtttatgaga aaatgccaac tggcaggatt    1560
cataagggag tgtgttccac ttggatgaag aatgctgtgc cttacgagaa gagtgaaaaa    1620
ctgttcctcg ggcggccgat atttgttagg caatccaact tcaagcttcc ttctgattct    1680
aaggtaccga tcatcatgat cggtccaggg actggattag ctccattcag aggattcctt    1740
caggaaagac tagcgttggt agaatctggt gttgaacttg gccatcagt tttgttcttt    1800
ggatgcagaa accgtagaat ggatttcatc tacgaggaag agctccagcg atttgttgag    1860
agtggtgctc tcgcagagct aagtgtcgcc ttctctcgtg aaggacccac caaagaatac    1920
gtacagcaca gatgatggga caaggcttct gatatctgga atatgatctc tcaaggagct    1980
tatttatatg tttgtggtga cgccaaaggc atggcaagag atgttcacag atctctccac    2040
acaatagctc aagaacaggg gtcaatggat tcaactaaag cagagggctt cgtgaagaat    2100
ctgcaaacga gtggaagata tcttagagat gtatggtaa                          2139
```

<210> SEQ ID NO 19
<211> LENGTH: 2115
<212> TYPE: DNA
<213> ORGANISM: Artemisia annua

<400> SEQUENCE: 19

```
atgcaatcaa caacttccgt taagttatct cccttcgatc taatgacggc gttacttaac     60
ggcaaggtat cgttcgacac atcaaacaca tccgatacga atattccgtt agcggtgttt    120
atggagaatc gtgagctttt gatgatttta actacttcag ttgcggtgtt gatcggatgc    180
gttgtggtgc ttgtgtggag acggtcgtcg tcggcggcga agagagcggc ggagtcgccg    240
gtgattgttg tgccgaagaa agtgacggag gatgaggttg atgatggacg gaagaaagtt    300
actgtgtttt ttggaactca gactggtact gctgaaggtt ttgctaaggc gcttgttgaa    360
gaagctaaag cgcgatatga aaaggcggtg tttaaagtga ttgatttgga tgattatgct    420
gctgaagatg atgagtatga ggagaagtta agaaagaat ctcttgcttt tttcttttta    480
gctacgtatg gagatggtga gccgacagat aatgctgcta gattctataa atggtttacc    540
gagggtgaag agaaaggtga atggcttgaa agcttcaat acgcagtgtt tggacttggt    600
aacagacagt atgagcattt caacaagatt gcgaaggtgg tcgatgaaaa acttacggaa    660
cagggtgcaa agcgccttgt tcctgttggc atggagacg acgatcaatg tattgaagac    720
gacttcactg catggaaaga gttggtgtgg cctgagttgg atcaattact tcgtgatgag    780
gatgatacat ctgttgccac cccatacaca gctgctgttg cagaataccg tgttgtgttc    840
catgataaac cagagacata tgatcaggat caactgacaa atggccatgc tgttcatgat    900
gctcaacatc catgcagatc caatgtagct gtcaaaaagg agctccattc ccctctatct    960
```

```
gaccgttctt gcactcattt ggaatttgat atctctaata ctggattatc gtatgaaact   1020 gggaccatg ttggagtcta cgttgagaat ctaagtgaag ttgtggacga agctgaaaaa   1080
ttaataggtt taccgccgca cacttatttc tcaatacacg ctgataacga agacgggaca   1140
ccacttggtg gagcctcttt gccacctcct ttccctccat gcactttaag aaaagcattg   1200
gcttcctatg ccgatgtttt gagctctcct aaaaagtcag ctttgcttgc tttagctgct   1260
catgctactg attctactga agctgataga ctgaaatttc ttgcgtctcc tgcgggaaag   1320
gatgaatatg ctcagtggat agttgcaagc cacagaagtc tccttgaggt catggaggcc   1380
ttcccatcag ctaagcctcc gcttggtgtt tttttttgcat ctgtcgcccc acgtttgcag   1440
ccgagatact attccatttc ttcttcccca agtttgcgc caaataggat tcatgtaact   1500
tgtgcattag tgtatgagca acaccatca ggccgcgttc acaagggagt ctgttcaaca   1560
tggatgaaga atgctgtgcc tatgacagaa agccaggatt gcagttgggc cccaatttat   1620
gttagaacat ccaatttcag acttccttct gatcctaagg tcccagttat catgattggc   1680
ccaggcactg gattggctcc atttagaggt ttccttcagg aaaggttagc tcagaaggaa   1740
gctgggactg agctcggaac agccatctta ttccttcggat gcaggaatcg caaagtggat   1800
ttcatatatg aggacgagct taataatttc gtggagactg gggctctttc cgagcttgtt   1860
acggccttct ctcgtgaagg tgccactaag gagtacgtgc aacacaagat gactcagaag   1920
acttcggata tctggaattt actctctgag ggagcatatt tgtatgtttg cggtgatgcc   1980
aaaggcatgg ccaaagatgt acatcggact ctgcacacta ttgtgcaaga cagggatct    2040 ctagactcct caaaggcgga gctctacgtg aagaatctac aaatggcagg aagatatctc   2100
cgtgatgtat ggtaa                                                     2115

<210> SEQ ID NO 20
<211> LENGTH: 2115
<212> TYPE: DNA
<213> ORGANISM: Artemisia annua

<400> SEQUENCE: 20
atgcaatcaa caacttccgt taagttatct cccttcgatc taatgacggc gttacttaac     60
ggcaaggtat cgttcgacac atcaaacaca tcggatacga atattccgtt agcggtgttt    120
atggagaatc gtgagctttt gatgatttta actactcgg ttgcggtttt gatcggatgc    180
gttgtggtgc ttgtgtggag acggtcgtcg tcggcggcga agaaagcggc ggagtcgccg    240
gtgattgttg tgccgaagaa agtgacggag gatgaggttg atgatggacg gaagaaagtt    300
actgtgtttt ttggaactca gactggtact gctgaaggtt ttgctaaggc gcttgttgaa    360
gaagctaaag cgcgatatga aaaggcggtg tttaaagtga ttgatttgga tgattatgct    420
gctgaggacg atgagtatga ggagaagtta agaaagaat ctcttgcttt tttcttttta    480
gctacgtatg gagatggtga gccgacagat aatgctgcta gattctataa atggtttacc    540
gagggtgaag agaaaggtga atggcttgac aagcttcaat acgcagtgtt tggacttggt    600
aacagacagt atgagcattt caacaagatt gcgaaggtgg tcgatgaaaa acttgtggag    660
cagggtgcaa agcgccttgt tcctgttggc atggagacg atgatcaatg tattgaagac    720
gacttcactg catggaaaga gttggtgtgg cctgagttgg atcaattact tcgtgatgag    780
gatgatacat ctgttgccac tccatacaca gctgctgttg cagaataccg tgttgtgttc    840
catgataaac cagagacata tgatcaggat caactgacaa atggccatgc tgttcatgat    900
```

```
gctcaacatc catgcagatc caatgtcgct gtcaaaaagg agctccattc ccctctatct    960
gaccggtctt gcactcattt ggaatttgat atctctaata ctggattatc gtatgaaact   1020
ggggaccatg ttggagtcta cgttgagaat ctaagtgaag ttgtggacga agctgaaaaa   1080
ttaataggtt taccgccgca cacttatttc tcagtacacg ctgataacga agacgggaca   1140
ccacttggtg gagcctcttt gccacctcct ttccctccat gcactttaag aaaagcattg   1200
gcttcctatg ccgatgtttt gagctctcct aaaaagtcag ctttgcttgc tttagctgct   1260
catgctactg attctactga agctgataga ctgaaatttc ttgcgtctcc tgcgggaaag   1320
gatgaatatg ctcagtggat agttgcaagc cacagaagtc tccttgaggt catggaggcc   1380
ttcccatcag ctaagcctcc gcttggtgtt ttttttgcat ctgtcgcccc acgtttgcag   1440
ccgagatact attccatttc ttcttcccca aggtttgcgc caaataggat tcatgtaact   1500
tgtgcattag tgtatgagca aacaccatca ggccgcgttc acaagggagt ctgttcaaca   1560
tggatgaaga atgccgtgcc tatgacagaa agccaggatt gcagttgggc cccaatttat   1620
gttagaacat ccaatttcag acttccttct gatcctaagg tcccagttat catgattggc   1680
ccaggcactg gattggctcc atttagaggt ttccttcagg aaaggttagc tcagaaggaa   1740
gctgggactg agctcggaac agccatctta ttcttcggat gcaggaatcg caaagtggat   1800
ttcatatatg aggacgagct taataatttc gtggagactg gggctctttc cgagcttgtt   1860
acggccttct ctcgtgaagg tgccactaag gagtacgtgc aacacaagat gactcagaag   1920
gcttcggata tctggaattt actctctgag ggagcatatt tgtatgtttg cggtgatgcc   1980
aaaggcatgg ccaaagatgt acatcggact ctgcacacta ttgtgcaaga cagggatct   2040
ctagactcct caaaggcgga gctctacgtg aagaatctac aaatggcagg aagatatctc   2100
cgtgatgtat ggtaa                                                    2115
```

<210> SEQ ID NO 21
<211> LENGTH: 2115
<212> TYPE: DNA
<213> ORGANISM: Artemisia annua

<400> SEQUENCE: 21

```
atgcaatcaa caacttccgt taagttatct cccttcgatc taatgacggc gttacttaac     60
ggcaaggtat cgttcgacac atcaaacaca tcggatacga atattccgtt agcggtgttt    120
atggagaatc gtgagctttt gatgattta actacttcgg ttgcggtgtt gatcggatgc    180
gttgtggtgc ttgtgtggag acggtcgtcg tcggcggcga agaaagcggc ggagtcgccg    240
gtgattgttg tgccgaagaa agtgacggag gatgaggttg atgacggacg gaagaaagtt    300
actgtgtttt ttggaactca gactggtact gctgaaggtt ttgctaaggc gcttgttgaa    360
gaagctaaag cgcgatatga aaaggcggtg tttaaagtga ttgatttgga tgattatgct    420
gctgaagatg atgagtatga ggagaagtta agaaagaat ctcttgcttt tttctttta    480
gctacgtatg gagatggtga gccgacagat aatgctgcta gattctataa atggttttacc   540
gagggtgaag agaaaggtga atggcttgac aagcttcaat acgcagtgtt tggacttggt    600
aacagacagt atgagcattt caacaagatt gcgaaggtgg tcgatgaaaa acttgtggag    660
cagggtgcaa agcgccttgt tcctgttggc atgggagacg atgatcaatg tatcgaagac    720
gacttcactg catggaaaga gttggtgtgg cctgagttgg atcaattact tcgtgatgag    780
gatgatacat ctgttgccac tccatacaca gctgctgttg agaataccg tgttgtgttc    840
catgacaaac cagagacata tgatcaggat caactgacaa atggccatgc tgttcatgat    900
```

```
gctcaacatc catgcagatc caatgtcgct gtcaaaaagg agctccattc ccctctatct      960
gaccggtctt gcactcattt ggaatttgat atctctaata ctggattatc gtatgaaact     1020
ggggaccatg ttggagtcta cgttgagaat ctaagtgaag ttgtggacga agctgaaaaa     1080
ttaataggtt taccgccgca cacttatttc tcagtacata ctgataacga agacgggaca     1140
ccacttggtg gagcctcttt gccacctcct ttccctccat gcactttaag aaaagcattg     1200
gcttcctatg ccgatgtttt gagctctcct aaaaagtcag ctttgcttgc tttagctgct     1260
catgctactg attctactga agctgataga ctgaaatttt ttgcgtctcc tgctggaaag     1320
gatgaatatg ctcagtggat agttgcaagc cacagaagtc tccttgaggt catggaggcc     1380
ttcccatcag ctaagcctcc gcttggtgtt tttttgcat ctgtcgcccc acgtttgcag      1440
ccgagatact attccatttc ttcttcccca aagtttgcgc caaataggat tcatgtaact     1500
tgtgcattag tgtatgagca aacaccatca ggccgcgttc acagggagt ctgttcaaca      1560
tggatgaaga atgccgtgcc tatgacagaa agccaggatt gcagttgggc cccaatttat     1620
gttagaacat ccaatttcag acttccttct gatcctaagg tcccagttat catgattggc     1680
ccaggcactg gattggctcc atttagaggt ttccttcagg aaaggttagc tcagaaggaa     1740
gctgggactg agctcggaac agccatctta ttcttcggat gcaggaatcg caaagtggat     1800
ttcatatatg aggacgagct taataatttc gtggagacgg gggctctttc cgagcttgtt     1860
acggccttct ctcgtgaagg tgccactaag gagtacgtgc aacacaagat gactcagaag     1920
gcttcggata tctggaattt actctctgag ggagcatatt tgtatgtttg cggtgatgcc     1980
aaaggcatgg ccaaagatgt acatcggact ctgcacacta ttgtgcaaga acagggatct     2040
ctagactcct caaaggcgga gctctacgtg aagaatctac aaatggcagg aagatatctc     2100
cgtgatgtat ggtaa                                                     2115
```

<210> SEQ ID NO 22
<211> LENGTH: 2079
<212> TYPE: DNA
<213> ORGANISM: Hybrid poplar

<400> SEQUENCE: 22

```
atgagttcag gtggttcaaa tttggcgagg ttcgttcaat cagtgctagg gatatctttt       60
ggcgactccc tgtctgactc agttgttgtg ataattacca cgtcgtttgc tgctctagtt      120
ggattggtgg tgcttgtatt gaagagatcg tccgatcgga gcaaagacgt caagccgttg      180
gtggttccta agtcactttc aattaaggac gaggaggatg agtccgaggc tctgggtggg      240
aaaactaagg ttactatctt ttatgggact cagaccggaa ctgcggaggg ttttgctaag      300
gctttagctg aagaggtcaa agcaagatat gagaaagcag ctgttaaagt gtttgacctg      360
gatgattatg ctatggaaga tgatcaatat gaagaaaaat gaagaaaga ctttggca         420
ttattcatgt ttgccactta tggagatgga gagccaactg ataacgctgc gagattttat      480
aagtggttta ctgagggaaa tgaaggggga atctggcttc aacagctttc ttatggtgtt      540
tttggtcttg gtaaccgtca atatgaacat tttaataaga tagcgaaggt gcttgatgac      600
ctgctctatg aacaaggagg aaagcgtctc gttcctgttg tcttggcga cgatgatcaa       660
tgcatagagg atgatttttc tgcttggaaa gaattttttgt ggcctgagct agaccagttg      720
ctcagagatg aagatgatgt gaatgctcca tctactcctt atacagctgc tatacctgaa      780
tatcgattag tgattcatga tccttctata atatctgttg aggataaatt ctcaaacttg      840
```

```
gcaaatggga atgtgtcttt tgatattcac catccatgca gagtcaatgt tgctgtccaa    900
aaagagcttc acaaagcaga gtctgaccgg tcttgcatac atctggaatt tgacatcaca    960
gggactggaa ttacatatga aactggagac catttggggg tgtatgctga aatagtgat   1020 gaaactgttg aagaagcagg gaagttgcta gataaacctt tagatttgtt gttttctatt   1080
catgctgata tgaggatgg cacagctatt ggaagctcat tgccgcctcc tttcccaggt   1140
ccctgcacac ttcacactgc attggcatgc tatgcagatc tcttgagccc tcctaaaaag   1200
gctgctttgc ttgctttggc tgctcatgcc agtgaaccta gcgaggcaga tagactcaag   1260
tttttatcat caccgcaagg aaagaatgaa tactctcact gggtcatggc aagtcagaga   1320
agtcttctcg aggtaatggc tgagttccca tcttcgaaac ctccccttgg tatctttttt   1380
gctgcagtgg ctcctcgcct acagcctcgc tactattcta tctcatcctc tcctagatat   1440
actcccaata gagtacatgt gacctgtgct ttagtatatg gtccaactcc cactggtaga   1500
attcacaaag gggtgtgttc aacttggatg aagaatgcag ttcctctgga gaaaagttat   1560
gaatgtagtt gggctcccat tttcaccaga acatctaatt tcaagttacc agcagatcct   1620
tcaactccaa ttataatggt gggtcctggt actggattgg cacctttcag aggatttta   1680 caggaaagaa tagccctgaa agaggatggt gtgaagcttg gtcccgccct gcttttcttt   1740
ggatgcagaa atcgccgaat ggatttcata tatgaggatg agctcaataa ttttgtcgag   1800
caaggtgtga tatccgagtt gatagttgca ttctcaaggg aggggccaca gaaggaatat   1860
gttcaacata agatggtgga tagagcagca gagatatgga ctataatttc tcaaggaggt   1920
tatttttacg tgtgcggtga tgccaagggt atggctagaa atgttcatag gactctgcac   1980
actattgtgc aagagcaggg aggcctggac tcgtcgaaaa ccgagtctat ggtgaagaag   2040
ctccaaatgg aaggacggta tctaagagat gtctggtga                          2079
```

<210> SEQ ID NO 23
<211> LENGTH: 2139
<212> TYPE: DNA
<213> ORGANISM: Hybrid poplar

<400> SEQUENCE: 23

```
atgcaatcat caagcagctc gatgaaagtg tcaccacttg aacttatgca agccataatc     60
aaaggcaaag tggacccaac aaatgtttca tcggaatccg gtggttctgc tgctgagatg    120
gcaactttga tccgcgagaa tcgtgagttt gttattatct taactacttc catagcggtt    180
ttgatcggct acgttgtcgt tttaatttgg agaaagatcat ccggctatca gaaacctaaa   240
gtccctgtcc ctcctaagcc gttgattgtt aaagacctcg aacctgaagt tgatgatggc    300
aagaaaaagg tcaccatctt tttcggcacc caaactggta ctgctgaagg atttgctaag    360
gctctagctg aggaggcaaa agctcggtat gagaaggcta tatttaaaac tgttgatttg    420
gatgattatg cggaggatga cgatgaatac aagagaaat tgaagaaaga gtctctggcc    480 atttctcttct tggccacata tggagatggt gagcctacag ataacgccgc gaggttttat    540
aaatggttta cagatggcaa tgagaggggg gaatggctta aggaacttcc atatgctgtt    600
tttggtcttg caacaggca atacgagcat tttaataaga ttgccatagt ggtgataaa     660 atccttggca accagggtgg gaagcagctt gttccagtgg gtcttggtga tgatgatcaa    720
tgcatggaag atgactttgc cgcatggcga gaattgttgt ggcctgagtt ggaccagttg    780
cttcttgatg gggatgatcc aactggtgtt tctaccccctt atactgctgc cgtggcagaa    840
tatcgggttg tattgcatga ccctgaagat gcaccattag aggatgataa ctggagtaat    900
```

```
gcgaatggtc atgctattta tgatgctcag catccatgca gggctaatgt tactgtgagg    960
agggagcttc atacccctgc atctgatcgt tcatgtaccc atttggagtt cgacatatct   1020
ggcactggac ttgtatatgg aactggtgat catgttggtg tgtactgtga aaatctaagt   1080
gaaattgttg aggaagcact gcagttgttg ggtttatcgc cagatattta cttcactatc   1140
catactgata atgaggatgg cacaccactt agtggaagtg ccttgccacc tccattccca   1200
tcgtccacct aagaacagc tctaactcga tatgctgatc ttttgagttc acccaaaaag   1260
tctgctttaa tggctttagc agctcatgct actaatccaa ccgaagctga tcggctaaga   1320
catcttgcat cacctgctgg aaaggatgaa tatgcacaat ggatagttgc aaatcataga   1380
agcctcctgg aagtcatggc tgaatttcca tcagccaaac ccccacttgg agtcttcttt   1440
gcttcagttg ccccgcgatt gctgccaaga tactattcta tttcatcatc tccaagcatg   1500
gcaccttcaa ggattcatgt tacatgtgca ctggttcttg agaaaacacc agcaggtcga   1560
attcacaaag gagtgtgctc aacttggatg aagaatgctg tgcctttaga gaaaagccat   1620
gattgcagct gggcacctat ttttgttaga caatcaaact tcaaacttcc agcagatact   1680
aaagttccca tcattatgat tggccctgga actggtttag ctccttttcag ggtttccttt   1740
caggaaagat tagcccagaa agaagcagga gcagaactgg gatcctctgt attattcttt   1800
ggttgcagga accgtcaaat ggattttatc tatgaagatg agctcaacaa tttcgttgaa   1860
agtggtgcac tttctgaact atctgtagcc ttctcacgtg agggacctac caaggaatat   1920
gtgcagcata agatgatgca gaaggcttct gatatctgga acatgatttc tcaaggagga   1980
tatttatatg tttgtggaga tgccaagggc atggctaaag atgtccacag aactctccac   2040
actatcgtgc aagagcaggg atctcttgac aactccaaga cagagagctt tgtgaagggt   2100
ctgcaaatga atggcaggta tctgcgtgat gtatggtaa                          2139

<210> SEQ ID NO 24
<211> LENGTH: 2139
<212> TYPE: DNA
<213> ORGANISM: Hybrid poplar

<400> SEQUENCE: 24
atggagtcat caagcagctc gatcaaagtg tctccacttg atcttatgca agccataatc    60
aaaggcaaag tggaccccgc gaatgtttca tcggagtccg gtggttctgt tgctgaggta   120
gcaactttga tcctcgagaa tcgtgagttt gttatgatct taactacttc catcgctgtt   180
ttgatcggct gcgtcgtcgt tttgatttgg agaagatcat ctgggtatca gagacccaaa   240
gtacctgtgc ctcccaagcc cttgattgtt aaagaccttg aacctgaagt tgacgatggc   300
aagaaaaagg tcaccatctt tttcggcacc caaaccggta cggcagaagg atttgctaag   360
gctctagctg aggaggcaaa agctcggtat gacaaggcta catttaaaac tgttgatatg   420
gatgattacg cgggtgatga tgatgaatac aagagaaat tgaagaaaga ggatctggtt   480
atttttcttct tggccacata cggagatggt gagcctactg ataatgcggc aaggttctac   540
aaatggttta cagagggaaa tgagagaggg aatggctca aggaccttcc atatgcagtt   600
tttggccttg gcaacaggca gtacgagcat tttaacaaga ttgctatagt ggtggataaa   660
atctttgctg accagggtgg gaagcgcctt gccccagtgg gtcttggtga tgatgatcaa   720
tgcatggaag atgactttgc tgcatggcgg gaattgttgt ggcctgagat ggaccagttg   780
cttcttgatg gagacgatcc aacagctgtt tctactcctt atgctgccac tgtatcagaa   840
```

```
tatcgggttg tattccatag ccctgaagat gccccattag aggatgataa ctggagtaat      900
gcaaatggcc atgctgtcta tgatgctcag catccatgca gggctaatgt tgctgtgagg      960
agggagcttc ataccccggc atctgatcgt tcatgtaccc atctggagtt tgaaatatca     1020
ggcaccggac ttgcatatgg aactggggat catgttggtg tgtactgtga aaatctaagt     1080
gaaactgtag aggaagcact gcagttgttg ggtttatcac cagatactta tttctctatc     1140
cacaatgata atgaggatgg cacgccactt agtggaggcg ccttgccacc tccattccca     1200
ccgtccacct taaaaactgc tctagctcga tatgctgatc ttttgagttt gcccaaaaag     1260
tctgctctaa tggctttagc agctcatgct actgatccaa cagaagctga tcgactaagg     1320
catcttgcat cgcctgctgg aaggatgaa tatgcacaat tgttagttgc aaatcagaga      1380
agcctccttg aggtcatggc tgaatttcca tcagccaagc ccccacttgg tgtcttcttt     1440
gcttcagttg cacctcggtt gcagccaaga tactactcta tttcatcatc tccaaggatg     1500
gctccatcaa gaattcatgt tacatgtgca ctggttcttg agaaaacact aggaggtcgt     1560
attcacaaag gagtttgctc aacttggatg aagaacgctg tgcctctgga gaaaagccat     1620
gattgcagct gggcacctgt ttttgttagg caatcaaact tcaaacttcc agcagatgct     1680
aaagttccca tcattatgat tggccctgga actggtttag ctcccttcag aggtttcctc     1740
caggaaagat tagccctgaa agaagcagga tcagaactgg gatcctctgt attattcttt     1800
ggttgcagga accgcaaaat ggattttatc tatgaagacg agctcaacaa cttcgttgaa     1860
agtggtgcac tttctgaact agttgttgcc ttctcccgtg agggacctac caaggaatac     1920
gtgcagcata agatgatgca gaaggcttct gatatctgga acatgatttc acaaggtgga     1980
tatttatatg tttgtggtga tgccaaaggc atggctaaag atgtccacag agcgctccac     2040
actattgtgc aagagcaggg atcccttgac aactcgaaga cggaaagctt tgtgaagagt     2100
ctgcaaatga atggcaggta tctacgtgat gtatggtaa                           2139
```

<210> SEQ ID NO 25
<211> LENGTH: 2073
<212> TYPE: DNA
<213> ORGANISM: Vigna radiata

<400> SEQUENCE: 25

```
atggcttcca attccgattt ggtgcgcgcc gttgagtcgt tccttggcgt ttctctagga       60
gattccgttt cggattcgct gcttctcatc gccaccacct ccgcggcggt tgtagtcggt      120
cttctcgtgt ttttatggaa gaaatcttcg gatcggagca aggaggtgaa gccggtggtt      180
gtgccgaggg atttaatgat ggaggaggaa gaggaagttg acgttgccgc cggcaagact      240
aaggtcacca ttttcttcgg tactcagacc ggtactgctg aaggctttgc taaggcgttg      300
gcagaggaga tcaaggcaag gtatgaaaaa gcggctgtca agttgttga cctggatgac       360 tatgcagctg atgatgatct atatgaggag aagctgaaga aagagagtct tgtattttc       420 atgctagcaa cttacgggga tgagaaacca atagacaatg ctgcaagatt ctacaaatgg      480
tttactgagg ggaaagacga aggggaatc tggcttcaaa aactcaccta tggagttttc       540
ggcctaggta caggcaata cgaacatttt aataagatag taagttgt ggatgaagaa         600 cttgctgaac aaggtgcaaa gcgtctagtt gcagttggat taggtgatga tgatcaatcc      660
attgaagatg attttctgc ctggaaagaa agtttatggt ctgagttgga tcagttgctc       720
agagatgagg atgatgctaa tactgtctct actcccctata cagctgctat tcttgaatac    780
cgagtagtga ttcacgatcc cactgcagca tcaacctatg ataatcactc aaccgtggca      840
```

| | |
|---|---:|
| aatgggaata ctgagtttga tattcatcat ccttgcaggg tgaatgttgc tgtacaaaag | 900 |
| gagcttcaca aacctgagtc tgatcgttct tgcatacatt tggaatttga tatatcgggg | 960 |
| acgagcataa catatgatac tggagaccat gtgggtgttt atgctgagaa ctgcaatgaa | 1020 |
| actgtcgaag aaactgggaa gttgttgggt cagaatttgg atctattttt ttctcttcac | 1080 |
| acagacaagg atgatggcac ttccctaggt ggttctctcc tacctccttt ccctggccct | 1140 |
| tgttcactgc gaactgcatt agcacgttat gctgatctct gaaccccccc acgaaaggct | 1200 |
| gctttacttg cattggctac tcatgcctct gaacctagcg acgaaagatt aaagttcctt | 1260 |
| tcatctcctc aggggaagga tgagtattcc aaatgggtgg ttggaagcca gaggagtctc | 1320 |
| gttgaggtga tggctgagtt ccatcagca aaacctcctc ttggtgtgtt ttttgctgca | 1380 |
| atagcccctc gttacagcc tcgttattat tctatttcat cctctccaag gtttgctcct | 1440 |
| caaagggtac atgtaacttg tgctttggtg tatggtccaa ctcccactgg tagaattcac | 1500 |
| aaaggtgtat gttcaacttg gatgaagaat gctattccct cagaaaaaag tcaagactgt | 1560 |
| agctcggctc ctatttttat taggccatca aatttcaagc ttccagttga tcattcaata | 1620 |
| cctattatta tggttggacc tggtaccggt cttgcacctt tcaggggatt tttgcaggaa | 1680 |
| agatatgctc tcaaagagga tggtgttcaa cttggccctg cattactctt ctttggatgt | 1740 |
| agaaatcgtc aaatggattt catttatgag gatgagctaa agagttttgt ggaacaaggt | 1800 |
| tctctttcag aattgatagt tgcattctct agagaggggg ctgaaaagga atatgttcaa | 1860 |
| cacaagatga tggacaaagc tgcgcacctt tggagtttga tttctcaagg aggttatctt | 1920 |
| tacgtctgtg gagatgccaa gggcatggcc agagatgtcc atcgaactct tcattccatt | 1980 |
| gtccaggagc aggaaaacgt ggactcaaca aaagctgaag ctatagtgaa aaaactccag | 2040 |
| atggacggac gttaccttag agatgtatgg tga | 2073 |

```
<210> SEQ ID NO 26
<211> LENGTH: 2100
<212> TYPE: DNA
<213> ORGANISM: Petroselinum crispum

<400> SEQUENCE: 26
```

| | |
|---|---:|
| atgcaatcgg aatcaatgga agtgtcgccg gtggatttgc tggcgtcgat tctgaagatt | 60 |
| gattcggttg aatcgatgac gttgctgctc gagaaccgtg acgtcttgat gttacttacg | 120 |
| acgtcgtttg cggtgttgat tggattagga ttggtgatga tgtggcggag atcaacgacg | 180 |
| atgacgaaga gcgcgaagaa gctcgagccg gcgaagattg atcccgaa atttgaaatg | 240 |
| gaggaggaag ttgatgacgg taaaaagaag gttacgatttt tttacggtac tcagaccggt | 300 |
| actgctgaag gttttgctaa ggcacttgcg gaggaggcga agcaagata tcaggatgct | 360 |
| atctttaaaa ctattgattt ggatgattat gcgggtgatg atgacgagta tgagacgaaa | 420 |
| cttaagaaag aatctatggt gttcttcttc ttagccacgt atggtgatgg tgaaccaacc | 480 |
| gacaatgcag cgagatttta caagtggttt tgtgagggca agagagagg ggagtggctt | 540 |
| aacaatcttc aatatggtgt gtttggcctt ggcaacaggc aatatgagca tttcaacaag | 600 |
| attgcagtgg ttgtggatga cggccttgtt gagcagggtg ccaagcgtct tgttccagtt | 660 |
| ggtatgggag atgacgacca atgtattgaa gatgactta ctgcatggcg ggagttagtc | 720 |
| tggcctgagt tggatcaact gctccttgac gaggagtcta aggctgctgc aactccatat | 780 |
| acagctgctg tgctagaata tcgtgttcag ttttataatc aaactgatac atcatctcca | 840 |

```
ctggttcgga gtatgagcaa attaaatggc catgctgtat atgatgctca acatccctgc    900
agggctaatg tggctgtaag aagagagctt catacacctg catcggatcg ttcctgcacc    960
catctggagt tcgatatttc ctctactgga cttgcatatg aaactggtga ccatgtagga   1020
gtctacactg aaaatctgat tgaaattgtt gaggaggctg aaagattgat tgatatatcg   1080
ccagatactt atttctccat tcatactgaa atgaagatg gaacacccct tagtggggga   1140
tccctgccac cccccttttcc cccatgcagc tttagaactg cacttactag atatgcagat   1200
cttttgagta ctccaaagaa gtctgcttta gttgcgttgg cggctcatgc atctgatcct   1260
agcgaagctg aacgattgag atttcttgca tctcctgttg aaaggatga atatgcgcag   1320 tggctcgtcg ctagtcagag gagcctgcta gaagtcttgg ctgcgtttcc atcagccaaa   1380
cccccattgg gagttttctt tgcatctgtt gccccacgct tgcagcccag atactattcc   1440
atctcttcct caccaaggat ggctccatca agaattcatg taacttgtgc attagttcac   1500
gagacaacgc ctgcaggaag aatacacaaa gggctctgtt ctacttggat gaagaatgct   1560
gtctcattgg aggatgccca tgtgagtagc tgggctccta ttttgttag gcaatcaaac   1620 ttcaggcttc caactgattc gaaagtacct attattatga ttggtcctgg caccgggttg   1680 gctccttta ggggtttcat gcaggaaagg ttagctctta aggaatctgg agcagaactt   1740
ggatctgcag tactgtactt tggatgcagg aatagaaaat tggatttcat ttacgaggat   1800
gagcttaatc actttgttga aactggtgca atatctgaga tggttgttgc tttctcacgt   1860
gagggtcctg ctaaggaata tgtccaacat aagatgagtc aaaaggcttc agagatatgg   1920
gacatgatat ctcatggagc atatatttat gtctgtggtg atgccaaagg catgccagaa   1980
gacgtgcaca ggatgctcca cacaattgca caagagcagg gagctctgga cagtagccat   2040
gcagagagct tggtgaaaaa tcttcatatg agtggaagat atttacgtga tgtatggtaa   2100
```

<210> SEQ ID NO 27
<211> LENGTH: 2046
<212> TYPE: DNA
<213> ORGANISM: Petroselinum crispum

<400> SEQUENCE: 27

```
atgggtggtg agagcttggc cacgtcactg ccggcgacgc tcctcgagaa tcgtgacctg     60
ttaatgctcc tcaccacgtc aatcgccgtt ttgattggat gcgctgtcgt tttggtgtgg    120
cgcagatcga gcctgcgatc ggttaaatca gttgagccgc cgaagctgat tgtaccgaaa    180
gttgaaattg aagatgaagt tgatgacggt aaaaagaaag ttaccgtgtt tttcggcact    240
caaactggta ctgctgaagg cttttgctaag gcttttgcgg aggaggcgaa agcgcggtac    300
gagaaggcga aattcagagt tgttgattta gatgattatg cggcggagga tgaggagtac    360
gaggcgaaat ttaagaagga atcttttgcg ttttttcttct tagctacata tggtgacggt    420
gagccaactg acaatgcggc tagattctat aagtggtttt cggagggtga agagaaagga    480
gattggttaa ataagcttca atatggagtg tttggccttg aaataggca gtacgaacat    540 tttaacaaga tcgcgaaagt tgttgacgat ggtcttgcag atcagggagc caagcgtatt    600
gttgaagtgg gtatgggtga tgatgatcaa tgcattgaag atgacttcac cgcatggcgg    660
gaattggtct ggcctgaatt ggataagttg cttttggatg aggatgacac atctgctgca    720
actccttaca cagctgctgt tttggaatat cgggttgtgg tttatgacca acttgataca    780 gctacactg atcggagttt aagtacccaa aatggccata cagttcatga tgctcaacat    840
ccgtgcaggt ctagcgtagc tgcaaagaaa gagcttcata aacctgcatc tgatcgttcg    900
```

```
tgcattcact tggagtttga catttcacac accgggcttg catatgaaac tggtgaccac    960
gtcgggtct actgtgagaa tctggttgaa attgttgagg aggctgaaaa gctattaggc    1020
atgcaaccaa acacttactt ctctgtccat attgacgacg aagatggaac accacttact   1080
ggaggctctc tgccacctcc cttcccgcca tgcactgtga aagtgcact ggcaaaatat    1140
gcagatcttt tgagctctcc gaagaagtct gccttgcttg ctctggcggc acatgcttct   1200
gatcctaccg aggctgaccg attaagattg ttagcatctc ctgctggaaa ggatgaatat   1260
gcacaatggg tagttgctag ccacagaagc cttcttgaag tcttggctga atttccatca   1320
gccaaacccc cactgggagt attctttgca tcagttgcac cacgcttgca gcccagatac   1380
tattctatct cttcttcacc aaggatggta ccatcaagga ttcatgttac ttgtgcttta   1440
gtttatgaga aaacacctac ggggcgaatt cacaaaggag tgtgttcaac ttggatgaag   1500
aatgctgttt cttggagga aagccatgat tgcagttggg cacccatttt tgttagacaa    1560
tccaacttca agcttccttc tgatacgaaa gtccccatca ttatgattgg ccctggaact   1620
ggattagctc ctttcagggg tttcctgcag gaaaggcaag ctctgaagga tgctggagca   1680
gagctgggaa ctgctgtgtt atactttggg tgcaggaata gaaatttgga ttttatttac   1740
gaggatgagc taaataagtt tgtcgaaagt ggttcaatct ctgagctaat tgtagctttc   1800
tcacgtgagg ggcccactaa ggagtatgtg caacataaga tgttgcagaa agcgtcagag   1860
atctggaact tgatttctga gggtgcatat atttatgtct gcggtgatgc aaaaggcatg   1920
gccagggatc tccatcgcat gcttcacaca attgcacagg agcagggagc tcttgacagc   1980
agcaaggcgg agagctgggt taagaacctt caaatgactg ggaggtatct tcgtgatgta   2040
tggtaa                                                              2046

<210> SEQ ID NO 28
<211> LENGTH: 2082
<212> TYPE: DNA
<213> ORGANISM: Gossypium hirsutum

<400> SEQUENCE: 28
atgagttcga gttccgattt ggtgggtttt gttgaatcgg tattgggagt gtcgttagag    60
ggttcggtaa cggattctat gatagtgatc gcgacgacgt cgttagcggt gattctgggg   120
cttttggtgt ttttctggaa gaaatcgggt tccgaacgga gccgtgatgt caaaccgttg   180
gtggcaccta agcctgtttc actcaaggac gaggaagacg acgacgccgt tatcgctgcc   240
ggcaaaacta aagttaccat tttctacggc acacagacgg gaacggccga gggatttgct   300
aaggctttag ccgaagagat caaggcaaga tatgagaaag ctgctgtcaa agttgttgac   360
ctggatgatt atgccatgga cgatgaacaa tacgaagaga agctgaaaaa ggagactta    420
gcttttttca tggtggccac ttatggagac ggagagccaa ccgataacgc tgctaggttt   480
tacaaatggt ttactgaggg aaatgaaagg ctgccgtggc ttcaacaact cacatatggt   540
gtatttggtc tgggtaaccg tcaatatgaa catttttaata agatagcaaa ggtgcttgat   600
gagcaacttt ccgaacaagg tgctaaacgt cttattgaag ttggtcttgg agatgatgat   660
caatgcattg aagatgattt tactgcatgg agagaactgc tctggccaga gttagatcaa   720
ctgcttagag atgaagatga tgaaaatgct acctctaccc cgtatacggc agctattcct   780
gaatatagag tagtggttca tgatcctgct gtgatgcacg tagaggagaa ttactcaaat   840
aaggcaaatg ggaatgctac atatgacctc caccatccat gcagagttaa tgttgccgtt   900
```

```
cagagagagc tccacaagcc tgaatctgat cgctcctgta ttcatttgga gtttgacata      960
tcagggactg gtatcacata tgaaaccgga gatcacgttg gtgtctacgc ggataattgc     1020
gttgagactg ttgaggaagc tgcaagattg ttgggtcaac ctctggattt gctatttttct   1080
atacacactg acaatgagga cggcacatct gctggaagct cattgccgcc acctttgcc     1140
agtccatgta cactgcgaat ggcattggca cgatatgcag atcttttaaa ccctccacgg    1200
aaggctgctt tgattgcctt ggctgctcat gccactgaac ccagtgaagc agaaaagctt    1260
aagttcttat cgtcaccaca ggggaaggat gagtactcac aatgggttgt tgcaagtcag    1320
agaagtcttc ttgaggttat ggctgagttc ccatcagcaa aacctcctct tggtgtattt    1380
tttgctgcag tagctcctcg tttacagcct cgttattatt ctatctcatc ctcccctagg    1440
tttgtacctg ccagggttca tgtaacctgc gctttagttt atggtccaac tccaactgga    1500
agaattcacc ggggtgtgtg ctcaacatgg atgaagaatg cagttccttt agagaaaagc    1560
aatgattgta gctgggctcc tattttttatt cggcaatcca attttaagct accagcagat   1620
ccttcagttc caatcatcat ggttggaccc gggactggat tggcaccttt cagaggtttt    1680
ctacaggaaa gattggtcct caaagaagat ggtgcagaac ttggctcttc tctactcttt    1740
tttggatgta ggaatcggcg aatggatttc atttatgagg atgagctcaa taactttgtg    1800
gaacaaggtg ccctttctga gcttgttgtt gcattttcac gagaaggtcc gcagaaggaa    1860
tatgttcaac acaaaatgat ggataaagct gcagatatat ggaacctaat ttctaagggt    1920
ggatatcttt atgtttgtgg tgatgccaag ggtatggcaa gagatgttca tcgcactttg    1980
cacactatta ttcaggagca ggaaaatgtg gattcatcaa aggcggagtc tatggtgaag    2040
aaactccaga tggacggacg ataccttaga gatgtgtggt ga                       2082

<210> SEQ ID NO 29
<211> LENGTH: 2133
<212> TYPE: DNA
<213> ORGANISM: Gossypium hirsutum

<400> SEQUENCE: 29
atggattctt catcatcatc atcatcttca ggtccctcac ctctcgatct catgtcggct      60
ttagtcaagg ccaaaatgga cccttccaac gcttcctccg actctgctgc tcaagtaacc    120
accgtccttt tcgagaacag agagttcgtt atgattttaa ctacctccat tgctgtgctc    180
atcggctgcg tcgtcatttt gatctggcgt agatccgctt ctcaaaagcc taaacaaatc    240
cagcttcctc ttaagccttc gatcattaaa gaaccagaac ttgaagttga cgatggaaag    300
aaaaaagtca ccatcctctt cggtactcaa accggcaccg ccgaaggctt cgctaaggct    360
ctagtcgagg aggcaaaagc acgctatgaa aaggcgactt ttaatattgt agatttggat    420
gattatgcag cagatgatga agaatacgag gagaagatga gaaagataa tttggcttc      480
ttcttcttgg ccacttatgg agacggtgag ccaacagata tgcagccag gttctataaa    540
tggttcactg agggaaaaga gagggagaa tggcttcaga acatgaagta tgggattttc   600
ggccttggta acaaacagta tgaacatttt aacaaggttg caaggtggt tgatgaactc    660
cttaccgagc agggagcgaa gcgcatagtt ccttgggtc ttggagatga tgaccaatgc    720
atagaagatg acttcactgc atggcgtgaa ttagtgtggc ccgagttaga tcagcttctg   780
cgtgatgaag atgatgcaac tgttctacc ccgtacactg ctgctgtttt ggaataccgt    840
gttgtatttt atgatcctgc agatgcaccc cttgaggata gaactggag taatgcaaat    900
ggtcatgcta cttatgatgc tcaacatcct tgcaggtcta atgtggctgt gaggaaggag    960
```

```
cttcatgctc ctgaatctga tcggtcttgc acccaccttg aatttgacat tgctggaact      1020
ggactttcat acgagacagg cgatcatgtc ggtgtttact gtgagaacct ggatgaagtt      1080
gtagatgaag cattgagttt actgggctta tcacccgaca cttatttctc tgttcacact      1140
gataaagagg atggtacacc acttggtgga agttctttac cttcttcttt ccccccttgt      1200
actctgagaa cagcactggc acgatatgct gatcttttga gctcgccaaa aaaggctgcc      1260
ttacttgctt tggctgctca tgcctctgat ccaactgaag ccgatcgact aagacacctt      1320
gcatcacctg ctggaaagga tgagtatgct caatggattg ttgcaaacca gagaagtctc      1380
cttgaggtca tggcggaatt tccttcagcc aagcctccac ttggtgtttt ctttgcagct      1440
gttgctccaa ggttgcagcc tagatattat tcgatatcat cctcaccaag gttggcacca      1500
tcaaggattc atgtaacttg tgcattggtt tatgagaaaa cgccaacagg tcgtattcac      1560
aaaggtgttt gttcaacttg gatgaagaat gctgtgtcct cggggaaaag cgatgactgc      1620
ggctgggcac ccattttgt caggcaatca aactttaaac ttccttcaga tactaaagtg       1680
cccatcataa tgattggtcc tggtactgga ttggctcctt caggggatt ccttcaggaa       1740 aggcttgcac tgaaagaagc tggtgctgag ttgggtccat ctgtattgtt ctttggctgc      1800
agaaaccgga aaatggattt catatatgaa gatgagctca caactttgt caacagtggt       1860 gcactatctg agcttgtggt tgccttttca cgtgagggac ctaccaagga atatgtgcaa      1920
cataaaatga tggagaaggc caaggacata tgggacatga tttctcaggg aggttacctg     1980
tatgtgtgtg gtgatgccaa gggcatggct agagatgttc atcgagctct tcacactatt     2040
ttccaagagc agggatcact agacagctca aaggctgaga gcatggtgaa aaatctgcaa     2100
atgagcggca ggtacctacg cgatgtatgg tga                                   2133

<210> SEQ ID NO 30
<211> LENGTH: 1443
<212> TYPE: DNA
<213> ORGANISM: Vitis vinifera

<400> SEQUENCE: 30
atggaggtgt tcttcctctc cctgctcctc atctttgtgc tctcagtctc catcggactt        60
cacttgctct tctacaagca tagatcccac ttcactggcc ccaatctccc tcctggcaag       120
attggttggc ctatggttgg tgaaagccct gaattcctct ccaccggctg gaaaggccac       180
ccggaaaaat tcatcttcga tcgcatctcc aaatactcct ctgaagtctt caagacctcc       240
ctcctcggag agcctgctgc cgtctttgct ggcgctgcgg gcaacaagtt tttgttctcc       300
aacgaaaaca aacttgttca tgcgtggtgg cctagctctg tcgacaaggt cttcccctcc       360
tccacccaaa cctcatccaa agaggaggcc aagaagatga ggaagttgct ccctcagttc       420
tttaagcctg aagccttgca acgttacatt ggcatcatgg atcacattgc gcagaggcat       480
tttgctgata gctgggacaa cagagatgaa gtcattgtat ttccactggc caagaggttc       540
actttctggc tagcttgccg cctgtttatg agcatagaag atcctgccca cgtcgctaaa       600
tttgaaaagc ccttccatgt cttggcctca ggactcatca ccgtcccaat tgacttgcct       660
gggacacctt tccaccgcgc tatcaaggcc tccaacttca tcagaaagga gcttagagcc       720
atcatcaagc aaaggaagat cgatctggct gagggcaagg cctcacaaaa tcaagatata       780
ttgtcccaca tgcttctggc tacagatgaa gatggatgcc acatgaatga aatggaaatt       840
gctgataaaa tcctcggttt gttgattggt ggccatgaca ctgccagtgc tgccattaca       900
```

```
ttccttatca agtacatggc tgagctgcct cacatctacg agaaagtcta cgaggagcaa    960
atggaaattg ccaattcaaa agcaccaggt gaattgctga actgggatga tgttcaaaac   1020
atgagatatt catggaatgt tgcctgtgaa gtgatgagac ttgcaccccc actccaagga   1080
gctttccggg aagcaatcac tgacttcgtg ttcaacggtt tctccattcc taagggttgg   1140
aagctgtact ggagcgcaaa ctcaacccac aaaagcccag aatgcttccc tcaacccgaa   1200
aattttgacc ctacaagatt tgaaggaaac gggcctgctc cttacacatt cgttcccttt   1260
ggtggcggac ctaggatgtg ccctggtaaa gagtacgccc gcttggaaat actagtcttc   1320
atgcacaacg tggttaaaag gttcaaatgg gataaattgc ttcctgatga aagataatc    1380
gttgacccca tgcccatgcc tgctaaggga cttccagttc gcctccatcc tcacaaacca   1440
tag                                                                 1443

<210> SEQ ID NO 31
<211> LENGTH: 1443
<212> TYPE: DNA
<213> ORGANISM: Vitis vinifera

<400> SEQUENCE: 31
atggaggtgt tcttcctctc cctgctcctc atctctgtgc tctcagtctc catcagactt     60
tacttgctct tatacaagca tagatcccac ttcactggcc ccaatctccc tcctggcaag    120
attggttggc caatggttgg tgaaagcctt gaattcctct ccaccggctg gaaaggccac    180
ccggaaaaat tcatcttcga tcgcatctcc aaatactcct ctgaagtctt caagacctcc    240
ctcctcggag agcctgctgc cgtctttgct ggcgctgcgg caacaagttt tttgttctcc    300
aacgaaaaca aacttgttca tgcatggtgg cctagctccg tcgacaaggt cttcccctcc    360
tccacccaaa cctcatccaa agaggaggcc aagaagatga ggaagttgct ccctcagttc    420
cttaagcctg aagccttgca acgttacacc ggcatcatgg atcacattgc acagaggcat    480
tttgctgata gctgggacaa cagagatgaa gtcattgtat ttccactggc caagaggttc    540
actttctggc tagcttgccg cctgtttatg agcatagaag atcctgccca cgtcgctaaa    600
tttgaaaagc ccttccacgt cttggcctca ggactcatca ccatcccaat tgacctgcct    660
gggacacctt ccaccgcgc tatcaaggcc tccaacttca tcagaaagga gcttagagcc    720
atcatcaagc aaaggaagat cgatctggct gagagcaagg cctcaaaaac tcaagatata    780
ttgtcccaca tgcttctggc tacagatgaa gatggatgcc acatgaatga aatgagtatt    840
gctgataaaa tcctcggttt gttgattggt ggccatgaca ctgccagttc tgccattaca    900
ttccttgtca agtacatggc tgagctgcct cacatctacg agaaagtcta caaggagcaa    960
atggaaattg ccaattcaaa agcaccaggt gaattgctga actgggatga tgttcaaaag   1020
atgagatatt catggaatgt tgcctgtgaa gtgatgagac ttgcaccccc actccaagga   1080
gctttccggg aagcaatcac tgacttcgtg ttcaacggtt tctccattcc taagggttgg   1140
aagctgtact ggagcgcaaa ctcaacccac aaaagcctag aatgcttccc tcaacccgaa   1200
aaatttgacc ctacaagatt tgaaggagcc gggcctgctc cttacacatt cgttcccttt   1260
ggtggcggac ctaggatgtg ccctggtaaa gagtacgccc gcttggagat acttatcttc   1320
atgcacaact tggttaaaag gttcaaatgg gataaattgc ttcctgatga aagataatc    1380
gttgacccca tgcccatgcc tgctaaggga cttccagttc gcctccatcc tcacaaacca   1440
tag                                                                 1443
```

<210> SEQ ID NO 32
<211> LENGTH: 1440
<212> TYPE: DNA
<213> ORGANISM: Medicago truncatula

<400> SEQUENCE: 32

| | | | | | |
|---|---|---|---|---|---|
| atggagccta | atttctatct | ctcccttctc | cttctctttg | tcactttcat | atctctctct | 60 |
| cttttttca | tattctacaa | acagaaatct | ccattaaatt | tgccacctgg | taaaatgggt | 120 |
| tacccaatca | taggtgaaag | ccttgagttc | ttatcaacag | gatggaaagg | acatcctgaa | 180 |
| aaattcattt | tcgaccgtat | gcgtaaatat | tcctcagaac | tctttaaaac | atcaatcgta | 240 |
| ggagaatcta | cggtggtttg | ttgcggagca | gcaagtaaca | agttttttgtt | ttcaaacgag | 300 |
| aataaacttg | tgactgcatg | gtggccagat | agtgtaaaca | aaatcttccc | tactacttct | 360 |
| cttgactcta | acttgaagga | agaatccatc | aagatgagaa | aattgcttcc | acaattcttt | 420 |
| aaacccgaag | ctctacaacg | ttatgttggt | gtcatggatg | ttattgctca | aagacatttt | 480 |
| gttactcatt | gggataataa | aaatgaaatc | accgtctacc | ccttggccaa | gaggtacacc | 540 |
| tttttgttag | cttgtcggtt | gttcatgagc | gttgaagacg | agaatcatgt | agcaaaattt | 600 |
| agtgatccat | ttcagttaat | tgcggccgga | atcatatctc | taccaattga | tttgccagga | 660 |
| acaccattca | acaaagctat | aaaggcctca | aactttataa | gaaggagtt | gattaagatc | 720 |
| ataaagcaaa | ggagggtaga | tttggcagaa | gggacagcat | caccaacaca | agatatattg | 780 |
| tctcacatgt | tgttgacaag | tgatgaaaat | ggaaagagta | tgaatgaact | taatattgct | 840 |
| gataagattc | ttggccttt | gatcggagga | catgacactg | ctagcgtcgc | atgcactttc | 900 |
| cttgtcaaat | atctcggcga | gttacctcac | atttatgata | aagtctatca | agagcaaatg | 960 |
| gaaattgcaa | aatcgaaacc | agcaggagaa | ttgttgaatt | gggatgacct | gaagaaaatg | 1020 |
| aaatactctt | ggaacgtagc | ttgtgaagta | atgagacttt | cccctccact | ccaaggaggt | 1080 |
| ttcagggaag | ccatcactga | ctttatgttc | aatggattct | caattcctaa | gggatggaag | 1140 |
| ctttattgga | gtgcaaattc | aacacataag | aacgcagaat | gttttcccat | gccagagaaa | 1200 |
| tttgacccaa | caagatttga | aggaaatgga | ccagctcctt | atacttttgt | tcccttggt | 1260 |
| ggaggaccaa | ggatgtgtcc | tggaaaagag | tatgcaagat | tagaaatact | tgttttcatg | 1320 |
| cacaatttgg | tgaaaaggtt | taagtgggaa | aaggtgattc | cagatgagaa | gattattgtt | 1380 |
| gatccattcc | ccatccctgc | aaaggatctt | ccaattcgcc | tttatccaca | caaagcttaa | 1440 |

<210> SEQ ID NO 33
<211> LENGTH: 1443
<212> TYPE: DNA
<213> ORGANISM: Catharanthus roseus

<400> SEQUENCE: 33

| | | | | | |
|---|---|---|---|---|---|
| atggagatct | tctatgtcac | tctccttagc | ttattcgttc | tccttgtttc | cctttccttt | 60 |
| catttcctct | tctacaaaaa | caaatcaacc | ttgccgggac | cgttacctcc | gggccggacc | 120 |
| ggctggccga | tggtgggaga | agtcttcaa | tttctctcag | cgggctggaa | aggccatcct | 180 |
| gaaaaattca | tatttgatcg | tatggctaag | tattcttcga | atgtctttag | gtcacatcta | 240 |
| ctaggtgaac | ctgccgcggt | attttgtggt | gcaattggaa | ataaatttt | attctcaaat | 300 |
| gaaaataaac | ttgttcaagc | atggtggcct | gattcagtaa | acaaagtttt | cccatcttca | 360 |
| aatcaaactt | cttcaaaaga | agaagctatt | aaaatgcgaa | agatgcttcc | gaattttctt | 420 |
| aaaccggaag | ctttacaacg | ttacataggt | ttaatggacc | aaattgccca | aaaacatttt | 480 |

```
tcttccggtt gggaaaatag ggaacaagtt gaagttttc ctttagccaa aaattatact    540
ttttggttag cttcaagatt atttgttagt gttgaagatc caattgaagt tgcaaaatta    600
cttgaacct  ttaatgtttt ggcctcggga ctaatttctg tccctattga tttgcctggt    660
acacctttta atcgtgctat aaaggcatca aatcaagtaa gaaaaatgct tatttctata    720
attaaacaaa gaaaaattga tttagctgaa ggaaaagcat ctccaacaca agatattttg    780
tcacatatgc ttttaacaag tgatgaaaat ggtaaattca tgcatgaatt ggatattgct    840
gataaaatcc ttggtttgtt aattggtgga catgatactg caagttctgc atgtactttt    900
attgtcaagt ttcttggaga attgccagag atatatgaag gagtttataa agaacaaatg    960
gagattgcca actcaaaagc ccctggtgaa ttcttgaatt gggaagatat tcaaaagatg   1020
aaatattcat ggaatgtagc atgtgaagtg ttgagacttg caccacctct ccaaggtgct   1080
tttagagaag ccctaaatga tttcatgttc catggattct ctattccaaa aggatggaag   1140
atttactgga gtgtgaattc aacacacaga atccagaat  gttttccaga tccacttaaa   1200
tttgacccgt caagatttga tggatctgga cctgctccat atacatttgt accatttggt   1260
ggaggaccaa gaatgtgccc tggaaaagaa tacgctaggc tggaaattct ggttttatg    1320
cataatcttg tgaagagatt caagtgggaa aaaattatcc caaatgaaaa gattgttgtt   1380
gatccaatgc caattcctga aaaggactt  cctgttcgac tttatcctca cattaatgca   1440
taa                                                                1443

<210> SEQ ID NO 34
<211> LENGTH: 1446
<212> TYPE: DNA
<213> ORGANISM: Populus trichocarpa

<400> SEQUENCE: 34
atggagcttc tcttcctctc actcctcctc gccctctttg tttcctccgt cactattccc     60
ctctttctca tcttttacaa tcatcgatcc cagaacagcc accccaacct ccctccaggc    120
aagctaggcc ttccccttgt tggagaaagc tttgagttct tggccacggg atggaaaggc    180
catcctgaaa agttcatctt tgatcgcata gctaaatact catctcacat cttcaagaca    240
aatattcttg gtcaaccagc agttgtcttt tgtggtgttg cttgtaacaa gttttgttt    300
tccaatgaga acaagctcgt tgtatcctgg tgccccgact ctgttaacaa aatctttccc    360
tcttcacttc aaacatcatc taaagaggaa gccaagaaaa tgagaaaact tctcccctcag    420
ttcttgaaac ctgaggcctt gcaaggatac attggtatca tggataccat tgcacaaaga    480
cacttcgcct cggaatggga acataaagaa caagtgctgg tgttcccttt gtcaaagaat    540
tacacctttc gtttggcttg tagattgttt ctgagtattg aagatccaag ccacgtagct    600
aaattttctg accccttaa  tctttttagc ctcgggtatca tttccatccc cattgatttg    660
cccgggactc cattcaaccg agctatcaaa gcctcaaact tcatcagaac tgagctttta    720
gcttttataa gacaaagaaa gaaggatctt gcagagggaa aagcttcccc cacgcaggat    780
atattgtcac acatgttgtt gacatgtgat gaaaatggaa aatgcatgaa tgagcttgat    840
attgctgata gatcattgg  attgttgatt ggtgggcatg atacagccag cgctgcttgt    900
accttcattg tcaagtatct tgcagagctt ccacatatat atgaggaagt ttacaaggaa    960
caaatggaga tagccaaatc caaaactcct ggtgaattct tgaattggga tgacattcag   1020
aagatgaaat actcatggaa agtagcttgt gaagtgatga ggatctcacc accgcttcaa   1080
ggtgctttta gggaagctct caatgatttc attttcaatg gctttaccat tccaagggt    1140
```

```
tggaagttat attggagcac caactcaacc catagagatc ccgtctactt tcctgaacct    1200
gagaaatttg atcctaggag gtttgaagga agtgggccag ctccatacac gtttgtcccc    1260
ttcggtggag gacctcggat gtgccctgga aaggagtatg ctcgcttgga aatactcgtt    1320
ttcatgcata atttggtcag aaggtttaaa tttgataagt tgattcaaga tgaaaagatt    1380
gtagtgaatc cactgccaat ccctgataaa ggacttcctg ttcgccttca tcctcacaag    1440
gcctag                                                               1446

<210> SEQ ID NO 35
<211> LENGTH: 1449
<212> TYPE: DNA
<213> ORGANISM: Glycine max

<400> SEQUENCE: 35
atggaccata ataacttgta cctctccctc cttctcctct tcgtttcttt cgtgaccctc      60
tccctcttct tcctcttcta caaacacagg tctccattcg tggccccgaa cctgccacct     120
ggagcaaccg gttacccggt gatcggggag agcctggagt tcctgtcaac aggatggaag     180
ggtcatccgg agaagttcat cttcgaccgg atgatcaggt actcctccca actgttcaag     240
acctccatct tcggggaacc cgcggtcata ttctgtgggg ccacctgcaa caagttcttg     300
ttctctaacg agaacaagct tgttgcagcg tggtggccca acagcgtcaa caaggtgttc     360
ccctccacgc ttcagagcaa ctccaaagaa gagtccaaaa agatgaggaa gttgctccct     420
cagttcctca gcccgaggc tctccaacgc tacgttggca tcatgacac catcgctcaa      480 aaccacttcg cttcccttg ggacaacaag acggaactca ccgtctatcc cttggctaag      540
aggtacacgt tcttgttggc ttgtcgtttg tttatgagcg ttgaggatgt gaatcacgta     600
gcaaaatttg agaaccccttt tcacctgttg gcgtctggaa tcatatcagt gcctattgat    660
cttcctggaa cgccgttcaa caaagcaatc aaggcagcaa acgcaatcag gaaggaactg    720
ttaaagatca ttagacagag gaaggttgat ttagctgaag gaaaagcttc accaacacaa    780 gacatttat ctcacatgtt gttaacatgc aatgagaatg acaattcat gaatgaattg       840 gatattgccg acaagattct tggccttttg attggaggcc atgacactgc tagtgctgca    900
tgcactttca ttgtcaaata tcttgctgaa ctccctcaca tttatgatag tgtctatcaa     960
gaacaaatgg aaatcgcaaa atcgaaattg cccggagagt tattgaattg ggatgatatc    1020
aacaggatga agtattcttg gaatgtagct tgtgaagtaa tgagaatcgc tcctccactt    1080
caaggaggtt ttagggaagc tatcaatgac tttattttca atggcttctc aattccaaag    1140
ggatggaagt tgtattggag tgcaaattca acacataaaa atccggaata ctttccagag    1200
ccagagaaat tcgatccaac tagattcgaa ggacaagggc cagctccttt tacttttgta    1260
ccatttggtg gaggaccaag gatgtgcccc ggaaaagagt atgctcgatt ggaaatattg    1320
gttttcatgc acaacctagt gaagaggttt aagtgggaaa aattgattcc agatgagaag    1380
attatcgttg atcccttgcc cgtacctgca aagaacctcc caattcgtct tcatcctcac    1440
aaaccctga                                                            1449

<210> SEQ ID NO 36
<211> LENGTH: 1449
<212> TYPE: DNA
<213> ORGANISM: Bupleurum chinense

<400> SEQUENCE: 36
```

```
atgatgatgt acttgtattt ttcagtcatc agcattcttg ttctacttcc ttgtgtatgg    60
ctcttcttct tacactcgaa cagaaaatca acccaacaat catacaaatc tctcccacca   120
ggagaaacgg gctattttct catcggagaa agcttagaat ttctgtccac aggaaggaaa   180
ggccatcctg aaaagttcat ttttgatcgc atgacaaagt acgcctctaa aattttcaaa   240
tcatcgctat ttggagagaa acaatagtc ttttgtggtg ctgctaacaa caagttttg     300
ttttctgacg aaaacaagct ggtgcagtcg tggtggccta actccgtaaa caaactcttc   360
ccttcctcta cacaaacttc ttcgaaagaa gaagccatca aaatgaggaa aatgcttcca   420
aacttcttca acccgaggc cttgcaaaga tatgttggtg ttatggatga aatagctcaa    480
aaacactttg attcttgttg ggaaaacaaa cacacggtca ttgttgcacc tctcaccaag   540
cgtttcacct tttggcttgc ttgtcgtttg tttgtcagcc ttgaagatcc tacacaggta   600
gctaaatttg ctgagccttt caatctattg gcctctggag tttttctat tcctattgat    660
ttaccgggaa cagcattcaa tcgagctatt aaagcctcta acttcattcg aaaaacgctt   720
attggcatca ttaaaaaaag aaaggttgat ttagaggatg gaactgcatc agccacacaa   780
gatattttgt cgcatatgct cttgacaagc gatgagactg aaagttcat gactgaagcc     840
gatattgctg ataaaatatt aggtttgttg ataggaggtc atgatactgc tagctctgct   900
tgtgctttga ttgtcaagta tcttgctgaa ctccctcaca tatatgatgg agtctataga   960
gagcaaatgg aaattgcaaa atctaaatct ccaggggagt gctaaactg ggatgatgta   1020
caaaagatga atattcatg gaatgtagca tgtgaagttt tgagacttgc accacccctc    1080
caaggaagtt ttagagaagt actttctgat ttcatgcaca atggtttctc catacccaag   1140
ggatggaaga tctattggag tgcgaattcg acacataaaa gttcagaata tttcccagag   1200
ccagaaaagt ttgatccgag acgatttgaa gggtcaggac cagcacccta cacatttgtg   1260
ccatttggag gtggaccaag aatgtgccct ggaaaagaat atggtagatt ggagatactt   1320
gtattcatgc accacttggt gaagaggttc agatggcaaa aaatatatcc tctggagaag   1380
attactgtta atccaatgcc tttccctgac aaggatcttc caattcgcct atttcctcac   1440
aaagcatag                                                           1449
```

<210> SEQ ID NO 37
<211> LENGTH: 1452
<212> TYPE: DNA
<213> ORGANISM: Cucumis sativus

<400> SEQUENCE: 37

```
atggagcttt tcctcatctc tctcttaatc cttttgttct tctttctttc tcttactctt    60
ttcatcctct tccacaatca caatccttta ttctcttatc ccaacactcc tcctggcgcc   120
atcggccttc ccatactcgg cgagagcgtc gagttcttat catctggttg gaaaggccat   180
cctgagaagt tcatcttcga tcgtttgaat aagtacaagt cagatgtgtt caaaacctcg   240
atcgtgggag ttccagccgc cattttctgc ggccctattt gtaacaagtt cctcttctct   300
aacgagaata aactggttac tccttggtgg ccagattccg tgaacaagat cttcccctct   360
acaactcaga ctagcaccaa agaagaagct aagaaactca gaaactcct tccgcaattc   420
cttaaacccg aagcgcttca gcgttatatt ggaattatgg acgaacttgc tgaacgccat   480
ttcaattcct tttggaagaa cagagaagag gtcctcgtgt ttcctcttgc taaaagcttc   540
acattctcaa tagcgtgccg actgttcatg agcgtggaag atgaaattca cgtgagaga   600
ttatcgggac cattcgagca cattgcagca ggaatcatat cgatgccgat cgatttacca   660
```

```
ggaacgccat tcaatagagc aataaaggcg tcaaagttca tcagaaagga agtggtggcg      720
atcgtgaggc agaggaaaca ggatttggcg gaaggaaagg cgttggcgac gcaggatatt      780
ttgtcccaca tgcttctaac gtgcgatgag aatggtgtgt acatgaacga atcagatatc      840
accgataaga ttcttgggtt gttgatcggc ggccatgaca ctgccagtgt tgcatgcacc      900
ttcatcgtta agttcctcgc tgagcttcct catatctacg atgctgtata tacagagcaa      960
atggaaatag caagagcaaa agcggaaggg gaaacgttga agtgggaaga cattaagaag     1020
atgaaatatt catggaatgt ggcttgtgag gttctaagaa ttgcttcccc actccaaggt     1080
gcctttaggg aagccttaag tgacttcgtt ttcaatggtt ttttcattcc caagggttgg     1140
aagctatatt ggagtgcaaa ctcgacacac aaaaaccccg agtacttccc agaaccttat     1200
aagttcgatc cgggaagatt tgaaggaaat ggaccattac cctacacatt tgtgccgttt     1260
gggggagggc caaggatgtg ccctggtaag gagtatgcaa agcttgagat tttggtgttc     1320
atgcataatt tggtgaagag attcaaatgg acaaagcttc ttgaaaatga aaacatcatt     1380
gttaacccaa tgccaatccc tcaaaaaggt ctcccagttc gccttttttcc tcatcaacct     1440 ctttctcttt aa                                                         1452

<210> SEQ ID NO 38
<211> LENGTH: 1446
<212> TYPE: DNA
<213> ORGANISM: Panax notoginseng

<400> SEQUENCE: 38
atggaactct tctatgtccc tctcctctcc ctctttgttc tcttcatctc tttatcattc       60
cacttcctct tctacaagtc caaatccagc tcctccgtcg ggcttcctct cccgccgggc      120
aagaccggat ggcccattat cggcgagagc tacgagtttc tctccacggg gtggaaaggc      180
tacccggaga agtttatatt tgaccgtatg accaagtact cctcaaatgt ctttaaaacc      240
tctattttcg gagagcccgc cgcagtattc tgcggcgcgk cttgtaacaa gttcttgttc      300
tcgaacgaaa acaagcttgt tcaggcgtgg tggcctgact ccgtaaacaa gttttttcct      360
tcttcaactc aaacctcttc gaaagaagag gcgattaaga tgcgaaaaat gctgccaaac      420
ttctttaaac cggaggcctt gcagcgctac atcggcctca tggaccaaat cgctgcaaag      480
cactttgaat ccggttggga aaataaagac gaagtggttg tatttcccct ggcaaaatcc      540
tayacgtttt ggatcgcgtg taaggtattt gttagcgtag aggaacctgc gcaggttgcg      600
gagctgttgg aaccatttag cgcgattgct tctgggatta tatccgtgcc aatagatttg      660
cccggcacgc cgtttaacag tgccataaaa tcatcgaaaa ttgttaggag aaagcttgtg      720
gggattatta accagaggaa aattgattta ggggagggaa aggcttcacc aacacaagac      780
atattgtcac acatgttgtt gacgagtgat gaaagtggca agtttatggg tgagggggaa      840
attgctgata agatattggg gttgttgatt ggaggacatg acactgcaag ttctgcatgt      900 actttttgttg tcaagtttct tgctgagctg cctcagattt atgrgggagt ctaccaggag      960
caaatggaga tagtgaaatc taaaaaggca ggagaattat tgaagtggga ggacatacaa     1020
aagatgaaat attcgtggaa tgtagcctgt gaagtgctga gcttgcacc accccttcaa     1080 ggagctttta gagaagccct ctccgatttc acctacaacg gtttctcaat ccccaaaggc     1140
tggaagctat attggagtgc aaattcaacc cacagaaact cagaagtttt cccggagcca     1200
ctaaaatttg atccatcaag attcgacgga gccgggccgc cgccgttctc gttcgtgccg     1260
```

-continued

| | |
|---|---|
| ttcggcggcg ggccgagaat gtgccccgga aaagagtatg cccggctgga aatactggtg | 1320 |
| tttatgcacc atcttgtcaa gaggttcaag tgggaaaagg ttattcctga tgagaaaatt | 1380 |
| gttgttaatc ccatgccaat tcctgccaac ggacttcctg ttcgcctatt ccacacaaa | 1440 |
| gcctaa | 1446 |

<210> SEQ ID NO 39
<211> LENGTH: 1446
<212> TYPE: DNA
<213> ORGANISM: Panax ginseng

<400> SEQUENCE: 39

| | |
|---|---|
| atggaactct tctatgtccc tctcctctca ctctttgttc tcttcatctc tttatcattc | 60 |
| cacttcctct tctacaagtc caaacccagc tcctccggcg ggtttcctct cccgccgggc | 120 |
| aagactgggt ggcccattat tggagagagc tacgagtttc tctccacggg atggaaaggc | 180 |
| tacccggaga agttcatatt tgaccgtatg accaagtact cctcaaatgt ctttaaaacc | 240 |
| tctattttcg gagagcccgc cgcagtattc tgcggcgcgg cttgtaacaa gttcttgttc | 300 |
| tcgaacgaga ataagcttgt tcaggcctgg tggcctgact ccgtgaacaa agttttttcct | 360 |
| tcatcaaccc aaacctcttc gaaagaagag gcgattaaga tgcgaaaaat gctgccaaac | 420 |
| ttctttaaac cggaggcttt gcagcgctac atcggcctca tggaccaaat cgctgcaaat | 480 |
| cactttgaat ccggttggga aaataaaaac gaagtggttg tatttcccct ggcaaaatcc | 540 |
| tacacgtttt ggatcgcgtg taaggtattt gttagcgtag aggaacctgc gcaggttgcg | 600 |
| gagctgttgg aaccattcag cgcgattgct tctgggatta tatccgtccc aatagatttg | 660 |
| cccggcacgc cgtttaacag tgccataaaa tcatcgaaaa ttgttaggag gaagcttgtg | 720 |
| gggattatta gcagaggaa aattgattta ggggagggaa aggcttcagc aacacaagac | 780 |
| atattgtcac acatgctgtt gacaagtgat gaaagtggca agtttatggg tgagggggat | 840 |
| attgccgata agatattggg gttgttgatt ggaggccatg acactgcaag ttctgcatgt | 900 |
| acttttgttg tcaagtttct tgctgagctg cctcagattt atgagggagt ctaccaggag | 960 |
| caaatggaga tagtgaaatc taaaaaggca ggagaattat tgaagtggga ggacatacaa | 1020 |
| aagatgaaat attcgtggaa tgtagcctgt gaagtgctga acttgcacc acctcttcaa | 1080 |
| ggagctttta gaagcccct ctccgatttc acctacaacg gttctcaat ccctaaaggc | 1140 |
| tggaagctat attggagtgc aaattcaacc cacataaact cagaagtttt cccggagcca | 1200 |
| ctaaaatttg atccatcaag attcgacgga gccggccgc cgccgttctc gttcgtgccg | 1260 |
| ttcggcggcg ggccgagaat gtgccccgga aaagagtatg cccggctgga aatactggtg | 1320 |
| tttatgcacc atcttgtcaa gaggttcaag tgggaaaagg ttattcctga tgagaaaatt | 1380 |
| gttgttaatc ccatgccaat tcctgccaac ggacttcctg ttcgcctatt ccacacaaa | 1440 |
| gcctaa | 1446 |

<210> SEQ ID NO 40
<211> LENGTH: 1443
<212> TYPE: DNA
<213> ORGANISM: Ricinus communis

<400> SEQUENCE: 40

| | |
|---|---|
| atggaccact tctatcttac ccttcttttc ctcttcgttt ccttcatcac cttttcaatt | 60 |
| tttatcatat tttacaagca caaatctcaa tacaattatc caagtcttcc tccagggaag | 120 |
| cctggcctcc cttttgttgg tgaaagcctt gaatttttgt cttcaggttg gaagggtcac | 180 |

-continued

```
cctgaaaagt tgtgtttga tagaacttct aaatattctt ctgagatttt taaaactaat      240
cttcttggcc aacctgctgc tgtcttctgt ggtgcttctg ccaacaagtt tttgttctcc      300
aatgaaaaca agcttgttca ggcctggtgg cctgattctg ttaacaaaat attcccttct      360
tctcttcaaa cttcttctaa agaagaagcc attaaaatga aaagcttct ccctcagttc      420 atgaaacctg aagccctcca gcgttatatt ggtatcatgg atacaattgc tcagaggcac      480
tttgcttcgg gatgggaaaa aaaaaatgaa gtagttgtgt ttcctctagc gaagaattac      540
accttctggt tagcgtgcag actgtttgtc agcctggaag atccagatca catcgctaaa      600
tttgcagacc cttttcagga attggcttca ggaatcattt ccgtgccaat agatttgcct      660
ggaacaccat tcagaagagc aatcaaagct tcaaacttca tcaggaaaga gcttataagt      720
attataaagc aaagaaagat tgatctagca gaagggaaag cttctggtac acaggatata      780
ttgtcccata tgttgttaac atcagatgag gatggaaagt ttatgaatga gatggatatt      840
gccgacaaaa ttcttggatt gctgattggt gggcatgata ctgctagtgc tgcttgtact      900
ttcattatca agtaccttgc tgagctccct caaatctatg atgcagttta caagagcaa       960 atggagattg caaaatcaaa aggagaagga gagttgttga attgggaaga catacagaag    1020
atgaaatatt catggaatgt ggcatgtgaa gttatgagag ttgcaccacc ccttcaaggt    1080
gctttcaggg aagctatcaa tgactttatc tttaatggct tctatattcc aaaaggctgg    1140
aagctatatt ggagtgcaaa ctcaacacac aaaagtgcaa catactttga agaaccagag    1200
aaatttgatc caagtagatt tgaagggaaa ggaccagccc catacacatt tgtaccattt    1260
ggaggaggac aagaatgtg ccctgggaaa gagtatgcta gactggaaat tcttgttttc    1320
atgcataatc tggtcaaaag attcaatttc caaaagataa ttcctgatga aacatcatt    1380 gttaatcctt tgcctatccc tgctaagggt cttccagttc gccttcttcc tcatcaaatt    1440
tag                                                                 1443
```

<210> SEQ ID NO 41
<211> LENGTH: 1443
<212> TYPE: DNA
<213> ORGANISM: Vitis vinifera

<400> SEQUENCE: 41

```
atggaggtgt tcttcctctc cctgctcctc atctgtgtgc tctcagtctc catcagactt       60
tacttgctct tatacaagca tagatcccac ttcactggcc ccaatctccc tcctggcaag      120
attggttggc caatggttgg tgaaagcctt gaattcctct ccaccggctg gaaaggccac      180
ccggaaaaat tcatcttcga tcgcatctcc aaatactcct ctgaagtctt caagacctcc      240
ctcctcggag agcctgctgc cgtctttgct ggcgctgcgg gcaacaagtt tttgttctcc      300
aacgaaaaca aacttgttca tgcgtggtgg cctagctctg tcgacaaggt cttcccctcc      360
tccacccaaa cctcatccaa agaggaggcc aagaagatga ggaagttgct ccctcagttc      420
cttaagcctg aagccttgca acgttacacc ggcatcatgg atcacattgc acagaggcat      480
tttgctgata gctgggacaa cagagatgaa gtcattgtat ttccactggc caagaggttc      540
actttctggc tagcttgccg cctgtttatg agcatagaag atcctgccca cgtcgctaaa      600
tttgaaaagc ccttccacgt cttggcctcr ggactcatca ccatcccaat tgacctgcct      660
gggacacctt tccaccgcgc tatcaaggcc tccaacttca tcagaaagga gcttagagcc      720
atcatcaagc aaaggaagat cgatctggct gagagcaagg cctcaaaaac tcaagatata      780
```

```
ttgtcccaca tgcttctggc tacagatgaa gatggatgcc acatgaatga aatgartatt       840
gctgataaaa tcctcggttt gttgattggt ggccatgaca ctgccagttc tgccattaca       900
ttccttgtca agtacatggc tgagctgcct cacatctacg agaaagtcta caaggagcaa       960
atggaaattg ccaattcaaa agcaccaggt gaattgctga actgggatga tgttcaaaag      1020
atgagatatt catggaatgt tgcctgtgaa gtgatgagac ttgcacccccc actccaagga    1080 gctttccggg aagcaatcac tgacttcgtg ttcaacggtt ctccattcc taagggttgg      1140 aagctgtact ggagcgcaaa ctcaacccac aaaagcctag aatgcttccc tcaacccgaa     1200
aaatttgacc ctacaagatt tgaaggagcc gggcctgctc cttacacatt cgttcccttt     1260
ggtggcggac ctaggatgtg ccctggtaaa gagtacgccc gcttggarat acttatcttc     1320
atgcacaact tggttaaaag gttcaaatgg gataaattgc ttcctgatga aagataatc      1380 gttgacccca tgcccatgcc tgctaaggga cttccagttc gcctccatcc tcacaaacca     1440
tag                                                                                                                 1443

<210> SEQ ID NO 42
<211> LENGTH: 1443
<212> TYPE: DNA
<213> ORGANISM: Vitis vinifera

<400> SEQUENCE: 42
atggaggtgt tcttcctctc cctgctcctc atctgtgtgc tctcagtctc catcggactt       60
cagttcctct tctacaagca cagatcccac ttcactggcc ccaacctccc ccctggcagg      120
attggttggc ctatggttgg tgaaagcctt gaattcctct ccaccggctg gaaaggccac      180
ccggaaaaat tcatcttcga tcgcatctcc aaatactcct ctgaagtctt caagacctcc      240
ctcctcggag agcctgctgc cgtctttgct ggcgctgcgg gcaacaagtt tttgttctcc      300
aacgaaaaca agcttgttca tgcgtggtgg cctagctccg tggacaaggt cttcccctcc      360
tccacccaaa cctcatccaa agaggaggcc aagaagatga ggaagttgct ccctcggttc      420
cttaagcctg aagccttgca acgttacatc ggcatcatgg atcacattgc gcagaggcac      480
tttgctgata gctgggacaa cagagatgaa gtcattgtgt ttccactgtc caagaggttc      540
actttctggc tagcttgccg cctctttatg agcatagaag atcctgacca catcgctaaa     600
tttgaaaagc ccttccatgt cttggcctca ggactcatca ccgtcccgat tgacttgcct     660
gggacaccct tccaccgcgc tatcaaggcc tccaacttca tcagaaagga gcttagagcc     720
atcatcaagc aaaggaagat cgatctggcc gagggaaaag cctcaccaac tcaagatata    780
ttgtccgacc tgcttctggc cacagatgaa gatggacgcc acatgaacga aattaatatt      840
gctgataaaa tccttggctt gttgattggt ggccatgata cggccagttc tgccattaca     900
ttcattgtta agtacatggc tgagctgcct catatgtacg agaaagtcta cgaagagcaa     960
atggaaattg ccaattcaaa agcaccaggt gaattattga actgggatga tgttcaaaag    1020
atgagatatt catggaatgt tgcttgtgaa gtgatgagac ttgcacccccc actccaagga   1080 gctttccgag aagcaatcac tgacttcgtg ttcaatggtt ctccattcc taagggttgg     1140 aagttgtact ggagcacaag ctcaacccac aaaagcccaa atgcttccc tgaacctgaa     1200 aaatttgacc ctacaagatt tgaaggagct gggcctgctc cttacacatt cgttcccttt     1260
ggtggtggac ctaggatgtg ccctggtaaa gagtacgccc gcttggaaat acttgtcttc    1320
atgcataacg tggttaaaag gttcaaatgg gataaattgc ttcctgatga aagataata    1380 attgacccca tgcgcatgcc tgctaaggga cttccagttc gcctccgtct tcacaaacca   1440
```

```
taa                                                             1443

<210> SEQ ID NO 43
<211> LENGTH: 1416
<212> TYPE: DNA
<213> ORGANISM: Ricinus communis

<400> SEQUENCE: 43
atgtttccct tgccgtcct cctcatcgct ctttcaatct cataccctcat cttcaaacac    60 aagtccaacg cctccagcag gaagaatctc ccacctggca ataccggttg gcctctcata   120
ggcgaaagca tagagttcct aagcaccggg cgaaagggtc acccggagaa gttcatattt   180
gaccgaatgg agaagttctc gagcaaggtg ttcaagacct cattgcttct ggagccggca   240
gcagtgtttt gtggggcagc agggaacaag ttcttgttct ccaatgagaa taaactagtc   300
actgcatggt ggcctaactc tgttaataaa atcttcccat cctctctcca aacctcttca   360
caggaggaat ccaagagaat gagaaagctt cttcctcaat ttctgaagcc agaagctctt   420
caaagatata taagtatcat ggatgttatt gcacaaagac atttcgcatt cggatggaac   480
aacaaacaac aagtgacagt tttccctcta gctaagatgt atactttctg gttagcctgt   540
cggttgtttc taagcatgga agaccgggaa gaagtcgaaa agtttgcaaa gccattcgat   600
gtattggcat caggtattat atcgatacct attgatttc cagggacgcc atttaaccga   660
gggatcaaag catcaaatga ggtaagaagg gagctgataa agatgatcga acagaggaag   720
attgatctag ccgagaataa ggcatcccca acacaggata tattgtctca catgctaacc   780
acagcagacg agtacatgaa tgaaatggat atagctgata agattcttgg tttgcttatt   840
ggaggccacg acacagccag tgctgccata acgtttgttg tcaagtatct tgcggagatg   900
cctcaagtct acaataaggt gttagaggaa caaatggaga ttgcgaaagc aaaagcagct   960
ggagagctgt tgaactggga agacatccaa aagatgagat attcatgaa cgtagcatgt  1020 gaagtgatga gacttgctcc tccgctacaa ggagccttta gagaggccat gacagacttc  1080
acctatgcag gtttcactat tcctaaagga tggaagttgt actggggtgc taactctaca  1140
cacagaaacc ccgagtgttt cccagaacca gaaaagttcg acccctcaag gtttgaaggc  1200
aagggacctg ccccttacac attcgttcct tttggaggcg acccagaat gtgccctgga  1260 aaagaatatg ctagattgga gatcctcgtt ttcatgcaca acattgtcaa aaagttcaga  1320
tgggagaagc tgcttcctga agagaagatt attgttgatc ctctcccgat tccgctaaa  1380 ggccttcccc ttcgtcttca tccccacacc tcctag                           1416

<210> SEQ ID NO 44
<211> LENGTH: 1440
<212> TYPE: DNA
<213> ORGANISM: Medicago truncatula

<400> SEQUENCE: 44
atggagccta atttctatct ctcccttctc cttctctttg tcactttcat atctctctct    60 cttttttttca tattctacaa acagaaatct ccattaaatt tgccacctgg taaaatgggt   120
tacccaatca taggtgaaag ccttgagttc ttatcaacag gatggaaagg acatcctgaa   180
aaattcattt tcgaccgtat gcgtaaatat tcctcagaac tctttaaaac atcaatcgta   240
ggagaatcta cggtggtttg ttgcggagca gcaagtaaca agttttttgtt ttcaaacgag   300 aataaacttg tgactgcatg gtggccagat agtgtaaaca aaatcttccc tactacttct   360
```

```
cttgactcta acttgaagga agaatccatc aagatgagaa aattgcttcc acaattcttt      420
aaacccgaag ctctacaacg ttatgttggt gtcatggatg ttattgctca aagacatttt      480
gttactcatt gggataataa aaatgaaacc accgtctacc ccttggccaa gaggtacacc      540
tttttgttag cttgtcggtt gttcatgagc gttgaagacg agaatcatgt agcaaaattt      600
agtgatccat ttcagttaat tgcggccgga atcatatctc taccaattga tttgccagga      660
acaccattca acaaagctat aaaggcctca aactttataa gaaaggagtt gattaagatc      720
ataaagcaaa ggagggtaga tttggcagaa gggacagcat caccaacaca agatatattg      780
tctcacatgt tgttgacaag tgatgaaaat ggaaagagta tgaatgaact taatattgct      840
gataagattc ttggccttttt gatcggagga catgacactg ctagcgtcgc atgcactttc      900
cttgtcaaat atctcggcga gttacctcac atttatgata agtctatca agagcaaatg       960
gaaattgcaa aatcgaaacc agcaggagaa ttgttgaatt gggatgacct gaagaaaatg     1020
aaatactctt ggaacgtagc ttgtgaagta atgagacttt cccctccact ccaaggaggt     1080
ttcagggaag ccatcactga cttttatgttc aatggattct caattcctaa gggatggaag     1140
cttttattgga gtgcaaattc aacacataag aacgcagaat gttttcccat gccagagaaa     1200
tttgacccaa caagatttga aggaaatgga ccagctcctt atactttttgt tcccttttggt     1260
ggaggaccaa ggatgtgtcc tggaaaagag tatgcaagat tagaaatact tgttttcatg     1320
cacaattttgg cgaaaaggtt taagtgggaa aaggtgattc cagatgagaa gattattgtt     1380
gatccattcc ccatccctgc aaaggatctt ccaattcgcc tttatccaca caaagcttaa     1440
```

<210> SEQ ID NO 45
<211> LENGTH: 1449
<212> TYPE: DNA
<213> ORGANISM: Glycine max

<400> SEQUENCE: 45

```
atggaggata taacttgca tctctccctc cttctcctct tcgtttctat agtgaccctc        60
tccctcttcg tcctcttcta caagcacagg tctgcatttg cggccccgaa cctgccaccg       120
ggagccaccg gttacccggt gatcggggag agcctggagt tcctgtccac aggatggaag       180
ggtcatccgg agaagttcat cttcgaccgg atgatcaggt actcctccca gctgttcaag       240
acctccatcc tgggggaacc ggcggtaata ttctgtgggg ccacctgcaa caagttctta       300
ttttcgaacg agaacaagct tgttgcagcg tggtggccca acagcgtcaa caaggtgttc       360
cccaccacgc ttcttagcaa ctccaaacaa gagtccaaaa agatgaggaa gttgctccct       420
cagttcctta agcccgaggc tctccaacgc tacgttggaa tcatggacac cattgctcga       480
aaccacttcg cttcccttttg gacaacaag acggaactca ccgtctatcc cttggccaag       540
aggtacacgt tcttgttggc ttgtcgtttg tttatgagca ttgaggacgt gaatcacgta       600
gcaaaatttg agaaccctttt tcacctgttg gcgtctggaa tcatatcagt gcctattgat       660
cttcccggaa cgccgttcaa caaagcaatt aaagcagcaa acgcaatcag gaaggagctg       720
ttgaagatca ttagacagag gaaggtggat ttagctgaag ggaaagcatc gccaacacaa       780
gacattttgt ctcatatgtt gttaacatgc gatgagaagg acagttcat gaatgaattg       840
gatattgccg acaagattct tggccttttg attggaggcc atgacactgc tagtgctgca       900
atcactttca ttgtcaaata tcttgctgaa ctccctcaca tttatgatag agtctatcaa       960
gagcaaatgg aaattgcaaa actgaaatcg ccaggagagt tattgaattg ggatgatgtc      1020
aacaggatgc agtattcttg gaatgtagct tgtgaagtaa tgagaatcgc tcctccactt      1080
```

```
caaggaggtt ttagggaagc tatcaatgac tttattttcg atggcttttc aataccaaag    1140
ggatggaagt tgtattggag tgcaaattca acacataaaa gtccagaata ttttccagag    1200
ccagagaaat tcgatccaac tagattcgaa ggacaagggc cagctcctta cttttgta      1260 ccatttggtg gaggaccaag gatgtgcccc ggaaaagagt atgctcgatt ggaaatattg    1320
gttttcatgc acaacctagt gaagaggttt aagtggcaaa aattgattcc agatgagaaa    1380
attatcgttg atcccttgcc catacctgca agaaccttc caattcgtct tcatcctcac     1440
aaaccctga                                                            1449

<210> SEQ ID NO 46
<211> LENGTH: 1335
<212> TYPE: DNA
<213> ORGANISM: Soybean

<400> SEQUENCE: 46
atggaggata taacttgca tctctccctc cttctcctct tcgtttctat agtgaccctc      60
tccctcttcg tcctcttcta caagcacagg tctgcatttg cggccccgaa cctgccaccg    120
ggagccaccg gttacccggt gatcggggag agcctggagt tcctgtccac aggatggaag    180
ggtcatccgg agaagttcat cttcgaccgg atgatcaggt actcctccca gctgttcaag    240
acctccatcc tggggaacc ggcggtaata ttctgtgggg ccacctgcaa caagttctta    300
ttttcgaacg agaacaagct tgttgcagcg tggtggccca acagcgtcaa caaggtgttc    360
cccaccacgc ttcttagcaa ctccaaacaa gagtccaaaa agatgaggaa gttgctccct    420
cagttcctta agcccgaggc tctccaacgc tacgttggaa tcatggacac cattgctcga    480
aaccacttcg cttcccttgg gacaacaag acggaactca ccgtctatcc cttggccaag    540
aggtacacgt tcttgttggc ttgtcgtttg tttatgagca ttgaggacgt gaatcacgta    600
gcaaaatttg agaaccccttt tcacctgttg gcgtctggaa tcatatcagt gcctattgat    660
cttcccggaa cgccgttcaa caaagcaatt aaagcagcga acgcaatcag gaaggagctg    720
ttgaagatca ttagacagag gaaggtggat ttagctgaag ggaaagcatc gccaacacaa    780
gacattttgt ctcatatgtt gttaacatgc gatgagaagg gacagttcat gaatgaattg    840
gatattgccg acaagattct tggccttttg attggaggcc atgacactgc tagtgctgca    900
atcactttca ttgtcaaata tcttgctgaa ctccctcaca tttatgatag agtctatcaa    960
gagcaaatgg aaattgcaaa actgaaatcg ccaggagagt tattgaattg ggatgatgtc   1020
aacaggatgc agtattcttg gaatgtagct tgtgaagtaa tgagaatcgc tcctccactt   1080
caaggaggtt ttagggaagc tatcaatgac tttattttcg atggcttttc aataccaaag   1140
ggatggaagt tgtattggag tgcaaattca acacataaaa gtccagaata ttttccagag   1200
ccagagaaat tcgatccaac tagattcgaa ggacaagggc cagctcctta cttttgta     1260 ccatttggtg gaggaccaag gatgtgcccc ggaaaagagt atgctcgatt ggaaatattg   1320
gttttcatgt acaac                                                    1335

<210> SEQ ID NO 47
<211> LENGTH: 1449
<212> TYPE: DNA
<213> ORGANISM: Vitis vinifera

<400> SEQUENCE: 47
atggagctct ctttactcca catacttcca tgggccaccc tcttcaccac tctttctctt      60
```

```
tcattcctca tctacaagct catgatcatc tcccatggca cacccagaaa ccttccgtcc      120
ggcaataccg gtctgcccta tatcggagaa agcatccagt tcctctccaa tggcagaaag      180
ggtcatcccg agaagttcat ttctgagaga atgttgaagt tctcatccaa agttttcaag      240
acctcactct tcggagaaac tgctgcagtc ttctgtggct cggccgggaa caagttcttg      300
ttctccaacg agaacaagct tgtgaccgca tggtggccga gctccgtaaa caaaatcttc      360
ccttcctctc tgcaaacctc ctcgcaggaa gaatcaaaga aaatgagaaa gctgcttccg      420
ggctttctca aacccgaagc cctccaaaga tatatcagta tcatggacgt gatagctcag      480
aggcactttg agtccagctg gaacaacaag gaagaagtca cagtcttccc gctagccaag      540
atgttcacat tctggctggc ttgtcgtctg tttttgagcg tagaagaccc cgaccatgtc      600
gaaaagcttg cagagccctt caacgaactg gccgccggaa tcatagccct acctattgat      660
ttgcctggga cgtcatttaa caaggggatc aaagcttcaa acctggtcag aaaggagctt      720
catgcaataa tcaagaagag gaagatgaat cttgcggaca acaaggcgtc gacgacgcag      780
gacatattgt cacatatgct tctcacttgt gatgagaatg gagagtacat gaatgaagag      840
gatatagctg ataaaattct tgggttgctc gtcggaggtc atgacacagc cagtgctacc      900
attactttta ttgtcaagtt tcttgcagag ctgcctcatg tttacgatga agttttcaag      960
gaacaaatgg agatagcaaa atcaaaggcc ccaggtgagc tgttgaattg ggaggacatt      1020
ccaaagatga ggtattcatg gaatgtagca tgtgaagtga tgagactggc accaccgtt      1080 caaggagctt tccgagaagc catgaatgac ttcatcttcg agggtttctc cattccaaag      1140
ggatggaagc tgtactggag cacgcactcg acccaccgga acccggagtt cttccccaag      1200
ccggaaaaat tcgacccctc gaggtttgac ggaaagggac cagccccta cacctatgtg       1260 cctttcggag gaggacccag gatgtgccct ggcaaagagt atgctagatt ggaagtacta      1320
gtgttcatgc acaatttagt gagaaggttc aaatgggaga agctgctgcc agatgagaag      1380
attatagtag accccatgcc cattcctgca aaaggccttc ccattcgcct ccatcatcac      1440
caaccctag                                                              1449

<210> SEQ ID NO 48
<211> LENGTH: 1455
<212> TYPE: DNA
<213> ORGANISM: Populus trichocarpa

<400> SEQUENCE: 48
atggaacttc ccttcatctc cctgcttccc tatggaatcc tcttcatcat ctctgcagtt       60
tcactatcat acctcataaa caaacacaaa tattatctct cctccctcaa caacctcccg      120
cctggtaata ccggtttgcc attaatcggt gaaagtctgg agttcctgac cacggggcaa      180
aagggtcagc cggagaagtt catattagac agaatggcaa agttctcatc caaagtcttc      240
aaaacctcgt tgttttgtga accaactgca gtattctgtg gtgcagcagg gaacaagttc      300
ttgttctcta atgagaataa gcttgtcact gcatggtggc tgattctgt caacaaaatc      360 ttcccttcct ctcaacaaac ttcttcacaa gaagaatcca agaaaatgag aaagcttttc      420
ccactttttt tcaagccaga atcacttcaa agatatatta gtgtgatgga tgtgattgca      480
caaaggcact ggcttctga ttgggaaggc aaacaggaag tcagtgtttt ccctctggct      540
aagacgtaca cttttggtt agcttgccgc ttatttctaa gcatggaaga tcctgaggaa      600
gtccaaaagt tcgccaaacc cttcaatgat ttagccgctg ggattatatc catacccatt      660
gatttgccct ggacacccc ttaatcgcggg gtcaaagcat caaatgtggt gcacaaggag      720
```

```
cttctaaaga tcataaagca gaggaagatt gatctagcgg agaacaaggc atccccaca      780 caagatatac tgtcccatat gctaaccaca gcagacgata tgggcaatg catgaaaaag      840 atcgatattg ccgataagat acttggtttg cttgttggag gtcacgacac agccagtgct     900
gctataactt ttattgtcaa gtatcttgca gagttgcctc atgtctacaa caagctcttg     960
gaagaacaaa gagagatcgc aaaaacgaaa acacctggag agctgttgaa ttgggaggac     1020
atacaaagga tgagatattc atggaacgtt gcctgtgaag tgatgagagt tgctccccca    1080
ctccaaggag ctttccgaga ggccatgacc gagttcaact acgcaggttt tacaattccg    1140
aagggatgga agctgtattg gagcgcaaac actacacaca aaaatcctga atgtttccct    1200
gagccagaga attttgaccc atcaagattc gaaggcaatg accggcccc atacacctttt    1260 gttccatttg gaggaggtcc taggatgtgt ccaggcaaaa aatatgctag actggaaata    1320
cttgttttct tgcacaactt ggttaaaaag ttcagatggg agaagctgct tcctaaagag    1380
aggataattg tagatccaat gccaatacct tcaaaaggcc ttccgatccg cctccaccct    1440
cacgaggctg cctaa                                                     1455

<210> SEQ ID NO 49
<211> LENGTH: 1440
<212> TYPE: DNA
<213> ORGANISM: Medicago truncatula

<400> SEQUENCE: 49
atggagccta atttctatct ctcccttctc cttctctttg tcactttcat atctctctct      60 cttttttca tattctacaa acagaaatct ccattaaatt tgccacctgg taaaatgggt     120
tacccaatca taggtgaaag ccttgagttc ttatcaacag gatggaaagg acatcctgaa    180
aaattcattt tcgaccgtat gcgtaaatat tcctcagaac tctttaaaac atcaatcgta    240
ggagaatcta cggtggtttg ttgcggagca gcaagtaaca agtttttgtt ttcaaacgag    300
aataaacttg tgactgcatg gtggccagat agtgtaaaca aaatcttccc tactacttct    360
cttgactcta acttgaagga agaatccatc aagatgagaa aattgcttcc acaattcttt    420
aaacccgaag ctctacaacg ttatgttggt gtcatggatg ttattgctca agacattttt    480
gttactcatt gggataataa aaatgaaacc accgtctacc ccttggccaa gaggtacacc    540
tttttgttag cttgtcggtt gttcatgagc gttgaagacg agaatcatgt agcaaaattt    600
agtgatccat ttcagttaat tgcggccgga atcatatctc taccaattga tttgccagga    660
acaccattca acaaagctat aaaggcctca aactttataa gaaaggagtt gattaagatc    720
ataaagcaaa ggagggtaga tttggcagaa gggacagcat caccaacaca agatatattg    780
tctcacatgt tgttgacaag tgatgaaaat ggaaagagta tgaatgaact taatattgct    840
gataagattc ttggcctttt gaccggagga catgacactg ctagcgtcgc atgcactttc    900
cttgtcaaat atctcggcga gttacctcac atttatgata agtctatca agagcaaatg    960 gaaattgcaa atcgaaacc agcaggagaa ttgttgaatt gggatgacct gaagaaaatg    1020
aaatactctt ggaacgtagc ttgtgaagta atgagacttt cccctccact ccaaggaggt    1080
ttcagggaag ccatcactga cttttatgttc aatggattct caattcctaa gggatggaag    1140
ctttattgga gtgcaaattc aacacataag aacgcagaat gttttcccat gccagagaaa    1200
tttgacccaa caagatttga aggaaatgga ccagctcctt atacttttgt tccctttggt    1260
ggaggaccaa ggatgtgtcc tggaaaagag tatgcaagat tagaaaatact tgttttcatg    1320
```

```
cacaatttgg cgaaaaggtt taagtgggaa aaggtgattc cagatgagaa gattattgtt    1380
gatccattcc ccatccctgc aaaggatctt ccaattcgcc tttatccaca caaagcttaa    1440

<210> SEQ ID NO 50
<211> LENGTH: 1434
<212> TYPE: DNA
<213> ORGANISM: Ricinus communis

<400> SEQUENCE: 50
atggagttgt tctttctcat agccttaacc cttttcatta ttcttgtcac tcttccaatt      60
ctggctgtct tatacagacc aaatattatc aatctaccac caggcaagac gggcttgcca     120
tacataggag agagcctgga atttctttcc acaggcagaa aaggtcatcc tgagaagttt     180
ttatcagata gaatggaaaa attctcacgt caagttttca ggacttcaat tcttggtgaa     240
caaactgcag tcgtctgtgg cgcacaaggc aacaagttct tgttctctaa tgagaacaag     300
cttgtcactg cttggtggcc aaaatcaatc ctgagactct tcccttcctc taatcaaagc     360
actatcctag ctgaaggcat gaggatgagg aagatgctac ctcactttct caaacctgag     420
gccctgcaaa gatacatagg tgtaatggac catatggcac aagttcactt tcaggatagc     480
tgggaaaaca agcaagaagt cacagtttat ccgcttgcaa agatgtatac attttcagtt     540
gcttgcaaag tgttcttgag catggatgac ccaaaggagg tcgcaaagtt cgctgctcct     600
ttcaatgata tggcctcagg aattatttct attcctatca attttcctgg aacatctttc     660
aatcgtggac tcaaggcctc gaagattata aggaacgaaa tgttgcgtat gattaagcaa     720
agaagaaaag atcttgctga gaataaagca actcctatgc aagatatact gtcccatatg     780
ctggtagcaa ctgatgaaga aggtcagaga ttgggagaag ttgggattgc tgataagatc     840
atctctttgc tcattggtgg ccacgacaca gcaagtgcta caatcacttt cgttgtcaag     900
tttcttgccg agctcccaga tatctacgat caagtcttga agagcaatt ggagattgct     960 aaatcaaaag aaccaggaga attattgacc tgggaagaca ttcagaagat gaagtactcg    1020
tggaatgttg cttgtgaagt aatgagatta gccccacctc ttcagggttc tttcagagaa    1080
gccttacatg acttcgacta tgctggtttc tctattccaa agggttggaa attatattgg    1140
agcacacata caacacacaa aaatccagaa tattttttcgg atcctgaaaa gtttgatcct    1200
tcaagatttg aaggatcagg gccagcacct tacacatttg ttccatttgg aggagggcca    1260
aggatgtgtc ctggaaaaga gtatgcaaga ttggaaattc ttgttttcat gcacaatata    1320
gcgaagaggt tcaagtggaa caaggttatt cctgacgaga aaattgttgt tgacccatg     1380 ccaataccag ctaaaggcct tccagttcac ctctatcctc aaaaacatga gtaa          1434

<210> SEQ ID NO 51
<211> LENGTH: 1458
<212> TYPE: DNA
<213> ORGANISM: Vitis vinifera

<400> SEQUENCE: 51
atgatcatgc agcaaagcga catggagctc ttgctcctct cctttctcct cctcatggct      60
ctctctctct cttttggat tcgcttcttt gtccataaac tcgaaaaaag cagtggtatt     120
aacctgcctc cagggaaaat gggttttcca ttcattggtg aaagtctaga attccttcgg     180
atgggcagga agggaacccc tgaaaggttc attcaagata ggatggccaa atactcaacc     240
cagatcttca aaacttgctt actcggagaa ccaactgcag ttgtgtgtgg ggctgctgga     300
aacaagttgt tgttctccaa cgagaacaag cttgttactt catggtggcc gcgctctgtg     360
```

```
gagaagatat ttccctcttc tcttcagact tcgaccaaag aagagtccat gaaaactcgt      420
aagttgcttc cagcctttct caaacccgag gcgttgcaaa agtatgtggg gatcatggat      480
tccatagcga agtggcattt ggataaccac tgggacttga atgaaaccgt tactgttttc      540
cctcttgcca agcaatacac cttcatggtg gcttgtagat tgttcttgag catagatgac      600
cctaagcaca ttgcaaaatt cgctaaccca tttcatattt tggctgctgg ggtcatgtca      660
atacctataa acttccctgg gaccccattc aaccgtgcta tcaaggctgc ggattccgta      720
agaaaggagc tcagagcaat aatcaagcaa aggaaaattc aagttttagc ggggaaaagt      780
tcatcctcta agcatgatat actgtcccat atgctcacca caacagatga aatggacag       840 ttcttgaatg agatggacat tgcggataag atacttggtt tgctaattgg tggccatgac      900
actgcaagtg ctgtcataac tttcatcatc aagtatcttg cagagttgcc acaagtctac      960
aatgaggttt taaaggagca aatggaggtt gcagccggga agaaaagtgg agagatgctt     1020
gattgggagg acatacaaaa gatgaagtat tcatggaatg tggcaaatga agtaatgagg     1080
ctggcaccac cacttcaagg tagtttccga gaggccataa ctgacttcac ctatgctggt     1140
ttctccattc ccaaagggtg gaagttgtac tggagcacaa atgcaacaca caagaaccct     1200
gactacttcc ctgatccgga gaaatttgat ccttcaaggt ttgaaggaaa tggacccatt     1260
ccttacacct atgttccttt cggaggagga ccacgaatgt gccctgggaa agagtatgct     1320
cgtttggaaa tacttgtttt catacacaat gttgtgagac ggttcagttg gtataaactg     1380
catccaaatg aagatgtcat agtggatcca atgccaatgc ctgcaaaagg acttcccatt     1440
cgccttcgtc accattaa                                                    1458

<210> SEQ ID NO 52
<211> LENGTH: 1455
<212> TYPE: DNA
<213> ORGANISM: Populus trichocarpa

<400> SEQUENCE: 52
atggagactc tctatttcat ccttctcctc tttgtcccca tcattctctc cctcgttgcc       60
ataatttaca agcacagata ccaggataaa ctccaaaacg ttcctccagg caatctaggc      120 ctccctttg tgggagagag cctagatttc ctgtcaaaag gatggaaagg ttgcccagaa       180
aacttcatat tcgatcgcat tcggaaatat tcgtcagaaa tattcaaaac aaatcttttt      240
cttcagcctg tagtgatgtt aaatggtgtt gccggaaaca agttcttatt ctccaacgag      300
aacagacttg ttgaaacatg gtggcctgat tttgtgaaca ggatatttcc atctgcagta      360
gaaacgtcac ccaaagaaga agcgaaaaga atgcgtaggt tgttccctcg attcttgaaa      420
cctgaggcct tgcagaggta tataggtacc atggatatgg ttaccaaaag cactttgcc      480 ttggagtggg gaaacaaagc agaggtggtt gtcttccctc tggcaaaaag ctacacattc      540
gagttggctt gccgcttgtt tctaagtatt gaagatccca gccacatagc cagattttcc      600
cacccattca accaaataac ctctggtatt tttaccatcc ccattgattt tcctggaact      660
ccatttaatc gagccatcaa ggcctcaaag ttaatcagaa ttgagctttt ggccattatc      720
aggcaaagaa agaaggatct tgcagaagga aaggcatccc caacccagga cattttgtca      780
cacatgctgt tgagcaatga tgcggatgga aagtacatga atgaggtgca gatttctgac      840
aagattcttg cattattgat gggtggacat gaaagcactg ctgcttcttg tactttcatt      900
gtcaaatatc ttgctgagct gcctcatatc tatgaagcag tttacaagga acaagctgag      960
```

```
atcattaaat ccaaagcacc cggtgagttg ttgaattggg atgacattca aaagatgaaa    1020
tattcatgga atgtagcttg tgaaacgttg agactctcac caccgcttat tggtaacttc    1080
aaagaagcca tcaaggactt cacattcaac gggttctcca tcccaagggg ctggaaggca    1140
agtcattttc tcactttgta ttggagtgca agctcgaccc ataaaaatcc tgaatacttt    1200
tctgagcctg aaaagttcga tcccagtaga tttgaaggga aaggaccagc tccttacacg    1260
tttattccat ttggtggagg accaaggatg tgccctggaa atgaatatgc tcgattagaa    1320
attcttgttt tcatgcataa cttggtgaag aggttcaaat ttgaaagatt gattctcgat    1380
gagaagatag tattcgatcc aacgccaaaa ccagaaatgg gacttccagt tcgtctgctt    1440
cctcacaaag cttga                                                    1455

<210> SEQ ID NO 53
<211> LENGTH: 1449
<212> TYPE: DNA
<213> ORGANISM: Glycine max

<400> SEQUENCE: 53
atggagcagt tgtactacct caccct tgtg ctactgtttg tgtccttcgt ctctgtctct      60
tttttcatca tttctacag gcatcgttct ccgttcagcg tccccaactt gccgccgggg     120
aaggcggggt ttccggtgat cggcgagagc ctggagtttc tgtcggcggg acggaagggg     180
cttccggaga agttcttctc cgatcgcatg acagagtact cttccaaagt gttcaagacc     240
tccatcttag gggagcctac agtgattttc tgtggagccg catgtaacaa gttcttgttt     300
tctaacgaga caaacacgt catttcgtgg tggcctgaaa atgtcaagaa gttgttccca     360
acgaatattc aaacaaactc taaggaagaa gccaagaagt tgagaaacat tctccctcag     420
ttcctcagcg ccaaagccat ccaacgttac gttggtatta tggacactgt tgcccaagaa     480
cactttgctc tggagtggga gaacaacacc caagtcaccg tattgcccct tggccaagag     540
tatacctttg gggtggctag ccgtgtgttc atgagcattg atgatttgaa tcaagtggcg     600
aaattggcag aacct ttaaa tcaggtgaat gcaggaatta tatcaatgcc cattaacttc     660
cccggaactg tgttcaaccg aggaatcaag gcctccaagt tcattaggag ggagctgttg     720
aggattgtca agcagaggaa ggtggaacta gctaatggaa tgtccacacc aacacaagac     780
attttgtctc acatgctaat atattgtgat gagaatggac aatatttggc tgaacatgat     840
attgtcaaca agatccttgg cttgctgata ggtagccatg aaaccacaag tactgtttgc     900
actttcgttg tcaaatacct tgccgagctc cctcaaaata tttatgaaaa tgtctatcaa     960
gaacaaatgg cgattgcaaa atccaaagct ccaggagagt tgttgaattg ggatgacatc    1020
cagaagatga atattcatg gaatgtagct tgtgaagtaa taggcttaa ccctccagcc    1080 caaggagctt ttagggaagc catcaatgac tttatcttcg atggattctc aattccaaaa    1140
ggctggaagt tgtattggag tgcaaattca actcacaaaa atccagagta cttccctgag    1200
ccagagaaat ttgatccaag cagatttgaa ggaactggac cagctcctta tcttatgtg    1260 ccatttggtg gagggccaag tatgtgccct ggaaagagt atgcgcgaat ggaactattg    1320
gtgttcatgc acaacttagt gaagaggttc aagtgtgaaa ctcttttcc taatggaaat    1380 gttacttata accctacgcc tattcctgcc aagggccttc ctgttcgtct tattcctcac    1440
cgatcatga                                                          1449

<210> SEQ ID NO 54
<211> LENGTH: 755
```

<212> TYPE: PRT
<213> ORGANISM: Betula platyphylla

<400> SEQUENCE: 54

Met Trp Lys Leu Lys Ile Ala Glu Gly Gly Pro Gly Leu Val Ser Gly
1               5                   10                  15

Asn Asp Phe Ile Gly Arg Gln His Trp Glu Phe Asp Pro Asp Ala Gly
            20                  25                  30

Thr Pro Gln Glu Arg Ala Glu Val Glu Lys Val Arg Glu Glu Phe Thr
        35                  40                  45

Lys Asn Arg Phe Gln Met Lys Gln Ser Ala Asp Leu Leu Met Arg Met
    50                  55                  60

Gln Leu Arg Lys Glu Asn Pro Cys Gln Pro Ile Pro Pro Pro Val Lys
65                  70                  75                  80

Val Lys Glu Thr Glu Val Ile Thr Glu Glu Ala Val Ile Thr Thr Leu
                85                  90                  95

Arg Arg Ser Leu Ser Phe Tyr Ser Ser Ile Gln Ala His Asp Gly His
            100                 105                 110

Trp Pro Gly Glu Ser Ala Gly Pro Leu Phe Phe Leu Gln Pro Phe Val
        115                 120                 125

Met Ala Leu Tyr Ile Thr Gly Asp Leu Asn Thr Ile Phe Ser Pro Ala
130                 135                 140

His Gln Lys Glu Ile Ile Arg Tyr Leu Tyr Asn His Gln Asn Glu Asp
145                 150                 155                 160

Gly Gly Trp Gly Phe His Ile Glu Gly His Ser Thr Met Phe Gly Ser
                165                 170                 175

Ala Leu Ser Tyr Ile Ala Leu Arg Ile Leu Gly Glu Gly Leu Glu Asp
            180                 185                 190

Gly Glu Asp Gly Ala Met Ala Lys Ser Arg Lys Trp Ile Leu Asp His
        195                 200                 205

Gly Gly Leu Val Ala Ile Pro Ser Trp Gly Lys Phe Trp Val Thr Val
210                 215                 220

Leu Gly Leu Tyr Glu Trp Ser Gly Cys Asn Pro Leu Pro Pro Glu Phe
225                 230                 235                 240

Trp Phe Leu Pro Asp Ile Phe Pro Ile His Pro Gly Lys Met Leu Cys
                245                 250                 255

Tyr Cys Arg Leu Val Tyr Met Pro Met Ser Tyr Leu Tyr Gly Lys Arg
            260                 265                 270

Phe Val Gly Pro Ile Thr Gly Leu Ile Gln Ser Leu Arg Gln Glu Leu
        275                 280                 285

Tyr Asn Glu Pro Tyr His Gln Ile Asn Trp Asn Lys Ala Arg Ser Thr
290                 295                 300

Val Ala Lys Glu Asp Leu Tyr Tyr Pro His Pro Leu Ile Gln Asp Leu
305                 310                 315                 320

Leu Trp Gly Phe Leu His His Val Ala Glu Pro Val Leu Thr Arg Trp
                325                 330                 335

Pro Phe Ser Met Leu Arg Glu Lys Ala Leu Lys Ala Ala Ile Gly His
            340                 345                 350

Val His Tyr Glu Asp Glu Asn Ser Lys Tyr Leu Cys Ile Gly Ser Val
        355                 360                 365

Glu Lys Val Leu Cys Leu Ile Ala Cys Trp Ala Glu Asp Pro Asn Gly
370                 375                 380

Glu Ala Tyr Lys Leu His Leu Gly Arg Ile Pro Asp Asn Tyr Trp Val
385                 390                 395                 400

Ala Glu Asp Gly Leu Lys Ile Gln Ser Phe Gly Cys Gln Met Trp Asp
                405                 410                 415

Ala Gly Phe Ala Ile Gln Ala Ile Leu Ser Cys Asn Leu Asn Glu Glu
            420                 425                 430

Tyr Trp Pro Thr Leu Arg Lys Ala His Glu Phe Val Lys Ala Ser Gln
        435                 440                 445

Val Pro Glu Asn Pro Ser Gly Asp Phe Lys Ala Met Tyr Arg His Ile
    450                 455                 460

Asn Lys Gly Ala Trp Thr Phe Ser Met Gln Asp His Gly Trp Gln Val
465                 470                 475                 480

Ser Asp Cys Thr Ala Glu Gly Leu Lys Val Ala Ile Leu Phe Ser Gln
                485                 490                 495

Met Pro Pro Asp Leu Val Gly Glu Lys Ile Glu Lys Glu Arg Leu Tyr
            500                 505                 510

Asp Ala Val Asn Val Ile Leu Ser Leu Gln Ser Ser Asn Gly Gly Phe
        515                 520                 525

Pro Ala Trp Glu Pro Gln Arg Ala Tyr Gly Trp Leu Glu Lys Phe Asn
    530                 535                 540

Pro Thr Glu Phe Phe Glu Asp Thr Leu Ile Glu Arg Glu Tyr Val Glu
545                 550                 555                 560

Cys Thr Ser Pro Ala Val His Gly Leu Ala Leu Phe Arg Lys Phe Tyr
                565                 570                 575

Pro Arg His Arg Gly Thr Glu Ile Asp Ser Ser Ile Tyr Arg Gly Ile
            580                 585                 590

Gln Tyr Ile Glu Asp Val Gln Glu Pro Asp Gly Ser Trp Tyr Gly His
        595                 600                 605

Trp Gly Ile Cys Tyr Thr Tyr Gly Thr Trp Phe Ala Val Gly Ala Leu
    610                 615                 620

Ala Ala Cys Gly Arg Asn Tyr Lys Asn Cys Pro Ala Leu Arg Lys Ser
625                 630                 635                 640

Cys Glu Phe Leu Leu Ser Lys Gln Leu Pro Asn Gly Gly Trp Gly Glu
                645                 650                 655

Ser Tyr Leu Ser Ser Gln Asn Lys Val Trp Thr Asn Ile Glu Gly Asn
            660                 665                 670

Arg Ala Asn Leu Val Gln Thr Ala Trp Ala Leu Leu Ser Leu Ile Asp
        675                 680                 685

Ala Arg Gln Ala Glu Ile Asp Pro Thr Pro Ile His Arg Gly Val Arg
    690                 695                 700

Val Leu Ile Asn Ser Gln Met Glu Asp Gly Asp Phe Pro Gln Gln Glu
705                 710                 715                 720

Ile Thr Gly Val Phe Met Arg Asn Cys Thr Leu Asn Tyr Ser Ser Tyr
                725                 730                 735

Arg Asn Ile Phe Pro Ile Trp Ala Leu Gly Glu Tyr Arg Arg Arg Val
            740                 745                 750

Leu Phe Ala
        755

<210> SEQ ID NO 55
<211> LENGTH: 758
<212> TYPE: PRT
<213> ORGANISM: Olea europaea

<400> SEQUENCE: 55

Met Trp Lys Leu Lys Ile Ala Asp Gly Thr Gly Pro Trp Leu Thr Thr

-continued

```
  1               5                  10                 15
Thr Asn Asn His Ile Gly Arg Gln His Trp Glu Phe Asp Pro Glu Ala
             20                 25                 30
Gly Thr Pro Asp Glu Arg Val Glu Val Glu Arg Leu Arg Glu Glu Phe
             35                 40                 45
Lys Lys Asn Arg Phe Arg Thr Lys Gln Ser Ala Asp Leu Leu Met Arg
         50                 55                 60
Met Gln Leu Val Lys Glu Asn Gln Arg Val Gln Ile Pro Pro Ala Ile
 65                 70                 75                 80
Lys Ile Lys Glu Thr Glu Gly Ile Thr Glu Glu Ala Val Ile Thr Thr
                 85                 90                 95
Leu Arg Arg Ala Ile Ser Phe Tyr Ser Thr Ile Gln Ala His Asp Gly
                100                105                110
His Trp Pro Ala Glu Ser Ala Gly Pro Leu Phe Phe Leu Pro Pro Leu
                115                120                125
Val Leu Ala Leu Tyr Val Thr Gly Ala Ile Asn Val Val Leu Ser Arg
            130                135                140
Glu His Gln Lys Glu Ile Thr Arg Tyr Ile Tyr Asn His Gln Asn Glu
145                150                155                160
Asp Gly Gly Trp Gly Ile His Ile Glu Gly His Ser Thr Met Phe Gly
                165                170                175
Ser Val Leu Ser Tyr Ile Thr Leu Arg Leu Leu Gly Glu Gly Gln Glu
            180                185                190
Asp Gly Glu Asp Lys Ala Val Ala Arg Gly Arg Lys Trp Ile Leu Asp
            195                200                205
His Gly Gly Ala Val Gly Ile Pro Ser Trp Gly Lys Phe Trp Leu Thr
210                215                220
Val Leu Gly Val Tyr Glu Trp Asp Gly Cys Asn Pro Met Pro Pro Glu
225                230                235                240
Phe Trp Leu Leu Pro Asn Phe Ser Pro Ile His Pro Gly Lys Met Leu
                245                250                255
Cys Tyr Cys Arg Leu Val Tyr Met Pro Met Ser Tyr Leu Tyr Gly Lys
                260                265                270
Arg Phe Val Gly Pro Ile Thr Gly Leu Val Leu Ser Leu Arg Gln Glu
            275                280                285
Ile Tyr Thr Glu Pro Tyr His Gly Ile Asn Trp Asn Arg Ala Arg Asn
            290                295                300
Thr Cys Ala Lys Glu Asp Leu Tyr Tyr Pro His Pro Leu Ala Gln Asp
305                310                315                320
Met Leu Trp Gly Phe Leu His His Phe Ala Glu Pro Val Leu Thr Arg
                325                330                335
Trp Pro Phe Ser Lys Leu Arg Glu Lys Ala Leu Lys Val Ala Met Glu
            340                345                350
His Val His Tyr Glu Asp Met Asn Ser Arg Tyr Leu Cys Ile Gly Cys
            355                360                365
Val Glu Lys Val Leu Cys Leu Ile Ala Cys Trp Val Glu Asp Pro Asn
            370                375                380
Ser Glu Ala Tyr Lys Arg His Ile Ala Arg Ile Pro Asp Tyr Phe Trp
385                390                395                400
Val Ala Glu Asp Gly Leu Lys Met Gln Ser Phe Gly Cys Gln Met Trp
                405                410                415
Asp Ala Ala Phe Ala Ile Gln Ala Ile Leu Ser Ser Asn Leu Ala Glu
                420                425                430
```

Glu Tyr Gly Pro Thr Leu Met Lys Ala His Asn Phe Val Lys Ala Ser
            435                 440                 445

Gln Val Gln Glu Asn Pro Ser Gly Asp Phe Asn Glu Met Tyr Arg His
450                 455                 460

Thr Ser Lys Gly Ala Trp Thr Phe Ser Met Gln Asp His Gly Trp Gln
465                 470                 475                 480

Val Ser Asp Cys Thr Ala Glu Gly Leu Lys Ala Leu Leu Phe Ser
                485                 490                 495

Gln Met Pro Ile Glu Leu Val Gly Ala Glu Ile Glu Thr Gly His Leu
            500                 505                 510

Tyr Asp Ala Val Asn Val Ile Leu Thr Leu Gln Ser Ala Ser Gly Gly
            515                 520                 525

Phe Pro Ala Trp Glu Pro Gln Lys Ala Tyr Arg Trp Leu Glu Lys Leu
            530                 535                 540

Asn Pro Thr Glu Phe Phe Glu Asp Val Leu Ile Glu Arg Asp Tyr Val
545                 550                 555                 560

Glu Cys Thr Ser Ser Ala Val Gln Ala Leu Lys Leu Phe Lys Gln Leu
                565                 570                 575

His Pro Gly His Arg Arg Lys Glu Ile Ala Ser Cys Ile Ser Lys Ala
            580                 585                 590

Ile Gln Tyr Ile Glu Ala Thr Gln Asn Pro Asp Gly Ser Trp Asp Gly
            595                 600                 605

Ser Trp Gly Ile Cys Phe Thr Tyr Gly Thr Trp Phe Ala Val Glu Gly
            610                 615                 620

Leu Val Ala Cys Gly Lys Asn Tyr His Asn Ser Pro Thr Leu Arg Arg
625                 630                 635                 640

Ala Cys Glu Phe Leu Leu Ser Lys Gln Leu Pro Asp Gly Gly Trp Ser
                645                 650                 655

Glu Ser Tyr Leu Ser Ser Ser Asn Lys Val Tyr Thr Asn Leu Glu Gly
            660                 665                 670

Asn Arg Ser Asn Leu Val Gln Thr Ser Trp Ala Leu Leu Ser Leu Ile
            675                 680                 685

Lys Ala Gly Gln Val Glu Ile Asp Pro Gly Pro Ile His Arg Gly Ile
            690                 695                 700

Lys Leu Leu Val Asn Ser Gln Met Glu Asp Gly Asp Phe Pro Gln Glu
705                 710                 715                 720

Glu Ile Thr Gly Ala Phe Met Lys Asn Cys Thr Leu Asn Tyr Ser Ser
                725                 730                 735

Tyr Arg Asn Ile Phe Pro Ile Trp Ala Leu Gly Glu Tyr Arg Arg Arg
            740                 745                 750

Ile Leu His Ala Gln Thr
            755

<210> SEQ ID NO 56
<211> LENGTH: 758
<212> TYPE: PRT
<213> ORGANISM: Glycyrrhiza uralensis

<400> SEQUENCE: 56

Met Trp Lys Leu Lys Ile Gly Glu Gly Gly Ala Gly Leu Ile Ser Val
1               5                   10                  15

Asn Asn Phe Ile Gly Arg Gln His Trp Glu Phe Asp Pro Asn Ala Gly
            20                  25                  30

Thr Pro Gln Glu His Ala Glu Ile Glu Arg Leu Arg Arg Glu Phe Thr

```
                35                  40                  45
Lys Asn Arg Phe Ser Ile Lys Gln Ser Ala Asp Leu Leu Met Arg Met
 50                  55                  60
Gln Leu Arg Lys Glu Asn His Tyr Gly Thr Asn Asn Ile Pro Ala
 65                  70                  75                  80
Ala Val Lys Leu Ser Asp Ala Glu Asn Ile Thr Val Glu Ala Leu Val
                 85                  90                  95
Thr Thr Ile Arg Arg Ala Ile Ser Phe Tyr Ser Ser Ile Gln Ala His
                100                 105                 110
Asp Gly His Trp Pro Ala Glu Ser Ala Gly Pro Leu Phe Phe Leu Gln
                115                 120                 125
Pro Leu Val Met Ala Leu Tyr Ile Thr Gly Ser Leu Asp Asp Val Leu
                130                 135                 140
Gly Pro Glu His Lys Lys Glu Ile Val Arg Tyr Leu Tyr Asn His Gln
145                 150                 155                 160
Asn Glu Asp Gly Gly Trp Gly Phe His Ile Glu Gly His Ser Thr Met
                165                 170                 175
Phe Gly Ser Ala Leu Ser Tyr Val Ala Leu Arg Ile Leu Gly Glu Gly
                180                 185                 190
Pro Glu Asp Lys Ala Met Ala Lys Gly Arg Lys Trp Ile Leu Asp His
                195                 200                 205
Gly Gly Leu Val Ala Ile Pro Ser Trp Gly Lys Phe Trp Val Thr Val
210                 215                 220
Leu Gly Ala Tyr Glu Trp Ser Gly Cys Asn Pro Leu Pro Pro Glu Leu
225                 230                 235                 240
Trp Leu Leu Pro Lys Phe Thr Pro Phe His Pro Gly Lys Met Leu Cys
                245                 250                 255
Tyr Cys Arg Leu Val Tyr Met Pro Met Ser Tyr Leu Tyr Gly Lys Lys
                260                 265                 270
Phe Val Gly Pro Ile Thr Ala Leu Ile Arg Ser Leu Arg Glu Glu Leu
                275                 280                 285
Tyr Asn Glu Pro Tyr Asn Gln Ile Asn Trp Asn Thr Ala Arg Asn Thr
290                 295                 300
Val Ala Lys Glu Asp Leu Tyr Tyr Pro His Pro Leu Ile Gln Asp Met
305                 310                 315                 320
Leu Trp Gly Phe Leu Tyr His Val Gly Glu Arg Phe Leu Asn Cys Trp
                325                 330                 335
Pro Phe Ser Met Leu Arg Arg Lys Ala Leu Glu Ile Ala Ile Asn His
                340                 345                 350
Val His Tyr Glu Asp Glu Asn Ser Arg Tyr Leu Cys Ile Gly Ser Val
                355                 360                 365
Glu Lys Val Leu Cys Leu Ile Ala Arg Trp Val Glu Asp Pro Asn Ser
                370                 375                 380
Glu Ala Tyr Lys Leu His Leu Ala Arg Ile Pro Asp Tyr Phe Trp Leu
385                 390                 395                 400
Ala Glu Asp Gly Leu Lys Ile Gln Ser Phe Gly Cys Gln Met Trp Asp
                405                 410                 415
Ala Ala Phe Ala Ile Gln Ala Ile Leu Ala Cys Asn Val Ser Glu Glu
                420                 425                 430
Tyr Gly Pro Thr Leu Arg Lys Ala His His Phe Val Lys Ala Ser Gln
                435                 440                 445
Val Arg Glu Asn Pro Ser Gly Asp Phe Asn Ala Met Tyr Arg His Ile
450                 455                 460
```

```
Ser Lys Gly Ala Trp Thr Phe Ser Met His Asp His Gly Trp Gln Val
465                 470                 475                 480

Ser Asp Cys Thr Ala Glu Gly Leu Lys Ala Leu Leu Leu Ser Glu
            485                 490                 495

Met Pro Ser Glu Leu Val Gly Gly Lys Met Glu Thr Gly Arg Phe Tyr
                500                 505                 510

Asp Ala Val Asn Val Ile Leu Ser Leu Gln Ser Ser Asn Gly Gly Phe
            515                 520                 525

Pro Ala Trp Glu Pro Gln Lys Ala Tyr Arg Trp Leu Glu Lys Phe Asn
530                 535                 540

Pro Thr Glu Phe Phe Glu Asp Thr Met Ile Glu Arg Glu Tyr Val Glu
545                 550                 555                 560

Cys Thr Gly Ser Ala Met Gln Gly Leu Ala Leu Phe Arg Lys Gln Tyr
                565                 570                 575

Pro Gln His Arg Ser Lys Glu Ile Asp Arg Cys Ile Ala Lys Ala Ile
            580                 585                 590

Arg Tyr Ile Glu Asn Met Gln Asn Pro Asp Gly Ser Trp Tyr Gly Cys
            595                 600                 605

Trp Gly Ile Cys Tyr Thr Tyr Gly Thr Trp Phe Ala Val Glu Gly Leu
610                 615                 620

Thr Ala Cys Gly Lys Asn Cys His Asn Ser Leu Ser Leu Arg Lys Ala
625                 630                 635                 640

Cys Gln Phe Leu Leu Ser Lys Gln Leu Pro Asn Ala Gly Trp Gly Glu
                645                 650                 655

Ser Tyr Leu Ser Ser Gln Asn Lys Val Tyr Thr Asn Leu Glu Gly Asn
            660                 665                 670

Arg Ala Asn Leu Val Gln Ser Ser Trp Ala Leu Leu Ser Leu Thr His
            675                 680                 685

Ala Gly Gln Ala Glu Ile Asp Pro Thr Pro Ile His Arg Gly Met Lys
690                 695                 700

Leu Leu Ile Asn Ser Gln Met Glu Asp Gly Asp Phe Pro Gln Gln Glu
705                 710                 715                 720

Ile Thr Gly Val Phe Met Arg Asn Cys Thr Leu Asn Tyr Ser Ser Tyr
                725                 730                 735

Arg Asn Ile Phe Pro Ile Trp Ala Met Gly Glu Tyr Arg Arg Gln Val
            740                 745                 750

Leu Cys Ala His Ser Tyr
            755

<210> SEQ ID NO 57
<211> LENGTH: 757
<212> TYPE: PRT
<213> ORGANISM: Arabidopsis thaliana

<400> SEQUENCE: 57

Met Trp Lys Leu Lys Ile Gly Lys Gly Asn Gly Glu Asp Pro His Leu
1               5                   10                  15

Phe Ser Asn Asn Phe Val Gly Arg Gln Thr Trp Lys Phe Asp His
            20                  25                  30

Lys Ala Gly Ser Pro Glu Glu Arg Ala Val Glu Ala Arg Arg
            35                  40                  45

Gly Phe Leu Asp Asn Arg Phe Arg Val Lys Gly Cys Ser Asp Leu Leu
        50                  55                  60

Trp Arg Met Gln Phe Leu Arg Glu Lys Lys Phe Glu Gln Gly Ile Pro
```

-continued

```
                65                  70                  75                  80
        Gln Leu Lys Ala Thr Asn Ile Glu Glu Ile Thr Tyr Glu Thr Thr Thr
                        85                  90                  95

Asn Ala Leu Arg Arg Gly Val Arg Tyr Phe Thr Ala Leu Gln Ala Ser
                        100                 105                 110

Asp Gly His Trp Pro Gly Glu Ile Thr Gly Pro Leu Phe Phe Leu Pro
                        115                 120                 125

Pro Leu Ile Phe Cys Leu Tyr Ile Thr Gly His Leu Glu Glu Val Phe
                        130                 135                 140

Asp Ala Glu His Arg Lys Glu Met Leu Arg His Ile Tyr Cys His Gln
        145                 150                 155                 160

Asn Glu Asp Gly Gly Trp Gly Leu His Ile Glu Ser Lys Ser Val Met
                        165                 170                 175

Phe Cys Thr Val Leu Asn Tyr Ile Cys Leu Arg Met Leu Gly Glu Asn
                        180                 185                 190

Pro Glu Gln Asp Ala Cys Lys Arg Ala Arg Gln Trp Ile Leu Asp Arg
                        195                 200                 205

Gly Gly Val Ile Phe Ile Pro Ser Trp Gly Lys Phe Trp Leu Ser Ile
                        210                 215                 220

Leu Gly Val Tyr Asp Trp Ser Gly Thr Asn Pro Thr Pro Pro Glu Leu
        225                 230                 235                 240

Leu Met Leu Pro Ser Phe Leu Pro Ile His Pro Gly Lys Ile Leu Cys
                        245                 250                 255

Tyr Ser Arg Met Val Ser Ile Pro Met Ser Tyr Leu Tyr Gly Lys Arg
                        260                 265                 270

Phe Val Gly Pro Ile Thr Pro Leu Ile Leu Leu Arg Glu Glu Leu
                        275                 280                 285

Tyr Leu Glu Pro Tyr Glu Glu Ile Asn Trp Lys Lys Ser Arg Arg Leu
                        290                 295                 300

Tyr Ala Lys Glu Asp Met Tyr Tyr Ala His Pro Leu Val Gln Asp Leu
        305                 310                 315                 320

Leu Ser Asp Thr Leu Gln Asn Phe Val Glu Pro Leu Leu Thr Arg Trp
                        325                 330                 335

Pro Leu Asn Lys Leu Val Arg Glu Lys Ala Leu Gln Leu Thr Met Lys
                        340                 345                 350

His Ile His Tyr Glu Asp Glu Asn Ser His Tyr Ile Thr Ile Gly Cys
                        355                 360                 365

Val Glu Lys Val Leu Cys Met Leu Ala Cys Trp Val Glu Asn Pro Asn
                        370                 375                 380

Gly Asp Tyr Phe Lys Lys His Leu Ala Arg Ile Pro Asp Tyr Met Trp
        385                 390                 395                 400

Val Ala Glu Asp Gly Met Lys Met Gln Ser Phe Gly Cys Gln Leu Trp
                        405                 410                 415

Asp Thr Gly Phe Ala Ile Gln Ala Leu Leu Ala Ser Asn Leu Pro Asp
                        420                 425                 430

Glu Thr Asp Asp Ala Leu Lys Arg Gly His Asn Tyr Ile Lys Ala Ser
                        435                 440                 445

Gln Val Arg Glu Asn Pro Ser Gly Asp Phe Arg Ser Met Tyr Arg His
                        450                 455                 460

Ile Ser Lys Gly Ala Trp Thr Phe Ser Asp Arg Asp His Gly Trp Gln
        465                 470                 475                 480

Val Ser Asp Cys Thr Ala Glu Ala Leu Lys Cys Cys Leu Leu Leu Ser
                        485                 490                 495
```

Met Met Ser Ala Asp Ile Val Gly Gln Lys Ile Asp Glu Gln Leu
                500                 505                 510

Tyr Asp Ser Val Asn Leu Leu Ser Leu Gln Ser Gly Asn Gly Gly
            515                 520                 525

Val Asn Ala Trp Glu Pro Ser Arg Ala Tyr Lys Trp Leu Glu Leu
530                 535                 540

Asn Pro Thr Glu Phe Met Ala Asn Thr Met Val Glu Arg Glu Phe Val
545                 550                 555                 560

Glu Cys Thr Ser Ser Val Ile Gln Ala Leu Asp Leu Phe Arg Lys Leu
                565                 570                 575

Tyr Pro Asp His Arg Lys Glu Ile Asn Arg Ser Ile Glu Lys Ala
            580                 585                 590

Val Gln Phe Ile Gln Asp Asn Gln Thr Pro Asp Gly Ser Trp Tyr Gly
        595                 600                 605

Asn Trp Gly Val Cys Phe Ile Tyr Ala Thr Trp Phe Ala Leu Gly Gly
    610                 615                 620

Leu Ala Ala Ala Gly Glu Thr Tyr Asn Asp Cys Leu Ala Met Arg Asn
625                 630                 635                 640

Gly Val His Phe Leu Leu Thr Thr Gln Arg Asp Asp Gly Gly Trp Gly
                645                 650                 655

Glu Ser Tyr Leu Ser Cys Ser Glu Gln Arg Tyr Ile Pro Ser Glu Gly
            660                 665                 670

Glu Arg Ser Asn Leu Val Gln Thr Ser Trp Ala Met Met Ala Leu Ile
        675                 680                 685

His Thr Gly Gln Ala Glu Arg Asp Leu Ile Pro Leu His Arg Ala Ala
    690                 695                 700

Lys Leu Ile Ile Asn Ser Gln Leu Glu Asn Gly Asp Phe Pro Gln Gln
705                 710                 715                 720

Glu Ile Val Gly Ala Phe Met Asn Thr Cys Met Leu His Tyr Ala Thr
                725                 730                 735

Tyr Arg Asn Thr Phe Pro Leu Trp Ala Leu Ala Glu Tyr Arg Lys Val
            740                 745                 750

Val Phe Ile Val Asn
        755

<210> SEQ ID NO 58
<211> LENGTH: 755
<212> TYPE: PRT
<213> ORGANISM: Lotus japonicus

<400> SEQUENCE: 58

Met Trp Lys Leu Lys Val Ala Glu Gly Gly Lys Gly Leu Val Ser Val
1               5                   10                  15

Ser Asn Phe Ile Gly Arg Gln His Trp Val Phe Asp Pro Asn Ala Gly
                20                  25                  30

Thr Pro Gln Glu His Glu Glu Ile Glu Arg Met Arg Gln Glu Phe Thr
            35                  40                  45

Lys Asn Arg Phe Ser Ile Lys Gln Ser Ala Asp Leu Leu Met Arg Met
        50                  55                  60

Gln Leu Arg Lys Glu Asn Pro Cys Gly Pro Ile Pro Pro Ala Val Lys
65                  70                  75                  80

Leu Arg Asp Val Glu Lys Val Thr Ala Glu Ala Leu Ile Thr Thr Ile
                85                  90                  95

Arg Arg Ser Ile Thr Phe Tyr Ser Ser Ile Gln Ala His Asp Gly His

```
              100                 105                 110
Trp Pro Ala Glu Ser Ala Gly Pro Leu Phe Phe Val Gln Pro Leu Val
              115                 120                 125
Met Ala Leu Tyr Ile Thr Gly Ser Leu Asp Asp Val Leu Gly Pro Gln
              130                 135                 140
His Lys Lys Glu Ile Ile Arg Tyr Leu Tyr Asn His Gln Asn Glu Asp
145               150                 155                 160
Gly Gly Trp Gly Phe His Ile Glu Gly His Ser Thr Met Phe Gly Ser
              165                 170                 175
Ala Leu Ser Tyr Ile Ala Leu Arg Val Leu Gly Gln Ser Leu Glu Asp
              180                 185                 190
Gly Glu Asp Met Ala Val Ala Arg Gly Arg Lys Trp Ile Leu Asp His
              195                 200                 205
Gly Gly Leu Val Ala Ile Pro Ser Trp Gly Lys Phe Trp Val Thr Val
              210                 215                 220
Leu Gly Val Tyr Glu Trp Ser Gly Cys Asn Pro Leu Pro Pro Glu Phe
225               230                 235                 240
Trp Leu Leu Pro Lys Ile Phe Pro Ile His Pro Gly Lys Met Leu Cys
              245                 250                 255
Tyr Cys Arg Leu Val Tyr Met Pro Met Ser Tyr Leu Tyr Gly Lys Lys
              260                 265                 270
Phe Val Gly Pro Ile Thr Ala Leu Val Arg Ser Leu Arg Lys Glu Leu
              275                 280                 285
Tyr Asn Glu Pro Tyr Asp Arg Val Asp Trp Asn Lys Ala Arg Asn Thr
              290                 295                 300
Val Ala Lys Glu Asp Leu Tyr Tyr Pro His Pro Leu Ile Gln Asp Met
305               310                 315                 320
Leu Trp Gly Phe Leu His His Val Gly Glu Arg Val Leu Asn Thr Trp
              325                 330                 335
Pro Phe Ser Met Leu Arg Gln Lys Ala Ile Glu Val Ala Ile Asn His
              340                 345                 350
Val Arg Tyr Glu Asp Glu Thr Thr Arg Tyr Leu Cys Ile Gly Ser Val
              355                 360                 365
Glu Lys Val Leu Tyr Leu Ile Ala Arg Trp Val Glu Asp Pro Asn Ser
              370                 375                 380
Glu Ala Tyr Lys Leu His Leu Ala Arg Ile Pro Asp Tyr Phe Trp Leu
385               390                 395                 400
Ala Glu Asp Gly Leu Lys Ile Gln Ser Phe Gly Cys Gln Met Trp Asp
              405                 410                 415
Ala Ala Phe Ala Ile Gln Ala Ile Leu Ser Gly Asn Val Ser Glu Glu
              420                 425                 430
Tyr Gly Pro Thr Leu Lys Lys Ala His His Phe Val Lys Ala Ser Gln
              435                 440                 445
Val Arg Glu Asn Pro Ser Gly Asp Phe Lys Ala Met Tyr Arg His Ile
              450                 455                 460
Ser Lys Gly Ala Trp Thr Phe Ser Met His Asp His Gly Trp Gln Val
465               470                 475                 480
Ser Asp Cys Thr Ala Glu Gly Leu Lys Val Ala Leu Leu Leu Ser Glu
              485                 490                 495
Met Ser Asp Asp Leu Val Gly Ala Lys Met Glu Thr Glu Gln Phe Tyr
              500                 505                 510
Asp Ala Val Asn Val Ile Leu Ser Leu Gln Ser Ser Asn Gly Gly Phe
              515                 520                 525
```

Pro Ala Trp Glu Pro Gln Arg Ala Tyr Gln Trp Leu Glu Lys Phe Asn
                530                 535                 540

Pro Thr Glu Phe Phe Glu Thr Leu Ile Glu Arg Glu Tyr Val Glu
545                 550                 555                 560

Cys Thr Gly Ser Ala Met Gln Ala Leu Ala Leu Phe Arg Lys Leu Tyr
                565                 570                 575

Pro Lys His Arg Arg Lys Glu Ile Asp Arg Cys Ile Ser Lys Ala Ile
                580                 585                 590

Arg Tyr Ile Glu Asn Thr Gln Asn Pro Asp Gly Ser Trp Tyr Gly Cys
                595                 600                 605

Trp Gly Ile Cys Tyr Thr Tyr Gly Thr Trp Phe Ala Val Glu Gly Leu
                610                 615                 620

Thr Ala Cys Gly Lys Asn Phe Gln Asn Ser Val Thr Leu Arg Arg Ala
625                 630                 635                 640

Cys Lys Phe Leu Leu Ser Lys Gln Leu Pro Asn Gly Gly Trp Gly Glu
                645                 650                 655

Ser Tyr Leu Ser Ser Gln Asp Lys Val Tyr Thr Asn Ile Glu Gly Lys
                660                 665                 670

Arg Ala Asn Leu Val Gln Ser Ser Trp Ala Leu Leu Ser Leu Met Arg
                675                 680                 685

Ala Gly Gln Ala Glu Ile Asp Pro Thr Pro Ile His Arg Gly Ile Arg
690                 695                 700

Leu Leu Ile Asn Ser Gln Met Asp Asp Gly Asp Phe Pro Gln Gln Glu
705                 710                 715                 720

Ile Thr Gly Val Phe Met Arg Asn Cys Thr Leu Asn Tyr Ser Ser Tyr
                725                 730                 735

Arg Asn Ile Phe Pro Ile Trp Ala Leu Gly Glu Tyr Arg Arg Arg Val
                740                 745                 750

Leu Cys Ala
        755

<210> SEQ ID NO 59
<211> LENGTH: 769
<212> TYPE: PRT
<213> ORGANISM: Ricinus communis

<400> SEQUENCE: 59

Met Trp Arg Ile Lys Ile Ala Glu Gly Gly Asn Asn Pro Tyr Ile Tyr
1               5                   10                  15

Ser Thr Asn Asn Phe Gln Gly Arg Gln Ile Trp Val Phe Asp Pro Asn
                20                  25                  30

Ala Gly Thr Pro Glu Glu Gln Ala Glu Val Glu Glu Ala Arg Gln Asn
                35                  40                  45

Phe Trp Lys Asn Arg Phe Gln Val Lys Pro Asn Ser Asp Leu Leu Trp
    50                  55                  60

Gln Leu Gln Phe Leu Arg Glu Lys Asn Phe Lys Gln Lys Ile Pro Lys
65                  70                  75                  80

Val Lys Val Glu Asp Gly Glu Glu Ile Thr Ser Glu Ile Ala Ala Ala
                85                  90                  95

Ala Leu Arg Arg Ser Val His Leu Phe Ser Ala Leu Gln Ala Ser Asp
                100                 105                 110

Gly His Trp Cys Ala Glu Asn Gly Gly Leu Leu Phe Phe Leu Pro Pro
                115                 120                 125

Leu Val Phe Ala Val Tyr Ile Thr Gly His Leu Asn Thr Val Phe Ser

```
                130             135             140
Pro Glu His Arg Lys Glu Ile Leu Arg Tyr Ile Tyr Cys His Gln Asn
145                 150                 155                 160

Glu Asp Gly Gly Trp Gly Ile His Ile Glu Gly His Ser Thr Met Phe
                165                 170                 175

Cys Thr Val Leu Asn Tyr Ile Cys Met Arg Ile Leu Gly Glu Ala Arg
                180                 185                 190

Asp Gly Gly Ile Glu Asn Ala Cys Glu Arg Gly Arg Lys Trp Ile Leu
                195                 200                 205

Asp His Gly Gly Ala Thr Gly Ile Ser Ser Trp Gly Lys Thr Trp Leu
        210                 215                 220

Ser Ile Leu Gly Val Tyr Glu Trp Asp Gly Thr Asn Pro Met Pro Pro
225                 230                 235                 240

Glu Phe Trp Ala Phe Pro Ser Ser Phe Pro Leu His Pro Ala Lys Met
                245                 250                 255

Phe Cys Tyr Cys Arg Ile Thr Tyr Met Pro Met Ser Tyr Leu Tyr Gly
                260                 265                 270

Lys Arg Phe Val Gly Pro Ile Thr Pro Leu Ile Leu Gln Ile Arg Glu
                275                 280                 285

Glu Ile Tyr Asn Glu Pro Tyr Asn Lys Ile Lys Trp Asn Ser Val Arg
        290                 295                 300

His Leu Cys Ala Lys Glu Asp Asn Tyr Phe Pro His Pro Thr Ile Gln
305                 310                 315                 320

Lys Leu Leu Trp Asp Ala Leu Tyr Thr Phe Ser Glu Pro Leu Phe Ser
                325                 330                 335

Arg Trp Pro Phe Asn Lys Leu Arg Glu Lys Ala Leu Lys Ile Thr Met
                340                 345                 350

Asp His Ile His Tyr Glu Asp His Asn Ser Arg Tyr Ile Thr Ile Gly
        355                 360                 365

Cys Val Glu Lys Pro Leu Cys Met Leu Ala Cys Trp Ile Glu Asp Pro
370                 375                 380

His Gly Glu Ala Phe Lys Lys His Leu Ala Arg Ile Ala Asp Tyr Ile
385                 390                 395                 400

Trp Val Gly Glu Asp Gly Ile Lys Met Gln Ser Phe Gly Ser Gln Thr
                405                 410                 415

Trp Asp Thr Ser Leu Ala Leu Gln Ala Leu Ile Ala Ser Asp Leu Ser
                420                 425                 430

His Glu Ile Gly Pro Thr Leu Lys Gln Gly His Val Phe Thr Lys Asn
        435                 440                 445

Ser Gln Ala Thr Glu Asn Pro Ser Gly Asp Phe Arg Lys Met Phe Arg
450                 455                 460

His Ile Ser Lys Gly Ala Trp Thr Phe Ser Asp Lys Asp Gln Gly Trp
465                 470                 475                 480

Gln Val Ser Asp Cys Thr Ala Glu Ser Leu Lys Cys Cys Leu Leu Phe
                485                 490                 495

Ser Met Met Pro Pro Glu Ile Val Gly Glu Lys Met Glu Pro Glu Lys
                500                 505                 510

Val Tyr Asp Ser Val Asn Val Ile Leu Ser Leu Gln Ser Gln Asn Gly
        515                 520                 525

Gly Phe Thr Ala Trp Glu Pro Ala Arg Ala Gly Ser Trp Met Glu Trp
        530                 535                 540

Leu Asn Pro Val Glu Phe Met Glu Asp Leu Val Val Glu His Glu Tyr
545                 550                 555                 560
```

```
Val Glu Cys Thr Ser Ser Ala Ile Gln Ala Leu Val Leu Phe Lys Lys
                565                 570                 575

Leu Tyr Pro Arg His Arg Asn Lys Glu Ile Glu Asn Cys Ile Ile Asn
            580                 585                 590

Ala Ala Gln Phe Ile Glu Asn Ile Gln Glu Pro Asp Gly Ser Trp Tyr
            595                 600                 605

Gly Asn Trp Gly Ile Cys Phe Ser Tyr Gly Thr Trp Phe Ala Leu Lys
            610                 615                 620

Gly Leu Ala Ala Ala Gly Arg Thr Tyr Glu Asn Cys Ser Ala Ile Arg
625                 630                 635                 640

Lys Gly Val Asp Phe Leu Leu Lys Ser Gln Arg Asp Asp Gly Gly Trp
                645                 650                 655

Ala Glu Ser Tyr Leu Ser Cys Pro Lys Lys Val Tyr Val Pro Phe Glu
                660                 665                 670

Gly Asn Arg Ser Asn Leu Val Gln Thr Ala Trp Ala Met Met Gly Leu
                675                 680                 685

Ile Tyr Gly Gly Gln Ala Lys Arg Asp Pro Met Pro Leu His Arg Ala
            690                 695                 700

Ala Lys Leu Leu Ile Asn Ser Gln Thr Asp Leu Gly Asp Phe Pro Gln
705                 710                 715                 720

Gln Glu Leu Thr Gly Ala Phe Met Arg Asn Cys Met Leu His Tyr Ala
                725                 730                 735

Leu Phe Arg Asn Thr Phe Pro Ile Trp Ala Leu Ala Glu Tyr Arg Arg
            740                 745                 750

His Val Leu Phe Pro Ser Ala Gly Phe Gly Phe Gly Phe Thr Asn Asn
            755                 760                 765

Leu

<210> SEQ ID NO 60
<211> LENGTH: 758
<212> TYPE: PRT
<213> ORGANISM: Taraxacum officinale

<400> SEQUENCE: 60

Met Trp Lys Leu Lys Ile Ala Glu Gly Gly Asp Asp Glu Trp Leu Thr
1               5                   10                  15

Thr Thr Asn Asn His Val Gly Arg Gln His Trp Gln Phe Asp Pro Asp
                20                  25                  30

Ala Gly Thr Glu Glu Arg Ala Glu Ile Glu Lys Ile Arg Leu Asn
            35                  40                  45

Phe Lys Leu Asn Arg Phe Gln Phe Lys Gln Ser Ala Asp Leu Leu Met
50                  55                  60

Arg Thr Gln Leu Arg Lys Glu Asn Pro Ile Asn Lys Ile Pro Asp Ala
65                  70                  75                  80

Ile Lys Leu Asn Glu Thr Glu Glu Val Thr Asn Asp Ala Val Thr Thr
                85                  90                  95

Thr Leu Lys Arg Ala Ile Ser Phe Tyr Ser Thr Ile Gln Ala His Asp
            100                 105                 110

Gly His Trp Pro Ala Glu Ser Ala Gly Pro Leu Phe Phe Leu Pro Pro
            115                 120                 125

Leu Val Ile Ala Leu Tyr Val Thr Gly Ala Met Asn Asp Ile Leu Thr
            130                 135                 140

Pro Ala His Gln Leu Glu Ile Lys Arg Tyr Ile Tyr Asn His Gln Asn
145                 150                 155                 160
```

```
Glu Asp Gly Gly Trp Gly Leu His Ile Glu Gly His Ser Thr Ile Phe
                165                 170                 175

Gly Ser Val Leu Ser Tyr Ile Thr Leu Arg Leu Leu Gly Glu Ala
        180                 185                 190

Asp Ser Val Ala Glu Asp Met Ala Leu Val Lys Gly Arg Lys Trp Ile
            195                 200                 205

Leu Asp His Gly Gly Ala Val Gly Ile Pro Ser Trp Gly Lys Phe Trp
        210                 215                 220

Leu Thr Ile Leu Gly Val Tyr Glu Trp Gly Gly Cys Asn Pro Met Pro
225                 230                 235                 240

Pro Glu Phe Trp Leu Met Pro Lys Phe Phe Pro Ile His Pro Gly Lys
            245                 250                 255

Met Leu Cys Tyr Cys Arg Leu Val Tyr Met Pro Met Ser Tyr Leu Tyr
            260                 265                 270

Gly Lys Arg Phe Val Gly Lys Ile Thr Glu Leu Val Arg Asp Leu Arg
        275                 280                 285

Gln Glu Leu Tyr Thr Asp Pro Tyr Asp Glu Ile Asn Trp Asn Lys Ala
        290                 295                 300

Arg Asn Thr Cys Ala Lys Glu Asp Leu Tyr Tyr Pro His Pro Phe Val
305                 310                 315                 320

Gln Asp Met Val Trp Gly Val Leu His Asn Val Val Glu Pro Val Leu
            325                 330                 335

Thr Ser Arg Pro Ile Ser Thr Leu Arg Glu Lys Ala Leu Lys Val Ala
            340                 345                 350

Met Asp His Val His Tyr Glu Asp Lys Ser Ser Arg Tyr Leu Cys Ile
        355                 360                 365

Gly Cys Val Glu Lys Val Leu Cys Leu Ile Ala Thr Trp Val Glu Asp
    370                 375                 380

Pro Asn Gly Asp Ala Tyr Lys Arg His Leu Ala Arg Ile Pro Asp Tyr
385                 390                 395                 400

Phe Trp Val Ala Glu Asp Gly Met Lys Met Gln Ser Phe Gly Cys Gln
            405                 410                 415

Met Trp Asp Ala Ala Phe Ala Ile Gln Ala Ile Phe Ser Ser Asn Leu
            420                 425                 430

Thr Glu Glu Tyr Gly Pro Thr Leu Lys Lys Ala His Glu Phe Val Lys
        435                 440                 445

Ala Ser Gln Val Arg Asp Asn Pro Pro Gly Asp Phe Ser Lys Met Tyr
450                 455                 460

Arg His Thr Ser Lys Gly Ala Trp Thr Phe Ser Ile Gln Asp His Gly
465                 470                 475                 480

Trp Gln Val Ser Asp Cys Thr Ala Glu Gly Leu Lys Val Ser Leu Leu
            485                 490                 495

Tyr Ser Gln Met Asn Pro Lys Leu Val Gly Glu Lys Val Glu Thr Glu
            500                 505                 510

His Leu Tyr Asp Ala Val Asn Val Ile Leu Ser Leu Gln Ser Glu Asn
        515                 520                 525

Gly Gly Phe Pro Ala Trp Glu Pro Gln Arg Ala Tyr Ala Trp Leu Glu
    530                 535                 540

Lys Phe Asn Pro Thr Glu Phe Phe Glu Asp Val Leu Ile Glu Arg Glu
545                 550                 555                 560

Tyr Val Glu Cys Thr Ser Ser Ala Ile Gln Gly Leu Thr Leu Phe Lys
            565                 570                 575
```

```
Lys Leu His Pro Gly His Arg Thr Lys Glu Ile Glu His Cys Ile Ser
                580                 585                 590

Arg Ala Val Lys Tyr Val Glu Asp Thr Gln Glu Ser Asp Gly Ser Trp
            595                 600                 605

Tyr Gly Cys Trp Gly Ile Cys Tyr Thr Tyr Gly Thr Trp Phe Ala Val
        610                 615                 620

Asp Ala Leu Val Ala Cys Gly Lys Asn Tyr His Asn Cys Pro Ala Leu
625                 630                 635                 640

Gln Lys Ala Cys Lys Phe Leu Leu Ser Lys Gln Leu Pro Asp Gly Gly
                645                 650                 655

Trp Gly Glu Ser Tyr Leu Ser Ser Asn Lys Val Tyr Thr Asn Leu
            660                 665                 670

Glu Gly Asn Arg Ser Asn Leu Val His Thr Ser Trp Ala Leu Ile Ser
        675                 680                 685

Leu Ile Lys Ala Gly Gln Ala Glu Ile Asp Pro Thr Pro Ile Ser Asn
690                 695                 700

Gly Val Arg Leu Leu Ile Asn Ser Gln Met Glu Glu Gly Asp Phe Pro
705                 710                 715                 720

Gln Gln Glu Ile Thr Gly Val Phe Met Lys Asn Cys Asn Leu Asn Tyr
                725                 730                 735

Ser Ser Phe Arg Asn Ile Phe Pro Ile Trp Ala Leu Gly Glu Tyr Arg
            740                 745                 750

Arg Ile Val Gln Asn Ile
        755

<210> SEQ ID NO 61
<211> LENGTH: 758
<212> TYPE: PRT
<213> ORGANISM: Glycyrrhiza glabra

<400> SEQUENCE: 61

Met Trp Lys Leu Lys Ile Gly Glu Gly Ala Gly Leu Ile Ser Val
1               5                   10                  15

Asn Asn Phe Ile Gly Arg Gln His Trp Glu Phe Asp Pro Asn Ala Gly
                20                  25                  30

Thr Pro Gln Glu His Ala Glu Ile Glu Arg Leu Arg Arg Glu Phe Thr
            35                  40                  45

Lys Asn Arg Phe Ser Ile Lys Gln Ser Ala Asp Leu Leu Met Arg Met
        50                  55                  60

Gln Leu Arg Lys Glu Asn His Tyr Gly Thr Asn Asn Asn Ile Pro Ala
65                  70                  75                  80

Ala Val Lys Leu Ser Asp Ala Glu Asn Ile Thr Val Glu Ala Leu Val
                85                  90                  95

Thr Thr Ile Thr Arg Ala Ile Ser Phe Tyr Ser Ser Ile Gln Ala His
            100                 105                 110

Asp Gly His Trp Pro Ala Glu Ser Ala Gly Pro Leu Phe Phe Leu Gln
        115                 120                 125

Pro Leu Val Met Ala Leu Tyr Ile Thr Gly Ser Leu Asp Asp Val Leu
130                 135                 140

Gly Pro Glu His Lys Lys Glu Ile Val Arg Tyr Leu Tyr Asn His Gln
145                 150                 155                 160

Asn Glu Asp Gly Gly Trp Gly Phe His Ile Glu Gly His Ser Thr Met
                165                 170                 175

Phe Gly Ser Ala Leu Ser Tyr Val Ala Leu Arg Ile Leu Gly Glu Gly
            180                 185                 190
```

```
Pro Gln Asp Lys Ala Met Ala Lys Gly Arg Lys Trp Ile Leu Asp His
        195                 200                 205

Gly Gly Leu Val Ala Ile Pro Ser Trp Gly Lys Phe Trp Val Thr Val
        210                 215                 220

Leu Gly Ala Tyr Glu Trp Ser Gly Cys Asn Pro Leu Pro Pro Glu Leu
225                 230                 235                 240

Trp Leu Leu Pro Lys Phe Ala Pro Phe His Pro Gly Lys Met Leu Cys
                245                 250                 255

Tyr Cys Arg Leu Val Tyr Met Pro Met Ser Tyr Leu Tyr Gly Lys Lys
                260                 265                 270

Phe Val Gly Pro Ile Thr Ala Leu Ile Arg Ser Leu Arg Glu Glu Leu
                275                 280                 285

Tyr Asn Glu Pro Tyr Asn Gln Ile Asn Trp Asn Thr Ala Arg Asn Thr
            290                 295                 300

Val Ala Lys Glu Asp Leu Tyr Tyr Pro His Pro Leu Ile Gln Asp Met
305                 310                 315                 320

Leu Trp Gly Phe Leu Tyr His Val Gly Glu Arg Phe Leu Asn Cys Trp
                325                 330                 335

Pro Phe Ser Met Leu Arg Arg Lys Ala Leu Glu Ile Ala Ile Asn His
                340                 345                 350

Val His Tyr Glu Asp Glu Asn Ser Arg Tyr Leu Cys Ile Gly Ser Val
                355                 360                 365

Glu Lys Val Leu Cys Leu Ile Ala Arg Trp Val Glu Asp Pro Asn Ser
        370                 375                 380

Glu Ala Tyr Lys Leu His Leu Ala Arg Ile Pro Asp Tyr Phe Trp Leu
385                 390                 395                 400

Ala Glu Asp Gly Leu Lys Ile Gln Ser Phe Gly Cys Gln Met Trp Asp
                405                 410                 415

Ala Ala Phe Ala Ile Gln Ala Ile Leu Ala Cys Asn Val Ser Glu Glu
                420                 425                 430

Tyr Gly Pro Thr Leu Arg Lys Ala His His Phe Val Lys Ala Ser Gln
            435                 440                 445

Val Arg Glu Asn Pro Ser Gly Asp Phe Asn Ala Met Tyr Arg His Ile
        450                 455                 460

Ser Lys Gly Ala Trp Thr Phe Ser Met His Asp His Gly Trp Gln Val
465                 470                 475                 480

Ser Asp Cys Thr Ala Glu Gly Leu Lys Ala Ala Leu Leu Leu Ser Glu
                485                 490                 495

Met Pro Ser Glu Leu Val Gly Gly Lys Met Glu Thr Glu Arg Phe Tyr
            500                 505                 510

Asp Ala Val Asn Val Ile Leu Ser Leu Gln Ser Ser Asn Gly Gly Phe
        515                 520                 525

Pro Ala Trp Glu Pro Gln Lys Ala Tyr Arg Trp Leu Glu Lys Phe Asn
        530                 535                 540

Pro Thr Glu Phe Phe Glu Asp Thr Met Ile Glu Arg Glu Tyr Val Glu
545                 550                 555                 560

Cys Thr Gly Ser Ala Met Gln Gly Leu Ala Leu Phe Arg Lys Gln Phe
                565                 570                 575

Pro Gln His Arg Ser Lys Glu Ile Asp Arg Cys Ile Ala Lys Ala Ile
            580                 585                 590

Arg Tyr Ile Glu Asn Met Gln Asn Pro Asp Gly Ser Trp Tyr Gly Cys
        595                 600                 605
```

```
Trp Gly Ile Cys Tyr Thr Tyr Gly Thr Trp Phe Ala Val Glu Gly Leu
    610             615                 620
Thr Ala Cys Gly Lys Asn Cys His Asn Ser Leu Ser Leu Arg Lys Ala
625             630                 635                 640
Cys Gln Phe Leu Leu Ser Lys Gln Leu Pro Asn Ala Gly Trp Gly Glu
                645                 650                 655
Ser Tyr Leu Ser Ser Gln Asn Lys Val Tyr Thr Asn Leu Glu Gly Asn
            660                 665                 670
Arg Ala Asn Leu Val Gln Ser Ser Trp Ala Leu Leu Ser Leu Thr His
        675                 680                 685
Ala Gly Gln Ala Glu Ile Asp Pro Thr Pro Ile His Arg Gly Met Lys
    690                 695                 700
Leu Leu Ile Asn Ser Gln Met Glu Asp Gly Asp Phe Pro Gln Gln Glu
705             710                 715                 720
Ile Thr Gly Val Phe Met Arg Asn Cys Thr Leu Asn Tyr Ser Ser Tyr
                725                 730                 735
Arg Asn Ile Phe Pro Ile Trp Ala Met Gly Glu Tyr Arg Gln Val
            740                 745                 750
Leu Cys Ala His Ser Tyr
        755
```

```
<210> SEQ ID NO 62
<211> LENGTH: 763
<212> TYPE: PRT
<213> ORGANISM: Eleutherococcus trifoliatus

<400> SEQUENCE: 62

Met Trp Lys Leu Lys Ile Ala Glu Gly Asp Lys Asn Asp Pro Tyr Leu
1               5                   10                  15
Tyr Ser Thr Asn Asn Phe Val Gly Arg Gln Thr Trp Glu Phe Asp Pro
            20                  25                  30
Asp Tyr Val Gly Ser Pro Gly Glu Leu Glu Glu Val Glu Glu Ala Arg
        35                  40                  45
Arg Gln Phe Trp Glu Asn Arg Tyr Lys Val Lys Pro Cys Gly Asp Leu
    50                  55                  60
Leu Trp Arg Met Gln Phe Leu Arg Glu Lys Asn Phe Lys Gln Thr Ile
65              70                  75                  80
Pro Gln Val Lys Val Gly Asp Asp Glu Ala Val Thr Tyr Asp Ala Ala
                85                  90                  95
Thr Thr Thr Leu Arg Arg Ala Val His Phe Phe Ser Ala Leu Gln Ala
            100                 105                 110
Ser Asp Gly His Trp Pro Ala Glu Ile Ala Gly Pro Leu Phe Phe Leu
        115                 120                 125
Pro Pro Leu Val Met Cys Val Tyr Ile Thr Gly His Leu Asp Thr Val
    130                 135                 140
Phe Pro Ala Lys His Arg Lys Glu Ile Leu Arg Tyr Ile Tyr Cys His
145             150                 155                 160
Gln Asn Glu Asn Gly Gly Gly Leu His Ile Glu Gly His Ser Thr
                165                 170                 175
Met Phe Gly Thr Thr Phe Ser Tyr Ile Cys Met Arg Ile Leu Gly Lys
            180                 185                 190
Gly Pro Asp Gly Gly Val Asn Asn Ala Cys Ala Lys Gly Arg Lys Trp
        195                 200                 205
Ile Leu Asp His Gly Ser Ala Thr Ala Ile Pro Ser Trp Gly Lys Thr
    210                 215                 220
```

```
Trp Leu Ser Ile Leu Gly Val Tyr Glu Trp Thr Gly Ser Asn Pro Met
225                 230                 235                 240

Pro Pro Glu Phe Trp Leu Leu Pro Ser Ser Leu Ser Val His Pro Ala
            245                 250                 255

Lys Met Leu Cys Tyr Cys Arg Met Val Tyr Leu Pro Met Ser Tyr Leu
                260                 265                 270

Tyr Gly Lys Arg Phe Val Gly Pro Ile Thr Pro Leu Ile Leu Gln Leu
        275                 280                 285

Lys Glu Glu Leu Tyr Ala Gln Pro Tyr Asn Glu Ile Arg Trp Gly Lys
    290                 295                 300

Val Arg His Val Cys Ala Lys Glu Asp Ile Tyr Tyr Pro His Pro Leu
305                 310                 315                 320

Ile Gln Asp Leu Leu Trp Asp Ser Leu His Val Leu Ala Glu Pro Leu
                325                 330                 335

Leu Thr Arg Trp Pro Phe Asn Lys Leu Arg Glu Lys Ala Leu Gln Thr
            340                 345                 350

Thr Met Lys His Ile His Tyr Glu Asp Glu Asn Ser Arg Tyr Ile Thr
        355                 360                 365

Ile Gly Cys Val Glu Lys Ile Leu Cys Met Leu Ala Cys Trp Val Glu
    370                 375                 380

Asp Pro Asn Gly Asp Tyr Phe Lys Lys His Leu Ala Arg Ile Pro Asp
385                 390                 395                 400

Tyr Leu Trp Val Ala Glu Asp Gly Met Lys Met Gln Ser Phe Gly Ser
                405                 410                 415

Gln Glu Trp Asp Ile Gly Phe Gly Ile Gln Ala Leu Leu Ala Ser Asp
            420                 425                 430

Leu Thr His Glu Leu Gly Pro Thr Leu Met Lys Gly His Asp Phe Ile
        435                 440                 445

Lys Lys Ser Gln Val Lys Asp Asn Pro Ser Gly Asp Phe Lys Ser Met
    450                 455                 460

Tyr Arg His Ile Ser Lys Gly Ser Trp Thr Phe Ser Asp Gln Asp His
465                 470                 475                 480

Gly Trp Gln Val Ser Asp Cys Thr Ala Glu Gly Leu Lys Cys Cys Leu
                485                 490                 495

Ile Phe Ser Thr Met Pro Glu Glu Ile Val Gly Lys Lys Met Glu Pro
            500                 505                 510

Glu Leu Leu Tyr Asn Ser Val Asn Val Leu Leu Ser Leu Gln Ser Lys
        515                 520                 525

Asn Gly Gly Val Ala Ala Trp Glu Pro Ala Thr Ala Gln Asp Trp Leu
    530                 535                 540

Glu Leu Phe Asn Pro Thr Glu Phe Phe Ala Asp Thr Ile Ile Glu His
545                 550                 555                 560

Glu Tyr Val Glu Cys Thr Ser Ser Ala Ile Gln Ala Leu Thr Leu Phe
                565                 570                 575

Lys Lys Leu Tyr Pro Gly His Arg Lys Glu Ile Asp Asn Phe Ile
            580                 585                 590

Thr Asn Ala Ile Arg Phe Ile Glu Asp Ile Gln Ile Pro Asp Gly Ser
        595                 600                 605

Trp Tyr Gly Asn Trp Gly Val Cys Phe Thr Tyr Gly Thr Trp Phe Ala
    610                 615                 620

Leu Gly Gly Leu Ala Ala Gly Gly Lys Thr Tyr Asn Asn Cys Ala Ala
625                 630                 635                 640
```

```
Val Arg Lys Ala Val Asn Phe Leu Leu Glu Ser Gln Leu Asp Asp Gly
                645                 650                 655

Gly Trp Gly Glu Ser His Leu Ser Cys Pro Arg Lys Val Tyr Val Pro
            660                 665                 670

Leu Glu Gly Asn Arg Ser Asn Leu Val His Thr Gly Trp Ala Leu Met
            675                 680                 685

Gly Leu Ile His Ser Gly Gln Ala Glu Arg Asp Pro Thr Pro Leu His
            690                 695                 700

Arg Ala Ala Lys Leu Leu Ile Asn Ser Gln Met Glu Asp Gly Asp Phe
705                 710                 715                 720

Pro Gln Gln Glu Ile Thr Gly Ala Phe Met Lys Asn Cys Met Leu His
                725                 730                 735

Tyr Ala Val Tyr Arg Asn Ile Tyr Pro Leu Trp Ala Leu Ala Glu Tyr
                740                 745                 750

Arg Arg Arg Val Pro Leu Pro Thr Leu Gly Ala
                755                 760

<210> SEQ ID NO 63
<211> LENGTH: 765
<212> TYPE: PRT
<213> ORGANISM: Kalanchoe daigremontiana

<400> SEQUENCE: 63

Met Trp Lys Leu Lys Ile Ala Asp Gly Gly Ser Asn Pro Tyr Ile Phe
1               5                   10                  15

Thr Thr Asn Asn Phe Val Gly Arg Gln Ile Trp Glu Phe Asp Pro Gln
                20                  25                  30

Ala Thr Asp Pro Gln Gln Leu Ala Lys Val Glu Ala Ala Arg Leu Asp
            35                  40                  45

Phe Tyr His Asn Arg Tyr Lys Leu Lys Pro Asn Ser Asp Leu Leu Trp
    50                  55                  60

Arg Met Gln Phe Leu Glu Glu Lys Ala Phe Thr Gln Thr Ile Pro Gln
65                  70                  75                  80

Val Lys Val Glu Asp Gly Glu Glu Val Ser Tyr Glu Ala Val Thr Ala
                85                  90                  95

Ala Leu Arg Arg Gly Val His Leu Tyr Ser Ala Leu Gln Ala Ser Asp
            100                 105                 110

Gly His Trp Pro Ala Glu Asn Ala Gly Pro Met Phe Phe Met Pro Pro
        115                 120                 125

Met Val Met Cys Leu Tyr Ile Thr Gly His Leu Asn Ala Ile Phe Thr
130                 135                 140

Glu Glu His Arg Ser Glu Thr Leu Arg Tyr Ile Tyr Tyr His Gln Asn
145                 150                 155                 160

Glu Asp Gly Gly Trp Gly Phe His Ile Glu Gly His Ser Thr Met Phe
                165                 170                 175

Gly Thr Val Leu Asn Tyr Ile Cys Met Arg Leu Leu Gly Glu Gly Pro
            180                 185                 190

Glu Gly Gly Gln Asp Asn Ala Val Ser Arg Gly Arg Lys Trp Ile Leu
        195                 200                 205

Asp His Gly Gly Ala Thr Ser Ile Pro Ser Trp Gly Lys Thr Trp Leu
    210                 215                 220

Ser Ile Met Gly Leu Cys Asp Trp Ser Gly Cys Asn Pro Met Pro Pro
225                 230                 235                 240

Glu Phe Trp Leu Leu Pro Ser Tyr Leu Pro Met His Pro Gly Lys Met
                245                 250                 255
```

```
Trp Cys Tyr Cys Arg Met Val Tyr Met Pro Met Ser Tyr Leu Tyr Gly
            260                 265                 270

Lys Arg Phe Thr Ala Arg Ile Thr Pro Leu Ile Leu Gln Leu Arg Glu
            275                 280                 285

Glu Ile His Ile Gln Pro Tyr Asp Gln Ile Asp Trp Lys Lys Val Arg
            290                 295                 300

His Val Cys Cys Lys Glu Asp Met Tyr Tyr Pro His Pro Leu Leu Gln
305                 310                 315                 320

Asp Leu Leu Trp Asp Thr Leu Tyr Leu Thr Thr Glu Pro Leu Leu Thr
                    325                 330                 335

Arg Trp Pro Leu Asn Lys Leu Ile Arg Lys Arg Ala Leu Gln Thr Thr
            340                 345                 350

Met Lys His Ile His Tyr Glu Asp Glu Asn Ser Arg Tyr Ile Thr Ile
            355                 360                 365

Gly Cys Val Glu Lys Val Leu Cys Met Leu Ala Cys Trp Val Glu Asp
            370                 375                 380

Pro Asn Gly Asp Tyr Phe Lys Lys His Leu Ala Arg Ile Pro Asp Tyr
385                 390                 395                 400

Leu Trp Ile Ala Glu Asp Gly Met Lys Met Gln Ser Phe Gly Ser Gln
                    405                 410                 415

His Trp Asp Thr Ala Phe Ser Ile Gln Ala Leu Leu Ala Ser Asn Met
            420                 425                 430

Ala Glu Glu Ile Gly Ile Thr Leu Ala Lys Gly His Asp Phe Ile Lys
            435                 440                 445

Lys Ser Gln Val Lys Asp Asn Pro Ser Gly Asp Phe Lys Gly Met Tyr
450                 455                 460

Arg His Ile Ser Lys Gly Ala Trp Thr Phe Ser Asp Gln Asp His Gly
465                 470                 475                 480

Trp Gln Val Ser Asp Cys Thr Ala Glu Gly Leu Lys Cys Cys Leu Leu
                    485                 490                 495

Phe Ser Met Met Gln Pro Glu Val Val Gly Glu Ser Met Ala Pro Glu
            500                 505                 510

Ser Leu Tyr Asn Ser Val Asn Val Leu Leu Ser Leu Gln Ser Gln Asn
            515                 520                 525

Gly Gly Leu Pro Ala Trp Glu Pro Ala Gly Ala Pro Glu Trp Leu Glu
            530                 535                 540

Leu Leu Asn Pro Thr Glu Phe Phe Glu Asn Ile Val Ile Glu His Glu
545                 550                 555                 560

Tyr Val Glu Cys Thr Ser Ser Ala Val Gln Ala Leu Val Leu Phe Lys
                    565                 570                 575

Lys Leu Tyr Pro Leu His Arg Arg Lys Glu Val Glu Arg Phe Ile Thr
            580                 585                 590

Asn Gly Ala Lys Tyr Leu Glu Asp Ile Gln Met Pro Asp Gly Ser Trp
            595                 600                 605

Tyr Gly Asn Trp Gly Val Cys Phe Thr Tyr Gly Ala Trp Phe Ala Leu
            610                 615                 620

Glu Gly Leu Ser Ala Ala Gly Lys Thr Tyr Asn Asn Cys Ala Ala Val
625                 630                 635                 640

Arg Lys Gly Val Asp Phe Leu Leu Asn Ile Gln Leu Glu Asp Gly Gly
                    645                 650                 655

Trp Gly Glu Ser Tyr Gln Ser Cys Pro Asp Lys Lys Tyr Val Pro Leu
            660                 665                 670
```

-continued

```
Glu Asp Asn Arg Ser Asn Leu Val Gln Thr Ser Trp Ala Leu Met Gly
            675                 680                 685

Leu Ile Tyr Ala Gly Gln Ala Asp Arg Asp Pro Thr Pro Leu His Arg
        690                 695                 700

Ala Ala Gln Leu Leu Ile Asn Ser Gln Leu Glu Asp Gly Asp Phe Pro
705                 710                 715                 720

Gln Gln Glu Ile Thr Gly Val Phe Gln Arg Asn Cys Met Leu His Tyr
                725                 730                 735

Ala Ala Tyr Arg Asn Ile Phe Pro Leu Trp Ala Leu Ala Glu Tyr Arg
            740                 745                 750

Arg Gln Ile Gln Leu His Ser Glu Ala Thr Lys Met Val
        755                 760                 765

<210> SEQ ID NO 64
<211> LENGTH: 761
<212> TYPE: PRT
<213> ORGANISM: Bruguiera gymnorhiza

<400> SEQUENCE: 64

Met Trp Arg Leu Lys Ile Ala Glu Gly Gly Asn Asn Pro Tyr Ile Tyr
1               5                   10                  15

Ser Thr Asn Asn Phe Val Gly Arg Gln Thr Trp Glu Phe Asp Pro Glu
            20                  25                  30

Ala Gly Thr Pro Glu Glu Arg Ala Gln Val Glu Glu Ala Arg Glu Asn
        35                  40                  45

Phe Trp Arg Asp Arg Phe Leu Ile Lys Pro Ser Ser Asp Leu Leu Trp
    50                  55                  60

Arg Phe Gln Phe Leu Ser Glu Lys Lys Phe Lys Gln Arg Ile Pro Gln
65                  70                  75                  80

Val Lys Val Gln Asp Gly Glu Glu Ile Thr Arg Glu Ile Ala Thr Thr
                85                  90                  95

Ala Leu Arg Arg Ser Val His Leu Val Ser Ala Leu Gln Ala Ser Asp
            100                 105                 110

Gly His Trp Cys Ala Glu Asn Ser Gly Pro Met Phe Phe Val Pro Pro
        115                 120                 125

Met Val Phe Ser Leu Tyr Ile Thr Gly His Leu Asn Ala Val Phe Ser
    130                 135                 140

Ala Glu His Cys Lys Glu Ile Leu Arg Tyr Ile Tyr Cys His Pro Asn
145                 150                 155                 160

Glu Asp Gly Gly Trp Gly Leu His Ile Glu Gly His Ser Ala Met Phe
                165                 170                 175

Ser Thr Val Leu Asn Tyr Asn Trp Leu Gly Lys Leu Gly Glu Gly Arg
            180                 185                 190

Asp Gly Gly Lys Asp Asn Ala Cys Glu Arg Ala Arg Arg Ile Leu
        195                 200                 205

Asp His Gly Ser Ala Thr Ala Ile Ser Ser Trp Gly Lys Thr Trp Leu
    210                 215                 220

Ala Ile Leu Gly Val Tyr Glu Trp Asp Gly Cys Asn Pro Met Pro Pro
225                 230                 235                 240

Glu Phe Trp Ala Phe Pro Thr Phe Phe Pro Ile His Pro Ala Arg Met
                245                 250                 255

Leu Cys Tyr Cys Arg Leu Thr Tyr Met Ala Met Ser Tyr Leu Tyr Gly
            260                 265                 270

Lys Lys Phe Val Gly Pro Ile Thr Pro Leu Ile Leu Gln Leu Arg Glu
        275                 280                 285
```

```
Glu Ile Tyr Asn Glu Pro Tyr Asp Gln Ile Asn Trp Ser Arg Met Arg
    290                 295                 300

His Leu Cys Ala Lys Glu Asp Asn Tyr Tyr Ala His Thr Leu Thr Gln
305                 310                 315                 320

Ile Ile Leu Trp Asp Ala Ile Tyr Met Leu Gly Glu Pro Leu Leu Lys
                325                 330                 335

Arg Trp Pro Phe Asn Lys Leu Arg Glu Lys Ala Leu Lys Ile Thr Met
                340                 345                 350

Asp His Ile His Tyr Glu Asp Glu Asn Ser Gln Tyr Ile Thr Ile Gly
            355                 360                 365

Ser Val Glu Lys Pro Leu Leu Met Leu Ala Cys Trp His Glu Asp Pro
370                 375                 380

Asn Gly Asp Ala Phe Lys Lys His Leu Ala Arg Ile Pro Asp Tyr Val
385                 390                 395                 400

Trp Leu Gly Glu Asp Gly Ile Lys Ile Gln Ser Phe Gly Ser Gln Val
                405                 410                 415

Trp Asp Thr Ser Phe Val Leu Gln Ala Leu Ile Ala Ser Asn Leu Pro
                420                 425                 430

Ser Glu Thr Gly Pro Thr Leu Glu Lys Gly His Asn Phe Ile Lys Asn
                435                 440                 445

Ser Gln Val Thr Gln Asn Pro Ser Gly Asp Phe Arg Arg Met Phe Arg
450                 455                 460

His Ile Ser Lys Gly Ser Trp Thr Phe Ser Asp Lys Asp His Gly Trp
465                 470                 475                 480

Gln Val Ser Asp Cys Thr Ala Glu Ser Leu Lys Cys Cys Leu Leu Phe
                485                 490                 495

Ser Met Met Pro Pro Glu Leu Val Gly Glu Lys Met Gly Pro Gln Arg
                500                 505                 510

Met Tyr Asp Ala Val Asn Val Ile Ile Ser Leu Gln Ser Lys Asn Gly
            515                 520                 525

Gly Cys Ser Ala Trp Glu Pro Ala Gly Ala Gly Ser Trp Met Glu Trp
            530                 535                 540

Leu Asn Pro Val Glu Phe Leu Ala Asp Leu Val Ile Glu His Glu Tyr
545                 550                 555                 560

Val Glu Cys Thr Ser Ser Ser Leu Gln Ala Leu Val Leu Phe Lys Lys
                565                 570                 575

Leu Tyr Pro Glu His Arg Arg Lys Glu Ile Glu Ile Phe Ile Leu Asn
                580                 585                 590

Ala Val Arg Phe Thr Glu Glu Ile Gln Gln Pro Asp Gly Ser Trp Tyr
            595                 600                 605

Gly Asn Trp Gly Ile Cys Phe Leu Ser Gly Thr Trp Phe Gly Leu Lys
610                 615                 620

Gly Leu Ala Ala Ala Gly Lys Thr Tyr Tyr Asn Cys Thr Ala Val Arg
625                 630                 635                 640

Lys Gly Val Glu Phe Leu Leu Gln Thr Gln Arg Asp Asp Gly Gly Trp
                645                 650                 655

Gly Glu Ser Tyr Leu Ser Cys Pro Lys Lys Ile Tyr Val Pro Leu Glu
                660                 665                 670

Gly Asn Arg Ser Asn Leu Val Gln Thr Ala Leu Ala Met Met Gly Leu
                675                 680                 685

Ile Leu Gly Gly Gln Gly Glu Arg Asp Pro Thr Pro Leu His Arg Ala
            690                 695                 700
```

```
Ala Lys Leu Leu Ile Asn Ser Gln Thr Glu Leu Gly Asp Phe Pro Gln
705                 710                 715                 720

Gln Glu Leu Ser Gly Cys Phe Met Arg Asn Cys Met Leu His Tyr Ser
            725                 730                 735

Glu Tyr Arg Asp Ile Phe Pro Thr Trp Ala Leu Ala Glu Tyr Cys Lys
            740                 745                 750

Leu Phe Pro Leu Pro Ser Lys Asn Asp
            755                 760

<210> SEQ ID NO 65
<211> LENGTH: 779
<212> TYPE: PRT
<213> ORGANISM: Betula platyphylla

<400> SEQUENCE: 65

Met Trp Arg Leu Lys Ile Ala Asp Gly Gly Ser Asp Pro Tyr Ile Tyr
1               5                   10                  15

Ser Thr Asn Asn Phe Val Gly Arg Gln Thr Trp Glu Phe Asp Pro Gln
            20                  25                  30

Ala Gly Ser Pro Gln Glu Arg Ala Glu Val Glu Glu Ala Arg Arg Asn
        35                  40                  45

Phe Tyr Asp Asn Arg Tyr Gln Val Lys Pro Ser Gly Asp Leu Leu Trp
50                  55                  60

Arg Met Gln Phe Leu Lys Glu Lys Asn Phe Lys Gln Thr Ile Pro Pro
65                  70                  75                  80

Val Lys Val Glu Asp Gly Glu Glu Ile Thr Tyr Glu Lys Ser Thr Ala
                85                  90                  95

Ala Leu Arg Arg Ala Val His Phe Tyr Ser Ala Leu Gln Ala Ser Asp
            100                 105                 110

Gly His Trp Pro Ala Glu Asn Ala Gly Pro Leu Phe Phe Leu Pro Pro
        115                 120                 125

Leu Val Met Cys Met Tyr Ile Thr Gly His Leu Asn Thr Val Phe Pro
130                 135                 140

Ala Glu His Gln Lys Glu Ile Leu Arg Tyr Ile Tyr Tyr His Gln Asn
145                 150                 155                 160

Glu Asp Gly Gly Trp Gly Leu His Ile Glu Gly His Ser Thr Met Phe
                165                 170                 175

Cys Thr Ala Leu Ser Tyr Ile Cys Met Arg Ile Leu Gly Glu Gly Pro
            180                 185                 190

Asp Gly Gly Gln Asp Asn Ala Cys Ala Arg Ala Arg Lys Trp Ile Leu
        195                 200                 205

Asp His Gly Gly Val Thr His Met Pro Ser Trp Gly Lys Thr Trp Leu
210                 215                 220

Ser Ile Leu Gly Ile Phe Glu Trp Ile Gly Ser Asn Pro Met Pro Pro
225                 230                 235                 240

Glu Phe Trp Ile Leu Pro Ser Phe Leu Pro Met His Pro Ala Lys Met
                245                 250                 255

Trp Cys Tyr Cys Arg Met Val Tyr Met Pro Met Ser Tyr Leu Tyr Gly
            260                 265                 270

Lys Arg Phe Val Gly Pro Ile Thr Pro Leu Ile Leu Gln Leu Arg Glu
        275                 280                 285

Glu Leu Tyr Thr Gln Pro Tyr His Gln Val Asn Trp Lys Lys Val Arg
    290                 295                 300

His Leu Cys Ala Lys Glu Asp Ile Tyr Tyr Pro His Pro Leu Ile Gln
305                 310                 315                 320
```

```
Asp Leu Leu Trp Asp Ser Leu Tyr Ile Phe Thr Glu Pro Leu Leu Thr
                325                 330                 335

Arg Trp Pro Phe Asn Lys Leu Val Arg Glu Lys Ala Leu Gln Val Thr
            340                 345                 350

Met Lys His Ile His Tyr Glu Asp Glu Asn Ser Arg Tyr Ile Thr Ile
        355                 360                 365

Gly Cys Val Glu Lys Val Leu Cys Met Leu Ala Cys Trp Val Glu Asp
    370                 375                 380

Pro Asn Gly Asp Tyr Phe Lys Lys His Ile Ala Arg Ile Pro Asp Tyr
385                 390                 395                 400

Ile Trp Val Ala Glu Asp Gly Ile Lys Met Gln Ser Phe Gly Ser Gln
                405                 410                 415

Glu Trp Asp Thr Gly Phe Ala Ile Gln Ala Leu Leu Ala Ser Asn Leu
            420                 425                 430

Thr Asp Glu Ile Gly Pro Thr Leu Ala Arg Gly His Asp Phe Ile Lys
        435                 440                 445

Lys Ser Gln Val Lys Asp Asn Pro Ser Gly Asp Phe Glu Ser Met His
    450                 455                 460

Arg His Ile Ser Lys Gly Ser Trp Thr Phe Ser Asp Gln Asp His Gly
465                 470                 475                 480

Trp Gln Val Ser Asp Cys Thr Ala Glu Gly Leu Lys Cys Cys Leu Leu
                485                 490                 495

Phe Ser Ile Met Pro Pro Glu Ile Val Gly Glu Lys Met Glu Pro Glu
            500                 505                 510

Gln Leu Tyr Asp Ser Val Asn Val Leu Leu Ser Leu Gln Ser Lys Asn
        515                 520                 525

Gly Gly Leu Ala Ala Trp Glu Pro Ala Gly Ala Gln Glu Trp Leu Glu
    530                 535                 540

Leu Leu Asn Ser Thr Glu Phe Phe Ala Asp Ile Val Ile Glu His Glu
545                 550                 555                 560

Tyr Ile Glu Cys Thr Ala Ser Ala Met Gln Thr Leu Val Leu Phe Lys
                565                 570                 575

Lys Leu Tyr Pro Gly His Arg Lys Lys Glu Ile Glu Asn Phe Ile Lys
            580                 585                 590

Asn Ala Ala Gln Phe Leu Gln Val Ile Gln Met Pro Asp Gly Ser Trp
        595                 600                 605

Tyr Gly Asn Trp Gly Val Cys Phe Thr Tyr Gly Thr Trp Phe Ala Leu
    610                 615                 620

Gly Gly Leu Ala Ala Val Gly Lys Thr Tyr Asn Asn Cys Leu Ala Val
625                 630                 635                 640

Arg Arg Ala Val Asp Phe Leu Leu Arg Ala Gln Arg Asp Asn Gly Gly
                645                 650                 655

Trp Gly Glu Ser Tyr Leu Ser Cys Pro Lys Lys Glu Tyr Val Pro Leu
            660                 665                 670

Glu Gly Asn Lys Ser Asn Leu Val His Thr Ala Trp Ala Met Met Gly
        675                 680                 685

Leu Ile His Ala Gly Gln Ala Glu Arg Asp Pro Thr Pro Leu His Arg
    690                 695                 700

Ala Ala Lys Leu Ile Ile Asn Ser Gln Leu Glu Asp Gly Asp Phe Pro
705                 710                 715                 720

Gln Gln Glu Ile Thr Gly Val Phe Met Lys Asn Cys Met Leu His Tyr
                725                 730                 735
```

```
Ala Ala Tyr Lys Asn Ile Tyr Pro Leu Trp Ala Leu Ala Glu Tyr Arg
            740                 745                 750

Lys His Val Pro Leu Pro Leu Gly Lys Asn Leu Asn Gln Val Val Asn
            755                 760                 765

Cys Ile Gly Gln Ser Leu Tyr Lys Lys Tyr Lys
            770                 775

<210> SEQ ID NO 66
<211> LENGTH: 706
<212> TYPE: PRT
<213> ORGANISM: Lotus japonicus

<400> SEQUENCE: 66

Met Glu Glu Ser Ser Met Lys Ile Ser Pro Leu Asp Leu Met Ser
1               5                   10                  15

Ala Met Ile Lys Gly Thr Leu Asp Pro Ser Asn Val Ser Ser Thr Ser
            20                  25                  30

Gly Ala Gly Ser Val Phe Leu Glu Asn Arg Glu Phe Val Met Val Leu
        35                  40                  45

Thr Thr Ser Ile Ala Val Leu Ile Gly Cys Val Val Phe Ile Trp
50                  55                  60

Arg Arg Ser Thr Gly Asn Lys Ala Lys Ser Ile Glu Pro Pro Lys Arg
65              70                  75                  80

Val Val Glu Lys Leu Ser Asp Glu Ala Glu Val Asp Asp Gly Thr Arg
                85                  90                  95

Lys Val Thr Ile Phe Phe Gly Thr Gln Thr Gly Thr Ala Glu Gly Phe
            100                 105                 110

Ala Lys Ala Ile Ala Glu Glu Ala Lys Val Arg Tyr Glu Lys Ala Lys
        115                 120                 125

Phe Lys Ile Val Asp Met Asp Asp Tyr Ala Gln Asp Asp Glu Tyr
    130                 135                 140

Glu Glu Lys Leu Lys Lys Glu Thr Leu Ala Leu Phe Phe Leu Ala Thr
145                 150                 155                 160

Tyr Gly Asp Gly Glu Pro Thr Asp Asn Ala Ala Arg Phe Tyr Lys Trp
                165                 170                 175

Phe Leu Glu Gly Asp Glu Lys Glu Gly Trp Leu Arg Asn Leu Glu
            180                 185                 190

Tyr Ala Val Phe Gly Leu Gly Asn Arg Gln Tyr Glu His Phe Asn Lys
        195                 200                 205

Val Ala Ile Glu Val Asp Asp Lys Leu Ala Asp Phe Gly Gly Lys Arg
    210                 215                 220

Leu Val Lys Val Gly Leu Gly Asp Asp Gln Cys Ile Glu Asp Asp
225                 230                 235                 240

Phe Thr Ala Trp Lys Glu Glu Leu Trp Pro Ala Leu Asp Glu Leu Leu
                245                 250                 255

Arg Gly Asp Asp Asp Thr Thr Val Ser Thr Pro Tyr Thr Ala Ala Val
            260                 265                 270

Leu Glu Tyr Arg Val Val Ile His Asp Pro Leu Asp Ala Ser Val Asp
        275                 280                 285

Glu Lys Lys Trp His Asn Val Asn Gly His Ala Ile Val Asp Ala Gln
    290                 295                 300

His Pro Val Arg Ser Asn Val Ala Val Arg Lys Glu Leu His Thr Pro
305                 310                 315                 320

Val Ser Asp Arg Ser Cys Thr His Leu Glu Phe Asp Ile Ser Gly Thr
                325                 330                 335
```

Gly Val Ala Tyr Glu Thr Gly Asp His Val Gly Val Tyr Cys Glu Asn
                340                 345                 350

Leu Ser Glu Thr Val Glu Glu Ala Val Arg Leu Leu Gly Leu Ser Pro
            355                 360                 365

Asp Thr Tyr Phe Ser Val His Thr Asp Asp Glu Asp Gly Lys Pro Leu
        370                 375                 380

Ser Gly Ser Ser Leu Pro Pro Thr Phe Pro Pro Cys Thr Leu Arg Thr
385                 390                 395                 400

Ala Ile Ala Arg Tyr Ala Asp Val Leu Ser Ser Pro Lys Lys Ser Val
                405                 410                 415

Leu Leu Ala Leu Ala Ala His Ala Ser Asn Pro Ser Glu Ala Asp Arg
            420                 425                 430

Leu Arg His Leu Ala Ser Pro Ala Gly Lys Asp Glu Tyr Ser Glu Trp
        435                 440                 445

Val Ile Ala Ser Gln Arg Ser Leu Leu Glu Val Met Ala Glu Phe Pro
    450                 455                 460

Ser Ala Lys Pro Pro Ile Gly Val Phe Phe Ala Ala Ile Ala Pro Arg
465                 470                 475                 480

Leu Gln Pro Arg Phe Tyr Ser Ile Ser Ser Ser Pro Arg Met Ala Pro
                485                 490                 495

Ser Arg Ile His Val Thr Cys Ala Leu Val Asn Asp Lys Met Pro Thr
            500                 505                 510

Gly Arg Ile His Arg Gly Val Cys Ser Thr Trp Met Lys Asn Ser Val
        515                 520                 525

Pro Leu Glu Lys Ser Gln Asp Cys Ser Trp Ala Pro Ile Phe Val Arg
    530                 535                 540

Gln Ser Asn Phe Lys Leu Pro Ala Asp Asn Lys Val Pro Ile Ile Met
545                 550                 555                 560

Ile Gly Pro Gly Thr Gly Leu Ala Pro Phe Arg Gly Phe Leu Gln Glu
                565                 570                 575

Arg Leu Ala Leu Lys Glu Asp Gly Ala Glu Leu Gly Pro Ser Val Leu
            580                 585                 590

Phe Phe Gly Cys Arg Asn Arg Gln Met Asp Tyr Ile Tyr Glu Asp Glu
        595                 600                 605

Leu Asn His Phe Val Asn Ser Gly Ala Leu Ser Glu Leu Ile Val Ala
    610                 615                 620

Phe Ser Arg Glu Gly Pro Thr Lys Glu Tyr Val Gln His Lys Met Met
625                 630                 635                 640

Glu Lys Ala Ser Asp Ile Trp Asn Met Ile Ser Gln Gly Ala Tyr Ile
                645                 650                 655

Tyr Val Cys Gly Asp Ala Lys Gly Met Ala Arg Asp Val His Arg Thr
            660                 665                 670

Leu His Thr Ile Leu Gln Glu Gln Gly Ser Leu Asp Ser Ser Lys Ala
        675                 680                 685

Glu Gly Met Val Lys Asn Leu Gln Leu Asn Gly Arg Tyr Leu Arg Asp
    690                 695                 700

Val Trp
705

<210> SEQ ID NO 67
<211> LENGTH: 692
<212> TYPE: PRT
<213> ORGANISM: Arabidopsis thaliana

```
<400> SEQUENCE: 67

Met Thr Ser Ala Leu Tyr Ala Ser Asp Leu Phe Lys Gln Leu Lys Ser
1               5                   10                  15

Ile Met Gly Thr Asp Ser Leu Ser Asp Val Val Leu Val Ile Ala
            20                  25                  30

Thr Thr Ser Leu Ala Leu Val Ala Gly Phe Val Val Leu Leu Trp Lys
        35                  40                  45

Lys Thr Thr Ala Asp Arg Ser Gly Glu Leu Lys Pro Leu Met Ile Pro
    50                  55                  60

Lys Ser Leu Met Ala Lys Asp Glu Asp Asp Leu Asp Leu Gly Ser
65                  70                  75                  80

Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
            100                 105                 110

Lys Ala Ala Val Lys Val Ile Asp Leu Asp Asp Tyr Ala Ala Asp Asp
        115                 120                 125

Asp Gln Tyr Glu Glu Lys Leu Lys Lys Glu Thr Leu Ala Phe Phe Cys
    130                 135                 140

Val Ala Thr Tyr Gly Asp Gly Glu Pro Thr Asp Asn Ala Ala Arg Phe
145                 150                 155                 160

Ser Lys Trp Phe Thr Glu Glu Asn Glu Arg Asp Ile Lys Leu Gln Gln
                165                 170                 175

Leu Ala Tyr Gly Val Phe Ala Leu Gly Asn Arg Gln Tyr Glu His Phe
            180                 185                 190

Asn Lys Ile Gly Ile Val Leu Asp Glu Glu Leu Cys Lys Lys Gly Ala
        195                 200                 205

Lys Arg Leu Ile Glu Val Gly Leu Gly Asp Asp Gln Ser Ile Glu
    210                 215                 220

Asp Asp Phe Asn Ala Trp Lys Glu Ser Leu Trp Ser Glu Leu Asp Lys
225                 230                 235                 240

Leu Leu Lys Asp Glu Asp Asp Lys Ser Val Ala Thr Pro Tyr Thr Ala
                245                 250                 255

Val Ile Pro Glu Tyr Arg Val Val Thr His Asp Pro Arg Phe Thr Thr
            260                 265                 270

Gln Lys Ser Met Glu Ser Asn Val Ala Asn Gly Asn Thr Thr Ile Asp
        275                 280                 285

Ile His His Pro Cys Arg Val Asp Val Ala Val Gln Lys Glu Leu His
    290                 295                 300

Thr His Glu Ser Asp Arg Ser Cys Ile His Leu Glu Phe Asp Ile Ser
305                 310                 315                 320

Arg Thr Gly Ile Thr Tyr Glu Thr Gly Asp His Val Gly Val Tyr Ala
                325                 330                 335

Glu Asn His Val Glu Ile Val Glu Glu Ala Gly Lys Leu Leu Gly His
            340                 345                 350

Ser Leu Asp Leu Val Phe Ser Ile His Ala Asp Lys Glu Asp Gly Ser
        355                 360                 365

Pro Leu Glu Ser Ala Val Pro Pro Phe Pro Gly Pro Cys Thr Leu
    370                 375                 380

Gly Thr Gly Leu Ala Arg Tyr Ala Asp Leu Leu Asn Pro Pro Arg Lys
385                 390                 395                 400

Ser Ala Leu Val Ala Leu Ala Ala Tyr Ala Thr Glu Pro Ser Glu Ala
                405                 410                 415
```

Glu Lys Leu Lys His Leu Thr Ser Pro Asp Gly Lys Asp Glu Tyr Ser
                420                 425                 430

Gln Trp Ile Val Ala Ser Gln Arg Ser Leu Leu Glu Val Met Ala Ala
            435                 440                 445

Phe Pro Ser Ala Lys Pro Pro Leu Gly Val Phe Phe Ala Ala Ile Ala
450                 455                 460

Pro Arg Leu Gln Pro Arg Tyr Tyr Ser Ile Ser Ser Cys Gln Asp Trp
465                 470                 475                 480

Ala Pro Ser Arg Val His Val Thr Ser Ala Leu Val Tyr Gly Pro Thr
                485                 490                 495

Pro Thr Gly Arg Ile His Lys Gly Val Cys Ser Thr Trp Met Lys Asn
            500                 505                 510

Ala Val Pro Ala Glu Lys Ser His Glu Cys Ser Gly Ala Pro Ile Phe
        515                 520                 525

Ile Arg Ala Ser Asn Phe Lys Leu Pro Ser Asn Pro Ser Thr Pro Ile
    530                 535                 540

Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Glu Leu Gly Ser Ser
                565                 570                 575

Leu Leu Phe Phe Gly Cys Arg Asn Arg Gln Met Asp Phe Ile Tyr Glu
            580                 585                 590

Asp Glu Leu Asn Asn Phe Val Asp Gln Gly Val Ile Ser Glu Leu Ile
        595                 600                 605

Met Ala Phe Ser Arg Glu Gly Ala Gln Lys Glu Tyr Val Gln His Lys
    610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
                645                 650                 655

Arg Thr Leu His Thr Ile Val Gln Glu Gln Glu Gly Val Ser Ser Ser
            660                 665                 670

Glu Ala Glu Ala Ile Val Lys Lys Leu Gln Thr Glu Gly Arg Tyr Leu
        675                 680                 685

Arg Asp Val Trp
    690

<210> SEQ ID NO 68
<211> LENGTH: 714
<212> TYPE: PRT
<213> ORGANISM: Catharanthus roseus

<400> SEQUENCE: 68

Met Asp Ser Ser Ser Glu Lys Leu Ser Pro Phe Glu Leu Met Ser Ala
1               5                   10                  15

Ile Leu Lys Gly Ala Lys Leu Asp Gly Ser Asn Ser Ser Asp Ser Gly
            20                  25                  30

Val Ala Val Ser Pro Ala Val Met Ala Met Leu Leu Glu Asn Lys Glu
        35                  40                  45

Leu Val Met Ile Leu Thr Thr Ser Val Ala Val Leu Ile Gly Cys Val
    50                  55                  60

Val Val Leu Ile Trp Arg Arg Ser Ser Gly Ser Gly Lys Lys Val Val
65                  70                  75                  80

Glu Pro Pro Lys Leu Ile Val Pro Lys Ser Val Val Glu Pro Glu Glu

```
            85                  90                  95
Ile Asp Glu Gly Lys Lys Phe Thr Ile Phe Gly Thr Gln Thr
            100                 105                 110

Gly Thr Ala Glu Gly Phe Ala Lys Ala Leu Ala Glu Ala Lys Ala
            115                 120                 125

Arg Tyr Glu Lys Ala Val Ile Lys Val Ile Asp Ile Asp Tyr Ala
            130                 135                 140

Ala Asp Asp Glu Glu Tyr Glu Lys Phe Arg Lys Glu Thr Leu Ala
145                 150                 155                 160

Phe Phe Ile Leu Ala Thr Tyr Gly Asp Gly Glu Pro Thr Asn Ala
                165                 170                 175

Ala Arg Phe Tyr Lys Trp Phe Val Glu Gly Asn Asp Arg Gly Asp Trp
                180                 185                 190

Leu Lys Asn Leu Gln Tyr Gly Val Phe Gly Leu Gly Asn Arg Gln Tyr
                195                 200                 205

Glu His Phe Asn Lys Ile Ala Lys Val Val Asp Glu Lys Val Ala Glu
                210                 215                 220

Gln Gly Gly Lys Arg Ile Val Pro Leu Val Leu Gly Asp Asp Gln
225                 230                 235                 240

Cys Ile Glu Asp Asp Phe Ala Ala Trp Arg Glu Asn Val Trp Pro Glu
                245                 250                 255

Leu Asp Asn Leu Leu Arg Asp Glu Asp Thr Thr Val Ser Thr Thr
                260                 265                 270

Tyr Thr Ala Ala Ile Pro Glu Tyr Arg Val Val Phe Pro Asp Lys Ser
                275                 280                 285

Asp Ser Leu Ile Ser Glu Ala Asn Gly His Ala Asn Gly Tyr Ala Asn
                290                 295                 300

Gly Asn Thr Val Tyr Asp Ala Gln His Pro Cys Arg Ser Asn Val Ala
305                 310                 315                 320

Val Arg Lys Glu Leu His Thr Pro Ala Ser Asp Arg Ser Cys Thr His
                325                 330                 335

Leu Asp Phe Asp Ile Ala Gly Thr Gly Leu Ser Tyr Gly Thr Gly Asp
                340                 345                 350

His Val Gly Val Tyr Cys Asp Asn Leu Ser Glu Thr Val Glu Glu Ala
                355                 360                 365

Glu Arg Leu Leu Asn Leu Pro Pro Glu Thr Tyr Phe Ser Leu His Ala
                370                 375                 380

Asp Lys Glu Asp Gly Thr Pro Leu Ala Gly Ser Ser Leu Pro Pro
385                 390                 395                 400

Phe Pro Pro Cys Thr Leu Arg Thr Ala Leu Thr Arg Tyr Ala Asp Leu
                405                 410                 415

Leu Asn Thr Pro Lys Lys Ser Ala Leu Leu Ala Leu Ala Ala Tyr Ala
                420                 425                 430

Ser Asp Pro Asn Glu Ala Asp Arg Leu Lys Tyr Leu Ala Ser Pro Ala
                435                 440                 445

Gly Lys Asp Glu Tyr Ala Gln Ser Leu Val Ala Asn Gln Arg Ser Leu
                450                 455                 460

Leu Glu Val Met Ala Glu Phe Pro Ser Ala Lys Pro Pro Leu Gly Val
465                 470                 475                 480

Phe Phe Ala Ala Ile Ala Pro Arg Leu Gln Pro Arg Phe Tyr Ser Ile
                485                 490                 495

Ser Ser Ser Pro Arg Met Ala Pro Ser Arg Ile His Val Thr Cys Ala
                500                 505                 510
```

-continued

```
Leu Val Tyr Glu Lys Thr Pro Gly Gly Arg Ile His Lys Gly Val Cys
            515                 520                 525

Ser Thr Trp Met Lys Asn Ala Ile Pro Leu Glu Glu Ser Arg Asp Cys
        530                 535                 540

Ser Trp Ala Pro Ile Phe Val Arg Gln Ser Asn Phe Lys Leu Pro Ala
545                 550                 555                 560

Asp Pro Lys Val Pro Val Ile Met Ile Gly Pro Gly Thr Gly Leu Ala
                565                 570                 575

Pro Phe Arg Gly Phe Leu Gln Glu Arg Leu Ala Leu Lys Glu Glu Gly
            580                 585                 590

Ala Glu Leu Gly Thr Ala Val Phe Phe Gly Cys Arg Asn Arg Lys
        595                 600                 605

Met Asp Tyr Ile Tyr Glu Asp Glu Leu Asn His Phe Leu Glu Ile Gly
        610                 615                 620

Ala Leu Ser Glu Leu Leu Val Ala Phe Ser Arg Glu Gly Pro Thr Lys
625                 630                 635                 640

Gln Tyr Val Gln His Lys Met Ala Glu Lys Ala Ser Asp Ile Trp Arg
                645                 650                 655

Met Ile Ser Asp Gly Ala Tyr Val Tyr Val Cys Gly Asp Ala Lys Gly
            660                 665                 670

Met Ala Arg Asp Val His Arg Thr Leu His Thr Ile Ala Gln Glu Gln
        675                 680                 685

Gly Ser Met Asp Ser Thr Gln Ala Glu Gly Phe Val Lys Asn Leu Gln
        690                 695                 700

Met Thr Gly Arg Tyr Leu Arg Asp Val Trp
705                 710

<210> SEQ ID NO 69
<211> LENGTH: 692
<212> TYPE: PRT
<213> ORGANISM: Medicago truncatula

<400> SEQUENCE: 69

Met Thr Ser Ser Asn Ser Asp Leu Val Arg Thr Ile Glu Ser Val Leu
1               5                   10                  15

Gly Val Ser Leu Gly Asp Ser Val Ser Asp Ser Val Val Leu Ile Val
            20                  25                  30

Thr Thr Ser Ala Ala Val Ile Ile Gly Leu Leu Val Phe Leu Trp Lys
        35                  40                  45

Lys Ser Ser Asp Arg Ser Lys Glu Leu Lys Pro Val Ile Val Pro Lys
50                  55                  60

Ser Leu Val Lys Glu Glu Asp Asp Ala Asp Ile Ala Asp Gly Lys
65                  70                  75                  80

Thr Lys Val Thr Val Phe Phe Gly Thr Gln Thr Gly Thr Ala Glu Gly
                85                  90                  95

Phe Ala Lys Ala Leu Ala Glu Glu Ile Lys Ala Arg Tyr Glu Lys Ala
            100                 105                 110

Phe Val Lys Val Val Asp Met Asp Asp Tyr Ala Ala Asp Asp Gln
            115                 120                 125

Tyr Glu Glu Lys Leu Lys Lys Glu Thr Leu Ala Phe Phe Met Leu Ala
        130                 135                 140

Thr Tyr Gly Asp Gly Glu Pro Thr Asp Asn Ala Ala Arg Phe Tyr Lys
145                 150                 155                 160

Trp Phe Thr Glu Gly Lys Asp Glu Arg Gly Thr Trp Leu Gln Gln Leu
```

```
                165                 170                 175
Thr Tyr Gly Val Phe Gly Leu Gly Asn Arg Gln Tyr Glu His Phe Asn
            180                 185                 190
Lys Ile Gly Lys Val Val Asp Asp Leu Ser Glu Gln Gly Ala Lys
            195                 200                 205
Arg Leu Val Pro Leu Gly Met Gly Asp Asp Gln Ser Ile Glu Asp
            210                 215                 220
Asp Phe Asn Ala Trp Lys Glu Ser Leu Trp Pro Glu Leu Asp Gln Leu
225                 230                 235                 240
Leu Arg Asp Glu Asp Val Asn Thr Val Ser Thr Pro Tyr Thr Ala
            245                 250                 255
Ala Ile Ser Glu Tyr Arg Val Val Phe His Asp Pro Thr Val Thr Pro
            260                 265                 270
Ser Tyr Glu Asn His Phe Asn Ala Ala Asn Gly Gly Ala Val Phe Asp
            275                 280                 285
Ile His His Pro Cys Arg Ala Asn Val Ala Val Arg Arg Glu Leu His
            290                 295                 300
Lys Pro Gln Ser Asp Arg Ser Cys Ile His Leu Glu Phe Asp Val Ser
305                 310                 315                 320
Gly Thr Gly Val Thr Tyr Glu Thr Gly Asp His Val Gly Val Tyr Ala
            325                 330                 335
Asp Asn Cys Asp Glu Thr Val Lys Glu Ala Gly Lys Leu Leu Gly Gln
            340                 345                 350
Asp Leu Asp Leu Leu Phe Ser Leu His Thr Asp Asn Glu Asp Gly Thr
            355                 360                 365
Ser Leu Gly Gly Ser Leu Leu Pro Pro Phe Pro Gly Pro Cys Thr Val
370                 375                 380
Arg Thr Ala Leu Ala Arg Tyr Ala Asp Leu Leu Asn Pro Pro Arg Lys
385                 390                 395                 400
Ala Ala Leu Ile Ala Leu Ala Ala His Ala Ser Glu Pro Ser Glu Ala
            405                 410                 415
Glu Arg Leu Lys Phe Leu Ser Ser Pro Gln Gly Lys Asp Glu Tyr Ser
            420                 425                 430
Lys Trp Val Val Gly Ser His Arg Thr Leu Leu Glu Val Met Ala Asp
            435                 440                 445
Phe Pro Ser Ala Lys Pro Pro Leu Gly Val Phe Phe Ala Ala Ile Ala
            450                 455                 460
Pro Arg Leu Gln Pro Arg Tyr Tyr Ser Ile Ser Ser Ser Pro Arg Phe
465                 470                 475                 480
Ala Pro Gln Arg Val His Val Thr Cys Ala Leu Val Glu Gly Pro Thr
            485                 490                 495
Pro Thr Gly Arg Ile His Lys Gly Val Cys Ser Thr Trp Met Lys Asn
            500                 505                 510
Ala Ile Pro Ser Glu Glu Ser Arg Asp Cys Ser Trp Ala Pro Ile Phe
            515                 520                 525
Ile Arg Pro Ser Asn Phe Lys Leu Pro Ala Asp Pro Ser Ile Pro Ile
            530                 535                 540
Ile Met Val Gly Pro Gly Thr Gly Leu Ala Pro Phe Arg Gly Phe Leu
545                 550                 555                 560
Gln Glu Arg Phe Ala Leu Lys Glu Asp Gly Val Gln Leu Gly Pro Ala
            565                 570                 575
Leu Leu Phe Phe Gly Cys Arg Asn Arg Gln Met Asp Phe Ile Tyr Glu
            580                 585                 590
```

```
Glu Glu Leu Asn Asn Phe Val Glu Gln Gly Ser Leu Ser Glu Leu Ile
            595                 600                 605

Val Ala Phe Ser Arg Glu Gly Pro Glu Lys Glu Tyr Val Gln His Lys
610                 615                 620

Met Met Asp Lys Ala Ser Tyr Phe Trp Ser Leu Ile Ser Gln Gly Gly
625                 630                 635                 640

Tyr Leu Tyr Val Cys Gly Asp Ala Lys Gly Met Ala Arg Asp Val His
            645                 650                 655

Arg Thr Leu His Thr Ile Val Gln Gln Gln Glu Asn Ala Asp Ser Ser
            660                 665                 670

Lys Ala Glu Ala Thr Val Lys Lys Leu Gln Met Asp Gly Arg Tyr Leu
            675                 680                 685

Arg Asp Val Trp
            690

<210> SEQ ID NO 70
<211> LENGTH: 691
<212> TYPE: PRT
<213> ORGANISM: Saccharomyces cerevisiae

<400> SEQUENCE: 70

Met Pro Phe Gly Ile Asp Asn Thr Asp Phe Thr Val Leu Ala Gly Leu
1               5                   10                  15

Val Leu Ala Val Leu Leu Tyr Val Lys Arg Asn Ser Ile Lys Glu Leu
                20                  25                  30

Leu Met Ser Asp Asp Gly Asp Ile Thr Ala Val Ser Ser Gly Asn Arg
            35                  40                  45

Asp Ile Ala Gln Val Val Thr Glu Asn Asn Lys Asn Tyr Leu Val Leu
50                  55                  60

Tyr Ala Ser Gln Thr Gly Thr Ala Glu Asp Tyr Ala Lys Lys Phe Ser
65                  70                  75                  80

Lys Glu Leu Val Ala Lys Phe Asn Leu Asn Val Met Cys Ala Asp Val
                85                  90                  95

Glu Asn Tyr Asp Phe Glu Ser Leu Asn Asp Val Pro Val Ile Val Ser
            100                 105                 110

Ile Phe Ile Ser Thr Tyr Gly Glu Gly Asp Phe Pro Asp Gly Ala Val
            115                 120                 125

Asn Phe Glu Asp Phe Ile Cys Asn Ala Glu Ala Gly Ala Leu Ser Asn
130                 135                 140

Leu Arg Tyr Asn Met Phe Gly Leu Gly Asn Ser Thr Tyr Glu Phe Phe
145                 150                 155                 160

Asn Gly Ala Ala Lys Lys Ala Glu Lys His Leu Ser Ala Ala Gly Ala
                165                 170                 175

Ile Arg Leu Gly Lys Leu Gly Glu Ala Asp Asp Gly Ala Gly Thr Thr
            180                 185                 190

Asp Glu Asp Tyr Met Ala Trp Lys Asp Ser Ile Leu Glu Val Leu Lys
            195                 200                 205

Asp Glu Leu His Leu Asp Glu Gln Glu Ala Lys Phe Thr Ser Gln Phe
210                 215                 220

Gln Tyr Thr Val Leu Asn Glu Ile Thr Asp Ser Met Ser Leu Gly Glu
225                 230                 235                 240

Pro Ser Ala His Tyr Leu Pro Ser His Gln Leu Asn Arg Asn Ala Asp
                245                 250                 255

Gly Ile Gln Leu Gly Pro Phe Asp Leu Ser Gln Pro Tyr Ile Ala Pro
```

```
                  260                 265                 270
Ile Val Lys Ser Arg Glu Leu Phe Ser Ser Asn Asp Arg Asn Cys Ile
            275                 280                 285

His Ser Glu Phe Asp Leu Ser Gly Ser Asn Ile Lys Tyr Ser Thr Gly
        290                 295                 300

Asp His Leu Ala Val Trp Pro Ser Asn Pro Leu Glu Lys Val Glu Gln
305                 310                 315                 320

Phe Leu Ser Ile Phe Asn Leu Asp Pro Glu Thr Ile Phe Asp Leu Lys
                325                 330                 335

Pro Leu Asp Pro Thr Val Lys Val Pro Phe Pro Thr Pro Thr Thr Ile
            340                 345                 350

Gly Ala Ala Ile Lys His Tyr Leu Glu Ile Thr Gly Pro Val Ser Arg
        355                 360                 365

Gln Leu Phe Ser Ser Leu Ile Gln Phe Ala Pro Asn Ala Asp Val Lys
    370                 375                 380

Glu Lys Leu Thr Leu Leu Ser Lys Asp Lys Asp Gln Phe Ala Val Glu
385                 390                 395                 400

Ile Thr Ser Lys Tyr Phe Asn Ile Ala Asp Ala Leu Lys Tyr Leu Ser
                405                 410                 415

Asp Gly Ala Lys Trp Asp Thr Val Pro Met Gln Phe Leu Val Glu Ser
            420                 425                 430

Val Pro Gln Met Thr Pro Arg Tyr Tyr Ser Ile Ser Ser Ser Ser Leu
        435                 440                 445

Ser Glu Lys Gln Thr Val His Val Thr Ser Ile Val Glu Asn Phe Pro
    450                 455                 460

Asn Pro Glu Leu Pro Asp Ala Pro Val Val Gly Val Thr Thr Asn
465                 470                 475                 480

Leu Leu Arg Asn Ile Gln Leu Ala Gln Asn Asn Val Asn Ile Ala Glu
                485                 490                 495

Thr Asn Leu Pro Val His Tyr Asp Leu Asn Gly Pro Arg Lys Leu Phe
            500                 505                 510

Ala Asn Tyr Lys Leu Pro Val His Val Arg Arg Ser Asn Phe Arg Leu
        515                 520                 525

Pro Ser Asn Pro Ser Thr Pro Val Ile Met Ile Gly Pro Gly Thr Gly
    530                 535                 540

Val Ala Pro Phe Arg Gly Phe Ile Arg Glu Arg Val Ala Phe Leu Glu
545                 550                 555                 560

Ser Gln Lys Lys Gly Gly Asn Asn Val Ser Leu Gly Lys His Ile Leu
                565                 570                 575

Phe Tyr Gly Ser Arg Asn Thr Asp Asp Phe Leu Tyr Gln Asp Glu Trp
            580                 585                 590

Pro Glu Tyr Ala Lys Lys Leu Asp Gly Ser Phe Glu Met Val Val Ala
        595                 600                 605

His Ser Arg Leu Pro Asn Thr Lys Lys Val Tyr Val Gln Asp Lys Leu
    610                 615                 620

Lys Asp Tyr Glu Asp Gln Val Phe Glu Met Ile Asn Asn Gly Ala Phe
625                 630                 635                 640

Ile Tyr Val Cys Gly Asp Ala Lys Gly Met Ala Lys Gly Val Ser Thr
                645                 650                 655

Ala Leu Val Gly Ile Leu Ser Arg Gly Lys Ser Ile Thr Thr Asp Glu
            660                 665                 670

Ala Thr Glu Leu Ile Lys Met Leu Lys Thr Ser Gly Arg Tyr Gln Glu
        675                 680                 685
```

Asp Val Trp
    690

<210> SEQ ID NO 71
<211> LENGTH: 712
<212> TYPE: PRT
<213> ORGANISM: Arabidopsis thaliana]

<400> SEQUENCE: 71

Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
                20                  25                  30

Ser Ala Tyr Glu Ser Val Ala Ala Glu Leu Ser Ser Met Leu Ile Glu
            35                  40                  45

Asn Arg Gln Phe Ala Met Ile Val Thr Thr Ser Ile Ala Val Leu Ile
        50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
                100                 105                 110

Thr Gly Thr Ala Glu Gly Phe Ala Lys Ala Leu Gly Glu Glu Ala Lys
            115                 120                 125

Ala Arg Tyr Glu Lys Thr Arg Phe Lys Ile Val Asp Leu Asp Asp Tyr
        130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Thr Leu Ala Asn Gly Asn Gly Tyr
    290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
                325                 330                 335

Phe Asp Ile Ala Gly Ser Gly Leu Thr Met Lys Leu Gly Asp His Val
            340                 345                 350

Gly Val Leu Cys Asp Asn Leu Ser Glu Thr Val Asp Glu Ala Leu Arg

```
                355                 360                 365
Leu Leu Asp Met Ser Pro Asp Thr Tyr Phe Ser Leu His Ala Glu Lys
    370                 375                 380

Glu Asp Gly Thr Pro Ile Ser Ser Leu Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
                420                 425                 430

Thr Glu Ala Glu Arg Leu Lys His Leu Ala Ser Pro Ala Gly Lys Asp
                435                 440                 445

Glu Tyr Ser Lys Trp Val Val Glu Ser Gln Arg Ser Leu Leu Glu Val
    450                 455                 460

Met Ala Glu Phe Pro Ser Ala Lys Pro Pro Leu Gly Val Phe Phe Ala
465                 470                 475                 480

Gly Val Ala Pro Arg Leu Gln Pro Arg Phe Tyr Ser Ile Ser Ser Ser
                485                 490                 495

Pro Lys Ile Ala Glu Thr Arg Ile His Val Thr Cys Ala Leu Val Tyr
                500                 505                 510

Glu Lys Met Pro Thr Gly Arg Ile His Lys Gly Val Cys Ser Thr Trp
                515                 520                 525

Met Lys Asn Ala Val Pro Tyr Glu Lys Ser Glu Lys Leu Phe Leu Gly
                530                 535                 540

Arg Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
                580                 585                 590

Leu Gly Pro Ser Val Leu Phe Phe Gly Cys Arg Asn Arg Arg Met Asp
                595                 600                 605

Phe Ile Tyr Glu Glu Glu Leu Gln Arg Phe Val Glu Ser Gly Ala Leu
    610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
                660                 665                 670

Arg Asp Val His Arg Ser Leu His Thr Ile Ala Gln Glu Gln Gly Ser
                675                 680                 685

Met Asp Ser Thr Lys Ala Glu Gly Phe Val Lys Asn Leu Gln Thr Ser
    690                 695                 700

Gly Arg Tyr Leu Arg Asp Val Trp
705                 710

<210> SEQ ID NO 72
<211> LENGTH: 704
<212> TYPE: PRT
<213> ORGANISM: Artemisia annua

<400> SEQUENCE: 72

Met Gln Ser Thr Thr Ser Val Lys Leu Ser Pro Phe Asp Leu Met Thr
1               5                   10                  15
```

Ala Leu Leu Asn Gly Lys Val Ser Phe Asp Thr Ser Asn Thr Ser Asp
             20                  25                  30

Thr Asn Ile Pro Leu Ala Val Phe Met Glu Asn Arg Glu Leu Leu Met
         35                  40                  45

Ile Leu Thr Thr Ser Val Ala Val Leu Ile Gly Cys Val Val Val Leu
 50                  55                  60

Val Trp Arg Arg Ser Ser Ser Ala Ala Lys Arg Ala Ala Glu Ser Pro
65                  70                  75                  80

Val Ile Val Val Pro Lys Lys Val Thr Glu Asp Glu Val Asp Asp Gly
             85                  90                  95

Arg Lys Lys Val Thr Val Phe Phe Gly Thr Gln Thr Gly Thr Ala Glu
         100                 105                 110

Gly Phe Ala Lys Ala Leu Val Glu Glu Ala Lys Ala Arg Tyr Glu Lys
         115                 120                 125

Ala Val Phe Lys Val Ile Asp Leu Asp Asp Tyr Ala Ala Glu Asp Asp
         130                 135                 140

Glu Tyr Glu Glu Lys Leu Lys Lys Glu Ser Leu Ala Phe Phe Phe Leu
145                 150                 155                 160

Ala Thr Tyr Gly Asp Gly Glu Pro Thr Asp Asn Ala Ala Arg Phe Tyr
             165                 170                 175

Lys Trp Phe Thr Glu Gly Glu Glu Lys Gly Glu Trp Leu Glu Lys Leu
             180                 185                 190

Gln Tyr Ala Val Phe Gly Leu Gly Asn Arg Gln Tyr Glu His Phe Asn
         195                 200                 205

Lys Ile Ala Lys Val Val Asp Glu Lys Leu Thr Glu Gln Gly Ala Lys
 210                 215                 220

Arg Leu Val Pro Val Gly Met Gly Asp Asp Gln Cys Ile Glu Asp
225                 230                 235                 240

Asp Phe Thr Ala Trp Lys Glu Leu Val Trp Pro Glu Leu Asp Gln Leu
             245                 250                 255

Leu Arg Asp Glu Asp Asp Thr Ser Val Ala Thr Pro Tyr Thr Ala Ala
             260                 265                 270

Val Ala Glu Tyr Arg Val Val Phe His Asp Lys Pro Glu Thr Tyr Asp
         275                 280                 285

Gln Asp Gln Leu Thr Asn Gly His Ala Val His Asp Ala Gln His Pro
         290                 295                 300

Cys Arg Ser Asn Val Ala Val Lys Lys Glu Leu His Ser Pro Leu Ser
305                 310                 315                 320

Asp Arg Ser Cys Thr His Leu Glu Phe Asp Ile Ser Asn Thr Gly Leu
             325                 330                 335

Ser Tyr Glu Thr Gly Asp His Val Gly Val Tyr Val Glu Asn Leu Ser
             340                 345                 350

Glu Val Val Asp Glu Ala Glu Lys Leu Ile Gly Leu Pro Pro His Thr
         355                 360                 365

Tyr Phe Ser Ile His Ala Asp Asn Glu Asp Gly Thr Pro Leu Gly Gly
 370                 375                 380

Ala Ser Leu Pro Pro Pro Phe Pro Pro Cys Thr Leu Arg Lys Ala Leu
385                 390                 395                 400

Ala Ser Tyr Ala Asp Val Leu Ser Ser Pro Lys Lys Ser Ala Leu Leu
             405                 410                 415

Ala Leu Ala Ala His Ala Thr Asp Ser Thr Glu Ala Asp Arg Leu Lys
             420                 425                 430

Phe Leu Ala Ser Pro Ala Gly Lys Asp Glu Tyr Ala Gln Trp Ile Val

```
                435                 440                 445
Ala Ser His Arg Ser Leu Leu Glu Val Met Glu Ala Phe Pro Ser Ala
450                 455                 460

Lys Pro Pro Leu Gly Val Phe Phe Ala Ser Val Ala Pro Arg Leu Gln
465                 470                 475                 480

Pro Arg Tyr Tyr Ser Ile Ser Ser Pro Lys Phe Ala Pro Asn Arg
                    485                 490                 495

Ile His Val Thr Cys Ala Leu Val Tyr Glu Gln Thr Pro Ser Gly Arg
                500                 505                 510

Val His Lys Gly Val Cys Ser Thr Trp Met Lys Asn Ala Val Pro Met
            515                 520                 525

Thr Glu Ser Gln Asp Cys Ser Trp Ala Pro Ile Tyr Val Arg Thr Ser
        530                 535                 540

Asn Phe Arg Leu Pro Ser Asp Pro Lys Val Pro Val Ile Met Ile Gly
545                 550                 555                 560

Pro Gly Thr Gly Leu Ala Pro Phe Arg Gly Phe Leu Gln Glu Arg Leu
                    565                 570                 575

Ala Gln Lys Glu Ala Gly Thr Glu Leu Gly Thr Ala Ile Leu Phe Phe
                580                 585                 590

Gly Cys Arg Asn Arg Lys Val Asp Phe Ile Tyr Glu Asp Glu Leu Asn
            595                 600                 605

Asn Phe Val Glu Thr Gly Ala Leu Ser Glu Leu Val Thr Ala Phe Ser
        610                 615                 620

Arg Glu Gly Ala Thr Lys Glu Tyr Val Gln His Lys Met Thr Gln Lys
625                 630                 635                 640

Thr Ser Asp Ile Trp Asn Leu Leu Ser Glu Gly Ala Tyr Leu Tyr Val
                    645                 650                 655

Cys Gly Asp Ala Lys Gly Met Ala Lys Asp Val His Arg Thr Leu His
                660                 665                 670

Thr Ile Val Gln Glu Gln Gly Ser Leu Asp Ser Ser Lys Ala Glu Leu
            675                 680                 685

Tyr Val Lys Asn Leu Gln Met Ala Gly Arg Tyr Leu Arg Asp Val Trp
        690                 695                 700

<210> SEQ ID NO 73
<211> LENGTH: 704
<212> TYPE: PRT
<213> ORGANISM: Artemisia annua

<400> SEQUENCE: 73

Met Gln Ser Thr Thr Ser Val Lys Leu Ser Pro Phe Asp Leu Met Thr
1               5                   10                  15

Ala Leu Leu Asn Gly Lys Val Ser Phe Asp Thr Ser Asn Thr Ser Asp
                20                  25                  30

Thr Asn Ile Pro Leu Ala Val Phe Met Glu Asn Arg Glu Leu Leu Met
            35                  40                  45

Ile Leu Thr Thr Ser Val Ala Val Leu Ile Gly Cys Val Val Val Leu
        50                  55                  60

Val Trp Arg Arg Ser Ser Ser Ala Ala Lys Lys Ala Ala Glu Ser Pro
65                  70                  75                  80

Val Ile Val Val Pro Lys Lys Val Thr Glu Asp Glu Val Asp Asp Gly
                    85                  90                  95

Arg Lys Lys Val Thr Val Phe Phe Gly Thr Gln Thr Gly Thr Ala Glu
                100                 105                 110
```

```
Gly Phe Ala Lys Ala Leu Val Glu Ala Lys Ala Arg Tyr Glu Lys
            115                 120                 125

Ala Val Phe Lys Val Ile Asp Leu Asp Asp Tyr Ala Ala Glu Asp
130                 135                 140

Glu Tyr Glu Glu Lys Leu Lys Lys Glu Ser Leu Ala Phe Phe Phe Leu
145                 150                 155                 160

Ala Thr Tyr Gly Asp Gly Glu Pro Thr Asp Asn Ala Ala Arg Phe Tyr
                165                 170                 175

Lys Trp Phe Thr Glu Gly Glu Lys Gly Glu Trp Leu Asp Lys Leu
            180                 185                 190

Gln Tyr Ala Val Phe Gly Leu Gly Asn Arg Gln Tyr Glu His Phe Asn
                195                 200                 205

Lys Ile Ala Lys Val Val Asp Glu Lys Leu Val Glu Gln Gly Ala Lys
            210                 215                 220

Arg Leu Val Pro Val Gly Met Gly Asp Asp Asp Gln Cys Ile Glu Asp
225                 230                 235                 240

Asp Phe Thr Ala Trp Lys Glu Leu Val Trp Pro Glu Leu Asp Gln Leu
                245                 250                 255

Leu Arg Asp Glu Asp Asp Thr Ser Val Ala Thr Pro Tyr Thr Ala Ala
            260                 265                 270

Val Ala Glu Tyr Arg Val Val Phe His Asp Lys Pro Glu Thr Tyr Asp
                275                 280                 285

Gln Asp Gln Leu Thr Asn Gly His Ala Val His Asp Ala Gln His Pro
            290                 295                 300

Cys Arg Ser Asn Val Ala Val Lys Lys Glu Leu His Ser Pro Leu Ser
305                 310                 315                 320

Asp Arg Ser Cys Thr His Leu Glu Phe Asp Ile Ser Asn Thr Gly Leu
                325                 330                 335

Ser Tyr Glu Thr Gly Asp His Val Gly Val Tyr Val Glu Asn Leu Ser
            340                 345                 350

Glu Val Val Asp Glu Ala Glu Lys Leu Ile Gly Leu Pro Pro His Thr
                355                 360                 365

Tyr Phe Ser Val His Ala Asp Asn Glu Asp Gly Thr Pro Leu Gly Gly
370                 375                 380

Ala Ser Leu Pro Pro Pro Phe Pro Pro Cys Thr Leu Arg Lys Ala Leu
385                 390                 395                 400

Ala Ser Tyr Ala Asp Val Leu Ser Ser Pro Lys Lys Ser Ala Leu Leu
                405                 410                 415

Ala Leu Ala Ala His Ala Thr Asp Ser Thr Glu Ala Asp Arg Leu Lys
            420                 425                 430

Phe Leu Ala Ser Pro Ala Gly Lys Asp Glu Tyr Ala Gln Trp Ile Val
            435                 440                 445

Ala Ser His Arg Ser Leu Leu Glu Val Met Glu Ala Phe Pro Ser Ala
            450                 455                 460

Lys Pro Pro Leu Gly Val Phe Phe Ala Ser Val Ala Pro Arg Leu Gln
465                 470                 475                 480

Pro Arg Tyr Tyr Ser Ile Ser Ser Ser Pro Arg Phe Ala Pro Asn Arg
                485                 490                 495

Ile His Val Thr Cys Ala Leu Val Tyr Glu Gln Thr Pro Ser Gly Arg
            500                 505                 510

Val His Lys Gly Val Cys Ser Thr Trp Met Lys Asn Ala Val Pro Met
            515                 520                 525

Thr Glu Ser Gln Asp Cys Ser Trp Ala Pro Ile Tyr Val Arg Thr Ser
```

```
                530             535             540
Asn Phe Arg Leu Pro Ser Asp Pro Lys Val Pro Val Ile Met Ile Gly
545                 550                 555                 560

Pro Gly Thr Gly Leu Ala Pro Phe Arg Gly Phe Leu Gln Glu Arg Leu
                565                 570                 575

Ala Gln Lys Glu Ala Gly Thr Glu Leu Gly Thr Ala Ile Leu Phe Phe
                580                 585                 590

Gly Cys Arg Asn Arg Lys Val Asp Phe Ile Tyr Glu Asp Glu Leu Asn
            595                 600                 605

Asn Phe Val Glu Thr Gly Ala Leu Ser Glu Leu Val Thr Ala Phe Ser
            610                 615                 620

Arg Glu Gly Ala Thr Lys Glu Tyr Val Gln His Lys Met Thr Gln Lys
625                 630                 635                 640

Ala Ser Asp Ile Trp Asn Leu Leu Ser Glu Gly Ala Tyr Leu Tyr Val
                645                 650                 655

Cys Gly Asp Ala Lys Gly Met Ala Lys Asp Val His Arg Thr Leu His
            660                 665                 670

Thr Ile Val Gln Glu Gln Gly Ser Leu Asp Ser Ser Lys Ala Glu Leu
            675                 680                 685

Tyr Val Lys Asn Leu Gln Met Ala Gly Arg Tyr Leu Arg Asp Val Trp
690                 695                 700

<210> SEQ ID NO 74
<211> LENGTH: 704
<212> TYPE: PRT
<213> ORGANISM: Artemisia annua

<400> SEQUENCE: 74

Met Gln Ser Thr Thr Ser Val Lys Leu Ser Pro Phe Asp Leu Met Thr
1               5                   10                  15

Ala Leu Leu Asn Gly Lys Val Ser Phe Asp Thr Ser Asn Thr Ser Asp
                20                  25                  30

Thr Asn Ile Pro Leu Ala Val Phe Met Glu Asn Arg Glu Leu Leu Met
            35                  40                  45

Ile Leu Thr Thr Ser Val Ala Val Leu Ile Gly Cys Val Val Val Leu
        50                  55                  60

Val Trp Arg Arg Ser Ser Ser Ala Ala Lys Lys Ala Ala Glu Ser Pro
65                  70                  75                  80

Val Ile Val Val Pro Lys Lys Val Thr Glu Asp Glu Val Asp Asp Gly
                85                  90                  95

Arg Lys Lys Val Thr Val Phe Phe Gly Thr Gln Thr Gly Thr Ala Glu
            100                 105                 110

Gly Phe Ala Lys Ala Leu Val Glu Glu Ala Lys Ala Arg Tyr Glu Lys
        115                 120                 125

Ala Val Phe Lys Val Ile Asp Leu Asp Asp Tyr Ala Ala Glu Asp Asp
    130                 135                 140

Glu Tyr Glu Glu Lys Leu Lys Lys Glu Ser Leu Ala Phe Phe Phe Leu
145                 150                 155                 160

Ala Thr Tyr Gly Asp Gly Glu Pro Thr Asp Asn Ala Ala Arg Phe Tyr
                165                 170                 175

Lys Trp Phe Thr Glu Gly Glu Glu Lys Gly Glu Trp Leu Asp Lys Leu
            180                 185                 190

Gln Tyr Ala Val Phe Gly Leu Gly Asn Arg Gln Tyr Glu His Phe Asn
        195                 200                 205
```

Lys Ile Ala Lys Val Val Asp Glu Lys Leu Val Glu Gln Gly Ala Lys
210                 215                 220

Arg Leu Val Pro Val Gly Met Gly Asp Asp Gln Cys Ile Glu Asp
225                 230                 235                 240

Asp Phe Thr Ala Trp Lys Glu Leu Val Trp Pro Glu Leu Asp Gln Leu
            245                 250                 255

Leu Arg Asp Glu Asp Asp Thr Ser Val Ala Thr Pro Tyr Thr Ala Ala
        260                 265                 270

Val Gly Glu Tyr Arg Val Val Phe His Asp Lys Pro Glu Thr Tyr Asp
            275                 280                 285

Gln Asp Gln Leu Thr Asn Gly His Ala Val His Asp Ala Gln His Pro
290                 295                 300

Cys Arg Ser Asn Val Ala Val Lys Lys Glu Leu His Ser Pro Leu Ser
305                 310                 315                 320

Asp Arg Ser Cys Thr His Leu Glu Phe Asp Ile Ser Asn Thr Gly Leu
                325                 330                 335

Ser Tyr Glu Thr Gly Asp His Val Gly Val Tyr Val Glu Asn Leu Ser
            340                 345                 350

Glu Val Val Asp Glu Ala Glu Lys Leu Ile Gly Leu Pro Pro His Thr
        355                 360                 365

Tyr Phe Ser Val His Thr Asp Asn Glu Asp Gly Thr Pro Leu Gly Gly
370                 375                 380

Ala Ser Leu Pro Pro Pro Phe Pro Pro Cys Thr Leu Arg Lys Ala Leu
385                 390                 395                 400

Ala Ser Tyr Ala Asp Val Leu Ser Ser Pro Lys Lys Ser Ala Leu Leu
                405                 410                 415

Ala Leu Ala Ala His Ala Thr Asp Ser Thr Glu Ala Asp Arg Leu Lys
            420                 425                 430

Phe Phe Ala Ser Pro Ala Gly Lys Asp Glu Tyr Ala Gln Trp Ile Val
435                 440                 445

Ala Ser His Arg Ser Leu Leu Glu Val Met Glu Ala Phe Pro Ser Ala
        450                 455                 460

Lys Pro Pro Leu Gly Val Phe Phe Ala Ser Val Ala Pro Arg Leu Gln
465                 470                 475                 480

Pro Arg Tyr Tyr Ser Ile Ser Ser Ser Pro Lys Phe Ala Pro Asn Arg
                485                 490                 495

Ile His Val Thr Cys Ala Leu Val Tyr Glu Gln Thr Pro Ser Gly Arg
            500                 505                 510

Val His Lys Gly Val Cys Ser Thr Trp Met Lys Asn Ala Val Pro Met
        515                 520                 525

Thr Glu Ser Gln Asp Cys Ser Trp Ala Pro Ile Tyr Val Arg Thr Ser
530                 535                 540

Asn Phe Arg Leu Pro Ser Asp Pro Lys Val Pro Val Ile Met Ile Gly
545                 550                 555                 560

Pro Gly Thr Gly Leu Ala Pro Phe Arg Gly Phe Leu Gln Glu Arg Leu
                565                 570                 575

Ala Gln Lys Glu Ala Gly Thr Glu Leu Gly Thr Ala Ile Leu Phe Phe
            580                 585                 590

Gly Cys Arg Asn Arg Lys Val Asp Phe Ile Tyr Glu Asp Glu Leu Asn
        595                 600                 605

Asn Phe Val Glu Thr Gly Ala Leu Ser Glu Leu Val Thr Ala Phe Ser
610                 615                 620

Arg Glu Gly Ala Thr Lys Glu Tyr Val Gln His Lys Met Thr Gln Lys

```
                625            630           635            640
Ala Ser Asp Ile Trp Asn Leu Leu Ser Glu Gly Ala Tyr Leu Tyr Val
                    645               650               655

Cys Gly Asp Ala Lys Gly Met Ala Lys Asp Val His Arg Thr Leu His
                660               665               670

Thr Ile Val Gln Glu Gln Gly Ser Leu Asp Ser Ser Lys Ala Glu Leu
                    675               680               685

Tyr Val Lys Asn Leu Gln Met Ala Gly Arg Tyr Leu Arg Asp Val Trp
    690               695               700

<210> SEQ ID NO 75
<211> LENGTH: 692
<212> TYPE: PRT
<213> ORGANISM: Populus trichocarpa

<400> SEQUENCE: 75

Met Ser Ser Gly Gly Ser Asn Leu Ala Arg Phe Val Gln Ser Val Leu
1               5                   10                  15

Gly Ile Ser Phe Gly Asp Ser Leu Ser Asp Ser Val Val Ile Ile
                20                  25                  30

Thr Thr Ser Phe Ala Ala Leu Val Gly Leu Val Val Leu Val Leu Lys
            35                  40                  45

Arg Ser Ser Asp Arg Ser Lys Asp Val Lys Pro Leu Val Val Pro Lys
50                  55                  60

Ser Leu Ser Ile Lys Asp Glu Glu Asp Glu Ser Glu Ala Leu Gly Gly
65                  70                  75                  80

Lys Thr Lys Val Thr Ile Phe Tyr Gly Thr Gln Thr Gly Thr Ala Glu
                85                  90                  95

Gly Phe Ala Lys Ala Leu Ala Glu Glu Val Lys Ala Arg Tyr Glu Lys
            100                 105                 110

Ala Ala Val Lys Val Phe Asp Leu Asp Asp Tyr Ala Met Glu Asp Asp
        115                 120                 125

Gln Tyr Glu Glu Lys Leu Lys Lys Glu Thr Leu Ala Leu Phe Met Val
    130                 135                 140

Ala Thr Tyr Gly Asp Gly Glu Pro Thr Asp Asn Ala Ala Arg Phe Tyr
145                 150                 155                 160

Lys Trp Phe Thr Glu Gly Asn Glu Arg Gly Ile Trp Leu Gln Gln Leu
                165                 170                 175

Ser Tyr Gly Val Phe Gly Leu Gly Asn Arg Gln Tyr Glu His Phe Asn
            180                 185                 190

Lys Ile Ala Lys Val Leu Asp Asp Leu Leu Tyr Glu Gln Gly Gly Lys
        195                 200                 205

Arg Leu Val Pro Val Gly Leu Gly Asp Asp Gln Cys Ile Glu Asp
    210                 215                 220

Asp Phe Ser Ala Trp Lys Glu Phe Leu Trp Pro Glu Leu Asp Gln Leu
225                 230                 235                 240

Leu Arg Asp Glu Asp Val Asn Ala Pro Ser Thr Pro Tyr Thr Ala
                245                 250                 255

Ala Ile Pro Glu Tyr Arg Leu Val Ile His Asp Pro Ser Ile Ile Ser
            260                 265                 270

Val Glu Asp Lys Phe Ser Asn Leu Ala Asn Gly Asn Val Ser Phe Asp
        275                 280                 285

Ile His His Pro Cys Arg Val Asn Val Ala Val Gln Lys Glu Leu His
    290                 295                 300
```

```
Lys Ala Glu Ser Asp Arg Ser Cys Ile His Leu Glu Phe Asp Ile Thr
305                 310                 315                 320

Gly Thr Gly Ile Thr Tyr Glu Thr Gly Asp His Leu Gly Val Tyr Ala
            325                 330                 335

Glu Asn Ser Asp Glu Thr Val Glu Glu Ala Gly Lys Leu Leu Asp Lys
            340                 345                 350

Pro Leu Asp Leu Leu Phe Ser Ile His Ala Asp Asn Glu Asp Gly Thr
            355                 360                 365

Ala Ile Gly Ser Ser Leu Pro Pro Phe Pro Gly Pro Cys Thr Leu
370                 375                 380

His Thr Ala Leu Ala Cys Tyr Ala Asp Leu Leu Ser Pro Pro Lys Lys
385                 390                 395                 400

Ala Ala Leu Leu Ala Leu Ala Ala His Ala Ser Glu Pro Ser Glu Ala
            405                 410                 415

Asp Arg Leu Lys Phe Leu Ser Ser Pro Gln Gly Lys Asn Glu Tyr Ser
            420                 425                 430

His Trp Val Met Ala Ser Gln Arg Ser Leu Leu Glu Val Met Ala Glu
            435                 440                 445

Phe Pro Ser Ser Lys Pro Pro Leu Gly Ile Phe Phe Ala Ala Val Ala
450                 455                 460

Pro Arg Leu Gln Pro Arg Tyr Tyr Ser Ile Ser Ser Ser Pro Arg Tyr
465                 470                 475                 480

Thr Pro Asn Arg Val His Val Thr Cys Ala Leu Val Tyr Gly Pro Thr
            485                 490                 495

Pro Thr Gly Arg Ile His Lys Gly Val Cys Ser Thr Trp Met Lys Asn
            500                 505                 510

Ala Val Pro Leu Glu Lys Ser Tyr Glu Cys Ser Trp Ala Pro Ile Phe
            515                 520                 525

Thr Arg Thr Ser Asn Phe Lys Leu Pro Ala Asp Pro Ser Thr Pro Ile
530                 535                 540

Ile Met Val Gly Pro Gly Thr Gly Leu Ala Pro Phe Arg Gly Phe Leu
545                 550                 555                 560

Gln Glu Arg Ile Ala Leu Lys Glu Asp Gly Val Lys Leu Gly Pro Ala
            565                 570                 575

Leu Leu Phe Phe Gly Cys Arg Asn Arg Arg Met Asp Phe Ile Tyr Glu
            580                 585                 590

Asp Glu Leu Asn Asn Phe Val Glu Gln Gly Val Ile Ser Glu Leu Ile
            595                 600                 605

Val Ala Phe Ser Arg Glu Gly Pro Gln Lys Glu Tyr Val Gln His Lys
610                 615                 620

Met Val Asp Arg Ala Ala Glu Ile Trp Thr Ile Ile Ser Gln Gly Gly
625                 630                 635                 640

Tyr Phe Tyr Val Cys Gly Asp Ala Lys Gly Met Ala Arg Asp Val His
            645                 650                 655

Arg Thr Leu His Thr Ile Val Gln Glu Gln Gly Gly Leu Asp Ser Ser
            660                 665                 670

Lys Thr Glu Ser Met Val Lys Lys Leu Gln Met Glu Gly Arg Tyr Leu
            675                 680                 685

Arg Asp Val Trp
        690
```

<210> SEQ ID NO 76
<211> LENGTH: 712
<212> TYPE: PRT

<213> ORGANISM: Populus trichocarpa

<400> SEQUENCE: 76

| Met | Gln | Ser | Ser | Ser | Ser | Met | Lys | Val | Ser | Pro | Leu | Glu | Leu | Met |
|1| | | |5| | | |10| | | | |15| |

Gln Ala Ile Ile Lys Gly Lys Val Asp Pro Thr Asn Val Ser Ser Glu
         20                  25                  30

Ser Gly Gly Ser Ala Ala Glu Met Ala Thr Leu Ile Arg Glu Asn Arg
             35                  40                  45

Glu Phe Val Ile Ile Leu Thr Thr Ser Ile Ala Val Leu Ile Gly Tyr
 50                  55                  60

Val Val Val Leu Ile Trp Arg Arg Ser Ser Gly Tyr Gln Lys Pro Lys
 65                  70                  75                  80

Val Pro Val Pro Pro Lys Pro Leu Ile Val Lys Asp Leu Glu Pro Glu
                 85                  90                  95

Val Asp Asp Gly Lys Lys Val Thr Ile Phe Phe Gly Thr Gln Thr
                100                 105                 110

Gly Thr Ala Glu Gly Phe Ala Lys Ala Leu Ala Glu Glu Ala Lys Ala
            115                 120                 125

Arg Tyr Glu Lys Ala Ile Phe Lys Thr Val Asp Leu Asp Asp Tyr Ala
130                 135                 140

Glu Asp Asp Asp Glu Tyr Glu Glu Lys Leu Lys Lys Glu Ser Leu Ala
145                 150                 155                 160

Ile Phe Phe Leu Ala Thr Tyr Gly Asp Gly Glu Pro Thr Asp Asn Ala
                165                 170                 175

Ala Arg Phe Tyr Lys Trp Phe Thr Asp Gly Asn Glu Arg Gly Glu Trp
            180                 185                 190

Leu Lys Glu Leu Pro Tyr Ala Val Phe Gly Leu Gly Asn Arg Gln Tyr
        195                 200                 205

Glu His Phe Asn Lys Ile Ala Ile Val Val Asp Lys Ile Leu Gly Asn
210                 215                 220

Gln Gly Gly Lys Gln Leu Val Pro Val Gly Leu Gly Asp Asp Asp Gln
225                 230                 235                 240

Cys Met Glu Asp Asp Phe Ala Ala Trp Arg Glu Leu Leu Trp Pro Glu
                245                 250                 255

Leu Asp Gln Leu Leu Leu Asp Gly Asp Asp Pro Thr Gly Val Ser Thr
            260                 265                 270

Pro Tyr Thr Ala Ala Val Ala Glu Tyr Arg Val Val Leu His Asp Pro
        275                 280                 285

Glu Asp Ala Pro Leu Glu Asp Asn Trp Ser Asn Ala Asn Gly His
290                 295                 300

Ala Ile Tyr Asp Ala Gln His Pro Cys Arg Ala Asn Val Thr Val Arg
305                 310                 315                 320

Arg Glu Leu His Thr Pro Ala Ser Asp Arg Ser Cys Thr His Leu Glu
                325                 330                 335

Phe Asp Ile Ser Gly Thr Gly Leu Val Tyr Gly Thr Gly Asp His Val
            340                 345                 350

Gly Val Tyr Cys Glu Asn Leu Ser Glu Ile Val Glu Glu Ala Leu Gln
        355                 360                 365

Leu Leu Gly Leu Ser Pro Asp Ile Tyr Phe Thr Ile His Thr Asp Asn
    370                 375                 380

Glu Asp Gly Thr Pro Leu Ser Gly Ser Ala Leu Pro Pro Pro Phe Pro
385                 390                 395                 400

```
Ser Ser Thr Leu Arg Thr Ala Leu Thr Arg Tyr Ala Asp Leu Leu Ser
                405                 410                 415

Ser Pro Lys Lys Ser Ala Leu Met Ala Leu Ala Ala His Ala Thr Asn
            420                 425                 430

Pro Thr Glu Ala Asp Arg Leu Arg His Leu Ala Ser Pro Ala Gly Lys
        435                 440                 445

Asp Glu Tyr Ala Gln Trp Ile Val Ala Asn His Arg Ser Leu Leu Glu
    450                 455                 460

Val Met Ala Glu Phe Pro Ser Ala Lys Pro Pro Leu Gly Val Phe Phe
465                 470                 475                 480

Ala Ser Val Ala Pro Arg Leu Leu Pro Arg Tyr Tyr Ser Ile Ser Ser
                485                 490                 495

Ser Pro Ser Met Ala Pro Ser Arg Ile His Val Thr Cys Ala Leu Val
            500                 505                 510

Leu Glu Lys Thr Pro Ala Gly Arg Ile His Lys Gly Val Cys Ser Thr
        515                 520                 525

Trp Met Lys Asn Ala Val Pro Leu Glu Lys Ser His Asp Cys Ser Trp
    530                 535                 540

Ala Pro Ile Phe Val Arg Gln Ser Asn Phe Lys Leu Pro Ala Asp Thr
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Gln Lys Glu Ala Gly Ala Glu
            580                 585                 590

Leu Gly Ser Ser Val Leu Phe Phe Gly Cys Arg Asn Arg Gln Met Asp
        595                 600                 605

Phe Ile Tyr Glu Asp Glu Leu Asn Asn Phe Val Glu Ser Gly Ala Leu
    610                 615                 620

Ser Glu Leu Ser Val Ala Phe Ser Arg Glu Gly Pro Thr Lys Glu Tyr
625                 630                 635                 640

Val Gln His Lys Met Met Gln Lys Ala Ser Asp Ile Trp Asn Met Ile
                645                 650                 655

Ser Gln Gly Gly Tyr Leu Tyr Val Cys Gly Asp Ala Lys Gly Met Ala
            660                 665                 670

Lys Asp Val His Arg Thr Leu His Thr Ile Val Gln Glu Gln Gly Ser
        675                 680                 685

Leu Asp Asn Ser Lys Thr Glu Ser Phe Val Lys Gly Leu Gln Met Asn
    690                 695                 700

Gly Arg Tyr Leu Arg Asp Val Trp
705                 710

<210> SEQ ID NO 77
<211> LENGTH: 712
<212> TYPE: PRT
<213> ORGANISM: Populus trichocarpa

<400> SEQUENCE: 77

Met Glu Ser Ser Ser Ser Ile Lys Val Ser Pro Leu Asp Leu Met
1               5                   10                  15

Gln Ala Ile Ile Lys Gly Lys Val Asp Pro Ala Asn Val Ser Ser Glu
            20                  25                  30

Ser Gly Gly Ser Val Ala Glu Val Ala Thr Leu Ile Leu Glu Asn Arg
        35                  40                  45

Glu Phe Val Met Ile Leu Thr Thr Ser Ile Ala Val Leu Ile Gly Cys
    50                  55                  60
```

-continued

```
Val Val Val Leu Ile Trp Arg Arg Ser Ser Gly Tyr Gln Arg Pro Lys
 65                  70                  75                  80

Val Pro Val Pro Pro Lys Pro Leu Ile Val Lys Asp Leu Glu Pro Glu
             85                  90                  95

Val Asp Asp Gly Lys Lys Val Thr Ile Phe Phe Gly Thr Gln Thr
            100                 105                 110

Gly Thr Ala Glu Gly Phe Ala Lys Ala Leu Ala Glu Glu Ala Lys Ala
            115                 120                 125

Arg Tyr Asp Lys Ala Thr Phe Lys Thr Val Asp Met Asp Asp Tyr Ala
            130                 135                 140

Gly Asp Asp Asp Glu Tyr Glu Glu Lys Leu Lys Lys Glu Asp Leu Val
145                 150                 155                 160

Ile Phe Phe Leu Ala Thr Tyr Gly Asp Gly Glu Pro Thr Asp Asn Ala
                165                 170                 175

Ala Arg Phe Tyr Lys Trp Phe Thr Glu Gly Asn Glu Arg Gly Glu Trp
            180                 185                 190

Leu Lys Asp Leu Pro Tyr Ala Val Phe Gly Leu Gly Asn Arg Gln Tyr
            195                 200                 205

Glu His Phe Asn Lys Ile Ala Ile Val Val Asp Lys Ile Phe Ala Asp
            210                 215                 220

Gln Gly Gly Lys Arg Leu Ala Pro Val Gly Leu Gly Asp Asp Gln
225                 230                 235                 240

Cys Met Glu Asp Asp Phe Ala Ala Trp Arg Glu Leu Leu Trp Pro Glu
                245                 250                 255

Met Asp Gln Leu Leu Leu Asp Gly Asp Asp Pro Thr Ala Val Ser Thr
            260                 265                 270

Pro Tyr Ala Ala Thr Val Ser Glu Tyr Arg Val Val Phe His Ser Pro
            275                 280                 285

Glu Asp Ala Pro Leu Glu Asp Asp Asn Trp Ser Asn Ala Asn Gly His
            290                 295                 300

Ala Val Tyr Asp Ala Gln His Pro Cys Arg Ala Asn Val Ala Val Arg
305                 310                 315                 320

Arg Glu Leu His Thr Pro Ala Ser Asp Arg Ser Cys Thr His Leu Glu
                325                 330                 335

Phe Glu Ile Ser Gly Thr Gly Leu Ala Tyr Gly Thr Gly Asp His Val
            340                 345                 350

Gly Val Tyr Cys Glu Asn Leu Ser Glu Thr Val Glu Glu Ala Leu Gln
            355                 360                 365

Leu Leu Gly Leu Ser Pro Asp Thr Tyr Phe Ser Ile His Asn Asp Asn
            370                 375                 380

Glu Asp Gly Thr Pro Leu Ser Gly Gly Ala Leu Pro Pro Phe Pro
385                 390                 395                 400

Pro Ser Thr Leu Lys Thr Ala Leu Ala Arg Tyr Ala Asp Leu Leu Ser
            405                 410                 415

Leu Pro Lys Lys Ser Ala Leu Met Ala Leu Ala Ala His Ala Thr Asp
            420                 425                 430

Pro Thr Glu Ala Asp Arg Leu Arg His Leu Ala Ser Pro Ala Gly Lys
            435                 440                 445

Asp Glu Tyr Ala Gln Leu Leu Val Ala Asn Gln Arg Ser Leu Leu Glu
            450                 455                 460

Val Met Ala Glu Phe Pro Ser Ala Lys Pro Pro Leu Gly Val Phe Phe
465                 470                 475                 480
```

```
Ala Ser Val Ala Pro Arg Leu Gln Pro Arg Tyr Tyr Ser Ile Ser Ser
                485                 490                 495

Ser Pro Arg Met Ala Pro Ser Arg Ile His Val Thr Cys Ala Leu Val
            500                 505                 510

Leu Glu Lys Thr Leu Gly Gly Arg Ile His Lys Gly Val Cys Ser Thr
        515                 520                 525

Trp Met Lys Asn Ala Val Pro Leu Glu Lys Ser His Asp Cys Ser Trp
    530                 535                 540

Ala Pro Val Phe Val Arg Gln Ser Asn Phe Lys Leu Pro Ala Asp Ala
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Lys Glu Ala Gly Ser Glu
            580                 585                 590

Leu Gly Ser Ser Val Leu Phe Phe Gly Cys Arg Asn Arg Lys Met Asp
        595                 600                 605

Phe Ile Tyr Glu Asp Glu Leu Asn Asn Phe Val Glu Ser Gly Ala Leu
    610                 615                 620

Ser Glu Leu Val Val Ala Phe Ser Arg Glu Gly Pro Thr Lys Glu Tyr
625                 630                 635                 640

Val Gln His Lys Met Met Gln Lys Ala Ser Asp Ile Trp Asn Met Ile
                645                 650                 655

Ser Gln Gly Gly Tyr Leu Tyr Val Cys Gly Asp Ala Lys Gly Met Ala
            660                 665                 670

Lys Asp Val His Arg Ala Leu His Thr Ile Val Gln Glu Gln Gly Ser
        675                 680                 685

Leu Asp Asn Ser Lys Thr Glu Ser Phe Val Lys Ser Leu Gln Met Asn
    690                 695                 700

Gly Arg Tyr Leu Arg Asp Val Trp
705                 710

<210> SEQ ID NO 78
<211> LENGTH: 690
<212> TYPE: PRT
<213> ORGANISM: Vigna radiata

<400> SEQUENCE: 78

Met Ala Ser Asn Ser Asp Leu Val Arg Ala Val Glu Ser Phe Leu Gly
1               5                   10                  15

Val Ser Leu Gly Asp Ser Val Ser Asp Ser Leu Leu Leu Ile Ala Thr
            20                  25                  30

Thr Ser Ala Ala Val Val Gly Leu Leu Val Phe Leu Trp Lys Lys
        35                  40                  45

Ser Ser Asp Arg Ser Lys Glu Val Lys Pro Val Val Pro Arg Asp
    50                  55                  60

Leu Met Met Glu Glu Glu Glu Val Asp Val Ala Ala Gly Lys Thr
65                  70                  75                  80

Lys Val Thr Ile Phe Phe Gly Thr Gln Thr Gly Thr Ala Glu Gly Phe
                85                  90                  95

Ala Lys Ala Leu Ala Glu Glu Ile Lys Ala Arg Tyr Glu Lys Ala Ala
            100                 105                 110

Val Lys Val Val Asp Leu Asp Asp Tyr Ala Ala Asp Asp Asp Leu Tyr
        115                 120                 125

Glu Glu Lys Leu Lys Lys Glu Ser Leu Val Phe Phe Met Leu Ala Thr
    130                 135                 140
```

```
Tyr Gly Asp Gly Glu Pro Ile Asp Asn Ala Ala Arg Phe Tyr Lys Trp
145                 150                 155                 160

Phe Thr Glu Gly Lys Asp Glu Arg Gly Ile Trp Leu Gln Lys Leu Thr
            165                 170                 175

Tyr Gly Val Phe Gly Leu Gly Asn Arg Gln Tyr Glu His Phe Asn Lys
            180                 185                 190

Ile Gly Lys Val Val Asp Glu Glu Leu Ala Glu Gln Gly Ala Lys Arg
        195                 200                 205

Leu Val Ala Val Gly Leu Gly Asp Asp Gln Ser Ile Glu Asp Asp
    210                 215                 220

Phe Ser Ala Trp Lys Glu Ser Leu Trp Ser Glu Leu Asp Gln Leu Leu
225                 230                 235                 240

Arg Asp Glu Asp Ala Asn Thr Val Ser Thr Pro Tyr Thr Ala Ala
                245                 250                 255

Ile Leu Glu Tyr Arg Val Val Ile His Asp Pro Thr Ala Ala Ser Thr
            260                 265                 270

Tyr Asp Asn His Ser Thr Val Ala Asn Gly Asn Thr Glu Phe Asp Ile
            275                 280                 285

His His Pro Cys Arg Val Asn Val Ala Val Gln Lys Glu Leu His Lys
290                 295                 300

Pro Glu Ser Asp Arg Ser Cys Ile His Leu Glu Phe Asp Ile Ser Gly
305                 310                 315                 320

Thr Ser Ile Thr Tyr Asp Thr Gly Asp His Val Gly Val Tyr Ala Glu
            325                 330                 335

Asn Cys Asn Glu Thr Val Glu Glu Thr Gly Lys Leu Leu Gly Gln Asn
            340                 345                 350

Leu Asp Leu Phe Phe Ser Leu His Thr Asp Lys Asp Asp Gly Thr Ser
            355                 360                 365

Leu Gly Gly Ser Leu Leu Pro Pro Phe Pro Gly Pro Cys Ser Leu Arg
    370                 375                 380

Thr Ala Leu Ala Arg Tyr Ala Asp Leu Leu Asn Pro Pro Arg Lys Ala
385                 390                 395                 400

Ala Leu Leu Ala Leu Ala Thr His Ala Ser Glu Pro Ser Asp Glu Arg
                405                 410                 415

Leu Lys Phe Leu Ser Ser Pro Gln Gly Lys Asp Glu Tyr Ser Lys Trp
            420                 425                 430

Val Val Gly Ser Gln Arg Ser Leu Val Glu Val Met Ala Glu Phe Pro
        435                 440                 445

Ser Ala Lys Pro Pro Leu Gly Val Phe Phe Ala Ala Ile Ala Pro Arg
    450                 455                 460

Leu Gln Pro Arg Tyr Tyr Ser Ile Ser Ser Ser Pro Arg Phe Ala Pro
465                 470                 475                 480

Gln Arg Val His Val Thr Cys Ala Leu Val Tyr Gly Pro Thr Pro Thr
            485                 490                 495

Gly Arg Ile His Lys Gly Val Cys Ser Thr Trp Met Lys Asn Ala Ile
            500                 505                 510

Pro Ser Glu Lys Ser Gln Asp Cys Ser Ser Ala Pro Ile Phe Ile Arg
            515                 520                 525

Pro Ser Asn Phe Lys Leu Pro Val Asp His Ser Ile Pro Ile Ile Met
            530                 535                 540

Val Gly Pro Gly Thr Gly Leu Ala Pro Phe Arg Gly Phe Leu Gln Glu
545                 550                 555                 560
```

```
Arg Tyr Ala Leu Lys Glu Asp Gly Val Gln Leu Gly Pro Ala Leu Leu
            565             570             575

Phe Phe Gly Cys Arg Asn Arg Gln Met Asp Phe Ile Tyr Glu Asp Glu
            580             585             590

Leu Lys Ser Phe Val Glu Gln Gly Ser Leu Ser Glu Leu Ile Val Ala
            595             600             605

Phe Ser Arg Glu Gly Ala Glu Lys Glu Tyr Val Gln His Lys Met Met
            610             615             620

Asp Lys Ala Ala His Leu Trp Ser Leu Ile Ser Gln Gly Gly Tyr Leu
625             630             635             640

Tyr Val Cys Gly Asp Ala Lys Gly Met Ala Arg Asp Val His Arg Thr
            645             650             655

Leu His Ser Ile Val Gln Glu Gln Glu Asn Val Asp Ser Thr Lys Ala
            660             665             670

Glu Ala Ile Val Lys Lys Leu Gln Met Asp Gly Arg Tyr Leu Arg Asp
            675             680             685

Val Trp
    690

<210> SEQ ID NO 79
<211> LENGTH: 699
<212> TYPE: PRT
<213> ORGANISM: Petroselinum crispum

<400> SEQUENCE: 79

Met Gln Ser Glu Ser Met Glu Val Ser Pro Val Asp Leu Leu Ala Ser
1               5                   10                  15

Ile Leu Lys Ile Asp Ser Val Glu Ser Met Thr Leu Leu Glu Asn
            20                  25                  30

Arg Asp Val Leu Met Leu Leu Thr Thr Ser Phe Ala Val Leu Ile Gly
            35                  40                  45

Leu Gly Leu Val Met Met Trp Arg Arg Ser Thr Thr Met Thr Lys Ser
    50                  55                  60

Ala Lys Lys Leu Glu Pro Ala Lys Ile Val Ile Pro Lys Phe Glu Met
65              70                  75                  80

Glu Glu Glu Val Asp Asp Gly Lys Lys Lys Val Thr Ile Phe Tyr Gly
            85                  90                  95

Thr Gln Thr Gly Thr Ala Glu Gly Phe Ala Lys Ala Leu Ala Glu Glu
            100                 105                 110

Ala Lys Ala Arg Tyr Gln Asp Ala Ile Phe Lys Thr Ile Asp Leu Asp
            115                 120                 125

Asp Tyr Ala Gly Asp Asp Glu Tyr Glu Thr Lys Leu Lys Lys Glu
            130                 135                 140

Ser Met Val Phe Phe Phe Leu Ala Thr Tyr Gly Asp Gly Glu Pro Thr
145             150                 155                 160

Asp Asn Ala Ala Arg Phe Tyr Lys Trp Phe Cys Glu Gly Lys Glu Arg
            165                 170                 175

Gly Glu Trp Leu Asn Asn Leu Gln Tyr Gly Val Phe Gly Leu Gly Asn
            180                 185                 190

Arg Gln Tyr Glu His Phe Asn Lys Ile Ala Val Val Asp Asp Gly
            195                 200                 205

Leu Val Glu Gln Gly Ala Lys Arg Leu Val Pro Val Gly Met Gly Asp
    210                 215                 220

Asp Asp Gln Cys Ile Glu Asp Asp Phe Thr Ala Trp Arg Glu Leu Val
225             230                 235                 240
```

```
Trp Pro Glu Leu Asp Gln Leu Leu Asp Glu Ser Lys Ala Ala
            245                 250                 255

Ala Thr Pro Tyr Thr Ala Ala Val Leu Glu Tyr Arg Val Gln Phe Tyr
            260                 265                 270

Asn Gln Thr Asp Thr Ser Ser Pro Leu Val Arg Ser Met Ser Lys Leu
            275                 280                 285

Asn Gly His Ala Val Tyr Asp Ala Gln His Pro Cys Arg Ala Asn Val
            290                 295                 300

Ala Val Arg Arg Glu Leu His Thr Pro Ala Ser Asp Arg Ser Cys Thr
305                 310                 315                 320

His Leu Glu Phe Asp Ile Ser Ser Thr Gly Leu Ala Tyr Glu Thr Gly
                325                 330                 335

Asp His Val Gly Val Tyr Thr Glu Asn Leu Ile Glu Ile Val Glu Glu
                340                 345                 350

Ala Glu Arg Leu Ile Asp Ile Ser Pro Asp Thr Tyr Phe Ser Ile His
                355                 360                 365

Thr Glu Asn Glu Asp Gly Thr Pro Leu Ser Gly Gly Ser Leu Pro Pro
            370                 375                 380

Pro Phe Pro Pro Cys Ser Phe Arg Thr Ala Leu Thr Arg Tyr Ala Asp
385                 390                 395                 400

Leu Leu Ser Thr Pro Lys Lys Ser Ala Leu Val Ala Leu Ala Ala His
                405                 410                 415

Ala Ser Asp Pro Ser Glu Ala Glu Arg Leu Arg Phe Leu Ala Ser Pro
                420                 425                 430

Val Gly Lys Asp Glu Tyr Ala Gln Trp Leu Val Ala Ser Gln Arg Ser
            435                 440                 445

Leu Leu Glu Val Leu Ala Ala Phe Pro Ser Ala Lys Pro Pro Leu Gly
            450                 455                 460

Val Phe Phe Ala Ser Val Ala Pro Arg Leu Gln Pro Arg Tyr Tyr Ser
465                 470                 475                 480

Ile Ser Ser Ser Pro Arg Met Ala Pro Ser Arg Ile His Val Thr Cys
                485                 490                 495

Ala Leu Val His Glu Thr Thr Pro Ala Gly Arg Ile His Lys Gly Leu
                500                 505                 510

Cys Ser Thr Trp Met Lys Asn Ala Val Ser Leu Glu Asp Ala His Val
            515                 520                 525

Ser Ser Trp Ala Pro Ile Phe Val Arg Gln Ser Asn Phe Arg Leu Pro
            530                 535                 540

Thr Asp Ser Lys Val Pro Ile Ile Met Ile Gly Pro Gly Thr Gly Leu
545                 550                 555                 560

Ala Pro Phe Arg Gly Phe Met Gln Glu Arg Leu Ala Leu Lys Glu Ser
                565                 570                 575

Gly Ala Glu Leu Gly Ser Ala Val Leu Tyr Phe Gly Cys Arg Asn Arg
                580                 585                 590

Lys Leu Asp Phe Ile Tyr Glu Asp Glu Leu Asn His Phe Val Glu Thr
            595                 600                 605

Gly Ala Ile Ser Glu Met Val Val Ala Phe Ser Arg Glu Gly Pro Ala
610                 615                 620

Lys Glu Tyr Val Gln His Lys Met Ser Gln Lys Ala Ser Glu Ile Trp
625                 630                 635                 640

Asp Met Ile Ser His Gly Ala Tyr Ile Tyr Val Cys Gly Asp Ala Lys
                645                 650                 655
```

```
Gly Met Ala Arg Asp Val His Arg Met Leu His Thr Ile Ala Gln Glu
            660                 665                 670

Gln Gly Ala Leu Asp Ser Ser His Ala Glu Ser Leu Val Lys Asn Leu
            675                 680                 685

His Met Ser Gly Arg Tyr Leu Arg Asp Val Trp
            690                 695

<210> SEQ ID NO 80
<211> LENGTH: 681
<212> TYPE: PRT
<213> ORGANISM: Petroselinum crispum

<400> SEQUENCE: 80

Met Gly Gly Glu Ser Leu Ala Thr Ser Leu Pro Ala Thr Leu Leu Glu
1               5                   10                  15

Asn Arg Asp Leu Leu Met Leu Leu Thr Thr Ser Ile Ala Val Leu Ile
            20                  25                  30

Gly Cys Ala Val Val Leu Val Trp Arg Arg Ser Ser Leu Arg Ser Val
        35                  40                  45

Lys Ser Val Glu Pro Pro Lys Leu Ile Val Pro Lys Val Glu Ile Glu
    50                  55                  60

Asp Glu Val Asp Asp Gly Lys Lys Lys Val Thr Val Phe Phe Gly Thr
65                  70                  75                  80

Gln Thr Gly Thr Ala Glu Gly Phe Ala Lys Ala Phe Ala Glu Glu Ala
                85                  90                  95

Lys Ala Arg Tyr Glu Lys Ala Lys Phe Arg Val Val Asp Leu Asp Asp
            100                 105                 110

Tyr Ala Ala Glu Asp Glu Glu Tyr Glu Ala Lys Phe Lys Lys Glu Ser
            115                 120                 125

Phe Ala Phe Phe Phe Leu Ala Thr Tyr Gly Asp Gly Glu Pro Thr Asp
    130                 135                 140

Asn Ala Ala Arg Phe Tyr Lys Trp Phe Ser Glu Gly Glu Glu Lys Gly
145                 150                 155                 160

Asp Trp Leu Asn Lys Leu Gln Tyr Gly Val Phe Gly Leu Gly Asn Arg
                165                 170                 175

Gln Tyr Glu His Phe Asn Lys Ile Ala Lys Val Val Asp Asp Gly Leu
            180                 185                 190

Ala Asp Gln Gly Ala Lys Arg Ile Val Glu Val Gly Met Gly Asp Asp
            195                 200                 205

Asp Gln Cys Ile Glu Asp Asp Phe Thr Ala Trp Arg Glu Leu Val Trp
    210                 215                 220

Pro Glu Leu Asp Lys Leu Leu Leu Asp Glu Asp Asp Thr Ser Ala Ala
225                 230                 235                 240

Thr Pro Tyr Thr Ala Ala Val Leu Glu Tyr Arg Val Val Tyr Asp
                245                 250                 255

Gln Leu Asp Thr Ala Thr Leu Asp Arg Ser Leu Ser Thr Gln Asn Gly
            260                 265                 270

His Thr Val His Asp Ala Gln His Pro Cys Arg Ser Ser Val Ala Ala
        275                 280                 285

Lys Lys Glu Leu His Lys Pro Ala Ser Asp Arg Ser Cys Ile His Leu
    290                 295                 300

Glu Phe Asp Ile Ser His Thr Gly Leu Ala Tyr Glu Thr Gly Asp His
305                 310                 315                 320

Val Gly Val Tyr Cys Glu Asn Leu Val Glu Ile Val Glu Glu Ala Glu
                325                 330                 335
```

Lys Leu Leu Gly Met Gln Pro Asn Thr Tyr Phe Ser Val His Ile Asp
                340                 345                 350

Asp Glu Asp Gly Thr Pro Leu Thr Gly Gly Ser Leu Pro Pro Pro Phe
                355                 360                 365

Pro Pro Cys Thr Val Arg Ser Ala Leu Ala Lys Tyr Ala Asp Leu Leu
            370                 375                 380

Ser Ser Pro Lys Lys Ser Ala Leu Leu Ala Leu Ala Ala His Ala Ser
385                 390                 395                 400

Asp Pro Thr Glu Ala Asp Arg Leu Arg Leu Leu Ala Ser Pro Ala Gly
                405                 410                 415

Lys Asp Glu Tyr Ala Gln Trp Val Val Ala Ser His Arg Ser Leu Leu
                420                 425                 430

Glu Val Leu Ala Glu Phe Pro Ser Ala Lys Pro Pro Leu Gly Val Phe
                435                 440                 445

Phe Ala Ser Val Ala Pro Arg Leu Gln Pro Arg Tyr Tyr Ser Ile Ser
                450                 455                 460

Ser Ser Pro Arg Met Val Pro Ser Arg Ile His Val Thr Cys Ala Leu
465                 470                 475                 480

Val Tyr Glu Lys Thr Pro Thr Gly Arg Ile His Lys Gly Val Cys Ser
                485                 490                 495

Thr Trp Met Lys Asn Ala Val Ser Leu Glu Glu Ser His Asp Cys Ser
                500                 505                 510

Trp Ala Pro Ile Phe Val Arg Gln Ser Asn Phe Lys Leu Pro Ser Asp
            515                 520                 525

Thr Lys Val Pro Ile Ile Met Ile Gly Pro Gly Thr Gly Leu Ala Pro
530                 535                 540

Phe Arg Gly Phe Leu Gln Glu Arg Gln Ala Leu Lys Asp Ala Gly Ala
545                 550                 555                 560

Glu Leu Gly Thr Ala Val Leu Tyr Phe Gly Cys Arg Asn Arg Asn Leu
                565                 570                 575

Asp Phe Ile Tyr Glu Asp Glu Leu Asn Lys Phe Val Glu Ser Gly Ser
            580                 585                 590

Ile Ser Glu Leu Ile Val Ala Phe Ser Arg Glu Gly Pro Thr Lys Glu
            595                 600                 605

Tyr Val Gln His Lys Met Leu Gln Lys Ala Ser Glu Ile Trp Asn Leu
            610                 615                 620

Ile Ser Glu Gly Ala Tyr Ile Tyr Val Cys Gly Asp Ala Lys Gly Met
625                 630                 635                 640

Ala Arg Asp Val His Arg Met Leu His Thr Ile Ala Gln Glu Gln Gly
                645                 650                 655

Ala Leu Asp Ser Ser Lys Ala Glu Ser Trp Val Lys Asn Leu Gln Met
            660                 665                 670

Thr Gly Arg Tyr Leu Arg Asp Val Trp
            675                 680

<210> SEQ ID NO 81
<211> LENGTH: 693
<212> TYPE: PRT
<213> ORGANISM: Gossypium hirsutum

<400> SEQUENCE: 81

Met Ser Ser Ser Ser Asp Leu Val Gly Phe Val Glu Ser Val Leu Gly
1               5                   10                  15

Val Ser Leu Glu Gly Ser Val Thr Asp Ser Met Ile Val Ile Ala Thr

-continued

```
             20                  25                  30
Thr Ser Leu Ala Val Ile Leu Gly Leu Leu Val Phe Phe Trp Lys Lys
         35                  40                  45

Ser Gly Ser Glu Arg Ser Arg Asp Val Lys Pro Leu Val Ala Pro Lys
 50                  55                  60

Pro Val Ser Leu Lys Asp Glu Asp Asp Ala Val Ile Ala Ala
 65              70                  75                  80

Gly Lys Thr Lys Val Thr Ile Phe Tyr Gly Thr Gln Thr Gly Thr Ala
                     85                  90                  95

Glu Gly Phe Ala Lys Ala Leu Ala Glu Glu Ile Lys Ala Arg Tyr Glu
             100                 105                 110

Lys Ala Ala Val Lys Val Val Asp Leu Asp Asp Tyr Ala Met Asp Asp
         115                 120                 125

Glu Gln Tyr Glu Glu Lys Leu Lys Lys Glu Thr Leu Ala Phe Phe Met
     130                 135                 140

Val Ala Thr Tyr Gly Asp Gly Glu Pro Thr Asp Asn Ala Ala Arg Phe
145                 150                 155                 160

Tyr Lys Trp Phe Thr Glu Gly Asn Glu Arg Leu Pro Trp Leu Gln Gln
                 165                 170                 175

Leu Thr Tyr Gly Val Phe Gly Leu Gly Asn Arg Gln Tyr Glu His Phe
             180                 185                 190

Asn Lys Ile Ala Lys Val Leu Asp Glu Gln Leu Ser Glu Gln Gly Ala
         195                 200                 205

Lys Arg Leu Ile Glu Val Gly Leu Gly Asp Asp Gln Cys Ile Glu
     210                 215                 220

Asp Asp Phe Thr Ala Trp Arg Glu Leu Leu Trp Pro Glu Leu Asp Gln
225                 230                 235                 240

Leu Leu Arg Asp Glu Asp Glu Asn Ala Thr Ser Thr Pro Tyr Thr
                 245                 250                 255

Ala Ala Ile Pro Glu Tyr Arg Val Val His Asp Pro Ala Val Met
             260                 265                 270

His Val Glu Glu Asn Tyr Ser Asn Lys Ala Asn Gly Asn Ala Thr Tyr
         275                 280                 285

Asp Leu His His Pro Cys Arg Val Asn Val Ala Val Gln Arg Glu Leu
     290                 295                 300

His Lys Pro Glu Ser Asp Arg Ser Cys Ile His Leu Glu Phe Asp Ile
305                 310                 315                 320

Ser Gly Thr Gly Ile Thr Tyr Glu Thr Gly Asp His Val Gly Val Tyr
                 325                 330                 335

Ala Asp Asn Cys Val Glu Thr Val Glu Glu Ala Ala Arg Leu Leu Gly
             340                 345                 350

Gln Pro Leu Asp Leu Leu Phe Ser Ile His Thr Asp Asn Glu Asp Gly
         355                 360                 365

Thr Ser Ala Gly Ser Ser Leu Pro Pro Pro Phe Ala Ser Pro Cys Thr
     370                 375                 380

Leu Arg Met Ala Leu Ala Arg Tyr Ala Asp Leu Leu Asn Pro Pro Arg
385                 390                 395                 400

Lys Ala Ala Leu Ile Ala Leu Ala Ala His Ala Thr Glu Pro Ser Glu
                 405                 410                 415

Ala Glu Lys Leu Lys Phe Leu Ser Ser Pro Gln Gly Lys Asp Glu Tyr
             420                 425                 430

Ser Gln Trp Val Val Ala Ser Gln Arg Ser Leu Leu Glu Val Met Ala
         435                 440                 445
```

```
Glu Phe Pro Ser Ala Lys Pro Pro Leu Gly Val Phe Phe Ala Ala Val
    450                 455                 460

Ala Pro Arg Leu Gln Pro Arg Tyr Tyr Ser Ile Ser Ser Ser Pro Arg
465                 470                 475                 480

Phe Val Pro Ala Arg Val His Val Thr Cys Ala Leu Val Tyr Gly Pro
                485                 490                 495

Thr Pro Thr Gly Arg Ile His Arg Gly Val Cys Ser Thr Trp Met Lys
                500                 505                 510

Asn Ala Val Pro Leu Glu Lys Ser Asn Asp Cys Ser Trp Ala Pro Ile
                515                 520                 525

Phe Ile Arg Gln Ser Asn Phe Lys Leu Pro Ala Asp Pro Ser Val Pro
                530                 535                 540

Ile Ile Met Val Gly Pro Gly Thr Gly Leu Ala Pro Phe Arg Gly Phe
545                 550                 555                 560

Leu Gln Glu Arg Leu Val Leu Lys Glu Asp Gly Ala Glu Leu Gly Ser
                565                 570                 575

Ser Leu Leu Phe Phe Gly Cys Arg Asn Arg Arg Met Asp Phe Ile Tyr
                580                 585                 590

Glu Asp Glu Leu Asn Asn Phe Val Glu Gln Gly Ala Leu Ser Glu Leu
                595                 600                 605

Val Val Ala Phe Ser Arg Glu Gly Pro Gln Lys Glu Tyr Val Gln His
610                 615                 620

Lys Met Met Asp Lys Ala Ala Asp Ile Trp Asn Leu Ile Ser Lys Gly
625                 630                 635                 640

Gly Tyr Leu Tyr Val Cys Gly Asp Ala Lys Gly Met Ala Arg Asp Val
                645                 650                 655

His Arg Thr Leu His Thr Ile Ile Gln Glu Gln Glu Asn Val Asp Ser
                660                 665                 670

Ser Lys Ala Glu Ser Met Val Lys Lys Leu Gln Met Asp Gly Arg Tyr
                675                 680                 685

Leu Arg Asp Val Trp
                690

<210> SEQ ID NO 82
<211> LENGTH: 710
<212> TYPE: PRT
<213> ORGANISM: Gossypium hirsutum

<400> SEQUENCE: 82

Met Asp Ser Ser Ser Ser Ser Ser Gly Pro Ser Pro Leu Asp
1               5                   10                  15

Leu Met Ser Ala Leu Val Lys Ala Lys Met Asp Pro Ser Asn Ala Ser
                20                  25                  30

Ser Asp Ser Ala Ala Gln Val Thr Thr Val Leu Phe Glu Asn Arg Glu
                35                  40                  45

Phe Val Met Ile Leu Thr Thr Ser Ile Ala Val Leu Ile Gly Cys Val
                50                  55                  60

Val Ile Leu Ile Trp Arg Arg Ser Ala Ser Gln Lys Pro Lys Gln Ile
65                  70                  75                  80

Gln Leu Pro Leu Lys Pro Ser Ile Ile Lys Glu Pro Glu Leu Glu Val
                85                  90                  95

Asp Asp Gly Lys Lys Lys Val Thr Ile Leu Phe Gly Thr Gln Thr Gly
                100                 105                 110

Thr Ala Glu Gly Phe Ala Lys Ala Leu Val Glu Glu Ala Lys Ala Arg
```

-continued

```
            115                 120                 125
Tyr Glu Lys Ala Thr Phe Asn Ile Val Asp Leu Asp Tyr Ala Ala
            130                 135                 140
Asp Asp Glu Glu Tyr Glu Glu Lys Met Lys Lys Asp Asn Leu Ala Phe
145                 150                 155                 160
Phe Phe Leu Ala Thr Tyr Gly Asp Gly Glu Pro Thr Asp Asn Ala Ala
                    165                 170                 175
Arg Phe Tyr Lys Trp Phe Thr Glu Gly Lys Glu Arg Gly Glu Trp Leu
                180                 185                 190
Gln Asn Met Lys Tyr Gly Ile Phe Gly Leu Gly Asn Lys Gln Tyr Glu
                195                 200                 205
His Phe Asn Lys Val Ala Lys Val Val Asp Glu Leu Leu Thr Glu Gln
            210                 215                 220
Gly Ala Lys Arg Ile Val Pro Leu Gly Leu Gly Asp Asp Asp Gln Cys
225                 230                 235                 240
Ile Glu Asp Asp Phe Thr Ala Trp Arg Glu Leu Val Trp Pro Glu Leu
                    245                 250                 255
Asp Gln Leu Leu Arg Asp Glu Asp Ala Thr Val Ser Thr Pro Tyr
                260                 265                 270
Thr Ala Ala Val Leu Glu Tyr Arg Val Val Phe Tyr Asp Pro Ala Asp
            275                 280                 285
Ala Pro Leu Glu Asp Lys Asn Trp Ser Asn Ala Asn Gly His Ala Thr
290                 295                 300
Tyr Asp Ala Gln His Pro Cys Arg Ser Asn Val Ala Val Arg Lys Glu
305                 310                 315                 320
Leu His Ala Pro Glu Ser Asp Arg Ser Cys Thr His Leu Glu Phe Asp
                    325                 330                 335
Ile Ala Gly Thr Gly Leu Ser Tyr Glu Thr Gly Asp His Val Gly Val
                340                 345                 350
Tyr Cys Glu Asn Leu Asp Glu Val Val Asp Glu Ala Leu Ser Leu Leu
                355                 360                 365
Gly Leu Ser Pro Asp Thr Tyr Phe Ser Val His Thr Asp Lys Glu Asp
            370                 375                 380
Gly Thr Pro Leu Gly Gly Ser Ser Leu Pro Ser Ser Phe Pro Pro Cys
385                 390                 395                 400
Thr Leu Arg Thr Ala Leu Ala Arg Tyr Ala Asp Leu Leu Ser Ser Pro
                    405                 410                 415
Lys Lys Ala Ala Leu Leu Ala Leu Ala Ala His Ala Ser Asp Pro Thr
                420                 425                 430
Glu Ala Asp Arg Leu Arg His Leu Ala Ser Pro Ala Gly Lys Asp Glu
            435                 440                 445
Tyr Ala Gln Trp Ile Val Ala Asn Gln Arg Ser Leu Leu Glu Val Met
            450                 455                 460
Ala Glu Phe Pro Ser Ala Lys Pro Pro Leu Gly Val Phe Phe Ala Ala
465                 470                 475                 480
Val Ala Pro Arg Leu Gln Pro Arg Tyr Tyr Ser Ile Ser Ser Ser Pro
                    485                 490                 495
Arg Leu Ala Pro Ser Arg Ile His Val Thr Cys Ala Leu Val Tyr Glu
                500                 505                 510
Lys Thr Pro Thr Gly Arg Ile His Lys Gly Val Cys Ser Thr Trp Met
                515                 520                 525
Lys Asn Ala Val Ser Ser Gly Lys Ser Asp Asp Cys Gly Trp Ala Pro
            530                 535                 540
```

```
Ile Phe Val Arg Gln Ser Asn Phe Lys Leu Pro Ser Asp Thr Lys Val
545                 550                 555                 560

Pro Ile Ile Met Ile Gly Pro Gly Thr Gly Leu Ala Pro Phe Arg Gly
                565                 570                 575

Phe Leu Gln Glu Arg Leu Ala Leu Lys Glu Ala Gly Ala Glu Leu Gly
            580                 585                 590

Pro Ser Val Leu Phe Phe Gly Cys Arg Asn Arg Lys Met Asp Phe Ile
        595                 600                 605

Tyr Glu Asp Glu Leu Asn Asn Phe Val Asn Ser Gly Ala Leu Ser Glu
    610                 615                 620

Leu Val Val Ala Phe Ser Arg Glu Gly Pro Thr Lys Glu Tyr Val Gln
625                 630                 635                 640

His Lys Met Met Glu Lys Ala Lys Asp Ile Trp Asp Met Ile Ser Gln
                645                 650                 655

Gly Gly Tyr Leu Tyr Val Cys Gly Asp Ala Lys Gly Met Ala Arg Asp
            660                 665                 670

Val His Arg Ala Leu His Thr Ile Phe Gln Glu Gln Gly Ser Leu Asp
        675                 680                 685

Ser Ser Lys Ala Glu Ser Met Val Lys Asn Leu Gln Met Ser Gly Arg
    690                 695                 700

Tyr Leu Arg Asp Val Trp
705                 710

<210> SEQ ID NO 83
<211> LENGTH: 480
<212> TYPE: PRT
<213> ORGANISM: Vitis vinifera

<400> SEQUENCE: 83

Met Glu Val Phe Phe Leu Ser Leu Leu Leu Ile Phe Val Leu Ser Val
1               5                   10                  15

Ser Ile Gly Leu His Leu Leu Phe Tyr Lys Arg Ser His Phe Thr
                20                  25                  30

Gly Pro Asn Leu Pro Pro Gly Lys Ile Gly Trp Pro Met Val Gly Glu
            35                  40                  45

Ser Leu Glu Phe Leu Ser Thr Gly Trp Lys Gly His Pro Glu Lys Phe
50                  55                  60

Ile Phe Asp Arg Ile Ser Lys Tyr Ser Ser Glu Val Phe Lys Thr Ser
65                  70                  75                  80

Leu Leu Gly Glu Pro Ala Ala Val Phe Ala Gly Ala Ala Gly Asn Lys
                85                  90                  95

Phe Leu Phe Ser Asn Glu Asn Lys Leu Val His Ala Trp Trp Pro Ser
            100                 105                 110

Ser Val Asp Lys Val Phe Pro Ser Ser Thr Gln Thr Ser Ser Lys Glu
        115                 120                 125

Glu Ala Lys Lys Met Arg Lys Leu Leu Pro Gln Phe Phe Lys Pro Glu
    130                 135                 140

Ala Leu Gln Arg Tyr Ile Gly Ile Met Asp His Ile Ala Gln Arg His
145                 150                 155                 160

Phe Ala Asp Ser Trp Asp Asn Arg Asp Glu Val Ile Val Phe Pro Leu
                165                 170                 175

Ala Lys Arg Phe Thr Phe Trp Leu Ala Cys Arg Leu Phe Met Ser Ile
            180                 185                 190

Glu Asp Pro Ala His Val Ala Lys Phe Glu Lys Pro Phe His Val Leu
```

```
               195                 200                 205
Ala Ser Gly Leu Ile Thr Val Pro Ile Asp Leu Pro Gly Thr Pro Phe
    210                 215                 220

His Arg Ala Ile Lys Ala Ser Asn Phe Ile Arg Lys Glu Leu Arg Ala
225                 230                 235                 240

Ile Ile Lys Gln Arg Lys Ile Asp Leu Ala Glu Gly Lys Ala Ser Gln
                245                 250                 255

Asn Gln Asp Ile Leu Ser His Met Leu Leu Ala Thr Asp Glu Asp Gly
            260                 265                 270

Cys His Met Asn Glu Met Glu Ile Ala Asp Lys Ile Leu Gly Leu Leu
        275                 280                 285

Ile Gly Gly His Asp Thr Ala Ser Ala Ala Ile Thr Phe Leu Ile Lys
290                 295                 300

Tyr Met Ala Glu Leu Pro His Ile Tyr Glu Lys Val Tyr Glu Glu Gln
305                 310                 315                 320

Met Glu Ile Ala Asn Ser Lys Ala Pro Gly Glu Leu Leu Asn Trp Asp
                325                 330                 335

Asp Val Gln Asn Met Arg Tyr Ser Trp Asn Val Ala Cys Glu Val Met
            340                 345                 350

Arg Leu Ala Pro Pro Leu Gln Gly Ala Phe Arg Glu Ala Ile Thr Asp
        355                 360                 365

Phe Val Phe Asn Gly Phe Ser Ile Pro Lys Gly Trp Lys Leu Tyr Trp
370                 375                 380

Ser Ala Asn Ser Thr His Lys Ser Pro Glu Cys Phe Pro Gln Pro Glu
385                 390                 395                 400

Asn Phe Asp Pro Thr Arg Phe Glu Gly Asn Gly Pro Ala Pro Tyr Thr
                405                 410                 415

Phe Val Pro Phe Gly Gly Gly Pro Arg Met Cys Pro Gly Lys Glu Tyr
            420                 425                 430

Ala Arg Leu Glu Ile Leu Val Phe Met His Asn Val Val Lys Arg Phe
        435                 440                 445

Lys Trp Asp Lys Leu Leu Pro Asp Glu Lys Ile Ile Val Asp Pro Met
450                 455                 460

Pro Met Pro Ala Lys Gly Leu Pro Val Arg Leu His Pro His Lys Pro
465                 470                 475                 480

<210> SEQ ID NO 84
<211> LENGTH: 480
<212> TYPE: PRT
<213> ORGANISM: Vitis vinifera

<400> SEQUENCE: 84

Met Glu Val Phe Phe Leu Ser Leu Leu Leu Ile Ser Val Leu Ser Val
1               5                   10                  15

Ser Ile Arg Leu Tyr Leu Leu Leu Tyr Lys His Arg Ser His Phe Thr
            20                  25                  30

Gly Pro Asn Leu Pro Pro Gly Lys Ile Gly Trp Pro Met Val Gly Glu
        35                  40                  45

Ser Leu Glu Phe Leu Ser Thr Gly Trp Lys Gly His Pro Glu Lys Phe
    50                  55                  60

Ile Phe Asp Arg Ile Ser Lys Tyr Ser Ser Glu Val Phe Lys Thr Ser
65                  70                  75                  80

Leu Leu Gly Glu Pro Ala Ala Val Phe Ala Gly Ala Ala Gly Asn Lys
                85                  90                  95
```

```
Phe Leu Phe Ser Asn Glu Asn Lys Leu Val His Ala Trp Trp Pro Ser
            100                 105                 110

Ser Val Asp Lys Val Phe Pro Ser Ser Thr Gln Thr Ser Ser Lys Glu
        115                 120                 125

Glu Ala Lys Lys Met Arg Lys Leu Leu Pro Gln Phe Leu Lys Pro Glu
130                 135                 140

Ala Leu Gln Arg Tyr Thr Gly Ile Met Asp His Ile Ala Gln Arg His
145                 150                 155                 160

Phe Ala Asp Ser Trp Asp Asn Arg Asp Glu Val Ile Val Phe Pro Leu
                165                 170                 175

Ala Lys Arg Phe Thr Phe Trp Leu Ala Cys Arg Leu Phe Met Ser Ile
            180                 185                 190

Glu Asp Pro Ala His Val Ala Lys Phe Glu Lys Pro Phe His Val Leu
        195                 200                 205

Ala Ser Gly Leu Ile Thr Ile Pro Ile Asp Leu Pro Gly Thr Pro Phe
210                 215                 220

His Arg Ala Ile Lys Ala Ser Asn Phe Ile Arg Lys Glu Leu Arg Ala
225                 230                 235                 240

Ile Ile Lys Gln Arg Lys Ile Asp Leu Ala Glu Ser Lys Ala Ser Lys
                245                 250                 255

Thr Gln Asp Ile Leu Ser His Met Leu Leu Ala Thr Asp Glu Asp Gly
            260                 265                 270

Cys His Met Asn Glu Met Ser Ile Ala Asp Lys Ile Leu Gly Leu Leu
        275                 280                 285

Ile Gly Gly His Asp Thr Ala Ser Ser Ala Ile Thr Phe Leu Val Lys
290                 295                 300

Tyr Met Ala Glu Leu Pro His Ile Tyr Glu Lys Val Tyr Lys Glu Gln
305                 310                 315                 320

Met Glu Ile Ala Asn Ser Lys Ala Pro Gly Glu Leu Leu Asn Trp Asp
                325                 330                 335

Asp Val Gln Lys Met Arg Tyr Ser Trp Asn Val Ala Cys Glu Val Met
            340                 345                 350

Arg Leu Ala Pro Pro Leu Gln Gly Ala Phe Arg Glu Ala Ile Thr Asp
        355                 360                 365

Phe Val Phe Asn Gly Phe Ser Ile Pro Lys Gly Trp Lys Leu Tyr Trp
370                 375                 380

Ser Ala Asn Ser Thr His Lys Ser Leu Glu Cys Phe Pro Gln Pro Glu
385                 390                 395                 400

Lys Phe Asp Pro Thr Arg Phe Glu Gly Ala Gly Pro Ala Pro Tyr Thr
                405                 410                 415

Phe Val Pro Phe Gly Gly Gly Pro Arg Met Cys Pro Gly Lys Glu Tyr
            420                 425                 430

Ala Arg Leu Glu Ile Leu Ile Phe Met His Asn Leu Val Lys Arg Phe
        435                 440                 445

Lys Trp Asp Lys Leu Leu Pro Asp Glu Lys Ile Ile Val Asp Pro Met
450                 455                 460

Pro Met Pro Ala Lys Gly Leu Pro Val Arg Leu His Pro His Lys Pro
465                 470                 475                 480

<210> SEQ ID NO 85
<211> LENGTH: 479
<212> TYPE: PRT
<213> ORGANISM: Medicago truncatula

<400> SEQUENCE: 85
```

```
Met Glu Pro Asn Phe Tyr Leu Ser Leu Leu Leu Phe Val Thr Phe
1               5                   10                  15

Ile Ser Leu Ser Leu Phe Phe Ile Phe Tyr Lys Gln Lys Ser Pro Leu
            20                  25                  30

Asn Leu Pro Pro Gly Lys Met Gly Tyr Pro Ile Ile Gly Glu Ser Leu
        35                  40                  45

Glu Phe Leu Ser Thr Gly Trp Lys Gly His Pro Glu Lys Phe Ile Phe
    50                  55                  60

Asp Arg Met Arg Lys Tyr Ser Ser Glu Leu Phe Lys Thr Ser Ile Val
65                  70                  75                  80

Gly Glu Ser Thr Val Val Cys Cys Gly Ala Ala Ser Asn Lys Phe Leu
                85                  90                  95

Phe Ser Asn Glu Asn Lys Leu Val Thr Ala Trp Trp Pro Asp Ser Val
            100                 105                 110

Asn Lys Ile Phe Pro Thr Thr Ser Leu Asp Ser Asn Leu Lys Glu Glu
        115                 120                 125

Ser Ile Lys Met Arg Lys Leu Leu Pro Gln Phe Phe Lys Pro Glu Ala
    130                 135                 140

Leu Gln Arg Tyr Val Gly Val Met Asp Val Ile Ala Gln Arg His Phe
145                 150                 155                 160

Val Thr His Trp Asp Asn Lys Asn Glu Ile Thr Val Tyr Pro Leu Ala
                165                 170                 175

Lys Arg Tyr Thr Phe Leu Leu Ala Cys Arg Leu Phe Met Ser Val Glu
            180                 185                 190

Asp Glu Asn His Val Ala Lys Phe Ser Asp Pro Phe Gln Leu Ile Ala
        195                 200                 205

Ala Gly Ile Ile Ser Leu Pro Ile Asp Leu Pro Gly Thr Pro Phe Asn
    210                 215                 220

Lys Ala Ile Lys Ala Ser Asn Phe Ile Arg Lys Glu Leu Ile Lys Ile
225                 230                 235                 240

Ile Lys Gln Arg Arg Val Asp Leu Ala Glu Gly Thr Ala Ser Pro Thr
                245                 250                 255

Gln Asp Ile Leu Ser His Met Leu Leu Thr Ser Asp Glu Asn Gly Lys
            260                 265                 270

Ser Met Asn Glu Leu Asn Ile Ala Asp Lys Ile Leu Gly Leu Leu Ile
        275                 280                 285

Gly Gly His Asp Thr Ala Ser Val Ala Cys Thr Phe Leu Val Lys Tyr
    290                 295                 300

Leu Gly Glu Leu Pro His Ile Tyr Asp Lys Val Tyr Gln Glu Gln Met
305                 310                 315                 320

Glu Ile Ala Lys Ser Lys Pro Ala Gly Glu Leu Leu Asn Trp Asp Asp
                325                 330                 335

Leu Lys Lys Met Lys Tyr Ser Trp Asn Val Ala Cys Glu Val Met Arg
            340                 345                 350

Leu Ser Pro Pro Leu Gln Gly Gly Phe Arg Glu Ala Ile Thr Asp Phe
        355                 360                 365

Met Phe Asn Gly Phe Ser Ile Pro Lys Gly Trp Lys Leu Tyr Trp Ser
    370                 375                 380

Ala Asn Ser Thr His Lys Asn Ala Glu Cys Phe Pro Met Pro Glu Lys
385                 390                 395                 400

Phe Asp Pro Thr Arg Phe Glu Gly Asn Gly Pro Ala Pro Tyr Thr Phe
                405                 410                 415
```

```
Val Pro Phe Gly Gly Pro Arg Met Cys Pro Gly Lys Glu Tyr Ala
            420                 425                 430

Arg Leu Glu Ile Leu Val Phe Met His Asn Leu Val Lys Arg Phe Lys
        435                 440                 445

Trp Glu Lys Val Ile Pro Asp Glu Lys Ile Ile Val Asp Pro Phe Pro
    450                 455                 460

Ile Pro Ala Lys Asp Leu Pro Ile Arg Leu Tyr Pro His Lys Ala
465                 470                 475

<210> SEQ ID NO 86
<211> LENGTH: 480
<212> TYPE: PRT
<213> ORGANISM: Catharanthus roseus

<400> SEQUENCE: 86

Met Glu Ile Phe Tyr Val Thr Leu Leu Ser Leu Phe Val Leu Leu Val
1               5                   10                  15

Ser Leu Ser Phe His Phe Leu Phe Tyr Lys Asn Lys Ser Thr Leu Pro
            20                  25                  30

Gly Pro Leu Pro Pro Gly Arg Thr Gly Trp Pro Met Val Gly Glu Ser
        35                  40                  45

Leu Gln Phe Leu Ser Ala Gly Trp Lys Gly His Pro Glu Lys Phe Ile
    50                  55                  60

Phe Asp Arg Met Ala Lys Tyr Ser Ser Asn Val Phe Arg Ser His Leu
65                  70                  75                  80

Leu Gly Glu Pro Ala Ala Val Phe Cys Gly Ala Ile Gly Asn Lys Phe
                85                  90                  95

Leu Phe Ser Asn Glu Asn Lys Leu Val Gln Ala Trp Trp Pro Asp Ser
            100                 105                 110

Val Asn Lys Val Phe Pro Ser Ser Asn Gln Thr Ser Ser Lys Glu Glu
        115                 120                 125

Ala Ile Lys Met Arg Lys Met Leu Pro Asn Phe Leu Lys Pro Glu Ala
    130                 135                 140

Leu Gln Arg Tyr Ile Gly Leu Met Asp Gln Ile Ala Gln Lys His Phe
145                 150                 155                 160

Ser Ser Gly Trp Glu Asn Arg Glu Gln Val Glu Val Phe Pro Leu Ala
                165                 170                 175

Lys Asn Tyr Thr Phe Trp Leu Ala Ser Arg Leu Phe Val Ser Val Glu
            180                 185                 190

Asp Pro Ile Glu Val Ala Lys Leu Leu Glu Pro Phe Asn Val Leu Ala
        195                 200                 205

Ser Gly Leu Ile Ser Val Pro Ile Asp Leu Pro Gly Thr Pro Phe Asn
    210                 215                 220

Arg Ala Ile Lys Ala Ser Asn Gln Val Arg Lys Met Leu Ile Ser Ile
225                 230                 235                 240

Ile Lys Gln Arg Lys Ile Asp Leu Ala Glu Gly Lys Ala Ser Pro Thr
                245                 250                 255

Gln Asp Ile Leu Ser His Met Leu Leu Thr Ser Asp Glu Asn Gly Lys
            260                 265                 270

Phe Met His Glu Leu Asp Ile Ala Asp Lys Ile Leu Gly Leu Leu Ile
        275                 280                 285

Gly Gly His Asp Thr Ala Ser Ser Ala Cys Thr Phe Ile Val Lys Phe
    290                 295                 300

Leu Gly Glu Leu Pro Glu Ile Tyr Glu Gly Val Tyr Lys Glu Gln Met
305                 310                 315                 320
```

Glu Ile Ala Asn Ser Lys Ala Pro Gly Glu Phe Leu Asn Trp Glu Asp
                325                 330                 335

Ile Gln Lys Met Lys Tyr Ser Trp Asn Val Ala Cys Glu Val Leu Arg
            340                 345                 350

Leu Ala Pro Pro Leu Gln Gly Ala Phe Arg Glu Ala Leu Asn Asp Phe
        355                 360                 365

Met Phe His Gly Phe Ser Ile Pro Lys Gly Trp Lys Ile Tyr Trp Ser
    370                 375                 380

Val Asn Ser Thr His Arg Asn Pro Glu Cys Phe Pro Asp Pro Leu Lys
385                 390                 395                 400

Phe Asp Pro Ser Arg Phe Asp Gly Ser Gly Pro Ala Pro Tyr Thr Phe
                405                 410                 415

Val Pro Phe Gly Gly Pro Arg Met Cys Pro Gly Lys Glu Tyr Ala
            420                 425                 430

Arg Leu Glu Ile Leu Val Phe Met His Asn Leu Val Lys Arg Phe Lys
        435                 440                 445

Trp Glu Lys Ile Ile Pro Asn Glu Lys Ile Val Val Asp Pro Met Pro
    450                 455                 460

Ile Pro Glu Lys Gly Leu Pro Val Arg Leu Tyr Pro His Ile Asn Ala
465                 470                 475                 480

<210> SEQ ID NO 87
<211> LENGTH: 481
<212> TYPE: PRT
<213> ORGANISM: Populus trichocarpa

<400> SEQUENCE: 87

Met Glu Leu Leu Phe Leu Ser Leu Leu Leu Ala Leu Phe Val Ser Ser
1               5                   10                  15

Val Thr Ile Pro Leu Phe Leu Ile Phe Tyr Asn His Arg Ser Gln Asn
            20                  25                  30

Ser His Pro Asn Leu Pro Pro Gly Lys Leu Gly Leu Pro Leu Val Gly
        35                  40                  45

Glu Ser Phe Glu Phe Leu Ala Thr Gly Trp Lys Gly His Pro Glu Lys
    50                  55                  60

Phe Ile Phe Asp Arg Ile Ala Lys Tyr Ser Ser His Ile Phe Lys Thr
65                  70                  75                  80

Asn Ile Leu Gly Gln Pro Ala Val Val Phe Cys Gly Val Ala Cys Asn
                85                  90                  95

Lys Phe Leu Phe Ser Asn Glu Asn Lys Leu Val Val Ser Trp Trp Pro
            100                 105                 110

Asp Ser Val Asn Lys Ile Phe Pro Ser Ser Leu Gln Thr Ser Ser Lys
        115                 120                 125

Glu Glu Ala Lys Lys Met Arg Lys Leu Leu Pro Gln Phe Leu Lys Pro
    130                 135                 140

Glu Ala Leu Gln Gly Tyr Ile Gly Ile Met Asp Thr Ile Ala Gln Arg
145                 150                 155                 160

His Phe Ala Ser Glu Trp Glu His Lys Glu Gln Val Leu Val Phe Pro
                165                 170                 175

Leu Ser Lys Asn Tyr Thr Phe Arg Leu Ala Cys Arg Leu Phe Leu Ser
            180                 185                 190

Ile Glu Asp Pro Ser His Val Ala Lys Phe Ser Asp Pro Phe Asn Leu
        195                 200                 205

Leu Ala Ser Gly Ile Ile Ser Ile Pro Ile Asp Leu Pro Gly Thr Pro

Phe Asn Arg Ala Ile Lys Ala Ser Asn Phe Ile Arg Thr Glu Leu Leu
225                 230                 235                 240

Ala Phe Ile Arg Gln Arg Lys Lys Asp Leu Ala Glu Gly Lys Ala Ser
            245                 250                 255

Pro Thr Gln Asp Ile Leu Ser His Met Leu Leu Thr Cys Asp Glu Asn
        260                 265                 270

Gly Lys Cys Met Asn Glu Leu Asp Ile Ala Asp Lys Ile Ile Gly Leu
    275                 280                 285

Leu Ile Gly Gly His Asp Thr Ala Ser Ala Ala Cys Thr Phe Ile Val
290                 295                 300

Lys Tyr Leu Ala Glu Leu Pro His Ile Tyr Glu Glu Val Tyr Lys Glu
305                 310                 315                 320

Gln Met Glu Ile Ala Lys Ser Lys Thr Pro Gly Glu Phe Leu Asn Trp
            325                 330                 335

Asp Asp Ile Gln Lys Met Lys Tyr Ser Trp Lys Val Ala Cys Glu Val
        340                 345                 350

Met Arg Ile Ser Pro Pro Leu Gln Gly Ala Phe Arg Glu Ala Leu Asn
    355                 360                 365

Asp Phe Ile Phe Asn Gly Phe Thr Ile Pro Lys Gly Trp Lys Leu Tyr
370                 375                 380

Trp Ser Thr Asn Ser Thr His Arg Asp Pro Val Tyr Phe Pro Glu Pro
385                 390                 395                 400

Glu Lys Phe Asp Pro Arg Arg Phe Glu Gly Ser Gly Pro Ala Pro Tyr
            405                 410                 415

Thr Phe Val Pro Phe Gly Gly Gly Pro Arg Met Cys Pro Gly Lys Glu
        420                 425                 430

Tyr Ala Arg Leu Glu Ile Leu Val Phe Met His Asn Leu Val Arg Arg
    435                 440                 445

Phe Lys Phe Asp Lys Leu Ile Gln Asp Glu Lys Ile Val Val Asn Pro
450                 455                 460

Leu Pro Ile Pro Asp Lys Gly Leu Pro Val Arg Leu His Pro His Lys
465                 470                 475                 480

Ala

<210> SEQ ID NO 88
<211> LENGTH: 482
<212> TYPE: PRT
<213> ORGANISM: Glycine max

<400> SEQUENCE: 88

Met Asp His Asn Asn Leu Tyr Leu Ser Leu Leu Leu Phe Val Ser
1               5                   10                  15

Phe Val Thr Leu Ser Leu Phe Phe Leu Phe Tyr Lys His Arg Ser Pro
            20                  25                  30

Phe Val Ala Pro Asn Leu Pro Pro Gly Ala Thr Gly Tyr Pro Val Ile
        35                  40                  45

Gly Glu Ser Leu Glu Phe Leu Ser Thr Gly Trp Lys Gly His Pro Glu
    50                  55                  60

Lys Phe Ile Phe Asp Arg Met Ile Arg Tyr Ser Ser Gln Leu Phe Lys
65                  70                  75                  80

Thr Ser Ile Phe Gly Glu Pro Ala Val Ile Phe Cys Gly Ala Thr Cys
            85                  90                  95

Asn Lys Phe Leu Phe Ser Asn Glu Asn Lys Leu Val Ala Ala Trp Trp

```
                100             105                 110
Pro Asn Ser Val Asn Lys Val Phe Pro Ser Thr Leu Gln Ser Asn Ser
            115                 120                 125

Lys Glu Glu Ser Lys Lys Met Arg Lys Leu Leu Pro Gln Phe Leu Lys
130             135                 140

Pro Glu Ala Leu Gln Arg Tyr Val Gly Ile Met Asp Thr Ile Ala Gln
145                 150                 155                 160

Asn His Phe Ala Ser Leu Trp Asp Asn Lys Thr Glu Leu Thr Val Tyr
                165                 170                 175

Pro Leu Ala Lys Arg Tyr Thr Phe Leu Leu Ala Cys Arg Leu Phe Met
                180                 185                 190

Ser Val Glu Asp Val Asn His Val Ala Lys Phe Glu Asn Pro Phe His
            195                 200                 205

Leu Leu Ala Ser Gly Ile Ile Ser Val Pro Ile Asp Leu Pro Gly Thr
            210                 215                 220

Pro Phe Asn Lys Ala Ile Lys Ala Ala Asn Ala Ile Arg Lys Glu Leu
225                 230                 235                 240

Leu Lys Ile Ile Arg Gln Arg Lys Val Asp Leu Ala Glu Gly Lys Ala
                245                 250                 255

Ser Pro Thr Gln Asp Ile Leu Ser His Met Leu Leu Thr Cys Asn Glu
                260                 265                 270

Asn Gly Gln Phe Met Asn Glu Leu Asp Ile Ala Asp Lys Ile Leu Gly
            275                 280                 285

Leu Leu Ile Gly Gly His Asp Thr Ala Ser Ala Ala Cys Thr Phe Ile
            290                 295                 300

Val Lys Tyr Leu Ala Glu Leu Pro His Ile Tyr Asp Ser Val Tyr Gln
305                 310                 315                 320

Glu Gln Met Glu Ile Ala Lys Ser Lys Leu Pro Gly Glu Leu Leu Asn
                325                 330                 335

Trp Asp Asp Ile Asn Arg Met Lys Tyr Ser Trp Asn Val Ala Cys Glu
                340                 345                 350

Val Met Arg Ile Ala Pro Pro Leu Gln Gly Gly Phe Arg Glu Ala Ile
                355                 360                 365

Asn Asp Phe Ile Phe Asn Gly Phe Ser Ile Pro Lys Gly Trp Lys Leu
            370                 375                 380

Tyr Trp Ser Ala Asn Ser Thr His Lys Asn Pro Glu Tyr Phe Pro Glu
385                 390                 395                 400

Pro Glu Lys Phe Asp Pro Thr Arg Phe Glu Gly Gln Gly Pro Ala Pro
                405                 410                 415

Phe Thr Phe Val Pro Phe Gly Gly Pro Arg Met Cys Pro Gly Lys
                420                 425                 430

Glu Tyr Ala Arg Leu Glu Ile Leu Val Phe Met His Asn Leu Val Lys
                435                 440                 445

Arg Phe Lys Trp Glu Lys Leu Ile Pro Asp Glu Lys Ile Ile Val Asp
                450                 455                 460

Pro Leu Pro Val Pro Ala Lys Asn Leu Pro Ile Arg Leu His Pro His
465                 470                 475                 480

Lys Pro

<210> SEQ ID NO 89
<211> LENGTH: 482
<212> TYPE: PRT
<213> ORGANISM: Bupleurum chinense
```

<400> SEQUENCE: 89

```
Met Met Met Tyr Leu Tyr Phe Ser Val Ile Ser Ile Leu Val Leu Leu
1               5                   10                  15

Pro Cys Val Trp Leu Phe Phe Leu His Ser Asn Arg Lys Ser Thr Gln
            20                  25                  30

Gln Ser Tyr Lys Ser Leu Pro Pro Gly Glu Thr Gly Tyr Phe Leu Ile
        35                  40                  45

Gly Glu Ser Leu Glu Phe Leu Ser Thr Gly Arg Lys Gly His Pro Glu
    50                  55                  60

Lys Phe Ile Phe Asp Arg Met Thr Lys Tyr Ala Ser Lys Ile Phe Lys
65                  70                  75                  80

Ser Ser Leu Phe Gly Glu Lys Thr Ile Val Phe Cys Gly Ala Ala Asn
                85                  90                  95

Asn Lys Phe Leu Phe Ser Asp Glu Asn Lys Leu Val Gln Ser Trp Trp
            100                 105                 110

Pro Asn Ser Val Asn Lys Leu Phe Pro Ser Ser Thr Gln Thr Ser Ser
        115                 120                 125

Lys Glu Glu Ala Ile Lys Met Arg Lys Met Leu Pro Asn Phe Phe Lys
    130                 135                 140

Pro Glu Ala Leu Gln Arg Tyr Val Gly Val Met Asp Glu Ile Ala Gln
145                 150                 155                 160

Lys His Phe Asp Ser Cys Trp Glu Asn Lys His Thr Val Ile Val Ala
                165                 170                 175

Pro Leu Thr Lys Arg Phe Thr Phe Trp Leu Ala Cys Arg Leu Phe Val
            180                 185                 190

Ser Leu Glu Asp Pro Thr Gln Val Ala Lys Phe Ala Glu Pro Phe Asn
        195                 200                 205

Leu Leu Ala Ser Gly Val Phe Ser Ile Pro Ile Asp Leu Pro Gly Thr
    210                 215                 220

Ala Phe Asn Arg Ala Ile Lys Ala Ser Asn Phe Ile Arg Lys Thr Leu
225                 230                 235                 240

Ile Gly Ile Ile Lys Lys Arg Lys Val Asp Leu Glu Asp Gly Thr Ala
                245                 250                 255

Ser Ala Thr Gln Asp Ile Leu Ser His Met Leu Leu Thr Ser Asp Glu
            260                 265                 270

Thr Gly Lys Phe Met Thr Glu Ala Asp Ile Ala Asp Lys Ile Leu Gly
        275                 280                 285

Leu Leu Ile Gly Gly His Asp Thr Ala Ser Ser Ala Cys Ala Leu Ile
    290                 295                 300

Val Lys Tyr Leu Ala Glu Leu Pro His Ile Tyr Asp Gly Val Tyr Arg
305                 310                 315                 320

Glu Gln Met Glu Ile Ala Lys Ser Lys Ser Pro Gly Glu Leu Leu Asn
                325                 330                 335

Trp Asp Asp Val Gln Lys Met Lys Tyr Ser Trp Asn Val Ala Cys Glu
            340                 345                 350

Val Leu Arg Leu Ala Pro Pro Leu Gln Gly Ser Phe Arg Glu Val Leu
        355                 360                 365

Ser Asp Phe Met His Asn Gly Phe Ser Ile Pro Lys Gly Trp Lys Ile
    370                 375                 380

Tyr Trp Ser Ala Asn Ser Thr His Lys Ser Ser Glu Tyr Phe Pro Glu
385                 390                 395                 400

Pro Glu Lys Phe Asp Pro Arg Arg Phe Glu Gly Ser Gly Pro Ala Pro
                405                 410                 415
```

```
Tyr Thr Phe Val Pro Phe Gly Gly Pro Arg Met Cys Pro Gly Lys
            420             425             430

Glu Tyr Gly Arg Leu Glu Ile Leu Val Phe Met His His Leu Val Lys
            435             440             445

Arg Phe Arg Trp Gln Lys Ile Tyr Pro Leu Glu Lys Ile Thr Val Asn
450             455             460

Pro Met Pro Phe Pro Asp Lys Asp Leu Pro Ile Arg Leu Phe Pro His
465             470             475             480

Lys Ala

<210> SEQ ID NO 90
<211> LENGTH: 483
<212> TYPE: PRT
<213> ORGANISM: Cucumis sativus

<400> SEQUENCE: 90

Met Glu Leu Phe Leu Ile Ser Leu Leu Ile Leu Leu Phe Phe Phe Leu
1               5                   10                  15

Ser Leu Thr Leu Phe Ile Leu Phe His Asn His Lys Ser Leu Phe Ser
            20                  25                  30

Tyr Pro Asn Thr Pro Pro Gly Ala Ile Gly Leu Pro Ile Leu Gly Glu
            35                  40                  45

Ser Val Glu Phe Leu Ser Ser Gly Trp Lys Gly His Pro Glu Lys Phe
50                  55                  60

Ile Phe Asp Arg Leu Asn Lys Tyr Lys Ser Asp Val Phe Lys Thr Ser
65                  70                  75                  80

Ile Val Gly Val Pro Ala Ala Ile Phe Cys Gly Pro Ile Cys Asn Lys
                85                  90                  95

Phe Leu Phe Ser Asn Glu Asn Lys Leu Val Thr Pro Trp Trp Pro Asp
            100                 105                 110

Ser Val Asn Lys Ile Phe Pro Ser Thr Thr Gln Thr Ser Thr Lys Glu
            115                 120                 125

Glu Ala Lys Lys Leu Lys Lys Leu Leu Pro Gln Phe Leu Lys Pro Glu
130                 135                 140

Ala Leu Gln Arg Tyr Ile Gly Ile Met Asp Glu Leu Ala Glu Arg His
145                 150                 155                 160

Phe Asn Ser Phe Trp Lys Asn Arg Glu Glu Val Leu Val Phe Pro Leu
                165                 170                 175

Ala Lys Ser Phe Thr Phe Ser Ile Ala Cys Arg Leu Phe Met Ser Val
            180                 185                 190

Glu Asp Glu Ile His Val Glu Arg Leu Ser Gly Pro Phe Glu His Ile
            195                 200                 205

Ala Ala Gly Ile Ile Ser Met Pro Ile Asp Leu Pro Gly Thr Pro Phe
210                 215                 220

Asn Arg Ala Ile Lys Ala Ser Lys Phe Ile Arg Lys Glu Val Val Ala
225                 230                 235                 240

Ile Val Arg Gln Arg Lys Gln Asp Leu Ala Glu Gly Lys Ala Leu Ala
                245                 250                 255

Thr Gln Asp Ile Leu Ser His Met Leu Leu Thr Cys Asp Glu Asn Gly
            260                 265                 270

Val Tyr Met Asn Glu Ser Asp Ile Thr Asp Lys Ile Leu Gly Leu Leu
            275                 280                 285

Ile Gly Gly His Asp Thr Ala Ser Val Ala Cys Thr Phe Ile Val Lys
290                 295                 300
```

```
Phe Leu Ala Glu Leu Pro His Ile Tyr Asp Ala Val Tyr Thr Glu Gln
305                 310                 315                 320

Met Glu Ile Ala Arg Ala Lys Ala Glu Gly Glu Thr Leu Lys Trp Glu
                325                 330                 335

Asp Ile Lys Lys Met Lys Tyr Ser Trp Asn Val Ala Cys Glu Val Leu
            340                 345                 350

Arg Ile Ala Ser Pro Leu Gln Gly Ala Phe Arg Glu Ala Leu Ser Asp
            355                 360                 365

Phe Val Phe Asn Gly Phe Phe Ile Pro Lys Gly Trp Lys Leu Tyr Trp
370                 375                 380

Ser Ala Asn Ser Thr His Lys Asn Pro Glu Tyr Phe Pro Glu Pro Tyr
385                 390                 395                 400

Lys Phe Asp Pro Gly Arg Phe Glu Gly Asn Gly Pro Leu Pro Tyr Thr
                405                 410                 415

Phe Val Pro Phe Gly Gly Pro Arg Met Cys Pro Gly Lys Glu Tyr
                420                 425                 430

Ala Lys Leu Glu Ile Leu Val Phe Met His Asn Leu Val Lys Arg Phe
            435                 440                 445

Lys Trp Thr Lys Leu Leu Glu Asn Glu Asn Ile Ile Val Asn Pro Met
450                 455                 460

Pro Ile Pro Gln Lys Gly Leu Pro Val Arg Leu Phe Pro His Gln Pro
465                 470                 475                 480

Leu Ser Leu

<210> SEQ ID NO 91
<211> LENGTH: 481
<212> TYPE: PRT
<213> ORGANISM: Panax notoginseng
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (315)..(315)
<223> OTHER INFORMATION: Xaa can be any naturally occurring amino acid

<400> SEQUENCE: 91

Met Glu Leu Phe Tyr Val Pro Leu Leu Ser Leu Phe Val Leu Phe Ile
1               5                   10                  15

Ser Leu Ser Phe His Phe Leu Phe Tyr Lys Ser Lys Ser Ser Ser Ser
                20                  25                  30

Val Gly Leu Pro Leu Pro Pro Gly Lys Thr Gly Trp Pro Ile Ile Gly
            35                  40                  45

Glu Ser Tyr Glu Phe Leu Ser Thr Gly Trp Lys Gly Tyr Pro Glu Lys
    50                  55                  60

Phe Ile Phe Asp Arg Met Thr Lys Tyr Ser Ser Asn Val Phe Lys Thr
65                  70                  75                  80

Ser Ile Phe Gly Glu Pro Ala Ala Val Phe Cys Gly Ala Xaa Cys Asn
                85                  90                  95

Lys Phe Leu Phe Ser Asn Glu Asn Lys Leu Val Gln Ala Trp Trp Pro
            100                 105                 110

Asp Ser Val Asn Lys Val Phe Pro Ser Ser Thr Gln Thr Ser Ser Lys
        115                 120                 125

Glu Glu Ala Ile Lys Met Arg Lys Met Leu Pro Asn Phe Phe Lys Pro
    130                 135                 140
```

```
Glu Ala Leu Gln Arg Tyr Ile Gly Leu Met Asp Gln Ile Ala Ala Lys
145                 150                 155                 160

His Phe Glu Ser Gly Trp Glu Asn Lys Asp Glu Val Val Phe Pro
                165                 170                 175

Leu Ala Lys Ser Tyr Thr Phe Trp Ile Ala Cys Lys Val Phe Val Ser
            180                 185                 190

Val Glu Glu Pro Ala Gln Val Ala Glu Leu Leu Pro Phe Ser Ala
        195                 200                 205

Ile Ala Ser Gly Ile Ile Ser Val Pro Ile Asp Leu Pro Gly Thr Pro
    210                 215                 220

Phe Asn Ser Ala Ile Lys Ser Lys Ile Val Arg Arg Lys Leu Val
225                 230                 235                 240

Gly Ile Ile Asn Gln Arg Lys Ile Asp Leu Gly Glu Gly Lys Ala Ser
                245                 250                 255

Pro Thr Gln Asp Ile Leu Ser His Met Leu Leu Thr Ser Asp Glu Ser
            260                 265                 270

Gly Lys Phe Met Gly Glu Gly Glu Ile Ala Asp Lys Ile Leu Gly Leu
        275                 280                 285

Leu Ile Gly Gly His Asp Thr Ala Ser Ser Ala Cys Thr Phe Val Val
290                 295                 300

Lys Phe Leu Ala Glu Leu Pro Gln Ile Tyr Xaa Gly Val Tyr Gln Glu
305                 310                 315                 320

Gln Met Glu Ile Val Lys Ser Lys Lys Ala Gly Glu Leu Leu Lys Trp
                325                 330                 335

Glu Asp Ile Gln Lys Met Lys Tyr Ser Trp Asn Val Ala Cys Glu Val
            340                 345                 350

Leu Arg Leu Ala Pro Pro Leu Gln Gly Ala Phe Arg Glu Ala Leu Ser
        355                 360                 365

Asp Phe Thr Tyr Asn Gly Phe Ser Ile Pro Lys Gly Trp Lys Leu Tyr
370                 375                 380

Trp Ser Ala Asn Ser Thr His Arg Asn Ser Glu Val Phe Pro Glu Pro
385                 390                 395                 400

Leu Lys Phe Asp Pro Ser Arg Phe Asp Gly Ala Gly Pro Pro Phe
                405                 410                 415

Ser Phe Val Pro Phe Gly Gly Pro Arg Met Cys Pro Gly Lys Glu
            420                 425                 430

Tyr Ala Arg Leu Glu Ile Leu Val Phe Met His His Leu Val Lys Arg
        435                 440                 445

Phe Lys Trp Glu Lys Val Ile Pro Asp Glu Lys Ile Val Val Asn Pro
450                 455                 460

Met Pro Ile Pro Ala Asn Gly Leu Pro Val Arg Leu Phe Pro His Lys
465                 470                 475                 480

Ala

<210> SEQ ID NO 92
<211> LENGTH: 481
<212> TYPE: PRT
<213> ORGANISM: Panax ginseng

<400> SEQUENCE: 92

Met Glu Leu Phe Tyr Val Pro Leu Leu Ser Leu Phe Val Leu Phe Ile
1               5                   10                  15

Ser Leu Ser Phe His Phe Leu Phe Tyr Lys Ser Lys Pro Ser Ser
            20                  25                  30
```

```
Gly Gly Phe Pro Leu Pro Pro Gly Lys Thr Gly Trp Pro Ile Ile Gly
         35                  40                  45
Glu Ser Tyr Glu Phe Leu Ser Thr Gly Trp Lys Gly Tyr Pro Glu Lys
 50                  55                  60
Phe Ile Phe Asp Arg Met Thr Lys Tyr Ser Ser Asn Val Phe Lys Thr
 65                  70                  75                  80
Ser Ile Phe Gly Glu Pro Ala Ala Val Phe Cys Gly Ala Ala Cys Asn
                 85                  90                  95
Lys Phe Leu Phe Ser Asn Glu Asn Lys Leu Val Gln Ala Trp Trp Pro
                100                 105                 110
Asp Ser Val Asn Lys Val Phe Pro Ser Ser Thr Gln Thr Ser Ser Lys
                115                 120                 125
Glu Glu Ala Ile Lys Met Arg Lys Met Leu Pro Asn Phe Phe Lys Pro
130                 135                 140
Glu Ala Leu Gln Arg Tyr Ile Gly Leu Met Asp Gln Ile Ala Ala Asn
145                 150                 155                 160
His Phe Glu Ser Gly Trp Glu Asn Lys Asn Glu Val Val Val Phe Pro
                165                 170                 175
Leu Ala Lys Ser Tyr Thr Phe Trp Ile Ala Cys Lys Val Phe Val Ser
                180                 185                 190
Val Glu Glu Pro Ala Gln Val Ala Glu Leu Leu Glu Pro Phe Ser Ala
        195                 200                 205
Ile Ala Ser Gly Ile Ile Ser Val Pro Ile Asp Leu Pro Gly Thr Pro
        210                 215                 220
Phe Asn Ser Ala Ile Lys Ser Ser Lys Ile Val Arg Arg Lys Leu Val
225                 230                 235                 240
Gly Ile Ile Lys Gln Arg Lys Ile Asp Leu Gly Glu Gly Lys Ala Ser
                245                 250                 255
Ala Thr Gln Asp Ile Leu Ser His Met Leu Leu Thr Ser Asp Glu Ser
                260                 265                 270
Gly Lys Phe Met Gly Glu Gly Asp Ile Ala Asp Lys Ile Leu Gly Leu
                275                 280                 285
Leu Ile Gly Gly His Asp Thr Ala Ser Ser Ala Cys Thr Phe Val Val
        290                 295                 300
Lys Phe Leu Ala Glu Leu Pro Gln Ile Tyr Glu Gly Val Tyr Gln Glu
305                 310                 315                 320
Gln Met Glu Ile Val Lys Ser Lys Lys Ala Gly Glu Leu Leu Lys Trp
                325                 330                 335
Glu Asp Ile Gln Lys Met Lys Tyr Ser Trp Asn Val Ala Cys Glu Val
                340                 345                 350
Leu Arg Leu Ala Pro Pro Leu Gln Gly Ala Phe Arg Glu Ala Leu Ser
                355                 360                 365
Asp Phe Thr Tyr Asn Gly Phe Ser Ile Pro Lys Gly Trp Lys Leu Tyr
                370                 375                 380
Trp Ser Ala Asn Ser Thr His Ile Asn Ser Glu Val Phe Pro Glu Pro
385                 390                 395                 400
Leu Lys Phe Asp Pro Ser Arg Phe Asp Gly Ala Gly Pro Pro Pro Phe
                405                 410                 415
Ser Phe Val Pro Phe Gly Gly Pro Arg Met Cys Pro Gly Lys Glu
                420                 425                 430
Tyr Ala Arg Leu Glu Ile Leu Val Phe Met His His Leu Val Lys Arg
                435                 440                 445
Phe Lys Trp Glu Lys Val Ile Pro Asp Glu Lys Ile Val Val Asn Pro
```

```
            450                 455                 460
Met Pro Ile Pro Ala Asn Gly Leu Pro Val Arg Leu Phe Pro His Lys
465                 470                 475                 480

Ala

<210> SEQ ID NO 93
<211> LENGTH: 480
<212> TYPE: PRT
<213> ORGANISM: Ricinus communis

<400> SEQUENCE: 93

Met Asp His Phe Tyr Leu Thr Leu Leu Phe Leu Phe Val Ser Phe Ile
1               5                   10                  15

Thr Phe Ser Ile Phe Ile Ile Phe Tyr Lys His Lys Ser Gln Tyr Asn
                20                  25                  30

Tyr Pro Ser Leu Pro Pro Gly Lys Pro Gly Leu Pro Phe Val Gly Glu
            35                  40                  45

Ser Leu Glu Phe Leu Ser Ser Gly Trp Lys Gly His Pro Glu Lys Phe
50                  55                  60

Val Phe Asp Arg Thr Ser Lys Tyr Ser Ser Glu Ile Phe Lys Thr Asn
65                  70                  75                  80

Leu Leu Gly Gln Pro Ala Ala Val Phe Cys Gly Ala Ser Ala Asn Lys
                85                  90                  95

Phe Leu Phe Ser Asn Glu Asn Lys Leu Val Gln Ala Trp Trp Pro Asp
            100                 105                 110

Ser Val Asn Lys Ile Phe Pro Ser Ser Leu Gln Thr Ser Ser Lys Glu
        115                 120                 125

Glu Ala Ile Lys Met Arg Lys Leu Leu Pro Gln Phe Met Lys Pro Glu
130                 135                 140

Ala Leu Gln Arg Tyr Ile Gly Ile Met Asp Thr Ile Ala Gln Arg His
145                 150                 155                 160

Phe Ala Ser Gly Trp Glu Lys Lys Asn Glu Val Val Val Phe Pro Leu
                165                 170                 175

Ala Lys Asn Tyr Thr Phe Trp Leu Ala Cys Arg Leu Phe Val Ser Leu
            180                 185                 190

Glu Asp Pro Asp His Ile Ala Lys Phe Ala Asp Pro Phe Gln Glu Leu
        195                 200                 205

Ala Ser Gly Ile Ile Ser Val Pro Ile Asp Leu Pro Gly Thr Pro Phe
210                 215                 220

Arg Arg Ala Ile Lys Ala Ser Asn Phe Ile Arg Lys Glu Leu Ile Ser
225                 230                 235                 240

Ile Ile Lys Gln Arg Lys Ile Asp Leu Ala Glu Gly Lys Ala Ser Gly
                245                 250                 255

Thr Gln Asp Ile Leu Ser His Met Leu Leu Thr Ser Asp Glu Asp Gly
            260                 265                 270

Lys Phe Met Asn Glu Met Asp Ile Ala Asp Lys Ile Leu Gly Leu Leu
        275                 280                 285

Ile Gly Gly His Asp Thr Ala Ser Ala Ala Cys Thr Phe Ile Ile Lys
290                 295                 300

Tyr Leu Ala Glu Leu Pro Gln Ile Tyr Asp Ala Val Tyr Lys Glu Gln
305                 310                 315                 320

Met Glu Ile Ala Lys Ser Lys Gly Glu Gly Glu Leu Leu Asn Trp Glu
                325                 330                 335

Asp Ile Gln Lys Met Lys Tyr Ser Trp Asn Val Ala Cys Glu Val Met
```

Arg Val Ala Pro Pro Leu Gln Gly Ala Phe Arg Glu Ala Ile Asn Asp
            340                 345                 350
        355                 360                 365

Phe Ile Phe Asn Gly Phe Tyr Ile Pro Lys Gly Trp Lys Leu Tyr Trp
        370                 375                 380

Ser Ala Asn Ser Thr His Lys Ser Ala Thr Tyr Phe Glu Glu Pro Glu
385                 390                 395                 400

Lys Phe Asp Pro Ser Arg Phe Glu Gly Lys Gly Pro Ala Pro Tyr Thr
                405                 410                 415

Phe Val Pro Phe Gly Gly Gly Pro Arg Met Cys Pro Gly Lys Glu Tyr
                420                 425                 430

Ala Arg Leu Glu Ile Leu Val Phe Met His Asn Leu Val Lys Arg Phe
                435                 440                 445

Asn Phe Gln Lys Ile Ile Pro Asp Glu Asn Ile Ile Val Asn Pro Leu
            450                 455                 460

Pro Ile Pro Ala Lys Gly Leu Pro Val Arg Leu Leu Pro His Gln Ile
465                 470                 475                 480

<210> SEQ ID NO 94
<211> LENGTH: 480
<212> TYPE: PRT
<213> ORGANISM: Vitis vinifera
<220> FEATURE:
<221> NAME/KEY: misc_feature
<222> LOCATION: (279)..(279)
<223> OTHER INFORMATION: Xaa can be any naturally occurring amino acid

<400> SEQUENCE: 94

Met Glu Val Phe Phe Leu Ser Leu Leu Leu Ile Cys Val Leu Ser Val
1               5                   10                  15

Ser Ile Arg Leu Tyr Leu Leu Leu Tyr Lys His Arg Ser His Phe Thr
                20                  25                  30

Gly Pro Asn Leu Pro Pro Gly Lys Ile Gly Trp Pro Met Val Gly Glu
            35                  40                  45

Ser Leu Glu Phe Leu Ser Thr Gly Trp Lys Gly His Pro Glu Lys Phe
    50                  55                  60

Ile Phe Asp Arg Ile Ser Lys Tyr Ser Ser Glu Val Phe Lys Thr Ser
65                  70                  75                  80

Leu Leu Gly Glu Pro Ala Ala Val Phe Ala Gly Ala Ala Gly Asn Lys
                85                  90                  95

Phe Leu Phe Ser Asn Glu Asn Lys Leu Val His Ala Trp Trp Pro Ser
            100                 105                 110

Ser Val Asp Lys Val Phe Pro Ser Ser Thr Gln Thr Ser Ser Lys Glu
        115                 120                 125

Glu Ala Lys Lys Met Arg Lys Leu Leu Pro Gln Phe Leu Lys Pro Glu
    130                 135                 140

Ala Leu Gln Arg Tyr Thr Gly Ile Met Asp His Ile Ala Gln Arg His
145                 150                 155                 160

Phe Ala Asp Ser Trp Asp Asn Arg Asp Glu Val Ile Val Phe Pro Leu
                165                 170                 175

Ala Lys Arg Phe Thr Phe Trp Leu Ala Cys Arg Leu Phe Met Ser Ile
            180                 185                 190

Glu Asp Pro Ala His Val Ala Lys Phe Glu Lys Pro Phe His Val Leu
        195                 200                 205

Ala Ser Gly Leu Ile Thr Ile Pro Ile Asp Leu Pro Gly Thr Pro Phe
    210                 215                 220

His Arg Ala Ile Lys Ala Ser Asn Phe Ile Arg Lys Glu Leu Arg Ala
225                 230                 235                 240

Ile Ile Lys Gln Arg Lys Ile Asp Leu Ala Glu Ser Lys Ala Ser Lys
            245                 250                 255

Thr Gln Asp Ile Leu Ser His Met Leu Leu Ala Thr Asp Glu Asp Gly
        260                 265                 270

Cys His Met Asn Glu Met Xaa Ile Ala Asp Lys Ile Leu Gly Leu Leu
    275                 280                 285

Ile Gly Gly His Asp Thr Ala Ser Ser Ala Ile Thr Phe Leu Val Lys
290                 295                 300

Tyr Met Ala Glu Leu Pro His Ile Tyr Glu Lys Val Tyr Lys Glu Gln
305                 310                 315                 320

Met Glu Ile Ala Asn Ser Lys Ala Pro Gly Glu Leu Leu Asn Trp Asp
                325                 330                 335

Asp Val Gln Lys Met Arg Tyr Ser Trp Asn Val Ala Cys Glu Val Met
            340                 345                 350

Arg Leu Ala Pro Pro Leu Gln Gly Ala Phe Arg Glu Ala Ile Thr Asp
        355                 360                 365

Phe Val Phe Asn Gly Phe Ser Ile Pro Lys Gly Trp Lys Leu Tyr Trp
    370                 375                 380

Ser Ala Asn Ser Thr His Lys Ser Leu Glu Cys Phe Pro Gln Pro Glu
385                 390                 395                 400

Lys Phe Asp Pro Thr Arg Phe Glu Gly Ala Gly Pro Ala Pro Tyr Thr
                405                 410                 415

Phe Val Pro Phe Gly Gly Gly Pro Arg Met Cys Pro Gly Lys Glu Tyr
            420                 425                 430

Ala Arg Leu Glu Ile Leu Ile Phe Met His Asn Leu Val Lys Arg Phe
        435                 440                 445

Lys Trp Asp Lys Leu Leu Pro Asp Glu Lys Ile Ile Val Asp Pro Met
    450                 455                 460

Pro Met Pro Ala Lys Gly Leu Pro Val Arg Leu His Pro His Lys Pro
465                 470                 475                 480

<210> SEQ ID NO 95
<211> LENGTH: 480
<212> TYPE: PRT
<213> ORGANISM: Vitis vinifera

<400> SEQUENCE: 95

Met Glu Val Phe Phe Leu Ser Leu Leu Leu Ile Cys Val Leu Ser Val
1               5                   10                  15

Ser Ile Gly Leu Gln Phe Leu Phe Tyr Lys His Arg Ser His Phe Thr
            20                  25                  30

Gly Pro Asn Leu Pro Pro Gly Arg Ile Gly Trp Pro Met Val Gly Glu
        35                  40                  45

Ser Leu Glu Phe Leu Ser Thr Gly Trp Lys Gly His Pro Glu Lys Phe
    50                  55                  60

Ile Phe Asp Arg Ile Ser Lys Tyr Ser Ser Glu Val Phe Lys Thr Ser
65                  70                  75                  80

Leu Leu Gly Glu Pro Ala Ala Val Phe Ala Gly Ala Ala Gly Asn Lys
                85                  90                  95

Phe Leu Phe Ser Asn Glu Asn Lys Leu Val His Ala Trp Trp Pro Ser
            100                 105                 110

Ser Val Asp Lys Val Phe Pro Ser Ser Thr Gln Thr Ser Ser Lys Glu

```
            115                 120                 125
Glu Ala Lys Lys Met Arg Lys Leu Leu Pro Arg Phe Leu Lys Pro Glu
            130                 135                 140

Ala Leu Gln Arg Tyr Ile Gly Ile Met Asp His Ile Ala Gln Arg His
145                 150                 155                 160

Phe Ala Asp Ser Trp Asp Asn Arg Asp Glu Val Ile Val Phe Pro Leu
                165                 170                 175

Ser Lys Arg Phe Thr Phe Trp Leu Ala Cys Arg Leu Phe Met Ser Ile
                180                 185                 190

Glu Asp Pro Asp His Ile Ala Lys Phe Glu Lys Pro Phe His Val Leu
                195                 200                 205

Ala Ser Gly Leu Ile Thr Val Pro Ile Asp Leu Pro Gly Thr Pro Phe
210                 215                 220

His Arg Ala Ile Lys Ala Ser Asn Phe Ile Arg Lys Glu Leu Arg Ala
225                 230                 235                 240

Ile Ile Lys Gln Arg Lys Ile Asp Leu Ala Glu Gly Lys Ala Ser Pro
                245                 250                 255

Thr Gln Asp Ile Leu Ser Asp Leu Leu Leu Ala Thr Asp Glu Asp Gly
                260                 265                 270

Arg His Met Asn Glu Ile Asn Ile Ala Asp Lys Ile Leu Gly Leu Leu
        275                 280                 285

Ile Gly Gly His Asp Thr Ala Ser Ser Ala Ile Thr Phe Ile Val Lys
        290                 295                 300

Tyr Met Ala Glu Leu Pro His Met Tyr Glu Lys Val Tyr Glu Glu Gln
305                 310                 315                 320

Met Glu Ile Ala Asn Ser Lys Ala Pro Gly Glu Leu Leu Asn Trp Asp
                325                 330                 335

Asp Val Gln Lys Met Arg Tyr Ser Trp Asn Val Ala Cys Glu Val Met
                340                 345                 350

Arg Leu Ala Pro Pro Leu Gln Gly Ala Phe Arg Glu Ala Ile Thr Asp
        355                 360                 365

Phe Val Phe Asn Gly Phe Ser Ile Pro Lys Gly Trp Lys Leu Tyr Trp
370                 375                 380

Ser Thr Ser Ser Thr His Lys Ser Pro Lys Cys Phe Pro Glu Pro Glu
385                 390                 395                 400

Lys Phe Asp Pro Thr Arg Phe Glu Gly Ala Gly Pro Ala Pro Tyr Thr
                405                 410                 415

Phe Val Pro Phe Gly Gly Gly Pro Arg Met Cys Pro Gly Lys Glu Tyr
                420                 425                 430

Ala Arg Leu Glu Ile Leu Val Phe Met His Asn Val Val Lys Arg Phe
        435                 440                 445

Lys Trp Asp Lys Leu Leu Pro Asp Glu Lys Ile Ile Ile Asp Pro Met
        450                 455                 460

Arg Met Pro Ala Lys Gly Leu Pro Val Arg Leu Arg Leu His Lys Pro
465                 470                 475                 480

<210> SEQ ID NO 96
<211> LENGTH: 471
<212> TYPE: PRT
<213> ORGANISM: Ricinus communis

<400> SEQUENCE: 96

Met Phe Pro Phe Ala Val Leu Leu Ile Ala Leu Ser Ile Ser Tyr Leu
1               5                   10                  15
```

-continued

```
Ile Phe Lys His Lys Ser Asn Ala Ser Ser Arg Lys Asn Leu Pro Pro
        20                  25                  30
Gly Asn Thr Gly Trp Pro Leu Ile Gly Glu Ser Ile Glu Phe Leu Ser
            35                  40                  45
Thr Gly Arg Lys Gly His Pro Glu Lys Phe Ile Phe Asp Arg Met Glu
        50                  55                  60
Lys Phe Ser Ser Lys Val Phe Lys Thr Ser Leu Leu Leu Glu Pro Ala
65                  70                  75                  80
Ala Val Phe Cys Gly Ala Ala Gly Asn Lys Phe Leu Phe Ser Asn Glu
                85                  90                  95
Asn Lys Leu Val Thr Ala Trp Trp Pro Asn Ser Val Asn Lys Ile Phe
            100                 105                 110
Pro Ser Ser Leu Gln Thr Ser Ser Gln Glu Glu Ser Lys Arg Met Arg
        115                 120                 125
Lys Leu Leu Pro Gln Phe Leu Lys Pro Glu Ala Leu Gln Arg Tyr Ile
        130                 135                 140
Ser Ile Met Asp Val Ile Ala Gln Arg His Phe Ala Phe Gly Trp Asn
145                 150                 155                 160
Asn Lys Gln Gln Val Thr Val Phe Pro Leu Ala Lys Met Tyr Thr Phe
                165                 170                 175
Trp Leu Ala Cys Arg Leu Phe Leu Ser Met Glu Asp Arg Glu Glu Val
            180                 185                 190
Glu Lys Phe Ala Lys Pro Phe Asp Val Leu Ala Ser Gly Ile Ile Ser
        195                 200                 205
Ile Pro Ile Asp Phe Pro Gly Thr Pro Phe Asn Arg Gly Ile Lys Ala
        210                 215                 220
Ser Asn Glu Val Arg Arg Glu Leu Ile Lys Met Ile Glu Gln Arg Lys
225                 230                 235                 240
Ile Asp Leu Ala Glu Asn Lys Ala Ser Pro Thr Gln Asp Ile Leu Ser
                245                 250                 255
His Met Leu Thr Thr Ala Asp Glu Tyr Met Asn Glu Met Asp Ile Ala
            260                 265                 270
Asp Lys Ile Leu Gly Leu Leu Ile Gly Gly His Asp Thr Ala Ser Ala
        275                 280                 285
Ala Ile Thr Phe Val Val Lys Tyr Leu Ala Glu Met Pro Gln Val Tyr
        290                 295                 300
Asn Lys Val Leu Glu Glu Gln Met Glu Ile Ala Lys Ala Lys Ala Ala
305                 310                 315                 320
Gly Glu Leu Leu Asn Trp Glu Asp Ile Gln Lys Met Arg Tyr Ser Trp
                325                 330                 335
Asn Val Ala Cys Glu Val Met Arg Leu Ala Pro Pro Leu Gln Gly Ala
            340                 345                 350
Phe Arg Glu Ala Met Thr Asp Phe Thr Tyr Ala Gly Phe Thr Ile Pro
        355                 360                 365
Lys Gly Trp Lys Leu Tyr Trp Gly Ala Asn Ser Thr His Arg Asn Pro
        370                 375                 380
Glu Cys Phe Pro Glu Pro Glu Lys Phe Asp Pro Ser Arg Phe Glu Gly
385                 390                 395                 400
Lys Gly Pro Ala Pro Tyr Thr Phe Val Pro Phe Gly Gly Gly Pro Arg
                405                 410                 415
Met Cys Pro Gly Lys Glu Tyr Ala Arg Leu Glu Ile Leu Val Phe Met
            420                 425                 430
His Asn Ile Val Lys Lys Phe Arg Trp Glu Lys Leu Leu Pro Glu Glu
```

```
                         435                 440                 445
Lys Ile Ile Val Asp Pro Leu Pro Ile Pro Ala Lys Gly Leu Pro Leu
            450                 455                 460

Arg Leu His Pro His Thr Ser
465                 470

<210> SEQ ID NO 97
<211> LENGTH: 482
<212> TYPE: PRT
<213> ORGANISM: Glycine max

<400> SEQUENCE: 97

Met Glu Asp Asn Asn Leu His Leu Ser Leu Leu Leu Phe Val Ser
1               5                   10                  15

Ile Val Thr Leu Ser Leu Phe Val Leu Phe Tyr Lys His Arg Ser Ala
                20                  25                  30

Phe Ala Ala Pro Asn Leu Pro Pro Gly Ala Thr Gly Tyr Pro Val Ile
            35                  40                  45

Gly Glu Ser Leu Glu Phe Leu Ser Thr Gly Trp Lys Gly His Pro Glu
        50                  55                  60

Lys Phe Ile Phe Asp Arg Met Ile Arg Tyr Ser Ser Gln Leu Phe Lys
65                  70                  75                  80

Thr Ser Ile Leu Gly Glu Pro Ala Val Ile Phe Cys Gly Ala Thr Cys
                85                  90                  95

Asn Lys Phe Leu Phe Ser Asn Glu Asn Lys Leu Val Ala Ala Trp Trp
            100                 105                 110

Pro Asn Ser Val Asn Lys Val Phe Pro Thr Thr Leu Leu Ser Asn Ser
        115                 120                 125

Lys Gln Glu Ser Lys Lys Met Arg Lys Leu Leu Pro Gln Phe Leu Lys
130                 135                 140

Pro Glu Ala Leu Gln Arg Tyr Val Gly Ile Met Asp Thr Ile Ala Arg
145                 150                 155                 160

Asn His Phe Ala Ser Leu Trp Asp Asn Lys Thr Glu Leu Thr Val Tyr
                165                 170                 175

Pro Leu Ala Lys Arg Tyr Thr Phe Leu Leu Ala Cys Arg Leu Phe Met
            180                 185                 190

Ser Ile Glu Asp Val Asn His Val Ala Lys Phe Glu Asn Pro Phe His
        195                 200                 205

Leu Leu Ala Ser Gly Ile Ile Ser Val Pro Ile Asp Leu Pro Gly Thr
210                 215                 220

Pro Phe Asn Lys Ala Ile Lys Ala Ala Asn Ala Ile Arg Lys Glu Leu
225                 230                 235                 240

Leu Lys Ile Ile Arg Gln Arg Lys Val Asp Leu Ala Glu Gly Lys Ala
                245                 250                 255

Ser Pro Thr Gln Asp Ile Leu Ser His Met Leu Leu Thr Cys Asp Glu
            260                 265                 270

Lys Gly Gln Phe Met Asn Glu Leu Asp Ile Ala Asp Lys Ile Leu Gly
        275                 280                 285

Leu Leu Ile Gly Gly His Asp Thr Ala Ser Ala Ala Ile Thr Phe Ile
290                 295                 300

Val Lys Tyr Leu Ala Glu Leu Pro His Ile Tyr Asp Arg Val Tyr Gln
305                 310                 315                 320

Glu Gln Met Glu Ile Ala Lys Leu Lys Ser Pro Gly Glu Leu Leu Asn
                325                 330                 335
```

Trp Asp Asp Val Asn Arg Met Gln Tyr Ser Trp Asn Val Ala Cys Glu
                340                 345                 350

Val Met Arg Ile Ala Pro Pro Leu Gln Gly Gly Phe Arg Glu Ala Ile
        355                 360                 365

Asn Asp Phe Ile Phe Asp Gly Phe Ser Ile Pro Lys Gly Trp Lys Leu
370                 375                 380

Tyr Trp Ser Ala Asn Ser Thr His Lys Ser Pro Glu Tyr Phe Pro Glu
385                 390                 395                 400

Pro Glu Lys Phe Asp Pro Thr Arg Phe Glu Gly Gln Gly Pro Ala Pro
                405                 410                 415

Tyr Thr Phe Val Pro Phe Gly Gly Pro Arg Met Cys Pro Gly Lys
                420                 425                 430

Glu Tyr Ala Arg Leu Glu Ile Leu Val Phe Met His Asn Leu Val Lys
            435                 440                 445

Arg Phe Lys Trp Gln Lys Leu Ile Pro Asp Glu Lys Ile Val Asp
            450                 455                 460

Pro Leu Pro Ile Pro Ala Lys Asn Leu Pro Ile Arg Leu His Pro His
465                 470                 475                 480

Lys Pro

<210> SEQ ID NO 98
<211> LENGTH: 445
<212> TYPE: PRT
<213> ORGANISM: Glycine max

<400> SEQUENCE: 98

Met Glu Asp Asn Asn Leu His Leu Ser Leu Leu Leu Phe Val Ser
1               5                   10                  15

Ile Val Thr Leu Ser Leu Phe Val Leu Phe Tyr Lys His Arg Ser Ala
                20                  25                  30

Phe Ala Ala Pro Asn Leu Pro Pro Gly Ala Thr Gly Tyr Pro Val Ile
            35                  40                  45

Gly Glu Ser Leu Glu Phe Leu Ser Thr Gly Trp Lys Gly His Pro Glu
        50                  55                  60

Lys Phe Ile Phe Asp Arg Met Ile Arg Tyr Ser Ser Gln Leu Phe Lys
65                  70                  75                  80

Thr Ser Ile Leu Gly Glu Pro Ala Val Ile Phe Cys Gly Ala Thr Cys
                85                  90                  95

Asn Lys Phe Leu Phe Ser Asn Glu Asn Lys Leu Val Ala Ala Trp Trp
            100                 105                 110

Pro Asn Ser Val Asn Lys Val Phe Pro Thr Thr Leu Leu Ser Asn Ser
        115                 120                 125

Lys Gln Glu Ser Lys Lys Met Arg Lys Leu Leu Pro Gln Phe Leu Lys
130                 135                 140

Pro Glu Ala Leu Gln Arg Tyr Val Gly Ile Met Asp Thr Ile Ala Arg
145                 150                 155                 160

Asn His Phe Ala Ser Leu Trp Asp Asn Lys Thr Glu Leu Thr Val Tyr
                165                 170                 175

Pro Leu Ala Lys Arg Tyr Thr Phe Leu Leu Ala Cys Arg Leu Phe Met
            180                 185                 190

Ser Ile Glu Asp Val Asn His Val Ala Lys Phe Glu Asn Pro Phe His
        195                 200                 205

Leu Leu Ala Ser Gly Ile Ile Ser Val Pro Ile Asp Leu Pro Gly Thr
210                 215                 220

```
Pro Phe Asn Lys Ala Ile Lys Ala Ala Asn Ala Ile Arg Lys Glu Leu
225                 230                 235                 240

Leu Lys Ile Ile Arg Gln Arg Lys Val Asp Leu Ala Glu Gly Lys Ala
            245                 250                 255

Ser Pro Thr Gln Asp Ile Leu Ser His Met Leu Leu Thr Cys Asp Glu
        260                 265                 270

Lys Gly Gln Phe Met Asn Glu Leu Asp Ile Ala Asp Lys Ile Leu Gly
    275                 280                 285

Leu Leu Ile Gly Gly His Asp Thr Ala Ser Ala Ala Ile Thr Phe Ile
290                 295                 300

Val Lys Tyr Leu Ala Glu Leu Pro His Ile Tyr Asp Arg Val Tyr Gln
305                 310                 315                 320

Glu Gln Met Glu Ile Ala Lys Leu Lys Ser Pro Gly Glu Leu Leu Asn
                325                 330                 335

Trp Asp Asp Val Asn Arg Met Gln Tyr Ser Trp Asn Val Ala Cys Glu
            340                 345                 350

Val Met Arg Ile Ala Pro Pro Leu Gln Gly Gly Phe Arg Glu Ala Ile
        355                 360                 365

Asn Asp Phe Ile Phe Asp Gly Phe Ser Ile Pro Lys Gly Trp Lys Leu
370                 375                 380

Tyr Trp Ser Ala Asn Ser Thr His Lys Ser Pro Glu Tyr Phe Pro Glu
385                 390                 395                 400

Pro Glu Lys Phe Asp Pro Thr Arg Phe Glu Gly Gln Gly Pro Ala Pro
                405                 410                 415

Tyr Thr Phe Val Pro Phe Gly Gly Pro Arg Met Cys Pro Gly Lys
            420                 425                 430

Glu Tyr Ala Arg Leu Glu Ile Leu Val Phe Met Tyr Asn
    435                 440                 445

<210> SEQ ID NO 99
<211> LENGTH: 482
<212> TYPE: PRT
<213> ORGANISM: Vitis vinifera

<400> SEQUENCE: 99

Met Glu Leu Ser Leu Leu His Ile Leu Pro Trp Ala Thr Leu Phe Thr
1               5                   10                  15

Thr Leu Ser Leu Ser Phe Leu Ile Tyr Lys Leu Met Ile Ile Ser His
            20                  25                  30

Gly Thr Pro Arg Asn Leu Pro Ser Gly Asn Thr Gly Leu Pro Tyr Ile
        35                  40                  45

Gly Glu Ser Ile Gln Phe Leu Ser Asn Gly Arg Lys Gly His Pro Glu
    50                  55                  60

Lys Phe Ile Ser Glu Arg Met Leu Lys Phe Ser Lys Val Phe Lys
65                  70                  75                  80

Thr Ser Leu Phe Gly Glu Thr Ala Ala Val Phe Cys Gly Ser Ala Gly
                85                  90                  95

Asn Lys Phe Leu Phe Ser Asn Glu Asn Lys Leu Val Thr Ala Trp Trp
            100                 105                 110

Pro Ser Ser Val Asn Lys Ile Phe Pro Ser Ser Leu Gln Thr Ser Ser
        115                 120                 125

Gln Glu Glu Ser Lys Lys Met Arg Lys Leu Leu Pro Gly Phe Leu Lys
    130                 135                 140

Pro Glu Ala Leu Gln Arg Tyr Ile Ser Ile Met Asp Val Ile Ala Gln
145                 150                 155                 160
```

Arg His Phe Glu Ser Ser Trp Asn Asn Lys Glu Val Thr Val Phe
                165                 170                 175

Pro Leu Ala Lys Met Phe Thr Phe Trp Leu Ala Cys Arg Leu Phe Leu
            180                 185                 190

Ser Val Glu Asp Pro Asp His Val Glu Lys Leu Ala Glu Pro Phe Asn
195                 200                 205

Glu Leu Ala Ala Gly Ile Ile Ala Leu Pro Ile Asp Leu Pro Gly Thr
    210                 215                 220

Ser Phe Asn Lys Gly Ile Lys Ala Ser Asn Leu Val Arg Lys Glu Leu
225                 230                 235                 240

His Ala Ile Ile Lys Lys Arg Lys Met Asn Leu Ala Asp Asn Lys Ala
            245                 250                 255

Ser Thr Thr Gln Asp Ile Leu Ser His Met Leu Leu Thr Cys Asp Glu
                260                 265                 270

Asn Gly Glu Tyr Met Asn Glu Glu Asp Ile Ala Asp Lys Ile Leu Gly
            275                 280                 285

Leu Leu Val Gly Gly His Asp Thr Ala Ser Ala Thr Ile Thr Phe Ile
    290                 295                 300

Val Lys Phe Leu Ala Glu Leu Pro His Val Tyr Asp Glu Val Phe Lys
305                 310                 315                 320

Glu Gln Met Glu Ile Ala Lys Ser Lys Ala Pro Gly Glu Leu Leu Asn
            325                 330                 335

Trp Glu Asp Ile Pro Lys Met Arg Tyr Ser Trp Asn Val Ala Cys Glu
                340                 345                 350

Val Met Arg Leu Ala Pro Pro Val Gln Gly Ala Phe Arg Glu Ala Met
            355                 360                 365

Asn Asp Phe Ile Phe Glu Gly Phe Ser Ile Pro Lys Gly Trp Lys Leu
370                 375                 380

Tyr Trp Ser Thr His Ser Thr His Arg Asn Pro Glu Phe Phe Pro Lys
385                 390                 395                 400

Pro Glu Lys Phe Asp Pro Ser Arg Phe Asp Gly Lys Gly Pro Ala Pro
            405                 410                 415

Tyr Thr Tyr Val Pro Phe Gly Gly Gly Pro Arg Met Cys Pro Gly Lys
                420                 425                 430

Glu Tyr Ala Arg Leu Glu Val Leu Val Phe Met His Asn Leu Val Arg
            435                 440                 445

Arg Phe Lys Trp Glu Lys Leu Leu Pro Asp Glu Lys Ile Ile Val Asp
450                 455                 460

Pro Met Pro Ile Pro Ala Lys Gly Leu Pro Ile Arg Leu His His His
465                 470                 475                 480

Gln Pro

<210> SEQ ID NO 100
<211> LENGTH: 484
<212> TYPE: PRT
<213> ORGANISM: Populus trichocarpa

<400> SEQUENCE: 100

Met Glu Leu Pro Phe Ile Ser Leu Leu Pro Tyr Gly Ile Leu Phe Ile
1               5                   10                  15

Ile Ser Ala Val Ser Leu Ser Tyr Leu Ile Asn Lys His Lys Tyr Tyr
            20                  25                  30

Leu Ser Ser Leu Asn Asn Leu Pro Pro Gly Asn Thr Gly Leu Pro Leu
        35                  40                  45

```
Ile Gly Glu Ser Leu Glu Phe Leu Thr Thr Gly Gln Lys Gly Gln Pro
 50                  55                  60

Glu Lys Phe Ile Leu Asp Arg Met Ala Lys Phe Ser Ser Lys Val Phe
 65                  70                  75                  80

Lys Thr Ser Leu Phe Cys Glu Pro Thr Ala Val Phe Cys Gly Ala Ala
                 85                  90                  95

Gly Asn Lys Phe Leu Phe Ser Asn Glu Asn Lys Leu Val Thr Ala Trp
            100                 105                 110

Trp Pro Asp Ser Val Asn Lys Ile Phe Pro Ser Ser Gln Gln Thr Ser
        115                 120                 125

Ser Gln Glu Glu Ser Lys Lys Met Arg Lys Leu Phe Pro Leu Phe Phe
    130                 135                 140

Lys Pro Glu Ser Leu Gln Arg Tyr Ile Ser Val Met Asp Val Ile Ala
145                 150                 155                 160

Gln Arg His Leu Ala Ser Asp Trp Glu Gly Lys Gln Glu Val Ser Val
                165                 170                 175

Phe Pro Leu Ala Lys Thr Tyr Thr Phe Trp Leu Ala Cys Arg Leu Phe
            180                 185                 190

Leu Ser Met Glu Asp Pro Glu Glu Val Gln Lys Phe Ala Lys Pro Phe
        195                 200                 205

Asn Asp Leu Ala Ala Gly Ile Ile Ser Ile Pro Ile Asp Leu Pro Trp
    210                 215                 220

Thr Pro Phe Asn Arg Gly Val Lys Ala Ser Asn Val Val His Lys Glu
225                 230                 235                 240

Leu Leu Lys Ile Ile Lys Gln Arg Lys Ile Asp Leu Ala Glu Asn Lys
                245                 250                 255

Ala Ser Pro Thr Gln Asp Ile Leu Ser His Met Leu Thr Thr Ala Asp
            260                 265                 270

Asp Asn Gly Gln Cys Met Lys Lys Ile Asp Ile Ala Asp Lys Ile Leu
        275                 280                 285

Gly Leu Leu Val Gly Gly His Asp Thr Ala Ser Ala Ala Ile Thr Phe
    290                 295                 300

Ile Val Lys Tyr Leu Ala Glu Leu Pro His Val Tyr Asn Lys Leu Leu
305                 310                 315                 320

Glu Glu Gln Arg Glu Ile Ala Lys Thr Lys Thr Pro Gly Glu Leu Leu
                325                 330                 335

Asn Trp Glu Asp Ile Gln Arg Met Arg Tyr Ser Trp Asn Val Ala Cys
            340                 345                 350

Glu Val Met Arg Val Ala Pro Pro Leu Gln Gly Ala Phe Arg Glu Ala
        355                 360                 365

Met Thr Glu Phe Asn Tyr Ala Gly Phe Thr Ile Pro Lys Gly Trp Lys
    370                 375                 380

Leu Tyr Trp Ser Ala Asn Thr Thr His Lys Asn Pro Glu Cys Phe Pro
385                 390                 395                 400

Glu Pro Glu Asn Phe Asp Pro Ser Arg Phe Glu Gly Asn Gly Pro Ala
                405                 410                 415

Pro Tyr Thr Phe Val Pro Phe Gly Gly Gly Pro Arg Met Cys Pro Gly
            420                 425                 430

Lys Glu Tyr Ala Arg Leu Glu Ile Leu Val Phe Leu His Asn Leu Val
        435                 440                 445

Lys Lys Phe Arg Trp Glu Lys Leu Leu Pro Lys Glu Arg Ile Ile Val
    450                 455                 460
```

Asp Pro Met Pro Ile Pro Ser Lys Gly Leu Pro Ile Arg Leu His Pro
465                 470                 475                 480

His Glu Ala Ala

<210> SEQ ID NO 101
<211> LENGTH: 479
<212> TYPE: PRT
<213> ORGANISM: Medicago truncatula

<400> SEQUENCE: 101

Met Glu Pro Asn Phe Tyr Leu Ser Leu Leu Leu Phe Val Thr Phe
1               5                   10                  15

Ile Ser Leu Ser Leu Phe Phe Ile Phe Tyr Lys Gln Lys Ser Pro Leu
                20                  25                  30

Asn Leu Pro Pro Gly Lys Met Gly Tyr Pro Ile Ile Gly Glu Ser Leu
            35                  40                  45

Glu Phe Leu Ser Thr Gly Trp Lys Gly His Pro Glu Lys Phe Ile Phe
50                  55                  60

Asp Arg Met Arg Lys Tyr Ser Ser Glu Leu Phe Lys Thr Ser Ile Val
65                  70                  75                  80

Gly Glu Ser Thr Val Val Cys Cys Gly Ala Ala Ser Asn Lys Phe Leu
                85                  90                  95

Phe Ser Asn Glu Asn Lys Leu Val Thr Ala Trp Trp Pro Asp Ser Val
            100                 105                 110

Asn Lys Ile Phe Pro Thr Thr Ser Leu Asp Ser Asn Leu Lys Glu Glu
        115                 120                 125

Ser Ile Lys Met Arg Lys Leu Leu Pro Gln Phe Phe Lys Pro Glu Ala
130                 135                 140

Leu Gln Arg Tyr Val Gly Val Met Asp Val Ile Ala Gln Arg His Phe
145                 150                 155                 160

Val Thr His Trp Asp Asn Lys Asn Glu Thr Thr Val Tyr Pro Leu Ala
                165                 170                 175

Lys Arg Tyr Thr Phe Leu Leu Ala Cys Arg Leu Phe Met Ser Val Glu
            180                 185                 190

Asp Glu Asn His Val Ala Lys Phe Ser Asp Pro Phe Gln Leu Ile Ala
        195                 200                 205

Ala Gly Ile Ile Ser Leu Pro Ile Asp Leu Pro Gly Thr Pro Phe Asn
210                 215                 220

Lys Ala Ile Lys Ala Ser Asn Phe Ile Arg Lys Glu Leu Ile Lys Ile
225                 230                 235                 240

Ile Lys Gln Arg Arg Val Asp Leu Ala Glu Gly Thr Ala Ser Pro Thr
                245                 250                 255

Gln Asp Ile Leu Ser His Met Leu Leu Thr Ser Asp Glu Asn Gly Lys
            260                 265                 270

Ser Met Asn Glu Leu Asn Ile Ala Asp Lys Ile Leu Gly Leu Leu Thr
        275                 280                 285

Gly Gly His Asp Thr Ala Ser Val Ala Cys Thr Phe Leu Val Lys Tyr
290                 295                 300

Leu Gly Glu Leu Pro His Ile Tyr Asp Lys Val Tyr Gln Glu Gln Met
305                 310                 315                 320

Glu Ile Ala Lys Ser Lys Pro Ala Gly Glu Leu Leu Asn Trp Asp Asp
                325                 330                 335

Leu Lys Lys Met Lys Tyr Ser Trp Asn Val Ala Cys Glu Val Met Arg
            340                 345                 350

Leu Ser Pro Pro Leu Gln Gly Gly Phe Arg Glu Ala Ile Thr Asp Phe
                355                 360                 365

Met Phe Asn Gly Phe Ser Ile Pro Lys Gly Trp Lys Leu Tyr Trp Ser
370                 375                 380

Ala Asn Ser Thr His Lys Asn Ala Glu Cys Phe Pro Met Pro Glu Lys
385                 390                 395                 400

Phe Asp Pro Thr Arg Phe Glu Gly Asn Gly Pro Ala Pro Tyr Thr Phe
                405                 410                 415

Val Pro Phe Gly Gly Pro Arg Met Cys Pro Gly Lys Glu Tyr Ala
                420                 425                 430

Arg Leu Glu Ile Leu Val Phe Met His Asn Leu Ala Lys Arg Phe Lys
                435                 440                 445

Trp Glu Lys Val Ile Pro Asp Glu Lys Ile Val Asp Pro Phe Pro
450                 455                 460

Ile Pro Ala Lys Asp Leu Pro Ile Arg Leu Tyr Pro His Lys Ala
465                 470                 475

<210> SEQ ID NO 102
<211> LENGTH: 477
<212> TYPE: PRT
<213> ORGANISM: Ricinus communis

<400> SEQUENCE: 102

Met Glu Leu Phe Phe Leu Ile Ala Leu Thr Leu Phe Ile Ile Leu Val
1               5                   10                  15

Thr Leu Pro Ile Leu Ala Val Leu Tyr Arg Pro Asn Ile Ile Asn Leu
                20                  25                  30

Pro Pro Gly Lys Thr Gly Leu Pro Tyr Ile Gly Glu Ser Leu Glu Phe
            35                  40                  45

Leu Ser Thr Gly Arg Lys Gly His Pro Glu Lys Phe Leu Ser Asp Arg
    50                  55                  60

Met Glu Lys Phe Ser Arg Gln Val Phe Arg Thr Ser Ile Leu Gly Glu
65                  70                  75                  80

Gln Thr Ala Val Val Cys Gly Ala Gln Gly Asn Lys Phe Leu Phe Ser
                85                  90                  95

Asn Glu Asn Lys Leu Val Thr Ala Trp Trp Pro Lys Ser Ile Leu Arg
                100                 105                 110

Leu Phe Pro Ser Ser Asn Gln Ser Thr Ile Leu Ala Glu Gly Met Arg
            115                 120                 125

Met Arg Lys Met Leu Pro His Phe Leu Lys Pro Glu Ala Leu Gln Arg
130                 135                 140

Tyr Ile Gly Val Met Asp His Met Ala Gln Val His Phe Gln Asp Ser
145                 150                 155                 160

Trp Glu Asn Lys Gln Glu Val Thr Val Tyr Pro Leu Ala Lys Met Tyr
                165                 170                 175

Thr Phe Ser Val Ala Cys Lys Val Phe Leu Ser Met Asp Asp Pro Lys
            180                 185                 190

Glu Val Ala Lys Phe Ala Ala Pro Phe Asn Asp Met Ala Ser Gly Ile
        195                 200                 205

Ile Ser Ile Pro Ile Asn Phe Pro Gly Thr Ser Phe Asn Arg Gly Leu
    210                 215                 220

Lys Ala Ser Lys Ile Ile Arg Asn Glu Met Leu Arg Met Ile Lys Gln
225                 230                 235                 240

Arg Arg Lys Asp Leu Ala Glu Asn Lys Ala Thr Pro Met Gln Asp Ile
                245                 250                 255

Leu Ser His Met Leu Val Ala Thr Asp Glu Glu Gly Gln Arg Leu Gly
                260                 265                 270

Glu Val Gly Ile Ala Asp Lys Ile Ile Ser Leu Leu Ile Gly Gly His
            275                 280                 285

Asp Thr Ala Ser Ala Thr Ile Thr Phe Val Val Lys Phe Leu Ala Glu
290                 295                 300

Leu Pro Asp Ile Tyr Asp Gln Val Leu Lys Glu Gln Leu Glu Ile Ala
305                 310                 315                 320

Lys Ser Lys Glu Pro Gly Glu Leu Leu Thr Trp Glu Asp Ile Gln Lys
                325                 330                 335

Met Lys Tyr Ser Trp Asn Val Ala Cys Glu Val Met Arg Leu Ala Pro
            340                 345                 350

Pro Leu Gln Gly Ser Phe Arg Glu Ala Leu His Asp Phe Asp Tyr Ala
            355                 360                 365

Gly Phe Ser Ile Pro Lys Gly Trp Lys Leu Tyr Trp Ser Thr His Thr
370                 375                 380

Thr His Lys Asn Pro Glu Tyr Phe Ser Asp Pro Glu Lys Phe Asp Pro
385                 390                 395                 400

Ser Arg Phe Glu Gly Ser Gly Pro Ala Pro Tyr Thr Phe Val Pro Phe
                405                 410                 415

Gly Gly Gly Pro Arg Met Cys Pro Gly Lys Glu Tyr Ala Arg Leu Glu
            420                 425                 430

Ile Leu Val Phe Met His Asn Ile Ala Lys Arg Phe Lys Trp Asn Lys
            435                 440                 445

Val Ile Pro Asp Glu Lys Ile Val Val Asp Pro Pro Met Pro Ile Pro Ala
450                 455                 460

Lys Gly Leu Pro Val His Leu Tyr Pro Gln Lys His Glu
465                 470                 475

<210> SEQ ID NO 103
<211> LENGTH: 509
<212> TYPE: PRT
<213> ORGANISM: Vitis vinifera

<400> SEQUENCE: 103

Met Val Ser Phe Asp Leu Leu Tyr Ser Asn Leu Ile Phe Cys Leu Leu
1               5                   10                  15

Phe Ser Ala Ile Ala Ser Ile Gln Met Ile Met Gln Ser Asp Met
            20                  25                  30

Glu Leu Leu Leu Leu Ser Phe Leu Leu Leu Met Ala Leu Ser Leu Ser
            35                  40                  45

Phe Trp Ile Arg Phe Phe Val His Lys Leu Glu Lys Ser Ser Gly Ile
        50                  55                  60

Asn Leu Pro Pro Gly Lys Met Gly Phe Pro Phe Ile Gly Glu Ser Leu
65                  70                  75                  80

Glu Phe Leu Arg Met Gly Arg Lys Gly Thr Pro Glu Arg Phe Ile Gln
                85                  90                  95

Asp Arg Met Ala Lys Tyr Ser Thr Gln Ile Phe Lys Thr Cys Leu Leu
            100                 105                 110

Gly Glu Pro Thr Ala Val Val Cys Gly Ala Ala Gly Asn Lys Leu Leu
            115                 120                 125

Phe Ser Asn Glu Asn Lys Leu Val Thr Ser Trp Trp Pro Arg Ser Val
130                 135                 140

Glu Lys Ile Phe Pro Ser Ser Leu Gln Thr Ser Thr Lys Glu Glu Ser

```
             145                 150                 155                 160
Met Lys Thr Arg Lys Leu Leu Pro Ala Phe Leu Lys Pro Glu Ala Leu
                165                 170                 175

Gln Lys Tyr Val Gly Ile Met Asp Ser Ile Ala Lys Trp His Leu Asp
                180                 185                 190

Asn His Trp Asp Leu Asn Glu Thr Val Thr Val Phe Pro Leu Ala Lys
                195                 200                 205

Gln Tyr Thr Phe Met Val Ala Cys Arg Leu Phe Leu Ser Ile Asp Asp
                210                 215                 220

Pro Lys His Ile Ala Lys Phe Ala Asn Pro Phe His Ile Leu Ala Ala
225                 230                 235                 240

Gly Val Met Ser Ile Pro Ile Asn Phe Pro Gly Thr Pro Phe Asn Arg
                245                 250                 255

Ala Ile Lys Ala Ala Asp Ser Val Arg Lys Glu Leu Arg Ala Ile Ile
                260                 265                 270

Lys Gln Arg Lys Ile Gln Val Leu Ala Gly Lys Ser Ser Ser Ser Lys
                275                 280                 285

His Asp Ile Leu Ser His Met Leu Thr Thr Thr Asp Glu Asn Gly Gln
                290                 295                 300

Phe Leu Asn Glu Met Asp Ile Ala Asp Lys Ile Leu Gly Leu Leu Ile
305                 310                 315                 320

Gly Gly His Asp Thr Ala Ser Ala Val Ile Thr Phe Ile Ile Lys Tyr
                325                 330                 335

Leu Ala Glu Leu Pro Gln Val Tyr Asn Glu Val Leu Lys Glu Gln Met
                340                 345                 350

Glu Val Ala Ala Gly Lys Lys Ser Gly Glu Met Leu Asp Trp Glu Asp
                355                 360                 365

Ile Gln Lys Met Lys Tyr Ser Trp Asn Val Ala Asn Glu Val Met Arg
                370                 375                 380

Leu Ala Pro Pro Leu Gln Gly Ser Phe Arg Glu Ala Ile Thr Asp Phe
385                 390                 395                 400

Thr Tyr Ala Gly Phe Ser Ile Pro Lys Gly Trp Lys Leu Tyr Trp Ser
                405                 410                 415

Thr Asn Ala Thr His Lys Asn Pro Asp Tyr Phe Pro Asp Pro Glu Lys
                420                 425                 430

Phe Asp Pro Ser Arg Phe Glu Gly Asn Gly Pro Ile Pro Tyr Thr Tyr
                435                 440                 445

Val Pro Phe Gly Gly Pro Arg Met Cys Pro Gly Lys Glu Tyr Ala
450                 455                 460

Arg Leu Glu Ile Leu Val Phe Ile His Asn Val Val Arg Arg Phe Ser
465                 470                 475                 480

Trp Tyr Lys Leu His Pro Asn Glu Asp Val Ile Val Asp Pro Met Pro
                485                 490                 495

Met Pro Ala Lys Gly Leu Pro Ile Arg Leu Arg His His
                500                 505

<210> SEQ ID NO 104
<211> LENGTH: 484
<212> TYPE: PRT
<213> ORGANISM: Populus trichocarpa

<400> SEQUENCE: 104

Met Glu Thr Leu Tyr Phe Ile Leu Leu Leu Phe Val Pro Ile Ile Leu
1               5                   10                  15
```

```
Ser Leu Val Ala Ile Ile Tyr Lys His Arg Tyr Gln Asp Lys Leu Gln
                20                  25                  30

Asn Val Pro Pro Gly Asn Leu Gly Leu Pro Phe Val Gly Glu Ser Leu
            35                  40                  45

Asp Phe Leu Ser Lys Gly Trp Lys Gly Cys Pro Glu Asn Phe Ile Phe
 50                  55                  60

Asp Arg Ile Arg Lys Tyr Ser Ser Glu Ile Phe Lys Thr Asn Leu Phe
 65                  70                  75                  80

Leu Gln Pro Val Val Met Leu Asn Gly Val Ala Gly Asn Lys Phe Leu
                85                  90                  95

Phe Ser Asn Glu Asn Arg Leu Val Glu Thr Trp Trp Pro Asp Phe Val
            100                 105                 110

Asn Arg Ile Phe Pro Ser Ala Val Glu Thr Ser Pro Lys Glu Glu Ala
            115                 120                 125

Lys Arg Met Arg Arg Leu Phe Pro Arg Phe Leu Lys Pro Glu Ala Leu
            130                 135                 140

Gln Arg Tyr Ile Gly Thr Met Asp Met Val Thr Lys Arg His Phe Ala
145                 150                 155                 160

Leu Glu Trp Gly Asn Lys Ala Glu Val Val Phe Pro Leu Ala Lys
                165                 170                 175

Ser Tyr Thr Phe Glu Leu Ala Cys Arg Leu Phe Leu Ser Ile Glu Asp
                180                 185                 190

Pro Ser His Ile Ala Arg Phe Ser His Pro Phe Asn Gln Ile Thr Ser
            195                 200                 205

Gly Ile Phe Thr Ile Pro Ile Asp Phe Pro Gly Thr Pro Phe Asn Arg
210                 215                 220

Ala Ile Lys Ala Ser Lys Leu Ile Arg Ile Glu Leu Leu Ala Ile Ile
225                 230                 235                 240

Arg Gln Arg Lys Lys Asp Leu Ala Glu Gly Lys Ala Ser Pro Thr Gln
                245                 250                 255

Asp Ile Leu Ser His Met Leu Leu Ser Asn Asp Ala Asp Gly Lys Tyr
            260                 265                 270

Met Asn Glu Val Gln Ile Ser Asp Lys Ile Leu Ala Leu Leu Met Gly
            275                 280                 285

Gly His Glu Ser Thr Ala Ala Ser Cys Thr Phe Ile Val Lys Tyr Leu
            290                 295                 300

Ala Glu Leu Pro His Ile Tyr Glu Ala Val Tyr Lys Glu Gln Ala Glu
305                 310                 315                 320

Ile Ile Lys Ser Lys Ala Pro Gly Glu Leu Leu Asn Trp Asp Asp Ile
                325                 330                 335

Gln Lys Met Lys Tyr Ser Trp Asn Val Ala Cys Glu Thr Leu Arg Leu
            340                 345                 350

Ser Pro Pro Leu Ile Gly Asn Phe Lys Glu Ala Ile Lys Asp Phe Thr
            355                 360                 365

Phe Asn Gly Phe Ser Ile Pro Lys Gly Trp Lys Ala Ser His Phe Leu
370                 375                 380

Thr Leu Tyr Trp Ser Ala Ser Ser Thr His Lys Asn Pro Glu Tyr Phe
385                 390                 395                 400

Ser Glu Pro Glu Lys Phe Asp Pro Ser Arg Phe Glu Gly Lys Gly Pro
                405                 410                 415

Ala Pro Tyr Thr Phe Ile Pro Phe Gly Gly Gly Pro Arg Met Cys Pro
            420                 425                 430

Gly Asn Glu Tyr Ala Arg Leu Glu Ile Leu Val Phe Met His Asn Leu
```

```
                435                 440                 445
Val Lys Arg Phe Lys Phe Glu Arg Leu Ile Leu Asp Glu Lys Ile Val
450                 455                 460

Phe Asp Pro Thr Pro Lys Pro Glu Met Gly Leu Pro Val Arg Leu Leu
465                 470                 475                 480

Pro His Lys Ala

<210> SEQ ID NO 105
<211> LENGTH: 481
<212> TYPE: PRT
<213> ORGANISM: Glycine max

<400> SEQUENCE: 105

Met Glu Gln Leu Tyr Tyr Leu Thr Leu Val Leu Leu Phe Val Ser Phe
1               5                   10                  15

Val Ser Val Ser Phe Phe Ile Ile Phe Tyr Arg His Arg Ser Pro Phe
            20                  25                  30

Ser Val Pro Asn Leu Pro Pro Gly Lys Ala Gly Phe Pro Val Ile Gly
        35                  40                  45

Glu Ser Leu Glu Phe Leu Ser Ala Gly Arg Lys Gly Leu Pro Glu Lys
50                  55                  60

Phe Phe Ser Asp Arg Met Thr Glu Tyr Ser Ser Lys Val Phe Lys Thr
65                  70                  75                  80

Ser Ile Leu Gly Glu Pro Thr Val Ile Phe Cys Gly Ala Ala Cys Asn
                85                  90                  95

Lys Phe Leu Phe Ser Asn Glu Asn Lys His Val Ile Ser Trp Trp Pro
            100                 105                 110

Glu Asn Val Lys Lys Leu Phe Pro Thr Asn Ile Gln Thr Asn Ser Lys
        115                 120                 125

Glu Glu Ala Lys Lys Leu Arg Asn Ile Leu Pro Gln Phe Leu Ser Ala
130                 135                 140

Lys Ala Ile Gln Arg Tyr Val Gly Ile Met Asp Thr Val Ala Gln Arg
145                 150                 155                 160

His Phe Ala Leu Glu Trp Glu Asn Asn Thr Gln Val Thr Val Leu Pro
                165                 170                 175

Leu Ala Lys Arg Tyr Thr Phe Gly Val Ala Ser Arg Val Phe Met Ser
            180                 185                 190

Ile Asp Asp Leu Asn Gln Val Ala Lys Leu Ala Glu Pro Leu Asn Gln
        195                 200                 205

Val Asn Ala Gly Ile Ile Ser Met Pro Ile Asn Phe Pro Gly Thr Val
210                 215                 220

Phe Asn Arg Gly Ile Lys Ala Ser Lys Phe Ile Arg Arg Glu Leu Leu
225                 230                 235                 240

Arg Ile Val Lys Gln Arg Lys Val Glu Leu Ala Asn Gly Met Ser Thr
                245                 250                 255

Pro Thr Gln Asp Ile Leu Ser His Met Leu Ile Tyr Cys Asp Glu Asn
            260                 265                 270

Gly Gln Tyr Leu Ala Glu His Asp Ile Val Asn Lys Ile Leu Gly Leu
        275                 280                 285

Leu Ile Gly Ser His Glu Thr Thr Ser Thr Val Cys Thr Phe Val Val
290                 295                 300

Lys Tyr Leu Ala Glu Leu Pro Gln Asn Ile Tyr Glu Asn Val Tyr Gln
305                 310                 315                 320

Glu Gln Met Ala Ile Ala Lys Ser Lys Ala Pro Gly Glu Leu Leu Asn
```

-continued

```
                    325                 330                 335
Trp Asp Asp Ile Gln Lys Met Lys Tyr Ser Trp Asn Val Ala Cys Glu
            340                 345                 350

Val Ile Arg Leu Asn Pro Pro Ala Gln Gly Ala Phe Arg Glu Ala Ile
            355                 360                 365

Asn Asp Phe Ile Phe Asp Gly Phe Ser Ile Pro Lys Gly Trp Lys Leu
            370                 375                 380

Tyr Trp Ser Ala Asn Ser Thr His Lys Asn Pro Glu Tyr Phe Pro Glu
385                 390                 395                 400

Pro Glu Lys Phe Asp Pro Ser Arg Phe Glu Gly Thr Gly Pro Ala Pro
                405                 410                 415

Tyr Thr Tyr Val Pro Phe Gly Gly Gly Pro Ser Met Cys Pro Gly Lys
            420                 425                 430

Glu Tyr Ala Arg Met Glu Leu Leu Val Phe Met His Asn Leu Val Lys
            435                 440                 445

Arg Phe Lys Cys Glu Thr Leu Phe Pro Asn Gly Asn Val Thr Tyr Asn
            450                 455                 460

Pro Thr Pro Ile Pro Ala Lys Gly Leu Pro Val Arg Leu Ile Pro His
465                 470                 475                 480

Arg
```

The invention claimed is:

1. A modified yeast strain for production of pentacyclic triterpenoids, comprising:
   i. at least one copy of a gene for encoding an oxidosqualene cyclase,
      wherein the oxidosqualene cyclase has an amino acid sequence with at least 95% sequence identity to SEQ ID NO: 55;
   ii. at least one copy of a gene for encoding a NADPH-cytochrome P450 reductase,
      wherein the NADPH-cytochrome P450 reductase has an amino acid sequence with at least 95% sequence identity to SEQ ID NO: 66, 68 or 69; and
   iii. at least one copy of a gene for encoding a cytochrome P450 monooxygenase,
      wherein the cytochrome P450 monooxygenase has an amino acid sequence with at least 95% sequence identity to SEQ ID NO: 83, 84 or 88.

2. The modified yeast strain according to claim 1,
   wherein the oxidosqualene cyclase has an amino acid sequence with at least 95% sequence identity to SEQ ID NO: 55;
   wherein the NADPH-cytochrome P450 reductase has an amino acid sequence with at least 95% sequence identity to SEQ ID NO: 66; and
   wherein the cytochrome P450 monooxygenase has an amino acid sequence with at least 95% sequence identity to SEQ ID NO: 83.

3. The modified yeast strain according to claim 1,
   wherein the oxidosqualene cyclase has an amino acid sequence of SEQ ID NO: 55;
   wherein the NADPH-cytochrome P450 reductase has an amino acid sequence of SEQ ID NO: 66; and
   wherein the cytochrome P450 monooxygenase has an amino acid sequence of SEQ ID NO: 83.

4. The modified yeast strain according to claim 1,
   wherein the oxidosqualene cyclase has an amino acid sequence with at least 95% sequence identity to SEQ ID NO: 55;
   wherein the NADPH-cytochrome P450 reductase has an amino acid sequence with at least 95% sequence identity to SEQ ID NO: 66; and
   wherein the cytochrome P450 monooxygenase has an amino acid sequence with at least 95% sequence identity to SEQ ID NO: 84.

5. The modified yeast strain according to claim 1,
   wherein the oxidosqualene cyclase has an amino acid sequence of SEQ ID NO: 55;
   wherein the NADPH-cytochrome P450 reductase has an amino acid sequence of SEQ ID NO: 66; and
   wherein the cytochrome P450 monooxygenase has an amino acid sequence of SEQ ID NO: 84.

6. The modified yeast strain according to claim 1,
   wherein the oxidosqualene cyclase has an amino acid sequence with at least 95% sequence identity to SEQ ID NO: 55;
   wherein the NADPH-cytochrome P450 reductase has an amino acid sequence with at least 95% sequence identity to SEQ ID NO: 66; and
   wherein the cytochrome P450 monooxygenase has an amino acid sequence with at least 95% sequence identity to SEQ ID NO: 88.

7. The modified yeast strain according to claim 1,
   wherein the oxidosqualene cyclase has an amino acid sequence of SEQ ID NO: 55;
   wherein the NADPH-cytochrome P450 reductase has an amino acid sequence of SEQ ID NO: 66; and
   wherein the cytochrome P450 monooxygenase has an amino acid sequence of SEQ ID NO: 88.

8. The modified yeast strain according to claim 1,
   wherein the oxidosqualene cyclase has an amino acid sequence with at least 95% sequence identity to SEQ ID NO: 55;
   wherein the NADPH-cytochrome P450 reductase has an amino acid sequence with at least 95% sequence identity to SEQ ID NO: 68; and wherein the cytochrome P450 monooxygenase has an amino acid sequence with at least 95% sequence identity to SEQ ID NO: 83.

9. The modified yeast strain according to claim 1,
wherein the oxidosqualene cyclase has an amino acid sequence of SEQ ID NO: 55;
wherein the NADPH-cytochrome P450 reductase has an amino acid sequence of SEQ ID NO: 68; and
wherein the cytochrome P450 monooxygenase has an amino acid sequence of SEQ ID NO: 83.

10. The modified yeast strain according to claim 1,
wherein the oxidosqualene cyclase has an amino acid sequence with at least 95% sequence identity to SEQ ID NO: 55;
wherein the NADPH-cytochrome P450 reductase has an amino acid sequence with at least 95% sequence identity to SEQ ID NO: 68; and
wherein the cytochrome P450 monooxygenase has an amino acid sequence with at least 95% sequence identity to SEQ ID NO: 84.

11. The modified yeast strain according to claim 1,
wherein the oxidosqualene cyclase has an amino acid sequence of SEQ ID NO: 55;
wherein the NADPH-cytochrome P450 reductase has an amino acid sequence of SEQ ID NO: 68; and
wherein the cytochrome P450 monooxygenase has an amino acid sequence of SEQ ID NO: 84.

12. The modified yeast strain according to claim 1,
wherein the oxidosqualene cyclase has an amino acid sequence with at least 95% sequence identity to SEQ ID NO: 55;
wherein the NADPH-cytochrome P450 reductase has an amino acid sequence with at least 95% sequence identity to SEQ ID NO: 68; and
wherein the cytochrome P450 monooxygenase has an amino acid sequence with at least 95% sequence identity to SEQ ID NO: 88.

13. The modified yeast strain according to claim 1,
wherein the oxidosqualene cyclase has an amino acid sequence of SEQ ID NO: 55;
wherein the NADPH-cytochrome P450 reductase has an amino acid sequence of SEQ ID NO: 68; and
wherein the cytochrome P450 monooxygenase has an amino acid sequence of SEQ ID NO: 88.

14. The modified yeast strain according to claim 1,
wherein the oxidosqualene cyclase has an amino acid sequence with at least 95% sequence identity to SEQ ID NO: 55;
wherein the NADPH-cytochrome P450 reductase has an amino acid sequence with at least 95% sequence identity to SEQ ID NO: 69; and
wherein the cytochrome P450 monooxygenase has an amino acid sequence with at least 95% sequence identity to SEQ ID NO: 83.

15. The modified yeast strain according to claim 1,
wherein the oxidosqualene cyclase has an amino acid sequence of SEQ ID NO: 55;
wherein the NADPH-cytochrome P450 reductase has an amino acid sequence of SEQ ID NO: 69; and
wherein the cytochrome P450 monooxygenase has an amino acid sequence of SEQ ID NO: 83.

16. The modified yeast strain according to claim 1,
wherein the oxidosqualene cyclase has an amino acid sequence with at least 95% sequence identity to SEQ ID NO: 55;
wherein the NADPH-cytochrome P450 reductase has an amino acid sequence with at least 95% sequence identity to SEQ ID NO: 69; and
wherein the cytochrome P450 monooxygenase has an amino acid sequence with at least 95% sequence identity to SEQ ID NO: 84.

17. The modified yeast strain according to claim 1,
wherein the oxidosqualene cyclase has an amino acid sequence of SEQ ID NO: 55;
wherein the NADPH-cytochrome P450 reductase has an amino acid sequence of SEQ ID NO: 69; and
wherein the cytochrome P450 monooxygenase has an amino acid sequence of SEQ ID NO: 84.

18. The modified yeast strain according to claim 1,
wherein the oxidosqualene cyclase has an amino acid sequence with at least 95% sequence identity to SEQ ID NO: 55;
wherein the NADPH-cytochrome P450 reductase has an amino acid sequence with at least 95% sequence identity to SEQ ID NO: 69; and
wherein the cytochrome P450 monooxygenase has an amino acid sequence with at least 95% sequence identity to SEQ ID NO: 88.

19. The modified yeast strain according to claim 1,
wherein the oxidosqualene cyclase has an amino acid sequence of SEQ ID NO: 55;
wherein the NADPH-cytochrome P450 reductase has an amino acid sequence of SEQ ID NO: 69; and
wherein the cytochrome P450 monooxygenase has an amino acid sequence of SEQ ID NO: 88.

20. The modified yeast strain according to claim 1, wherein the strain is capable of producing betulin with an intracellular concentration of more than 1 mg per gram of dry biomass.

21. The modified yeast strain according to claim 1, wherein the strain is capable of producing betulin with an intracellular concentration of more than 3 mg per gram of dry biomass.

22. The modified yeast strain according to claim 1, wherein the strain is capable of producing betulin with an intracellular concentration of more than 10 mg per gram of dry biomass.

23. The modified yeast strain according to claim 1, wherein the strain is capable of producing betulin with a concentration of more than 50 mg per liter of culture medium.

24. The modified yeast strain according to claim 1, wherein the strain is capable of producing betulin aldehyde with an intracellular concentration of more than 1 mg per gram of dry biomass.

25. The modified yeast strain according to claim 1, wherein the strain is capable of producing betulin aldehyde with an intracellular concentration of more than 2 mg per gram of dry biomass.

26. The modified yeast strain according to claim 1, wherein the strain is capable of producing betulin aldehyde with an intracellular concentration of more than 3 mg per gram of dry biomass.

27. The modified yeast strain according to claim 1, wherein the strain is capable of producing betulin aldehyde with a concentration of more than 25 mg per liter of culture medium.

28. The modified yeast strain according to claim 1, wherein the strain is capable of producing betulinic acid with an intracellular concentration of more than 1 mg per gram of dry biomass.

29. The modified yeast strain according to claim 1, wherein the strain is capable of producing betulinic acid with an intracellular concentration of more than 2 mg per gram of dry biomass.

30. The modified yeast strain according to claim 1, wherein the strain is capable of producing betulinic acid with an intracellular concentration of more than 5 mg per gram of dry biomass.

31. The modified yeast strain according to claim 1, wherein the strain is capable of producing betulinic acid with a concentration of more than 25 mg per liter of culture medium.

32. The modified yeast strain according to claim 1, wherein the yeast strain comprises a tHMG1 expression cassette.

33. The modified yeast strain according to claim 1, wherein this strain is *Saccharomyces cerevisiae*.

34. The modified yeast strain according to claim 1, wherein the strain is a *Saccharomyces cerevisiae* GEN.PK, CEN.PK111-61A or AH22tH3ura8 strain.

35. A method for producing the modified yeast strain according to claim 1 comprising:
   a) providing a *Saccharomyces cerevisiae* strain,
   b) transforming the strain with a vector comprising a gene for encoding an oxidosqualene cyclase, wherein the oxidosqualene cyclase has an amino acid sequence with at least 95% sequence identity to SEQ ID NO: 55;
   c) transforming the strain with a vector comprising a gene for encoding an NADPH-cytochrome P450 reductase, wherein the NADPH-cytochrome P450 reductase has an amino acid sequence with at least 95% sequence identity to SEQ ID NO: 66, 68 or 69; and
   d) transforming the strain with a vector comprising a gene for encoding a cytochrome P450 monooxygenase, wherein the cytochrome P450 monooxygenase has an amino acid sequence with at least 95% sequence identity to SEQ ID NO: 83, 84 or 88.

36. A method for producing a triterpene and/or triterpenoid, comprising cultivating the modified yeast strain according to claim 1 in a medium.

* * * * *